US007763775B2

(12) United States Patent
Puthigae et al.

(10) Patent No.: US 7,763,775 B2
(45) Date of Patent: Jul. 27, 2010

(54) COMPOSITIONS AND METHODS FOR PRODUCING PLANTS WITH IMPROVED STRESS TOLERANCE

(75) Inventors: Sathish Puthigae, Auckland (NZ); Jonathan Robert Phillips, Bonn (NZ); Claudia Jeannette Smith-Espinoza, Bonn (NZ); Catherine Jane Bryant, Auckland (NZ); Kieran Michael Elborough, Franklin (NZ); Colin Robert South, Lexington, MA (US)

(73) Assignee: Vialactia Biosciences (NZ) Limited, Auckland (NZ)

( * ) Notice: Subject to any disclaimer, the term of this patent is extended or adjusted under 35 U.S.C. 154(b) by 336 days.

(21) Appl. No.: 11/584,820

(22) Filed: Oct. 20, 2006

(65) Prior Publication Data

US 2007/0231903 A1 Oct. 4, 2007

Related U.S. Application Data

(60) Provisional application No. 60/729,316, filed on Oct. 21, 2005.

(51) Int. Cl.

| | |
|---|---|
| ***C12N 15/82*** | (2006.01) |
| ***C12N 15/29*** | (2006.01) |
| ***A01H 5/00*** | (2006.01) |
| ***A01H 5/10*** | (2006.01) |

(52) U.S. Cl. ...................... 800/289; 800/298; 536/23.6; 435/320.1; 435/252.3; 435/419; 435/468; 435/6; 435/7.1

(58) Field of Classification Search ....................... None
See application file for complete search history.

(56) References Cited

U.S. PATENT DOCUMENTS

2006/0123516 A1* 6/2006 Ronen et al. ................ 800/289

OTHER PUBLICATIONS

Whisstock J.C. et al. Prediction of protein function from protein sequence and structure. Q Rev Biophys. Aug. 2003;36(3):307-40. Review.*

Heim et al. The basic helix-loop-helix transcription factor family in plants: a genome-wide study of protein structure and functional diversity Mol Biol Evol. May 2003;20(5):735-47. Epub Apr 2, 2003.*

Konishi et al. Identification of the C-terminal activation domain of the NeuroD-related factor (NDRF). Nucleic Acids Res. Jun. 15, 2000;28(12):2406-12.*

Tamura T et al. Osmotic stress tolerance of transgenic tobacco expressing a gene encoding a membrane-located receptor-like protein from tobacco plants. Plant Physiol. Feb. 2003;131(2):454-62.*

Duek et al. The degradation of HFR1, a putative bHLH class transcription factor involved in light signaling, is regulated by phosphorylation and requires COP1. Curr Biol. Dec. 29, 2004;14(24):2296-301.*

Gaxiola et al., "Drought- and salt-tolerant plants result from overexpression of the AVP1 H+-pump", Proceedings of the National Academy of Sciences, 2001, vol. 98, No. 20, pp. 11444-11449.

Kasuga at al., "Improving plant drought, salt, and freezing tolerance by gene transfer of a single stress-inducible transcription factor", Nature Biotechnology, 1999, vol. 17, pp. 287-291.

Shinozaki et al., "Gene networks involved in drought stress response and tolerance", Journal of Experimental Botany, 2006, vol. 58, No. 2, pp. 221-227.

Liu et al., "Two Transcription Factors, DREB1 and DREB2, with an EREBP/AP2 DNA Binding Domain Separate Two Cellular Signal Transduction Pathways in Drought- and Low-Temperature-Responsive Gene Expression, Respectively, in Arabidopsis", The Plant Cell, 1998, vol. 10, pp. 1391-1406.

* cited by examiner

*Primary Examiner*—Cynthia Collins
(74) *Attorney, Agent, or Firm*—Knobbe, Martens Olson & Bear, LLP

(57) ABSTRACT

The invention provides compositions and methods useful for producing a plant cell or plant with altered tolerance to drought by transformation of the plant cell or plant with a genetic construct encoding a polypeptide with at least 90% identity to the amino acid sequence of SEQ ID NO:4.

19 Claims, 53 Drawing Sheets

Figure 1

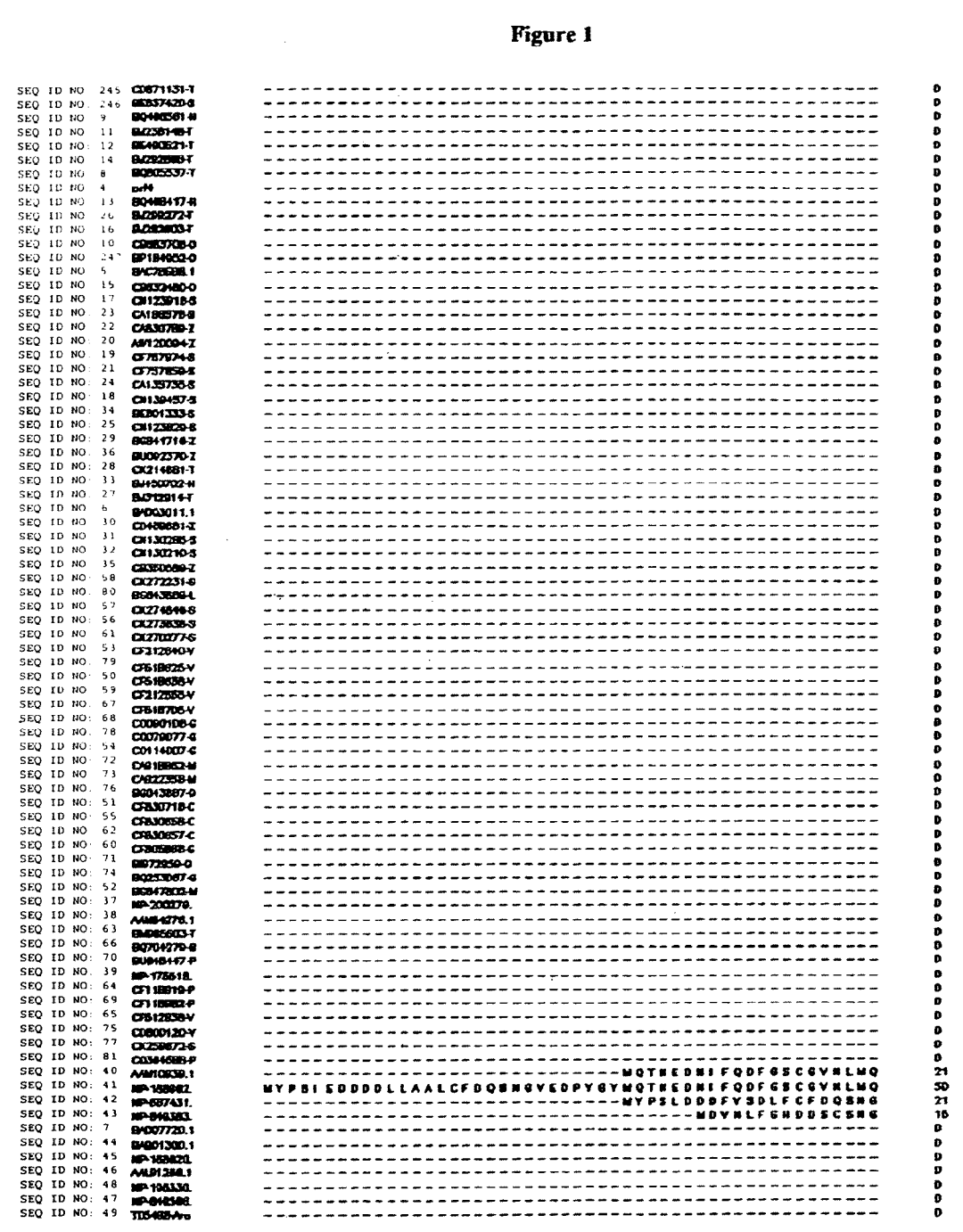

| | | | |
|---|---|---|---|
| SEQ ID NO 245 | CD871131-T | -------------------------------------------------- | 0 |
| SEQ ID NO. 246 | BE837420-G | -------------------------------------------------- | 0 |
| SEQ ID NO 9 | BQ486561-H | -------------------------------------------------- | 0 |
| SEQ ID NO 11 | BM258148-T | -------------------------------------------------- | 0 |
| SEQ ID NO: 12 | BE490521-T | -------------------------------------------------- | 0 |
| SEQ ID NO 14 | BM292880-T | -------------------------------------------------- | 0 |
| SEQ ID NO 8 | BQ805537-T | -------------------------------------------------- | 0 |
| SEQ ID NO 4 | orf4 | -------------------------------------------------- | 0 |
| SEQ ID NO 13 | BQ488417-R | -------------------------------------------------- | 0 |
| SEQ ID NO 26 | BM292272-T | -------------------------------------------------- | 0 |
| SEQ ID NO 16 | BM292803-T | -------------------------------------------------- | 0 |
| SEQ ID NO 10 | CD883708-O | -------------------------------------------------- | 0 |
| SEQ ID NO 247 | BP184952-O | -------------------------------------------------- | 0 |
| SEQ ID NO 5 | BAC78588.1 | -------------------------------------------------- | 0 |
| SEQ ID NO 15 | CD832480-O | -------------------------------------------------- | 0 |
| SEQ ID NO 17 | CN123918-S | -------------------------------------------------- | 0 |
| SEQ ID NO. 23 | CA186578-B | -------------------------------------------------- | 0 |
| SEQ ID NO 22 | CA830789-Z | -------------------------------------------------- | 0 |
| SEQ ID NO: 20 | AW120094-Z | -------------------------------------------------- | 0 |
| SEQ ID NO. 19 | CF787974-S | -------------------------------------------------- | 0 |
| SEQ ID NO: 21 | CF757858-E | -------------------------------------------------- | 0 |
| SEQ ID NO: 24 | CA135735-S | -------------------------------------------------- | 0 |
| SEQ ID NO· 18 | CN139457-S | -------------------------------------------------- | 0 |
| SEQ ID NO: 34 | BG601333-S | -------------------------------------------------- | 0 |
| SEQ ID NO: 25 | CN123829-S | -------------------------------------------------- | 0 |
| SEQ ID NO: 29 | BG841716-Z | -------------------------------------------------- | 0 |
| SEQ ID NO. 36 | BU092370-Z | -------------------------------------------------- | 0 |
| SEQ ID NO: 28 | CK214881-T | -------------------------------------------------- | 0 |
| SEQ ID NO· 33 | BJ430702-H | -------------------------------------------------- | 0 |
| SEQ ID NO. 27 | BJ712914-T | -------------------------------------------------- | 0 |
| SEQ ID NO 6 | BAD03011.1 | -------------------------------------------------- | 0 |
| SEQ ID NO 30 | CD459881-I | -------------------------------------------------- | 0 |
| SEQ ID NO 31 | CN130285-S | -------------------------------------------------- | 0 |
| SEQ ID NO 32 | CN130210-S | -------------------------------------------------- | 0 |
| SEQ ID NO 35 | CB350080-Z | -------------------------------------------------- | 0 |
| SEQ ID NO· 58 | CK272231-G | -------------------------------------------------- | 0 |
| SEQ ID NO. 80 | BG843589-L | -------------------------------------------------- | 0 |
| SEQ ID NO 57 | CK274846-S | -------------------------------------------------- | 0 |
| SEQ ID NO: 56 | CK273838-S | -------------------------------------------------- | 0 |
| SEQ ID NO 61 | CK270277-S | -------------------------------------------------- | 0 |
| SEQ ID NO 53 | CF212840-V | -------------------------------------------------- | 0 |
| SEQ ID NO. 79 | CF518825-V | -------------------------------------------------- | 0 |
| SEQ ID NO· 50 | CF518858-V | -------------------------------------------------- | 0 |
| SEQ ID NO 59 | CF212555-V | -------------------------------------------------- | 0 |
| SEQ ID NO. 67 | CF518706-V | -------------------------------------------------- | 0 |
| SEQ ID NO: 68 | CO090108-C | -------------------------------------------------- | 0 |
| SEQ ID NO. 78 | CO079077-C | -------------------------------------------------- | 0 |
| SEQ ID NO: 54 | CO114007-C | -------------------------------------------------- | 0 |
| SEQ ID NO· 72 | CA918852-M | -------------------------------------------------- | 0 |
| SEQ ID NO 73 | CA922358-M | -------------------------------------------------- | 0 |
| SEQ ID NO. 76 | BG043887-D | -------------------------------------------------- | 0 |
| SEQ ID NO: 51 | CF830718-C | -------------------------------------------------- | 0 |
| SEQ ID NO· 55 | CF830858-C | -------------------------------------------------- | 0 |
| SEQ ID NO 62 | CF830857-C | -------------------------------------------------- | 0 |
| SEQ ID NO· 60 | CF805868-C | -------------------------------------------------- | 0 |
| SEQ ID NO· 71 | BB972950-O | -------------------------------------------------- | 0 |
| SEQ ID NO: 74 | BQ253067-G | -------------------------------------------------- | 0 |
| SEQ ID NO: 52 | BG847802-M | -------------------------------------------------- | 0 |
| SEQ ID NO: 37 | NP_200279. | -------------------------------------------------- | 0 |
| SEQ ID NO: 38 | AAM64276.1 | -------------------------------------------------- | 0 |
| SEQ ID NO: 63 | BM065603-T | -------------------------------------------------- | 0 |
| SEQ ID NO: 66 | BQ704279-B | -------------------------------------------------- | 0 |
| SEQ ID NO: 70 | BU048447-P | -------------------------------------------------- | 0 |
| SEQ ID NO. 39 | NP_175518. | -------------------------------------------------- | 0 |
| SEQ ID NO: 64 | CF118819-P | -------------------------------------------------- | 0 |
| SEQ ID NO: 69 | CF118882-P | -------------------------------------------------- | 0 |
| SEQ ID NO: 65 | CF512838-V | -------------------------------------------------- | 0 |
| SEQ ID NO: 75 | CO800120-Y | -------------------------------------------------- | 0 |
| SEQ ID NO: 77 | CK258672-S | -------------------------------------------------- | 0 |
| SEQ ID NO: 81 | CO344588-P | -------------------------------------------------- | 0 |
| SEQ ID NO: 40 | AAM10839.1 | -----------------------------MQTHEDHIFQDFGSCGVHLMQ | 21 |
| SEQ ID NO: 41 | NP_188882. | MYPHISDDDDLLAALCFDQSHGVEDPYGYMQTHEDHIFQDFGSCGVHLMQ | 50 |
| SEQ ID NO: 42 | NP_687431. | -----------------------------MYPSLDDDFYSDLFCFDQSHG | 21 |
| SEQ ID NO: 43 | NP_848383. | -----------------------------------MDVHLFGHDDSCSHG | 16 |
| SEQ ID NO: 7 | BAD07720.1 | -------------------------------------------------- | 0 |
| SEQ ID NO: 44 | BAB01300.1 | -------------------------------------------------- | 0 |
| SEQ ID NO: 45 | NP_189820. | -------------------------------------------------- | 0 |
| SEQ ID NO: 46 | AAL91288.1 | -------------------------------------------------- | 0 |
| SEQ ID NO: 48 | NP_196330. | -------------------------------------------------- | 0 |
| SEQ ID NO: 47 | NP_848586. | -------------------------------------------------- | 0 |
| SEQ ID NO: 49 | TD5488-Ara | -------------------------------------------------- | 0 |

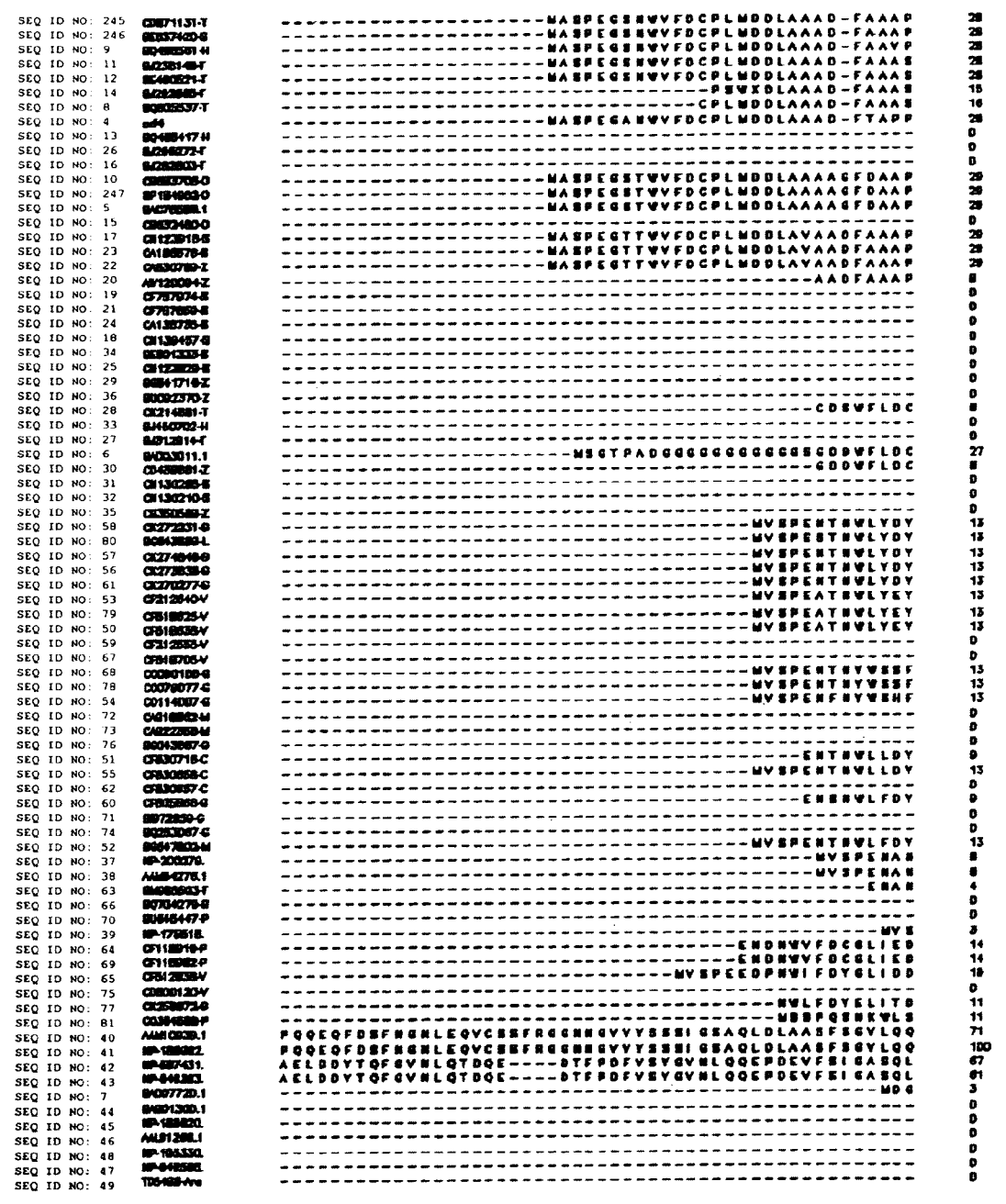

| | | | |
|---|---|---|---|
| SEQ ID NO: 245 | [illegible] | ---------------------MASPEGSNVVFDCPLMDDLAAAD-FAAAP | 28 |
| SEQ ID NO: 246 | [illegible] | ---------------------MASPEGSNVVFDCPLMDDLAAAD-FAAAP | 28 |
| SEQ ID NO: 9 | [illegible] | ---------------------MASPEGSNVVFDCPLMDDLAAAD-FAAVP | 28 |
| SEQ ID NO: 11 | [illegible] | ---------------------MASPEGSNVVFDCPLMDDLAAAD-FAAAS | 28 |
| SEQ ID NO: 12 | [illegible] | ---------------------MASPEGSNVVFDCPLMDDLAAAD-FAAAS | 28 |
| SEQ ID NO: 14 | [illegible] | ----------------------------------PSVXDLAAAD-FAAAS | 15 |
| SEQ ID NO: 8 | [illegible] | ---------------------------------CPLMDDLAAAD-FAAAS | 16 |
| SEQ ID NO: 4 | [illegible] | ---------------------MASPEGANVVFDCPLMDDLAAAD-FTAPP | 28 |
| SEQ ID NO: 13 | [illegible] | -------------------------------------------------- | 0 |
| SEQ ID NO: 26 | [illegible] | -------------------------------------------------- | 0 |
| SEQ ID NO: 16 | [illegible] | -------------------------------------------------- | 0 |
| SEQ ID NO: 10 | [illegible] | ---------------------MASPEGSTVVFDCPLMDDLAAAAGFDAAP | 29 |
| SEQ ID NO: 247 | [illegible] | ---------------------MASPEGSTVVFDCPLMDDLAAAAGFDAAP | 29 |
| SEQ ID NO: 5 | [illegible] | ---------------------MASPEGSTVVFDCPLMDDLAAAAGFDAAP | 29 |
| SEQ ID NO: 15 | [illegible] | -------------------------------------------------- | 0 |
| SEQ ID NO: 17 | [illegible] | ---------------------MASPEGTTVVFDCPLMDDLAVAADFAAAP | 29 |
| SEQ ID NO: 23 | [illegible] | ---------------------MASPEGTTVVFDCPLMDDLAVAADFAAAP | 29 |
| SEQ ID NO: 22 | [illegible] | ---------------------MASPEGTTVVFDCPLMDDLAVAADFAAAP | 29 |
| SEQ ID NO: 20 | [illegible] | ------------------------------------------AADFAAAP | 8 |
| SEQ ID NO: 19 | [illegible] | -------------------------------------------------- | 0 |
| SEQ ID NO: 21 | [illegible] | -------------------------------------------------- | 0 |
| SEQ ID NO: 24 | [illegible] | -------------------------------------------------- | 0 |
| SEQ ID NO: 18 | [illegible] | -------------------------------------------------- | 0 |
| SEQ ID NO: 34 | [illegible] | -------------------------------------------------- | 0 |
| SEQ ID NO: 25 | [illegible] | -------------------------------------------------- | 0 |
| SEQ ID NO: 29 | [illegible] | -------------------------------------------------- | 0 |
| SEQ ID NO: 36 | [illegible] | -------------------------------------------------- | 0 |
| SEQ ID NO: 28 | [illegible] | ------------------------------------------CDSVFLDC | 8 |
| SEQ ID NO: 33 | [illegible] | -------------------------------------------------- | 0 |
| SEQ ID NO: 27 | [illegible] | -------------------------------------------------- | 0 |
| SEQ ID NO: 6 | BAD33011.1 | -----------------------MSGTPADGGGGGGGGGGGSGDDVFLDC | 27 |
| SEQ ID NO: 30 | [illegible] | ------------------------------------------GDDVFLDC | 8 |
| SEQ ID NO: 31 | [illegible] | -------------------------------------------------- | 0 |
| SEQ ID NO: 32 | [illegible] | -------------------------------------------------- | 0 |
| SEQ ID NO: 35 | [illegible] | -------------------------------------------------- | 0 |
| SEQ ID NO: 58 | [illegible] | -------------------------------------MVSPENTNVLYDY | 13 |
| SEQ ID NO: 80 | [illegible] | -------------------------------------MVSPESTNVLYDY | 13 |
| SEQ ID NO: 57 | [illegible] | -------------------------------------MVSPENTNVLYDY | 13 |
| SEQ ID NO: 56 | [illegible] | -------------------------------------MVSPENTNVLYDY | 13 |
| SEQ ID NO: 61 | [illegible] | -------------------------------------MVSPENTNVLYDY | 13 |
| SEQ ID NO: 53 | [illegible] | -------------------------------------MVSPEATNVLYEY | 13 |
| SEQ ID NO: 79 | [illegible] | -------------------------------------MVSPEATNVLYEY | 13 |
| SEQ ID NO: 50 | [illegible] | -------------------------------------MVSPEATNVLYEY | 13 |
| SEQ ID NO: 59 | [illegible] | -------------------------------------------------- | 0 |
| SEQ ID NO: 67 | [illegible] | -------------------------------------------------- | 0 |
| SEQ ID NO: 68 | [illegible] | -------------------------------------MVSPENTNYVESF | 13 |
| SEQ ID NO: 78 | [illegible] | -------------------------------------MVSPENTNYVESF | 13 |
| SEQ ID NO: 54 | [illegible] | -------------------------------------MVSPENFNYVEHF | 13 |
| SEQ ID NO: 72 | [illegible] | -------------------------------------------------- | 0 |
| SEQ ID NO: 73 | [illegible] | -------------------------------------------------- | 0 |
| SEQ ID NO: 76 | [illegible] | -------------------------------------------------- | 0 |
| SEQ ID NO: 51 | [illegible] | -----------------------------------------ENTNVLLDY | 9 |
| SEQ ID NO: 55 | [illegible] | -------------------------------------MVSPENTNVLLDY | 13 |
| SEQ ID NO: 62 | [illegible] | -------------------------------------------------- | 0 |
| SEQ ID NO: 60 | [illegible] | -----------------------------------------ENSNVLFDY | 9 |
| SEQ ID NO: 71 | [illegible] | -------------------------------------------------- | 0 |
| SEQ ID NO: 74 | [illegible] | -------------------------------------------------- | 0 |
| SEQ ID NO: 52 | [illegible] | -------------------------------------MVSPENTNVLFDY | 13 |
| SEQ ID NO: 37 | [illegible] | ------------------------------------------MVSPENAN | 8 |
| SEQ ID NO: 38 | [illegible] | ------------------------------------------MVSPENAN | 8 |
| SEQ ID NO: 63 | [illegible] | ----------------------------------------------ENAN | 4 |
| SEQ ID NO: 66 | [illegible] | -------------------------------------------------- | 0 |
| SEQ ID NO: 70 | [illegible] | -------------------------------------------------- | 0 |
| SEQ ID NO: 39 | [illegible] | -----------------------------------------------MVS | 3 |
| SEQ ID NO: 64 | [illegible] | ------------------------------------ENDNVVFDCGLIED | 14 |
| SEQ ID NO: 69 | [illegible] | ------------------------------------ENDNVVFDCGLIED | 14 |
| SEQ ID NO: 65 | [illegible] | -------------------------------MVSPEEDPNVIFDYGLIDD | 19 |
| SEQ ID NO: 75 | [illegible] | -------------------------------------------------- | 0 |
| SEQ ID NO: 77 | [illegible] | ---------------------------------------NVLFDYELITD | 11 |
| SEQ ID NO: 81 | [illegible] | ---------------------------------------MSSFQSNKVLS | 11 |
| SEQ ID NO: 40 | [illegible] | PQQEQFDSFNGNLEQVCSSFRGGNNGVVYSSSIGSAQLDLAASFSGVLQQ | 71 |
| SEQ ID NO: 41 | [illegible] | PQQEQFDSFNGNLEQVCSSFRGGNNGVVYSSSIGSAQLDLAASFSGVLQQ | 100 |
| SEQ ID NO: 42 | [illegible] | AELDDYTQFGVNLQTDQE----DTFPDFVSYGVNLQQEPDEVFSIGASQL | 67 |
| SEQ ID NO: 43 | [illegible] | AELDDYTQFGVNLQTDQE----DTFPDFVSYGVNLQQEPDEVFSIGASQL | 61 |
| SEQ ID NO: 7 | [illegible] | -----------------------------------------------MDG | 3 |
| SEQ ID NO: 44 | [illegible] | -------------------------------------------------- | 0 |
| SEQ ID NO: 45 | [illegible] | -------------------------------------------------- | 0 |
| SEQ ID NO: 46 | [illegible] | -------------------------------------------------- | 0 |
| SEQ ID NO: 48 | [illegible] | -------------------------------------------------- | 0 |
| SEQ ID NO: 47 | [illegible] | -------------------------------------------------- | 0 |
| SEQ ID NO: 49 | [illegible] | -------------------------------------------------- | 0 |

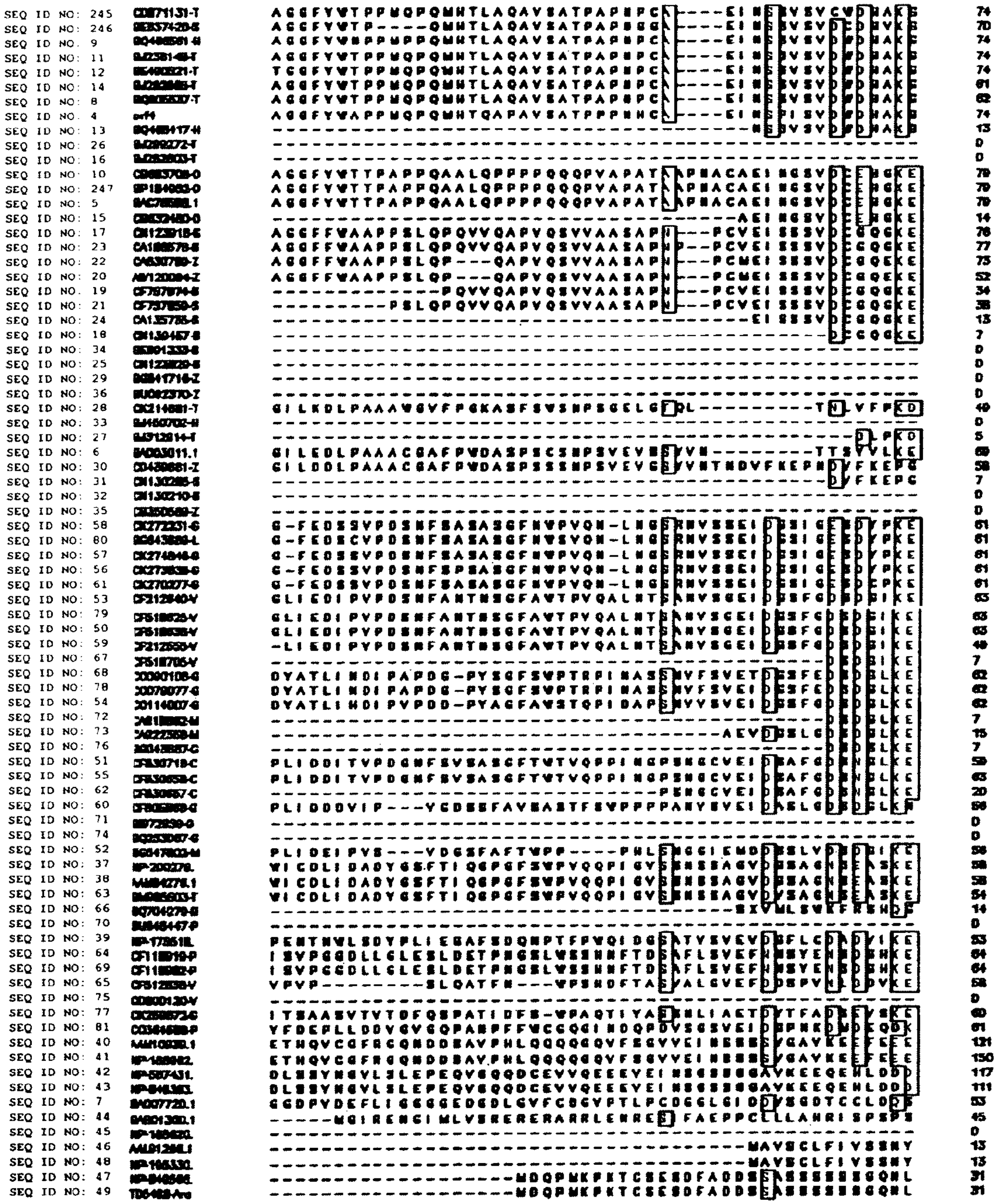

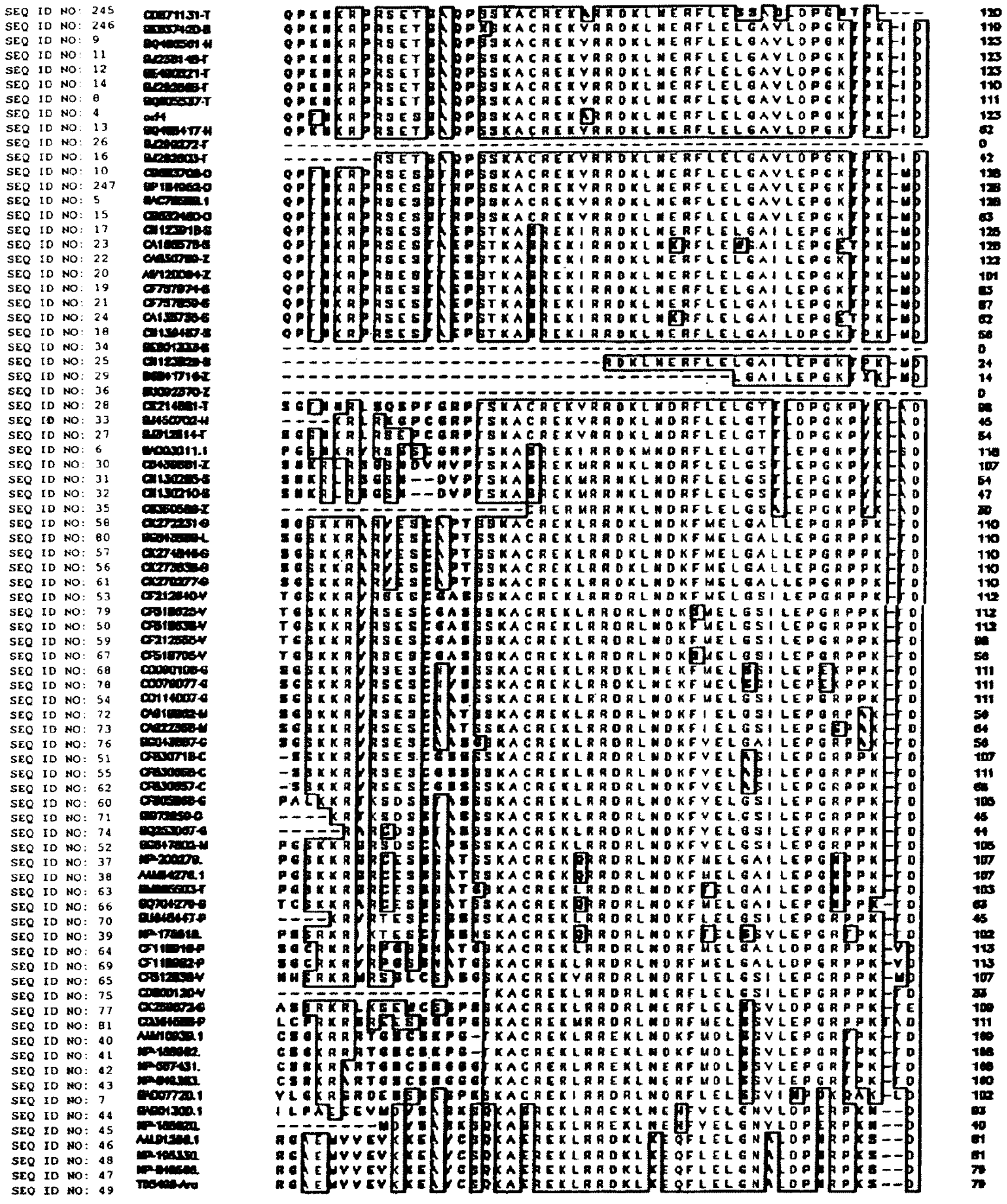

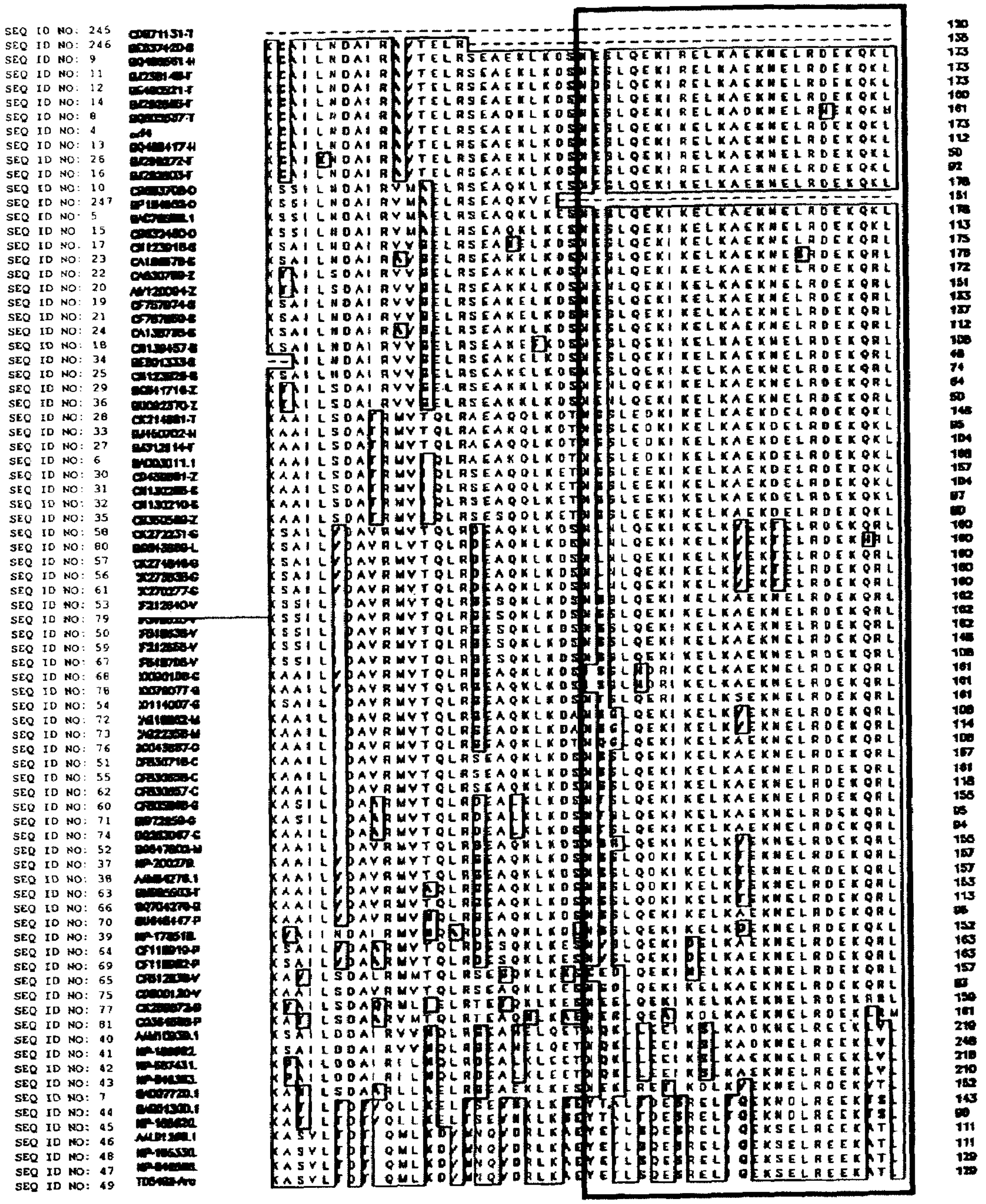

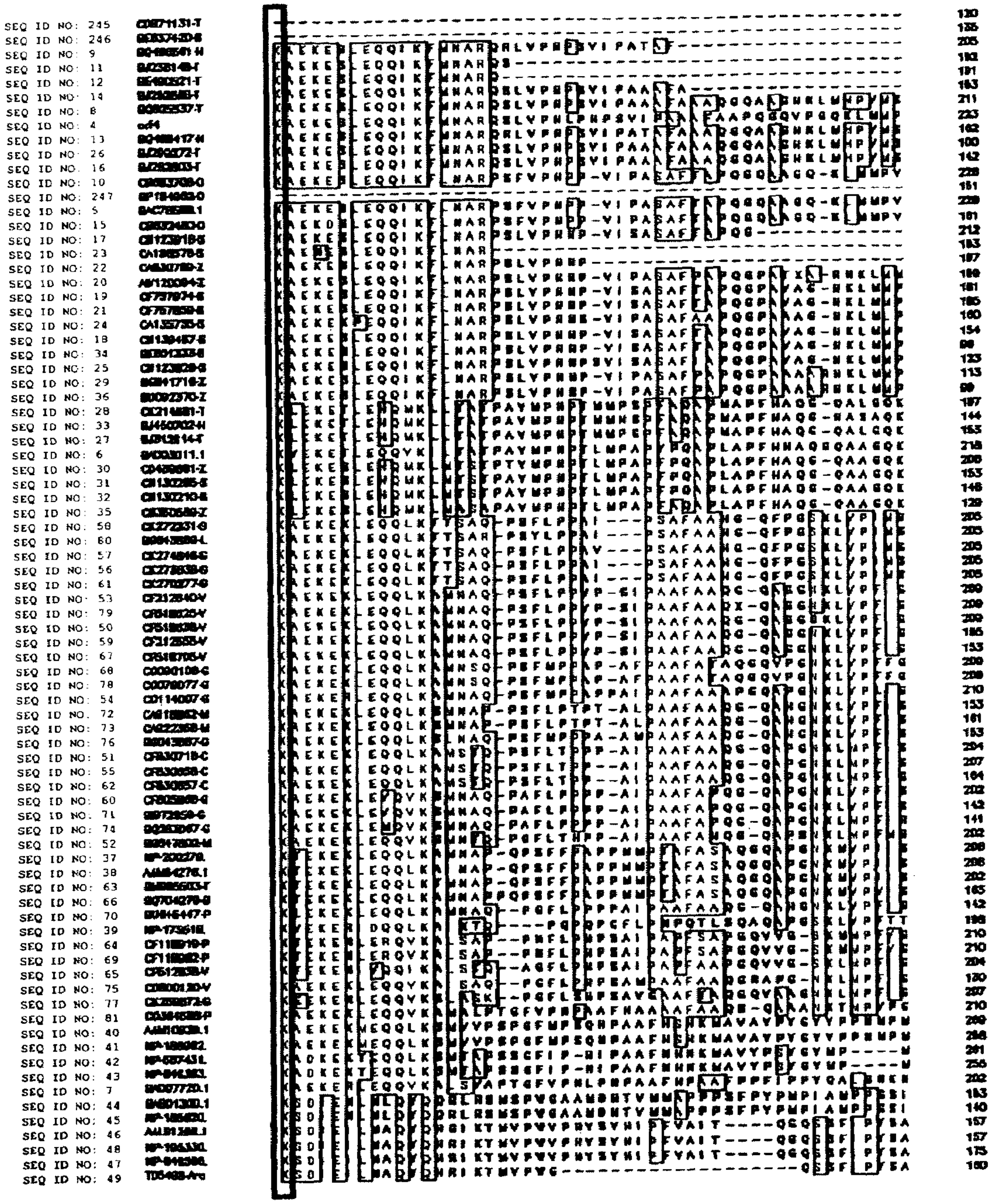

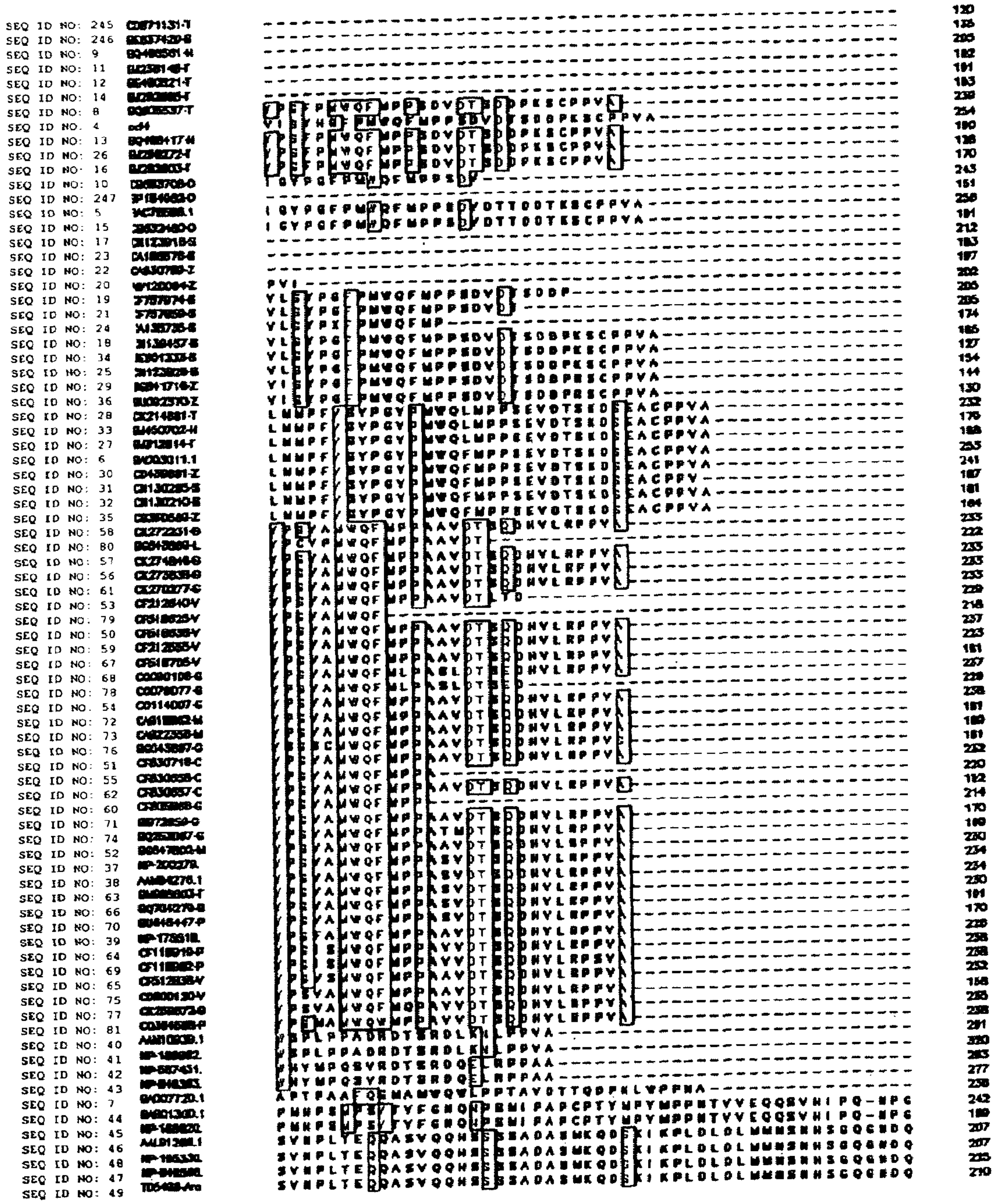
SEQ ID NO: 245
SEQ ID NO: 246
SEQ ID NO: 9
SEQ ID NO: 11
SEQ ID NO: 12
SEQ ID NO: 14
SEQ ID NO: 8
SEQ ID NO: 4
SEQ ID NO: 13
SEQ ID NO: 26
SEQ ID NO: 16
SEQ ID NO: 10
SEQ ID NO: 247
SEQ ID NO: 5
SEQ ID NO: 15
SEQ ID NO: 17
SEQ ID NO: 23
SEQ ID NO: 22
SEQ ID NO: 20
SEQ ID NO: 19
SEQ ID NO: 21
SEQ ID NO: 24
SEQ ID NO: 18
SEQ ID NO: 34
SEQ ID NO: 25
SEQ ID NO: 29
SEQ ID NO: 36
SEQ ID NO: 28
SEQ ID NO: 33
SEQ ID NO: 27
SEQ ID NO: 6
SEQ ID NO: 30
SEQ ID NO: 31
SEQ ID NO: 32
SEQ ID NO: 35
SEQ ID NO: 58
SEQ ID NO: 80
SEQ ID NO: 57
SEQ ID NO: 56
SEQ ID NO: 61
SEQ ID NO: 53
SEQ ID NO: 79
SEQ ID NO: 50
SEQ ID NO: 59
SEQ ID NO: 67
SEQ ID NO: 68
SEQ ID NO: 78
SEQ ID NO: 54
SEQ ID NO: 72
SEQ ID NO: 73
SEQ ID NO: 76
SEQ ID NO: 51
SEQ ID NO: 55
SEQ ID NO: 62
SEQ ID NO: 60
SEQ ID NO: 71
SEQ ID NO: 74
SEQ ID NO: 52
SEQ ID NO: 37
SEQ ID NO: 38
SEQ ID NO: 63
SEQ ID NO: 66
SEQ ID NO: 70
SEQ ID NO: 39
SEQ ID NO: 64
SEQ ID NO: 69
SEQ ID NO: 65
SEQ ID NO: 75
SEQ ID NO: 77
SEQ ID NO: 81
SEQ ID NO: 40
SEQ ID NO: 41
SEQ ID NO: 42
SEQ ID NO: 43
SEQ ID NO: 7
SEQ ID NO: 44
SEQ ID NO: 45
SEQ ID NO: 46
SEQ ID NO: 48
SEQ ID NO: 47
SEQ ID NO: 49

| | | | |
|---|---|---|---|
| SEQ ID NO: 245 | CD871131-T | -------------------------------------------------- | 120 |
| SEQ ID NO: 246 | BE837402D-S | -------------------------------------------------- | 155 |
| SEQ ID NO: 9 | BQ468581-H | -------------------------------------------------- | 205 |
| SEQ ID NO: 11 | BJ238145-T | -------------------------------------------------- | 192 |
| SEQ ID NO: 12 | BE490821-T | -------------------------------------------------- | 191 |
| SEQ ID NO: 14 | BJ282665-T | -------------------------------------------------- | 183 |
| SEQ ID NO: 8 | BQ805537-T | -------------------------------------------------- | 259 |
| SEQ ID NO: 4 | arf4 | -------------------------------------------------- | 284 |
| SEQ ID NO: 13 | BQ468417-H | -------------------------------------------------- | 190 |
| SEQ ID NO: 26 | BJ290272-T | -------------------------------------------------- | 128 |
| SEQ ID NO: 16 | BJ283803-T | -------------------------------------------------- | 170 |
| SEQ ID NO: 10 | CB837708-O | -------------------------------------------------- | 243 |
| SEQ ID NO: 247 | BP184583-O | -------------------------------------------------- | 151 |
| SEQ ID NO: 5 | BAC78588.1 | -------------------------------------------------- | 258 |
| SEQ ID NO: 15 | CB872480-O | -------------------------------------------------- | 191 |
| SEQ ID NO: 17 | CN123918-S | -------------------------------------------------- | 212 |
| SEQ ID NO: 23 | CA186578-S | -------------------------------------------------- | 183 |
| SEQ ID NO: 22 | CA630789-Z | -------------------------------------------------- | 187 |
| SEQ ID NO: 20 | AW120094-Z | -------------------------------------------------- | 202 |
| SEQ ID NO: 19 | CF787874-S | -------------------------------------------------- | 205 |
| SEQ ID NO: 21 | CF787859-S | -------------------------------------------------- | 206 |
| SEQ ID NO: 24 | CA138736-S | -------------------------------------------------- | 174 |
| SEQ ID NO: 18 | CN130457-S | -------------------------------------------------- | 188 |
| SEQ ID NO: 34 | BE801333-S | -------------------------------------------------- | 127 |
| SEQ ID NO: 25 | CN123829-S | -------------------------------------------------- | 184 |
| SEQ ID NO: 29 | BG841718-Z | -------------------------------------------------- | 144 |
| SEQ ID NO: 36 | BU092370-Z | -------------------------------------------------- | 130 |
| SEQ ID NO: 28 | CK214681-T | -------------------------------------------------- | 252 |
| SEQ ID NO: 33 | BM460702-H | -------------------------------------------------- | 179 |
| SEQ ID NO: 27 | BJ312814-T | -------------------------------------------------- | 188 |
| SEQ ID NO: 6 | BAD03011.1 | -------------------------------------------------- | 263 |
| SEQ ID NO: 30 | CD439881-Z | -------------------------------------------------- | 241 |
| SEQ ID NO: 31 | CN130285-S | -------------------------------------------------- | 187 |
| SEQ ID NO: 32 | CN130210-S | -------------------------------------------------- | 181 |
| SEQ ID NO: 35 | CB350580-Z | -------------------------------------------------- | 164 |
| SEQ ID NO: 58 | CK272231-G | -------------------------------------------------- | 223 |
| SEQ ID NO: 80 | BG843889-L | -------------------------------------------------- | 222 |
| SEQ ID NO: 57 | CK274848-G | -------------------------------------------------- | 233 |
| SEQ ID NO: 56 | CK273639-G | -------------------------------------------------- | 233 |
| SEQ ID NO: 61 | CK270277-G | -------------------------------------------------- | 233 |
| SEQ ID NO: 53 | CF212640-V | -------------------------------------------------- | 229 |
| SEQ ID NO: 79 | CF518625-V | -------------------------------------------------- | 218 |
| SEQ ID NO: 50 | CF518639-V | -------------------------------------------------- | 237 |
| SEQ ID NO: 59 | CF212555-V | -------------------------------------------------- | 223 |
| SEQ ID NO: 67 | CF518705-V | -------------------------------------------------- | 181 |
| SEQ ID NO: 68 | CD090108-G | -------------------------------------------------- | 237 |
| SEQ ID NO: 78 | CD079077-G | -------------------------------------------------- | 229 |
| SEQ ID NO: 54 | CD114007-G | -------------------------------------------------- | 238 |
| SEQ ID NO: 72 | CA618862-M | -------------------------------------------------- | 181 |
| SEQ ID NO: 73 | CA622358-M | -------------------------------------------------- | 189 |
| SEQ ID NO: 76 | BG043887-G | -------------------------------------------------- | 181 |
| SEQ ID NO: 51 | CF830718-C | -------------------------------------------------- | 232 |
| SEQ ID NO: 55 | CF830658-C | -------------------------------------------------- | 220 |
| SEQ ID NO: 62 | CF830687-C | -------------------------------------------------- | 182 |
| SEQ ID NO: 60 | CF805868-G | -------------------------------------------------- | 214 |
| SEQ ID NO: 71 | BE872860-G | -------------------------------------------------- | 170 |
| SEQ ID NO: 74 | BQ253067-G | -------------------------------------------------- | 189 |
| SEQ ID NO: 52 | BG547803-M | -------------------------------------------------- | 230 |
| SEQ ID NO: 37 | NP-200279. | -------------------------------------------------- | 234 |
| SEQ ID NO: 38 | AAM64276.1 | -------------------------------------------------- | 234 |
| SEQ ID NO: 63 | BM985603-T | -------------------------------------------------- | 230 |
| SEQ ID NO: 66 | BQ704279-S | -------------------------------------------------- | 181 |
| SEQ ID NO: 70 | BU846147-P | -------------------------------------------------- | 170 |
| SEQ ID NO: 39 | NP-173518. | -------------------------------------------------- | 228 |
| SEQ ID NO: 64 | CF118916-P | -------------------------------------------------- | 238 |
| SEQ ID NO: 69 | CF118982-F | -------------------------------------------------- | 238 |
| SEQ ID NO: 65 | CF512836-V | -------------------------------------------------- | 232 |
| SEQ ID NO: 75 | CD800120-V | -------------------------------------------------- | 188 |
| SEQ ID NO: 77 | CK269673-G | -------------------------------------------------- | 235 |
| SEQ ID NO: 81 | CO584589-P | -------------------------------------------------- | 238 |
| SEQ ID NO: 40 | AAM10639.1 | -------------------------------------------------- | 231 |
| SEQ ID NO: 41 | NP-186982. | -------------------------------------------------- | 300 |
| SEQ ID NO: 42 | NP-567431. | -------------------------------------------------- | 283 |
| SEQ ID NO: 43 | NP-641363. | -------------------------------------------------- | 277 |
| SEQ ID NO: 7 | BAD07720.1 | -------------------------------------------------- | 258 |
| SEQ ID NO: 44 | BAG01300.1 | MRSREPRAKVSRESRSEKAEDSNEVATQLELKTPGSTSDKDTLQRPEKTK | 282 |
| SEQ ID NO: 45 | NP-189920. | MRSREPRAKVSRESRSEKAEDSNEVATQLELKTPGSTSDKDTLQRPEKTK | 239 |
| SEQ ID NO: 46 | AAU81288.1 | KDDVRLKLELKIHASSLAQQDVSGKEKKVSLTTTASSSNSYSLSQAVQDS | 267 |
| SEQ ID NO: 48 | NP-193330. | KDDVRLKLELKIHASSLAQQDVSGKEKKVSLTTTASSSNSYSLSQAVQDS | 267 |
| SEQ ID NO: 47 | NP-919508. | KDDVRLKLELKIHASSLAQQDVSGKEKKVSLTTTASSSNSYSLSQAVQDS | 275 |
| SEQ ID NO: 49 | TD5488-Arc | KDDVRLKLELKIHASSLAQQVSDLFNSFANKLFNGLTRVVFNAGCFVKRE | 260 |

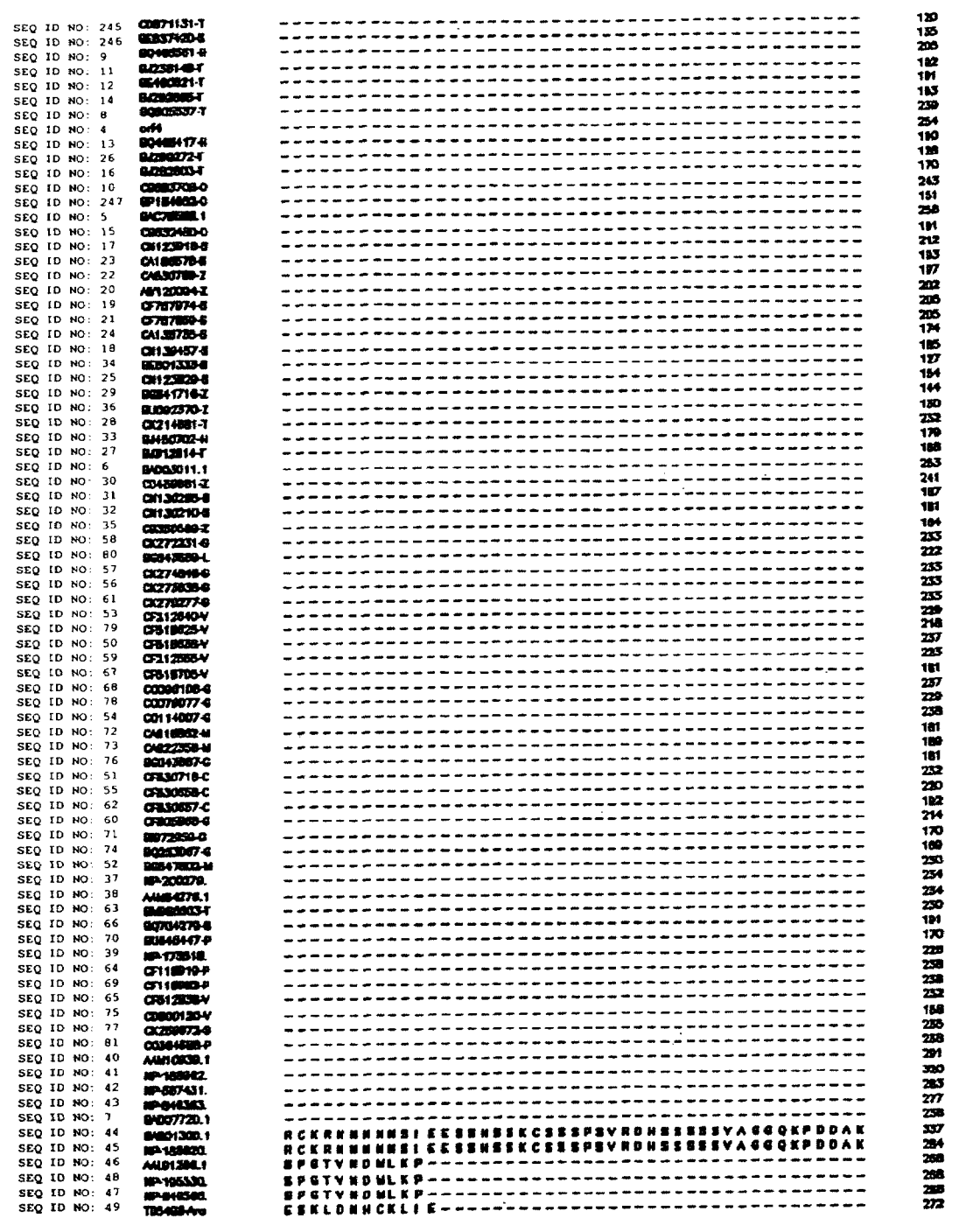

| | | | |
|---|---|---|---|
| SEQ ID NO: 245 | CD871131-T | --------------------------------------------- | 120 |
| SEQ ID NO: 246 | BE837420-S | --------------------------------------------- | 135 |
| SEQ ID NO: 9 | BQ485581-B | --------------------------------------------- | 205 |
| SEQ ID NO: 11 | BJ238148-T | --------------------------------------------- | 182 |
| SEQ ID NO: 12 | BE480821-T | --------------------------------------------- | 181 |
| SEQ ID NO: 14 | BJ282685-T | --------------------------------------------- | 183 |
| SEQ ID NO: 8 | BQ805537-T | --------------------------------------------- | 239 |
| SEQ ID NO: 4 | orf4 | --------------------------------------------- | 254 |
| SEQ ID NO: 13 | BQ485417-B | --------------------------------------------- | 190 |
| SEQ ID NO: 26 | BJ280272-T | --------------------------------------------- | 128 |
| SEQ ID NO: 16 | BJ282803-T | --------------------------------------------- | 170 |
| SEQ ID NO: 10 | CD883708-O | --------------------------------------------- | 243 |
| SEQ ID NO: 247 | BP184803-O | --------------------------------------------- | 151 |
| SEQ ID NO: 5 | BAC78588.1 | --------------------------------------------- | 258 |
| SEQ ID NO: 15 | CD832480-O | --------------------------------------------- | 191 |
| SEQ ID NO: 17 | CN123918-S | --------------------------------------------- | 212 |
| SEQ ID NO: 23 | CA188578-S | --------------------------------------------- | 183 |
| SEQ ID NO: 22 | CA630780-Z | --------------------------------------------- | 197 |
| SEQ ID NO: 20 | AW120004-Z | --------------------------------------------- | 202 |
| SEQ ID NO: 19 | CF787874-S | --------------------------------------------- | 208 |
| SEQ ID NO: 21 | CF787850-S | --------------------------------------------- | 205 |
| SEQ ID NO: 24 | CA138725-S | --------------------------------------------- | 174 |
| SEQ ID NO: 18 | CN139457-S | --------------------------------------------- | 185 |
| SEQ ID NO: 34 | BE801333-B | --------------------------------------------- | 127 |
| SEQ ID NO: 25 | CN123829-S | --------------------------------------------- | 154 |
| SEQ ID NO: 29 | BG841718-Z | --------------------------------------------- | 144 |
| SEQ ID NO: 36 | BU092370-Z | --------------------------------------------- | 130 |
| SEQ ID NO: 28 | CK214881-T | --------------------------------------------- | 232 |
| SEQ ID NO: 33 | BJ480702-H | --------------------------------------------- | 179 |
| SEQ ID NO: 27 | BJ912814-T | --------------------------------------------- | 188 |
| SEQ ID NO: 6 | BAD03011.1 | --------------------------------------------- | 263 |
| SEQ ID NO: 30 | CD458861-Z | --------------------------------------------- | 241 |
| SEQ ID NO: 31 | CN130285-S | --------------------------------------------- | 187 |
| SEQ ID NO: 32 | CN130210-S | --------------------------------------------- | 181 |
| SEQ ID NO: 35 | CO350589-Z | --------------------------------------------- | 184 |
| SEQ ID NO: 58 | CK272231-G | --------------------------------------------- | 233 |
| SEQ ID NO: 80 | BG343589-L | --------------------------------------------- | 222 |
| SEQ ID NO: 57 | CK274818-G | --------------------------------------------- | 233 |
| SEQ ID NO: 56 | CK273835-G | --------------------------------------------- | 233 |
| SEQ ID NO: 61 | CK278277-G | --------------------------------------------- | 233 |
| SEQ ID NO: 53 | CF312840-V | --------------------------------------------- | 229 |
| SEQ ID NO: 79 | CF518925-V | --------------------------------------------- | 218 |
| SEQ ID NO: 50 | CF518538-V | --------------------------------------------- | 237 |
| SEQ ID NO: 59 | CF212585-V | --------------------------------------------- | 225 |
| SEQ ID NO: 67 | CF518705-V | --------------------------------------------- | 181 |
| SEQ ID NO: 68 | CO090108-G | --------------------------------------------- | 237 |
| SEQ ID NO: 78 | CO079077-G | --------------------------------------------- | 229 |
| SEQ ID NO: 54 | CO114007-G | --------------------------------------------- | 238 |
| SEQ ID NO: 72 | CA818882-M | --------------------------------------------- | 181 |
| SEQ ID NO: 73 | CA822358-M | --------------------------------------------- | 189 |
| SEQ ID NO: 76 | BG043867-C | --------------------------------------------- | 181 |
| SEQ ID NO: 51 | CF830718-C | --------------------------------------------- | 232 |
| SEQ ID NO: 55 | CF830658-C | --------------------------------------------- | 220 |
| SEQ ID NO: 62 | CF830657-C | --------------------------------------------- | 182 |
| SEQ ID NO: 60 | CF805868-G | --------------------------------------------- | 214 |
| SEQ ID NO: 71 | BE872859-D | --------------------------------------------- | 170 |
| SEQ ID NO: 74 | BQ253067-G | --------------------------------------------- | 169 |
| SEQ ID NO: 52 | BG547822-M | --------------------------------------------- | 230 |
| SEQ ID NO: 37 | NP-200279. | --------------------------------------------- | 234 |
| SEQ ID NO: 38 | AAM64276.1 | --------------------------------------------- | 234 |
| SEQ ID NO: 63 | BM680603-T | --------------------------------------------- | 230 |
| SEQ ID NO: 66 | BQ704279-S | --------------------------------------------- | 191 |
| SEQ ID NO: 70 | BU848447-P | --------------------------------------------- | 170 |
| SEQ ID NO: 39 | NP-175518. | --------------------------------------------- | 228 |
| SEQ ID NO: 64 | CF118910-P | --------------------------------------------- | 238 |
| SEQ ID NO: 69 | CF118883-P | --------------------------------------------- | 238 |
| SEQ ID NO: 65 | CF512838-V | --------------------------------------------- | 232 |
| SEQ ID NO: 75 | CD800120-V | --------------------------------------------- | 158 |
| SEQ ID NO: 77 | CK258872-G | --------------------------------------------- | 235 |
| SEQ ID NO: 81 | CO364888-P | --------------------------------------------- | 238 |
| SEQ ID NO: 40 | AAM10838.1 | --------------------------------------------- | 291 |
| SEQ ID NO: 41 | NP-188982. | --------------------------------------------- | 320 |
| SEQ ID NO: 42 | NP-567431. | --------------------------------------------- | 283 |
| SEQ ID NO: 43 | NP-848363. | --------------------------------------------- | 277 |
| SEQ ID NO: 7 | BAD07720.1 | --------------------------------------------- | 238 |
| SEQ ID NO: 44 | BAB01300.1 | RCKRNNNNNSIEESSNSSKCSSSPSVRDHSSSSSVAGGQKPDDAK | 337 |
| SEQ ID NO: 45 | NP-188820. | RCKRNNNNNSIEESSNSSKCSSSPSVRDHSSSSSVAGGQKPDDAK | 284 |
| SEQ ID NO: 46 | AAL91286.1 | SPGTVNDMLKP---------------------------------- | 268 |
| SEQ ID NO: 48 | NP-195330. | SPGTVNDMLKP---------------------------------- | 268 |
| SEQ ID NO: 47 | NP-848580. | SPGTVNDMLKP---------------------------------- | 288 |
| SEQ ID NO: 49 | TB5408-Avo | GSKLDNNCKLIE--------------------------------- | 272 |

Figure 2

Alignment to dicotyledonous sequences:

| | | | |
|---|---|---|---|
| SEQ ID NO: 4 | orf4 | -------------------------------------------------- | 0 |
| SEQ ID NO 58 | CX272231-G | -------------------------------------------------- | 0 |
| SEQ ID NO: 80 | BG843589-L | -------------------------------------------------- | 0 |
| SEQ ID NO 57 | CX274848-G | -------------------------------------------------- | 0 |
| SEQ ID NO: 56 | CX273638-G | -------------------------------------------------- | 0 |
| SEQ ID NO: 61 | CX270277-G | -------------------------------------------------- | 0 |
| SEQ ID NO: 53 | CF212840-V | -------------------------------------------------- | 0 |
| SEQ ID NO 79 | CF518625-V | -------------------------------------------------- | 0 |
| SEQ ID NO 55 | CF618608-V | -------------------------------------------------- | 0 |
| SEQ ID NO 59 | CF212885-V | -------------------------------------------------- | 0 |
| SEQ ID NO: 67 | CF618786-V | -------------------------------------------------- | 0 |
| SEQ ID NO. 68 | CD090108-G | -------------------------------------------------- | 0 |
| SEQ ID NO: 78 | CD078077-G | -------------------------------------------------- | 0 |
| SEQ ID NO: 54 | CO114807-G | -------------------------------------------------- | 0 |
| SEQ ID NO: 72 | CA818882-M | -------------------------------------------------- | 0 |
| SEQ ID NO. 73 | CA822358-M | -------------------------------------------------- | 0 |
| SEQ ID NO. 76 | BG043867-C | -------------------------------------------------- | 0 |
| SEQ ID NO: 51 | CF830718-C | -------------------------------------------------- | 0 |
| SEQ ID NO: 55 | CF830658-C | -------------------------------------------------- | 0 |
| SEQ ID NO: 62 | CF830657-C | -------------------------------------------------- | 0 |
| SEQ ID NO: 60 | CF805868-G | -------------------------------------------------- | 0 |
| SEQ ID NO: 71 | BI972859-O | -------------------------------------------------- | 0 |
| SEQ ID NO: 74 | BQ253067-G | -------------------------------------------------- | 0 |
| SEQ ID NO: 52 | BG847802-M | -------------------------------------------------- | 0 |
| SEQ ID NO: 37 | NP-200279. | -------------------------------------------------- | 0 |
| SEQ ID NO: 38 | AAM64776.1 | -------------------------------------------------- | 0 |
| SEQ ID NO: 63 | BM985603-I | -------------------------------------------------- | 0 |
| SEQ ID NO: 66 | BQ704279-B | -------------------------------------------------- | 0 |
| SEQ ID NO: 70 | BU948447-P | -------------------------------------------------- | 0 |
| SEQ ID NO: 39 | NP-173818. | -------------------------------------------------- | 0 |
| SEQ ID NO. 64 | CF118919-P | -------------------------------------------------- | 0 |
| SEQ ID NO: 69 | CF118982-P | -------------------------------------------------- | 0 |
| SEQ ID NO: 65 | CF512838-V | -------------------------------------------------- | 0 |
| SEQ ID NO: 75 | CD800120-V | -------------------------------------------------- | 0 |
| SEQ ID NO: 77 | CK258672-G | -------------------------------------------------- | 0 |
| SEQ ID NO. 81 | CO384588-P | -------------------------------------------------- | 0 |
| SEQ ID NO: 40 | AAW10838.1 | -------------------------------------------------- | 0 |
| SEQ ID NO: 41 | NP-188842. | -----------------------------MQTNEDNIFQDFGSCGVNLMQ | 21 |
| SEQ ID NO: 42 | NP-587431. | MYPSIEDDDDLLAALCFDQNNGVEDPYGYMQTNEDNIFQDFGSCGVNLMQ | 50 |
| SEQ ID NO 43 | NP-849383. | -----------------------------MYPSLDDDFVSDLFCFDQSNG | 21 |
| SEQ ID NO: 44 | BAB01300.1 | -----------------------------------MDVNLFGHDDSCSNG | 15 |
| SEQ ID NO: 45 | NP-188820. | -------------------------------------------------- | 0 |
| SEQ ID NO: 46 | AAL91284.1 | -------------------------------------------------- | 0 |
| SEQ ID NO: 48 | NP-195330. | -------------------------------------------------- | 0 |
| SEQ ID NO: 47 | NP-849586. | -------------------------------------------------- | 0 |
| SEQ ID NO: 49 | T05488-Ara | -------------------------------------------------- | 0 |
| SEQ ID NO: 38 | | -------------------------------------------------- | 0 |

| | | | |
|---|---|---|---|
| SEQ ID NO. 4 | orf4 | ---------------------MASPEGANWVFDCPLMDDLAAAD-FTAPP | 28 |
| SEQ ID NO 58 | CK772231-G | -------------------------------------MVSPENTNWLYDY | 13 |
| SEQ ID NO 80 | BG843889-L | -------------------------------------MVSPESTNWLYDY | 13 |
| SEQ ID NO 57 | CK774848-G | -------------------------------------MVSPENTNWLYDY | 13 |
| SEQ ID NO 56 | CK775838-G | -------------------------------------MVSPENTNWLYDY | 13 |
| SEQ ID NO 61 | CK770277-G | -------------------------------------MVSPENTNWLYDY | 13 |
| SEQ ID NO 53 | CF212640-V | -------------------------------------MVSPEATNWLYEY | 13 |
| SEQ ID NO 79 | CF818828-V | -------------------------------------MVSPEATNWLYEY | 13 |
| SEQ ID NO 50 | CF818838-V | -------------------------------------MVSPEATNWLYEY | 13 |
| SEQ ID NO 59 | CF212555-V | -------------------------------------------------- | 0 |
| SEQ ID NO 67 | CF818705-V | -------------------------------------------------- | 0 |
| SEQ ID NO 68 | CD090108-G | -------------------------------------MVSPENTNYWSSF | 13 |
| SEQ ID NO 78 | CD079077-G | -------------------------------------MVSPENTNYWSSF | 13 |
| SEQ ID NO. 54 | CD114007-G | -------------------------------------MVSPENFNYWSHF | 13 |
| SEQ ID NO 72 | CA618862-M | -------------------------------------------------- | 0 |
| SEQ ID NO: 73 | CA822358-M | -------------------------------------------------- | 0 |
| SEQ ID NO 76 | BQ042887-G | -------------------------------------------------- | 0 |
| SEQ ID NO 51 | CF830718-C | -----------------------------------------ENTNWLLDY | 9 |
| SEQ ID NO: 55 | CF830658-C | -------------------------------------MVSPENTNWLLDY | 13 |
| SEQ ID NO. 62 | CF830857-C | -------------------------------------------------- | 0 |
| SEQ ID NO 60 | CF805868-G | -----------------------------------------ENSNWLFDY | 9 |
| SEQ ID NO 71 | BI072859-G | -------------------------------------------------- | 0 |
| SEQ ID NO. 74 | | | |
| SEQ ID NO 52 | BQ253067-G | -------------------------------------------------- | 0 |
| SEQ ID NO 37 | BG847803-M | -------------------------------------MVSPENTNWLFDY | 13 |
| SEQ ID NO: 38 | NP-200279. | ------------------------------------------MVSPENAN | 8 |
| SEQ ID NO: 63 | AAM64276.1 | ------------------------------------------MVSPENAN | 8 |
| SEQ ID NO: 66 | BM985603-T | ----------------------------------------------ENAN | 4 |
| SEQ ID NO 70 | BQ704279-B | -------------------------------------------------- | 0 |
| SEQ ID NO 39 | BU848447-P | -------------------------------------------------- | 0 |
| SEQ ID NO 64 | NP-178818. | -----------------------------------------------MVS | 3 |
| SEQ ID NO 69 | CF118919-P | ------------------------------------ENDNWVFDCGLIED | 14 |
| SEQ ID NO 65 | CF118862-P | ------------------------------------ENDNWVFDCGLIED | 14 |
| SEQ ID NO 75 | CF512838-V | -------------------------------MVSPEEDPNWIFDYGLIDD | 19 |
| SEQ ID NO 77 | CD800120-V | -------------------------------------------------- | 0 |
| SEQ ID NO 81 | CK259672-G | ---------------------------------------NWLFDYELITD | 11 |
| SEQ ID NO 40 | CO384588-P | ---------------------------------------MSSPQSNKVLS | 11 |
| SEQ ID NO 41 | AAM10939.1 | PQQEQFDSFNGNLEQVCSSFRGGNNGVVYSSSIGSAQLDLAASFSGVLQQ | 71 |
| SEQ ID NO 42 | NP-188982. | PQQEQFDSFNGNLEQVCSSFRGGNNGVVYSSSIGSAQLDLAASFSGVLQQ | 100 |
| SEQ ID NO 43 | NP-587431. | AELDDYTQFGVNLQTDQE----DTFPDFVSYGVNLQQEPDEVFSIGASQL | 67 |
| SEQ ID NO: 44 | NP-840363. | AELDDYTQFGVNLQTDQE----DTFPDFVSYGVNLQQEPDEVFSIGASQL | 61 |
| SEQ ID NO: 45 | BAB01300.1 | -------------------------------------------------- | 0 |
| SEQ ID NO. 46 | NP-188820. | -------------------------------------------------- | 0 |
| SEQ ID NO. 48 | AAB61288.1 | -------------------------------------------------- | 0 |
| SEQ ID NO. 47 | NP-196330. | -------------------------------------------------- | 0 |
| SEQ ID NO: 49 | NP-842588. | -------------------------------------------------- | 0 |
| SEQ ID NO: 38 | TD5488-Aro | -------------------------------------------------- | 0 |

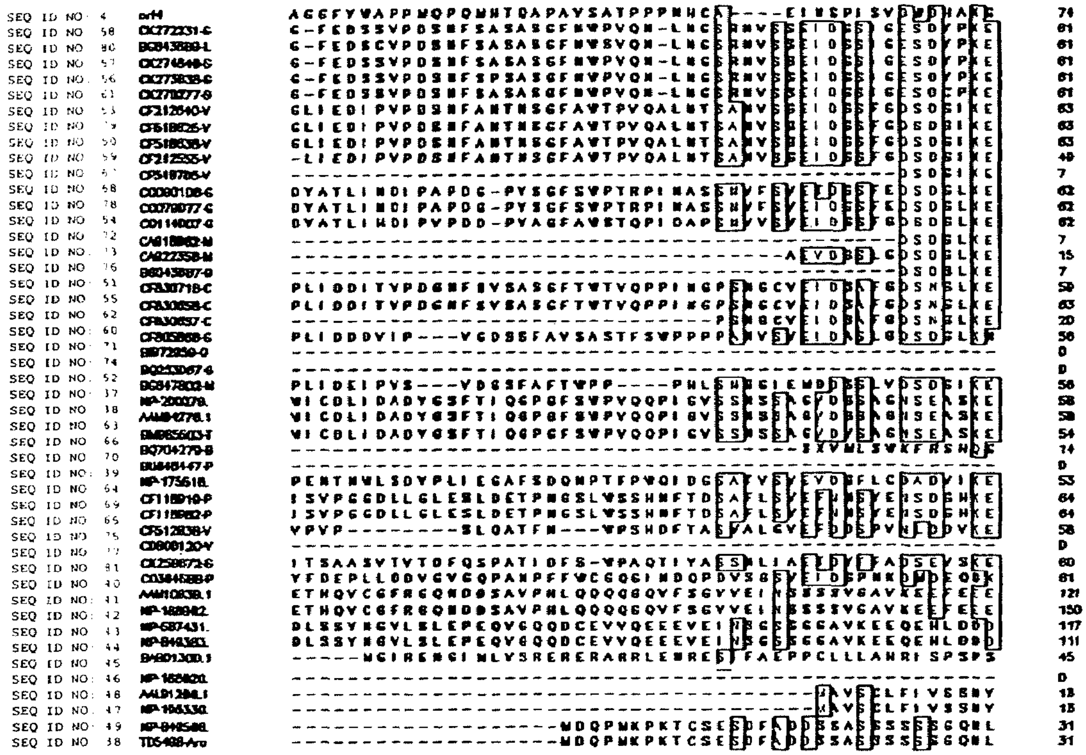

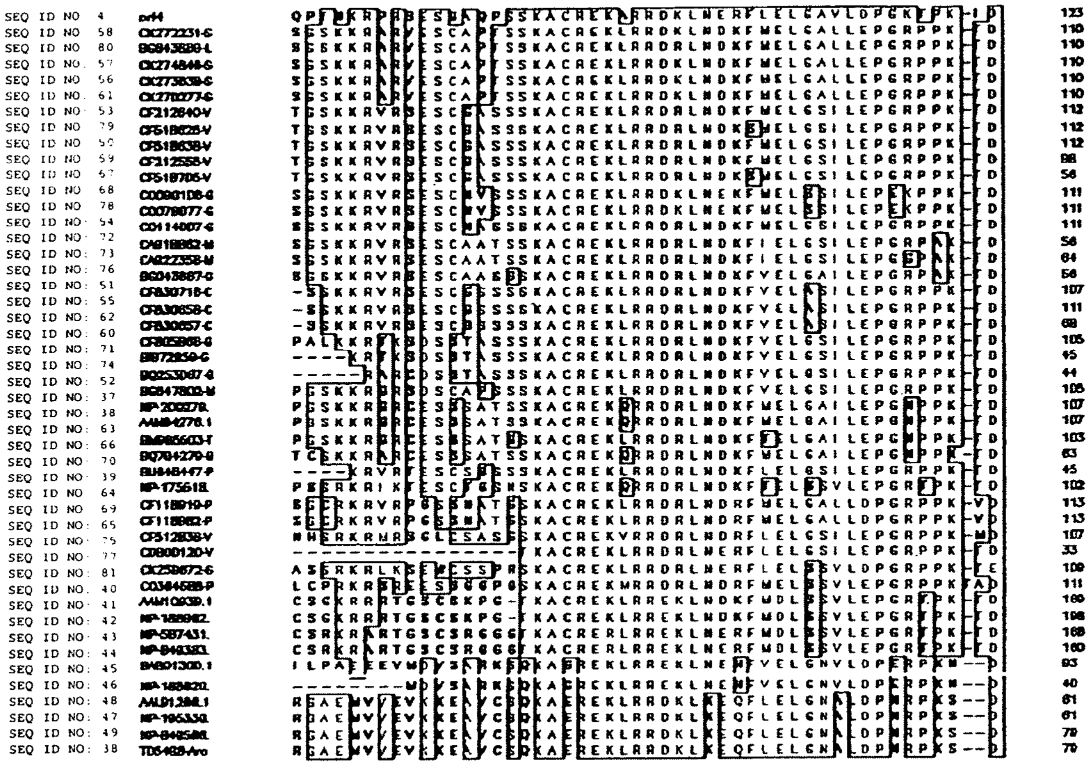

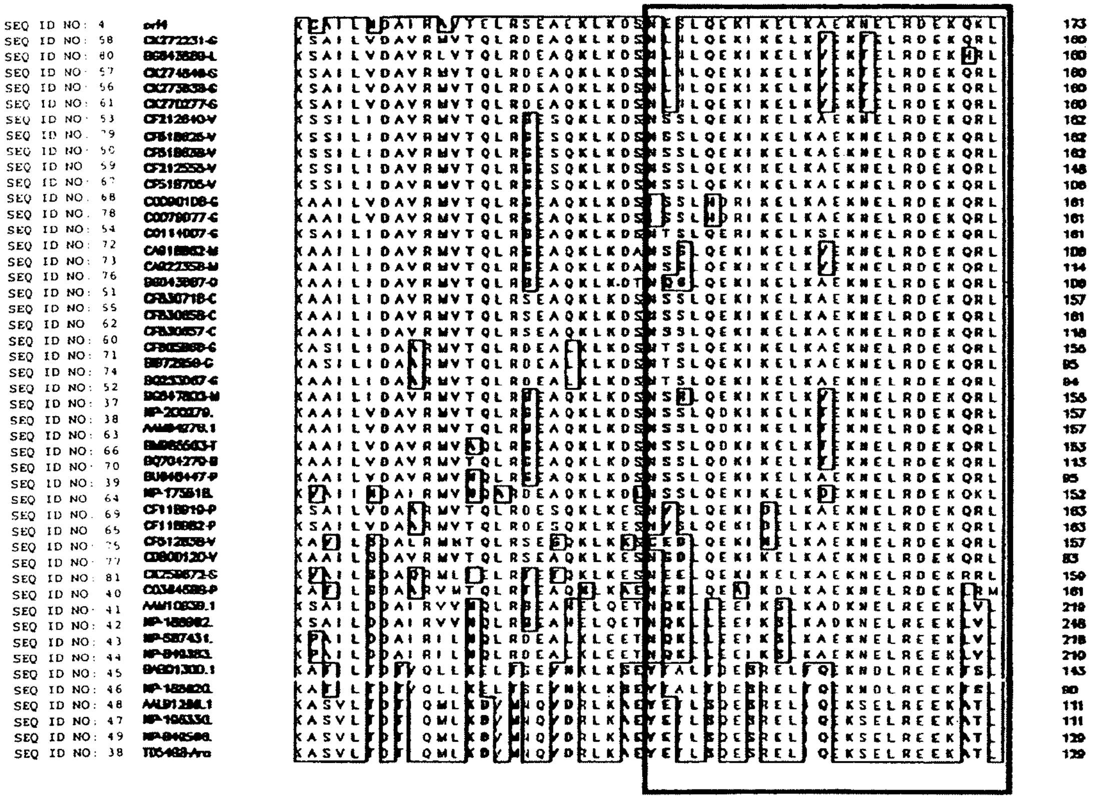

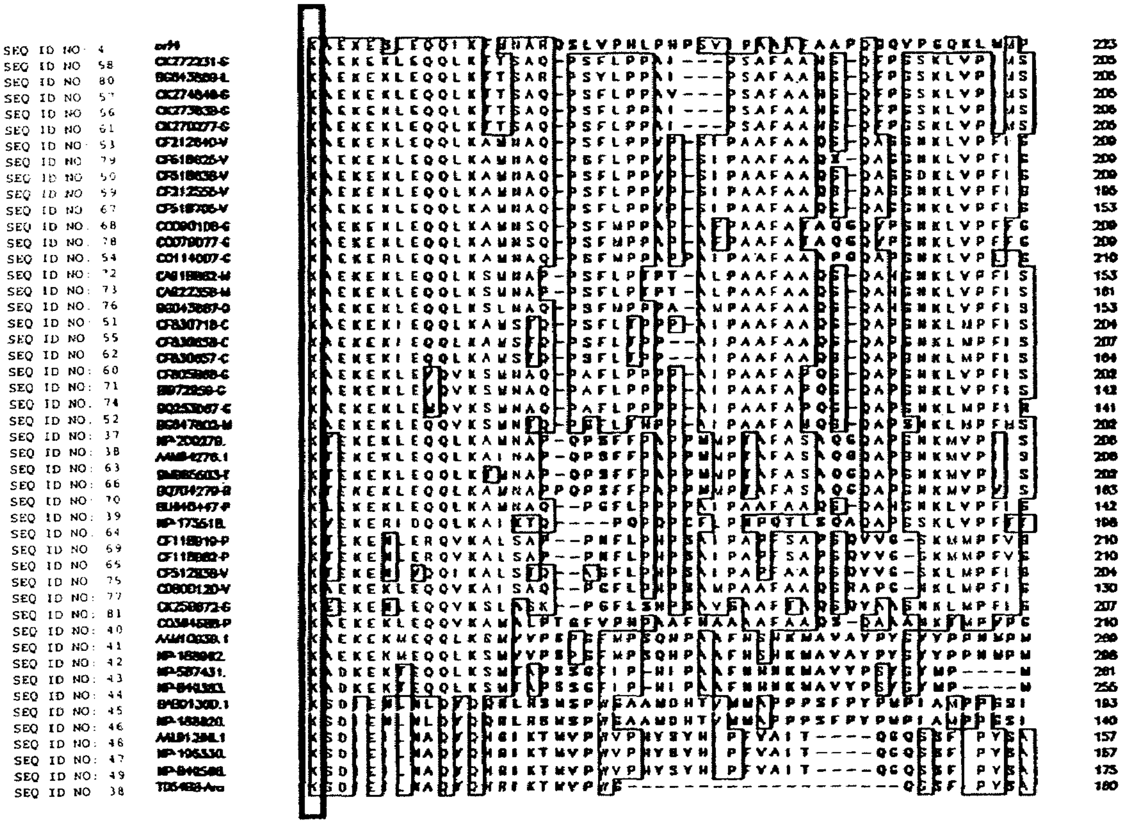

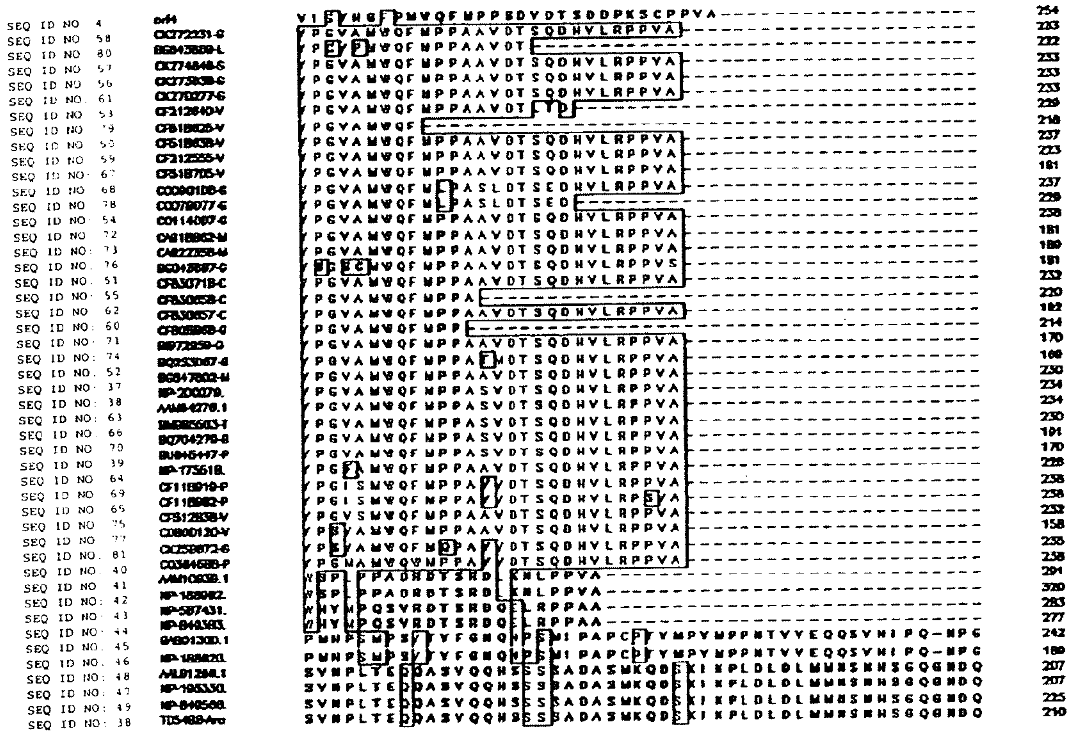
SEQ ID NO 4
SEQ ID NO 58
SEQ ID NO 80
SEQ ID NO 57
SEQ ID NO 56
SEQ ID NO. 61
SEQ ID NO 53
SEQ ID NO 79
SEQ ID NO 50
SEQ ID NO 59
SEQ ID NO· 67
SEQ ID NO 68
SEQ ID NO 78
SEQ ID NO· 54
SEQ ID NO 72
SEQ ID NO: 73
SEQ ID NO. 76
SEQ ID NO. 51
SEQ ID NO· 55
SEQ ID NO 62
SEQ ID NO: 60
SEQ ID NO· 71
SEQ ID NO: 74
SEQ ID NO. 52
SEQ ID NO· 37
SEQ ID NO: 38
SEQ ID NO: 63
SEQ ID NO. 66
SEQ ID NO 70
SEQ ID NO 39
SEQ ID NO 64
SEQ ID NO 69
SEQ ID NO 65
SEQ ID NO 75
SEQ ID NO 77
SEQ ID NO. 81
SEQ ID NO. 40
SEQ ID NO 41
SEQ ID NO: 42
SEQ ID NO· 43
SEQ ID NO· 44
SEQ ID NO. 45
SEQ ID NO. 46
SEQ ID NO: 48
SEQ ID NO: 47
SEQ ID NO: 49
SEQ ID NO: 38

| | | | |
|---|---|---|---|
| SEQ ID NO: 4 | orf4 | -------------------------------------------------- | 254 |
| SEQ ID NO: 58 | CX272231-G | -------------------------------------------------- | 233 |
| SEQ ID NO: 80 | BG843589-L | -------------------------------------------------- | 222 |
| SEQ ID NO: 57 | CX274540-G | -------------------------------------------------- | 233 |
| SEQ ID NO: 56 | CX273839-G | -------------------------------------------------- | 233 |
| SEQ ID NO: 61 | CX270277-G | -------------------------------------------------- | 233 |
| SEQ ID NO: 53 | CF212840-V | -------------------------------------------------- | 229 |
| SEQ ID NO: 79 | CF818625-V | -------------------------------------------------- | 218 |
| SEQ ID NO: 50 | CF518658-V | -------------------------------------------------- | 237 |
| SEQ ID NO: 59 | CF212558-V | -------------------------------------------------- | 223 |
| SEQ ID NO: 67 | CF518705-V | -------------------------------------------------- | 181 |
| SEQ ID NO: 68 | CD090108-G | -------------------------------------------------- | 237 |
| SEQ ID NO: 78 | CD078077-G | -------------------------------------------------- | 229 |
| SEQ ID NO: 54 | CD114007-G | -------------------------------------------------- | 238 |
| SEQ ID NO: 72 | CA818862-M | -------------------------------------------------- | 181 |
| SEQ ID NO: 73 | CA822358-M | -------------------------------------------------- | 189 |
| SEQ ID NO: 76 | BG043887-G | -------------------------------------------------- | 181 |
| SEQ ID NO: 51 | CF830718-C | -------------------------------------------------- | 232 |
| SEQ ID NO: 55 | CF830658-C | -------------------------------------------------- | 220 |
| SEQ ID NO: 62 | CF830657-C | -------------------------------------------------- | 182 |
| SEQ ID NO: 60 | CF805868-G | -------------------------------------------------- | 214 |
| SEQ ID NO: 71 | BI872838-G | -------------------------------------------------- | 170 |
| SEQ ID NO: 74 | | | |
| SEQ ID NO: 52 | BQ253067-G | -------------------------------------------------- | 180 |
| SEQ ID NO: 37 | BG847802-M | -------------------------------------------------- | 230 |
| SEQ ID NO: 38 | NP-200279. | -------------------------------------------------- | 234 |
| SEQ ID NO: 63 | AAM64276.1 | -------------------------------------------------- | 234 |
| SEQ ID NO: 66 | BM865603-T | -------------------------------------------------- | 230 |
| SEQ ID NO: 70 | BQ704279-B | -------------------------------------------------- | 191 |
| SEQ ID NO: 39 | BU845447-P | -------------------------------------------------- | 170 |
| SEQ ID NO: 64 | NP-178518. | -------------------------------------------------- | 228 |
| SEQ ID NO: 69 | CF118919-P | -------------------------------------------------- | 238 |
| SEQ ID NO: 65 | CF118862-P | -------------------------------------------------- | 238 |
| SEQ ID NO: 75 | CF512838-V | -------------------------------------------------- | 232 |
| SEQ ID NO: 77 | CD800120-V | -------------------------------------------------- | 158 |
| SEQ ID NO: 81 | CX258872-G | -------------------------------------------------- | 235 |
| SEQ ID NO: 40 | CD384688-P | -------------------------------------------------- | 238 |
| SEQ ID NO: 41 | AAM10838.1 | -------------------------------------------------- | 291 |
| SEQ ID NO: 42 | NP-188842. | -------------------------------------------------- | 300 |
| SEQ ID NO: 43 | NP-587431. | -------------------------------------------------- | 283 |
| SEQ ID NO: 44 | NP-840383. | -------------------------------------------------- | 277 |
| SEQ ID NO: 45 | BAB01300.1 | MRSREPRAKVSRESRSEKAEDSNEVATQLELKTPGSTSDKDTLQRPEKTK | 282 |
| SEQ ID NO: 46 | NP-188828. | MRSREPRAKVSRESRSEKAEDSNEVATQLELKTPGSTSDKDTLQRPEKTK | 239 |
| SEQ ID NO: 48 | AAL91284.1 | KDDVRLKLELKINASSLAQQDVSGKEKKVSLTTTASSSNSYSLSQAVQDS | 257 |
| SEQ ID NO: 47 | NP-196330. | KDDVRLKLELKINASSLAQQDVSGKEKKVSLTTTASSSNSYSLSQAVQDS | 257 |
| SEQ ID NO: 49 | NP-840568. | KDDVRLKLELKINASSLAQQDVSGKEKKVSLTTTASGSNSYSLSQAVQDS | 275 |
| SEQ ID NO: 38 | T06428-Ara | KDDVRLKLELKINASSLAQQVSDLFNSFAKKLFNGLTRVYFNAGCFWKRE | 260 |

| | | | |
|---|---|---|---|
| SEQ ID NO: 4 | orf4 | --------------------------------------------- | 284 |
| SEQ ID NO: 58 | CX272231-G | --------------------------------------------- | 233 |
| SEQ ID NO: 80 | BG843586-L | --------------------------------------------- | 222 |
| SEQ ID NO: 57 | CX274848-G | --------------------------------------------- | 233 |
| SEQ ID NO: 56 | CX278838-G | --------------------------------------------- | 233 |
| SEQ ID NO: 61 | CX270277-G | --------------------------------------------- | 233 |
| SEQ ID NO: 53 | CF212640-V | --------------------------------------------- | 229 |
| SEQ ID NO: 79 | CF518625-V | --------------------------------------------- | 218 |
| SEQ ID NO: 50 | CF518638-V | --------------------------------------------- | 237 |
| SEQ ID NO: 59 | CF212553-V | --------------------------------------------- | 233 |
| SEQ ID NO: 67 | CF518705-V | --------------------------------------------- | 181 |
| SEQ ID NO: 68 | CD090108-G | --------------------------------------------- | 237 |
| SEQ ID NO: 78 | CD078077-G | --------------------------------------------- | 229 |
| SEQ ID NO: 54 | CD114007-G | --------------------------------------------- | 238 |
| SEQ ID NO: 72 | CA818862-M | --------------------------------------------- | 181 |
| SEQ ID NO: 73 | CA822358-M | --------------------------------------------- | 189 |
| SEQ ID NO: 76 | BG043887-G | --------------------------------------------- | 181 |
| SEQ ID NO: 51 | CF830710-C | --------------------------------------------- | 232 |
| SEQ ID NO: 55 | CF830658-C | --------------------------------------------- | 220 |
| SEQ ID NO: 62 | CF830657-C | --------------------------------------------- | 182 |
| SEQ ID NO: 60 | CF808868-G | --------------------------------------------- | 214 |
| SEQ ID NO: 71 | BB772839-G | --------------------------------------------- | 170 |
| SEQ ID NO: 74 | BQ253067-G | --------------------------------------------- | 169 |
| SEQ ID NO: 52 | BG817602-M | --------------------------------------------- | 230 |
| SEQ ID NO: 37 | NP-200079. | --------------------------------------------- | 234 |
| SEQ ID NO: 38 | AAM64276.1 | --------------------------------------------- | 234 |
| SEQ ID NO: 63 | BM965603-T | --------------------------------------------- | 230 |
| SEQ ID NO: 66 | BQ704279-B | --------------------------------------------- | 191 |
| SEQ ID NO: 70 | BU846447-P | --------------------------------------------- | 170 |
| SEQ ID NO: 39 | NP-173518. | --------------------------------------------- | 228 |
| SEQ ID NO: 64 | CF118919-P | --------------------------------------------- | 238 |
| SEQ ID NO: 69 | CF118882-P | --------------------------------------------- | 238 |
| SEQ ID NO: 65 | CF312838-V | --------------------------------------------- | 232 |
| SEQ ID NO: 75 | CD800120-V | --------------------------------------------- | 158 |
| SEQ ID NO: 77 | CX258672-G | --------------------------------------------- | 235 |
| SEQ ID NO: 81 | CO384588-P | --------------------------------------------- | 238 |
| SEQ ID NO: 40 | AAM10839.1 | --------------------------------------------- | 291 |
| SEQ ID NO: 41 | NP-188982. | --------------------------------------------- | 320 |
| SEQ ID NO: 42 | NP-587431. | --------------------------------------------- | 283 |
| SEQ ID NO: 43 | NP-848383. | --------------------------------------------- | 277 |
| SEQ ID NO: 44 | BAB01300.1 | R C K R N N N N N S I E E S S H S S K C S S S P S V R D H S S S S S V A C G Q K P D D A K | 337 |
| SEQ ID NO: 45 | NP-188820. | R C K R N N N N N S I E E S S H S S K C S S S P S V R D H S S S S S V A C G Q K P D D A K | 284 |
| SEQ ID NO: 46 | AAL91284.1 | S P G T V N D M L K P ---------------------------------- | 288 |
| SEQ ID NO: 48 | NP-195330. | S P G T V N D M L K P ---------------------------------- | 288 |
| SEQ ID NO: 47 | NP-848588. | S P G T V N D M L K P ---------------------------------- | 288 |
| SEQ ID NO: 49 | T06489-Ara | E E K L D N H C K L I E --------------------------------- | 272 |
| SEQ ID NO: 38 | | | |

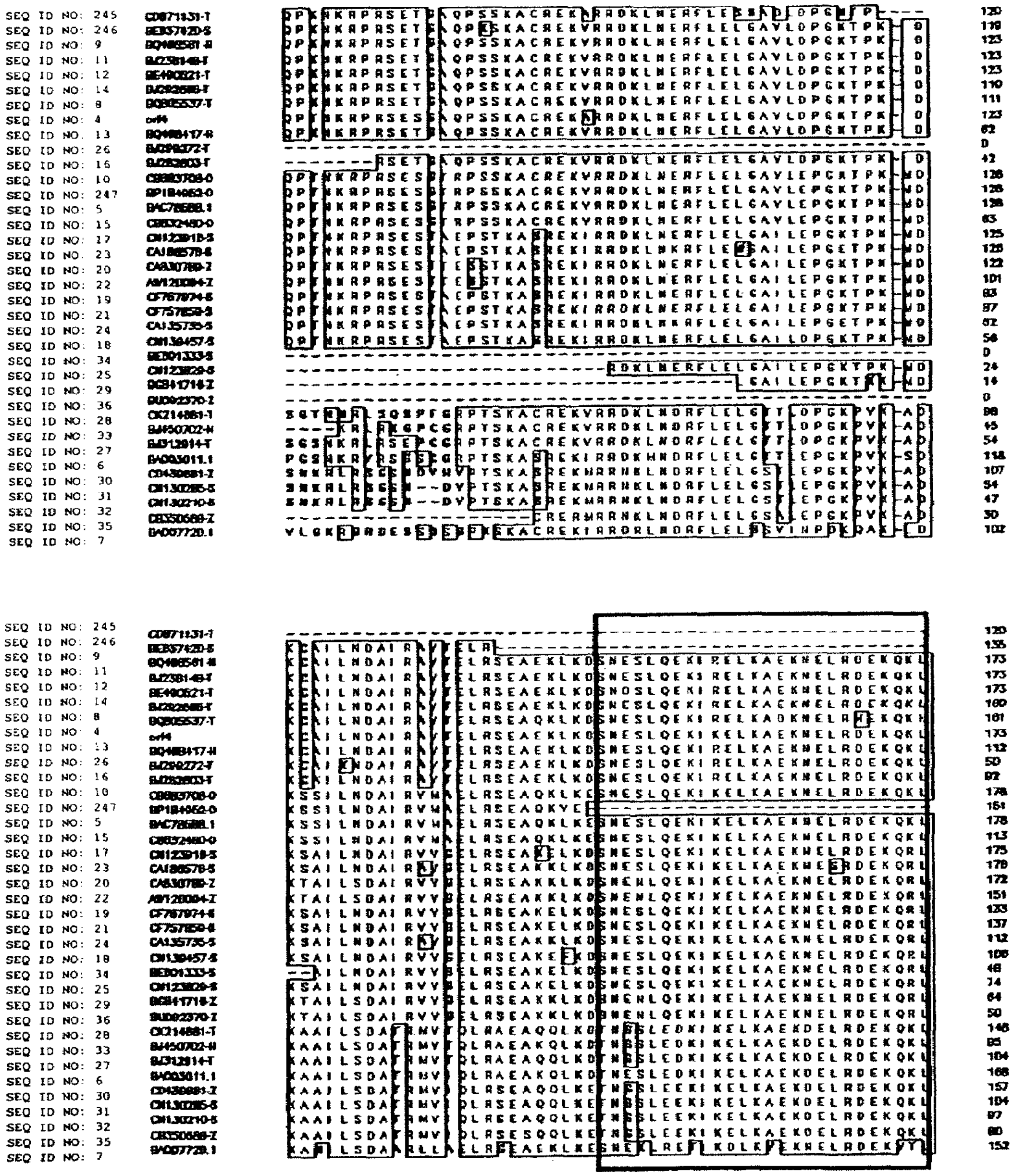
SEQ ID NO: 245
SEQ ID NO: 246
SEQ ID NO: 9
SEQ ID NO: 11
SEQ ID NO: 12
SEQ ID NO: 14
SEQ ID NO: 8
SEQ ID NO: 4
SEQ ID NO: 13
SEQ ID NO: 26
SEQ ID NO: 16
SEQ ID NO: 10
SEQ ID NO: 247
SEQ ID NO: 5
SEQ ID NO: 15
SEQ ID NO: 17
SEQ ID NO: 23
SEQ ID NO: 20
SEQ ID NO: 22
SEQ ID NO: 19
SEQ ID NO: 21
SEQ ID NO: 24
SEQ ID NO: 18
SEQ ID NO: 34
SEQ ID NO: 25
SEQ ID NO: 29
SEQ ID NO: 36
SEQ ID NO: 28
SEQ ID NO: 33
SEQ ID NO: 27
SEQ ID NO: 6
SEQ ID NO: 30
SEQ ID NO: 31
SEQ ID NO: 32
SEQ ID NO: 35
SEQ ID NO: 7
SEQ ID NO: 245
SEQ ID NO: 246
SEQ ID NO: 9
SEQ ID NO: 11
SEQ ID NO: 12
SEQ ID NO: 14
SEQ ID NO: 8
SEQ ID NO: 4
SEQ ID NO: 13
SEQ ID NO: 26
SEQ ID NO: 16
SEQ ID NO: 10
SEQ ID NO: 247
SEQ ID NO: 5
SEQ ID NO: 15
SEQ ID NO: 17
SEQ ID NO: 23
SEQ ID NO: 20
SEQ ID NO: 22
SEQ ID NO: 19
SEQ ID NO: 21
SEQ ID NO: 24
SEQ ID NO: 18
SEQ ID NO: 34
SEQ ID NO: 25
SEQ ID NO: 29
SEQ ID NO: 36
SEQ ID NO: 28
SEQ ID NO: 33
SEQ ID NO: 27
SEQ ID NO: 6
SEQ ID NO: 30
SEQ ID NO: 31
SEQ ID NO: 32
SEQ ID NO: 35
SEQ ID NO: 7

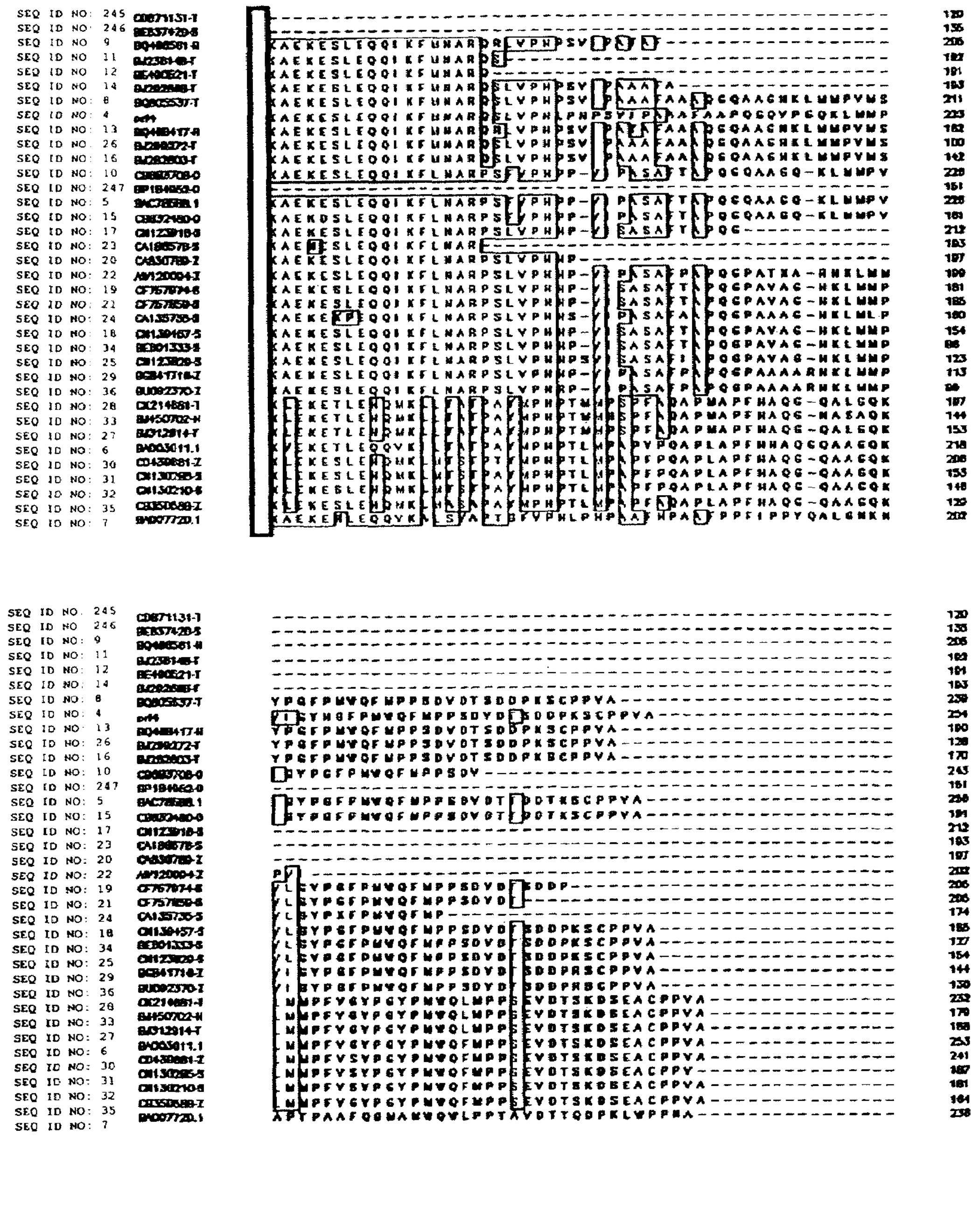

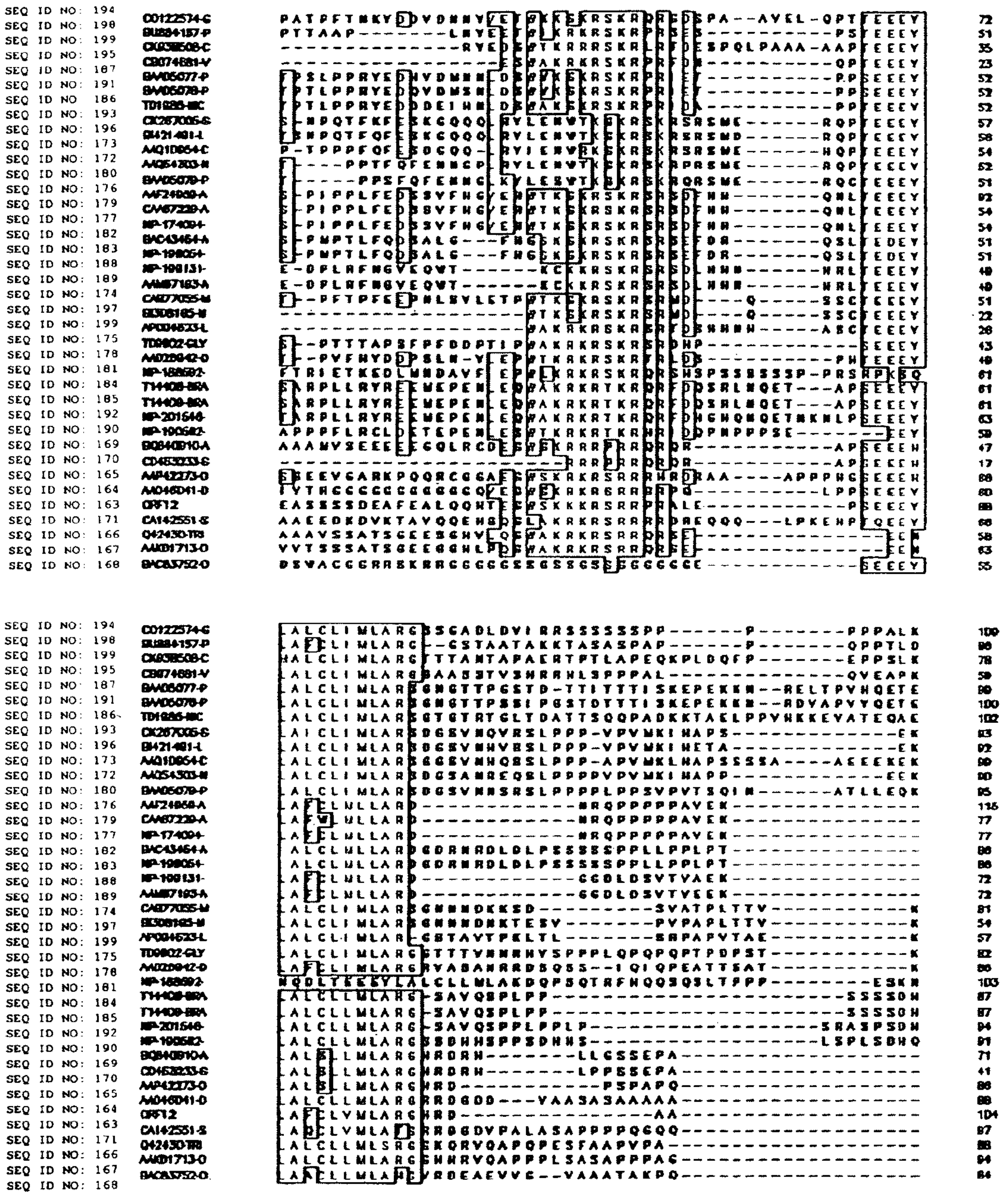

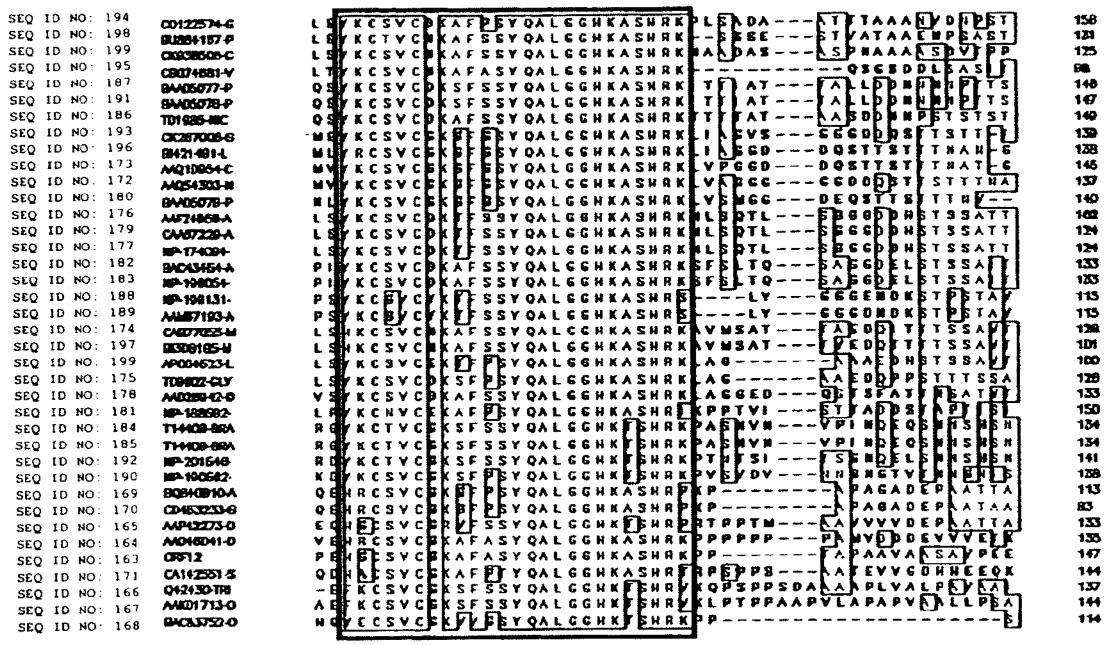
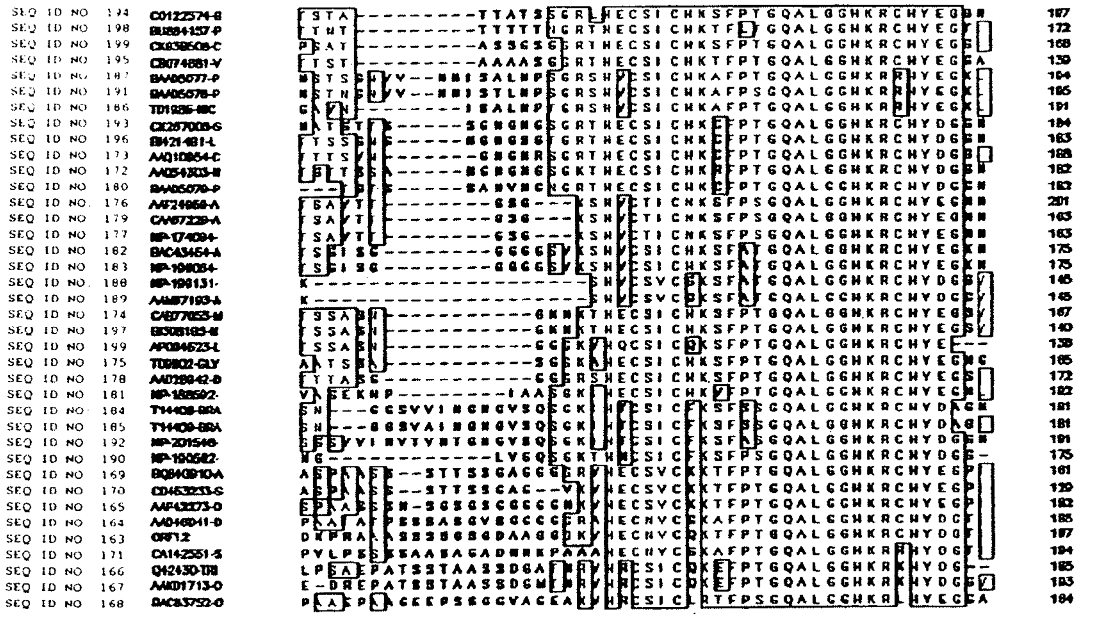

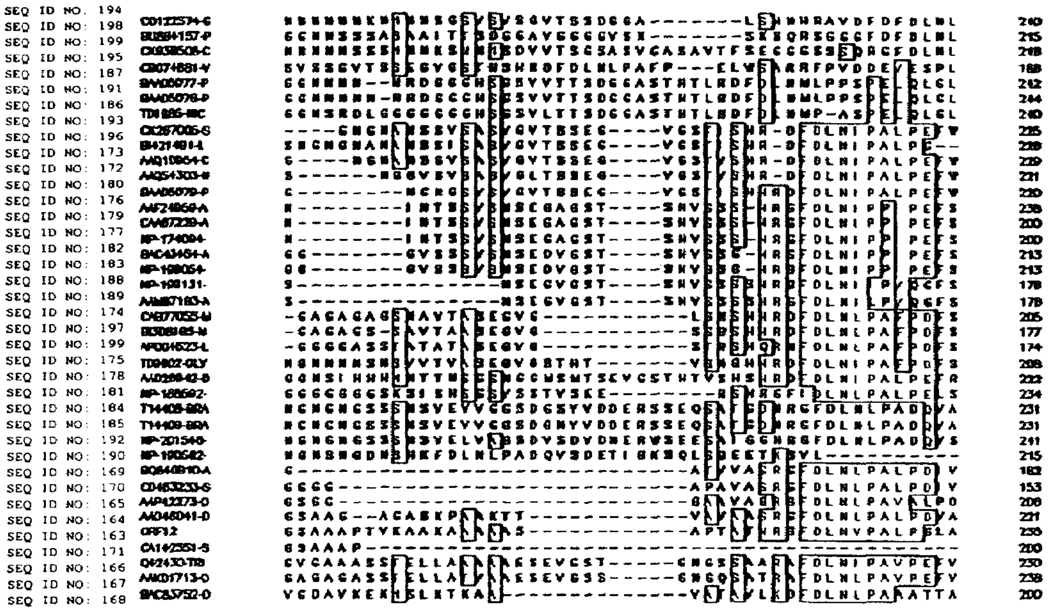
SEQ ID NO: 194
SEQ ID NO: 198
SEQ ID NO: 199
SEQ ID NO: 195
SEQ ID NO: 187
SEQ ID NO: 191
SEQ ID NO: 186
SEQ ID NO: 193
SEQ ID NO: 196
SEQ ID NO: 173
SEQ ID NO: 172
SEQ ID NO: 180
SEQ ID NO: 176
SEQ ID NO: 179
SEQ ID NO: 177
SEQ ID NO: 182
SEQ ID NO: 183
SEQ ID NO: 188
SEQ ID NO: 189
SEQ ID NO: 174
SEQ ID NO: 197
SEQ ID NO: 199
SEQ ID NO: 175
SEQ ID NO: 178
SEQ ID NO: 181
SEQ ID NO: 184
SEQ ID NO: 185
SEQ ID NO: 192
SEQ ID NO: 190
SEQ ID NO: 169
SEQ ID NO: 170
SEQ ID NO: 165
SEQ ID NO: 164
SEQ ID NO: 163
SEQ ID NO: 171
SEQ ID NO: 166
SEQ ID NO: 167
SEQ ID NO: 168

```
SEQ ID NO: 194  CO122574-6      PALPEFS_MYPDEEEVQSPLPTQKPRFLI--------------  269
SEQ ID NO: 198  BU884157-P      PALP----------------------------------------  219
SEQ ID NO: 199  CK838508-C      PALPEFVSDEVESPLPAKKKKLLM--------------------  240
SEQ ID NO: 195  CB074881-Y      PTKKPRLDM-----------------------------------  195
SEQ ID NO: 187  BAA05077-P      SIDCDLKS-DIPIEQEVESPMPLKKPRLLFSMD-----------  274
SEQ ID NO: 191  BAA05078-P      SIDCGLKSDQVPIEQEVESPMPLKKPRLLFSMD-----------  277
SEQ ID NO: 186  TD1886-MC       SIDCGRKSDE-PMVQEVESPMPAKKPRLLFSLG-----------  273
SEQ ID NO: 193  CX267006-S      PGF-GSGEDEVESPHPAKKSRLSL--------------------  248
SEQ ID NO: 196  B421481-L       --------------------------------------------  228
SEQ ID NO: 173  AAQ10954-C      LGF-GSGEDEVESPHPAKKSRLCLPPKYELFQH-----------  261
SEQ ID NO: 172  AAQ54303-H      PGF-GSGEDEVESPHPTKKSRLSLPPKFELFRE-----------  253
SEQ ID NO: 180  BAA05079-P      PGF-GSGEDEVESPHPAKKSRLSLPPKLELFKGL----------  253
SEQ ID NO: 176  AAF24858-A      MVN-G--DDEVMSPMPAKKPRFDFPVKLQL--------------  265
SEQ ID NO: 179  CAA67229-A      MVN-G--DDEVMSPMPAKKPRFDFPVKLQL--------------  227
SEQ ID NO: 177  NP-174094-      MVN-G--DDEVMSPMPAKKPRFDFPYKLQL--------------  227
SEQ ID NO: 182  BAC43454-A      MVN-G--DEEVMSPMPAKKLRFDFPGKP----------------  238
SEQ ID NO: 183  NP-198064-      MVN-G--DEEVMSPMPAKKLRFDFPEKP----------------  238
SEQ ID NO: 188  NP-199131-      PD-----DEVMSPMATKKPRLK----------------------  193
SEQ ID NO: 189  AAM57103-A      RD-----DEVMSPMATKKPRLK----------------------  193
SEQ ID NO: 174  CAB77055-H      K--KFFYDDEVFSPLPAAKKPCLFKLEIPSHY------------  235
SEQ ID NO: 197  BX306165-M      K--KFFYDDEVSSPLPAAKKPCL---------------------  196
SEQ ID NO: 199  AP004523-L      AS-KFFYEEEVSSPLPSKKPRLL---------------------  196
SEQ ID NO: 175  TD9802-GLY      T---KVGEDEVESPHPYMKKPRLFVIPKIEIPQFQ---------  240
SEQ ID NO: 178  AAD28942-D      SNFFISGDDEVESPHPAKKPRILMK-------------------  247
SEQ ID NO: 181  NP-188592-      LHHNPIVDEEILSPLTGKKPLLLTDHDQVIKKEDLSLKI-----  273
SEQ ID NO: 184  TI4408-BRA      VVIS----------------------------------------  235
SEQ ID NO: 185  TI4409-BRA      VVISKR--------------------------------------  237
SEQ ID NO: 192  NP-201548-      VTTS----------------------------------------  245
SEQ ID NO: 190  NP-190582-      --------------------------------------------  215
SEQ ID NO: 169  BQ840910-A      TERERCM-------------------------------------  189
SEQ ID NO: 170  CD453233-6      TERERCMPAPADEEEVLSPLAFKKPRLMIPA-------------  184
SEQ ID NO: 165  AAP42273-0      IMTERCLPAAAEEEEVLSPLASFKKPRLMIPA------------  238
SEQ ID NO: 164  AAD46041-0      AAADQRC--AAEDDEVLSPLAFKKPRLMIPA-------------  250
SEQ ID NO: 163  OSI2           EEGEEVLSPVSFKKPRLMITA-----------------------  258
SEQ ID NO: 171  CA142551-S      --------------------------------------------  200
SEQ ID NO: 166  Q42430-TB       WRPCAKGKMMWEDDEEVDSPLAFKKPRLLTA-------------  261
SEQ ID NO: 167  AAK01713-0      WRPCSKGKKMWDEEEEVDSPLAFKKPRLLTA-------------  269
SEQ ID NO: 168  BAC83752-0      GDEAESSPPEAKRARLLLLV------------------------  220
```

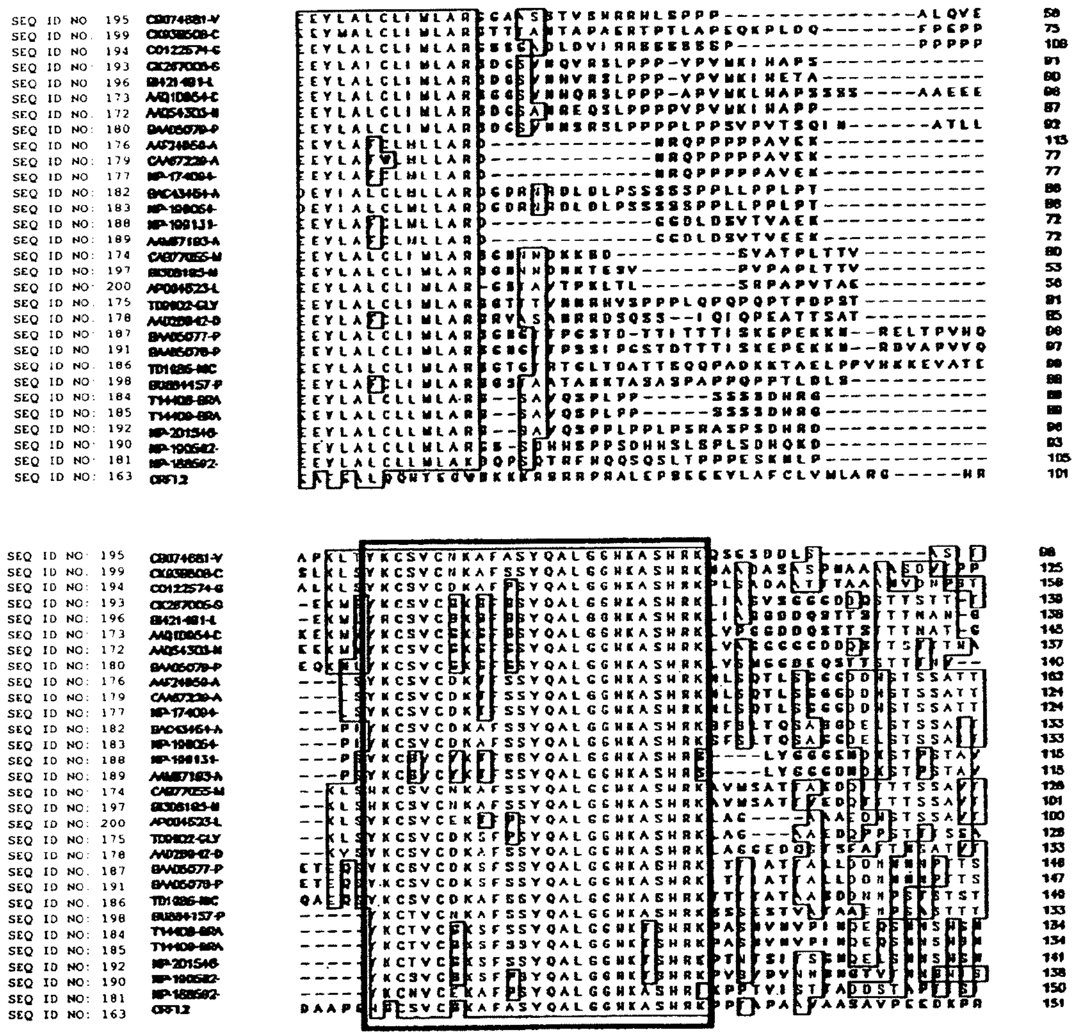

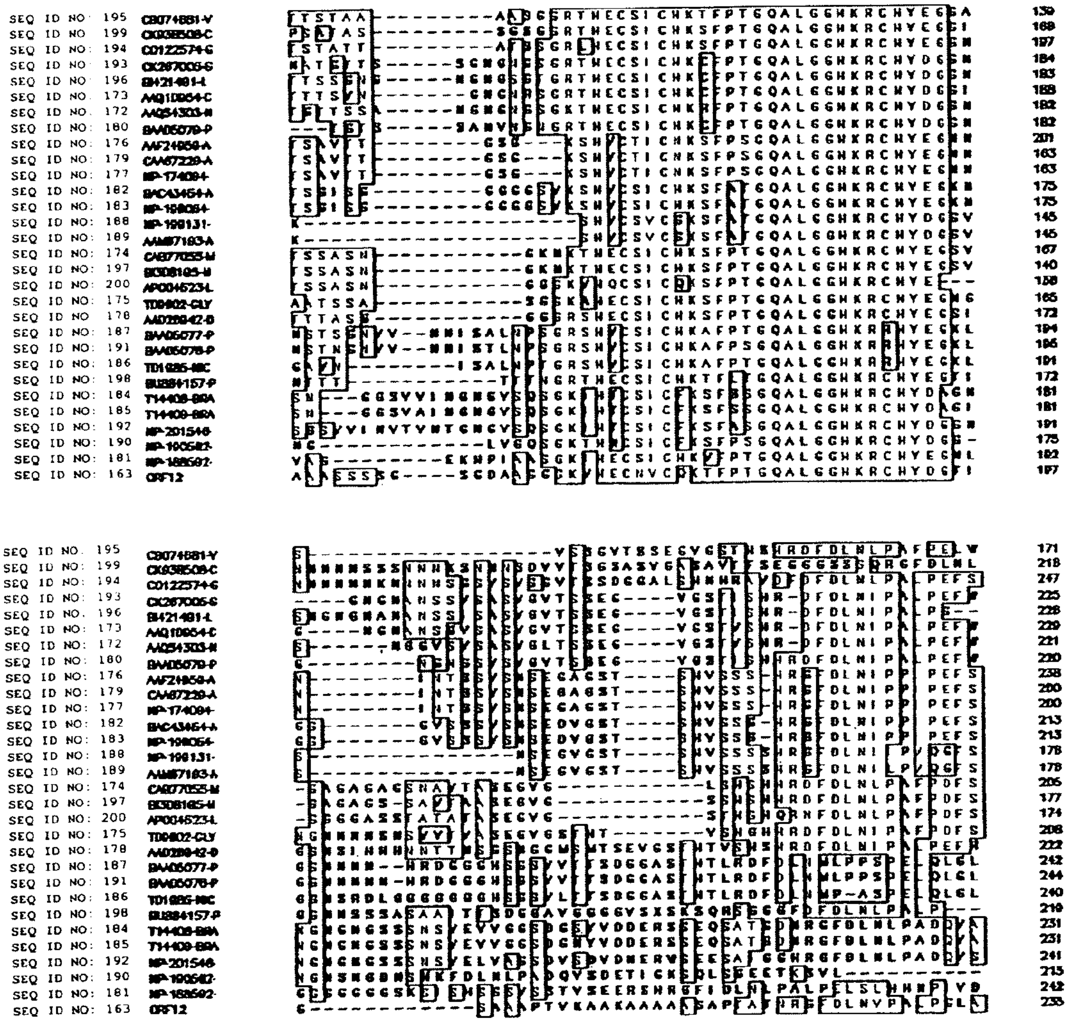

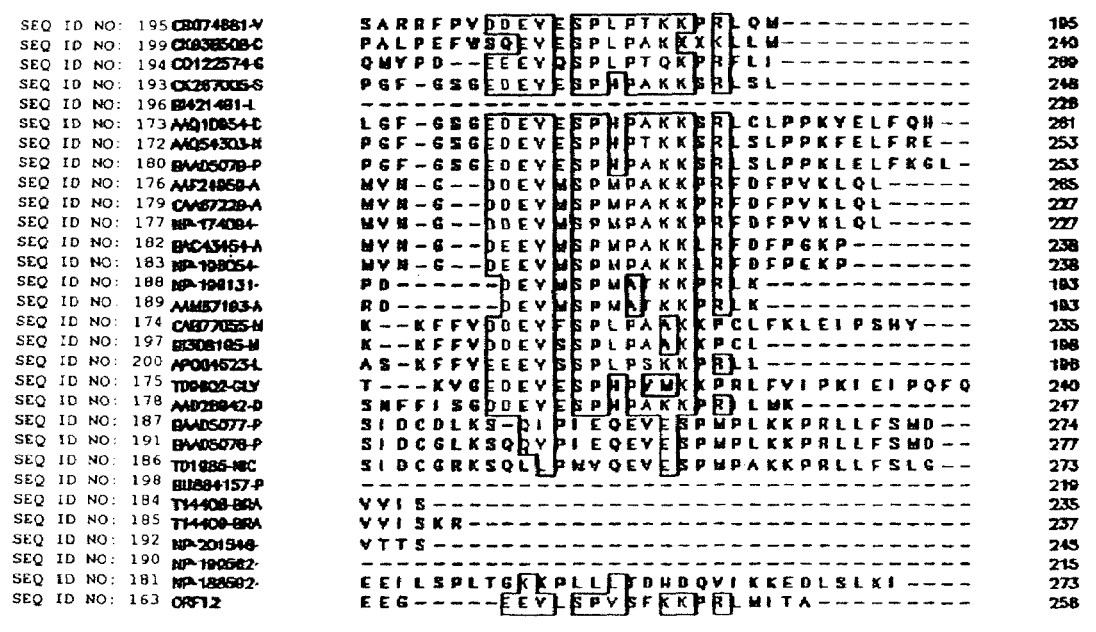

| | | | |
|---|---|---|---|
| SEQ ID NO: 195 | CB074881-V | SARRFPVDDEVESPLPTKKPRLQM----------- | 195 |
| SEQ ID NO: 199 | CK938508-C | PALPEFVSQEVESPLPAKKXKLLM----------- | 240 |
| SEQ ID NO: 194 | CD122574-G | QMYPD--EEEVQSPLPTQKPRFLI----------- | 289 |
| SEQ ID NO: 193 | CK267005-S | PGF-GSGEDEVESPHPAKKSRLSL----------- | 248 |
| SEQ ID NO: 196 | BI421481-L | ----------------------------------- | 228 |
| SEQ ID NO: 173 | AAQ10854-C | LGF-GSGEDEVESPHPAKKSRLCLPPKYELFQH-- | 281 |
| SEQ ID NO: 172 | AAQ54303-H | PGF-GSGEDEVESPHPTKKSRLSLPPKFELFRE-- | 253 |
| SEQ ID NO: 180 | BAA05079-P | PGF-GSGEDEVESPHPAKKSRLSLPPKLELFKGL- | 253 |
| SEQ ID NO: 176 | AAF24958-A | MVN-G--DDEVMSPMPAKKPRFDFPVKLQL----- | 285 |
| SEQ ID NO: 179 | CAA67229-A | MVN-G--DDEVMSPMPAKKPRFDFPVKLQL----- | 227 |
| SEQ ID NO: 177 | NP-174084- | MVN-G--DDEVMSPMPAKKPRFDFPVKLQL----- | 227 |
| SEQ ID NO: 182 | BAC43454-A | MVN-G--DEEVMSPMPAKKLRFDFPGKP------- | 238 |
| SEQ ID NO: 183 | NP-198054- | MVN-G--DEEVMSPMPAKKLRFDFPEKP------- | 238 |
| SEQ ID NO: 188 | NP-198131- | PD------DEVMSPMATKKPRLK------------ | 183 |
| SEQ ID NO: 189 | AAM67183-A | RD------DEVMSPMATKKPRLK------------ | 183 |
| SEQ ID NO: 174 | CAB77055-M | K--KFFVDDEVFSPLPAAKKPCLFKLEIPSHY--- | 235 |
| SEQ ID NO: 197 | BI308185-M | K--KFFVDDEVSSPLPAAKKPCL------------ | 188 |
| SEQ ID NO: 200 | AP004523-L | AS-KFFVEEEVSSPLPSKKPRLL------------ | 188 |
| SEQ ID NO: 175 | T09802-GLY | T---KVGEDEVESPHPVMKKPRLFVIPKIEIPQFQ | 240 |
| SEQ ID NO: 178 | AAD28842-D | SNFFISGDDEVESPHPAKKPR LMK---------- | 247 |
| SEQ ID NO: 187 | BAA05077-P | SIDCDLKS-QIPIEQEVESPMPLKKPRLLFSMD-- | 274 |
| SEQ ID NO: 191 | BAA05078-P | SIDCGLKSQDVPIEQEVESPMPLKKPRLLFSMD-- | 277 |
| SEQ ID NO: 186 | T01885-NIC | SIDCGRKSQLLPNVQEVESPMPAKKPRLLFSLG-- | 273 |
| SEQ ID NO: 198 | BU884157-P | ----------------------------------- | 219 |
| SEQ ID NO: 184 | T14408-BRA | VVIS------------------------------- | 235 |
| SEQ ID NO: 185 | T14409-BRA | VVISKR----------------------------- | 237 |
| SEQ ID NO: 192 | NP-201548- | VTTS------------------------------- | 245 |
| SEQ ID NO: 190 | NP-190582- | ----------------------------------- | 215 |
| SEQ ID NO: 181 | NP-188582- | EEILSPLTGKKPLLLFDHDQVIKKEDLSLKI---- | 273 |
| SEQ ID NO: 163 | ORF12 | EEG------EEVLSPVSFKKPRLMITA-------- | 258 |

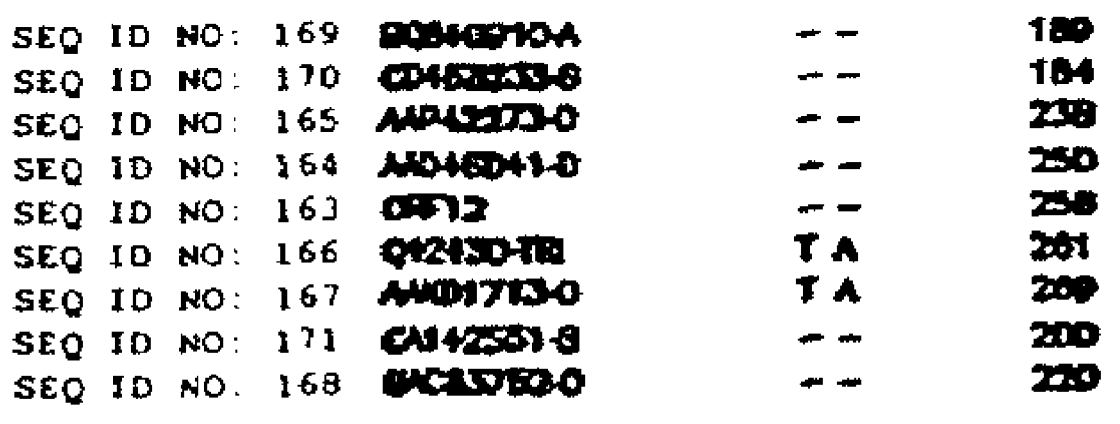

| | | | |
|---|---|---|---|
| SEQ ID NO: 169 | [illegible] | -- | 189 |
| SEQ ID NO: 170 | [illegible] | -- | 184 |
| SEQ ID NO: 165 | [illegible] | -- | 239 |
| SEQ ID NO: 164 | [illegible] | -- | 250 |
| SEQ ID NO: 163 | ORF12 | -- | 258 |
| SEQ ID NO: 166 | [illegible] | T A | 261 |
| SEQ ID NO: 167 | [illegible] | T A | 209 |
| SEQ ID NO: 171 | [illegible] | -- | 200 |
| SEQ ID NO: 168 | [illegible] | -- | 220 |

Figure 8

SEQ ID NO. 240

GGCGCGCCTTAATTAACGGGCTGGTAAAACAAATATAAGTATTAATATAAATATAATACAATAGAAGGAAAATAAATAAAATTTCCCTCTGTG
CCGTGCAAAAATGCACGGCAATGGGTTGGCCCGCACGGCAAAGGCATCGTTGCCCGTGTCCACGGCAATGGGTTGGCCCGCACGGCAAAGGCAT
CGTTGCCGTGTCCACGTCTTTGCCGTGCGCCTTGGCTCTATCTTTGCCGTGAAGCGTTCTTTGCCGTGTGCCTTTTATTTCTTTGCCGTGGGA
TGCTGCCTTTGCCGAGCGCTGAGCTGGCGCTTTGCCGTGCGCGTATTGTTTGCCGTGCGTCCTCCCAGAGCTGTACGGCAAAGAATTCATTGC
CGTGCACGAGGCACACGGGAAAGAAGTTTCGCATGGCAAAGGGCGCTGACAGCACACGGCAAAGAGCCCGGCACGGCATTGAGCTTTTTTTCC
CGTAATGATAGACGGCATAATATAATGGACGCACATGCTGATGTCAGGATGTCACCCACTCATCCTAGTATTTGTGGGACGTGAATTCTTTGT
GAGATGGGCAATGGGATGTGAACAAAATAAGTTTTGTACTAGTAGATAAACATTTTTACCCATAAACAATTGTTCTGTATTGAATGAAAAATT
ATTTTGTACTGGATGAAAATCTTCTGAGTAACTGTGTAAGATTAACATGAATCAAGAGACAAATCCAATGGCTACAAAGTCAACTAATACTTG
TTAAAAGTTCCGATACTTAAAATTATCAAAACTGATATATAGAATATTGCCCATCTCGCCACCGTGCTAGTTTAACAGACGATGGACGAATAT
CAGTCTTGTATTGGATAATCGATGCATGCGAGCTATCGGTCACCTGTCCATGCTTCCAGAAGGAGCCGAGACGTGGCGACTTCGTCCGACGCG
CCGACTATCTGCACACGGCCCGGCTTCTCGTCGTGGGCGAGTCAGCAGTCACAGGCTTTCCGCCTACCAACTCACACGTAGCGCCCTATCGTGG
CGCTTGATCGATGCAACAGCGATGCCTATCCCAGCTCCTCAAGCTGCTTATAAGTATGTCCTCGGCCATCACTGCTTACACAACAAACACAGC
TACTTATCGCAGTGTACTAAACAAGACGTACTAGCTAGATTTCGTGAGGTAAAATCAGTGCAATATCACTTGTGCAAGCCATTAGTTCCGTCG
CCATGGCGTCCCCGGAGGGCGCCAACTGGGTCTTCGACTGCCCGCTCATGGACGACCTTGCTGCCGCCGACTTCACCGCACCGCCCGCAGGAG
GCTTCTACTGGGCACCACCGATGCAGCCGCAGATGCACACCCAGGCCCCGGCCGTCTCCGCCACCCCGCCTCCCAACCACTGTGCCGAAATCA
ATAGCCCTATTTCTGTGGACTGGGACCATGCCAAAGGACAGCCAACAAATAAACGTCCTAGGTCAGAATCTGGTGCTCAACCCAGCTCCAAAG
CATGCAGGGAGAAAGCGAGAAGGGACAAGCTAAACGAGAGGTTCTTGGAATTGGGTGCTGTCTTGGATCCAGGGAAAACACCTAAAATCGACA
AGTGTGCTATATTGAATGATGCTATTCGTGCGGTGACTGAGCTACGTAGTGAAGCAGAGAAGCTGAAGGATTCAAACGAGTCTCTCCAAGAGA
AGATCAAAGAGCTGAAGGCTGAGAAGAATGAGCTGCGGGATGAGAAGCAAAAGCTGAAGGCAGAGAAAGAGAGCCTGGAGCAGCAGATCAAGT
TCATGAATGCCCGTCAGAGCCTCGTACCACACCTACCGCACCCTTCGGTTATCCCAGCGGCTGCATTTGCTGCTCCCCAAGGGCAAGTGCCAG
GGCAGAAGCTGATGATGCCTGTCATTGGCTACCATGGATTTCCCATGTGGCAATTCATGCCACCTTCTGATGTTGATACCTCCGATGATCCCA
AGTCGTGCCCTCCTGTTGCATAAGCCAGCTAAAGGCCTGGTTTCTCCATAATAATGTGTGAGTAGTTCCCAGATAAGGGAATTAGGGTTCCTA
TAGGGTTTCGCTCATGTGTTGAGCATATAAGAAACCCTTAGTATGTATTTGTATTTGTAAAATACTTCTATCAATAAAATTTCTAATTCCTAA
AACCAAAATCCAGTACTAAAATCCAGATCCCCCGAATTAATTCGGCGTTAATTCAGTATCGGCGCGCCTTAATTAAAATCGAATTTCGACCAT
ATGGGAGAGCTCCCAACGCGTTGGATGCATAGCTTGAGTATTCTATAGTGTCACCTAAATAGCTTGGCGTAATCATGGTCATAGCTGTTTCCT
GTGTGAAATTGTTATCCGCTCACAATTCCACACAACATACGAGCCGGAAGCATAAAGTGTAAAGCCTGGGGTGCCTAATGAGTGAGCTAACTC
ACATTAATTGCGTTGCGCTCACTGCCCGCTTTCCAGTCGGGAAACCTGTCGTGCCAGCTGCATTAATGAATCGGCCAACGCGCGGGGAGAGGC
GGTTTGCGTATTGGGCGCTCTTCCGCTTCCTCGCTCACTGACTCGCTGCGCTCGGTCGTTCGGCTGCGGCGAGCGGTATCAGCTCACTCAAAG
GCGGTAATACGGTTATCCACAGAATCAGGGGATAACGCAGGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCGACGCTCAAGTCAGAGGTGGCGAAACCCGACAGGACTA
TAAAGATACCAGGCGTTTCCCCCTGGAAGCTCCCTCGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAGGTCGTTCGCTCCAAGCTGGGCTGTGTGCACGAACCC
CCCGTTCAGCCCGACCGCTGCGCCTTATCCGGTAACTATCGTCTTGAGTCCAACCCGGTAAGACACGACTTATCGCCACTGGCAGCAGCCACT
GGTAACAGGATTAGCAGAGCGAGGTATGTAGGCGGTGCTACAGAGTTCTTGAAGTGGTGGCCTAACTACGGCTACACTAGAAGAACAGTATTT
GGTATCTGCGCTCTGCTGAAGCCAGTTACCTTCGGAAAAAGAGTTGGTAGCTCTTGATCCGGCAAACAAACCACCGCTGGTAGCGGTGGTTTT
TTTGTTTGCAAGCAGCAGATTACGCGCAGAAAAAAAGGATCTCAAGAAGATCCTTTGATCTTTTCTACGGGGTCTGACGCTCAGTGGAACGAA
AACTCACGTTAAGGGATTTTGGTCATGAGATTATCAAAAAGGATCTTCACCTAGATCCTTTTAAATTAAAAATGAAGTTTTAAATCAATCTAA
AGTATATATGAGTAAACTTGGTCTGACAGTTACCAATGCTTAATCAGTGAGGCACCTATCTCAGCGATCTGTCTATTTCGTTCATCCATAGTT
GCCTGACTCCCCGTCGTGTAGATAACTACGATACGGGAGGGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAGTGGTCCTGCAACTTTATCCGCCTCCATCCAGTCTATTAAT
TGTTGCCGGGAAGCTAGAGTAAGTAGTTCGCCAGTTAATAGTTTGCGCAACGTTGTTGCCATTGCTACAGGCATCGTGGTGTCACGCTCGTCG
TTTGGTATGGCTTCATTCAGCTCCGGTTCCCAACGATCAAGGCGAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGTTATGGCAGCACTGCATAATTCTCTTACTGTCATGCCATCCGTA
AGATGCTTTTCTGTGACTGGTGAGTACTCAACCAAGTCATTCTGAGAATAGTGTATGCGGCGACCGAGTTGCTCTTGCCCGGCGTCAATACGG
GATAATACCGCGCCACATAGCAGAACTTTAAAAGTGCTCATCATTGGAAAACGTTCTTCGGGGCGAAAACTCTCAAGGATCTTACCGCTGTTG
AGATCCAGTTCGATGTAACCCACTCGTGCACCCAACTGATCTTCAGCATCTTTTACTTTCACCAGCGTTTCTGGGTGAGCAAAAACAGGAAGG
CAAAATGCCGCAAAAAAGGGAATAAGGGCGACACGGAAATGTTGAATACTCATACTCTTCCTTTTTCAATATTATTGAAGCATTTATCAGGGT
TATTGTCTCATGAGCGGATACATATTTGAATGTATTTAGAAAAATAAACAAATAGGGGTTCCGCGCACATTTCCCCGAAAAGTGCCACCTGAT
GCGGTGTGAAATACCGCACAGATGCGTAAGGAGAAAATACCGCATCAGGAAATTGTAAGCGTTAATATTTTGTTAAAATTCGCGTTAAATTTT
TGTTAAATCAGCTCATTTTTTAACCAATAGGCCGAAATCGGCAAAATCCCTTATAAATCAAAAGAATAGACCGAGATAGGGTTGAGTGTTGTT
CCAGTTTGGAACAAGAGTCCACTATTAAAGAACGTGGACTCCAACGTCAAAGGGCGAAAAACCGTCTATCAGGGCGATGGCCCACTACGTGAA
CCATCACCCTAATCAAGTTTTTTGGGGTCGAGGTGCCGTAAAGCACTAAATCGGAACCCTAAAGGGAGCCCCCGATTTAGAGCTTGACGGGGA
AAGCCGGCGAACGTGGCGAGAAAGGAAGGGAAGAAAGCGAAAGGAGCGGGCGCTAGGGCGCTGGCAAGTGTAGCGGTCACGCTGCGCGTAACC
ACCACACCCGCCGCGCTTAATGCGCCGCTACAGGGCGCGTCCATTCGCCATTCAGGCTGCGCAACTGTTGGGAAGGGCGATCGGTGCGGGCCT
CTTCGCTATTACGCCAGCTGGCGAAAGGGGGATGTGCTGCAAGGCGATTAAGTTGGGTAACGCCAGGGTTTTCCCAGTCACGACGTTGTAAAA
CGACGGCCAGTGAATTGTAATACGACTCACTATAGGGCGAATTGGGCCCGACGTCGCATGCTCCCGGCCGCCATGGCGGCCGCGGGAATTCGA
TTGATT

SEQ ID NO. 241

Figure 10

GGCGCGCCTTAATTAACGGGCTGGTAAAACAAATATAAGTATTAATATAAATATAATACAATAGAAGGAAAATAAATAAAATTTCCCTCTGTG
CCGTGCAAAAATGCACGGCAATGGGTTGGCCCGCACGGCAAAGGCATCGTTGCCGTGTCCACGGCAATGGGTTGGCCCGCACGGCAAAGGCAT
CGTTGCCGTGTCCACGTCTTTGCCGTGCGCCTTGGCTCTATCTTTGCCGTGAAGCGTTCTTTGCCGTGTGCCTTTTATTTCTTTGCCGTGGGA
TGCTGCCTTTGCCGAGCGCTGAGCTGGCGCTTTGCCGTGCGCGTATTGTTTGCCGTGCGTCCTCCCAGAGCTGTACGGCAAAGAATTCATTGC
CGTGCACGAGGCACACGGGAAAGAAGTTTCGCATGGCAAAGGGCGCTGACAGCACACGGCAAAGAGCCCGGCACGGCATTGAGCTTTTTTTCC
CGTAATGATAGACGGCATAATATAATGGACGCACATGCTGATGTCAGGATGTCACCCACTCATCCTAGTATTTGTGGGACGTGAATTCTTTGT
GAGATGGGCAATGGGATGTGAACAAAATAAGTTTTGTACTAGTAGATAAACATTTTTACCCATAAACAATTGTTCTGTATTGAATGAAAAATT
ATTTTGTACTGGATGAAAATCTTCTGAGTAACTGTGTAAGATTAACATGAATCAAGAGACAAATCCAATGGCTACAAAGTCAACTAATACTTG
TTAAAAGTTCCGATACTTAAAATTATCAAAACTGATATATAGAATATTGCCCATCTCGCCACCGTGCTAGTTTAACAGACGATGGACGAATAT
CAGTCTTGTATTGGATAATCGATGCATGCGAGCTATCGGTCACCTGTCCATGCTTCCAGAAGGAGCCGAGACGTGGCGACTTCGTCCGACGCG
CCGACTATCTGCACACGCCCGGCTTCTCGTCGTGGGCGAGTCAGCAGTCACAGGCTTTCCGCCTACCAACTCACACGTAGCGCCCTATCGTGG
CGCTTGATCGATGCAACAGCGATGCCTATCCCAGCTCCTCAAGCTGCTTATAAGTATGTCCTCGGCCATCACTGCTTACACAACAAACACAGC
TACTTATCGCAGTGTACTAAACAAGACGTACTAGCTAGATTTCGTGAGGTAAAATCAGTGCAATATCACTTGTGCAAGCCATTAGTATGGCCG
TGGAGGCGGTTCTCGAAGCGGCGGCGATGATACAGTCGCCGCCGAGCAAGAAGATGGAGGCGTCTAGTAGCAGCGACGAGGCGTTCGAGGCGT
TGCAGCAGCACACGGAGGGGTGGTCCAAGAAGAAGCGCTCGAGGCGGCCACGGGCGCTCGAGCCCAGCGAGGAGGAGTACCTCGCGTTCTGCC
TCGTCATGCTGGCGCGCGGCCACCGCGACGCCGCGCCGGAGCACGGGTGCTCCGTCTGCGGCAAGGCGTTCGCGTCGTACCAGGCGCTCGGCG
GCCACAAGGCCAGCCACCGGAAGCCACCCACAGCTCCAGCCGCGGTGGCAGCAAGCGCCGTCCCCGAGGAGGACAAGCCACGGGCGGCTGCCT
CGTCCTCGTCTGGGTCCGGCGATGCCGCTGGCGGCGGCAAGGTCCACGAGTGCAACGTGTGCCAGAAGACGTTCCCGACGGGGCAGGCGCTGG
GCGGCCACAAGCGGTGCCACTACGACGGCACCATCGGCAGCGCCGCCGCGCCCACGGTGAAGGCTGCCAAGGCCGCCGCCGCGGCGAGCGCGC
CGACGGCGACGAACCGGGGGTTCGACCTGAACGTGCCGGCGCTGCCGGGACTCGCGGAGGAGGGGGAGGAGGTGCTCAGCCCGGTATCCTTCA
AGAAGCCGAGGCTCATGATCACCGCGTGAAGGCCTGGTTTCTCCATAATAATGTGTGAGTAGTTCCCAGATAAGGGAATTAGGGTTCCTATAG
GGTTTCGCTCATGTGTTGAGCATATAAGAAACCCTTAGTATGTATTTGTATTTGTAAAATACTTCTATCAATAAAATTTCTAATTCCTAAAAC
CAAAATCCAGTACTAAAATCCAGATCCCCCGAATTAATTCGGCGTTAATTCAGTATCGGCGCGCCTTAATTAAAATCGAATTTCGACCATATG
GGAGAGCTCCCAACGCGTTGGATGCATAGCTTGAGTATTCTATAGTGTCACCTAAATAGCTTGGCGTAATCATGGTCATAGCTGTTTCCTGTG
TGAAATTGTTATCCGCTCACAATTCCACACAACATACGAGCCGGAAGCATAAAGTGTAAAGCCTGGGGTGCCTAATGAGTGAGCTAACTCACA
TTAATTGCGTTGCGCTCACTGCCCGCTTTCCAGTCGGGAAACCTGTCGTGCCAGCTGCATTAATGAATCGGCCAACGCGCGGGGAGAGGCGGT
TTGCGTATTGGGCGCTCTTCCGCTTCCTCGCTCACTGACTCGCTGCGCTCGGTCGTTCGGCTGCGGCGAGCGGTATCAGCTCACTCAAAGGCG
GTAATACGGTTATCCACAGAATCAGGGGATAACGCAGGAAAGAACATGTGAGCAAAAGGCCAGCAAAAGGCCAGGAACCGTAAAAAGGCCGCG
TTGCTGGCGTTTTTCCATAGGCTCCGCCCCCCTGACGAGCATCACAAAAATCGACGCTCAAGTCAGAGGTGGCGAAACCCGACAGGACTATAA
AGATACCAGGCGTTTCCCCCTGGAAGCTCCCTCGTGCGCTCTCCTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGTGTAGGTCGTTCGCTCCAAGCTGGGCTGTGTGCACGAACCCCCC
GTTCAGCCCGACCGCTGCGCCTTATCCGGTAACTATCGTCTTGAGTCCAACCCGGTAAGACACGACTTATCGCCACTGGCAGCAGCCACTGGT
AACAGGATTAGCAGAGCGAGGTATGTAGGCGGTGCTACAGAGTTCTTGAAGTGGTGGCCTAACTACGGCTACACTAGAAGAACAGTATTTGGT
ATCTGCGCTCTGCTGAAGCCAGTTACCTTCGGAAAAAGAGTTGGTAGCTCTTGATCCGGCAAACAAACCACCGCTGGTAGCGGTGGTTTTTTT
GTTTGCAAGCAGCAGATTACGCGCAGAAAAAAAGGATCTCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCCTTTTAAATTAAAAATGAAGTTTTAAATCAATCTAAAGT
ATATATGAGTAAACTTGGTCTGACAGTTACCAATGCTTAATCAGTGAGGCACCTATCTCAGCGATCTGTCTATTTCGTTCATCCATAGTTGCC
TGACTCCCCGTCGTGTAGATAACTACGATACGGGAGGGCTTACCATCTGGCCCCAGTGCTGCAATGATACCGCGAGACCCACGCTCACCGGCT
CCAGATTTATCAGCAATAAACCAGCCAGCCGGAAGGGCCGAGCGCAGAAGTGGTCCTGCAACTTTATCCGCCTCCATCCAGTCTATTAATTGT
TGCCGGGAAGCTAGAGTAAGTAGTTCGCCAGTTAATAGTTTGCGCAACGTTGTTGCCATTGCTACAGGCATCGTGGTGTCACGCTCGTCGTTT
GGTATGGCTTCATTCAGCTCCGGTTCCCAACGATCAAGGCGAGTTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTATGGCAGCACTGCATAATTCTCTTACTGTCATGCCATCCGTAAGA
TGCTTTTCTGTGACTGGTGAGTACTCAACCAAGTCATTCTGAGAATAGTGTATGCGGCGACCGAGTTGCTCTTGCCCGGCGTCAATACGGGAT
AATACCGCGCCACATAGCAGAACTTTAAAAGTGCTCATCATTGGAAAACGTTCTTCGGGGCGAAAACTCTCAAGGATCTTACCGCTGTTGAGA
TCCAGTTCGATGTAACCCACTCGTGCACCCAACTGATCTTCAGCATCTTTTACTTTCACCAGCGTTTCTGGGTGAGCAAAAACAGGAAGGCAA
AATGCCGCAAAAAAGGGAATAAGGGCGACACGGAAATGTTGAATACTCATACTCTTCCTTTTTCAATATTATTGAAGCATTTATCAGGGTTAT
TGTCTCATGAGCGGATACATATTTGAATGTATTTAGAAAAATAAACAAATAGGGGTTCCGCGCACATTTCCCCGAAAAGTGCCACCTGATGCG
GTGTGAAATACCGCACAGATGCGTAAGGAGAAAATACCGCATCAGGAAATTGTAAGCGTTAATATTTTGTTAAAATTCGCGTTAAATTTTTGT
TAAATCAGCTCATTTTTTAACCAATAGGCCGAAATCGGCAAAATCCCTTATAAATCAAAAGAATAGACCGAGATAGGGTTGAGTGTTGTTCCA
GTTTGGAACAAGAGTCCACTATTAAAGAACGTGGACTCCAACGTCAAAGGGCGAAAAACCGTCTATCAGGGCGATGGCCCACTACGTGAACCA
TCACCCTAATCAAGTTTTTTGGGGTCGAGGTGCCGTAAAGCACTAAATCGGAACCCTAAAGGGAGCCCCCGATTTAGAGCTTGACGGGGAAAG
CCGGCGAACGTGGCGAGAAAGGAAGGGAAGAAAGCGAAAGGAGCGGGCGCTAGGGCGCTGGCAAGTGTAGCGGTCACGCTGCGCGTAACCACC
ACACCCGCCGCGCTTAATGCGCCGCTACAGGGCGCGTCCATTCGCCATTCAGGCTGCGCAACTGTTGGGAAGGGCGATCGGTGCGGGCCTCTT
CGCTATTACGCCAGCTGGCGAAAGGGGGATGTGCTGCAAGGCGATTAAGTTGGGTAACGCCAGGGTTTTCCCAGTCACGACGTTGTAAAACGA
CGGCCAGTGAATTGTAATACGACTCACTATAGGGCGAATTGGGCCCGACGTCGCATGCTCCCGGCCGCCATGGCGGCCGCGGGAATTCGATTG
ATT

SEQ ID NO: 242

Figure 12

GAATTTCTAGTTCTAGATGCATGCTCGAAATTCGATTGGCGCGCCTTAATTAATAAGAGCAGCTTGCCAACATG
GTGGAGCACGACACTCTCGTCTACTCCAAGAATATCAAAGATACAGTCTCAGAAGACCAAAGGGCTATTGAGAC
TTTTCAACAAAGGGTAATATCGGGAAACCTCCTCGGATTCCATTGCCCAGCTATCTGTCACTTCATCAAAAGGA
CAGTAGAAAAGGAAGGTGGCACCTACAAATGCCATCATTGCGATAAAGGAAAGGCTATCGTTCAAGATGCCTCT
GCCGACAGTGGTCCCAAAGATGGACCCCCACCCACGAGGAGCATCGTGGAAAAAGAAGACGTTCCAACCACGTC
TTCAAAGCAAGTGGATTGATGTGAACATGGTGGAGCACGACACTCTCGTCTACTCCAAGAATATCAAAGATACA
GTCTCAGAAGACCAAAGGGCTATTGAGACTTTTCAACAAAGGGTAATATCGGGAAACCTCCTCGGATTCCATTG
CCCAGCTATCTGTCACTTCATCAAAAGGACAGTAGAAAAGGAAGGTGGCACCTACAAATGCCATCATTGCGATA
AAGGAAAGGCTATCGTTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATATCTCCACTGACGTAAGGGAT
GACGCACAATCCCACTATCCTTCGCAAGACCCTTCCTCTATATAAGGAAGTTCATTTCATTTGGAGAGGACACG
CTGAAATCACCAGTCTCTCTCTACAAATCTATCTCTCTCCATTAGTTCCGTCGCCATGGCGTCCCCGGAGGCG
CCAACTGGGTCTTCGACTGCCCGCTCATGGACGACCTTGCTGCCGCCGACTTCACCGCACCGCCCGCAGGAGGC
TTCTACTGGGCACCACCGATGCAGCCGCAGATGCACACCCAGGCCCCGGCCGTCTCCGCCACCCCGCCTCCCAA
CCACTGTGCCGAAATCAATAGCCCTATTTCTGTGGACTGGGACCATGCCAAAGGACAGCCAACAAATAAACGTC
CTAGGTCAGAATCTGGTGCTCAACCCAGCTCCAAAGCATGCAGGGAGAAAGCGAGAAGGGACAAGCTAAACGAG
AGGTTCTTGGAATTGGGTGCTGTCTTGGATCCAGGGAAAACACCTAAAATCGACAAGTGTGCTATATTGAATGA
TGCTATTCGTGCGGTGACTGAGCTACGTAGTGAAGCAGAGAAGCTGAAGGATTCAAACGAGTCTCTCCAAGAGA
AGATCAAAGAGCTGAAGGCTGAGAAGAATGAGCTGCGGGATGAGAAGCAAAAGCTGAAGGCAGAGAAAGAGAGC
CTGGAGCAGCAGATCAAGTTCATGAATGCCCGTCAGAGCCTCGTACCACACCTACCGCACCCTTCGGTTATCCC
AGCGGCTGCATTTGCTGCTCCCCAAGGGCAAGTGCCAGGGCAGAAGCTGATGATGCCTGTCATTGGCTACCATG
GATTTCCCATGTGGCAATTCATGCCACCTTCTGATGTTGATACCTCCGATGATCCCAAGTCGTGCCCTCCTGTT
GCATAAGCCAGCTAAAGGCCTGGTTTCTCCATAATAATGTGTGAGTAGTTCCCAGATAAGGGAATTAGGGTTCC
TATAGGGTTTCGCTCATGTGTTGAGCATATAAGAAACCCTTAGTATGTATTTGTATTTGTAAAATACTTCTATC
AATAAAATTTCTAATTCCTAAAACCAAAATCCAGTACTAAAATCCAGATCCCCCGAATTAATTCGGCGTTAATT
CAGTATCGGCGCGCCTTAATTAAAATCGAATTTCGACCATACTAGTGGATCCCCCTCGGACTAGAAGCTTGGCA
CTGGCCGTCGTTTTACAACGTCGTGACTGGGAAAACCCTGGCGTTACCCAACTTAATCGCCTTGCAGCACATCC
CCCTTTCGCCAGCTGGCGTAATAGCGAAGAGGCCCGCACCGATCGCCCTTCCCAACAGTTGCGCAGCCTGAATG
GCGAATGCTAGAGCAGCTTGAGCTTGGATCAGATTGTCGTTTCCCGCCTTCAGTTTAAACTATCAGTGTTTGAC
AGGATATATTGGCGGGTAAACCTAAGAGAAAAGAGCGTTTATTAGAATAACGGATATTTAAAAGGGCGTGAAAA
GGTTTATCCGTTCGTCCATTTGTATGTGCATGCCAACCACAGGGTTCCCCTCGGGATCAAAGTACTTTGATCCA
ACCCCTCCGCTGCTATAGTGCAGTCGGCTTCTGACGTTCAGTGCAGCCGTCTTCTGAAAACGACATGTCGCACA
AGTCCTAAGTTACGCGACAGGCTGCCGCCCTGCCCTTTTCCTGGCGTTTTCTTGTCGCGTGTTTTAGTCGCATA
AAGTAGAATACTTGCGACTAGAACCGGAGACATTACGCCATGAACAAGAGCGCCGCCGCTGGCCTGCTGGGCTA
TGCCCGCGTCAGCACCGACGACCAGGACTTGACCAACCAACGGGCCGAACTGCACGCGGCCGGCTGCACCAAGC
TGTTTTCCGAGAAGATCACCGGCACCAGGCGCGACCGCCCGGAGCTGGCCAGGATGCTTGACCACCTACGCCCT
GGCGACGTTGTGACAGTGACCAGGCTAGACCGCCTGGCCCGCAGCACCCGCGACCTACTGGACATTGCCGAGCG
CATCCAGGAGGCCGGCGCGGGCCTGCGTAGCCTGGCAGAGCCGTGGGCCGACACCACCACGCCGGCCGGCCGCA
TGGTGTTGACCGTGTTCGCCGGCATTGCCGAGTTCGAGCGTTCCCTAATCATCGACCGCACCCGGAGCGGGCGC
GAGGCCGCCAAGGCCCGAGGCGTGAAGTTTGGCCCCCGCCCTACCCTCACCCCGGCACAGATCGCGCACGCCCG
CGAGCTGATCGACCAGGAAGGCCGCACCGTGAAAGAGGCGGCTGCACTGCTTGGCGTGCATCGCTCGACCCTGT
ACCGCGCACTTGAGCGCAGCGAGGAAGTGACGCCCACCGAGGCCAGGCGGCGCGGTGCCTTCCGTGAGGACGCA
TTGACCGAGGCCGACGCCCTGGCGGCCGCCGAGAATGAACGCCAAGAGGAACAAGCATGAAACCGCACCAGGAC
GGCCAGGACGAACCGTTTTTCATTACCGAAGAGATCGAGGCGGAGATGATCGCGGCCGGGTACGTGTTCGAGCC
GCCCGCGCACGTCTCAACCGTGCGGCTGCATGAAATCCTGGCCGGTTTGTCTGATGCCAAGCTGGCGGCCTGGC
CGGCCAGCTTGGCCGCTGAAGAAACCGAGCGCCGCCGTCTAAAAAGGTGATGTGTATTTGAGTAAAACAGCTTG
CGTCATGCGGTCGCTGCGTATATGATGCGATGAGTAAATAAACAAATACGCAAGGGGAACGCATGAAGGTTATC
GCTGTACTTAACCAGAAAGGCGGGTCAGGCAAGACGACCATCGCAACCCATCTAGCCCGCGCCCTGCAACTCGC
CGGGGCCGATGTTCTGTTAGTCGATTCCGATCCCCAGGGCAGTGCCCGCGATTGGGCGGCCGTGCGGGAAGATC
AACCGCTAACCGTTGTCGGCATCGACCGCCCGACGATTGACCGCGACGTGAAGGCCATCGGCCGGCGCGACTTC
GTAGTGATCGACGGAGCGCCCCAGGCGGCGGACTTGGCTGTGTCCGCGATCAAGGCAGCCGACTTCGTGCTGAT
TCCGGTGCAGCCAAGCCCTTACGACATATGGGCCACCGCCGACCTGGTGGAGCTGGTTAAGCAGCGCATTGAGG
TCACGGATGGAAGGCTACAAGCGGCCTTTGTCGTGTCGCGGGCGATCAAAGGCACGCGCATCGGCGGTGAGGT

GCCGAGGCGCTGGCCGGGTACGAGCTGCCCATTCTTGAGTCCCGTATCACGCAGCGCGTGAGCTACCCAGGCAC
TGCCGCCGCCGGCACAACCGTTCTTGAATCAGAACCCGAGGGCGACGCTGCCCGCGAGGTCCAGGCGCTGGCCG
CTGAAATTAAATCAAAACTCATTTGAGTTAATGAGGTAAAGAGAAAATGAGCAAAAGCACAAACACGCTAAGTG
CCGGCCGTCCGAGCGCACGCAGCAGCAAGGCTGCAACGTTGGCCAGCCTGGCAGACACGCCAGCCATGAAGCGG
GTCAACTTTCAGTTGCCGGCGGAGGATCACACCAAGCTGAAGATGTACGCGGTACGCCAAGGCAAGACCATTAC
CGAGCTGCTATCTGAATACATCGCGCAGCTACCAGAGTAAATGAGCAAATGAATAAATGAGTAGATGAATTTTA
GCGGCTAAAGGAGGCGGCATGGAAAATCAAGAACAACCAGGCACCGACGCCGTGGAATGCCCCATGTGTGGAGG
AACGGGCGGTTGGCCAGGCGTAAGCGGCTGGGTTGTCTGCCGGCCCTGCAATGGCACTGGAACCCCCAAGCCCG
AGGAATCGGCGTGACGGTCGCAAACCATCCGGCCCGGTACAAATCGGCGCGGCGCTGGGTGATGACCTGGTGGA
GAAGTTGAAGGCCGCGCAGGCCGCCCAGCGGCAACGCATCGAGGCAGAAGCACGCCCCGGTGAATCGTGGCAAG
CGGCCGCTGATCGAATCCGCAAAGAATCCCGGCAACCGCCGGCAGCCGGTGCGCCGTCGATTAGGAAGCCGCCC
AAGGGCGACGAGCAACCAGATTTTTTCGTTCCGATGCTCTATGACGTGGGCACCCGCGATAGTCGCAGCATCAT
GGACGTGGCCGTTTTCCGTCTGTCGAAGCGTGACCGACGAGCTGGCGAGGTGATCCGCTACGAGCTTCCAGACG
GGCACGTAGAGGTTTCCGCAGGGCCGGCCGGCATGGCCAGTGTGTGGGATTACGACCTGGTACTGATGGCGGTT
TCCCATCTAACCGAATCCATGAACCGATACCGGGAAGGGAAGGGAGACAAGCCCGGCCGCGTGTTCCGTCCACA
CGTTGCGGACGTACTCAAGTTCTGCCGGCGAGCCGATGGCGGAAAGCAGAAAGACGACCTGGTAGAAACCTGCA
TTCGGTTAAACACCACGCACGTTGCCATGCAGCGTACGAAGAAGGCCAAGAACGGCCGCCTGGTGACGGTATCC
GAGGGTGAAGCCTTGATTAGCCGCTACAAGATCGTAAAGAGCGAAACCGGGCGGCCGGAGTACATCGAGATCGA
GCTAGCTGATTGGATGTACCGCGAGATCACAGAAGGCAAGAACCCGGACGTGCTGACGGTTCACCCCGATTACT
TTTTGATCGATCCCGGCATCGGCCGTTTTCTCTACCGCCTGGCACGCCGCGCCGCAGGCAAGGCAGAAGCCAGA
TGGTTGTTCAAGACGATCTACGAACGCAGTGGCAGCGCCGGAGAGTTCAAGAAGTTCTGTTTCACCGTGCGCAA
GCTGATCGGGTCAAATGACCTGCCGGAGTACGATTTGAAGGAGGAGGCGGGGCAGGCTGGCCCGATCCTAGTCA
TGCGCTACCGCAACCTGATCGAGGGCGAAGCATCCGCCGGTTCCTAATGTACGGAGCAGATGCTAGGGCAAATT
GCCCTAGCAGGGGAAAAAGGTCGAAAAGGTCTCTTTCCTGTGGATAGCACGTACATTGGGAACCCAAAGCCGTA
CATTGGGAACCGGAACCCGTACATTGGGAACCCAAAGCCGTACATTGGGAACCGGTCACACATGTAAGTGACTG
ATATAAAAGAGAAAAAAGGCGATTTTTCCGCCTAAAACTCTTTAAAACTTATTAAAACTCTTAAAACCCGCCTG
GCCTGTGCATAACTGTCTGGCCAGCGCACAGCCGAAGAGCTGCAAAAAGCGCCTACCCTTCGGTCGCTGCGCTC
CCTACGCCCCGCCGCTTCGCGTCGGCCTATCGCGGCCGCTGGCCGCTCAAAAATGGCTGGCCTACGGCCAGGCA
ATCTACCAGGGCGCGGACAAGCCGCGCCGTCGCCACTCGACCGCCGGCGCCCACATCAAGGCACCCTGCCTCGC
GCGTTTCGGTGATGACGGTGAAAACCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGGGTGTCGGGGCGCAGCCATGACCCAG
TCACGTAGCGATAGCGGAGTGTATACTGGCTTAACTATGCGGCATCAGAGCAGATTGTACTGAGAGTGCACCAT
ATGCGGTGTGAAATACCGCACAGATGCGTAAGGAGAAAATACCGCATCAGGCGCTCTTCCGCTTCCTCGCTCAC
TGACTCGCTGCGCTCGGTCGTTCGGCTGCGGCGAGCGGTATCAGCTCACTCAAAGGCGGTAATACGGTTATCCA
CAGAATCAGGGGATAACGCAGGAAAGAACATGTGAGCAAAAGGCCAGCAAAAGGCCAGGAACCGTAAAAAGGCC
GCGTTGCTGGCGTTTTTCCATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCGTGCGCTCTCCTGTTCCGA
CCCTGCCGCTTACCGGATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTTGAAGTGGTGGCCTAACTACGGC
TACACTAGAAGGACAGTATTTGGTATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCAAGCAGCAGATTACGCGCAGAAAAA
AAGGATCTCAAGAAGATCCTTTGATCTTTTCTACGGGGTCTGACGCTCAGTGGAACGAAAACTCACGTTAAGGG
ATTTTGGTCATGCATTCTAGGTACTAAAACAATTCATCCAGTAAAATATAATATTTTATTTTCTCCCAATCAGG
CTTGATCCCCAGTAAGTCAAAAAATAGCTCGACATACTGTTCTTCCCCGATATCCTCCCTGATCGACCGGACGC
AGAAGGCAATGTCATACCACTTGTCCGCCCTGCCGCTTCTCCCAAGATCAATAAAGCCACTTACTTTGCCATCT
TTCACAAAGATGTTGCTGTCTCCCAGGTCGCCGTGGGAAAAGACAAGTTCCTCTTCGGGCTTTTCCGTCTTTAA
AAAATCATACAGCTCGCGCGGATCTTTAAATGGAGTGTCTTCTTCCCAGTTTTCGCAATCCACATCGGCCAGAT
CGTTATTCAGTAAGTAATCCAATTCGGCTAAGCGGCTGTCTAAGCTATTCGTATAGGGACAATCCGATATGTCG
ATGGAGTGAAAGAGCCTGATGCACTCCGCATACAGCTCGATAATCTTTTCAGGGCTTTGTTCATCTTCATACTC
TTCCGAGCAAAGGACGCCATCGGCCTCACTCATGAGCAGATTGCTCCAGCCATCATGCCGTTCAAAGTGCAGGA
CCTTTGGAACAGGCAGCTTTCCTTCCAGCCATAGCATCATGTCCTTTTCCCGTTCCACATCATAGGTGGTCCCT
TTATACCGGCTGTCCGTCATTTTTAAATATAGGTTTTCATTTTCTCCCACCAGCTTATATACCTTAGCAGGAGA
CATTCCTTCCGTATCTTTTACGCAGCGGTATTTTTCGATCAGTTTTTCAATTCCGGTGATATTCTCATTTTAG
CCATTTATTATTTCCTTCCTCTTTTCTACAGTATTTAAAGATACCCCAAGAAGCTAATTATAACAAGACGAACT

CCAATTCACTGTTCCTTGCATTCTAAAACCTTAAATACCAGAAAACAGCTTTTTCAAAGTTGTTTTCAAAGTTG
GCGTATAACATAGTATCGACGGAGCCGATTTTGAAACCGCGGTGATCACAGGCAGCAACGCTCTGTCATCGTTA
CAATCAACATGCTACCCTCCGCGAGATCATCCGTGTTTCAAACCCGGCAGCTTAGTTGCCGTTCTTCCGAATAG
CATCGGTAACATGAGCAAAGTCTGCCGCCTTACAACGGCTCTCCCGCTGACGCCGTCCCGGACTGATGGGCTGC
CTGTATCGAGTGGTGATTTTGTGCCGAGCTGCCGGTCGGGGAGCTGTTGGCTGGCTGGTGGCAGGATATATTGT
GGTGTAAACAAATTGACGCTTAGACAACTTAATAACACATTGCGGACGTTTTTAATGTACTGAATTAACGCCGA
ATTAATTCGGGGGATCTGGATTTTAGTACTGGATTTTGGTTTTAGGAATTAGAAATTTTATTGATAGAAGTATT
TTACAAATACAAATACATACTAAGGGTTTCTTATATGCTCAACACATGAGCGAAACCCTATAGGAACCCTAATT
CCCTTATCTGGGAACTACTCACACATTATTATGGAGAAACTCGAGCTTGTCGATCGACAGATCCGGTCGGCATC
TACTCTATTTCTTTGCCCTCGGACGAGTGCTGGGGCGTCGGTTTCCACTATCGGCGAGTACTTCTACACAGCCA
TCGGTCCAGACGGCCGCGCTTCTGCGGGCGATTTGTGTACGCCCGACAGTCCCGGCTCCGGATCGGACGATTGC
GTCGCATCGACCCTGCGCCCAAGCTGCATCATCGAAATTGCCGTCAACCAAGCTCTGATAGAGTTGGTCAAGAC
CAATGCGGAGCATATACGCCCGGAGTCGTGGCGATCCTGCAAGCTCCGGATGCCTCCGCTCGAAGTAGCGCGTC
TGCTGCTCCATACAAGCCAACCACGGCCTCCAGAAGAAGATGTTGGCGACCTCGTATTGGGAATCCCCGAACAT
CGCCTCGCTCCAGTCAATGACCGCTGTTATGCGGCCATTGTCCGTCAGGACATTGTTGGAGCCGAAATCCGCGT
GCACGAGGTGCCGGACTTCGGGGCAGTCCTCGGCCCAAAGCATCAGCTCATCGAGAGCCTGCGCGACGGACGCA
CTGACGGTGTCGTCCATCACAGTTTGCCAGTGATACACATGGGGATCAGCAATCGCGCATATGAAATCACGCCA
TGTAGTGTATTGACCGATTCCTTGCGGTCCGAATGGGCCGAACCCGCTCGTCTGGCTAAGATCGGCCGCAGCGA
TCGCATCCATAGCCTCCGCGACCGGTTGTAGAACAGCGGGCAGTTCGGTTTCAGGCAGGTCTTGCAACGTGACA
CCCTGTGCACGGCGGGAGATGCAATAGGTCAGGCTCTCGCTAAACTCCCCAATGTCAAGCACTTCCGGAATCGG
GAGCGCGGCCGATGCAAAGTGCCGATAAACATAACGATCTTTGTAGAAACCATCGGCGCAGCTATTTACCCGCA
GGACATATCCACGCCCTCCTACATCGAAGCTGAAAGCACGAGATTCTTCGCCCTCCGAGAGCTGCATCAGGTCG
GAGACGCTGTCGAACTTTTCGATCAGAAACTTCTCGACAGACGTCGCGGTGAGTTCAGGCTTTTTCATATCTCA
TTGCCCCCCCGGATCTGCGAAAGCTCGAGAGAGATAGATTTGTAGAGAGAGACTGGTGATTTCAGCGTGTCCTC
TCCAAATGAAATGAACTTCCTTATATAGAGGAAGGTCTTGCGAAGGATAGTGGGATTGTGCGTCATCCCTTACG
TCAGTGGAGATATCACATCAATCCACTTGCTTTGAAGACGTGGTTGGAACGTCTTCTTTTTCCACGATGCTCCT
CGTGGGTGGGGGTCCATCTTTGGGACCACTGTCGGCAGAGGCATCTTGAACGATAGCCTTTCCTTTATCGCAAT
GATGGCATTTGTAGGTGCCACCTTCCTTTTCTACTGTCCTTTTGATGAAGTGACAGATAGCTGGGCAATGGAAT
CCGAGGAGGTTTCCCGATATTACCCTTTGTTGAAAAGTCTCAATAGCCCTTTGGTCTTCTGAGACTGTATCTTT
GATATTCTTGGAGTAGACGAGAGTGTCGTGCTCCACCATGTTATCACATCAATCCACTTGCTTTGAAGACGTGG
TTGGAACGTCTTCTTTTTCCACGATGCTCCTCGTGGGTGGGGGTCCATCTTTGGGACCACTGTCGGCAGAGGCA
TCTTGAACGATAGCCTTTCCTTTATCGCAATGATGGCATTTGTAGGTGCCACCTTCCTTTTCTACTGTCCTTTT
GATGAAGTGACAGATAGCTGGGCAATGGAATCCGAGGAGGTTTCCCGATATTACCCTTTGTTGAAAAGTCTCAA
TAGCCCTTTGGTCTTCTGAGACTGTATCTTTGATATTCTTGGAGTAGACGAGAGTGTCGTGCTCCACCATGTTG
GCAAGCTGCTCTAGCCAATACGCAAACCGCCTCTCCCCGCGCGTTGGCCGATTCATTAATGCAGCTGGCACGAC
AGGTTTCCCGACTGGAAAGCGGGCAGTGAGCGCAACGCAATTAATGTGAGTTAGCTCACTCATTAGGCACCCCA
GGCTTTACACTTTATGCTTCCGGCTCGTATGTTGTGTGGAATTGTGAGCGGATAACAATTTCACACAGGAAACA
GCTATGACCATGATTAC

Figure 14

SEQ ID NO: 243

GAATTTCTAGTTCTAGATGCATGCTCGAAATTCGATTGGCGCGCCTTAATTAATAAGAGCAGCTTGCCAACATG
GTGGAGCACGACACTCTCGTCTACTCCAAGAATATCAAAGATACAGTCTCAGAAGACCAAAGGGCTATTGAGAC
TTTTCAACAAAGGGTAATATCGGGAAACCTCCTCGGATTCCATTGCCCAGCTATCTGTCACTTCATCAAAAGGA
CAGTAGAAAAGGAAGGTGGCACCTACAAATGCCATCATTGCGATAAAGGAAAGGCTATCGTTCAAGATGCCTCT
GCCGACAGTGGTCCCAAAGATGGACCCCCACCCACGAGGAGCATCGTGGAAAAAGAAGACGTTCCAACCACGTC
TTCAAAGCAAGTGGATTGATGTGAACATGGTGGAGCACGACACTCTCGTCTACTCCAAGAATATCAAAGATACA
GTCTCAGAAGACCAAAGGGCTATTGAGACTTTTCAACAAAGGGTAATATCGGGAAACCTCCTCGGATTCCATTG
CCCAGCTATCTGTCACTTCATCAAAAGGACAGTAGAAAAGGAAGGTGGCACCTACAAATGCCATCATTGCGATA
AAGGAAAGGCTATCGTTCAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATATCTCCACTGACGTAAGGGAT
GACGCACAATCCCACTATCCTTCGCAAGACCCTTCCTCTATATAAGGAAGTTCATTTCATTTGGAGAGGACACG
CTGAAATCACCAGTCTCTCTCTACAAATCTATCTCTCTCCATTAGTTTGCCCACTGCTTGCTGCTACTCTCTCG
ATCTGTAGTTGCTCAGGTGTGCAAGAAAGATACTCACACGCGAGCTTGCTTGGCATGGCCGTGGAGGCGGTTCT
CGAAGCGGCGGCGATGATACAGTCGCCGCCGAGCAAGAAGATGGAGGCGTCTAGTAGCAGCGACGAGGCGTTCG
AGGCGTTGCAGCAGCACACGGAGGGGTGGTCCAAGAAGAAGCGCTCGAGGCGGCCACGGGCGCTCGAGCCCAGC
GAGGAGGAGTACCTCGCGTTCTGCCTCGTCATGCTGGCGCGCGGCCACCGCGACGCCGCGCCGGAGCACGGGTG
CTCCGTCTGCGGCAAGGCGTTCGCGTCGTACCAGGCGCTCGGCGGCCACAAGGCCAGCCACCGGAAGCCACCCA
CAGCTCCAGCCGCGGTGGCAGCAAGCGCCGTCCCCGAGGAGGACAAGCCACGGGCGGCTGCCTCGTCCTCGTCT
GGGTCCGGCGATGCCGCTGGCGGCGGCAAGGTCCACGAGTGCAACGTGTGCCAGAAGACGTTCCCGACGGGGCA
GGCGCTGGGCGGCCACAAGCGGTGCCACTACGACGGCACCATCGGCAGCGCCGCCGCGCCCACGGTGAAGGCTG
CCAAGGCCGCCGCCGCGGCGAGCGCGCCGACGGCGACGAACCGGGGGTTCGACCTGAACGTGCCGGCGCTGCCG
GGACTCGCGGAGGAGGGGGAGGAGGTGCTCAGCCCGGTATCCTTCAAGAAGCCGAGGCTCATGATCACCGCGTG
ATTTGACCATACAATCTGCATATAGTTGGTCAAAATCAAGGGTTCTTCTGTAGCTTAGCTTCTGTTAGTGATTG
CCGTACATAGATTGTTGGTGATTGAAGGCCTGGTTTCTCCATAATAATGTGTGAGTAGTTCCCAGATAAGGGAA
TTAGGGTTCCTATAGGGTTTCGCTCATGTGTTGAGCATATAAGAAACCCTTAGTATGTATTTGTATTTGTAAAA
TACTTCTATCAATAAAATTTCTAATTCCTAAAACCAAAATCCAGTACTAAAATCCAGATCCCCCGAATTAATTC
GGCGTTAATTCAGTATCGGCGCGCCTTAATTAAAATCGAATTTCGACCATACTAGTGGATCCCCCTCGGACTAG
AAGCTTGGCACTGGCCGTCGTTTTACAACGTCGTGACTGGGAAAACCCTGGCGTTACCCAACTTAATCGCCTTG
CAGCACATCCCCCTTTCGCCAGCTGGCGTAATAGCGAAGAGGCCCGCACCGATCGCCCTTCCCAACAGTTGCGC
AGCCTGAATGGCGAATGCTAGAGCAGCTTGAGCTTGGATCAGATTGTCGTTTCCCGCCTTCAGTTTAAACTATC
AGTGTTTGACAGGATATATTGGCGGGTAAACCTAAGAGAAAAGAGCGTTTATTAGAATAACGGATATTTAAAAG
GGCGTGAAAAGGTTTATCCGTTCGTCCATTTGTATGTGCATGCCAACCACAGGGTTCCCCTCGGGATCAAAGTA
CTTTGATCCAACCCCTCCGCTGCTATAGTGCAGTCGGCTTCTGACGTTCAGTGCAGCCGTCTTCTGAAAACGAC
ATGTCGCACAAGTCCTAAGTTACGCGACAGGCTGCCGCCCTGCCCTTTTCCTGGCGTTTTCTTGTCGCGTGTTT
TAGTCGCATAAAGTAGAATACTTGCGACTAGAACCGGAGACATTACGCCATGAACAAGAGCGCCGCCGCTGGCC
TGCTGGGCTATGCCCGCGTCAGCACCGACGACCAGGACTTGACCAACCAACGGGCCGAACTGCACGCGGCCGGC
TGCACCAAGCTGTTTTCCGAGAAGATCACCGGCACCAGGCGCGACCGCCCGGAGCTGGCCAGGATGCTTGACCA
CCTACGCCCTGGCGACGTTGTGACAGTGACCAGGCTAGACCGCCTGGCCCGCAGCACCCGCGACCTACTGGACA
TTGCCGAGCGCATCCAGGAGGCCGGCGCGGGCCTGCGTAGCCTGGCAGAGCCGTGGGCCGACACCACCACGCCG
GCCGGCCGCATGGTGTTGACCGTGTTCGCCGGCATTGCCGAGTTCGAGCGTTCCCTAATCATCGACCGCACCCG
GAGCGGGCGCGAGGCCGCCAAGGCCCGAGGCGTGAAGTTTGGCCCCCGCCCTACCCTCACCCCGGCACAGATCG
CGCACGCCCGCGAGCTGATCGACCAGGAAGGCCGCACCGTGAAAGAGGCGGCTGCACTGCTTGGCGTGCATCGC
TCGACCCTGTACCGCGCACTTGAGCGCAGCGAGGAAGTGACGCCCACCGAGGCCAGGCGGCGCGGTGCCTTCCG
TGAGGACGCATTGACCGAGGCCGACGCCCTGGCGGCCGCCGAGAATGAACGCCAAGAGGAACAAGCATGAAACC
GCACCAGGACGGCCAGGACGAACCGTTTTTCATTACCGAAGAGATCGAGGCGGAGATGATCGCGGCCGGGTACG
TGTTCGAGCCGCCCGCGCACGTCTCAACCGTGCGGCTGCATGAAATCCTGGCCGGTTTGTCTGATGCCAAGCTG
GCGGCCTGGCCGGCCAGCTTGGCCGCTGAAGAAACCGAGCGCCGCCGTCTAAAAAGGTGATGTGTATTTGAGTA
AAACAGCTTGCGTCATGCGGTCGCTGCGTATATGATGCGATGAGTAAATAAACAAATACGCAAGGGGAACGCAT
GAAGGTTATCGCTGTACTTAACCAGAAAGGCGGGTCAGGCAAGACGACCATCGCAACCCATCTAGCCCGCGCCC
TGCAACTCGCCGGGGCCGATGTTCTGTTAGTCGATTCCGATCCCCAGGGCAGTGCCCGCGATTGGGCGGCCGTG
CGGGAAGATCAACCGCTAACCGTTGTCGGCATCGACCGCCCGACGATTGACCGCGACGTGAAGGCCATCGGCCG
GCGCGACTTCGTAGTGATCGACGGAGCGCCCCAGGCGGCGGACTTGGCTGTGTCCGCGATCAAGGCAGCCGACT

TCGTGCTGATTCCGGTGCAGCCAAGCCCTTACGACATATGGGCCACCGCCGACCTGGTGGAGCTGGTTAAGCAG
CGCATTGAGGTCACGGATGGAAGGCTACAAGCGGCCTTTGTCGTGTCGCGGGCGATCAAAGGCACGCGCATCGG
CGGTGAGGTTGCCGAGGCGCTGGCCGGGTACGAGCTGCCCATTCTTGAGTCCCGTATCACGCAGCGCGTGAGCT
ACCCAGGCACTGCCGGCCGCCGGCACAACCGTTCTTGAATCAGAACCCGAGGGCGACGCTGCCCGCGAGGTCCAG
GCGCTGGCCGCTGAAATTAAATCAAAACTCATTTGAGTTAATGAGGTAAAGAGAAAATGAGCAAAAGCACAAAC
ACGCTAAGTGCCGGCCGTCCGAGCGCACGCAGCAGCAAGGCTGCAACGTTGGCCAGCCTGGCAGACACGCCAGC
CATGAAGCGGGTCAACTTTCAGTTGCCGGCGGAGGATCACACCAAGCTGAAGATGTACGCGGTACGCCAAGGCA
AGACCATTACCGAGCTGCTATCTGAATACATCGCGCAGCTACCAGAGTAAATGAGCAAATGAATAAATGAGTAG
ATGAATTTTAGCGGCTAAAGGAGGCGGCATGGAAAATCAAGAACAACCAGGCACCGACGCCGTGGAATGCCCCA
TGTGTGGAGGAACGGGCGGTTGGCCAGGCGTAAGCGGCTGGGTTGTCTGCCGGCCCTGCAATGGCACTGGAACC
CCCAAGCCCGAGGAATCGGCGTGACGGTCGCAAACCATCCGGCCCGGTACAAATCGGCGCGGCGCTGGGTGATG
ACCTGGTGGAGAAGTTGAAGGCCGCGCAGGCCGCCCAGCGGCAACGCATCGAGGCAGAAGCACGCCCCGGTGAA
TCGTGGCAAGCGGCCGCTGATCGAATCCGCAAAGAATCCCGGCAACCGCCGGCAGCCGGTGCGCCGTCGATTAG
GAAGCCGCCCAAGGGCGACGAGCAACCAGATTTTTTCGTTCCGATGCTCTATGACGTGGGCACCCGCGATAGTC
GCAGCATCATGGACGTGGCCGTTTTCCGTCTGTCGAAGCGTGACCGACGAGCTGGCGAGGTGATCCGCTACGAG
CTTCCAGACGGGCACGTAGAGGTTTCCGCAGGGCCGGCCGGCATGGCCAGTGTGTGGGATTACGACCTGGTACT
GATGGCGGTTTCCCATCTAACCGAATCCATGAACCGATACCGGGAAGGGAAGGGAGACAAGCCCGGCCGCGTGT
TCCGTCCACACGTTGCGGACGTACTCAAGTTCTGCCGGCGAGCCGATGGCGGAAAGCAGAAAGACGACCTGGTA
GAAACCTGCATTCGGTTAAACACCACGCACGTTGCCATGCAGCGTACGAAGAAGGCCAAGAACGGCCGCCTGGT
GACGGTATCCGAGGGTGAAGCCTTGATTAGCCGCTACAAGATCGTAAAGAGCGAAACCGGGCGGCCGGAGTACA
TCGAGATCGAGCTAGCTGATTGGATGTACCGCGAGATCACAGAAGGCAAGAACCCGGACGTGCTGACGGTTCAC
CCCGATTACTTTTTGATCGATCCCGGCATCGGCCGTTTTCTCTACCGCCTGGCACGCCGCGCCGCAGGCAAGGC
AGAAGCCAGATGGTTGTTCAAGACGATCTACGAACGCAGTGGCAGCGCCGGAGAGTTCAAGAAGTTCTGTTTCA
CCGTGCGCAAGCTGATCGGGTCAAATGACCTGCCGGAGTACGATTTGAAGGAGGAGGCGGGGCAGGCTGGCCCG
ATCCTAGTCATGCGCTACCGCAACCTGATCGAGGGCGAAGCATCCGCCGGTTCCTAATGTACGGAGCAGATGCT
AGGGCAAATTGCCCTAGCAGGGGAAAAAGGTCGAAAAGGTCTCTTTCCTGTGGATAGCACGTACATTGGGAACC
CAAAGCCGTACATTGGGAACCGGAACCCGTACATTGGGAACCCAAAGCCGTACATTGGGAACCGGTCACACATG
TAAGTGACTGATATAAAAGAGAAAAAAGGCGATTTTTCCGCCTAAAACTCTTTAAAACTTATTAAAACTCTTAA
AACCCGCCTGGCCTGTGCATAACTGTCTGGCCAGCGCACAGCCGAAGAGCTGCAAAAAGCGCCTACCCTTCGGT
CGCTGCGCTCCCTACGCCCCGCCGCTTCGCGTCGGCCTATCGCGGCCGCTGGCCGCTCAAAAATGGCTGGCCTA
CGGCCAGGCAATCTACCAGGGCGCGGACAAGCCGCGCCGTCGCCACTCGACCGCCGGCGCCCACATCAAGGCAC
CCTGCCTCGCGCGTTTCGGTGATGACGGTGAAAACCTCTGACACATGCAGCTCCCGGAGACGGTCACAGCTTGT
CTGTAAGCGGATGCCGGGAGCAGACAAGCCCGTCAGGGCGCGTCAGCGGGTGTTGGCGGGTGTCGGGGCGCAGC
CATGACCCAGTCACGTAGCGATAGCGGAGTGTATACTGGCTTAACTATGCGGCATCAGAGCAGATTGTACTGAG
AGTGCACCATATGCGGTGTGAAATACCGCACAGATGCGTAAGGAGAAAATACCGCATCAGGCGCTCTTCCGCTT
CCTCGCTCACTGACTCGCTGCGCTCGGTCGTTCGGCTGCGGCGAGCGGTATCAGCTCACTCAAAGGCGGTAATA
CGGTTATCCACAGAATCAGGGGATAACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACGAGCATCACAAAAATCGACGCTCAA
GTCAGAGGTGGCGAAACCCGACAGGACTATAAAGATACCAGGCGTTTCCCCCTGGAAGCTCCCTCGTGCGCTCT
CCTGTTCCGACCCTGCCGCTTACCGGATACCTGTCCGCCTTTCTCCCTTCGGGAAGCGTGGCGCTTTCTCATAG
CTCACGCTGTAGGTATCTCAGTTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAAGACACGACTTATCGCCACTG
GCAGCAGCCACTGGTAACAGGATTAGCAGAGCGAGGTATGTAGGCGGTGCTACAGAGTTCTTGAAGTGGTGGCC
TAACTACGGCTACACTAGAAGGACAGTATTTGGTATCTGCGCTCTGCTGAAGCCAGTTACCTTCGGAAAAAGAG
TTGGTAGCTCTTGATCCGGCAAACAAACCACCGCTGGTAGCGGTGGTTTTTTTGTTTGCAAGCAGCAGATTACG
CGCAGAAAAAAAGGATCTCAAGAAGATCCTTTGATCTTTTCTACGGGGTCTGACGCTCAGTGGAACGAAAACTC
ACGTTAAGGGATTTTGGTCATGCATTCTAGGTACTAAAACAATTCATCCAGTAAAATATAATATTTTATTTTCT
CCCAATCAGGCTTGATCCCCAGTAAGTCAAAAAATAGCTCGACATACTGTTCTTCCCCGATATCCTCCCTGATC
GACCGGACGCAGAAGGCAATGTCATACCACTTGTCCGCCCTGCCGCTTCTCCCAAGATCAATAAAGCCACTTAC
TTTGCCATCTTTCACAAAGATGTTGCTGTCTCCCAGGTCGCCGTGGGAAAAGACAAGTTCCTCTTCGGGCTTTT
CCGTCTTTAAAAAATCATACAGCTCGCGCGGATCTTTAAATGGAGTGTCTTCTTCCCAGTTTTCGCAATCCACA
TCGGCCAGATCGTTATTCAGTAAGTAATCCAATTCGGCTAAGCGGCTGTCTAAGCTATTCGTATAGGGACAATC
CGATATGTCGATGGAGTGAAAGAGCCTGATGCACTCCGCATACAGCTCGATAATCTTTTCAGGGCTTTGTTCAT
CTTCATACTCTTCCGAGCAAAGGACGCCATCGGCCTCACTCATGAGCAGATTGCTCCAGCCATCATGCCGTTCA
AAGTGCAGGACCTTTGGAACAGGCAGCTTTCCTTCCAGCCATAGCATCATGTCCTTTTCCCGTTCCACATCATA
GGTGGTCCCTTTATACCGGCTGTCCGTCATTTTTAAATATAGGTTTTCATTTTCTCCCACCAGCTTATATACCT

TAGCAGGAGACATTCCTTCCGTATCTTTTACGCAGCGGTATTTTTCGATCAGTTTTTTCAATTCCGGTGATATT
CTCATTTTAGCCATTTATTATTTCCTTCCTCTTTTCTACAGTATTTAAAGATACCCCAAGAAGCTAATTATAAC
AAGACGAACTCCAATTCACTGTTCCTTGCATTCTAAAACCTTAAATACCAGAAAACAGCTTTTTCAAAGTTGTT
TTCAAAGTTGGCGTATAACATAGTATCGACGGAGCCGATTTTGAAACCGCGGTGATCACAGGCAGCAACGCTCT
GTCATCGTTACAATCAACATGCTACCCTCCGCGAGATCATCCGTGTTTCAAACCCGGCAGCTTAGTTGCCGTTC
TTCCGAATAGCATCGGTAACATGAGCAAAGTCTGCCGCCTTACAACGGCTCTCCCGCTGACGCCGTCCCGGACT
GATGGGCTGCCTGTATCGAGTGGTGATTTTGTGCCGAGCTGCCGGTCGGGGAGCTGTTGGCTGGCTGGTGGCAG
GATATATTGTGGTGTAAACAAATTGACGCTTAGACAACTTAATAACACATTGCGGACGTTTTTAATGTACTGAA
TTAACGCCGAATTAATTCGGGGGATCTGGATTTTAGTACTGGATTTTGGTTTTAGGAATTAGAAATTTTATTGA
TAGAAGTATTTTACAAATACAAATACATACTAAGGGTTTCTTATATGCTCAACACATGAGCGAAACCCTATAGG
AACCCTAATTCCCTTATCTGGGAACTACTCACACATTATTATGGAGAAACTCGAGCTTGTCGATCGACAGATCC
GGTCGGCATCTACTCTATTTCTTTGCCCTCGGACGAGTGCTGGGGCGTCGGTTTCCACTATCGGCGAGTACTTC
TACACAGCCATCGGTCCAGACGGCCGCGCTTCTGCGGGCGATTTGTGTACGCCCGACAGTCCCGGCTCCGGATC
GGACGATTGCGTCGCATCGACCCTGCGCCCAAGCTGCATCATCGAAATTGCCGTCAACCAAGCTCTGATAGAGT
TGGTCAAGACCAATGCGGAGCATATACGCCCGGAGTCGTGGCGATCCTGCAAGCTCCGGATGCCTCCGCTCGAA
GTAGCGCGTCTGCTGCTCCATACAAGCCAACCACGGCCTCCAGAAGAAGATGTTGGCGACCTCGTATTGGGAAT
CCCCGAACATCGCCTCGCTCCAGTCAATGACCGCTGTTATGCGGCCATTGTCCGTCAGGACATTGTTGGAGCCG
AAATCCGCGTGCACGAGGTGCCGGACTTCGGGGCAGTCCTCGGCCCAAAGCATCAGCTCATCGAGAGCCTGCGC
GACGGACGCACTGACGGTGTCGTCCATCACAGTTTGCCAGTGATACACATGGGGATCAGCAATCGCGCATATGA
AATCACGCCATGTAGTGTATTGACCGATTCCTTGCGGTCCGAATGGGCCGAACCCGCTCGTCTGGCTAAGATCG
GCCGCAGCGATCGCATCCATAGCCTCCGCGACCGGTTGTAGAACAGCGGGCAGTTCGGTTTCAGGCAGGTCTTG
CAACGTGACACCCTGTGCACGGCGGGAGATGCAATAGGTCAGGCTCTCGCTAAACTCCCCAATGTCAAGCACTT
CCGGAATCGGGAGCGCGGCCGATGCAAAGTGCCGATAAACATAACGATCTTTGTAGAAACCATCGGCGCAGCTA
TTTACCCGCAGGACATATCCACGCCCTCCTACATCGAAGCTGAAAGCACGAGATTCTTCGCCCTCCGAGAGCTG
CATCAGGTCGGAGACGCTGTCGAACTTTTCGATCAGAAACTTCTCGACAGACGTCGCGGTGAGTTCAGGCTTTT
TCATATCTCATTGCCCCCCCCGGATCTGCGAAAGCTCGAGAGAGATAGATTTGTAGAGAGAGACTGGTGATTTCA
GCGTGTCCTCTCCAAATGAAATGAACTTCCTTATATAGAGGAAGGTCTTGCGAAGGATAGTGGGATTGTGCGTC
ATCCCTTACGTCAGTGGAGATATCACATCAATCCACTTGCTTTGAAGACGTGGTTGGAACGTCTTCTTTTTCCA
CGATGCTCCTCGTGGGTGGGGGTCCATCTTTGGGACCACTGTCGGCAGAGGCATCTTGAACGATAGCCTTTCCT
TTATCGCAATGATGGCATTTGTAGGTGCCACCTTCCTTTTCTACTGTCCTTTTGATGAAGTGACAGATAGCTGG
GCAATGGAATCCGAGGAGGTTTCCCGATATTACCCTTTGTTGAAAAGTCTCAATAGCCCTTTGGTCTTCTGAGA
CTGTATCTTTGATATTCTTGGAGTAGACGAGAGTGTCGTGCTCCACCATGTTATCACATCAATCCACTTGCTTT
GAAGACGTGGTTGGAACGTCTTCTTTTTCCACGATGCTCCTCGTGGGTGGGGGTCCATCTTTGGGACCACTGTC
GGCAGAGGCATCTTGAACGATAGCCTTTCCTTTATCGCAATGATGGCATTTGTAGGTGCCACCTTCCTTTTCTA
CTGTCCTTTTGATGAAGTGACAGATAGCTGGGCAATGGAATCCGAGGAGGTTTCCCGATATTACCCTTTGTTGA
AAAGTCTCAATAGCCCTTTGGTCTTCTGAGACTGTATCTTTGATATTCTTGGAGTAGACGAGAGTGTCGTGCTC
CACCATGTTGGCAAGCTGCTCTAGCCAATACGCAAACCGCCTCTCCCCGCGCGTTGGCCGATTCATTAATGCAG
CTGGCACGACAGGTTTCCCGACTGGAAAGCGGGCAGTGAGCGCAACGCAATTAATGTGAGTTAGCTCACTCATT
AGGCACCCCAGGCTTTACACTTTATGCTTCCGGCTCGTATGTTGTGTGGAATTGTGAGCGGATAACAATTTCAC
ACAGGAAACAGCTATGACCATGATTAC

At the end of fourteen days of drought-stress

At the end of 24 h recovery from drought-stress

COMPOSITIONS AND METHODS FOR PRODUCING PLANTS WITH IMPROVED STRESS TOLERANCE

REFERENCE TO RELATED APPLICATIONS

The present application claims priority to U.S. Provisional Application No. 60/729,316, filed Oct. 21, 2005, which is hereby incorporated by reference in its entirety.

TECHNICAL FIELD

The present invention relates to compositions and methods for producing plants with improved stress tolerance.

BACKGROUND ART

Environmental abiotic stresses, including drought stress, cold stress, freezing stress, heat stress and salinity stress are major factors limiting plant growth and productivity. Crop losses and reduction in yield of major crops including maize, wheat and rice caused by such stresses represent significant economic issues and also lead to food shortages in several underdeveloped countries.

The development of stress tolerant plants has the potential to reduce or solve at least some of these problems. The use of traditional plant breeding strategies to produce new lines of plants that exhibit tolerance to these types of stresses has been slow. Lack of sufficient germplasm resources and incompatibility between distantly related plant species, present significant problems in conventional breeding. Further, the cellular processes leading to tolerance to such stresses are complex and involve multiple mechanisms of cellular adaptation and numerous metabolic pathways. This limits the success of both traditional breeding and that of genetic engineering approaches to development of stress tolerant plants. It would be beneficial to identify genes and proteins involved in controlling the complex processes leading to stress tolerance.

Regulators of gene expression, such as transcription factors, involved in controlling stress tolerance may be particularly useful in genetic engineering of plants, as a single gene may control a whole cascade of genes leading to the tolerance phenotype. Furthermore, there is sometimes commonality in many aspects of the different types of stress tolerant responses referred above. For example, genes that increase tolerance to cold or salt may also improve drought stress tolerance. This has been demonstrated in the case of the transcription factor At CBF/DREB 1 (Kasuga et al., 1999 Nature Biotech 17: 287-91) and the vacuolar pyrophosphatase AVP1 (Gaxiola et al., 2001 PNAS 98:11444-19).

Whilst some potentially useful genes have been identified, the identification and cloning of plant genes that confer tolerance to stress remains fragmented and incomplete. Although it is assumed that stress induced proteins may have a role in stress tolerance, evidence is still lacking and the function of many such stress responsive genes is unknown.

The hot and dry weather conditions in New Zealand and other countries in the summer period can have significant effect upon the yield of ryegrass. This is invariably during the dairy milking season and therefore has real effects on cost of dairy production through either reduced milk yield or the use of supplementary feeds and/or irrigation systems.

It would be beneficial to identify genes which have the capacity to confer stress tolerance in stress susceptible plant species. The development of stress tolerant crops will provide many advantages such as increasing yield and producing plants that may be cultivated in previously unsuitable environmental conditions. Thus, there exists a need for compositions and methods for producing plants with improved stress tolerance relative to their wild-type counterparts.

It is an object of the invention to provide improved compositions and methods for developing plant varieties with improved tolerance of at least one of the following stresses; drought, cold, freezing, heat and salinity, or at least to provide the public with a useful choice.

SUMMARY OF THE INVENTION

In the first aspect, the invention provides an isolated polynucleotide comprising:

a) a sequence encoding a polypeptide with at least 70% identity to the amino acid sequence of SEQ ID NO:4 or SEQ ID NO:163, wherein the polypeptide is capable of modulating in a plant, tolerance to at least one environmental stress selected from drought, cold, freezing, heat and salinity; or b) the complement of the sequence of a).

Preferably the polypeptide has at least 70% identity to the amino acid sequence of SEQ ID NO:4. More preferably the polypeptide has the amino acid sequence of SEQ ID NO:4.

Preferably the sequence encoding the polypeptide in a) has at least 70% identity to the sequence of SEQ ID NO:82. More preferably the sequence encoding the polypeptide in a) has at least 70% identity to the coding sequence of SEQ ID NO:82. More preferably the sequence encoding the polypeptide in a) has the sequence of SEQ ID NO:82. More preferably the sequence encoding the polypeptide in a) has the coding sequence of SEQ ID NO:82.

In one embodiment the polypeptide is derived from a plant species and comprises the sequence of SEQ ID NO:1.

In a further embodiment the polypeptide is derived from a *dicotyledonous* species and comprises the sequence of SEQ ID NO:2.

In a further embodiment the polypeptide is derived from a *monocotyledonous* species and comprises the sequence of SEQ ID NO:3.

Alternatively the polypeptide has at least 70% identity to the amino acid sequence of SEQ ID NO:163. Preferably the polypeptide has the amino acid sequence of SEQ ID NO:163.

Preferably the sequence encoding the polypeptide in a) has at least 70% identity to the sequence of SEQ ID NO:201. More preferably the sequence encoding the polypeptide in a) has at least 70% identity to the coding sequence of SEQ ID NO:201. More preferably the sequence encoding the polypeptide in a) has the sequence of SEQ ID NO:201. More preferably the sequence encoding the polypeptide in a) has the coding sequence of SEQ ID NO:201.

In one embodiment the polypeptide is derived from a plant species and comprises the sequence of SEQ ID NO:4.

In a further embodiment the polypeptide is derived from a *dicotyledonous* species and comprises the sequence of SEQ ID NO:5.

In a further embodiment the polypeptide is derived from a *monocotyledonous* species and comprises the sequence of SEQ ID NO:6.

In a further embodiment the polypeptide comprises at least two repeats of the amino acid sequence motif QALGGHK (SEQ ID NO:242), the repeated moiety being separated by between 26 and 63 residues.

In a further aspect the invention provides an isolated polynucleotide comprising:

a) a sequence with at least 70% identity to the nucleotide sequence of SEQ ID NO:82 or 201, wherein the sequence encodes a polypeptide capable of modulating in a plant, tolerance to at least one environmental stress selected from drought, cold, freezing, heat and salinity; or b) the complement of the sequence of a).

Preferably the sequence in a) has at least 70% identity to the sequence of SEQ ID NO:82. More preferably the sequence in a) has at least 70% identity to the coding sequence of SEQ ID NO:82. More preferably the sequence in a) has the sequence of SEQ ID NO:82. More preferably the sequence in a) has the coding sequence of SEQ ID NO:82.

Alternatively the sequence in a) has at least 70% identity to the sequence of SEQ ID NO:201. More preferably the sequence in a) has at least 70% identity to the coding sequence of SEQ ID NO:201. More preferably the sequence in a) has the sequence of SEQ ID NO:201. More preferably the sequence in a) has the coding sequence of SEQ ID NO:201.

In a further aspect the invention provides an isolated polypeptide comprising:

a) a sequence with at least 70% identity to the amino acid sequence of SEQ ID NO:4 or 163, wherein the polypeptide is capable of modulating in a plant, tolerance to at least one environmental stress selected from drought, cold, freezing, heat and salinity.

Preferably the sequence in a) has at least 70% sequence identity to the amino acid sequence of SEQ ID NO: 4. More preferably the sequence in a) has the sequence of SEQ ID NO: 4.

Alternatively the sequence in a) has at least 70% sequence identity to the amino acid sequence of SEQ ID NO: 163. Preferably the sequence in a) has the sequence of SEQ ID NO: 163.

In a further aspect the invention provides an isolated polypeptide comprising a fragment of at least 5 contiguous amino acids of the polypeptide of the invention, wherein the fragment has essentially the same activity as the polypeptide.

In a further aspect the invention provides a polynucleotide encoding a polypeptide of the invention.

In a further aspect the invention provides an antibody raised against a polypeptide of the invention.

In a further aspect the invention provides a probe or primer capable of hybridizing to a polynucleotide of the invention, or a complement thereof, under stringent hybridization conditions.

Preferably the probe or primer comprises at least 15 contiguous nucleotides of polynucleotide of the invention.

In a further aspect the invention provides a genetic construct comprising a polynucleotide of the invention.

Preferably the genetic construct comprises a promoter operably linked to the polynucleotide. Preferably the promoter is the double CaMV 35S promoter. More preferably the promoter is the ryegrass promoter of SEQ ID NO:239. Alternatively the promoter is a portion of the ryegrass promoter of SEQ ID NO:239 that provides essentially the same expression pattern as the ryegrass promoter of SEQ ID NO:239.

In a further aspect the invention provides a vector comprising the genetic construct of the invention.

In a further aspect the invention provides a host cell comprising a genetic construct of the invention.

In a further aspect the invention provides a host cell genetically modified to express the polynucleotide of the invention.

In a further aspect the invention provides a plant cell comprising the genetic construct of the invention.

In a further aspect the invention provides a plant cell genetically modified to express a polynucleotide of the invention.

In a further aspect the invention provides a plant which comprises the plant cell of the invention.

In a further aspect the invention provides a method for producing a polypeptide of the invention, the method comprising culturing a host cell comprising a genetic construct of the invention designed to express the polypeptide.

In a further aspect the invention provides a method for producing a plant cell or plant with altered tolerance to at least one environmental stress selected from drought, cold, freezing, heat and salinity; the method comprising the step of transformation of a plant cell or plant with a genetic construct including:

a) at least one polynucleotide of the invention; or b) at least one polynucleotide comprising a fragment, of at least 15 nucleotides in length, of the polynucleotide of a);

In a further aspect the invention provides a plant produced by the method of the invention.

In a further aspect the invention provides a method for selecting a plant with altered tolerance to at least one environmental stress selected from drought, cold, freezing, heat and salinity, the method comprising testing of a plant for altered expression of a polynucleotide of the invention.

In a further aspect the invention provides a method for selecting a plant with altered tolerance to at least one environmental stress selected from drought, cold, freezing, heat and salinity, the method comprising testing of a plant for altered expression of a polypeptide of the invention.

In a further aspect the invention provides a plant selected by a selection method of the invention.

In a further aspect the invention provides a plant part, propagule, progeny or seed of the plant of the invention.

In preferred embodiments of the invention the environmental stress is drought stress.

In a further aspect the invention provides an isolated polynucleotide comprising the sequence of SEQ ID NO:82 or a variant thereof, wherein the variant encodes a polypeptide which modulates in a plant, tolerance to at least one environmental stress selected from drought, cold, freezing, heat and salinity.

Preferably the variant of SEQ ID NO:82 encodes a polypeptide comprising the amino acid sequence:

$LX_1X_2$ $X_3X_4X_5$ $X_6$ $LX_7$ $X_8X_9$ $KX_{10}$ $X_{11}X_{12}$ $RX_{13}EKX_{14}X_{15}X_{16}K$ (Seq ID NO.: 1) wherein $X_1$=Q, E, H, L, R, T or S, $X_2$=E, D or Q, $X_3$=K, R, A, E or T, $X_4$=I or S, $X_5$=K, R, D or N, $X_6$=E, D or S, $X_7$=K, T or I, $X_8$=A, V, S, T, D, V or Q, $X_9$=E or D, $X_{10}$=N, D, T or S, $X_{11}$=E or D, $X_{12}$=L or S, $X_{13}$=D, H or E, $X_{14}$=Q, H, R, L, V, T or A and $X_{15}$=K, R, V, T or S, $X_{16}$=L or M, the polypeptide modulating, in a plant, tolerance to at least one environmental stress selected from drought, cold, freezing, heat and salinity.

Alternatively the variant of SEQ ID NO:82 encodes a polypeptide comprising the amino acid sequence:

$LX_1$ $X_2X_3$ $X_4X_5X_6LX_7X_8X_9KX_{10}X_{11}LRX_{12}EKX_{13}X_{14}$ $X_{15}K$ (SEQ ID NO: 2) wherein $X_1$=Q, H, L, R, T or S, $X_2$=E, D or Q, $X_3$=K, R, A or E, $X_4$=I or S, $X_5$=K, R, D or N, $X_6$=E, D or S, $X_7$=K, T or I, $X_8$=A, V, S, T, D, or Q, $X_9$=E or D, $X_{10}$=N, T or S, $X_{11}$=E or D, $X_{12}$=D or E, $X_{13}$=Q, H, R, L, T or A, $X_{14}$=K, R, V, T or S and $X_{15}$=L or M, the polypeptide modulating, in a *dicotyledonous* plant, tolerance to at least one environmental stress selected from drought, cold, freezing, heat and salinity.

Alternatively the variant of SEQ ID NO:82 encodes a polypeptide comprising the amino acid sequence:

$LX_1X_2X_3IX_4X_5LKKX_6X_7KX_8EX_9RX_{10}EKX_{11}X_{12}X_{13}K$ (SEQ ID NO: 3) where $X_1$=Q, E or R, $X_2$=E or D, $X_3$=K or T, $X_4$=K or R, $X_5$=E or D, $X_6$=A or V, $X_7$=E or D, $X_8$=N or D, $X_9$=L or s, $X_{10}$=D or H, $X_{11}$=Q or V, $X_{12}$=K, R or T and $X_{13}$=L or M, the polypeptide modulating, in a *monocotyledonous* plant, tolerance to at least one environmental stress selected from drought, cold, freezing, heat and salinity.

Exemplary polynucleotide variants of SEQ ID NO: 82 are disclosed herein and identified as SEQ ID NOs: 83-159 of the sequence listing.

In a further aspect the invention provides an isolated polynucleotide comprising the sequence of SEQ ID NO:82.

In a further aspect the invention provides an isolated polynucleotide consisting of the sequence of SEQ ID NO:82.

In a further aspect the invention provides polynucleotides comprising fragments of SEQ ID NO: 82. Polynucleotides comprising fragments of the polynucleotide variants also form part of the invention.

In a further aspect the invention provides an isolated polynucleotide comprising the sequence of SEQ ID NO: 201 or a variant thereof, wherein the variant encodes a polypeptide which modulates in a plant, tolerance to at least one environmental stress selected from drought, cold, freezing, heat and salinity.

Preferably the variant of SEQ ID NO:201 encodes a polypeptide comprising the amino acid sequence:

$X_1X_2CX_3VCX_4X_5X_6$ $X_7X_8X_9YQALGGHKX_{10}SHRX_{11}$ (SEQ ID NO: 160) where $X_1$=H, F or Y, $X_2$=G, A, K, E or R, $X_3$=S, T, N or G, $X_4$=G, E, D, N or Y, $X_5$=K or R, $X_6$=A, S, V, G, or T, $X_7$=F or Y, $X_8$=A, P, S or G, $X_9$=S or T, $X_{10}$=A or T and $X_{11}$=K, S, I, P, T or V the polypeptide modulating, in a plant, tolerance to at least one environmental stress selected from drought, cold, freezing, heat and salinity.

Alternatively the variant of SEQ ID NO:201 encodes a polypeptide comprising the amino acid sequence:

$X_1X_2CX_3VCX_4KX_5FX_6SYQALGGHKX_7SHRX_8$(SEQ ID NO: 161) where $X_1$=H, F or Y, $X_2$=G, A, K, E or R, $X_3$=S, T, N or G, $X_4$=G, E, D, N or Y, $X_5$=A, S, G, or T, $X_6$=A, P, S or G, $X_7$=A or T and $X_8$=K, S, I, P, T or V the polypeptide modulating, in a *dicotyledonous* plant, tolerance to at least one environmental stress selected from drought, cold, freezing, heat and salinity. Alternatively the variant of SEQ ID NO:201 encodes a polypeptide comprising the amino acid sequence:

$X_1X_2CSVCGX_3X_4X_5X_6SYQALGGHKX_7SHRX_8$ (SEQ ID NO: 162) where $X_1$=H, F or Y, $X_2$=G, A, K, E or R, $X_3$=K or R, $X_4$=A, S, V, or G, $X_5$=F or Y, $X_6$=A, P, S or G, $X_7$=A or T, $X_8$=K, P, T or V.

the polypeptide modulating, in a *monocotyledonous* plant, tolerance to at least one environmental stress selected from drought, cold, freezing, heat and salinity.

Alternatively the variant of SEQ ID NO:201 encodes a polypeptide comprising at least two repeats of the amino acid sequence motif QALGGHK (SEQ ID NO:244), the repeated sequence motif being separated by about 36 to about 60 residues, wherein the polypeptide modulates, in a plant, tolerance to at least one environmental stress selected from drought, cold, freezing, heat and salinity. Preferably the motif is separated by about 40 to about 60 residues, more preferably by about 50 to about 60 residues, most preferably by about 56 residues. Preferably the polypeptide encoded by the variant modulates tolerance to the environmental stress in a *dicotyledonous* plant. More preferably the polypeptide encoded by the variant modulates tolerance to the environmental stress in a *monocotyledonous* plant.

Exemplary polynucleotide variants of SEQ ID NO: 201 are disclosed herein and identified as SEQ ID NOs: 202-238 of the sequence listing.

In a further aspect the invention provides an isolated polynucleotide comprising the sequence of SEQ ID NO: 201.

In a further aspect the invention provides an isolated polynucleotide consisting of the sequence of SEQ ID NO: 201.

In a further aspect the invention provides polynucleotides comprising fragments of SEQ ID NO: 201. Polynucleotides comprising fragments of the polynucleotide variants also form part of the invention.

The isolated polynucleotides of the invention are also useful in methods for selecting plants tolerant to at least one environmental stress selected from drought, cold, freezing, heat and salinity.

In a further aspect the invention provides an isolated polypeptide comprising the sequence of SEQ ID NO: 4 or a variant thereof, wherein the variant modulates in a plant, tolerance to at least one environmental stress selected from drought, cold, freezing, heat and salinity.

Preferably the variant of SEQ ID NO: 4 comprises the amino acid sequence:

$LX_1X_2X_3X_4X_5X_6LX_7X_8X_9KX_{10}X_{11}X_{12}RX_{13}EKX_{14}X_{15}X_{16}K$ (SEQ ID NO: 1) wherein $X_1$=Q, E, H, L, R, T or S, $X_2$=E, D or Q, $X_3$=K, R, A, E or T, $X_4$=I or S, $X_5$=K, R, D or N, $X_6$=E, D or S, $X_7$=K, T or I, $X_8$=A, V, S, T, D, V or Q, $X_9$=E or D, $X_{10}$=N, D, T or S, $X_{11}$=E or D, $X_{12}$=L or S, $X_{13}$=D, H or E, $X_{14}$=Q, H, R, L, V, T or A, $X_{15}$=K, R, V, T or S and $X_{16}$=L or M, and modulates in a plant, tolerance to at least one environmental stress selected from drought, cold, freezing, heat and salinity.

Alternatively the variant of SEQ ID NO: 4 comprises the amino acid sequence:

$LX_1X_2X_3X_4X_5X_6LX_7X_8X_9KX_{10}X_{11}LRX_{12}EKX_{13}X_{14}X_{15}K$ (SEQ ID NO: 2) wherein $X_1$=Q, H, L, R, T or S, $X_2$=E, D or Q, $X_3$=K, R, A or E, $X_4$=I or S, $X_5$=K, R, D or N, $X_6$=E, D or S, $X_7$=K, T or I, $X_8$=A, V, S, T, D, or Q, $X_9$=E or D, $X_{10}$=N, T or S, $X_{11}$=E or D, $X_{12}$=D or E, $X_{13}$=Q, H, R, L, T or A, $X_{14}$=K, R, V, T or S and $X_{15}$=L or M, and modulates in a *dicotyledonous* plant, tolerance to at least one environmental stress selected from drought, cold, freezing, heat and salinity.

Alternatively the variant of SEQ ID NO: 4 comprises the amino acid sequence:

$LX_1X_2X_3IX_4X_5LKX_6X_7KX_8EX_9RX_{10}EKX_{11}X_{12}X_{13}K$ (SEQ ID NO: 3) where $X_1$=Q, E or R, $X_2$=E or D, $X_3$=K or T, $X_4$=K or R, $X_5$=E or D, $X_6$=A or V, $X_7$=E or D, $X_8$=N or D, $X_9$=L or s, $X_{10}$=D or H, $X_{11}$=Q or V, $X_{12}$=K, R or T, $X_{13}$=L or M, and modulates in a in a *monocotyledonous* plant, tolerance to at least one environmental stress selected from drought, cold, freezing, heat and salinity.

Exemplary polypeptide variants of SEQ ID NO: 4 are disclosed herein and identified as SEQ ID NOs: 5-81 of the sequence listing.

In a further aspect the invention provides an isolated polypeptide comprising the sequence of SEQ ID NO: 4.

In a further aspect the invention provides an isolated polypeptide consisting of the sequence of SEQ ID NO: 4.

In a further aspect the invention provides polypeptides comprising fragments of SEQ ID NO: 4. Polypeptides comprising fragments of variants, also form part of the invention.

In a further aspect the invention provides an isolated polypeptide comprising the sequence of SEQ ID NO: 163 or a variant thereof, wherein the variant modulates in a plant, tolerance to at least one environmental stress selected from drought, cold, freezing, heat and salinity.

Preferably the variant of SEQ ID NO: 163 comprises the amino acid sequence:

$X_1X_2CX_3VCX_4X_5X_6$ $X_7X_8X_9$YQALGGHK$X_{10}$SHR$X_{11}$ (SEQ ID NO:160) wherein $X_1$=H, F or Y; $X_2$=G, A, K, E or R; $X_3$=S, T, N or G; $X_4$=G, E, D, N or Y; $X_5$=K or R; $X_6$=A, S, V, G, or T; $X_7$=F or Y; $X_8$=A, P, S or G; $X_9$=S or T; $X_{10}$=A or T; $X_{11}$=K, S, I, P, T or V.

and modulates in a plant, tolerance to at least one environmental stress selected from drought, cold, freezing, heat and salinity.

Alternatively the variant of SEQ ID NO: 163 comprises the amino acid sequence:

$X_1X_2CX_3VCX_4KX_5FX_6$SYQALGGHK$X_7$SHR$X_8$(SEQ ID NO: 161) where $X_1$=H, F or Y, $X_2$=G, A, K, E or R, $X_3$=S, T, N or G, $X_4$=G, E, D, N or Y, $X_5$=A, S, G, or T, $X_6$=A, P, S or G, $X_7$=A or T, $X_8$=K, S, I, P, T or V.

and modulates in a *dicotyledonous* plant, tolerance to at least one environmental stress selected from drought, cold, freezing, heat and salinity.

Alternatively the variant of SEQ ID NO: 163 comprises the amino acid sequence:

$X_1X_2$CSVCG$X_3X_4X_5X_6$SYQALGGHK$X_7$SHR$X_8$(SEQ ID NO: 162) where $X_1$=H, F or Y, $X_2$=G, A, K, E or R, $X_3$=K or R, $X_4$=A, S, V, or G, $X_5$=F or Y, $X_6$=A, P, S or G, $X_7$=A or T, $X_8$=K, P, T or V.

and modulates in a *monocotyledonous* plant, tolerance to at least one environmental stress selected from drought, cold, freezing, heat and salinity.

Alternatively the variant of SEQ ID NO: 163 comprises at least two repeats of the amino acid sequence motif QALGGHK (SEQ ID NO:244), the repeated sequence motif being separated by about 36 to about 63 residues, wherein the polypeptide modulates, in a plant, tolerance to at least one environmental stress selected from drought, cold, freezing, heat and salinity. Preferably the motif is separated by about 40 to about 60 residues, more preferably by about 50 to about 60 residues, most preferably by about 56 residues. Preferably the polypeptide modulates tolerance to the environmental stress in a *dicotyledonous* plant. More preferably the polypeptide modulates tolerance to the environmental stress in a *monocotyledonous* plant.

Exemplary polypeptide variants of SEQ ID NO: 163 are disclosed herein and identified as SEQ ID NOs: 164-200 of the sequence listing.

In a further aspect the invention provides an isolated polypeptide comprising the sequence of SEQ ID NO: 163.

In a further aspect the invention provides an isolated polypeptide consisting of the sequence of SEQ ID NO: 163.

In a further aspect the invention provides polypeptides comprising fragments of SEQ ID NO: 163. Polypeptides comprising fragments of variants, also form part of the invention.

In a further aspect the invention provides a polynucleotide encoding a polypeptide of the invention.

In a further aspect the invention provides a genetic construct which comprises a polynucleotide of the invention.

In a further aspect the invention provides a genetic construct which comprises a polynucleotide encoding a polypeptide of the invention.

In a further aspect the invention provides a genetic construct which comprises a polynucleotide of any one of SEQ ID NOs: 82-159, or a variant or fragment thereof.

In a further aspect the invention provides a genetic construct which comprises a polynucleotide of any one of SEQ ID NOs: 201-238, or a variant or fragment thereof.

In a further aspect the invention provides a genetic construct which comprises the polynucleotide sequence of SEQ ID NO: 82, or a variant or fragment thereof.

In a further aspect the invention provides a genetic construct which comprises the polynucleotide sequence of SEQ ID NO: 82.

In a further aspect the invention provides a genetic construct which comprises the polynucleotide sequence of SEQ ID NO: 201, or a variant or fragment thereof.

In a further aspect the invention provides a genetic construct which comprises the polynucleotide sequence of SEQ ID NO: 201.

Preferably the constructs of the invention are expression constructs as herein defined. Preferably expression constructs of the invention include an environmental stress responsive promoter operably linked polynucleotide sequence. Preferably the environmental stress responsive promoter is responsive to at least one environmental stress selected from drought, cold, freezing, heat and salinity.

Preferably the expression construct includes a promoter comprising the sequence of SEQ ID NO: 239 or a fragment, region, cis-element or variant of the sequence capable of regulating transcription of an operably linked polynucleotide sequence.

In a further aspect the invention provides a vector which comprises a genetic construct of the invention.

In a further aspect the invention provides a host cell which comprises a genetic construct of the invention.

In a further aspect the invention provides methods for the recombinant production of polypeptide of the invention comprising the steps of:

a) culturing a host cell comprising a genetic construct of the invention, such as an expression construct as defined herein, capable of expressing a polypeptide of the invention, and b) separating the expressed polypeptide.

In a further aspect the invention provides a plant cell which comprises one or more of the genetic constructs of the invention. In a preferred embodiment the genetic construct comprises the polynucleotide sequence of SEQ ID NO: 82 or a variant or fragment thereof.

In a further aspect the invention provides a plant cell which comprises one or more of the genetic constructs of the invention. In a preferred embodiment the genetic construct comprises the polynucleotide sequence of SEQ ID NOs: 201 or a variant or fragment thereof.

In a further aspect the invention provides a plant cell with altered expression of a polynucleotide or polypeptide of the invention.

In a further aspect the invention provides a plant cell genetically modified to alter expression of a polynucleotide or polypeptide of the invention.

In a further aspect the invention provides a plant which comprises a plant cell of the invention.

In a further aspect the invention provides methods for altering in a plant, tolerance to at least one environmental stress selected from drought, cold, freezing, heat and salinity, the method comprising transformation of a plant cell, or plant with a genetic construct of the invention capable of altering expression of a polynucleotide/polypeptide of the invention.

In a further aspect the invention provides methods for altering tolerance to drought stress in a plant, the method comprising transformation of a plant with a genetic construct of the invention capable of altering expression of a polynucleotide/polypeptide of the invention.

In a further aspect the invention provides methods for altering tolerance to cold stress in a plant, the method comprising transformation of a plant with a genetic construct of the invention capable of altering expression of a polynucleotide/polypeptide of the invention.

In a further aspect the invention provides methods for altering tolerance to freezing stress in a plant, the method comprising transformation of a plant with a genetic construct of the invention capable of altering expression of a polynucleotide/polypeptide of the invention.

In a further aspect the invention provides methods for altering tolerance to heat stress in a plant, the method comprising transformation of a plant with a genetic construct of the invention capable of altering expression of a polynucleotide/polypeptide of the invention.

In a further aspect the invention provides methods for altering tolerance to salinity stress in a plant, the method comprising transformation of a plant with a genetic construct of the invention capable of altering expression of a polynucleotide/polypeptide of the invention.

In a further aspect the invention provides methods for altering tolerance to at least one environmental stress selected from drought, cold, freezing, heat and salinity in a plant, the method comprising transformation of a plant with a genetic construct of the invention capable of altering expression of a polynucleotide involved in modulation in a plant of tolerance to at least one environmental stress selected from drought, cold, freezing, heat and salinity.

In a further aspect the invention provides methods for altering tolerance to drought stress in a plant, the method comprising transformation of a plant with a genetic construct of the invention capable of altering expression of a polynucleotide involved in modulation tolerance to drought stress in a plant.

In a further aspect the invention provides methods for altering tolerance to cold stress in a plant the method comprising transformation of a plant with a genetic construct of the invention capable of altering expression of a polynucleotide involved in modulation of tolerance to cold stress in a plant.

In a further aspect the invention provides methods for altering tolerance to freezing stress in a plant, the method comprising transformation of a plant with a genetic construct of the invention capable of altering expression of a polynucleotide involved in modulation of tolerance to freezing stress in a plant.

In a further aspect the invention provides methods for altering tolerance to heat stress in a plant, the method comprising transformation of a plant with a genetic construct of the invention capable of altering expression of a polynucleotide involved in modulation of tolerance to freezing stress in a plant.

In a further aspect the invention provides methods for altering tolerance to salinity stress in a plant, the method comprising transformation of a plant with a genetic construct of the invention capable of altering expression of a polynucleotide involved in modulation of tolerance to salinity stress in a plant.

It will be understood by those skilled in the art that transformation of a plant may involve transforming a plant cell/s and regenerating a transformed plant from the transformed plant cell/s.

In a further aspect the invention provides a method for selecting a plant with increased tolerance to at least one environmental stress selected from drought, cold, freezing, heat and salinity, the method comprising testing of a plant for altered expression of a polynucleotide of the invention.

In a further aspect the invention provides a method for selecting a plant with increased tolerance to drought stress, the method comprising testing of a plant for altered expression of a polynucleotide of the invention.

In a further aspect the invention provides a method for selecting a plant with increased tolerance to cold stress, the method comprising testing of a plant for altered expression of a polynucleotide of the invention.

In a further aspect the invention provides a method for selecting a plant with increased tolerance to freezing stress, the method comprising testing of a plant for altered expression of a polynucleotide of the invention.

In a further aspect the invention provides a method for selecting a plant with increased tolerance to heat stress, the method comprising testing of a plant for altered expression of a polynucleotide of the invention.

In a further aspect the invention provides a method for selecting a plant with increased tolerance to salinity stress, the method comprising testing of a plant for altered expression of a polynucleotide of the invention.

In a further aspect the invention provides a method for selecting a plant with increased tolerance to at least one environmental stress selected from drought, cold, freezing, heat and salinity, the method comprising testing of a plant for altered expression of a polypeptide of the invention.

In a further aspect the invention provides a method for selecting a plant with increased tolerance to drought stress, the method comprising testing of a plant for altered expression of a polypeptide of the invention.

In a further aspect the invention provides a method for selecting a plant with increased tolerance to cold stress, the method comprising testing of a plant for altered expression of a polypeptide of the invention.

In a further aspect the invention provides a method for selecting a plant with increased tolerance to freezing stress, the method comprising testing of a plant for altered expression of a polypeptide of the invention.

In a further aspect the invention provides a method for selecting a plant with increased tolerance to heat stress, the method comprising testing of a plant for altered expression of a polypeptide of the invention.

In a further aspect the invention provides a method for selecting a plant with increased tolerance to salinity stress, the method comprising testing of a plant for altered expression of a polypeptide of the invention.

In a further aspect the invention provides a plant cell or plant produced by a method of the invention.

The polynucleotides and polynucleotide variants, of the invention may be derived from any species and/or may be produced recombinantly or synthetically.

In one embodiment the polynucleotide or variant, is derived from a plant species.

In a further embodiment the polynucleotide or variant, is derived from a *gymnosperm* plant species.

In a further embodiment the polynucleotide or variant, is derived from an *angiosperm* plant species.

In a further embodiment the polynucleotide or variant, is derived from a from *dicotyledonous* plant species.

In a further embodiment the polynucleotide or variant, is derived from a *monocotyledonous* plant species.

The polypeptide and polypeptide variants, of the invention may be derived from any species and/or may be produced recombinantly or synthetically.

In one embodiment the polypeptide or variant, is derived from a plant species.

In a further embodiment the polypeptide or variant, is derived from a *gymnosperm* plant species.

In a further embodiment the polypeptide or variant, is derived from an *angiosperm* plant species.

In a further embodiment the polypeptide or variant, is derived from a from *dicotyledonous* plant species.

In a further embodiment the polypeptide or variant, is derived from a *monocotyledonous* plant species.

The plant cell or plant may be derived from any plant species.

In a further embodiment the plant cell or plant, is derived from a *gymnosperm* plant species.

In a further embodiment the plant cell or plant, is derived from an *angiosperm* plant species.

In a further embodiment the plant cell or plant, is derived from a from *dicotyledonous* plant species.

In a further embodiment the plant cell or plant, is derived from a *monocotyledonous* plant species.

Preferred *dicotyledonous genera* include: *Amygdalus, Anacardium, Arachis, Brassica, Cajanus, Cannabis, Carthamus, Carya, Ceiba, Cicer, Cocos, Coriandrum, Coronilla, Crotalaria, Dolichos, Elaeis, lycine, Gossypium, Helianthus, Lathyrus, Lens, Lespedeza, Linum, Lotus, Lupinus, Macadamia, Medicago, Melilotus, Mucuna, Olea, Onobrychis, Ornithopus, Papaver, Phaseolus, Phoenix, Pistacia, Pisum, Prunus, Pueraria, Ribes, Ricinus, Sesamum, Theobroma, Trifblium, Trigonella, Vicia* and *Vigna.*

Preferred *dicotyledonous* species include: *Amygdalus communis, Anacardium occidentale, Arachis hypogaea, Arachis hypogea, Brassica napus Rape, Brassica. nigra. Brassica campestris, Cajanus cajan, Cajanus indicus, Cannabis saliva, Carthamus tinctorius, Carya illinoinensis, Ceiba pentandra, Cicer arietinum, Cocos nucifera, Coriandrum sativum, Coronilla varia, Crotalaria juncea, Dolichos lablab, Elaeis guineensis, Gossypium arboreum, Gossypium nanking, Gossypium barbadense, Gossypium herbaceum, Gossypium hirsutum, Glycine max, Glycine ussuriensis, Glycine gracilis, Helianthus annus, Lupinus angustifolius, Lupinus luteus, Lupinus mutabilis, Lespedeza sericea, Lespedeza striata, Lotus uliginosus, Lathyrus sativus, Lens culinaris, Lespedeza stipulacea, Linum usitatissimum, Lotus corniculatus, Lupinus albus, Medicago arborea, Medicago falcate, Medicago hispida, Medicago officinalis, Medicago. sativa Alfalfa, Medicago tribuloides, Macadamia integrifolia, Medicago arabica, Melilotus albus, Mucuna pruriens, Olea europaea, Onobrychis viciifolia, Ornithopus sativus, Phaseolus aureus, Prunus cerasifera, Prunus cerasus, Phaseolus coccineus, Prunus domestica, Phaseolus lunatus, Prunus. maheleb, Phaseolus mungo, Prunus. persica, Prunus. pseudocerasus, Phaseolus vulgaris, Papaver somniferum, Phaseolus acutifolius, Phoenix dactylifera, Pistacia vera, Pisum sativum, Prunus amygdalus, Prunus armeniaca, Pueraria thunbergiana, Ribes nigrum, Ribes rubrum, Ribes grossularia, Ricinus communis, Sesamum indicum, Trifolium augustifolium, Trifolium diffusum, Trifolium hybridum, Trifolium incarnatum, Trifolium ingrescens, Trifolium pratense, Trifolium repens, Trifolium resupinatum, Trifolium subterraneuni, Theobroma cacao, Trifolium alexandrinum, Trigonella foenumgraecum, Vicia angustifolia, Vicia atropurpurea, Vicia calcarata, Vicia dasycarpa, Vicia enilia, Vaccinium oxycoccos, Vicia pannonica, Vigna sesquipedalis, Vigna sinensis, Vicia villosa, Vicia faba, Vicia sative and Vigna angularis.*

Preferred *monocotyledonous genera* include: *Agropyron, Allium, Alopecurus, Andropogon, Arrhenatherum, Asparagus, Avena, Bambusa, Bothrichloa, Bouteloua, Bromus, Calamovilfa, Cenchrus, Chloris, Cymbopogon, Cynodon, Dactylis, Dichanthium, Digitaria, Eleusine, Eragrostis, Fagopyrum, Festuca, Helianthus, Hordeum, Lolium, Miscanthis, Miscanthus x giganteus, Oryza, Panicum, Paspalum, Pennisetum, Phalaris, Phleum, Poa, Saccharum, Secale, Setaria, Sorgahastum, Sorghum, Triticum, Vanilla, X Triticosecale Triticale* and *Zea.*

Preferred *monocotyledonous* species include: *Agropyron cristatum, Agropyron desertorum, Agropyron elongatum, Agropyron intermedium, Agropyron smithii, Agropyron spicatum, Agropyron trachycaulum, Agropyron trichophorum, Allium ascalonicum, Allium cepa, Allium chinense, Allium porrum, Allium schoenoprasum, Allium. fistulosum, Allium. sativum, Alopecurus pratensis, Andropogon gerardi, Andropogon Gerardii, Andropogon scoparious, Arrhenatherum elatius, Asparagus officinalis, Avena nuda, Avena sativa, Bambusa vulgaris, Bothrichloa barbinodis, Bothrichloa ischaemum, Bothrichloa saccharoides, Bouteloua curipendula, Bouteloua eriopoda, Bouteloua gracilis, Bromus erectus, Bromus inermis, Bromus riparius, Calamovilfa longifilia, Cenchrus ciliaris, Chloris gayana, Cymbopogon nardus, Cynodon dactylon, Dactylis glomerata, Dichanthium annulatum, Dichanthium aristatum, Dichanthium sericeum, Digitaria decumbens, Digitaria smutsii, Eleusine coracan, Elymus angustus, Elymus junceus, Eragrostis curvula, Eragrostis tef, Fagopyrum esculentum, Fagopyrum tataricum, Festuca arundinacea, Festuca ovina, Festuca pratensis, Festuca rubra, Helianthus annuus sunflower, Hordeum distichum, Hordeum vulgare, Lolium multiflorum, Lolium perenne, Miscanthis sinensis, Miscanthus x giganteus, Oryza sativa, Panicum italicium, Panicum maximum, Panicum miliaceum, Panicum purpurascens, Panicum virgatum, Panicum virgatum, Paspalum dilatatum, Paspalum notatum, Pennisetum clandestinum, Pennisetum glaucum, Pennisetum purpureum, Pennisetum spicatum, Phalaris arundinacea, Phleum bertolinii, Phleum pratense, Poa fendleriana, Poa pratensis, Poa. nemoralis, Saccharum officinarum, Saccharum robustum, Saccharum sinense, Saccharum spontaneum, Secale cereale, Setaria sphacelata, Sorgahastum nutans, Sorghastrum nutans, Sorghum dochna, Sorghum halepense, Sorghum sudanense, Sorghum bicolor, Triticum aestivum, Triticum dicoccum, Triticum durum, Triticum monococcum, Vanilla fragrans, X Triticosecale* and *Zea mays.*

Preferred plants are forage plant species from a group comprising but not limited to the following genera: *Lolium, Festuca, Dactylis, Bromus, Trifolium, Medicago, Phleum, Phalaris, Holcus, Lotus, Plantago* and *Cichorium.*

Particularly preferred plants are from the genera *Lolium* and *Trifolium*. Particularly preferred species are *Lolium perenne* and *Trifolium repens.*

Particularly preferred *monocotyledonous* plant species are: *Lolium perenne* and *Oryza sativa.*

The term "plant" is intended to include a whole plant, any part of a plant, propagules and progeny of a plant.

The term 'propagule' means any part of a plant that may be used in reproduction or propagation, either sexual or asexual, including seeds and cuttings.

BRIEF DESCRIPTION OF THE DRAWINGS

The present invention will be better understood with reference to the accompanying drawings in which:

FIG. 1 shows an alignment of polypeptides of the invention, including SEQ ID NO: 4 and sequences which are variants SEQ ID NO: 4 from several species and illustrates a consensus region (shown within bold box) identified by the applicants which is present in all of the such sequences.

FIG. 2 shows an alignment of polypeptides of the invention, including SEQ ID NO: 4 and sequences which are variants SEQ ID NO: 4 from several *dicotyledonous* species and illustrates a consensus region (shown within bold box) identified by the applicants which is present in all of the such sequences.

FIG. 8 shows the sequence of a vector, for plant transformation, comprising ORF4 and corresponding to the map in FIG. 7. Sequence in bold corresponds to the *Lolium perenne* promoter (SEQ ID NO:239). Sequence in italics corresponds to ORF4. Sequence underlined corresponds to 3'terminator sequence from CaMV35S gene. Sequence in regular font corresponds to vector sequence.

FIG. 10 shows the sequence of a vector, for plant transformation, comprising ORF12 and corresponding to the map in FIG. 9. Sequence in bold corresponds to the *Lolium perenne* promoter (SEQ ID NO:239). Sequence in italics corresponds to ORF12. Sequence underlined corresponds to the 3'terminator sequence from CaMV35S gene. Sequence in regular font corresponds to vector sequence.

FIG. 12 shows the sequence of a vector, for plant transformation, comprising ORF4 (SEQ ID NO:82) and corresponding to the map in FIG. 11. Sequence in bold corresponds to the double CaMV35S promoter. Sequence in italics corresponds to ORF4 (SEQ ID NO:82). Sequence underlined corresponds to 3' terminator sequence from CaM V35S gene. Sequence in regular font corresponds to vector sequence.

FIG. 14 shows the sequence of a vector, for plant transformation, comprising ORF12 (SEQ ID NO:201) and corresponding to the map in FIG. 13. Sequence in bold corresponds to the double CaM V35S promoter. Sequence in italics corresponds to ORF 12 (SEQ ID NO:201). Sequence underlined corresponds to the 3' terminator sequence from CaM V35S gene. Sequence in regular font corresponds to vector sequence.

DETAILED DESCRIPTION

Figure 3:
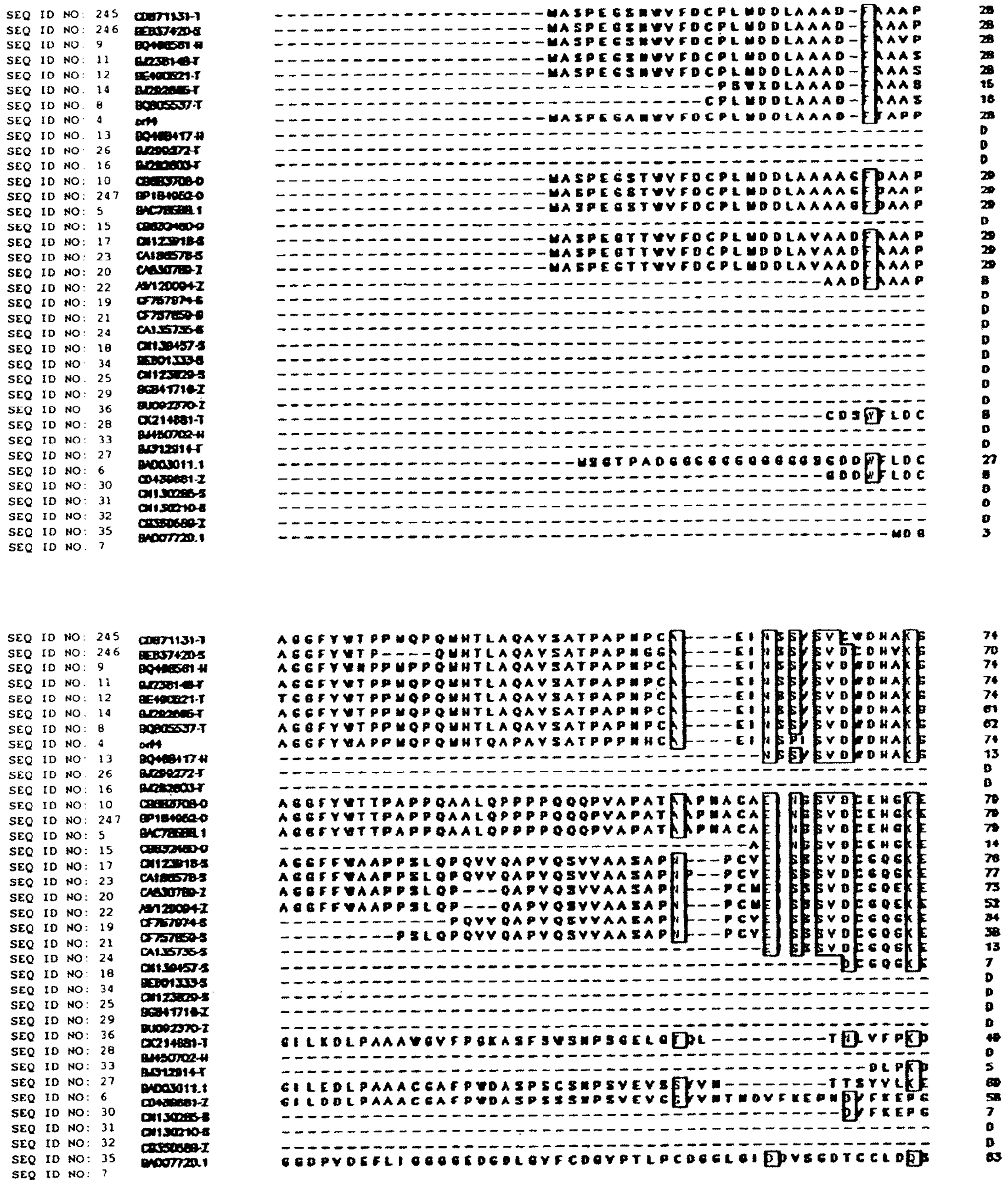
FIG. 3 shows an alignment of polypeptides of the invention, including SEQ ID NO: 4 and sequences which are variants SEQ ID NO: 4 from several *monocotyledonous* species and illustrates a consensus region (shown within bold box) identified by the applicants which is present in all of the such sequences.

The term "plant" is intended to include a whole plant, any part of a plant, propagules and progeny of a plant.

The term 'propagule' means any part of a plant that may be used in reproduction or propagation, either sexual or asexual, including seeds and cuttings.

The term "tolerance or tolerant to drought stress" is intended to describe a plant or plants which perform more favourably in any aspect of their growth and development under sub-optimal hydration conditions than do suitable control plants in the same conditions.

The term "tolerance or tolerant to cold stress" is intended to describe a plant or plants which perform more favourably in any aspect of their growth and development under sub-optimal-reduced reduced temperature conditions than suitable control plants in the same conditions.

The term "tolerance or tolerant to freezing stress" is intended to describe a plant or plants which perform more favourably in any aspect of their growth and development under temperature conditions of less than or equal to 0° C., than do suitable control plants in the same conditions.

The term "tolerance or tolerant to heat stress" is intended to describe a plant or plants which perform more favourably in any aspect of their growth and development under sub-optimal elevated temperature conditions than do suitable control plants in the same conditions.

The term "tolerance or tolerant to salinity" is intended to describe a plant or plants which perform more favourably in any aspect of their growth and development under sub-optimal elevated salinity conditions than do in the same conditions.

Suitable control plants may include non-transformed plants of the same species and variety, or plants of the same species or variety transformed with a control construct.

With reference to the selection methods of the invention, a plant with increased tolerance to environmental stress refers to a plant, selected from a population of plants, which performs more favourably in any aspect of growth and development under stress conditions than does an average member of the population under the same conditions.

The term "comprising" as used in this specification and claims means "consisting at least in part of"; that is to say when interpreting statements in this specification and claims which include "comprising", the features prefaced by this term in each statement all need to be present but other features can also be present. Related terms such as "comprise" and "comprised" are to be interpreted in similar manner.

Polynucleotides and Fragments

The term "polynucleotide(s)," as used herein, means a single or double-stranded deoxyribonucleotide or ribonucleotide polymer of any length, and include as non-limiting examples, coding and non-coding sequences of a gene, sense and antisense sequences, exons, introns, genomic DNA, cDNA, pre-mRNA, mRNA, rRNA, siRNA, miRNA, tRNA, ribozymes, recombinant polynucleotides, isolated and purified naturally occurring DNA or RNA sequences, synthetic RNA and DNA sequences, nucleic acid probes, primers, and fragments.

A "fragment" of a polynucleotide sequence provided herein is a subsequence of contiguous nucleotides that is capable of specific hybridization to a target of interest, e.g., a sequence that is at least 15 nucleotides in length. The fragments of the invention comprise 15 nucleotides, preferably at least 20 nucleotides, more preferably at least 30 nucleotides, more preferably at least 50 nucleotides, more preferably at least 50 nucleotides and most preferably at least 60 nucleotides of contiguous nucleotides of a polynucleotide of the invention. A fragment of a polynucleotide sequence can be used in antisense, gene silencing, triple helix or ribozyme technology, or as a primer, a probe, included in a microarray, or used in polynucleotide-based selection methods of the invention.

The term "primer" refers to a short polynucleotide, usually having a free 3'OH group, that is hybridized to a template and used for priming polymerization of a polynucleotide complementary to the target.

The term "probe" refers to a short polynucleotide that is used to detect a polynucleotide sequence, that is complementary to the probe, in a hybridization-based assay. The probe may consist of a "fragment" of a polynucleotide as defined herein.

Polypeptides and Fragments

The term "polypeptide", as used herein, encompasses amino acid chains of any length, but preferably at least 5 amino acids in length, including full-length proteins, in which amino acid residues are linked by covalent peptide bonds. Polypeptides of the present invention may be purified natural products, or may be produced partially or wholly using recombinant or synthetic techniques. The term may refer to a polypeptide, an aggregate of a polypeptide such as a dimer or other multimer, a fusion polypeptide, a polypeptide fragment, a polypeptide variant, or derivative thereof.

A "fragment" of a polypeptide is a subsequence of the polypeptide that performs a function that is required for the biological activity and/or provides three dimensional structure of the polypeptide. The term may refer to a polypeptide, an aggregate of a polypeptide such as a dimer or other multimer, a fusion polypeptide, a polypeptide fragment, a polypeptide variant, or derivative thereof capable of performing the above enzymatic activity.

The term "isolated" as applied to the polynucleotide or polypeptide sequences disclosed herein is used to refer to sequences that are removed from their natural cellular environment. An isolated molecule may be obtained by any method or combination of methods including biochemical, recombinant, and synthetic techniques.

The term "recombinant" refers to a polynucleotide sequence that is removed from sequences that surround it in its natural context and/or is recombined with sequences that are not present in its natural context.

A "recombinant" polypeptide sequence is produced by translation from a "recombinant" polynucleotide sequence.

The term "derived from" with respect to polynucleotides and polypeptides of the invention being "derived from" a particular genera or species, means that the polynucleotide or polypeptide has the same sequence as a polynucleotide or polypeptide found naturally in that genera or species. The polynucleotide or polypeptide which is derived from a genera or species may therefore be produced synthetically or recombinantly.

Variant

As used herein, the term "variant" refers to polynucleotide or polypeptide sequences different from the specifically identified sequences, wherein one or more nucleotides or amino acid residues is deleted, substituted, or added. Variants may be naturally occurring allelic variants, or non-naturally occurring variants. Variants may be from the same or from other species and may encompass homologues, paralogues and orthologues. In certain embodiments, variants of the inventive polypeptides and polynucleotides possess biological activities that are the same or similar to those of the inventive polypeptides or polynucleotides. The term "variant" with reference to polynucleotides and polypeptides encompasses all forms of polynucleotides and polypeptides as defined herein.

Polynucleotide Variants

Variant polynucleotide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least %, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a specified polynucleotide sequence. Identity is found over a comparison window of at least 20 nucleotide positions, preferably at least 50 nucleotide positions, more preferably at least 100 nucleotide positions, and most preferably over the entire length of the specified polynucleotide sequence.

Polynucleotide sequence identity can be determined in the following manner. The subject polynucleotide sequence is compared to a candidate polynucleotide sequence using BLASTN (from the BLAST suite of programs, version 2.2.5 [November 2002]) in bl2seq (Tatiana A. Tatusova, Thomas L. Madden (1999), "Blast 2 sequences—a new tool for comparing protein and nucleotide sequences", FEMS Microbiol Lett. 174:247-250), which is publicly available from NCBI (ftp://ftp.ncbi.nih.gov/blast/). The default parameters of bl2seq are utilized except that filtering of low complexity parts should be turned off.

The identity of polynucleotide sequences may be examined using the following UNIX command line parameters:

bl2seq-i nucleotideseq1-j nucleotideseq2-F F-p blastn

The parameter-F F turns off filtering of low complexity sections. The parameter-p selects the appropriate algorithm for the pair of sequences. The bl2seq program reports sequence identity as both the number and percentage of identical nucleotides in a line "Identities=".

Polynucleotide sequence identity may also be calculated over the entire length of the overlap between a candidate and subject polynucleotide sequences using global sequence alignment programs (e.g. Needleman, S. B. and Wunsch, C. D. (1970) J. Mol. Biol. 48, 443-453). A full implementation of the Needleman-Wunsch global alignment algorithm is found in the needle program in the EMBOSS package (Rice, P. Longden, I. and Bleasby, A. EMBOSS: The European Molecular Biology Open Software Suite, Trends in Genetics June 2000, vol 16, No 6. pp. 276-277) which can be obtained from http://www.hgmp.mrc.ac.uk/Software/EMBOSS/. The European Bioinformatics Institute server also provides the facility to perform EMBOSS-needle global alignments between two sequences on line at http:/www.ebi.ac.uk/emboss/align/.

Alternatively the GAP program may be used which computes an optimal global alignment of two sequences without penalizing terminal gaps. GAP is described in the following paper: Huang, X. (1994) On Global Sequence Alignment. Computer Applications in the Biosciences 10, 227-235.

Polynucleotide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polynucleotides may be determined using the publicly available bl2seq program from the BLAST suite of programs (version 2.2.5 [November 2002]) from NCBI (ftp://ftp.ncbi.nih.govblast/).

The similarity of polynucleotide sequences may be examined using the following UNIX command line parameters:

bl2seq-i nucleotideseq1-j nucleotideseq2-F F-p tblastx

The parameter-F F turns off filtering of low complexity sections. The parameter-p selects the appropriate algorithm for the pair of sequences. This program finds regions of similarity between the sequences and for each such region reports an "E value" which is the expected number of times one could expect to see such a match by chance in a database of a fixed reference size containing random sequences. The size of this database is set by default in the bl2seq program. For small E values, much less than one, the E value is approximately the probability of such a random match.

Variant polynucleotide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1-10^{-100}$ when compared with any one of the specifically identified sequences.

Alternatively, variant polynucleotides of the present invention hybridize to a specified polynucleotide sequence, or complements thereof under stringent conditions.

The term "hybridize under stringent conditions", and grammatical equivalents thereof, refers to the ability of a polynucleotide molecule to hybridize to a target polynucleotide molecule (such as a target polynucleotide molecule immobilized on a DNA or RNA blot, such as a Southern blot or Northern blot) under defined conditions of temperature and salt concentration. The ability to hybridize under stringent hybridization conditions can be determined by initially hybridizing under less stringent conditions then increasing the stringency to the desired stringency.

With respect to polynucleotide molecules greater than about 100 bases in length, typical stringent hybridization conditions are no more than 25 to 30° C. (for example, 10° C.) below the melting temperature (Tm) of the native duplex (see generally, Sambrook et al., Eds, 1987, Molecular Cloning, A Laboratory Manual, 2nd Ed. Cold Spring Harbor Press; Ausubel et al., 1987, Current Protocols in Molecular Biology, Greene Publishing,). Tm for polynucleotide molecules greater than about 100 bases can be calculated by the formula Tm=81. 5+0.41% (G+C−log (Na+). (Sambrook et al., Eds, 1987, Molecular Cloning, A Laboratory Manual, 2nd Ed. Cold Spring Harbor Press; Bolton and McCarthy, 1962, PNAS 84:1390). Typical stringent conditions for polynucleotide of greater than 100 bases in length would be hybridization conditions such as prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

With respect to polynucleotide molecules having a length less than 100 bases, exemplary stringent hybridization conditions are 5 to 10° C. below Tm. On average, the Tm of a polynucleotide molecule of length less than 100 bp is reduced by approximately (500/oligonucleotide length)° C.

With respect to the DNA mimics known as peptide nucleic acids (PNAs) (Nielsen et al., Science. Dec. 6, 1991; 254 (5037):1497-500) Tm values are higher than those for DNA-DNA or DNA-RNA hybrids, and can be calculated using the formula described in Giesen et al., Nucleic Acids Res. Nov. 1, 1998; 26(21):5004-6. Exemplary stringent hybridization conditions for a DNA-PNA hybrid having a length less than 100 bases are 5 to 10° C. below the Tm.

Variant polynucleotides of the present invention also encompasses polynucleotides that differ from the sequences of the invention but that, as a consequence of the degeneracy of the genetic code, encode a polypeptide having similar activity to a polypeptide encoded by a polynucleotide of the present invention. A sequence alteration that does not change the amino acid sequence of the polypeptide is a "silent variation". Except for ATG (methionine) and TGG (tryptophan), other codons for the same amino acid may be changed by art recognized techniques, e.g., to optimize codon expression in a particular host organism.

Polynucleotide sequence alterations resulting in conservative substitutions of one or several amino acids in the encoded polypeptide sequence without significantly altering its biological activity are also included in the invention. A skilled artisan will be aware of methods for making phenotypically silent amino acid substitutions (see, e.g., Bowie et al., 1990, Science 247, 1306).

Variant polynucleotides due to silent variations and conservative substitutions in the encoded polypeptide sequence may be determined using the publicly available bl2seq program from the BLAST suite of programs (version 2.2.5 [November 2002]) from NCBI (ftp://ftp.ncbi.nih.gov/blast/) via the tblastx algorithm as previously described.

Polypeptide Variants

The term "variant" with reference to polypeptides encompasses naturally occurring, recombinantly and synthetically produced polypeptides. Variant polypeptide sequences preferably exhibit at least 50%, more preferably at least 51%, more preferably at least 52%, more preferably at least 53%, more preferably at least 54%, more preferably at least 55%, more preferably at least 56%, more preferably at least 57%, more preferably at least 58%, more preferably at least 59%, more preferably at least 60%, more preferably at least 61%, more preferably at least 62%, more preferably at least 63%, more preferably at least 64%, more preferably at least 65%, more preferably at least 66%, more preferably at least 67%, more preferably at least 68%, more preferably at least 69%, more preferably at least 70%, more preferably at least 71%, more preferably at least 72%, more preferably at least 73%, more preferably at least 74%, more preferably at least 75%, more preferably at least 76%, more preferably at least 77%, more preferably at least 78%, more preferably at least 79%, more preferably at least 80%, more preferably at least 81%, more preferably at least 82%, more preferably at least 83%, more preferably at least 84%, more preferably at least 85%, more preferably at least 86%, more preferably at least 87%, more preferably at least 88%, more preferably at least 89%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, and most preferably at least 99% identity to a sequences of the present invention. Identity is found over a comparison window of at least 20 amino acid positions, preferably at least 50 amino acid positions, more preferably at least 100 amino acid positions, and most preferably over the entire length of the specified polypeptide sequence.

Polypeptide sequence identity can be determined in the following manner. The subject polypeptide sequence is compared to a candidate polypeptide sequence using BLASTP (from the BLAST suite of programs, version 2.2.5 [November 2002]) in bl2seq, which is publicly available from NCBI (ftp://ftp.ncbi.nih.gov/blast/). The default parameters of bl2seq are utilized except that filtering of low complexity regions should be turned off.

Polypeptide sequence identity may also be calculated over the entire length of the overlap between a candidate and subject polynucleotide sequences using global sequence alignment programs. EMBOSS-needle (available at http://www.ebi.ac.uk/emboss/align/) and GAP (Huang, X. (1994) On Global Sequence Alignment. Computer Applications in the Biosciences 10, 227-235. ) as discussed above are also suitable global sequence alignment programs for calculating polypeptide sequence identity.

Polypeptide variants of the present invention also encompass those which exhibit a similarity to one or more of the specifically identified sequences that is likely to preserve the functional equivalence of those sequences and which could not reasonably be expected to have occurred by random chance. Such sequence similarity with respect to polypeptides may be determined using the publicly available bl2seq program from the BLAST suite of programs (version 2.2.5 [November 2002]) from NCBI (ftp://ftp.ncbi.nih.gov/blast/). The similarity of polypeptide sequences may be examined using the following UNIX command line parameters:

bl2seq-i peptideseq1-j peptideseq2-F F-p blastp

Variant polypeptide sequences preferably exhibit an E value of less than $1\times10^{-10}$ more preferably less than $1\times10^{-20}$, more preferably less than $1\times10^{-30}$, more preferably less than $1\times10^{-40}$, more preferably less than $1\times10^{-50}$, more preferably less than $1\times10^{-60}$, more preferably less than $1\times10^{-70}$, more preferably less than $1\times10^{-80}$, more preferably less than $1\times10^{-90}$ and most preferably less than $1\times10^{-100}$ when compared with any one of the specifically identified sequences.

The parameter-F F turns off filtering of low complexity sections. The parameter-p selects the appropriate algorithm for the pair of sequences. This program finds regions of similarity between the sequences and for each such region reports an "E value" which is the expected number of times one could expect to see such a match by chance in a database of a fixed reference size containing random sequences. For small E values, much less than one, this is approximately the probability of such a random match.

Conservative substitutions of one or several amino acids of a described polypeptide sequence without significantly altering its biological activity are also included in the invention. A skilled artisan will be aware of methods for making phenotypically silent amino acid substitutions (see, e.g., Bowie et al., 1990, Science 247, 1306).

Constructs, Vectors and Components Thereof

The term "genetic construct" refers to a polynucleotide molecule, usually double-stranded DNA, which may have inserted into it another polynucleotide molecule (the insert polynucleotide molecule) such as, but not limited to, a cDNA molecule. A genetic construct may contain the necessary elements that permit transcribing the insert polynucleotide molecule, and, optionally, translating the transcript into a polypeptide. The insert polynucleotide molecule may be derived from the host cell, or may be derived from a different cell or organism and/or may be a recombinant polynucleotide. Once inside the host cell the genetic construct may become integrated in the host chromosomal DNA. The genetic construct may be linked to a vector.

The term “vector” refers to a polynucleotide molecule, usually double stranded DNA, which is used to transport the genetic construct into a host cell. The vector may be capable of replication in at least one additional host system, such as *E. coli.*

The term “expression construct” refers to a genetic construct that includes the necessary elements that permit transcribing the insert polynucleotide molecule, and, optionally, translating the transcript into a polypeptide. An expression construct typically comprises in a 5' to 3' direction:

a) a promoter functional in the host cell into which the construct will be transformed, b) the polynucleotide to be expressed, and c) a terminator functional in the host cell into which the construct will be transformed.

The term “coding region” or “open reading frame” (ORF) refers to the sense strand of a genomic DNA sequence or a cDNA sequence that is capable of producing a transcription product and/or a polypeptide under the control of appropriate regulatory sequences. The coding sequence is identified by the presence of a 5' translation start codon and a 3' translation stop codon. When inserted into a genetic construct, a “coding sequence” is capable of being expressed when it is operably linked to promoter and terminator sequences.

“Operably-linked” means that the sequenced to be expressed is placed under the control of regulatory elements that include promoters, tissue-specific regulatory elements, temporal regulatory elements, enhancers, repressors and terminators.

The term “noncoding region” refers to untranslated sequences that are upstream of the translational start site and downstream of the translational stop site. These sequences are also referred to respectively as the 5' UTR and the 3' UTR. These regions include elements required for transcription initiation and termination and for regulation of translation efficiency.

Terminators are sequences, which terminate transcription, and are found in the 3' untranslated ends of genes downstream of the translated sequence. Terminators are important determinants of mRNA stability and in some cases have been found to have spatial regulatory functions.

The term “promoter” refers to nontranscribed cis-regulatory elements upstream of the coding region that regulate gene transcription. Promoters comprise cis-initiator elements which specify the transcription initiation site and conserved boxes such as the TATA box, and motifs that are bound by transcription factors.

A “transgene” is a polynucleotide that is taken from one organism and introduced into a different organism by transformation. The transgene may be derived from the same species or from a different species as the species of the organism into which the transgene is introduced.

An “inverted repeat” is a sequence that is repeated, where the second half of the repeat is in the complementary strand, e.g.,

```
(5')GATCTA . . . TAGATC(3')

(3')CTAGAT . . . ATCTAG(5')
```

Read-through transcription will produce a transcript that undergoes complementary base-pairing to form a hairpin structure provided that there is a 3-5 bp spacer between the repeated regions.

A “transgenic plant” refers to a plant which contains new genetic material as a result of genetic manipulation or transformation. The new genetic material may be derived from a plant of the same species as the resulting transgenic plant or from a different species.

The terms “to alter expression of” and “altered expression” of a polynucleotide or polypeptide of the invention, are intended to encompass the situation where genomic DNA corresponding to a polynucleotide of the invention is modified thus leading to altered expression of a polynucleotide or polypeptide of the invention. Modification of the genomic DNA may be through genetic transformation or other methods known in the art for inducing mutations. The “altered expression” can be related to an increase or decrease in the amount of messenger RNA and/or polypeptide produced and may also result in altered activity of a polypeptide due to alterations in the sequence of a polynucleotide and polypeptide produced.

The applicants have identified a polynucleotide from ryegrass (SEQ ID NO: 82) encoding a polypeptide (SEQ ID NO: 4) which modulates in plants, tolerance to at least one environmental stress selected from drought, cold, freezing, heat and salinity. The applicants have also identified polynucleotide variants of SEQ ID NO: 82 (SEQ ID NOs: 83-159) encoding polypeptide variants of SEQ ID NOs: 4 (SEQ ID NOs: 5-81) which modulate in plants, tolerance to at least one environmental stress selected from drought, cold, freezing, heat and salinity. The applicants identified consensus sequences (SEQ ID NO:1) present in all of polypeptides encoded by such polynucleotides, as shown in FIG. 1. Further the applicants have identified a consensus sequence (SEQ ID NO:2) specific to *dicotyledonous* polypeptide sequences (FIG. 2) and a consensus sequence (SEQ ID NO:3) specific to *monocotyledonous* sequences (FIG. 3).

Figure 4:
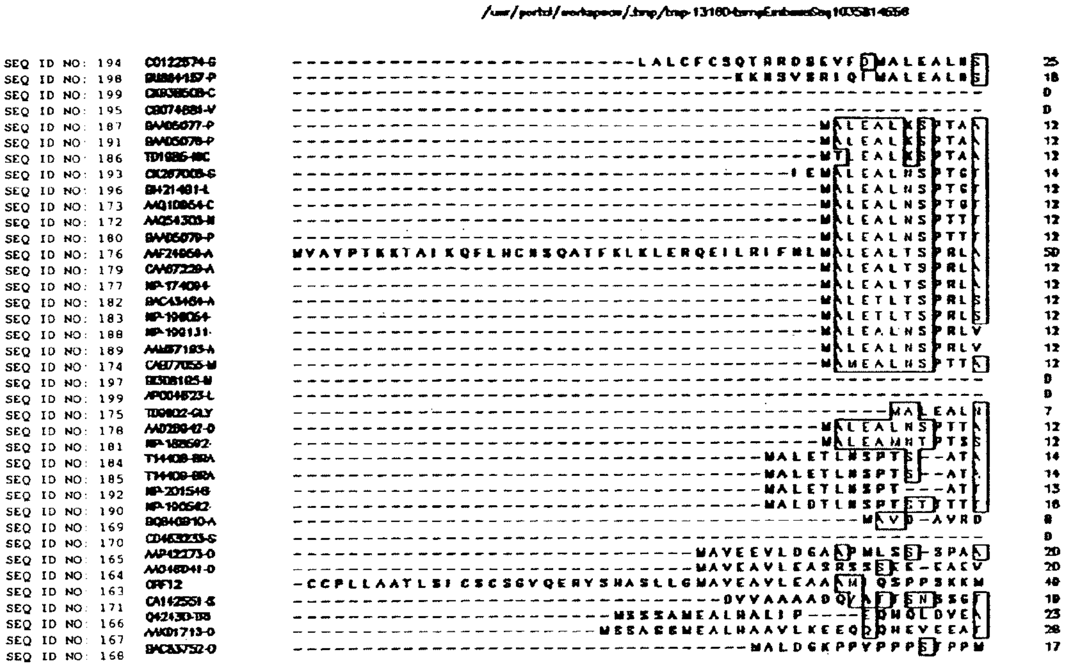
FIG. 4 shows an alignment of polypeptides of the invention, including SEQ ID NO: 163 and sequences which are variants SEQ ID NO: 163 from several species and illustrates a consensus region (shown within bold box) identified by the applicants which is present in all of the such sequences.

The applicants have identified a polynucleotide from ryegrass (SEQ ID NO:201) encoding a polypeptide (SEQ ID NO: 163) which modulates in plants, tolerance to at least one environmental stress selected from drought, cold, freezing, heat and salinity. The applicants have also identified polynucleotide variants of SEQ ID NO: 201 (SEQ ID NOs: 202-238) encoding polypeptide variants of SEQ ID NOs: 163 (SEQ ID NOs: 164-200) which modulate in plants, tolerance to at least one environmental stress selected from drought, cold, freezing, heat and salinity. The applicants identified consensus sequences (SEQ ID NO:160) present in all of polypeptides encoded by such polynucleotides, as shown in FIG. 4. Further the applicants have identified a consensus sequence (SEQ ID NO:161) specific to *dicotyledonous* polypeptide sequences (FIG. 5) and a consensus sequence (SEQ ID NO:162) specific to *monocotyledonous* sequences (FIG. 6).

The invention provides plants altered relative to wild-type plants in tolerance to at least one environmental stress selected from drought, cold, freezing, heat and salinity. The invention provides both plants with both increased tolerance to the above and plants with decreased tolerance to above characteristic stresses. The invention also provides methods for the production or selection of such plants.

The polynucleotide molecules of the invention can be isolated by using a variety of techniques known to those of ordinary skill in the art. By way of example, such polynucleotides can be isolated through use of the polymerase chain reaction (PCR) described in Mullis et al., Eds. 1994 The Polymerase Chain Reaction, Birkhauser, incorporated herein by reference. The polynucleotides of the invention can be amplified using primers, as defined herein, derived from the polynucleotide sequences of the invention.

The polynucleotide fragments of the invention may be produced by techniques well-known in the art such as restriction endonuclease digestion and oligonucleotide synthesis.

A partial polynucleotide sequence may be used, in methods well-known in the art to identify the corresponding full length polynucleotide sequence. Such methods would include PCR-based methods, 5'RACE (Frohman Mass., 1993, Methods Enzymol. 218: 340-56) and hybridization-based method, computer/database-based methods. Further, by way of example, inverse PCR permits acquisition of unknown sequences, flanking the polynucleotide sequences disclosed herein, starting with primers based on a known region (Triglia et al., 1998, *Nucleic Acids Res* 16, 8186, incorporated herein by reference). The method uses several restriction enzymes to generate a suitable fragment in the known region of a gene. The fragment is then circularized by intramolecular ligation and used as a PCR template. Divergent primers are designed from the known region. In order to physically assemble full-length clones, standard molecular biology approaches can be utilized (Sambrook et al., Molecular Cloning: A Laboratory Manual, 2nd Ed. Cold Spring Harbor Press, 1987).

It may be beneficial, when producing a transgenic plant from a particular species, to transform such a plant with a sequence or sequences derived from that species. The benefit may be to alleviate public concerns regarding cross-species transformation in generating transgenic organisms. Additionally when down-regulation of a gene is the desired result, it may be necessary to utilise a sequence identical (or at least highly similar) to that in the plant, for which reduced expression is desired. For these reasons among others, it is desirable to be able to identify and isolate orthologues of a particular gene in several different plant species. Variants (including orthologues) may be identified by the methods described.

Methods for Identifying Variants

Physical Methods

Variant polynucleotides may be identified using PCR-based methods (Mullis et al., Eds. 1994 The Polymerase Chain Reaction, Birkhauser). Typically, the polynucleotide sequence of a primer, useful to amplify variant polynucleotide molecules by PCR, may be based on a sequence encoding a conserved region of the corresponding amino acid sequence.

Alternatively library screening methods will be known to those skilled in the art (Sambrook et al., Molecular Cloning: A Laboratory Manual, 2nd Ed. Cold Spring Harbor Press, 1987) may be employed. When identifying variants of the probe sequence hybridisation and/or wash stringency conditions will typically be reduced relative to when exact sequence matches are sought.

Polypeptide variants of the invention may be identified by physical methods, for example by screening expression libraries using antibodies raised against polypeptides of the invention (Sambrook et al., Molecular Cloning: A Laboratory Manual, 2nd Ed. Cold Spring Harbor Press, 1987) or by identifying polypeptides from natural sources with the aid of such antibodies.

Computer Based Methods

The variant sequences of the invention, including both polynucleotide and polypeptide variants, may also be identified by computer-based methods well-known to those skilled in the art, using public domain sequence alignment algorithms and sequence similarity search tools to search sequence databases (public domain databases include Genbank, EMBL, Swiss-Prot, PIR and others). See, e.g., Nucleic Acids Res. 29: 1-10 and 11-16, 2001 for examples of online resources. Similarity searches retrieve and align target sequences for comparison with a sequence to be analyzed (i.e., a query sequence). Sequence comparison algorithms use scoring matrices to assign an overall score to each of the alignments.

An exemplary family of programs useful for identifying variants in sequence databases is the BLAST suite of programs (version 2.2.5 [November 2002]) including BLASTN, BLASTP, BLASTX, tBLASTN and tBLASTX, which are publicly available from (ftp://ftp.ncbi.nih.gov/blast/) or from the National Center for Biotechnology Information (NCBI), National Library of Medicine, Building 38A, Room 8N805, Bethesda, Md. 20894 USA. The NCBI server also provides the facility to use the programs to screen a number of publicly available sequence databases. BLASTN compares a nucleotide query sequence against a nucleotide sequence database. BLASTP compares an amino acid query sequence against a protein sequence database. BLASTX compares a nucleotide query sequence translated in all reading frames against a protein sequence database. tBLASTN compares a protein query sequence against a nucleotide sequence database dynamically translated in all reading frames. tBLASTX compares the six-frame translations of a nucleotide query sequence against the six-frame translations of a nucleotide sequence database. The BLAST programs may be used with default parameters or the parameters may be altered as required to refine the screen.

The use of the BLAST family of algorithms, including BLASTN, BLASTP, and BLASTX, is described in the publication of Altschul et al., Nucleic Acids Res. 25: 3389-3402, 1997.

The "hits" to one or more database sequences by a queried sequence produced by BLASTN, BLASTP, BLASTX, tBLASTN, tBLASTX, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN, BLASTP, BLASTX, tBLASTN and tBLASTX algorithms also produce "Expect" values for alignments. The Expect value (E) indicates the number of hits one can "expect" to see by chance when searching a database of the same size containing random contiguous sequences. The Expect value is used as a significance threshold for determining whether the hit to a database indicates true similarity. For example, an E value of 0.1 assigned to a polynucleotide hit is interpreted as meaning that in a database of the size of the database screened, one might expect to see 0.1 matches over the aligned portion of the sequence with a similar score simply by chance. For sequences having an E value of 0.01 or less over aligned and matched portions, the probability of finding a match by chance in that database is 1% or less using the BLASTN, BLASTP, BLASTX, tBLASTN or TBLASTX algorithm.

Multiple sequence alignments of a group of related sequences can be carried out with CLUSTALW (Thompson, J. D., Higgins, D. G. and Gibson, T. J. (1994) CLUSTALW: improving the sensitivity of progressive multiple sequence alignment through sequence weighting, positions-specific gap penalties and weight matrix choice. Nucleic Acids Research, 22:4673-4680, http://www-igbmc.u-strasbg.fr/BioInfo/ClustalW/Top.html) or T-COFFEE (Cedric Notredame, Desmond G. Higgins, Jaap Heringa, T-Coffee: A novel method for fast and accurate multiple sequence alignment, J. Mol. Biol. (2000) 302: 205-217)) or PILEUP, which uses progressive, pairwise alignments. (Feng and Doolittle, 1987, J. Mol. Evol. 25, 351).

Pattern recognition software applications are available for finding motifs or signature sequences. For example, MEME (Multiple Em for Motif Elicitation) finds motifs and signature sequences in a set of sequences, and MAST (Motif Alignment and Search Tool) uses these motifs to identify similar or the same motifs in query sequences. The MAST results are provided as a series of alignments with appropriate statistical data and a visual overview of the motifs found. MEME and MAST were developed at the University of California, San Diego.

PROSITE (Bairoch and Bucher, 1994, Nucleic Acids Res. 22, 3583; Hofmann et al., 1999, Nucleic Acids Res. 27, 215) is a method of identifying the functions of uncharacterized proteins translated from genomic or cDNA sequences. The PROSITE database (www.expasy.org/prosite) contains biologically significant patterns and profiles and is designed so that it can be used with appropriate computational tools to assign a new sequence to a known family of proteins or to determine which known domain(s) are present in the sequence (Falquet et al., 2002, Nucleic Acids Res. 30, 235). Prosearch is a tool that can search SWISS-PROT and EMBL databases with a given sequence pattern or signature.

The function of a variant polynucleotide of the invention in modulating tolerance to environmental stresses in a plant may be assessed by expressing the polynucleotide in a plant and for example, analyzing the effect on stress tolerance by methods provided in the Example section. Further plant transformation protocols for several species are known to those skilled in the art. A list of such protocols is provided herein.

Methods for Isolating Polypeptides

The polypeptides of the invention, including variant polypeptides, may be prepared using peptide synthesis methods well known in the art such as direct peptide synthesis using solid phase techniques (e.g. Stewart et al., 1969, in Solid-Phase. Peptide Synthesis, WH Freeman Co, San Francisco Calif., or automated synthesis, for example using an Applied Biosystems 431A Peptide Synthesizer (Foster City, Calif.). Mutated forms of the polypeptides may also be produced during such syntheses.

The polypeptides and variant polypeptides of the invention may also be purified from natural sources using a variety of techniques that are well known in the art (e.g. Deutscher, 1990, Ed, Methods in Enzymology, Vol. 182, *Guide to Protein Purification,*).

Alternatively the polypeptides and variant polypeptides of the invention may be expressed recombinantly in suitable host cells and separated from the cells as discussed below.

Methods for Producing Constructs and Vectors

The genetic constructs of the present invention comprise one or more polynucleotide sequences of the invention and/or polynucleotides encoding polypeptides of the invention, and may be useful for transforming, for example, bacterial, fungal, insect, mammalian or plant organisms. The genetic constructs of the invention are intended to include expression constructs as herein defined.

Methods for producing and using genetic constructs and vectors are well known in the art and are described generally in Sambrook et al., Molecular Cloning: A Laboratory Manual, 2nd Ed. Cold Spring Harbor Press, 1987; Ausubel et al., Current Protocols in Molecular Biology, Greene Publishing, 1987).

Methods for Producing Host Cells Comprising Constructs and Vectors

The invention provides a host cell which comprises a genetic construct or vector of the invention. Host cells may be derived from, for example, bacterial, fungal, insect, mammalian or plant organisms.

Host cells comprising genetic constructs, such as expression constructs, of the invention are useful in methods well known in the art (e.g. Sambrook et al., Molecular Cloning: A Laboratory Manual, 2nd Ed. Cold Spring Harbor Press, 1987 ; Ausubel et al., Current Protocols in Molecular Biology, Greene Publishing, 1987) for recombinant production of polypeptides of the invention. Such methods may involve the culture of host cells in an appropriate medium in conditions suitable for or conducive to expression of a polypeptide of the invention. The expressed recombinant polypeptide, which may optionally be secreted into the culture, may then be separated from the medium, host cells or culture medium by methods well known in the art (e.g. Deutscher, Ed, 1990, Methods in Enzymology, Vol 182, Guide to Protein Purification).

Methods for Producing Plant Cells and Plants Comprising Constructs and Vectors

The invention further provides plant cells which comprise a genetic construct of the invention, and plant cells modified to alter expression of a polynucleotide or polypeptide of the invention. Plants comprising such cells also form an aspect of the invention.

Tolerance to at least one environmental stress selected from drought, cold, freezing, heat and salinity in a plant, may also be altered through methods of the invention. Such methods may involve the transformation of plant cells and plants, with a construct of the invention designed to alter expression of a polynucleotide or polypeptide which modulates for example, tolerance to drought stress, in such plant cells and plants. Such methods also include the transformation of plant cells and plants with a combination of the construct of the invention and one or more other constructs designed to alter expression of one or more polynucleotides or polypeptides which modulate for example, tolerance to drought stress in such plant cells and plants.

Methods for transforming plant cells, plants and portions thereof with polynucleotides are described in Draper et al., 1988, Plant Genetic Transformation and Gene Expression. A Laboratory Manual. Blackwell Sci. Pub. Oxford, p. 365; Potrykus and Spangenberg, 1995, Gene Transfer to Plants. Springer-Verlag, Berlin.; and Gelvin et al., 1993, Plant Molecular Biol. Manual. Kluwer Acad. Pub. Dordrecht. A review of transgenic plants, including transformation techniques, is provided in Galun and Breiman, 1997, Transgenic Plants. Imperial College Press, London.

Methods for Genetic Manipulation of Plants

A number of plant transformation strategies are available (e.g. Birch, 1997, Ann Rev Plant Phys Plant Mol Biol, 48, 297). For example, strategies may be designed to increase expression of a polynucleotide/polypeptide in a plant cell, organ and/or at a particular developmental stage where/when it is normally expressed or to ectopically express a polynucleotide/polypeptide in a cell, tissue, organ and/or at a particular developmental stage which/when it is not normally expressed. The expressed polynucleotide/polypeptide may be derived from the plant species to be transformed or may be derived from a different plant species.

Transformation strategies may be designed to reduce expression of a polynucleotide/polypeptide in a plant cell, tissue, organ or at a particular developmental stage which/when it is normally expressed. Such strategies are known as gene silencing strategies.

Genetic constructs for expression of genes in transgenic plants typically include promoters for driving the expression of one or more cloned polynucleotide, terminators and selectable marker sequences to detest presence of the genetic construct in the transformed plant.

The promoters suitable for use in the constructs of this invention are functional in a cell, tissue or organ of a monocot or dicot plant and include cell-, tissue- and organ-specific promoters, cell cycle specific promoters, temporal promoters, inducible promoters, constitutive promoters that are active in most plant tissues, and recombinant promoters. Choice of promoter will depend upon the temporal and spatial expression of the cloned polynucleotide, so desired. The promoters may be those normally associated with a transgene of interest, or promoters which are derived from genes of other plants, viruses, and plant pathogenic bacteria and fungi. Those skilled in the art will, without undue experimentation, be able to select promoters that are suitable for use in modifying and modulating plant traits using genetic constructs comprising the polynucleotide sequences of the invention. Examples of constitutive plant promoters include the CaMV 35S promoter, the nopaline synthase promoter and the octopine synthase promoter, and the Ubi 1 promoter from maize. Plant promoters which are active in specific tissues, respond to internal developmental signals or external abiotic or biotic stresses are described in the scientific literature. Exemplary promoters are described, e.g., in WO 02/00894, which is herein incorporated by reference.

Exemplary terminators that are commonly used in plant transformation genetic construct include, e.g., the cauliflower mosaic virus (CaMV) 35S terminator, the *Agrobacterium tumefaciens* nopaline synthase or octopine synthase terminators, the *Zea mays* zein gene terminator, the *Oryza sativa* ADP-glucose pyrophosphorylase terminator and the *Solanum tuberosum* PI-II terminator.

Selectable markers commonly used in plant transformation include the neomycin phophotransferase II gene (NPT II) which confers kanamycin resistance, the aadA gene, which confers spectinomycin and streptomycin resistance, the phosphinothricin acetyl transferase (bar gene) for Ignite (AgrEvo) and Basta (Hoechst) resistance, and the hygromycin phosphotransferase gene (hpt) for hygromycin resistance.

Use of genetic constructs comprising reporter genes (coding sequences which express an activity that is foreign to the host, usually an enzymatic activity and/or a visible signal (e.g., luciferase, GUS, GFP) which may be used for promoter expression analysis in plants and plant tissues are also contemplated. The reporter gene literature is reviewed in Herrera-Estrella et al., 1993, Nature 303, 209, and Schrott, 1995, In: Gene Transfer to Plants (Potrykus, T., Spangenberg. Eds) Springer Verlag. Berline, pp. 325-336.

Gene silencing strategies may be focused on the gene itself or regulatory elements which effect expression of the encoded polypeptide. "Regulatory elements" is used here in the widest possible sense and includes other genes which interact with the gene of interest.

Genetic constructs designed to decrease or silence the expression of a polynucleotide/polypeptide of the invention may include an antisense copy of a polynucleotide of the invention. In such constructs the polynucleotide is placed in an antisense orientation with respect to the promoter and terminator.

An "antisense" polynucleotide is obtained by inverting a polynucleotide or a segment of the polynucleotide so that the transcript produced will be complementary to the mRNA transcript of the gene, e.g.,

```
5'GATCTA 3'            3'CTAGAT 5'
(coding strand)        (antisense strand)

3'CUAGAU 5'            5'GAUCUA 3'
mRNA                   antisense RNA
```

Genetic constructs designed for gene silencing may also include an inverted repeat as herein defined. The preferred approach to achieve this is via RNA-interference strategies using genetic constructs encoding self-complementary "hairpin" RNA (Wesley et al., 2001, Plant Journal, 27: 581-590).

The transcript formed may undergo complementary base pairing to form a hairpin structure. Usually a spacer of at least 3-5 bp between the repeated regions is required to allow hairpin formation.

Another silencing approach involves the use of a small antisense RNA targeted to the transcript equivalent to an miRNA (Llave et al., 2002, Science 297, 2053). Use of such small antisense RNA corresponding to polynucleotide of the invention is expressly contemplated.

The term genetic construct as used herein also includes small antisense RNAs and other such polynucleotides effecting gene silencing.

Transformation with an expression construct, as herein defined, may also result in gene silencing through a process known as sense suppression (e.g. Napoli et al., 1990, Plant Cell 2, 279; de Carvalho Niebel et al., 1995, Plant Cell, 7, 347). In some cases sense suppression may involve overexpression of the whole or a partial coding sequence but may also involve expression of non-coding region of the gene, such as an intron or a 5' or 3' untranslated region (UTR). Chimeric partial sense constructs can be used to coordinately silence multiple genes (Abbott et al., 2002, Plant Physiol. 128(3): 844-53; Jones et al., 1998, Planta 204: 499-505). The use of such sense suppression strategies to silence the expression of a polynucleotide of the invention is also contemplated.

The polynucleotide inserts in genetic constructs designed for gene silencing may correspond to coding sequence and/or non-coding sequence, such as promoter and/or intron and/or 5' or 3' UTR sequence, or the corresponding gene.

Other gene silencing strategies include dominant negative approaches and the use of ribozyme constructs (McIntyre, 1996, Transgenic Res, 5, 257)

Pre-transcriptional silencing may be brought about through mutation of the gene itself or its regulatory elements. Such mutations may include point mutations, frameshifts, insertions, deletions and substitutions.

The following are representative publications disclosing genetic transformation protocols that can be used to genetically transform the following plant species: Rice (Alam et al., 1999, Plant Cell Rep. 18, 572); maize (U.S. Pat. Ser. Nos. 5,177,010 and 5,981,840); wheat (Ortiz et al., 1996, Plant Cell Rep. 15, 1996, 877); tomato (U.S. Pat. Ser. No. 5,159,135); potato (Kumar et al., 1996 Plant J. 9,: 821); cassava (Li et al., 1996 Nat. Biotechnology 14, 736); lettuce (Michelmore et al., 1987, Plant Cell Rep. 6, 439); tobacco (Horsch et al., 1985, Science 227, 1229); cotton (U.S. Pat. Ser. Nos. 5,846,797 and 5,004,863); grasses (U.S. Pat. Nos. 5,187,073 and 6,020,539); peppermint (Niu et al., 1998, Plant Cell Rep. 17, 165); citrus plants (Pena et al., 1995, Plant Sci. 104, 183); caraway (Krens et al., 1997, Plant Cell Rep, 17, 39); banana (U.S. Pat. Ser. No. 5,792,935); soybean (U.S. Pat. Nos. 5,416, 011; 5,569,834; 5,824,877 ; 5,563,04455 and 5,968,830); pineapple (U.S. Pat. Ser. No. 5,952,543); poplar (U.S. Pat. No. 4,795,855); monocots in general (U.S. Pat. Nos. 5,591,616 and 6,037,522); brassica (U.S. Pat. Nos. 5,188,958 ; 5,463,174 and 5,750,871); and cereals (U.S. Pat. No. 6,074,877). Other species are contemplated and suitable methods and protocols are available in the scientific literature for use by those skilled in the art.

Several further methods known in the art may be employed to alter expression of a nucleotide and/or polypeptide of the invention. Such methods include but are not limited to Tilling (Till et al., 2003, Methods Mol Biol, 2%, 205), so called "Deletagene" technology (Li et al., 2001, Plant Journal 27(3), 235) and the use of artificial transcription factors such as synthetic zinc finger transcription factors. (e.g. Jouvenot et al., 2003, Gene Therapy 10, 513). Additionally antibodies or fragments thereof, targeted to a particular polypeptide may also be expressed in plants to modulate the activity of that polypeptide (Jobling et al., 2003, Nat. Biotechnol., 21(1), 35). Transposon tagging approaches may also be applied. Additionally peptides interacting with a polypeptide of the invention may be identified through technologies such as phase-display (Dyax Corporation). Such interacting peptides may be expressed in or applied to a plant to affect activity of a polypeptide of the invention. Use of each of the above approaches in alteration of expression of a nucleotide and/or polypeptide of the invention is specifically contemplated.

Methods for Selecting Plants

Methods are also provided for selecting plants altered tolerance to at least one environmental stress selected from drought, cold, freezing, heat and salinity. Such methods involve testing of plants for altered for the expression of a polynucleotide or polypeptide of the invention. Such methods may be applied at a young age or early developmental stage to accelerate breeding programs directed toward at least one of the characteristics described which may not be easily assessed until a later age or developmental stage.

The expression of a polynucleotide, such as a messenger RNA, is often used as an indicator of expression of a corresponding polypeptide. Exemplary methods for measuring the expression of a polynucleotide include but are not limited to Northern analysis, RT-PCR and dot-blot analysis (Sambrook et al., Molecular Cloning: A Laboratory Manual, 2nd Ed. Cold Spring Harbor Press, 1987). Polynucleotides or portions of the polynucleotides of the invention are thus useful as probes or primers, as herein defined, in methods for the identification of plants with altered tolerance to at least one environmental stress selected from drought, cold, freezing, heat and salinity. For example an altered level in a plant, of a polypeptide involved in modulating tolerance to drought stress may be used as an indicator of eventual tolerance to drought stress in such a plant. The polynucleotides of the invention may be used as probes in hybridization experiments, or as primers in PCR based experiments, designed to identify such plants.

Alternatively antibodies may be raised against polypeptides of the invention. Methods for raising and using antibodies are standard in the art (see for example: Antibodies, A Laboratory Manual, Harlow A Lane, Eds, Cold Spring Harbour Laboratory, 1998). Such antibodies may be used in methods to detect altered expression of polypeptides which modulate flower size in plants. Such methods may include ELISA (Kemeny, 1991, A Practical Guide to ELISA, NY Pergamon Press) and Western analysis (Towbin & Gordon, 1994, J Immunol Methods, 72, 313).

These approaches for analysis of polynucleotide or polypeptide expression and the selection of plants with altered expression are useful in conventional breeding programs designed to produce varieties with altered in tolerance to at least one environmental stress selected from drought, cold, freezing, heat and salinity.

Plants

The plants of the invention may be grown and either selfed or crossed with a different plant strain and the resulting hybrids, with the desired phenotypic characteristics, may be identified. Two or more generations may be grown to ensure that the subject phenotypic characteristics are stably maintained and inherited. Plants resulting from such standard breeding approaches also form an aspect of the present invention.

EXAMPLES

The invention will now be illustrated with reference to the following non-limiting examples.

Example 1

Identification of Polynucleotides which Modulate Tolerance to Environmental Stresses Introduction Transcript identification in different tissue and developmental stages is based mainly by the use of EST (expressed sequence tag)-based methods (Adams et al. 1991, *Science* 252:1651-1656). SAGE (serial analysis of gene expression) (Velculescu et al. 1995, *Science* 270: 484-487) is a modification of conventional EST methods and has many advantages over that of other methods, such as microarray (Richmond and Somerville 2000, *Current Opinion in Plant Biology*. 3:108-116). Transcript profiling by SAGE is not limited to studying known genes and is estimated to be 26 times more sensitive than EST method (Sun et al. 2004, *BMC Genomics* 5: 1.1-1.4). Unlike microarray, SAGE is free from cross-hybridization problem and accurate because of dimer-formation prior to amplification (Ruan et al. 2004, *Trends in Biotechnology* 22: 23-30.). Alternative splicing of the transcript is a well-known phenomenon, whose impact is not fully understood yet (Lee et al. 2003, *PNAS* 99:12257-12262). These splice variants can be identified by SAGE. SAGE is also able to detect antisense RNAs, since the orientation of the SAGE tag on the transcripts can be readily determined. Antisense transcripts are likely to represent novel genes whose function may or may not be related to regulation of the expression of the genes transcribed from the sense strand (Chen et al. 2002, *Nucleic Acids Res.* 31:101-105). Although SAGE is widely used in the analysis of transcriptomes from cancerous human cells, it is not widely applied in other organisms, including plants. To date only a handful of papers have appeared where SAGE has been applied to characterize plant transcriptome, for example; Lee and Lee, 2003 *Plant Physiol.* 132: 517-529. Most of the plant transcriptome analysed using SAGE has been confined to the two fully sequenced genomes, namely *Arabidopsis* and rice.

Perennial ryegrass (*Lolium perenne L.*) is a cool temperate pasture plant from the family Gramineae and the tribe Festucaceae. To generate a profile of relative gene expression patterns in ryegrass, RNA was extracted from samples obtained from ambient temperature growth, cold grown, hydrated, dehydrated and rehydrated or dehydration pre- and post-grazed plants during autumn, summer, spring and winter, and used for constructing a SAGE library.

Materials and Methods:

Perennial ryegrass (*Lolium perenne L.*) cv. Bronsyn was used throughout this study. Field grown samples were collected from active paddocks at Dexcel, Hamilton, New Zealand during the peak of each season. Grass samples were collected from pre-grazed (15 days post grazing) and post-grazed (1 day post grazing) ryegrass swards. Tufts of grass samples were harvested from 3-6 randomly chosen sites and stored in dry-ice after snap-freezing with liquid nitrogen. During spring, immature spike and floral initials were also harvested. For stress-treatment, the following conditions were used on lab-grown ryegrass: Mature lab-grown perennial ryegrass that was grown in growth chamber for 15 months at 85% RH, 20° C./18° C. and 16 h/8 h day/night regime; Hydrated control grown for 55 days at 85% RH, 20° C./18° C. and 16 h/8 h day/night regime; 6 days at 70% RH, 22° C. C./16° C. and 16 h/8 h day/night regime, seedlings were kept watered throughout their life; Dehydrated sample watered only for 55 days at 85% RH, 20° C./18° C. and 16 h/8 h day/night regime; 3 days at 70% RH, 28° C./20° C. and 16 h/8 h day/night regime; 3 days at 50% RH, 28° C. and 16 h/8 h day/night regime; Rehydrated samples were from dehydrated plants that was watered for 24 hours and grown at 70% RH, 22° C./16° C. and 16 h/8 h day/night regime; Cold-stressed plants were grown for 55 days at 85% RH, 20° C./18° C. and 16 h/8 h day/night regime; 7 days at 70% RH, 22° C./16° C. and 16 h/8 h day/night regime; 7 days at 70% RH, 6° C./2° C. and 16 h/8 h day/night regime, seedlings were kept watered throughout their life.

Construction of SAGE Libraries

RNA was extracted using TRIZOL® reagent (Invitrogen, Calif., USA) and by the protocol described by the manufacturer from tissue that was ground in liquid nitrogen. For each SAGE library 100 μg of total RNA was used and the libraries were created using I-SAGE™ or I-SAGE™ Long kit (Invitrogen, Calif., USA) according to manufacturer's protocol. From each library 960-1,920 clones were sequenced (Australian Genome Research Facility, Brisbane, Australia) and the tags extracted using the SAGE2000 software.

SAGE Bioinformatics:

The relational database was designed to hold tags, libraries and expression counts of the SAGE experiments. Each tag sequence (including enzyme sequence) was searched against the whole Ryegrass non-overlapping Gene thresher and the EST sets. The search was carried out in both direction and used exact match only. Results were loaded to the relational database using General Feature Format (GFF) approach (htt://www3.ebi.ac.uk/Services/WebFeat)

All Ryegrass Gene thresher and the EST sequences were annotated using homology searches against some or all the following public and propriety databases:

AGI TIGR Gene Indices, *Arabidopsis*, release 11, January 2004

OGI TIGR Gene Indices, Rice, release 14-1, January 2004

GENESEQN Derwent patent DNA sequences Dec. 7, 2002

GENESEQP Derwent patent amino acid sequences Dec. 7, 2002

Os_unigene *Oryza sativa* Unigene unique sequences Mar. 18, 2004 est_others Other EST sequences (mammal, fungi, prokaryote) Mar. 11, 2003 est_plant Viridiplantae subset of Non-redundant Database of GenBank+EMBL+DDBJ EST Divisions Mar. 15, 2004 nr All non-redundant GenBank CDS translations+PDB+SwissProt+PIR Mar. 11, 2003 nr_plant Plant subset of HS subset of BT subset of All non-redundant GenBank CDS translations+PDB+SwissProt+PIR Aug. 8, 2003 nt All Non-redundant GenBank+EMBL+DDBJ+PDB sequences (but no EST, STS, GSS, or HTGS sequences) Mar. 11, 2003 nt_monocots Monocot subset of All Non-redundant GenBank+EMBL+DDBJ+PDB sequences (but no EST, STS, GSS, or HTGS sequences) Mar. 11, 2003 swissprot The last major release of the SWISS-PROT protein sequence database (no updates) Mar. 28, 2003

A cutoff of E value less than E-05 was used and maximum of 10 targets per database were stored in the relational database.

Tags Annotation:

Tags with hits to the Ryegrass sets were annotated by creating a summary of all the annotations of the involved sequences. The summary was generated using an algorithm to calculate the frequency of the occurrence of each word in the annotations and rank them in descending order based on the number off occurrences. The summary was limited to 10 words and a void word list was used to filter out insignificant information. The resulting summary line was used as an indication of what the tags were likely to be. Actual numbers are displayed; giving additional information that could be used to evaluate the significance of each of the words in the summary. This method of automatic annotation using keyword counts is similar to the Automatic comment that is used by the ProDom database (http://protein.toulouse.inra.fr/prodom/current/html/home.php) to annotate the automatically generated protein domain families.

Detailed annotation based on the top hits of the involved sequences was displayed when viewing tags data.

Two polynucleotide sequences of particular interest were identified in the above analysis. These are ORF4 (corresponds to SEQ ID NO: 82) and ORF12 (corresponding to SEQ ID NO: 201).

ORF4 appears to encode a helix-loop-helix transcription factor. The transcript accumulates in cold, dehydrated and rehydrating tissues. The full transcript profile is shown in table 1.

TABLE 1

| SAGE_TAG | TGACACCGTT |
|---|---|
| LPWPRE | 0 |
| LPWPOS | 0 |
| LPRWIN | 0 |
| LPSPRE | 0 |
| LPSPOS | 2 |
| LPISFI | 1 |
| LPUPOS | 2 |
| LPAPRE | 2 |

TABLE 1-continued

| SAGE_TAG | TGACACCGTT |
|---|---|
| LPAPOS | 1 |
| LPMALF | 0 |
| LPCOLD | 2 |
| LPHYDR | 0 |
| LPDEHY | 4 |
| LPREHY | 2 |
| Total | 15 |

ORF12 appears to encode a zinc finger protein and the transcript accumulates in response to drought stimulus. The full transcript profile is shown in table 2 below.

TABLE 2

| SAGE_TAG | TGTATCATTA |
|---|---|
| LPWPRE | 0 |
| LPWPOS | 0 |
| LPRWIN | 0 |
| LPSPRE | 0 |
| LPISFI | 0 |
| LPUPOS | 0 |
| LPAPRE | 0 |
| LPAPOS | 0 |
| LPMALF | 2 |
| LPCOLD | 0 |
| LPHYDR | 0 |
| LPDEHY | 6 |
| LPREHY | 0 |
| Total | 8 |

ORF 12 appears to be a C2H2 class zinc finger transcription factor with two zinc fingers. The first zinc finger is contained in the polypeptide between amino acid residue 81 and 101 of SEQ. ID NO:163 while the second zinc finger is contained in the polypeptide sequence between amino acid residue 144 and 164. Within the first zinc finger a conserved amino acid sequence motif QALGGHK was identified which is directly repeated in the second zinc finger domain, the conserved motif being separated by 56 residues. The H residue in this motif, in the first zinc finger, appears to be the first of the two H residues that is reported to be the active site in the C2H2 class zinc finger transcription factors.

Example 2

Identification variants of ORF 4 and ORF 12

The polypeptide sequence encoded by the ORF4 and ORF12 were used as seed sequences to perform BLASTP search against NR_PLANT database (release date 30 Jul. 2004). Besides BLASTP, a TBLASTN search was also performed against EST_PLANT database (release date 15 Jul. 2004) and NT_PLANT database (release date 15 Jul. 2004). To identify the variants cut-off e value was generally set at greater than 1e-05, which was determined based upon the associated score value.

Selected variant sequences were aligned using the EMBOSS tool EMMA (Thompson, J. D., Higgins, D. G. and Gibson, T. J. 1994, CABIOS, 10, 19-29.), which is an interface to the popular multiple alignment program ClustalW. Aligned sequences were visualised using another EMBOSS tool called prettyplot, which displays aligned sequences with colouring and boxing.

All the ORF4 variant polypeptide sequences above were aligned as described above with ORF4 and a consensus motif (SEQ ID NO:1) common to ORF4 and ORF4 variants from all plant (both *monocotyledonous* and *dicotyledonous*) sequences was identified as shown in FIG. 1.

A similar consensus motif (SEQ ID NO:2) was identified which was specific to ORF4 and all of the *dicotyledonous* variant sequences as shown in FIG. 2.

A further consensus motif (SEQ ID NO:3) was identified which was specific to ORF4 and all of the *monocotyledonous* variant sequences as shown in FIG. 3.

All the ORF12 variant polypeptide sequences above were aligned as described above with ORF12 and a consensus motif (SEQ ID NO:4) common to ORF12 and ORF12 variants from all plant (both *monocotyledonous* and *dicotyledonous*) sequences was identified as shown in FIG. 4.

Figure 5:
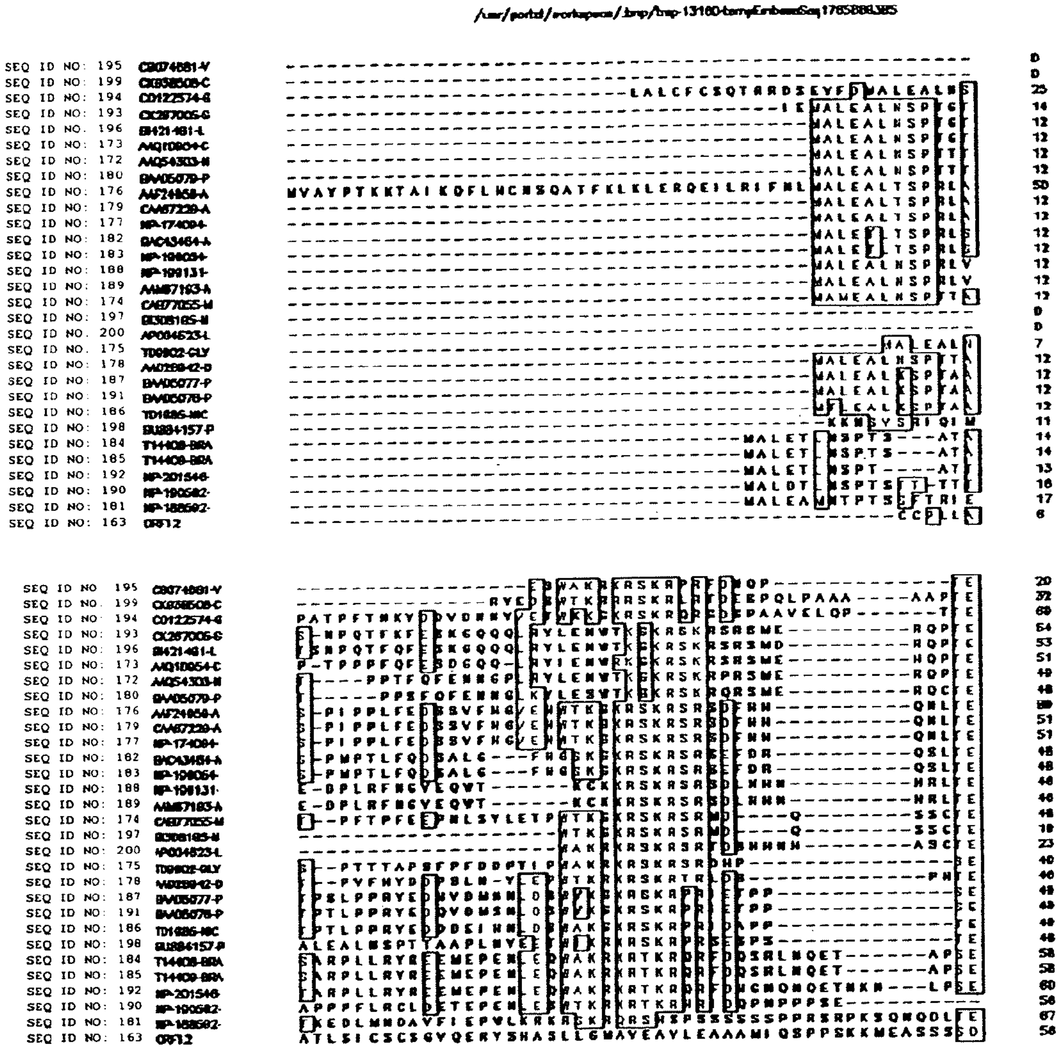
FIG. 5 shows an alignment of polypeptides of the invention, including SEQ ID NO: 163 and sequences which are variants SEQ ID NO: 163 from several *dicotyledonous* species and illustrates a consensus region (shown within bold box) identified by the applicants which is present in all of the such sequences.
Figure 6:
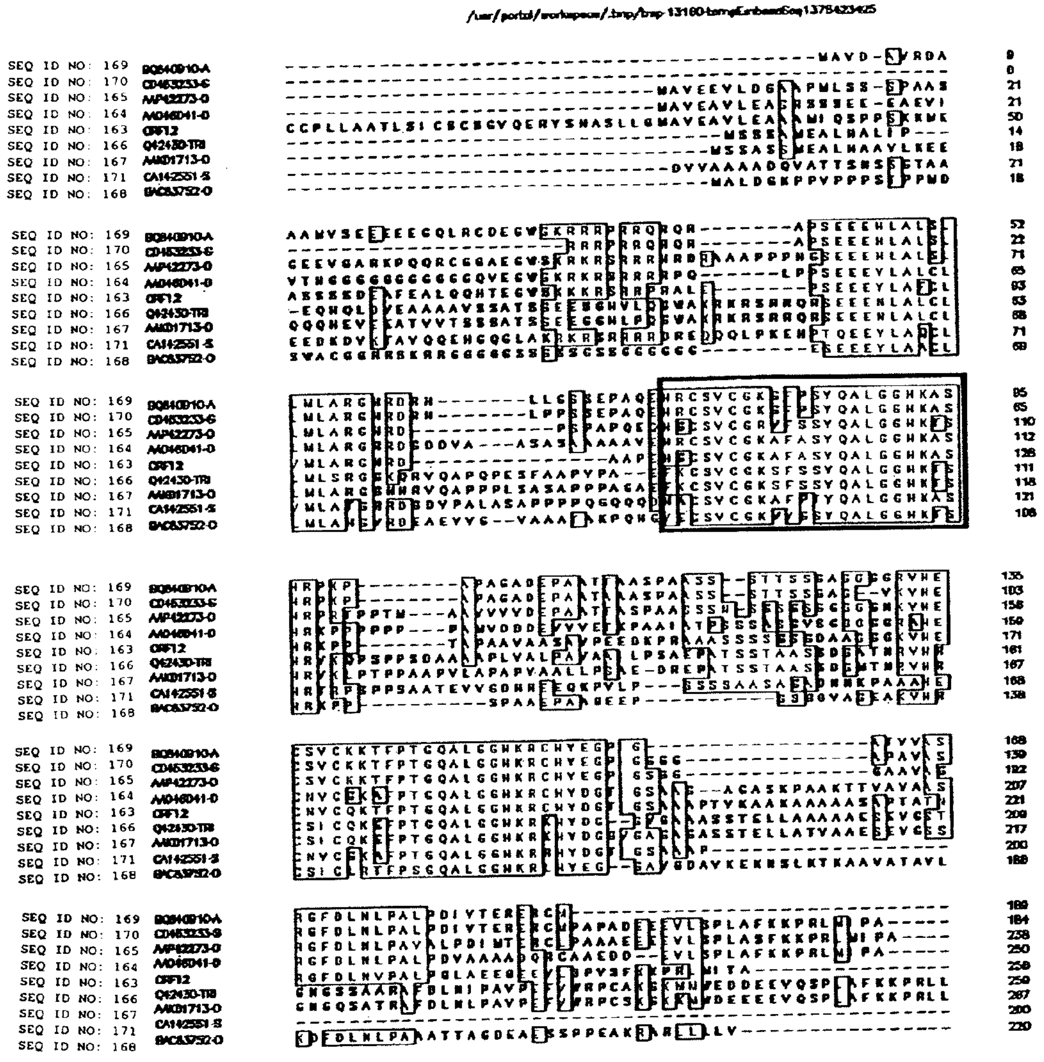
FIG. 6 shows an alignment of polypeptides of the invention, including SEQ ID NO: 163 and sequences which are variants SEQ ID NO: 163 from several *monocotyledonous* species and illustrates a consensus region (shown within bold box) identified by the applicants which is present in all of the such sequences.

A similar consensus motif (SEQ ID NO:5) was identified which was specific to ORF4 and all of the *dicotyledonous* variant sequences as shown in FIG. 5.

A further consensus motif (SEQ ID NO:6) was identified which was specific to ORF4 and all of the *monocotyledonous* variant sequences as shown in FIG. 6.

We note that the repeated QALGGHK motif discussed above which was identified in ORF12 is also repeated in all of the ORF12 polypeptide variants being separated by between 36 and 63 amino acid residues. This is thus a distinctive feature of ORF12 and all of the ORF12 variant sequences identified.

Example 3

Preparation of Vectors Comprising Polynucleotides of the Invention for Plant Transformation Vectors Comprising ORF4

Figure 7:
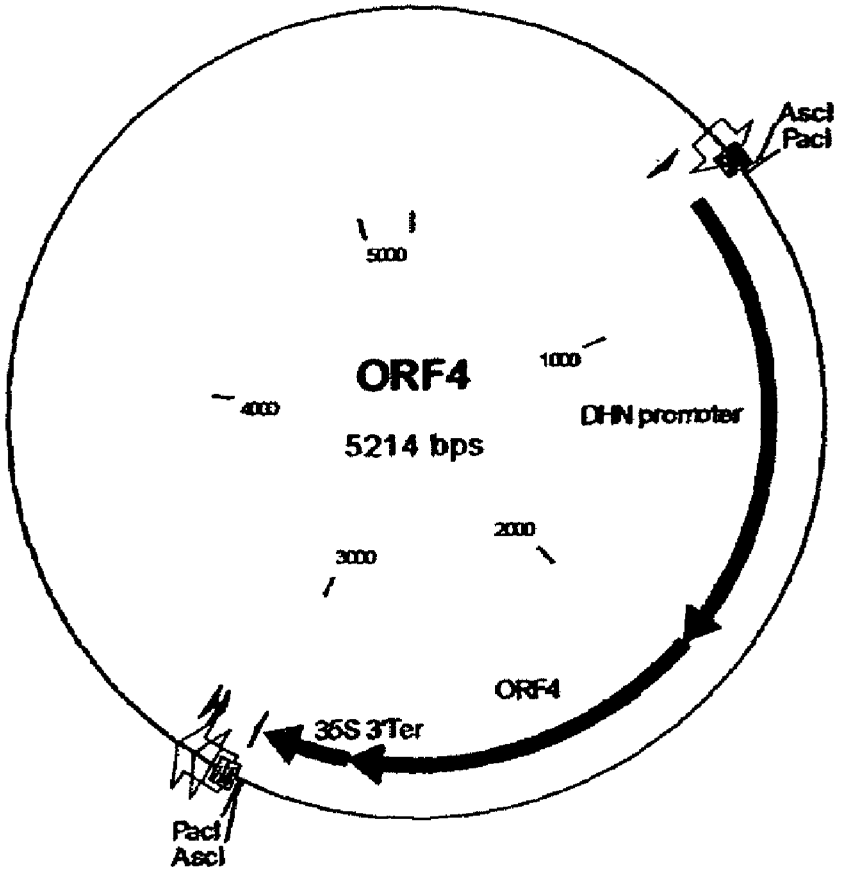
FIG. 7 shows a map of a vector, for plant transformation, comprising ORF4 (SEQ ID NO:82) driven by the ryegrass promoter of SEQ ID NO:239.

A vector comprising ORF4 driven by the ryegrass promoter of SEQ ID NO:239 was produced by standard molecular biology techniques. A map to vectors is shown in FIG. 7. The sequence of the vector (SEQ ID NO:240) is shown in FIG. 8.

Figure 11:
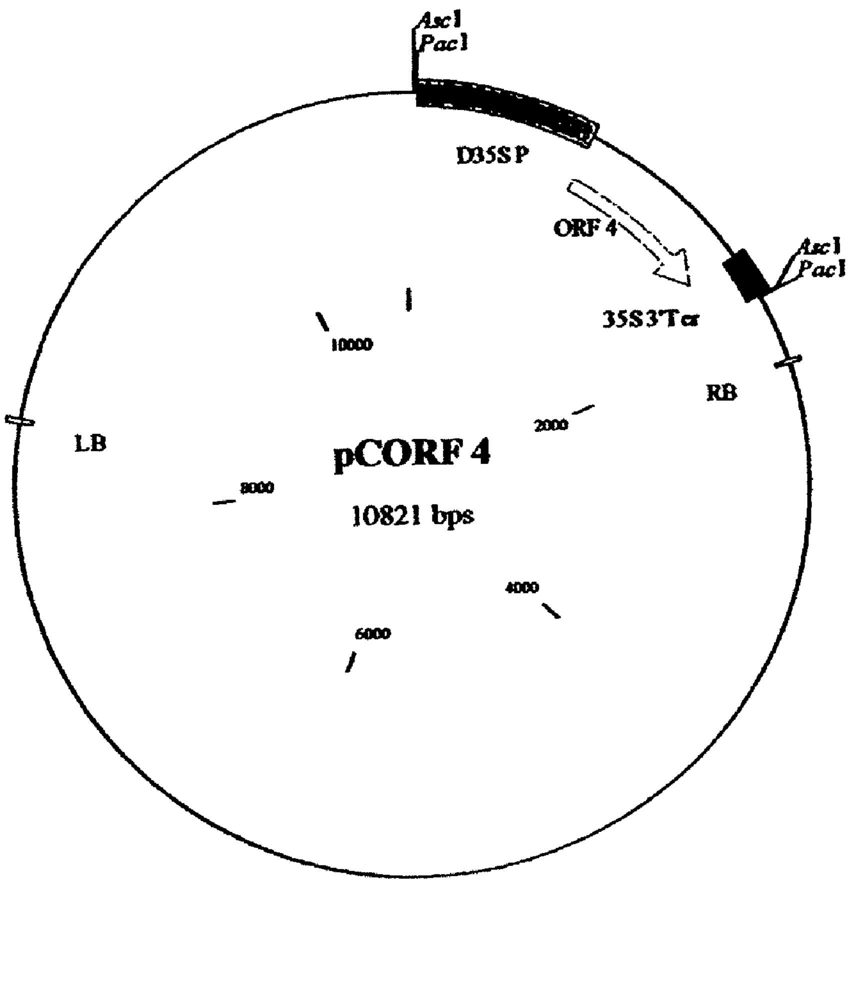
FIG. 11 shows a map of a vector, for plant transformation, comprising ORF4 (SEQ ID NO:82) driven by the double CaMV35S promoter.

A vector comprising ORF4 driven by the double CaMV35S promoter was produced by standard molecular biology techniques. A map to vectors is shown in FIG. 11. The sequence of the vector (SEQ ID NO:242) is shown in FIG. 12.

Vector Comprising ORF 12

Figure 9:
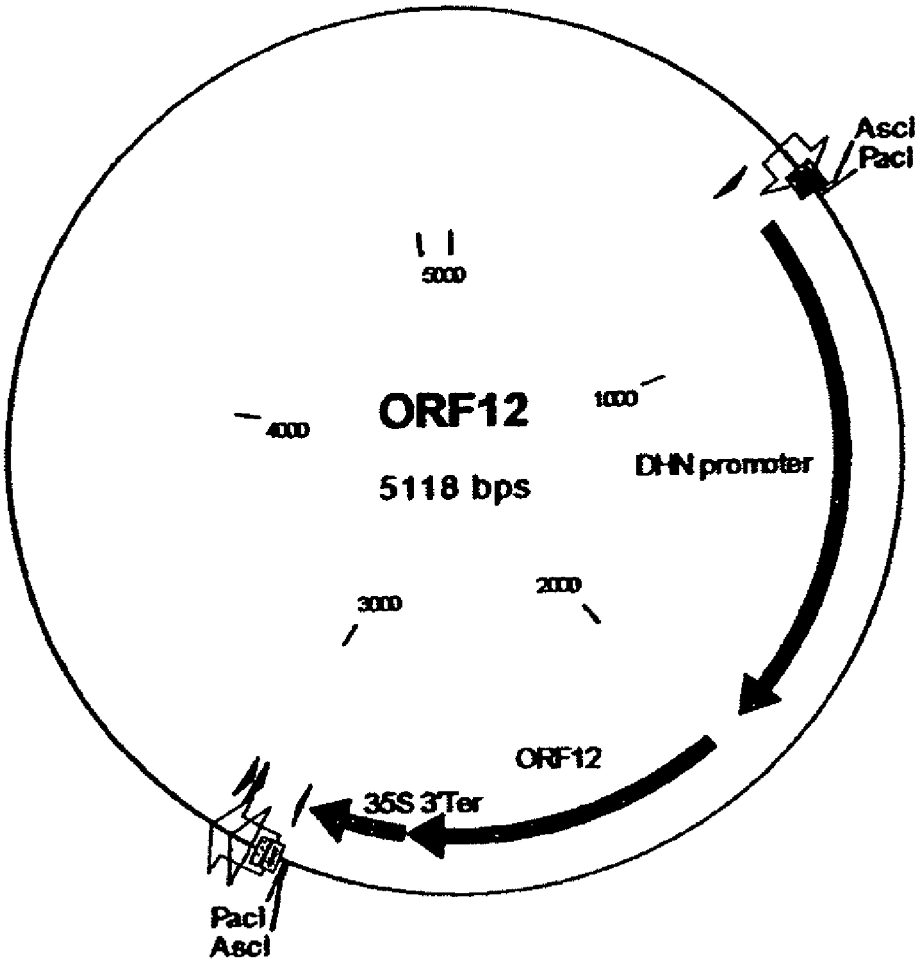
FIG. 9 shows a map of a vector, for plant transformation, comprising ORF12 (SEQ ID NO:201) driven by the ryegrass promoter of SEQ ID NO:243

A vector comprising ORF12 driven the by the ryegrass promoter of SEQ ID NO:239 was produced by standard molecular biology techniques. A map of the vector is shown in FIG. 9. The sequence (SEQ ID NO:241) and features of the vector is shown in FIG. 10.

Figure 13:
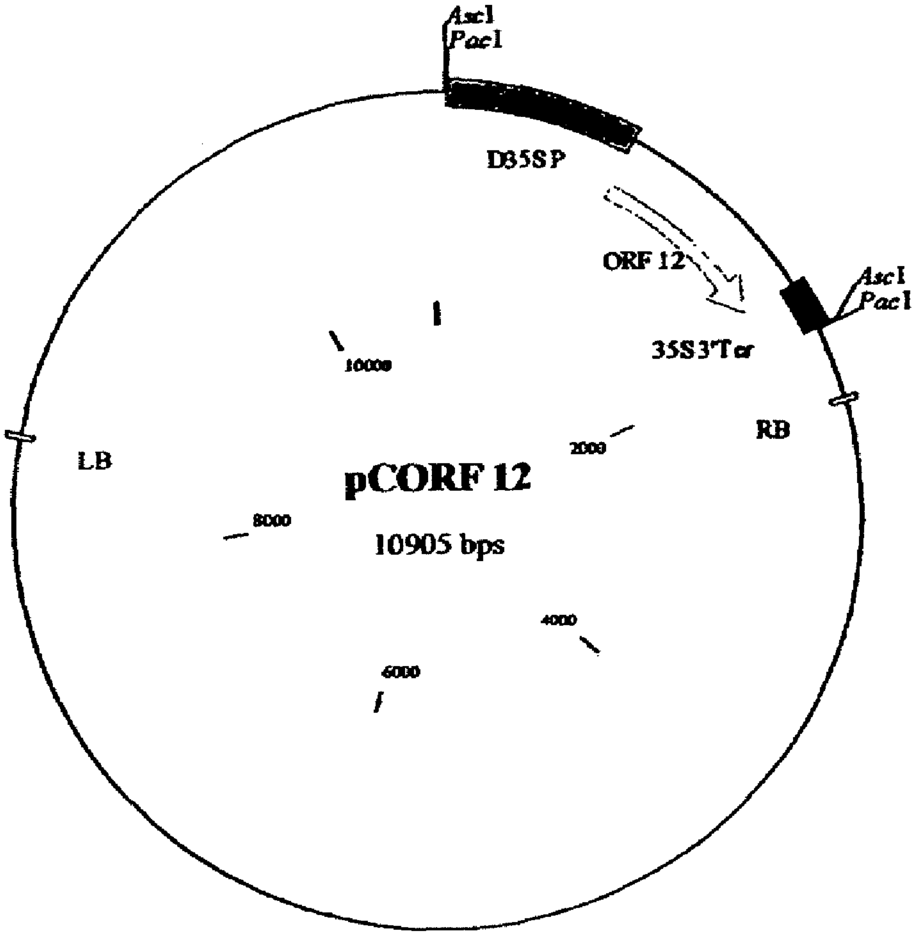
FIG. 13 shows a map of a vector, for plant transformation, comprising ORF12 (SEQ ID NO:201) driven by the double CaMV35S promoter.

A vector comprising ORF12 driven the by the double CaMV35S promoter was produced by standard molecular biology techniques. A map of the vector is shown in FIG. 13. The sequence (SEQ ID NO:243) and features of the vector is shown in FIG. 14.

Example 4

Transformation of Plants within the Polynucleotides of the Invention

Donor Plant Production to Obtain Tissue Culture Explants

Seeds to establish contamination free in-vitro cultures were surface sterilized for 3 minutes with 70% (v/v) ethanol; followed by 60 minutes with sodium hypochlorite solution (2.4% active Chlorine) supplemented with a surfactant (0.1% (w/v) of Tween-20 and five rinses with autoclaved distilled water. Plantlets of perennial ryegrass (*Lolium perenne L.*) cultivar 'Limes' (DSV Lippstadt/Germany) were clonally propagated in a 90 mm Petridish, containing Murashige and Skoog (Murashige, T and Skoog, F (1962) *Physiol. Plant* 15(3): 473-497) basal medium supplemented with 0.1 mg/l Benzylaminopurine; pH 5.8 and was solidified with 3.0 g/l phytagel (Sigma), at 16° C. during night and 20° C. during the day with 14/12 h light/dark cycle. Light intensity of at least 360 $\mu Em^{-2}s^{-1}$ at plant height was maintained with sodium vapor lights (SON-T AGRO 400, Phillips). Axillary buds approximately 4-10 mm in size were excised and placed on callus induction medium. 12 explants were cultured per 90mm petri-dish at 20 $\mu Em^{-2}s^{-1}$ and 25° C. for 28 to 56 days and calli sub-cultured to fresh medium every 14 days.

Biolistic Gene Transfer, Selection and Regeneration of Transgenic Plants

Calli were bombarded with DNA-coated particles six to ten weeks after culture of explants. Four to six hours prior to biolistic gene transfer calli were sub-cultured on medium with additional 64 $g.l^{-1}$ mannitol and retransferred to mannitol free callus subculture medium after the particle bombardment. Regeneration medium differed from the callus induction medium in the phytohormone composition (no 2,4-D and BAP) and the carbohydrate source and concentration (20 $g\text{-}l^{-1}$ sucrose). Calli were cultured in low light at 20 $\mu E.m^{-2}s^{-1}$ and 24° C. and regenerated initially at 50 $\mu E.m^{-}s^{-1}$ with a 16 h day, 8 h night cycle at 24° C. Two weeks after transfer to regeneration media light intensity was increased to 130 $\mu E.m^{-2}.s^{-1}$ with fluorescent lamps (Philips TL-D 58 W/840R).

The plasmid pJFnpt contains the selectable nptII gene, encoding the enzyme neomycin phosphotransferase II under control of the maize ubiquitin promoter and first intron (Christensen and Quail 1996, Transgenic Res., 5, 213-218). The nptII expression cassette from pJFnpt was inserted into the pPZP 111 vector [P Hajdukiewicz, Z Svab, and P Maliga, 1994 Plant Molecular Biology 25: 989-994,]. The plasmids pPZP 111, pCORF4, pCORF12, pDORF4 and pDORF12 were isolated as supercoiled DNA using commercially available DNA Maxiprep Kit. Vector backbone was removed from both the selectable marker gene expression cassette as well as from the target gene expression cassette by restriction digest, gel electrophoresis and gel purification prior gene transfer. Genetic transformation of perennial ryegrass was essentially carried out as described previously (Altpeter, F., Xu, J. and Ahmed S. 2000, Molecular Breeding, 6, 519-528). In brief, minimal transgene expression cassettes without vector backbone were precipitated on gold particles and delivered to target tissue in a 2:1 molar ratio (target gene expression cassette: selectable marker gene expression cassette) using a DuPont PDS-1000/He (BioRad, USA) device and 1100 psi rupture disks [Kikkert, J. R., 1993, Plant Cell, Tissue and Organ Culture, 33.(3) 221-226]. Particle density was adjusted by the final volume of ethanol in the gold-DNA suspension to 50 µg per bombardment. Five µl of the DNA coated particles were spread on the surface of the macrocarrier. Thirty to 35 callus pieces were put in the center of a petridish per bombardment six to ten weeks after callus initiation.

Selection was initiated five to seven days after biolistic gene transfer into calli. Two to three biweekly callus subcultures on CIM medium with 50 $mg.l^{-1}$ paromomycin were followed by two to three biweekly subcultures on 50 mg 1-1 paromomycin containing SRM medium. Four to eight weeks after transfer of selected calli to light, rooted transgenic plants were screened by performing an ELISA for nptII expression using leaf protein extracts. nptII positive plants were further screened by performing a genomic PCR involving ORF4 or ORF12 specific primers as appropriate. Positive primary transformants were transferred to soil under controlled environment conditions and kept at 15° C./12° C. day/night with a 12 hour photoperiod and 400 $\mu E.m^{-2}.s^{-1}$. Illumination was provided by sodium vapor lamps (Philips SON-T AGRO 400) and vegetatively propagated to produce clones of uniform size and growth. RT-PCR was carried out using standard methodology on regenerated plants to determine the transgene expression levels and lines for drought screening were selected based on the transgene expression level.

Transgenic lines transformed with the double CaMV 35-driven ORF4 cassette used in further experiments included: C4 14, C4-19 and C4-20.

Transgenic lines transformed with the ryegrass promoter (SEQ ID NO:239)-driven ORF4 cassette, used in further experiments included D4-1, D4-5, D4-7 and D4-32.

Transgenic lines transformed with the ryegrass promoter (SEQ ID NO:239)-driven ORF12 cassette, used in further experiments included D12-58, D12-60 and D12-61.

Example 5

Alteration in Tolerance to Environmental Stress in Plants Transformed with Polynucleotides of the Invention Drought Screening in Growth Chamber Based Hydroponics System.

Figure 15:
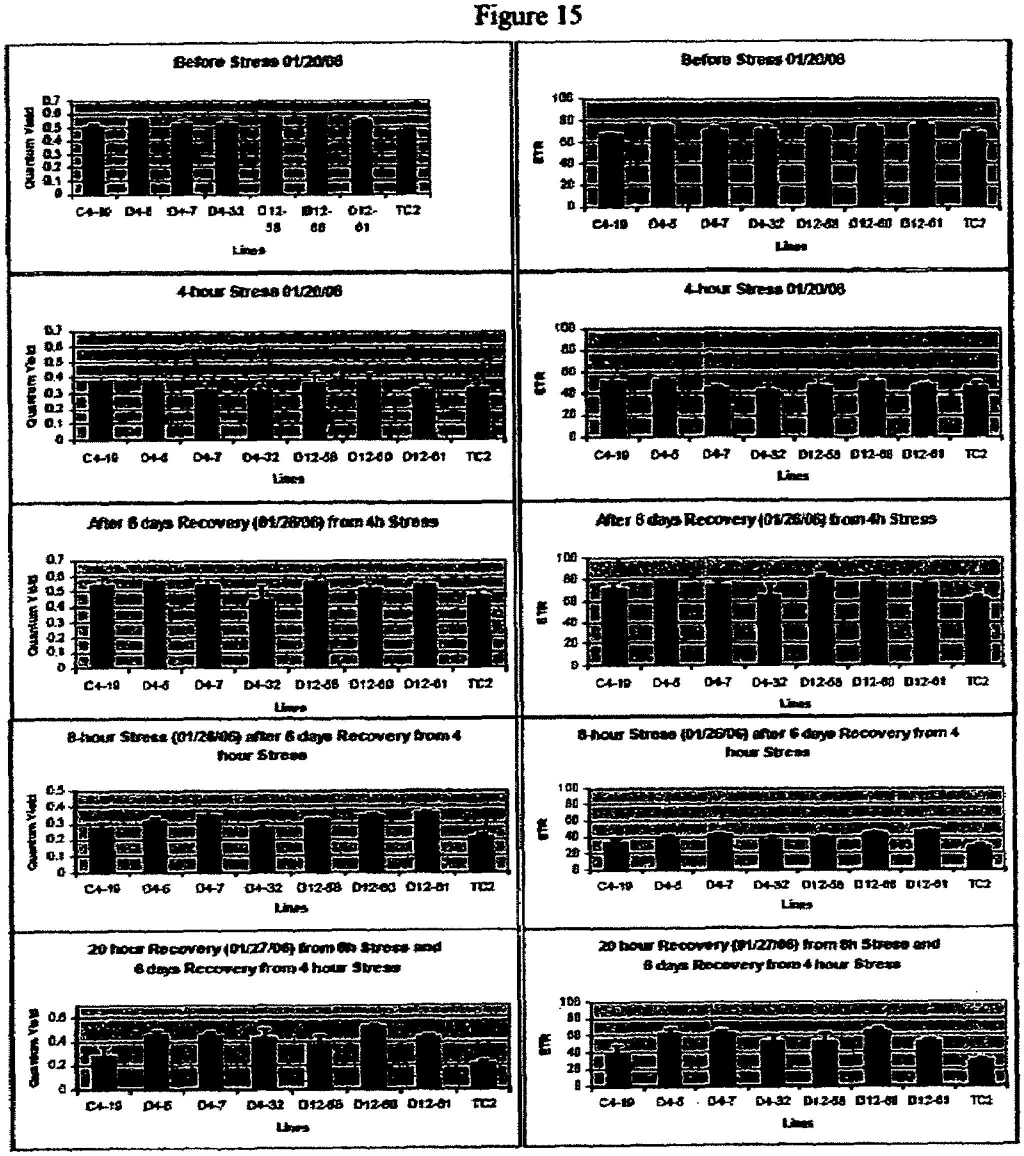
FIG. 15 shows measurements of Electron Transfer Rate (ETR) and Quantum Yield of PSII (Quantum yield), measured with PAM2000, in the leaves of transgenic (C4-14, D4-5, D4-7, D4-32, D12-58, D12-60 and D12-61) and non-transgenic (TC2) perennial ryegrass lines
Figure 16:
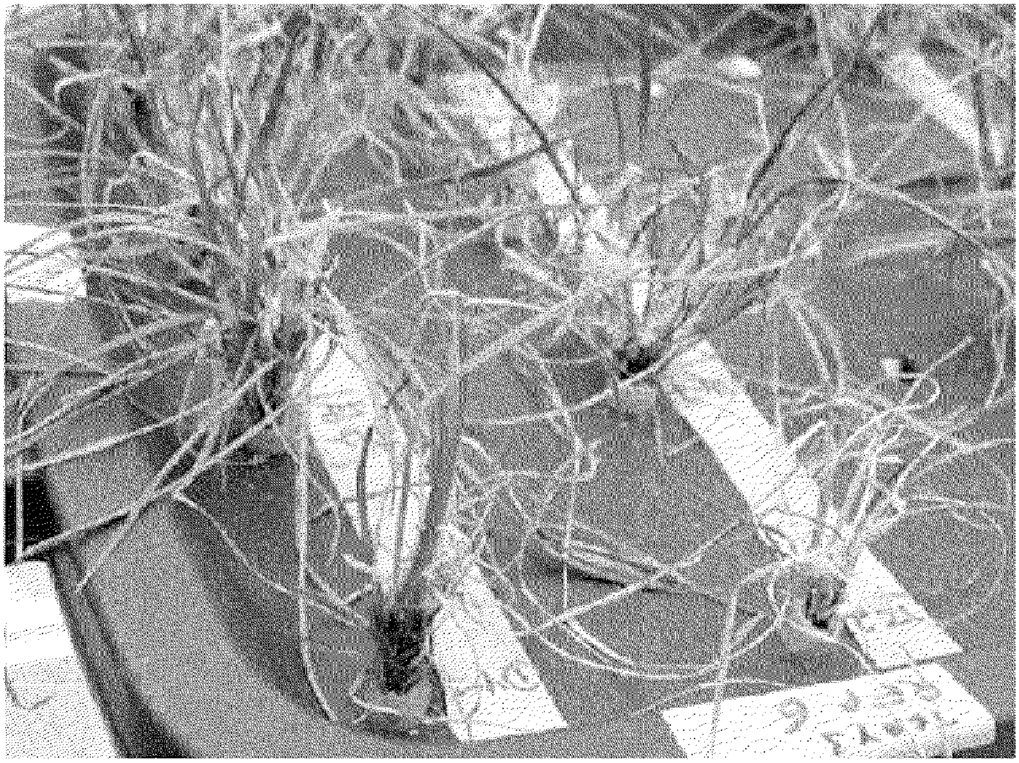
FIG. 16 shows phenotypic response at recovery stage following two cycles of drought (4-h drought, 6-days recovery, 8-hour drought, 20-h recovery) in transgenic (D4-5 bottom left, D12-58—above D4-5, and D4-7—above TC2) and non-transgenic (TC2—bottom right) perennial ryegrass lines

Clones of selected lines and a non-transgenic control line were established in a hydroponics system that was set up in a growth chamber. The experimental setup involved four replications. After establishment, the plants were exposed to two rounds of drought-stress (plants lifted up from the hydroponic system) comprising of 4 h drought followed by 6 days of recovery in the first cycle and then by 8 hours of drought and 20 h recovery in the second cycle. Biometric parameters such as Quantum yield of Photosystem II (yield) and Electron Transfer Rate (ETR) were measured using a Pulse Modulated Fluorometer (PAM2000) before the drought stress, at the end of the first drought cycle, at the end of the first recovery period, at the end of the second drought stress and finally at the end of the second recovery period (FIG. 15). Each data point in the figure represents the average of 12 measurements (three measurements per plant and four plants per line). The non-transgenic control fared poorly as when compared with its transgenic counterparts expressing either ORF4 or ORF12. FIG. 16 shows the condition of non-transgenic plant (TC 2, bottom right) and some of the transgenic lines at the end of the second recovery period.

Drought Screening in Glasshouse Based Potted Plants.

Figure 17:
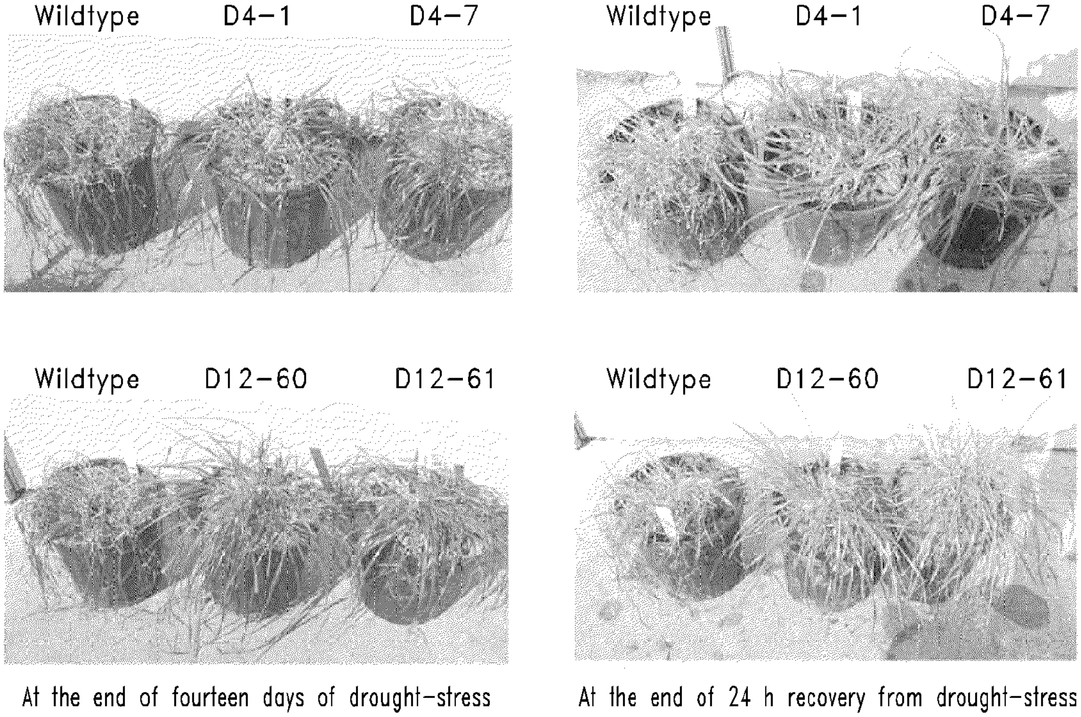
FIG. 17 shows phenotypic response of transgenic ryegrass lines (D4-1, D4-7, D12-60 and D12-61) in comparison to a non-transgenic line wildtype) at the end of 14-day drought-stress (left) and at the end of 1-day recovery from drought-stress (right)

Equal sized transgenic and non-transgenic clones were produced and established in pots filled with soil. Drought screening was carried out by withholding water for fourteen days and then the recovery observed after a day after irrigating the plants. Once again non-transgenic plants fared worse than the transgenic lines expressing either ORF4 or ORF12. FIG. 17 is a representative image of the outcome of this trial.

Drought Screening in SUN-Lit Chambers

Transgenic lines over-expressing ORF 4, or 12 were selected for a detailed physiological analysis in SUN-LIT chambers following their performance in hydroponic culture and soil (pots) under controlled environment conditions (growth chamber and greenhouse respectively). Six lines of transgenic ryegrass and a wildtype ryegrass (WT) were vegetatively propagated in the greenhouse before transplanting to the SPAR chamber, i.e., C4-19, C4-20, D4-1, D4-7, D12-60, D12-61, non-transgenic WT. These lines were randomized in a block design of 4 replications per chamber.

Soil Moisture Monitoring

Figure 18:
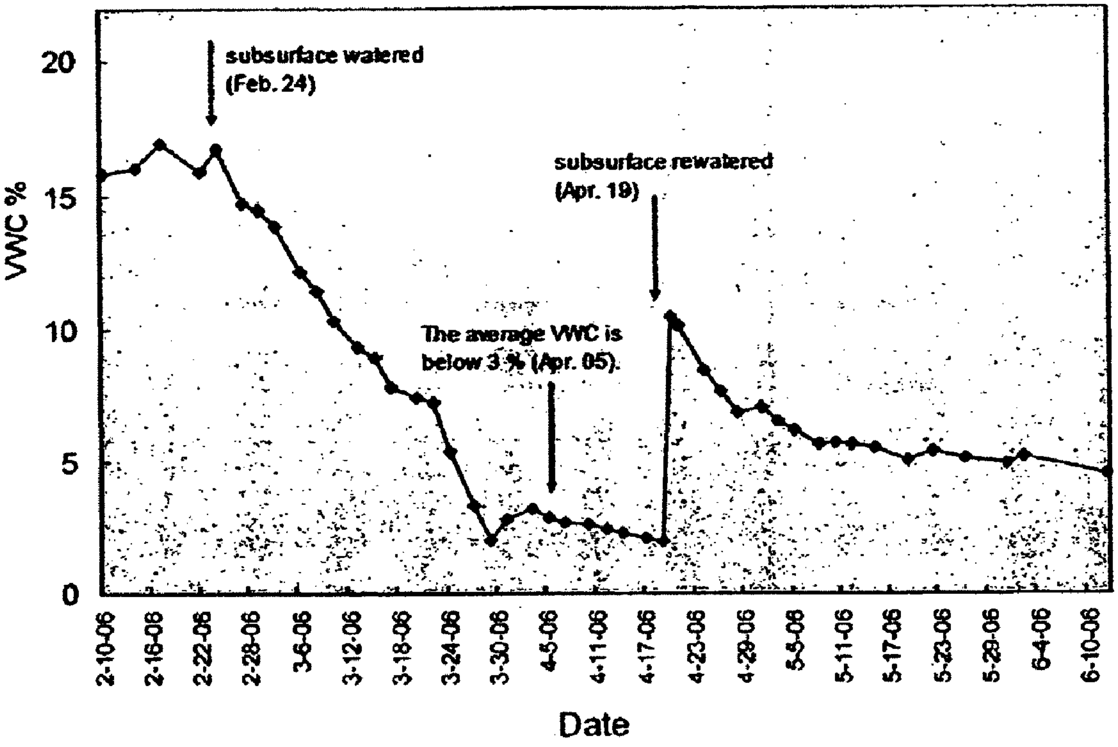
FIG. 18 shows measurement of Volumetric Water Content (VWC) of the soil during the experimental stage in the SUNLIT chamber as measured with a TDR300.
Figure 19:
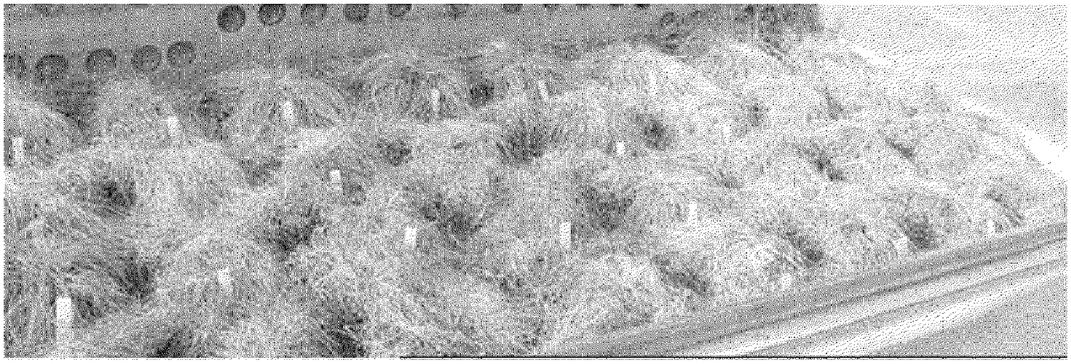
FIG. 19 shows phenotypic response of transgenic and non-transgenic ryegrass lines in the SUNLIT chamber after 54 days of sub-surface irrigation

The soil moisture (VWC, volumetric water content) was recorded with a TDR300 at an interval of two to three days starting $10^{th}$ Feb. 2006. Measurements were taken in each row between each of the plants at 20 cm depth (there were 28 positions for monitoring soil water status in each chamber). The time course of the VWC (every data point represents the VWC average of 28 positions) is shown in FIG. 18 and the dates for subsurface irrigation are indicated. Following the establishment period subsurface irrigation was cut on $24^{th}$ Feb. 2006. Soil moisture content declined and reached a VWC below 3% on $5^{th}$ Apr. 2006. A 54 days period of no-irrigation was followed by a re-growth period coupled with weekly biomass harvest during the second dry down cycle. Plants showed progressive wilting from $20^{th}$ Mar. 2006 and severe necrosis after 12Apr. 2006 (FIG. 19).

Chlorophyll Content in Different Lines

The chlorophyll content of leaves was measured with a chlorophyll meter (SPAD-502, Konica Minolta Sensing, Inc., Japan). For each plant, the second youngest, fully expanded leaf from three different tillers per plant was measured. Each data point in Table 3 represented the average of 12 measurements from the four clones of each transgenic line or wild type. The statistical significance levels of the difference in chlorophyll content between transgenic lines and wild type are shown: * significant difference at P<0.05; ** significant difference at P<0.01. The data indicate that three transgenic lines displayed higher chlorophyll contents than the wild type over the majority of time points: C4-20, D4-1 and D4-7 and that the chlorophyll content of D4-1 and D4-7 actually increased after the drought cycles (19 May 2006) as compared to pre-drought state (14 Feb. 2006).

TABLE 3

Different Levels Of Chlorophyll Contents In Non-Transgenic And Transgenic Lines

| Date | WT | C4-19 | C4-20 | D12-60 | D12-61 | D4-1 | D4-7 |
|---|---|---|---|---|---|---|---|
| 02-14 | 40.2 | 40.8 | 49.5** | 42.9 | 43.1* | 40.2 | 46.9** |
| 03-09 | 47.9 | 47.5 | 54.0* | 49.8** | 49.7 | 49.4 | 51.8* |
| 03-20 | 45.7 | 44.0 | 53.0* | 50.1 | 48.1 | 46.5 | 49.1* |
| 04-05 | 49.2 | 51.3 | 56.2* | 52.4 | 51.5 | 53.8 | 56.8* |
| 04-13 | 48.5 | 44.8** | 59.0** | 49.3 | 49.0 | 56.7** | 58.1** |
| 04-18 | 33.0 | 35.4 | 49.5** | 32.0 | 34.5 | 49.4** | 51.0** |
| 04-20 | 34.0 | 32.6 | 41.0** | 38.6 | 36.0 | 41.0* | 39.9* |
| 04-28 | 41.0 | 39.4 | 47.2** | 45.1* | 41.6 | 45.3** | 52.6** |
| 05-05 | 45.1 | 43.8 | 50.7* | 47.1 | 44.8 | 46.8 | 51.6* |
| 05-12 | 44.2 | 45.0 | 49.9** | 44.9 | 44.9 | 46.3 | 49.1* |
| 05-19 | 40.2 | 38.8 | 47.8** | 37.3 | 34.4 | 43.7 | 47.5 |

Chlorophyll fluorescence parameters (ETR & yield)

Figure 20:
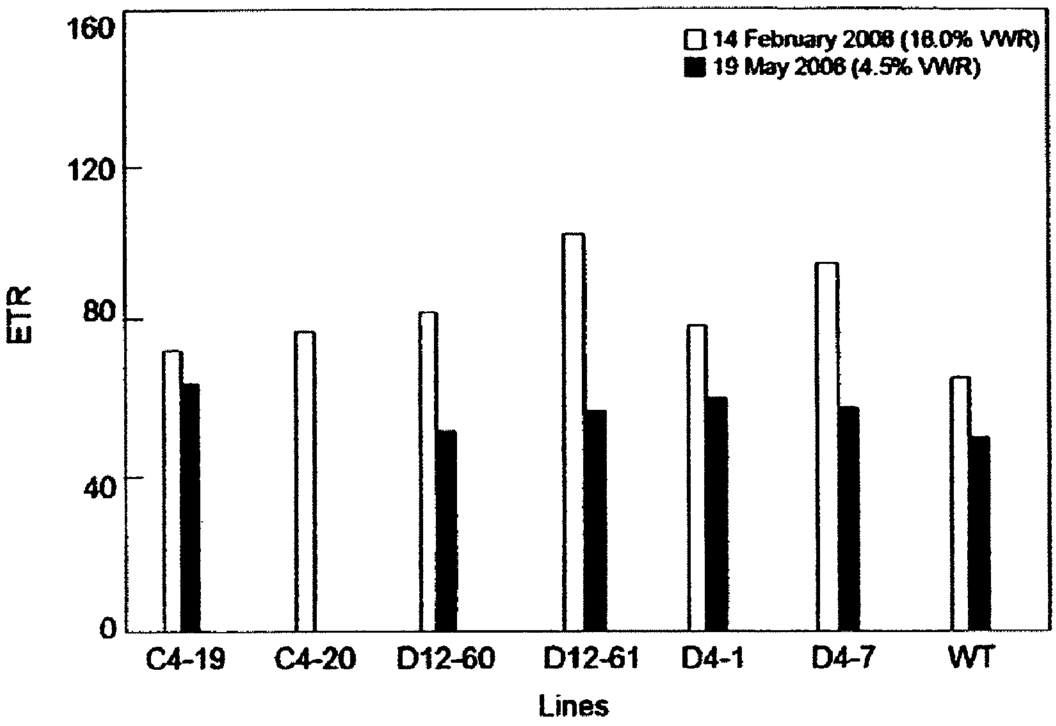
FIG. 20 shows measurements of Electron Transfer Rate (ETR) in the leaves of transgenic (C4-19, C4-20, D12-60, D12-61, D4-1 and D4-7) and non-transgenic (WT) perennial ryegrass lines grown in the SUNLIT chamber before drought-stress (white column) and at the end of the drought-stress (black column)
Figure 21:
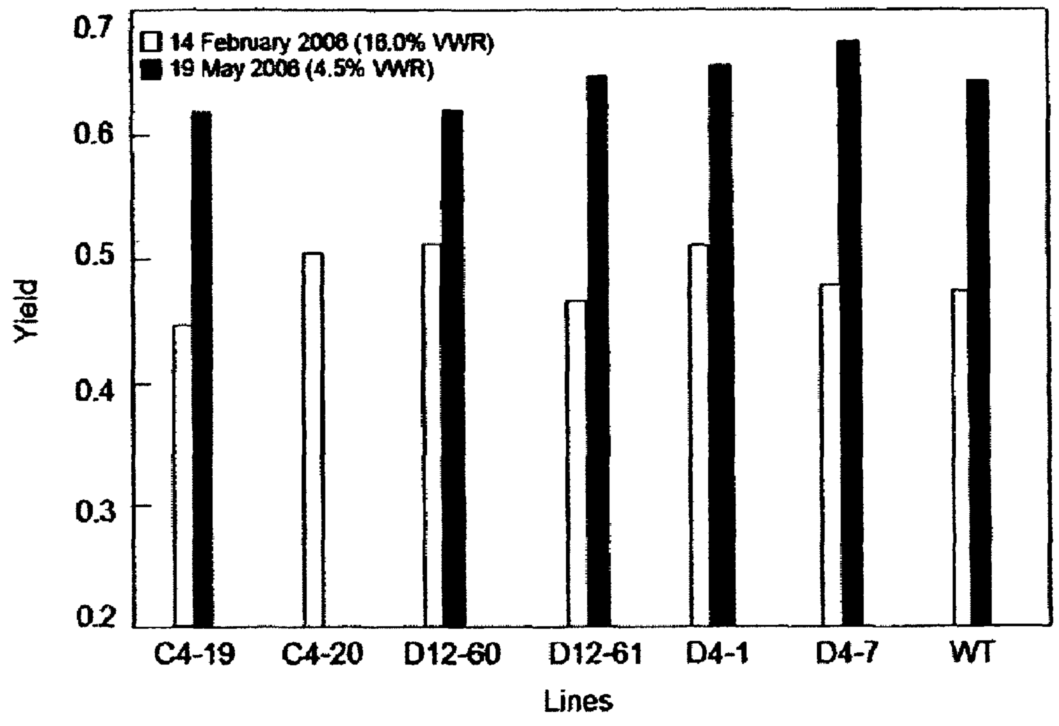
FIG. 21 shows measurements of Quantum Yield of PSII (Yield) in the leaves of transgenic (C4-19, C4-20, D12-60, D12-61, D4-1 and D4-7) and non-transgenic (WT) perennial ryegrass lines grown in the SUNLIT chamber before drought-stress (white column) and at the end of the drought-stress (black column)

The chlorophyll fluorescence parameters, electron transport rate (ETR) and quantum yield (Yield), were measured with the PAM2000 fluorometer and are presented in FIGS. 20 and 21, respectively. The second fully expanded leaf was measured from three tillers per plant. Each data point in the figures represents the average of 12 measurements (3 measurements per clone, four clones per line) for each line. The volumetric water content of the soil is given in brackets in the figure legend. The absence of data for C4-20 during the second round of drought period indicates that the leaves of these transgenic plants were too small or narrow to be measured. During severe stress (VWC less than 3%) the wildtype did not show a statistically lower ETR or yield than the transgenic lines although there were statistically significant differences in the chlorophyll contents.

Above-Ground Biomass

Figure 22:
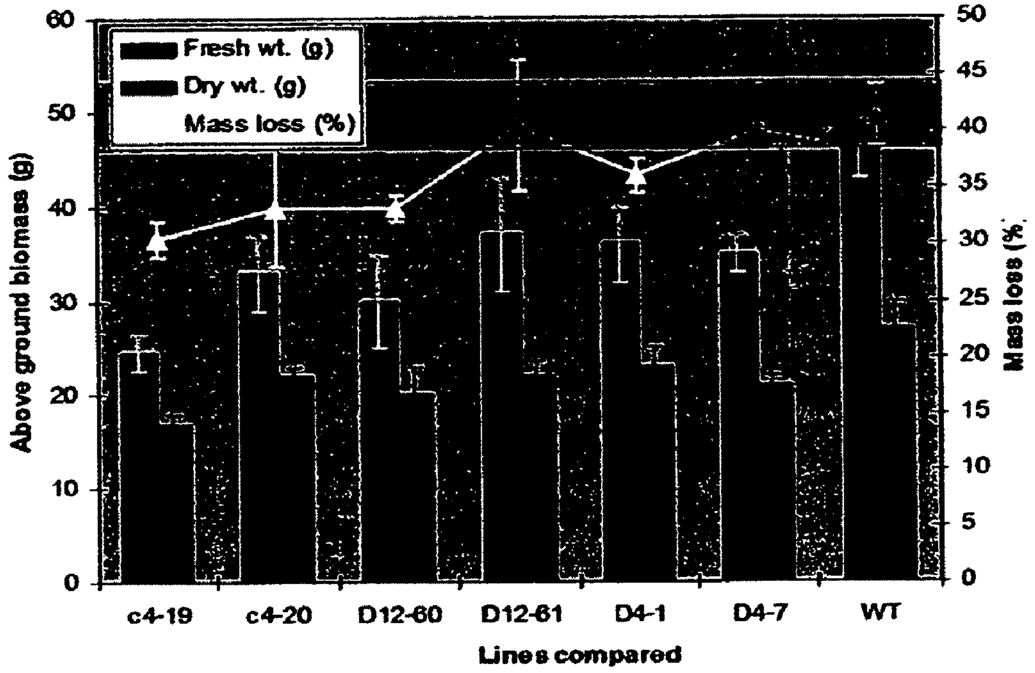
FIG. 22 shows measurement of above ground biomass (dark bars represent fresh weight and light bars represent dry weight) and % mass loss, two days after re-watering, post drought regime for transgenic (C4-19, C4-20, D12-60, D12-61, D4-1 and D4-7) and non-transgenic (WT) perennial ryegrass lines.

All leaves were cut 2 days after re-watering at 2.5 cm clipping height. The fresh weights (FW) of leaves were measured immediately, then leaves were dried at 80° C. for 48 h and the dry weight (DW) was measured. The difference between fresh weight and dry weight was used as an indicator of early recovery from drought stress. The aboveground biomass in chamber 1 and 2 produced since during the first dry down cycle is shown in FIG. 22. Mass loss indicates the difference of fresh weight and dry weight over fresh weight. No transgenic line produced significantly more biomass than wildtype in the first dry down cycle. However, transgenic lines C4-19, C4-20, D4-1 and D12-60 exhibited comparatively less biomass loss.

Figure 23:
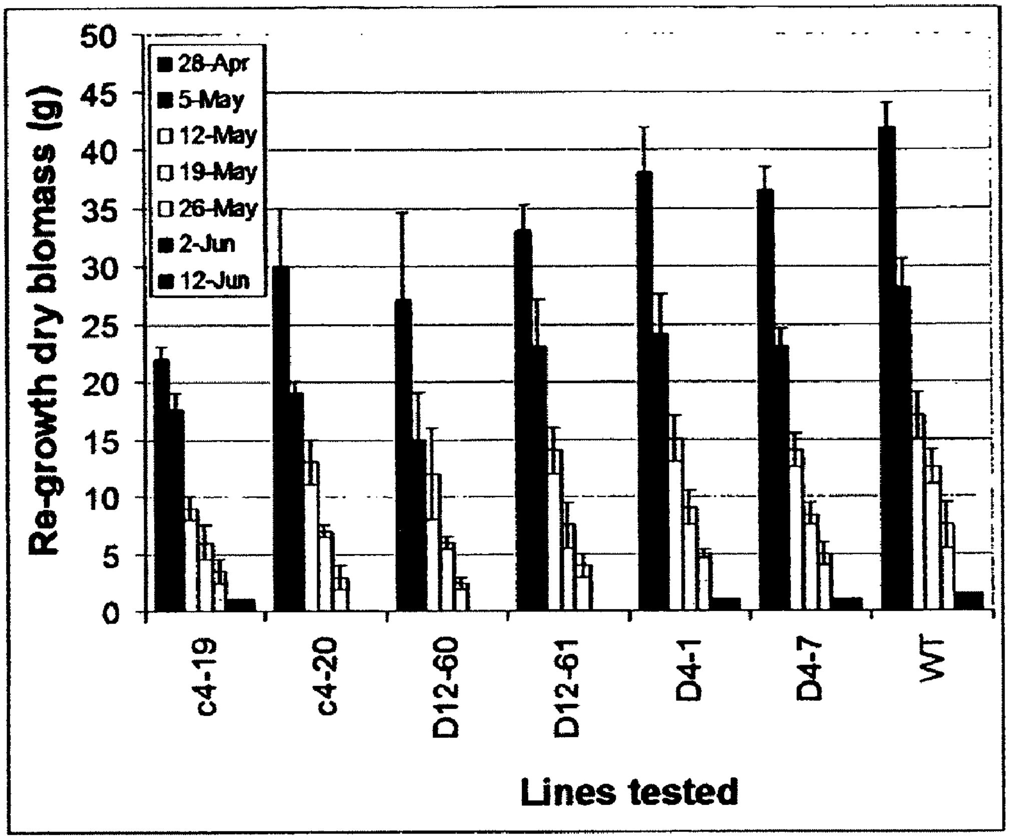
FIG. 23 shows newly produced above ground biomass during the during the drought screen, for transgenic (C4-19, C4-20, D12-60, D12-61, D4-1 and D4-7) and non-transgenic (WT) perennial ryegrass lines.

The time course of the newly produced leaf biomass (DW) during the second dry down cycle with clipping intervals of 7 to 10 days are shown in FIG. 23. The bars indicate the SE of four readings from four replications of each line in one chamber. With decreasing of soil moisture, the newly produced biomass of each line decreased. Wild type line, which had the highest biomass before the beginning of the trial, always had the highest amount of DW among all lines at any clipping time, but the differences declined with progressive drought stress and there was no significant difference between wildtype and transgenic lines at the $2^{nd}$ Jun. 2006 harvest. This indicates that the loss in the ability to produce aboveground biomass in the transgenic plants is lower than wild type under drought stress conditions.

The above examples illustrate practice of the invention. It will be appreciated by those skilled in the art that numerous variations and modifications may be made without departing from the spirit and scope of the invention.

-continued

SUMMARY OF SEQUENCES

| SEQ ID NO: | TYPE | SPECIES | REFERENCE |
|---|---|---|---|
| 1 | Polypeptide | Plant | Consensus |
| 2 | Polypeptide | Dicotyledonous | Consensus |
| 3 | Polypeptide | Monocotyledonous | Consensus |
| 4 | Polypeptide | *Lolium perenne* | ORF4 |
| 5 | Polypeptide | *Oryza sativa* | BAC8588.1 |
| 6 | Polypeptide | *Oryza sativa* | BAD03011.1 |
| 7 | Polypeptide | *Oryza sativa* | BAD07720.1 |
| 8 | Polypeptide | *Triticum aestivum* | BQ805537 |
| 9 | Polypeptide | *Hordeum vulgare* | BQ466561 |
| 10 | Polypeptide | *Oryza sativa* | CB683708 |
| 11 | Polypeptide | *Triticum aestivum* | BJ236148 |
| 12 | Polypeptide | *Triticum aestivum* | BE490521 |
| 13 | Polypeptide | *Hordeum vulgare* | BQ468417 |
| 14 | Polypeptide | *Triticum aestivum* | BJ292865 |
| 15 | Polypeptide | *Oryza sativa* | CB632480 |
| 16 | Polypeptide | *Triticum aestivum* | BJ282803 |
| 17 | Polypeptide | *Sorghum bicolor* | CN123916 |
| 18 | Polypeptide | *Sorghum bicolor* | CN139457 |
| 19 | Polypeptide | *Sorghum bicolor* | CF757974 |
| 20 | Polypeptide | *Zea mays* | CA830789 |
| 21 | Polypeptide | *Sorghum bicolor* | CF757859 |
| 22 | Polypeptide | *Zea mays* | AW120094 |
| 23 | Polypeptide | *Saccharum officinarum* | CA186576 |
| 24 | Polypeptide | *Saccharum officinarum* | CA135735 |
| 25 | Polypeptide | *Sorghum bicolor* | CN123829 |
| 26 | Polypeptide | *Triticum aestivum* | BJ299272 |
| 27 | Polypeptide | *Triticum aestivum* | BJ312914 |
| 28 | Polypeptide | *Triticum aestivum* | CK214681 |
| 29 | Polypeptide | *Zea mays* | BG841716 |
| 30 | Polypeptide | *Zea mays* | CD439661 |
| 31 | Polypeptide | *Sorghum bicolor* | CN130285 |
| 32 | Polypeptide | *Sorghum bicolor* | CN130210 |
| 33 | Polypeptide | *Hordeum vulgare* | BJ450702 |
| 34 | Polypeptide | *Sorghum bicolor* | BE601333 |
| 35 | Polypeptide | *Zea mays* | CB350589 |
| 36 | Polypeptide | *Zea mays* | BU092370 |
| 37 | Polypeptide | *Arabidopsis thaliana* | NP 200279.1 |
| 38 | Polypeptide | *Arabidopsis thaliana* | AAM64276.1 |
| 39 | Polypeptide | *Arabidopsis thaliana* | NP 175518.1 |
| 40 | Polypeptide | *Arabidopsis thaliana* | AAM10939.1 |
| 41 | Polypeptide | *Arabidopsis thaliana* | NP 188962.2 |
| 42 | Polypeptide | *Arabidopsis thaliana* | NP 567431.1 |
| 43 | Polypeptide | *Arabidopsis thaliana* | NP 849383.1 |
| 44 | Polypeptide | *Arabidopsis thaliana* | BAB01300.1 |
| 45 | Polypeptide | *Arabidopsis thaliana* | NP 188620.1 |
| 46 | Polypeptide | *Arabidopsis thaliana* | AAL91266.1 |
| 47 | Polypeptide | *Arabidopsis thaliana* | NP 849566.1 |
| 48 | Polypeptide | *Arabidopsis thaliana* | NP 195330.2 |
| 49 | Polypeptide | *Arabidopsis thaliana* | T05498 |
| 50 | Polypeptide | *Vitis vinifera* | CF518638 |
| 51 | Polypeptide | *Citrus reticulata* | CF830716 |
| 52 | Polypeptide | *Medicago trunculata* | BG647802 |
| 53 | Polypeptide | *Vitis vinifera* | CF212640 |
| 54 | Polypeptide | *Gossypium raimondii* | CO114007 |
| 55 | Polypeptide | *Citrus reticulata* | CF830658 |
| 56 | Polypeptide | *Solanum tuberosum* | CK273638 |
| 57 | Polypeptide | *Solanum tuberosum* | CK274846 |
| 58 | Polypeptide | *Solanum tubersoum* | CK272231 |
| 59 | Polypeptide | *Vitis vinifera* | CF212555 |
| 60 | Polypeptide | *Glycine max* | CF805866 |
| 61 | Polypeptide | *Solanum tuberosum* | CK270277 |
| 62 | Polypeptide | *Citrus reticulata* | CF830657 |
| 63 | Polypeptide | *Thellungiella halophila* | BM985503 |
| 64 | Polypeptide | *Populus tremuloides* | CF118919 |
| 65 | Polypeptide | *Vitis vinifera* | CF512838 |
| 66 | Polypeptide | *Brassica napus* | BQ704279 |
| 67 | Polypeptide | *Vitis vinifera* | CF518705 |
| 68 | Polypeptide | *Gossypium raimondii* | CO090106 |
| 69 | Polypeptide | *Populus tremuloides* | CF118982 |
| 70 | Polypeptide | *Prunus dulcis* | BU645447 |
| 71 | Polypeptide | *Glycine max* | BI972959 |
| 72 | Polypeptide | *Medicago trunculata* | CA918862 |
| 73 | Polypeptide | *Medicago trunculata* | CA922356 |
| 74 | Polypeptide | *Glycine max* | BQ253067 |
| 75 | Polypeptide | *Vitis vinifera* | CD800120 |
| 76 | Polypeptide | *Glycine soja* | BG043667 |
| 77 | Polypeptide | *Solanum tuberosum* | CK259672 |
| 78 | Polypeptide | *Gossypium raimondii* | CO079077 |
| 79 | Polypeptide | *Vitis vinifera* | CF518625 |
| 80 | Polypeptide | *Lycopersicon esculentum* | BG643869 |
| 81 | Polypeptide | *Pinus taeda* | CO364588 |
| 82 | Polynucleotide | *Lolium perenne* | ORF4 |
| 83 | polynucleotide | *Oryza sativa* | AB110196 |
| 84 | Polynucleotide | *Oryza sativa* | AP003876 |
| 85 | Polynucleotide | *Oryza sativa* | AP004121 |
| 86 | Polynucleotide | *Triticum aestivum* | BQ805537 |
| 87 | Polynucleotide | *Hordeum vulgare* | BQ466561 |
| 88 | Polynucleotide | *Oryza sativa* | CB683708 |
| 89 | Polynucleotide | *Triticum aestivum* | BJ236148 |
| 90 | Polynucleotide | *Triticum aestivum* | BE490521 |
| 91 | Polynucleotide | *Hordeum vulgare* | BQ468417 |
| 92 | Polynucleotide | *Triticum aestivum* | BJ292865 |
| 93 | Polynucleotide | *Oryza sativa* | CB632480 |
| 94 | Polynucleotide | *Triticum aestivum* | BJ282803 |
| 95 | Polynucleotide | *Sorghum bicolor* | CN123916 |
| 96 | Polynucleotide | *Sorghum bicolor* | CN139457 |
| 97 | Polynucleotide | *Sorghum bicolor* | CF757974 |
| 98 | Polynucleotide | *Zea mays* | CA830789 |
| 99 | Polynucleotide | *Sorghum bicolor* | CF757859 |
| 100 | Polynucleotide | *Zea mays* | AW120094 |
| 101 | Polynucleotide | *Saccharum officinarum* | CA186576 |
| 102 | Polynucleotide | *Saccharum officinarum* | CA135735 |
| 103 | Polynucleotide | *Sorghum bicolor* | CN123829 |
| 104 | Polynucleotide | *Triticum aestivum* | BJ299272 |
| 105 | Polynucleotide | *Triticum aestivum* | BJ312914 |
| 106 | Polynucleotide | *Triticum aestivum* | CK214681 |
| 107 | Polynucleotide | *Zea mays* | BG841716 |
| 108 | Polynucleotide | *Zea mays* | CD439661 |
| 109 | Polynucleotide | *Sorghum bicolor* | CN130285 |
| 110 | Polynucleotide | *Sorghum bicolor* | CN130210 |
| 111 | Polynucleotide | *Hordeum vulgare* | BJ450702 |
| 112 | Polynucleotide | *Sorghum bicolor* | BE601333 |
| 113 | Polynucleotide | *Zea mays* | CB350589 |
| 114 | Polynucleotide | *Zea mays* | BU092370 |
| 115 | Polynucleotide | *Arabidopsis thaliana* | NM 124849 |
| 116 | Polynucleotide | *Arabidopsis thaliana* | AY086197 |
| 117 | Polynucleotide | *Arabidopsis thaliana* | NM 103985 |
| 118 | Polynucleotide | *Arabidopsis thaliana* | AF488573 |
| 119 | Polynucleotide | *Arabidopsis thaliana* | NM 113222 |
| 120 | Polynucleotide | *Arabidopsis thaliana* | NM 117520 |
| 121 | Polynucleotide | *Arabidopsis thaliana* | NM 179052 |
| 122 | Polynucleotide | *Arabidopsis thaliana* | AB025631 |
| 123 | Polynucleotide | *Arabidopsis thaliana* | NM 112876 |
| 124 | Polynucleotide | *Arabidopsis thaliana* | AY090362 |
| 125 | Polynucleotide | *Arabidopsis thaliana* | NM 179235 |
| 126 | Polynucleotide | *Arabidopsis thaliana* | NM 119773 |
| 127 | Polynucleotide | *Arabidopsis thaliana* | AL022373 |
| 128 | Polynucleotide | *Vitis vinifera* | CF518638 |
| 129 | Polynucleotide | *Citrus reticulate* | CF830716 |
| 130 | Polynucleotide | *Medicago trunculata* | BG647802 |
| 131 | Polynucleotide | *Vitis vinifera* | CF212640 |
| 132 | Polynucleotide | *Gossypium raimondii* | CO114007 |
| 133 | Polynucleotide | *Citrus reticulata* | CF830658 |
| 134 | Polynucleotide | *Solanum tuberosum* | CK273638 |
| 135 | Polynucleotide | *Solanum tuberosum* | CK274846 |
| 136 | Polynucleotide | *Solanum tuberosum* | CK272231 |
| 137 | Polynucleotide | *Vitis vinifera* | CF212555 |
| 138 | Polynucleotide | *Glycine max* | CF805866 |
| 139 | Polynucleotide | *Solanum tuberosum* | CK270277 |
| 140 | Polynucleotide | *Citrus reticulata* | CF830657 |
| 141 | Polynucleotide | *Thellungiella halophila* | BM985503 |
| 142 | Polynucleotide | *Populus tremuloides* | CF118919 |
| 143 | Polynucleotide | *Vitis vinifera* | CF512838 |
| 144 | Polynucleotide | *Brassica napus* | BQ704279 |
| 145 | Polynucleotide | *Vitis vinifera* | CF518705 |
| 146 | Polynucleotide | *Gossypium raimondii* | CO090106 |
| 147 | Polynucleotide | *Populus tremuloides* | CF118982 |
| 148 | Polynucleotides | *Prunus dulcis* | BU645447 |

SUMMARY OF SEQUENCES

| SEQ ID NO: | TYPE | SPECIES | REFERENCE |
|---|---|---|---|
| 149 | Polynucleotide | Glycine max | BI972959 |
| 150 | Polynucleotide | Medicago trunculata | CA918862 |
| 151 | Polynucleotide | Medicago trunculata | CA922356 |
| 152 | Polynucleotide | Glycine max | BQ253067 |
| 153 | Polynucleotide | Vitis vinifera | CD800120 |
| 154 | Polynucleotide | Glycine soja | BG043667 |
| 155 | Polynucleotide | Solanum tuberosum | CK259672 |
| 156 | Polynucleotide | Gossypium raimondii | CO079077 |
| 157 | Polynucleotide | Vitis vinifera | CF518625 |
| 158 | Polynucleotide | Lycopersicon esculentum | BG643869 |
| 159 | Polynucleotide | Pinus taeda | CO364588 |
| 160 | Polypeptide | Plant | Consensus |
| 161 | Polypeptide | Dicotyledonous | Consensus |
| 162 | Polypeptide | Monocotyledonous | Consensus |
| 163 | Polypeptide | Lolium perenne | ORF12 |
| 164 | Polypeptide | Oryza sativa | AAO46041 |
| 165 | Polypeptide | Oryza sativa | AAP42273.1 |
| 166 | Polypeptide | Triticum aestivum | Q42430 |
| 167 | Polypeptide | Oryza sativa | AAK01713 |
| 168 | Polypeptide | Oryza sativa | BAC83752 |
| 169 | Polypeptide | Aegilops speltoides | BQ840910 |
| 170 | Polypeptide | Secale cereale | CD453233 |
| 171 | Polypeptide | Saccharum officinarum | CA142551 |
| 172 | Polypeptide | Nicotiana Benthamiana | AAQ54303 |
| 173 | Polypeptide | Capsicum annum | AAQ10954 |
| 174 | Polypeptide | Medicago sativa | CAB77055 |
| 175 | Polypeptide | Glycine max | T09602 |
| 176 | Polypeptide | Arabidopsis thaliana | AAF24959 |
| 177 | Polypeptide | Arabidopsis thaliana | NP 174094 |
| 178 | Polypeptide | Datisca glomerata | AAD26942 |
| 179 | Polypeptide | Arabidopsis thaliana | CAA67229 |
| 180 | Polypeptide | Petunia X hybrida | BAA05079 |
| 181 | Polypeptide | Arabidopsis thaliana | NP 188952 |
| 182 | Polypeptide | Arabidopsis thaliana | BAC43454 |
| 183 | Polypeptide | Arabidopsis thaliana | NP 196054 |
| 184 | Polypeptide | Brassica rapa | T14408 |
| 185 | Polypeptide | Brassica rapa | T14409 |
| 186 | Polypeptide | Nicotiana tabacum | T01985 |
| 187 | Polypeptide | Petunia X Hybrida | BAA05077 |
| 188 | Polypeptide | Arabidopsis thaliana | NP 199131 |
| 189 | Polypeptide | Arabidopsis thaliana | AAM67193 |
| 190 | Polypeptide | Arabidopsis thaliana | NP 190562 |
| 191 | Polypeptide | Petunia X hybrida | BAA05076 |
| 192 | Polypeptide | Arabidopsis thaliana | NP 201546 |
| 193 | Polypeptide | Solanum tuberosum | CK267005 |
| 194 | Polypeptide | Gossypium raimondii | CO122574 |
| 195 | Polypeptide | Vitis aestivalis | CB074681 |
| 196 | Polypeptide | Lycopersicon esculentum | BI421491 |
| 197 | Polypeptide | Medicago trunculata | BI308195 |
| 198 | Polypeptide | Populus sp. | BU884157 |
| 199 | Polypeptide | Citrus sinensis | CK938508 |
| 200 | Polypeptide | Lotus corniculatus | AP004523 |
| 201 | Polynucleotide | Lolium perenne | ORF12 |
| 202 | Polynucleotide | Oryza sativa | AY219847 |
| 203 | Polynucleotide | Oryza sativa | AY289189 |
| 204 | Polynucleotide | Triticum aestivum | D16415 |
| 205 | Polynucleotide | Oryza sativa | AF332876 |
| 206 | Polynucleotide | Oryza sativa | AP005149 |
| 207 | Polynucleotide | Aegilops speltoides | BQ840910 |
| 208 | Polynucleotide | Secale cereale | CD453233 |
| 209 | Polynucleotide | Saccarum officinarum | CA142551 |
| 210 | Polynucleotide | Nicotiana benthamiana | AY290702 |
| 211 | Polynucleotide | Capsicum annuum | AF539746 |
| 212 | Polynucleotide | Medicago sativa | Y18788 |
| 213 | Polynucleotide | Glycine max | GMU68763 |
| 214 | Polynucleotide | Arabidopsis thaliana | AC012375 |
| 215 | Polynucleotide | Arabidopsis thaliana | NM 102538 |
| 216 | Polynucleotide | Datisca glomerata | AF119050 |
| 217 | Polynucleotide | Arabidopsis thaliana | X98671 |
| 218 | Polynucleotide | Petunia X hybrida | D26086 |
| 219 | Polynucleotide | Arabidopsis thaliana | NM 112848 |
| 220 | Polynucleotide | Arabidopsis thaliana | AK118868 |
| 221 | Polynucleotide | Arabidopsis thaliana | NM 120516 |
| 222 | Polynucleotide | Brassica rapa | BRU76554 |
| 223 | Polynucleotide | Brassica rapa | BRU76555 |
| 224 | Polynucleotide | Nicotiana tabacum | AF053077 |
| 225 | Polynucleotide | Petunia X hybrida | D26084 |
| 226 | Polynucleotide | Arabidopsis Thaliana | NM 123683 |
| 227 | Polynucleotide | Arabidopsis thaliana | AY088887 |
| 228 | Polynucleotide | Arabidopsis thaliana | NM 114853 |
| 229 | Polynucleotide | Petunia x hybrida | D26083 |
| 230 | Polynucleotide | Arabidopsis thaliana | NM 126145 |
| 231 | Polynucleotide | Solanum tuberosum | CK267005 |
| 232 | Polynucleotide | Gossypium raimondii | CO122574 |
| 233 | Polynucleotide | Vitis aestivalis | CB074681 |
| 234 | Polynucleotide | Lycopersicon esculentum | BI421491 |
| 235 | Polynucleotide | Medicago trunculata | BI308195 |
| 236 | Polynucleotide | Populus sp. | BU884157 |
| 237 | Polynucleotide | Citrus sinensis | CK938508 |
| 238 | Polynucleotide | Lotus corniculatus | AP004523 |
| 239 | Polynucleotide | Lolium perenne | Promoter |
| 240 | Polynucleotide | — | Genetic construct ORF4 (FIG. 7/8) |
| 241 | Polynucleotide | — | Genetic Construct ORF 12 (FIG. 9/10) |
| 242 | Polynucleotide | — | Genetic construct pCORF 4 (FIG. 11/12) |
| 243 | Polynucleotide | — | Genetic construct (FIG. 13/14) pCORF 12 |
| 244 | Polypeptide | — | Motif |

What we claim is:

1. An isolated polynucleotide comprising a) a sequence encoding a polypeptide with at least 95% identity to the amino acid sequence of SEQ ID NO:4; or b) the complement of the sequence of a).

2. The isolated polynucleotide of claim 1, wherein the polypeptide has the amino acid sequence of SEQ ID NO:4.

3. The isolated polynucleotide of claim 1, wherein the sequence encoding the polypeptide in a) has at least 95% identity to the sequence of SEQ ID NO:82.

4. The isolated polynucleotide of claim 1, wherein the sequence encoding the polypeptide in a) has at least 95% identity to the coding sequence of SEQ ID NO:82.

5. The isolated polynucleotide of claim 1, wherein the sequence encoding the polypeptide in a) has the sequence of SEQ ID NO:82.

6. The isolated polynucleotide of claim 1, wherein the sequence encoding the polypeptide in a) has the coding sequence of SEQ ID NO:82.

7. The isolated polynucleotide of claim 1, wherein the polypeptide is derived from a plant species, and comprises the sequence of SEQ ID NO:1.

8. The isolated polynucleotide of claim 1, wherein the polypeptide is derived from a *dicotyledonous* species, and comprises the sequence of SEQ ID NO:2.

9. The isolated polynucleotide of claim 1, wherein the polypeptide is derived from a *monocotyledonous* species and comprises the sequence of SEQ ID NO:3.

10. An isolated polynucleotide encoding a polypeptide consisting of:

a) a sequence with at least 95% identity to the amino acid sequence of SEQ ID NO:4.

11. A genetic construct comprising the polynucleotide of claim 1.

12. A genetic construct comprising the polynucleotide of claim 10.

13. A host cell comprising a genetic construct of claim 11.

14. The host cell of claim 13 genetically modified to express an isolated polynucleotide comprising a) a sequence encoding a polypeptide with at least 95% identity to the amino acid sequence of SEQ ID NO:4; or b) the complement of the sequence of a).

15. A plant cell or plant comprising the genetic construct of claim 11, or a plant part, propagule, progeny or seed of the plant, wherein the plant part, propagule, progeny or seed of the plant comprises the genetic construct.

16. The plant cell or plant of claim 15 genetically modified to express a polynucleotide of claim 1, or a plant part, propagule, progeny or seed of the plant, wherein the plant part, propagule, progeny or seed of the plant expresses the polynucleotide.

17. A method for producing a plant cell or plant with altered tolerance to drought relative to a control plant, the method comprising the step of transformation of a plant cell or plant with a genetic construct including:

a) at least one polynucleotide comprising:

i) a sequence encoding a polypeptide with at least 95% identity to the amino acid sequence of SEQ ID NO:4; or ii) the complement of the sequence of a).

18. A method for selecting a plant with altered tolerance to drought relative to a control plant, the method comprising the steps:

i) testing of the plant for altered expression of a polynucleotide comprising:

a) a sequence encoding a polypeptide with at least 95% identity to the amino acid sequence of SEQ ID NO:4; or b) the complement of the sequence of a);

wherein altered expression of the polypeptide is indicative of the altered tolerance; and ii) selecting the plant with the altered expression.

19. A method for selecting a plant with altered tolerance to drought relative to a control plant, the method comprising the steps:

(i) testing of a plant for altered expression of a polypeptide comprising:

a) a sequence with at least 95% identity to the amino acid sequence of SEQ ID NO:4, wherein altered expression of the polypeptide is indicative of the altered tolerance; and (ii) selecting the plant with the altered expression.

* * * * *

SEQUENCE LISTING

```
<160> NUMBER OF SEQ ID NOS: 247

<210> SEQ ID NO 1
<211> LENGTH: 23
<212> TYPE: PRT
<213> ORGANISM: Artificial
<220> FEATURE:
<223> OTHER INFORMATION: plant consensus
<220> FEATURE:
<221> NAME/KEY: MISC_FEATURE
<222> LOCATION: (2)..(2)
<223> OTHER INFORMATION: Q, E, H, L, R, T or S
<220> FEATURE:
```

-continued

```
<221> NAME/KEY: MISC_FEATURE
<222> LOCATION: (3)..(3)
<223> OTHER INFORMATION: E, D or Q
<220> FEATURE:
<221> NAME/KEY: MISC_FEATURE
<222> LOCATION: (4)..(4)
<223> OTHER INFORMATION: K, R, A, E or T
<220> FEATURE:
<221> NAME/KEY: MISC_FEATURE
<222> LOCATION: (5)..(5)
<223> OTHER INFORMATION: I or S
<220> FEATURE:
<221> NAME/KEY: MISC_FEATURE
<222> LOCATION: (6)..(6)
<223> OTHER INFORMATION: K, R, D or N
<220> FEATURE:
<221> NAME/KEY: MISC_FEATURE
<222> LOCATION: (7)..(7)
<223> OTHER INFORMATION: E, D or S
<220> FEATURE:
<221> NAME/KEY: MISC_FEATURE
<222> LOCATION: (9)..(9)
<223> OTHER INFORMATION: K, T or I
<220> FEATURE:
<221> NAME/KEY: MISC_FEATURE
<222> LOCATION: (10)..(10)
<223> OTHER INFORMATION: A, V, S, T, D, V or Q
<220> FEATURE:
<221> NAME/KEY: MISC_FEATURE
<222> LOCATION: (11)..(11)
<223> OTHER INFORMATION: E or D
<220> FEATURE:
<221> NAME/KEY: MISC_FEATURE
<222> LOCATION: (13)..(13)
<223> OTHER INFORMATION: N, D, T or S
<220> FEATURE:
<221> NAME/KEY: MISC_FEATURE
<222> LOCATION: (14)..(14)
<223> OTHER INFORMATION: E or D
<220> FEATURE:
<221> NAME/KEY: MISC_FEATURE
<222> LOCATION: (15)..(15)
<223> OTHER INFORMATION: L or S
<220> FEATURE:
<221> NAME/KEY: MISC_FEATURE
<222> LOCATION: (17)..(17)
<223> OTHER INFORMATION: D, H or E
<220> FEATURE:
<221> NAME/KEY: MISC_FEATURE
<222> LOCATION: (20)..(20)
<223> OTHER INFORMATION: Q, H, R, L, V, T or A
<220> FEATURE:
<221> NAME/KEY: MISC_FEATURE
<222> LOCATION: (21)..(21)
<223> OTHER INFORMATION: K, R, V, T or S
<220> FEATURE:
<221> NAME/KEY: MISC_FEATURE
<222> LOCATION: (22)..(22)
<223> OTHER INFORMATION: L or M

<400> SEQUENCE: 1

Leu Xaa Xaa Xaa Xaa Xaa Xaa Leu Xaa Xaa Xaa Lys Xaa Xaa Xaa Arg
1               5                   10                  15

Xaa Glu Lys Xaa Xaa Xaa Lys
            20


<210> SEQ ID NO 2
<211> LENGTH: 23
<212> TYPE: PRT
<213> ORGANISM: Artificial
<220> FEATURE:
<223> OTHER INFORMATION: dicotyledonous consensus
<220> FEATURE:
<221> NAME/KEY: MISC_FEATURE
<222> LOCATION: (2)..(2)
<223> OTHER INFORMATION: Q, H, L, R, T or S
```

-continued

<220> FEATURE:
<221> NAME/KEY: MISC_FEATURE
<222> LOCATION: (3)..(3)
<223> OTHER INFORMATION: E, D or Q
<220> FEATURE:
<221> NAME/KEY: MISC_FEATURE
<222> LOCATION: (4)..(4)
<223> OTHER INFORMATION: K, R, A or E
<220> FEATURE:
<221> NAME/KEY: MISC_FEATURE
<222> LOCATION: (5)..(5)
<223> OTHER INFORMATION: I or S
<220> FEATURE:
<221> NAME/KEY: MISC_FEATURE
<222> LOCATION: (6)..(6)
<223> OTHER INFORMATION: K, R, D or N
<220> FEATURE:
<221> NAME/KEY: MISC_FEATURE
<222> LOCATION: (7)..(7)
<223> OTHER INFORMATION: E, D or S
<220> FEATURE:
<221> NAME/KEY: MISC_FEATURE
<222> LOCATION: (9)..(9)
<223> OTHER INFORMATION: K, T or I
<220> FEATURE:
<221> NAME/KEY: MISC_FEATURE
<222> LOCATION: (10)..(10)
<223> OTHER INFORMATION: A, V, S, T, D or Q
<220> FEATURE:
<221> NAME/KEY: MISC_FEATURE
<222> LOCATION: (11)..(11)
<223> OTHER INFORMATION: E or D
<220> FEATURE:
<221> NAME/KEY: MISC_FEATURE
<222> LOCATION: (13)..(13)
<223> OTHER INFORMATION: N, T or S
<220> FEATURE:
<221> NAME/KEY: MISC_FEATURE
<222> LOCATION: (14)..(14)
<223> OTHER INFORMATION: E or D
<220> FEATURE:
<221> NAME/KEY: MISC_FEATURE
<222> LOCATION: (17)..(17)
<223> OTHER INFORMATION: D or E
<220> FEATURE:
<221> NAME/KEY: MISC_FEATURE
<222> LOCATION: (20)..(20)
<223> OTHER INFORMATION: Q, H, R, L, T or A
<220> FEATURE:
<221> NAME/KEY: MISC_FEATURE
<222> LOCATION: (21)..(21)
<223> OTHER INFORMATION: K, R, V, T or S
<220> FEATURE:
<221> NAME/KEY: MISC_FEATURE
<222> LOCATION: (22)..(22)
<223> OTHER INFORMATION: L or M

<400> SEQUENCE: 2

```
Leu Xaa Xaa Xaa Xaa Xaa Xaa Leu Xaa Xaa Xaa Lys Xaa Xaa Leu Arg
1               5                   10                  15

Xaa Glu Lys Xaa Xaa Xaa Lys
            20
```

<210> SEQ ID NO 3
<211> LENGTH: 23
<212> TYPE: PRT
<213> ORGANISM: Artificial
<220> FEATURE:
<223> OTHER INFORMATION: monocotyledonous consensus
<220> FEATURE:
<221> NAME/KEY: MISC_FEATURE
<222> LOCATION: (2)..(2)
<223> OTHER INFORMATION: Q, E or R
<220> FEATURE:
<221> NAME/KEY: MISC_FEATURE
<222> LOCATION: (3)..(3)

-continued

<223> OTHER INFORMATION: E or D
<220> FEATURE:
<221> NAME/KEY: MISC_FEATURE
<222> LOCATION: (4)..(4)
<223> OTHER INFORMATION: K or T
<220> FEATURE:
<221> NAME/KEY: MISC_FEATURE
<222> LOCATION: (6)..(6)
<223> OTHER INFORMATION: K or R
<220> FEATURE:
<221> NAME/KEY: MISC_FEATURE
<222> LOCATION: (7)..(7)
<223> OTHER INFORMATION: E or D
<220> FEATURE:
<221> NAME/KEY: MISC_FEATURE
<222> LOCATION: (10)..(10)
<223> OTHER INFORMATION: A or V
<220> FEATURE:
<221> NAME/KEY: MISC_FEATURE
<222> LOCATION: (11)..(11)
<223> OTHER INFORMATION: E or D
<220> FEATURE:
<221> NAME/KEY: MISC_FEATURE
<222> LOCATION: (13)..(13)
<223> OTHER INFORMATION: N or D
<220> FEATURE:
<221> NAME/KEY: MISC_FEATURE
<222> LOCATION: (15)..(15)
<223> OTHER INFORMATION: L or S
<220> FEATURE:
<221> NAME/KEY: MISC_FEATURE
<222> LOCATION: (17)..(17)
<223> OTHER INFORMATION: D or H
<220> FEATURE:
<221> NAME/KEY: MISC_FEATURE
<222> LOCATION: (20)..(20)
<223> OTHER INFORMATION: Q or V
<220> FEATURE:
<221> NAME/KEY: MISC_FEATURE
<222> LOCATION: (21)..(21)
<223> OTHER INFORMATION: K, R or T
<220> FEATURE:
<221> NAME/KEY: MISC_FEATURE
<222> LOCATION: (22)..(22)
<223> OTHER INFORMATION: L or M

<400> SEQUENCE: 3

```
Leu Xaa Xaa Xaa Ile Xaa Xaa Leu Lys Xaa Xaa Lys Xaa Glu Xaa Arg
1               5                   10                  15

Xaa Glu Lys Xaa Xaa Xaa Lys
            20
```

<210> SEQ ID NO 4
<211> LENGTH: 254
<212> TYPE: PRT
<213> ORGANISM: Lolium perenne

<400> SEQUENCE: 4

```
Met Ala Ser Pro Glu Gly Ala Asn Trp Val Phe Asp Cys Pro Leu Met
1               5                   10                  15

Asp Asp Leu Ala Ala Ala Asp Phe Thr Ala Pro Pro Ala Gly Gly Phe
            20                  25                  30

Tyr Trp Ala Pro Pro Met Gln Pro Gln Met His Thr Gln Ala Pro Ala
        35                  40                  45

Val Ser Ala Thr Pro Pro Pro Asn His Cys Ala Glu Ile Asn Ser Pro
    50                  55                  60

Ile Ser Val Asp Trp Asp His Ala Lys Gly Gln Pro Thr Asn Lys Arg
65                  70                  75                  80

Pro Arg Ser Glu Ser Gly Ala Gln Pro Ser Ser Lys Ala Cys Arg Glu
                85                  90                  95
```

-continued

```
Lys Ala Arg Arg Asp Lys Leu Asn Glu Arg Phe Leu Glu Leu Gly Ala
            100                 105                 110

Val Leu Asp Pro Gly Lys Thr Pro Lys Ile Asp Lys Cys Ala Ile Leu
        115                 120                 125

Asn Asp Ala Ile Arg Ala Val Thr Glu Leu Arg Ser Glu Ala Glu Lys
    130                 135                 140

Leu Lys Asp Ser Asn Glu Ser Leu Gln Glu Lys Ile Lys Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln Ser
            180                 185                 190

Leu Val Pro His Leu Pro His Pro Ser Val Ile Pro Ala Ala Ala Phe
        195                 200                 205

Ala Ala Pro Gln Gly Gln Val Pro Gly Gln Lys Leu Met Met Pro Val
    210                 215                 220

Ile Gly Tyr His Gly Phe Pro Met Trp Gln Phe Met Pro Pro Ser Asp
225                 230                 235                 240

Val Asp Thr Ser Asp Asp Pro Lys Ser Cys Pro Pro Val Ala
                245                 250


<210> SEQ ID NO 5
<211> LENGTH: 256
<212> TYPE: PRT
<213> ORGANISM: Oryza sativa

<400> SEQUENCE: 5

Met Ala Ser Pro Glu Gly Ser Thr Trp Val Phe Asp Cys Pro Leu Met
1               5                   10                  15

Asp Asp Leu Ala Ala Ala Ala Gly Phe Asp Ala Ala Pro Ala Gly Gly
            20                  25                  30

Phe Tyr Trp Thr Thr Pro Ala Pro Pro Gln Ala Ala Leu Gln Pro Pro
        35                  40                  45

Pro Pro Gln Gln Gln Pro Val Ala Pro Ala Thr Ala Ala Pro Asn Ala
    50                  55                  60

Cys Ala Glu Ile Asn Gly Ser Val Asp Cys Glu His Gly Lys Glu Gln
65                  70                  75                  80

Pro Thr Asn Lys Arg Pro Arg Ser Glu Ser Gly Thr Arg Pro Ser Ser
                85                  90                  95

Lys Ala Cys Arg Glu Lys Val Arg Arg Asp Lys Leu Asn Glu Arg Phe
            100                 105                 110

Leu Glu Leu Gly Ala Val Leu Glu Pro Gly Lys Thr Pro Lys Met Asp
        115                 120                 125

Lys Ser Ser Ile Leu Asn Asp Ala Ile Arg Val Met Ala Glu Leu Arg
    130                 135                 140

Ser Glu Ala Gln Lys Leu Lys Glu Ser Asn Glu Ser Leu Gln Glu Lys
145                 150                 155                 160

Ile Lys Glu Leu Lys Ala Glu Lys Asn Glu Leu Arg Asp Glu Lys Gln
                165                 170                 175

Lys Leu Lys Ala Glu Lys Glu Ser Leu Glu Gln Gln Ile Lys Phe Leu
            180                 185                 190

Asn Ala Arg Pro Ser Phe Val Pro His Pro Pro Val Ile Pro Ala Ser
        195                 200                 205

Ala Phe Thr Ala Pro Gln Gly Gln Ala Ala Gly Gln Lys Leu Met Met
```

-continued

```
    210                 215                 220

Pro Val Ile Gly Tyr Pro Gly Phe Pro Met Trp Gln Phe Met Pro Pro
225                 230                 235                 240

Ser Asp Val Asp Thr Thr Asp Asp Thr Lys Ser Cys Pro Pro Val Ala
                245                 250                 255


<210> SEQ ID NO 6
<211> LENGTH: 253
<212> TYPE: PRT
<213> ORGANISM: Oryza sativa

<400> SEQUENCE: 6

Met Ser Gly Thr Pro Ala Asp Gly Gly Gly Gly Gly Gly Gly Gly Gly
1               5                   10                  15

Gly Gly Ser Gly Asp Asp Trp Phe Leu Asp Cys Gly Ile Leu Glu Asp
            20                  25                  30

Leu Pro Ala Ala Ala Cys Gly Ala Phe Pro Trp Asp Ala Ser Pro Ser
        35                  40                  45

Cys Ser Asn Pro Ser Val Glu Val Ser Ser Tyr Val Asn Thr Thr Ser
    50                  55                  60

Tyr Val Leu Lys Glu Pro Gly Ser Asn Lys Arg Val Arg Ser Gly Ser
65                  70                  75                  80

Cys Gly Arg Pro Thr Ser Lys Ala Ser Arg Glu Lys Ile Arg Arg Asp
                85                  90                  95

Lys Met Asn Asp Arg Phe Leu Glu Leu Gly Thr Thr Leu Glu Pro Gly
            100                 105                 110

Lys Pro Val Lys Ser Asp Lys Ala Ala Ile Leu Ser Asp Ala Thr Arg
        115                 120                 125

Met Val Ile Gln Leu Arg Ala Glu Ala Lys Gln Leu Lys Asp Thr Asn
    130                 135                 140

Glu Ser Leu Glu Asp Lys Ile Lys Glu Leu Lys Ala Glu Lys Asp Glu
145                 150                 155                 160

Leu Arg Asp Glu Lys Gln Lys Leu Lys Val Glu Lys Glu Thr Leu Glu
                165                 170                 175

Gln Gln Val Lys Ile Leu Thr Ala Thr Pro Ala Tyr Met Pro His Pro
            180                 185                 190

Thr Leu Met Pro Ala Pro Tyr Pro Gln Ala Pro Leu Ala Pro Phe His
        195                 200                 205

His Ala Gln Gly Gln Ala Ala Gly Gln Lys Leu Met Met Pro Phe Val
    210                 215                 220

Gly Tyr Pro Gly Tyr Pro Met Trp Gln Phe Met Pro Pro Ser Glu Val
225                 230                 235                 240

Asp Thr Ser Lys Asp Ser Glu Ala Cys Pro Pro Val Ala
                245                 250


<210> SEQ ID NO 7
<211> LENGTH: 236
<212> TYPE: PRT
<213> ORGANISM: Oryza sativa

<400> SEQUENCE: 7

Met Asp Gly Gly Gly Asp Pro Val Asp Glu Phe Leu Ile Gly Gly Gly
1               5                   10                  15

Gly Glu Asp Gly Asp Leu Gly Val Phe Cys Asp Gly Val Pro Thr Leu
            20                  25                  30

Pro Cys Asp Gly Gly Leu Gly Ile Asp Asp Val Ser Gly Asp Thr Cys
```

-continued

```
        35                  40                  45

Cys Leu Asp Gln Ser Val Leu Gly Lys Arg Gly Arg Asp Glu Ser Ser
    50                  55                  60

Ser Ser Gly Pro Lys Ser Lys Ala Cys Arg Glu Lys Ile Arg Arg Asp
65                  70                  75                  80

Arg Leu Asn Asp Arg Phe Leu Glu Leu Ser Ser Val Ile Asn Pro Asp
                85                  90                  95

Lys Gln Ala Lys Leu Asp Lys Ala Asn Ile Leu Ser Asp Ala Ala Arg
            100                 105                 110

Leu Leu Ala Glu Leu Arg Gly Glu Ala Glu Lys Leu Lys Glu Ser Asn
        115                 120                 125

Glu Lys Leu Arg Glu Thr Ile Lys Asp Leu Lys Val Glu Lys Asn Glu
    130                 135                 140

Leu Arg Asp Glu Lys Val Thr Leu Lys Ala Glu Lys Glu Arg Leu Glu
145                 150                 155                 160

Gln Gln Val Lys Ala Leu Ser Val Ala Pro Thr Gly Phe Val Pro His
                165                 170                 175

Leu Pro His Pro Ala Ala Phe His Pro Ala Ala Phe Pro Pro Phe Ile
            180                 185                 190

Pro Pro Tyr Gln Ala Leu Gly Asn Lys Asn Ala Pro Thr Pro Ala Ala
        195                 200                 205

Phe Gln Gly Met Ala Met Trp Gln Trp Leu Pro Pro Thr Ala Val Asp
    210                 215                 220

Thr Thr Gln Asp Pro Lys Leu Trp Pro Pro Asn Ala
225                 230                 235


<210> SEQ ID NO 8
<211> LENGTH: 239
<212> TYPE: PRT
<213> ORGANISM: Triticum aestivum

<400> SEQUENCE: 8

Cys Pro Leu Met Asp Asp Leu Ala Ala Ala Asp Phe Ala Ala Ala Ser
1               5                   10                  15

Ala Gly Gly Phe Tyr Trp Thr Pro Pro Met Gln Pro Gln Met His Thr
            20                  25                  30

Leu Ala Gln Ala Val Ser Ala Thr Pro Ala Pro Asn Pro Cys Ala Glu
        35                  40                  45

Ile Asn Ser Ser Val Ser Val Asp Trp Asp His Ala Lys Gly Gln Pro
    50                  55                  60

Lys Asn Lys Arg Pro Arg Ser Glu Thr Gly Ala Gln Pro Ser Ser Lys
65                  70                  75                  80

Ala Cys Arg Glu Lys Val Arg Arg Asp Lys Leu Asn Glu Arg Phe Leu
                85                  90                  95

Glu Leu Gly Ala Val Leu Asp Pro Gly Lys Thr Pro Lys Ile Asp Lys
            100                 105                 110

Cys Ala Ile Leu Asn Asp Ala Ile Arg Ala Val Thr Glu Leu Arg Ser
        115                 120                 125

Glu Ala Gln Lys Leu Lys Asp Ser Asn Glu Ser Leu Gln Glu Lys Ile
    130                 135                 140

Arg Glu Leu Lys Ala Asp Lys Asn Glu Leu Arg His Glu Lys Gln Lys
145                 150                 155                 160

Met Lys Ala Glu Lys Glu Ser Leu Glu Gln Gln Ile Lys Phe Met Asn
                165                 170                 175
```

-continued

```
Ala Arg Gln Ser Leu Val Pro His Pro Ser Val Ile Pro Ala Ala Ala
            180                 185                 190

Phe Ala Ala Ala Gln Gly Gln Ala Ala Gly His Lys Leu Met Met Pro
        195                 200                 205

Val Met Ser Tyr Pro Gly Phe Pro Met Trp Gln Phe Met Pro Pro Ser
    210                 215                 220

Asp Val Asp Thr Ser Asp Asp Pro Lys Ser Cys Pro Pro Val Ala
225                 230                 235


<210> SEQ ID NO 9
<211> LENGTH: 205
<212> TYPE: PRT
<213> ORGANISM: Hordeum vulgare

<400> SEQUENCE: 9

Met Ala Ser Pro Glu Gly Ser Asn Trp Val Phe Asp Cys Pro Leu Met
1               5                   10                  15

Asp Asp Leu Ala Ala Ala Asp Phe Ala Ala Val Pro Ala Gly Gly Phe
            20                  25                  30

Tyr Trp Asn Pro Pro Met Pro Pro Gln Met His Thr Leu Ala Gln Ala
        35                  40                  45

Val Ser Ala Thr Pro Ala Pro Asn Pro Cys Ala Glu Ile Asn Ser Ser
    50                  55                  60

Val Ser Val Asp Trp Asp His Ala Lys Gly Gln Pro Lys Asn Lys Arg
65                  70                  75                  80

Pro Arg Ser Glu Thr Gly Ala Gln Pro Ser Ser Lys Ala Cys Arg Glu
                85                  90                  95

Lys Val Arg Arg Asp Lys Leu Asn Glu Arg Phe Leu Glu Leu Gly Ala
            100                 105                 110

Val Leu Asp Pro Gly Lys Thr Pro Lys Ile Asp Lys Cys Ala Ile Leu
        115                 120                 125

Asn Asp Ala Ile Arg Ala Val Thr Glu Leu Arg Ser Glu Ala Glu Lys
    130                 135                 140

Leu Lys Asp Ser Asn Glu Ser Leu Gln Glu Lys Ile Arg Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln Arg
            180                 185                 190

Leu Val Pro His Pro Ser Val Ile Pro Ala Thr Ala Phe
        195                 200                 205


<210> SEQ ID NO 10
<211> LENGTH: 243
<212> TYPE: PRT
<213> ORGANISM: Oryza sativa

<400> SEQUENCE: 10

Met Ala Ser Pro Glu Gly Ser Thr Trp Val Phe Asp Cys Pro Leu Met
1               5                   10                  15

Asp Asp Leu Ala Ala Ala Ala Gly Phe Asp Ala Ala Pro Ala Gly Gly
            20                  25                  30

Phe Tyr Trp Thr Thr Pro Ala Pro Pro Gln Ala Ala Leu Gln Pro Pro
        35                  40                  45

Pro Pro Gln Gln Gln Pro Val Ala Pro Ala Thr Ala Ala Pro Asn Ala
    50                  55                  60
```

-continued

```
Cys Ala Glu Ile Asn Gly Ser Val Asp Cys Glu His Gly Lys Glu Gln
65                  70                  75                  80

Pro Thr Asn Lys Arg Pro Arg Ser Glu Ser Gly Thr Arg Pro Ser Ser
                85                  90                  95

Lys Ala Cys Arg Glu Lys Val Arg Arg Asp Lys Leu Asn Glu Arg Phe
            100                 105                 110

Leu Glu Leu Gly Ala Val Leu Glu Pro Gly Lys Thr Pro Lys Met Asp
        115                 120                 125

Lys Ser Ser Ile Leu Asn Asp Ala Ile Arg Val Met Ala Glu Leu Arg
    130                 135                 140

Ser Glu Ala Gln Lys Leu Lys Glu Ser Asn Glu Ser Leu Gln Glu Lys
145                 150                 155                 160

Ile Lys Glu Leu Lys Ala Glu Lys Asn Glu Leu Arg Asp Glu Lys Gln
                165                 170                 175

Lys Leu Lys Ala Glu Lys Glu Ser Leu Glu Gln Gln Ile Lys Phe Leu
            180                 185                 190

Asn Ala Arg Pro Ser Phe Val Pro His Pro Pro Val Ile Pro Ala Ser
        195                 200                 205

Ala Phe Thr Ala Pro Gln Gly Gln Ala Ala Gly Gln Lys Leu Met Met
    210                 215                 220

Pro Val Ile Gly Tyr Pro Gly Phe Pro Met Trp Gln Phe Met Pro Pro
225                 230                 235                 240

Ser Asp Val


<210> SEQ ID NO 11
<211> LENGTH: 192
<212> TYPE: PRT
<213> ORGANISM: Triticum aestivum

<400> SEQUENCE: 11

Met Ala Ser Pro Glu Gly Ser Asn Trp Val Phe Asp Cys Pro Leu Met
1               5                   10                  15

Asp Asp Leu Ala Ala Ala Asp Phe Ala Ala Ala Ser Ala Gly Gly Phe
            20                  25                  30

Tyr Trp Thr Pro Pro Met Gln Pro Gln Met His Thr Leu Ala Gln Ala
        35                  40                  45

Val Ser Ala Thr Pro Ala Pro Asn Pro Cys Ala Glu Ile Asn Ser Ser
    50                  55                  60

Val Ser Val Asp Trp Asp His Ala Lys Gly Gln Pro Lys Asn Lys Arg
65                  70                  75                  80

Pro Arg Ser Glu Thr Gly Ala Gln Pro Ser Ser Lys Ala Cys Arg Glu
                85                  90                  95

Lys Val Arg Arg Asp Lys Leu Asn Glu Arg Phe Leu Glu Leu Gly Ala
            100                 105                 110

Val Leu Asp Pro Gly Lys Thr Pro Lys Ile Asp Lys Cys Ala Ile Leu
        115                 120                 125

Asn Asp Ala Ile Arg Ala Val Thr Glu Leu Arg Ser Glu Ala Glu Lys
    130                 135                 140

Leu Lys Asp Ser Asn Glu Ser Leu Gln Glu Lys Ile Arg Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln Ser
            180                 185                 190
```

-continued

<210> SEQ ID NO 12
<211> LENGTH: 191
<212> TYPE: PRT
<213> ORGANISM: Triticum aestivum

<400> SEQUENCE: 12

```
Met Ala Ser Pro Glu Gly Ser Asn Trp Val Phe Asp Cys Pro Leu Met
1               5                   10                  15

Asp Asp Leu Ala Ala Ala Asp Phe Ala Ala Ala Ser Thr Gly Gly Phe
            20                  25                  30

Tyr Trp Thr Pro Pro Met Gln Pro Gln Met His Thr Leu Ala Gln Ala
        35                  40                  45

Val Ser Ala Thr Pro Ala Pro Asn Pro Cys Ala Glu Ile Asn Ser Ser
    50                  55                  60

Val Ser Val Asp Trp Asp His Ala Lys Gly Gln Pro Lys Asn Lys Arg
65                  70                  75                  80

Pro Arg Ser Glu Thr Gly Ala Gln Pro Ser Ser Lys Ala Cys Arg Glu
                85                  90                  95

Lys Val Arg Arg Asp Lys Leu Asn Glu Arg Phe Leu Glu Leu Gly Ala
            100                 105                 110

Val Leu Asp Pro Gly Lys Thr Pro Lys Ile Asp Lys Cys Ala Ile Leu
        115                 120                 125

Asn Asp Ala Ile Arg Ala Val Thr Glu Leu Arg Ser Glu Ala Glu Lys
    130                 135                 140

Leu Lys Asp Ser Asn Asp Ser Leu Gln Glu Lys Ile Arg Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln
            180                 185                 190
```

<210> SEQ ID NO 13
<211> LENGTH: 190
<212> TYPE: PRT
<213> ORGANISM: Hordeum vulgare

<400> SEQUENCE: 13

```
Asn Ser Ser Val Ser Val Asp Trp Asp His Ala Lys Gly Gln Pro Lys
1               5                   10                  15

Asn Lys Arg Pro Arg Ser Glu Thr Gly Ala Gln Pro Ser Ser Lys Ala
            20                  25                  30

Cys Arg Glu Lys Val Arg Arg Asp Lys Leu Asn Glu Arg Phe Leu Glu
        35                  40                  45

Leu Gly Ala Val Leu Asp Pro Gly Lys Thr Pro Lys Ile Asp Lys Cys
    50                  55                  60

Ala Ile Leu Asn Asp Ala Ile Arg Ala Val Thr Glu Leu Arg Ser Glu
65                  70                  75                  80

Ala Glu Lys Leu Lys Asp Ser Asn Glu Ser Leu Gln Glu Lys Ile Arg
                85                  90                  95

Glu Leu Lys Ala Glu Lys Asn Glu Leu Arg Asp Glu Lys Gln Lys Leu
            100                 105                 110

Lys Ala Glu Lys Glu Ser Leu Glu Gln Gln Ile Lys Phe Met Asn Ala
        115                 120                 125

Arg Gln Arg Leu Val Pro His Pro Ser Val Ile Pro Ala Thr Ala Phe
    130                 135                 140
```

-continued

```
Ala Ala Ala Gln Gly Gln Ala Ala Gly His Lys Leu Met Met Pro Val
145                 150                 155                 160

Met Ser Tyr Pro Gly Phe Pro Met Trp Gln Phe Met Pro Pro Ser Asp
                165                 170                 175

Val Asp Thr Ser Asp Asp Pro Lys Ser Cys Pro Pro Val Ala
            180                 185                 190
```

<210> SEQ ID NO 14
<211> LENGTH: 193
<212> TYPE: PRT
<213> ORGANISM: Triticum aestivum
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

```
Pro Ser Trp Xaa Asp Leu Ala Ala Ala Asp Phe Ala Ala Ala Ser Ala
1               5                   10                  15

Gly Gly Phe Tyr Trp Thr Pro Pro Met Gln Pro Gln Met His Thr Leu
            20                  25                  30

Ala Gln Ala Val Ser Ala Thr Pro Ala Pro Asn Pro Cys Ala Glu Ile
        35                  40                  45

Asn Ser Ser Val Ser Val Asp Trp Asp His Ala Lys Gly Gln Pro Lys
    50                  55                  60

Asn Lys Arg Pro Arg Ser Glu Thr Gly Ala Gln Pro Ser Ser Lys Ala
65                  70                  75                  80

Cys Arg Glu Lys Val Arg Arg Asp Lys Leu Asn Glu Arg Phe Leu Glu
                85                  90                  95

Leu Gly Ala Val Leu Asp Pro Gly Lys Thr Pro Lys Ile Asp Lys Cys
            100                 105                 110

Ala Ile Leu Asn Asp Ala Ile Arg Ala Val Thr Glu Leu Arg Ser Glu
        115                 120                 125

Ala Glu Lys Leu Lys Asp Ser Asn Glu Ser Leu Gln Glu Lys Ile Arg
    130                 135                 140

Glu Leu Lys Ala Glu Lys Asn Glu Leu Arg Asp Glu Lys Gln Lys Leu
145                 150                 155                 160

Lys Ala Glu Lys Glu Ser Leu Glu Gln Gln Ile Lys Phe Met Asn Ala
                165                 170                 175

Arg Gln Ser Leu Val Pro His Pro Ser Val Ile Pro Ala Ala Ala Phe
            180                 185                 190

Ala
```

<210> SEQ ID NO 15
<211> LENGTH: 191
<212> TYPE: PRT
<213> ORGANISM: Oryza sativa

<400> SEQUENCE: 15

```
Ala Glu Ile Asn Gly Ser Val Asp Cys Glu His Gly Lys Glu Gln Pro
1               5                   10                  15

Thr Asn Lys Arg Pro Arg Ser Glu Ser Gly Thr Arg Pro Ser Ser Lys
            20                  25                  30

Ala Cys Arg Glu Lys Val Arg Arg Asp Lys Leu Asn Glu Arg Phe Leu
        35                  40                  45

Glu Leu Gly Ala Val Leu Glu Pro Gly Lys Thr Pro Lys Met Asp Lys
    50                  55                  60
```

-continued

```
Ser Ser Ile Leu Asn Asp Ala Ile Arg Val Met Ala Glu Leu Arg Ser
65                  70                  75                  80

Glu Ala Gln Lys Leu Lys Glu Ser Asn Glu Ser Leu Gln Glu Lys Ile
                85                  90                  95

Lys Glu Leu Lys Ala Glu Lys Asn Glu Leu Arg Asp Glu Lys Gln Lys
            100                 105                 110

Leu Lys Ala Glu Lys Asp Ser Leu Glu Gln Gln Ile Lys Phe Leu Asn
        115                 120                 125

Ala Arg Pro Ser Phe Val Pro His Pro Pro Val Ile Pro Ala Ser Ala
    130                 135                 140

Phe Thr Ala Pro Gln Gly Gln Ala Ala Gly Gln Lys Leu Met Met Pro
145                 150                 155                 160

Val Ile Gly Tyr Pro Gly Phe Pro Met Trp Gln Phe Met Pro Pro Ser
                165                 170                 175

Asp Val Asp Thr Thr Asp Asp Thr Lys Ser Cys Pro Pro Val Ala
            180                 185                 190


<210> SEQ ID NO 16
<211> LENGTH: 170
<212> TYPE: PRT
<213> ORGANISM: Triticum aestivum

<400> SEQUENCE: 16

Arg Ser Glu Thr Gly Ala Gln Pro Ser Ser Lys Ala Cys Arg Glu Lys
1               5                   10                  15

Val Arg Arg Asp Lys Leu Asn Glu Arg Phe Leu Glu Leu Gly Ala Val
            20                  25                  30

Leu Asp Pro Gly Lys Thr Pro Lys Ile Asp Lys Cys Ala Ile Leu Asn
        35                  40                  45

Asp Ala Ile Arg Ala Val Thr Glu Leu Arg Ser Glu Ala Glu Lys Leu
    50                  55                  60

Lys Asp Ser Asn Glu Ser Leu Gln Glu Lys Ile Arg Glu Leu Lys Ala
65                  70                  75                  80

Glu Lys Asn Glu Leu Arg Asp Glu Lys Gln Lys Leu Lys Ala Glu Lys
                85                  90                  95

Glu Ser Leu Glu Gln Gln Ile Lys Phe Met Asn Ala Arg Gln Ser Leu
            100                 105                 110

Val Pro His Pro Ser Val Ile Pro Ala Ala Ala Phe Ala Ala Ala Gln
        115                 120                 125

Gly Gln Ala Ala Gly His Lys Leu Met Met Pro Val Met Ser Tyr Pro
    130                 135                 140

Gly Phe Pro Met Trp Gln Phe Met Pro Pro Ser Asp Val Asp Thr Ser
145                 150                 155                 160

Asp Asp Pro Lys Ser Cys Pro Pro Val Ala
                165                 170


<210> SEQ ID NO 17
<211> LENGTH: 212
<212> TYPE: PRT
<213> ORGANISM: Sorghum bicolor
<220> FEATURE:
<221> NAME/KEY: misc_feature
<222> LOCATION: (145)..(145)
<223> OTHER INFORMATION: Xaa can be any naturally occurring amino acid

<400> SEQUENCE: 17

Met Ala Ser Pro Glu Gly Thr Thr Trp Val Phe Asp Cys Pro Leu Met
1               5                   10                  15
```

-continued

```
Asp Asp Leu Ala Val Ala Ala Asp Phe Ala Ala Ala Pro Ala Gly Gly
            20                  25                  30

Phe Phe Trp Ala Ala Pro Pro Ser Leu Gln Pro Gln Val Val Gln Ala
        35                  40                  45

Pro Val Gln Ser Val Val Ala Ala Ser Ala Pro Asn Pro Cys Val Glu
    50                  55                  60

Ile Ser Ser Ser Val Asp Cys Gly Gln Gly Lys Glu Gln Pro Thr Asn
65                  70                  75                  80

Lys Arg Pro Arg Ser Glu Ser Thr Ala Glu Pro Ser Thr Lys Ala Ser
                85                  90                  95

Arg Glu Lys Ile Arg Arg Asp Lys Leu Asn Glu Arg Phe Leu Glu Leu
            100                 105                 110

Gly Ala Ile Leu Glu Pro Gly Lys Thr Pro Lys Met Asp Lys Ser Ala
        115                 120                 125

Ile Leu Asn Asp Ala Ile Arg Val Val Gly Glu Leu Arg Ser Glu Ala
    130                 135                 140

Xaa Glu Leu Lys Asp Ser Asn Glu Ser Leu Gln Glu Lys Ile Lys Glu
145                 150                 155                 160

Leu Lys Ala Glu Lys Asn Glu Leu Arg Asp Glu Lys Gln Arg Leu Lys
                165                 170                 175

Ala Glu Lys Glu Ser Leu Glu Gln Gln Ile Lys Phe Leu Asn Ala Arg
            180                 185                 190

Pro Ser Leu Val Pro His His Pro Val Ile Ser Ala Ser Ala Phe Thr
        195                 200                 205

Ala Pro Gln Gly
    210


<210> SEQ ID NO 18
<211> LENGTH: 185
<212> TYPE: PRT
<213> ORGANISM: Sorghum bicolor

<400> SEQUENCE: 18

Asp Cys Gly Gln Gly Lys Glu Gln Pro Thr Asn Lys Arg Pro Arg Ser
1               5                   10                  15

Glu Ser Thr Ala Glu Pro Ser Thr Lys Ala Ser Arg Glu Lys Ile Arg
            20                  25                  30

Arg Asp Lys Leu Asn Glu Arg Phe Leu Glu Leu Gly Ala Ile Leu Asp
        35                  40                  45

Pro Gly Lys Thr Pro Lys Met Asp Lys Ser Ala Ile Leu Asn Asp Ala
    50                  55                  60

Ile Arg Val Val Gly Glu Leu Arg Ser Glu Ala Lys Glu Phe Lys Asp
65                  70                  75                  80

Ser Asn Glu Ser Leu Gln Glu Lys Ile Lys Glu Leu Lys Ala Glu Lys
                85                  90                  95

Asn Glu Leu Arg Asp Glu Lys Gln Arg Leu Lys Ala Glu Lys Glu Ser
            100                 105                 110

Leu Glu Gln Gln Ile Lys Phe Leu Asn Ala Arg Pro Ser Leu Val Pro
        115                 120                 125

His His Pro Val Ile Ser Ala Ser Ala Phe Thr Ala Pro Gln Gly Pro
    130                 135                 140

Ala Val Ala Gly His Lys Leu Met Met Pro Val Leu Gly Tyr Pro Gly
145                 150                 155                 160

Phe Pro Met Trp Gln Phe Met Pro Pro Ser Asp Val Asp Thr Ser Asp
```

-continued

```
                165                 170                 175

Asp Pro Lys Ser Cys Pro Pro Val Ala
            180                 185


<210> SEQ ID NO 19
<211> LENGTH: 205
<212> TYPE: PRT
<213> ORGANISM: Sorghum bicolor

<400> SEQUENCE: 19

Pro Gln Val Val Gln Ala Pro Val Gln Ser Val Val Ala Ala Ser Ala
1               5                   10                  15

Pro Asn Pro Cys Val Glu Ile Ser Ser Ser Val Asp Cys Gly Gln Gly
            20                  25                  30

Lys Glu Gln Pro Thr Asn Lys Arg Pro Arg Ser Glu Ser Thr Ala Glu
        35                  40                  45

Pro Ser Thr Lys Ala Ser Arg Glu Lys Ile Arg Arg Asp Lys Leu Asn
    50                  55                  60

Glu Arg Phe Leu Glu Leu Gly Ala Ile Leu Glu Pro Gly Lys Thr Pro
65                  70                  75                  80

Lys Met Asp Lys Ser Ala Ile Leu Asn Asp Ala Ile Arg Val Val Gly
                85                  90                  95

Glu Leu Arg Ser Glu Ala Lys Glu Leu Lys Asp Ser Asn Glu Ser Leu
            100                 105                 110

Gln Glu Lys Ile Lys Glu Leu Lys Ala Glu Lys Asn Glu Leu Arg Asp
        115                 120                 125

Glu Lys Gln Arg Leu Lys Ala Glu Lys Glu Ser Leu Glu Gln Gln Ile
    130                 135                 140

Lys Phe Leu Asn Ala Arg Pro Ser Leu Val Pro His His Pro Val Ile
145                 150                 155                 160

Ser Ala Ser Ala Phe Thr Ala Pro Gln Gly Pro Ala Val Ala Gly His
                165                 170                 175

Lys Leu Met Met Pro Val Leu Gly Tyr Pro Gly Phe Pro Met Trp Gln
            180                 185                 190

Phe Met Pro Pro Ser Asp Val Asp Thr Ser Asp Asp Pro
        195                 200                 205


<210> SEQ ID NO 20
<211> LENGTH: 197
<212> TYPE: PRT
<213> ORGANISM: Zea mays

<400> SEQUENCE: 20

Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
            20                  25                  30

Phe Phe Trp Ala Ala Pro Pro Ser Leu Gln Pro Gln Ala Pro Val Gln
        35                  40                  45

Ser Val Val Ala Ala Ser Ala Pro Asn Pro Cys Met Glu Ile Ser Ser
    50                  55                  60

Ser Val Asp Cys Gly Gln Glu Lys Glu Gln Pro Thr Asn Lys Arg Pro
65                  70                  75                  80

Arg Ser Glu Ser Thr Thr Glu Ser Ser Thr Lys Ala Ser Arg Glu Lys
                85                  90                  95

Ile Arg Arg Asp Lys Leu Asn Glu Arg Phe Leu Glu Leu Gly Ala Ile
```

-continued

```
            100                 105                 110

Leu Glu Pro Gly Lys Thr Pro Lys Met Asp Lys Thr Ala Ile Leu Ser
        115                 120                 125

Asp Ala Ile Arg Val Val Gly Glu Leu Arg Ser Glu Ala Lys Lys Leu
    130                 135                 140

Lys Asp Ser Asn Glu Asn Leu Gln Glu Lys Ile Lys Glu Leu Lys Ala
145                 150                 155                 160

Glu Lys Asn Glu Leu Arg Asp Glu Lys Gln Arg Leu Lys Ala Glu Lys
                165                 170                 175

Glu Ser Leu Glu Gln Gln Ile Lys Phe Leu Asn Ala Arg Pro Ser Leu
            180                 185                 190

Val Pro His His Pro
        195
```

<210> SEQ ID NO 21
<211> LENGTH: 205
<212> TYPE: PRT
<213> ORGANISM: Sorghum bicolor

<400> SEQUENCE: 21

```
Pro Ser Leu Gln Pro Gln Val Val Gln Ala Pro Val Gln Ser Val Val
1               5                   10                  15

Ala Ala Ser Ala Pro Asn Pro Cys Val Glu Ile Ser Ser Ser Val Asp
            20                  25                  30

Cys Gly Gln Gly Lys Glu Gln Pro Thr Asn Lys Arg Pro Arg Ser Glu
        35                  40                  45

Ser Thr Ala Glu Pro Ser Thr Lys Ala Ser Arg Glu Lys Ile Arg Arg
    50                  55                  60

Asp Lys Leu Asn Glu Arg Phe Leu Glu Leu Gly Ala Ile Leu Glu Pro
65                  70                  75                  80

Gly Lys Thr Pro Lys Met Asp Lys Ser Ala Ile Leu Asn Asp Ala Ile
                85                  90                  95

Arg Val Val Gly Glu Leu Arg Ser Glu Ala Lys Glu Leu Lys Asp Ser
            100                 105                 110

Asn Glu Ser Leu Gln Glu Lys Ile Lys Glu Leu Lys Ala Glu Lys Asn
        115                 120                 125

Glu Leu Arg Asp Glu Lys Gln Arg Leu Lys Ala Glu Lys Glu Ser Leu
    130                 135                 140

Glu Gln Gln Ile Lys Phe Leu Asn Ala Arg Pro Ser Leu Val Pro His
145                 150                 155                 160

His Pro Val Ile Ser Ala Ser Ala Phe Thr Ala Pro Gln Gly Pro Ala
                165                 170                 175

Val Ala Gly His Lys Leu Met Met Pro Val Leu Gly Tyr Pro Gly Phe
            180                 185                 190

Pro Met Trp Gln Phe Met Pro Pro Ser Asp Val Asp Thr
        195                 200                 205
```

<210> SEQ ID NO 22
<211> LENGTH: 202
<212> TYPE: PRT
<213> ORGANISM: Zea mays
<220> FEATURE:
<221> NAME/KEY: misc_feature
<222> LOCATION: (192)..(192)
<223> OTHER INFORMATION: Xaa can be any naturally occurring amino acid

<400> SEQUENCE: 22

-continued

```
Ala Ala Asp Phe Ala Ala Ala Pro Ala Gly Gly Phe Phe Trp Ala Ala
1               5                   10                  15

Pro Pro Ser Leu Gln Pro Gln Ala Pro Val Gln Ser Val Val Ala Ala
            20                  25                  30

Ser Ala Pro Asn Pro Cys Met Glu Ile Ser Ser Ser Val Asp Cys Gly
        35                  40                  45

Gln Glu Lys Glu Gln Pro Thr Asn Lys Arg Pro Arg Ser Glu Ser Thr
    50                  55                  60

Thr Glu Ser Ser Thr Lys Ala Ser Arg Glu Lys Ile Arg Arg Asp Lys
65                  70                  75                  80

Leu Asn Glu Arg Phe Leu Glu Leu Gly Ala Ile Leu Glu Pro Gly Lys
                85                  90                  95

Thr Pro Lys Met Asp Lys Thr Ala Ile Leu Ser Asp Ala Ile Arg Val
            100                 105                 110

Val Gly Glu Leu Arg Ser Glu Ala Lys Lys Leu Lys Asp Ser Asn Glu
        115                 120                 125

Asn Leu Gln Glu Lys Ile Lys Glu Leu Lys Ala Glu Lys Asn Glu Leu
    130                 135                 140

Arg Asp Glu Lys Gln Arg Leu Lys Ala Glu Lys Glu Ser Leu Glu Gln
145                 150                 155                 160

Gln Ile Lys Phe Leu Asn Ala Arg Pro Ser Leu Val Pro His His Pro
                165                 170                 175

Val Ile Pro Ala Ser Ala Phe Pro Ala Pro Gln Gly Pro Ala Thr Xaa
            180                 185                 190

Ala Arg His Lys Leu Met Met Pro Val Ile
        195                 200


<210> SEQ ID NO 23
<211> LENGTH: 193
<212> TYPE: PRT
<213> ORGANISM: Saccharum officinarum

<400> SEQUENCE: 23

Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
            20                  25                  30

Phe Phe Trp Ala Ala Pro Pro Ser Leu Gln Pro Gln Val Val Gln Ala
        35                  40                  45

Pro Val Gln Ser Val Val Ala Ala Ser Ala Pro Asn Pro Pro Cys Val
    50                  55                  60

Glu Ile Ser Ser Ser Val Asp Cys Gly Gln Gly Lys Glu Gln Pro Thr
65                  70                  75                  80

Asn Lys Arg Pro Arg Ser Glu Ser Thr Ala Glu Pro Ser Thr Lys Ala
                85                  90                  95

Ser Arg Glu Lys Ile Arg Arg Asp Lys Leu Asn Lys Arg Phe Leu Glu
            100                 105                 110

Trp Gly Ala Ile Leu Glu Pro Gly Glu Thr Pro Lys Met Asp Lys Ser
        115                 120                 125

Ala Ile Leu Asn Asp Ala Ile Arg Ala Val Gly Glu Leu Arg Ser Glu
    130                 135                 140

Ala Lys Lys Leu Lys Asp Ser Asn Glu Ser Leu Gln Glu Lys Ile Lys
145                 150                 155                 160

Glu Leu Lys Ala Glu Lys Asn Glu Ser Arg Asp Glu Lys Gln Arg Leu
                165                 170                 175
```

-continued

```
Lys Ala Glu Asn Glu Ser Leu Glu Gln Gln Ile Lys Phe Leu Asn Ala
            180                 185                 190

Arg


<210> SEQ ID NO 24
<211> LENGTH: 174
<212> TYPE: PRT
<213> ORGANISM: Saccharum officinarum
<220> FEATURE:
<221> NAME/KEY: misc_feature
<222> LOCATION: (166)..(166)
<223> OTHER INFORMATION: Xaa can be any naturally occurring amino acid

<400> SEQUENCE: 24

Glu Ile Ser Ser Ser Val Asp Cys Gly Gln Gly Lys Glu Gln Pro Thr
1               5                   10                  15

Asn Lys Arg Pro Arg Ser Glu Ser Thr Ala Glu Pro Ser Thr Lys Ala
            20                  25                  30

Ser Arg Glu Lys Ile Arg Arg Asp Lys Leu Asn Lys Arg Phe Leu Glu
        35                  40                  45

Leu Gly Ala Ile Leu Glu Pro Gly Glu Thr Pro Lys Met Asp Lys Ser
    50                  55                  60

Ala Ile Leu Asn Asp Ala Ile Arg Ala Val Gly Glu Leu Arg Ser Glu
65                  70                  75                  80

Ala Lys Lys Leu Lys Asp Ser Asn Glu Ser Leu Gln Glu Lys Ile Lys
                85                  90                  95

Glu Leu Lys Ala Glu Lys Asn Glu Leu Arg Asp Glu Lys Gln Arg Leu
            100                 105                 110

Lys Ala Glu Lys Glu Lys Pro Glu Gln Gln Ile Lys Phe Leu Asn Ala
        115                 120                 125

Arg Pro Ser Leu Val Pro His His Ser Val Ile Pro Ala Ser Ala Phe
    130                 135                 140

Ala Ala Pro Gln Gly Pro Ala Ala Ala Gly His Lys Leu Met Leu Pro
145                 150                 155                 160

Val Leu Gly Tyr Pro Xaa Phe Pro Met Trp Gln Phe Met Pro
                165                 170


<210> SEQ ID NO 25
<211> LENGTH: 154
<212> TYPE: PRT
<213> ORGANISM: Sorghum bicolor

<400> SEQUENCE: 25

Arg Asp Lys Leu Asn Glu Arg Phe Leu Glu Leu Gly Ala Ile Leu Glu
1               5                   10                  15

Pro Gly Lys Thr Pro Lys Met Asp Lys Ser Ala Ile Leu Asn Asp Ala
            20                  25                  30

Ile Arg Val Val Gly Glu Leu Arg Ser Glu Ala Lys Glu Leu Lys Asp
        35                  40                  45

Ser Asn Glu Ser Leu Gln Glu Lys Ile Lys Glu Leu Lys Ala Glu Lys
    50                  55                  60

Asn Glu Leu Arg Asp Glu Lys Gln Arg Leu Lys Ala Glu Lys Glu Ser
65                  70                  75                  80

Leu Glu Gln Gln Ile Lys Phe Leu Asn Ala Arg Pro Ser Leu Val Pro
                85                  90                  95

His His Pro Ser Val Ile Ser Ala Ser Ala Phe Ile Ala Pro Gln Gly
            100                 105                 110
```

Pro Ala Val Ala Gly His Lys Leu Met Met Pro Val Leu Gly Tyr Pro
115 120 125

Gly Phe Pro Met Trp Gln Phe Met Pro Pro Ser Asp Val Asp Thr Ser
130 135 140

Asp Asp Pro Lys Ser Cys Pro Pro Val Ala
145 150

<210> SEQ ID NO 26
<211> LENGTH: 128
<212> TYPE: PRT
<213> ORGANISM: Triticum aestivum
<220> FEATURE:
<221> NAME/KEY: misc_feature
<222> LOCATION: (5)..(5)
<223> OTHER INFORMATION: Xaa can be any naturally occurring amino acid

<400> SEQUENCE: 26

Lys Cys Ala Ile Xaa Asn Asp Ala Ile Arg Ala Val Thr Glu Leu Arg
1 5 10 15

Ser Glu Ala Glu Lys Leu Lys Asp Ser Asn Glu Ser Leu Gln Glu Lys
20 25 30

Ile Arg Glu Leu Lys Ala Glu Lys Asn Glu Leu Arg Asp Glu Lys Gln
35 40 45

Lys Leu Lys Ala Glu Lys Glu Ser Leu Glu Gln Gln Ile Lys Phe Met
50 55 60

Asn Ala Arg Gln Ser Leu Val Pro His Pro Ser Val Ile Pro Ala Ala
65 70 75 80

Ala Phe Ala Ala Ala Gln Gly Gln Ala Ala Gly His Lys Leu Met Met
85 90 95

Pro Val Met Ser Tyr Pro Gly Phe Pro Met Trp Gln Phe Met Pro Pro
100 105 110

Ser Asp Val Asp Thr Ser Asp Asp Pro Lys Ser Cys Pro Pro Val Ala
115 120 125

<210> SEQ ID NO 27
<211> LENGTH: 188
<212> TYPE: PRT
<213> ORGANISM: Triticum aestivum

<400> SEQUENCE: 27

Asp Leu Pro Lys Asp Ser Gly Ser Asn Lys Arg Leu Arg Ser Glu Pro
1 5 10 15

Cys Gly Arg Pro Thr Ser Lys Ala Cys Arg Glu Lys Val Arg Arg Asp
20 25 30

Lys Leu Asn Asp Arg Phe Leu Glu Leu Gly Thr Thr Leu Asp Pro Gly
35 40 45

Lys Pro Val Lys Ala Asp Lys Ala Ala Ile Leu Ser Asp Ala Thr Arg
50 55 60

Met Val Thr Gln Leu Arg Ala Glu Ala Gln Gln Leu Lys Asp Thr Asn
65 70 75 80

Gly Ser Leu Glu Asp Lys Ile Lys Glu Leu Lys Ala Glu Lys Asp Glu
85 90 95

Leu Arg Asp Glu Lys Gln Lys Leu Lys Leu Glu Lys Glu Thr Leu Glu
100 105 110

His Gln Met Lys Leu Leu Thr Ala Thr Pro Ala Tyr Met Pro His Pro
115 120 125

Thr Met Met Pro Ser Pro Phe Ala Gln Ala Pro Met Ala Pro Phe His

-continued

```
    130                 135                 140

Ala Gln Gly Gln Ala Leu Gly Gln Lys Leu Met Met Pro Phe Val Gly
145                 150                 155                 160

Tyr Pro Gly Tyr Pro Met Trp Gln Leu Met Pro Pro Ser Glu Val Asp
                165                 170                 175

Thr Ser Lys Asp Ser Glu Ala Cys Pro Pro Val Ala
            180                 185


<210> SEQ ID NO 28
<211> LENGTH: 232
<212> TYPE: PRT
<213> ORGANISM: Triticum aestivum

<400> SEQUENCE: 28

Cys Asp Ser Trp Phe Leu Asp Cys Gly Ile Leu Lys Asp Leu Pro Ala
1               5                   10                  15

Ala Ala Trp Gly Val Phe Pro Gly Lys Ala Ser Phe Ser Trp Ser Asn
            20                  25                  30

Pro Ser Gly Glu Leu Gly Thr Gln Leu Thr Asn Leu Val Phe Pro Lys
        35                  40                  45

Asp Ser Gly Thr Asn Asn Arg Leu Ser Gln Ser Pro Phe Gly Arg Pro
    50                  55                  60

Thr Ser Lys Ala Cys Arg Glu Lys Val Arg Arg Asp Lys Leu Asn Asp
65                  70                  75                  80

Arg Phe Leu Glu Leu Gly Thr Thr Leu Asp Pro Gly Lys Pro Val Lys
                85                  90                  95

Ala Asp Lys Ala Ala Ile Leu Ser Asp Ala Thr Arg Met Val Thr Gln
            100                 105                 110

Leu Arg Ala Glu Ala Gln Gln Leu Lys Asp Thr Asn Gly Ser Leu Glu
        115                 120                 125

Asp Lys Ile Lys Glu Leu Lys Ala Glu Lys Asp Glu Leu Arg Asp Glu
    130                 135                 140

Lys Gln Lys Leu Lys Leu Glu Lys Glu Thr Leu Glu His Gln Met Lys
145                 150                 155                 160

Leu Leu Thr Ala Thr Pro Ala Tyr Met Pro His Pro Thr Met Met Pro
                165                 170                 175

Ser Pro Phe Ala Gln Ala Pro Met Ala Pro Phe His Ala Gln Gly Gln
            180                 185                 190

Ala Leu Gly Gln Lys Leu Met Met Pro Phe Val Gly Tyr Pro Gly Tyr
        195                 200                 205

Pro Met Trp Gln Leu Met Pro Pro Ser Glu Val Asp Thr Ser Lys Asp
    210                 215                 220

Ser Glu Ala Cys Pro Pro Val Ala
225                 230


<210> SEQ ID NO 29
<211> LENGTH: 144
<212> TYPE: PRT
<213> ORGANISM: Zea mays
<220> FEATURE:
<221> NAME/KEY: misc_feature
<222> LOCATION: (11)..(11)
<223> OTHER INFORMATION: Xaa can be any naturally occurring amino acid

<400> SEQUENCE: 29

Leu Gly Ala Ile Leu Glu Pro Gly Lys Thr Xaa Lys Met Asp Lys Thr
1               5                   10                  15
```

-continued

```
Ala Ile Leu Ser Asp Ala Ile Arg Val Val Gly Glu Leu Arg Ser Glu
            20                  25                  30

Ala Lys Lys Leu Lys Asp Ser Asn Glu Asn Leu Gln Glu Lys Ile Lys
        35                  40                  45

Glu Leu Lys Ala Glu Lys Asn Glu Leu Arg Asp Glu Lys Gln Arg Leu
    50                  55                  60

Lys Ala Glu Lys Glu Ser Leu Glu Gln Gln Ile Lys Phe Leu Asn Ala
65                  70                  75                  80

Arg Pro Ser Leu Val Pro His His Pro Val Ile Pro Ala Ser Ala Phe
                85                  90                  95

Pro Ala Pro Gln Gly Pro Ala Ala Ala Ala Arg His Lys Leu Met Met
            100                 105                 110

Pro Val Ile Gly Tyr Pro Gly Phe Pro Met Trp Gln Phe Met Pro Pro
        115                 120                 125

Ser Asp Val Asp Thr Ser Asp Asp Pro Arg Ser Cys Pro Pro Val Ala
    130                 135                 140


<210> SEQ ID NO 30
<211> LENGTH: 241
<212> TYPE: PRT
<213> ORGANISM: Zea mays

<400> SEQUENCE: 30

Gly Asp Asp Trp Phe Leu Asp Cys Gly Ile Leu Asp Asp Leu Pro Ala
1               5                   10                  15

Ala Ala Cys Gly Ala Phe Pro Trp Asp Ala Ser Pro Ser Ser Ser Asn
            20                  25                  30

Pro Ser Val Glu Val Gly Ser Tyr Val Asn Thr Asn Asp Val Phe Lys
        35                  40                  45

Glu Pro Asn Asp Val Phe Lys Glu Pro Gly Ser Asn Lys Arg Leu Arg
    50                  55                  60

Ser Gly Ser Asn Asp Val His Val Pro Thr Ser Lys Ala Ser Arg Glu
65                  70                  75                  80

Lys Met Arg Arg Asn Lys Leu Asn Asp Arg Phe Leu Glu Leu Gly Ser
                85                  90                  95

Thr Leu Glu Pro Gly Lys Pro Val Lys Ala Asp Lys Ala Ala Ile Leu
            100                 105                 110

Ser Asp Ala Thr Arg Met Val Ile Gln Leu Arg Ser Glu Ala Gln Gln
        115                 120                 125

Leu Lys Glu Thr Asn Gly Ser Leu Glu Glu Lys Ile Lys Glu Leu Lys
    130                 135                 140

Ala Glu Lys Asp Glu Leu Arg Asp Glu Lys Gln Lys Leu Lys Leu Glu
145                 150                 155                 160

Lys Glu Ser Leu Glu His Gln Met Lys Leu Met Thr Ser Thr Pro Thr
                165                 170                 175

Tyr Met Pro His Pro Thr Leu Met Pro Ala Pro Phe Pro Gln Ala Pro
            180                 185                 190

Leu Ala Pro Phe His Ala Gln Gly Gln Ala Ala Gly Gln Lys Leu Met
        195                 200                 205

Met Pro Phe Val Ser Tyr Pro Gly Tyr Pro Met Trp Gln Phe Met Pro
    210                 215                 220

Pro Ser Glu Val Asp Thr Ser Lys Asp Ser Glu Ala Cys Pro Pro Val
225                 230                 235                 240

Ala
```

-continued

<210> SEQ ID NO 31
<211> LENGTH: 187
<212> TYPE: PRT
<213> ORGANISM: Sorghum bicolor

<400> SEQUENCE: 31

```
Asp Val Phe Lys Glu Pro Gly Ser Asn Lys Arg Leu Arg Ser Gly Ser
1               5                   10                  15

Asn Asp Val Pro Thr Ser Lys Ala Ser Arg Glu Lys Met Arg Arg Asn
            20                  25                  30

Lys Leu Asn Asp Arg Phe Leu Glu Leu Gly Ser Thr Leu Glu Pro Gly
        35                  40                  45

Lys Pro Val Lys Ala Asp Lys Ala Ala Ile Leu Ser Asp Ala Thr Arg
    50                  55                  60

Met Val Ile Gln Leu Arg Ser Glu Ala Gln Gln Leu Lys Glu Thr Asn
65                  70                  75                  80

Gly Ser Leu Glu Glu Lys Ile Lys Glu Leu Lys Ala Glu Lys Asp Glu
                85                  90                  95

Leu Arg Asp Glu Lys Gln Lys Leu Lys Leu Glu Lys Glu Ser Leu Glu
            100                 105                 110

His Gln Met Lys Leu Met Thr Ser Thr Pro Ala Tyr Met Pro His Pro
        115                 120                 125

Thr Leu Met Pro Ala Pro Phe Pro Gln Ala Pro Leu Ala Pro Phe His
    130                 135                 140

Ala Gln Gly Gln Ala Ala Gly Gln Lys Leu Met Met Pro Phe Val Ser
145                 150                 155                 160

Tyr Pro Gly Tyr Pro Met Trp Gln Phe Met Pro Pro Ser Glu Val Asp
                165                 170                 175

Thr Ser Lys Asp Ser Glu Ala Cys Pro Pro Val
            180                 185
```

<210> SEQ ID NO 32
<211> LENGTH: 181
<212> TYPE: PRT
<213> ORGANISM: Sorghum bicolor

<400> SEQUENCE: 32

```
Ser Asn Lys Arg Leu Arg Ser Gly Ser Asn Asp Val Pro Thr Ser Lys
1               5                   10                  15

Ala Ser Arg Glu Lys Met Arg Arg Asn Lys Leu Asn Asp Arg Phe Leu
            20                  25                  30

Glu Leu Gly Ser Thr Leu Glu Pro Gly Lys Pro Val Lys Ala Asp Lys
        35                  40                  45

Ala Ala Ile Leu Ser Asp Ala Thr Arg Met Val Ile Gln Leu Arg Ser
    50                  55                  60

Glu Ala Gln Gln Leu Lys Glu Thr Asn Gly Ser Leu Glu Glu Lys Ile
65                  70                  75                  80

Lys Glu Leu Lys Ala Glu Lys Asp Glu Leu Arg Asp Glu Lys Gln Lys
                85                  90                  95

Leu Lys Leu Glu Lys Glu Ser Leu Glu His Gln Met Lys Leu Met Thr
            100                 105                 110

Ser Thr Pro Ala Tyr Met Pro His Pro Thr Leu Met Pro Ala Pro Phe
        115                 120                 125

Pro Gln Ala Pro Leu Ala Pro Phe His Ala Gln Gly Gln Ala Ala Gly
    130                 135                 140
```

-continued

```
Gln Lys Leu Met Met Pro Phe Val Ser Tyr Pro Gly Tyr Pro Met Trp
145                 150                 155                 160

Gln Phe Met Pro Pro Ser Glu Val Asp Thr Ser Lys Asp Ser Glu Ala
                165                 170                 175

Cys Pro Pro Val Ala
            180


<210> SEQ ID NO 33
<211> LENGTH: 179
<212> TYPE: PRT
<213> ORGANISM: Hordeum vulgare
<220> FEATURE:
<221> NAME/KEY: misc_feature
<222> LOCATION: (5)..(5)
<223> OTHER INFORMATION: Xaa can be any naturally occurring amino acid

<400> SEQUENCE: 33

Lys Arg Leu Arg Xaa Gly Pro Cys Gly Arg Pro Thr Ser Lys Ala Cys
1               5                   10                  15

Arg Glu Lys Val Arg Arg Asp Lys Leu Asn Asp Arg Phe Leu Glu Leu
            20                  25                  30

Gly Thr Thr Leu Asp Pro Gly Lys Pro Val Lys Ala Asp Lys Ala Ala
        35                  40                  45

Ile Leu Ser Asp Ala Thr Arg Met Val Thr Gln Leu Arg Ala Glu Ala
    50                  55                  60

Lys Gln Leu Lys Asp Thr Asn Gly Ser Leu Glu Asp Lys Ile Lys Glu
65                  70                  75                  80

Leu Lys Ala Glu Lys Asp Glu Leu Arg Asp Glu Lys Gln Lys Leu Lys
                85                  90                  95

Leu Glu Lys Glu Thr Leu Glu His Gln Met Lys Leu Leu Thr Ala Thr
            100                 105                 110

Pro Ala Tyr Met Pro His Pro Thr Met Met His Ser Pro Phe Ala Gln
        115                 120                 125

Ala Pro Met Ala Pro Phe His Ala Gln Gly His Ala Ser Ala Gln Lys
    130                 135                 140

Leu Met Met Pro Phe Val Gly Tyr Pro Gly Tyr Pro Met Trp Gln Leu
145                 150                 155                 160

Met Pro Pro Ser Glu Val Asp Thr Ser Lys Asp Ser Glu Ala Cys Pro
                165                 170                 175

Pro Val Ala


<210> SEQ ID NO 34
<211> LENGTH: 127
<212> TYPE: PRT
<213> ORGANISM: Sorghum bicolor

<400> SEQUENCE: 34

Ala Ile Leu Asn Asp Ala Ile Arg Val Val Gly Glu Leu Arg Ser Glu
1               5                   10                  15

Ala Lys Glu Leu Lys Asp Ser Asn Glu Ser Leu Gln Glu Lys Ile Lys
            20                  25                  30

Glu Leu Lys Ala Glu Lys Asn Glu Leu Arg Asp Glu Lys Gln Arg Leu
        35                  40                  45

Lys Ala Glu Lys Glu Ser Leu Glu Gln Gln Ile Lys Phe Leu Asn Ala
    50                  55                  60

Arg Pro Ser Leu Val Pro His His Pro Val Ile Ser Ala Ser Ala Phe
65                  70                  75                  80
```

-continued

```
Thr Ala Pro Gln Gly Pro Ala Val Ala Gly His Lys Leu Met Met Pro
                85                  90                  95

Val Leu Gly Tyr Pro Gly Phe Pro Met Trp Gln Phe Met Pro Pro Ser
            100                 105                 110

Asp Val Asp Thr Ser Asp Asp Pro Lys Ser Cys Pro Pro Val Ala
        115                 120                 125


<210> SEQ ID NO 35
<211> LENGTH: 164
<212> TYPE: PRT
<213> ORGANISM: Zea mays

<400> SEQUENCE: 35

Cys Arg Glu Arg Met Arg Arg Asn Lys Leu Asn Asp Arg Phe Leu Glu
1               5                   10                  15

Leu Gly Ser Ala Leu Glu Pro Gly Lys Pro Val Lys Ala Asp Lys Ala
            20                  25                  30

Ala Ile Leu Ser Asp Ala Thr Arg Met Val Ile Gln Leu Arg Ser Glu
        35                  40                  45

Ser Gln Gln Leu Lys Glu Thr Asn Gly Ser Leu Glu Glu Lys Ile Lys
    50                  55                  60

Glu Leu Lys Ala Glu Lys Asp Glu Leu Arg Asp Glu Lys Gln Lys Leu
65                  70                  75                  80

Lys Leu Glu Lys Glu Ser Leu Glu His Gln Met Lys Leu Met Ala Ser
                85                  90                  95

Ala Pro Ala Tyr Met Pro His Pro Thr Leu Met Pro Ala Pro Phe Ala
            100                 105                 110

Gln Ala Pro Leu Ala Pro Phe His Ala Gln Gly Gln Ala Ala Gly Gln
        115                 120                 125

Lys Leu Met Met Pro Phe Val Gly Tyr Pro Gly Tyr Pro Met Trp Gln
    130                 135                 140

Phe Met Pro Pro Ser Glu Val Asp Thr Ser Lys Asp Ser Glu Ala Cys
145                 150                 155                 160

Pro Pro Val Ala


<210> SEQ ID NO 36
<211> LENGTH: 130
<212> TYPE: PRT
<213> ORGANISM: Zea mays

<400> SEQUENCE: 36

Lys Thr Ala Ile Leu Ser Asp Ala Ile Arg Val Val Gly Glu Leu Arg
1               5                   10                  15

Ser Glu Ala Lys Lys Leu Lys Asp Ser Asn Glu Asn Leu Gln Glu Lys
            20                  25                  30

Ile Lys Glu Leu Lys Ala Glu Lys Asn Glu Leu Arg Asp Glu Lys Gln
        35                  40                  45

Arg Leu Lys Ala Glu Lys Glu Ser Leu Glu Gln Gln Ile Lys Phe Leu
    50                  55                  60

Asn Ala Arg Pro Ser Leu Val Pro His Arg Pro Val Ile Pro Ala Ser
65                  70                  75                  80

Ala Phe Pro Ala Pro Gln Gly Pro Ala Ala Ala Ala Arg His Lys Leu
                85                  90                  95

Met Met Pro Val Ile Gly Tyr Pro Gly Phe Pro Met Trp Gln Phe Met
            100                 105                 110

Pro Pro Ser Asp Val Asp Thr Ser Asp Asp Pro Arg Ser Cys Pro Pro
```

-continued

```
        115                 120                 125

Val Ala
    130


<210> SEQ ID NO 37
<211> LENGTH: 234
<212> TYPE: PRT
<213> ORGANISM: Arabidopsis thaliana

<400> SEQUENCE: 37

Met Val Ser Pro Glu Asn Ala Asn Trp Ile Cys Asp Leu Ile Asp Ala
1               5                   10                  15

Asp Tyr Gly Ser Phe Thr Ile Gln Gly Pro Gly Phe Ser Trp Pro Val
            20                  25                  30

Gln Gln Pro Ile Gly Val Ser Ser Asn Ser Ser Ala Gly Val Asp Gly
        35                  40                  45

Ser Ala Gly Asn Ser Glu Ala Ser Lys Glu Pro Gly Ser Lys Lys Arg
    50                  55                  60

Gly Arg Cys Glu Ser Ser Ser Ala Thr Ser Ser Lys Ala Cys Arg Glu
65                  70                  75                  80

Lys Gln Arg Arg Asp Arg Leu Asn Asp Lys Phe Met Glu Leu Gly Ala
                85                  90                  95

Ile Leu Glu Pro Gly Asn Pro Pro Lys Thr Asp Lys Ala Ala Ile Leu
            100                 105                 110

Val Asp Ala Val Arg Met Val Thr Gln Leu Arg Gly Glu Ala Gln Lys
        115                 120                 125

Leu Lys Asp Ser Asn Ser Ser Leu Gln Asp Lys Ile Lys Glu Leu Lys
    130                 135                 140

Thr Glu Lys Asn Glu Leu Arg Asp Glu Lys Gln Arg Leu Lys Thr Glu
145                 150                 155                 160

Lys Glu Lys Leu Glu Gln Gln Leu Lys Ala Met Asn Ala Pro Gln Pro
                165                 170                 175

Ser Phe Phe Pro Ala Pro Pro Met Met Pro Thr Ala Phe Ala Ser Ala
            180                 185                 190

Gln Gly Gln Ala Pro Gly Asn Lys Met Val Pro Ile Ile Ser Tyr Pro
        195                 200                 205

Gly Val Ala Met Trp Gln Phe Met Pro Pro Ala Ser Val Asp Thr Ser
    210                 215                 220

Gln Asp His Val Leu Arg Pro Pro Val Ala
225                 230


<210> SEQ ID NO 38
<211> LENGTH: 234
<212> TYPE: PRT
<213> ORGANISM: Arabidopsis thaliana

<400> SEQUENCE: 38

Met Val Ser Pro Glu Asn Ala Asn Trp Ile Cys Asp Leu Ile Asp Ala
1               5                   10                  15

Asp Tyr Gly Ser Phe Thr Ile Gln Gly Pro Gly Phe Ser Trp Pro Val
            20                  25                  30

Gln Gln Pro Ile Gly Val Ser Ser Asn Ser Ser Ala Gly Val Asp Gly
        35                  40                  45

Ser Ala Gly Asn Ser Glu Ala Ser Lys Glu Pro Gly Ser Lys Lys Arg
    50                  55                  60

Gly Arg Cys Glu Ser Ser Ser Ala Thr Ser Ser Lys Ala Cys Arg Glu
```

-continued

```
65                  70                  75                  80

Lys Gln Arg Arg Asp Arg Leu Asn Asp Lys Phe Met Glu Leu Gly Ala
                85                  90                  95

Ile Leu Glu Pro Gly Asn Pro Pro Lys Thr Asp Lys Ala Ala Ile Leu
            100                 105                 110

Val Asp Ala Val Arg Met Val Thr Gln Leu Arg Gly Glu Ala Gln Lys
        115                 120                 125

Leu Lys Asp Ser Asn Ser Ser Leu Gln Asp Lys Ile Lys Glu Leu Lys
    130                 135                 140

Thr Glu Lys Asn Glu Leu Arg Asp Glu Lys Gln Arg Leu Lys Thr Glu
145                 150                 155                 160

Lys Glu Lys Leu Glu Gln Gln Leu Lys Ala Ile Asn Ala Pro Gln Pro
                165                 170                 175

Ser Phe Phe Pro Ala Pro Pro Met Met Pro Thr Ala Phe Ala Ser Ala
            180                 185                 190

Gln Gly Gln Ala Pro Gly Asn Lys Met Val Pro Ile Ile Ser Tyr Pro
        195                 200                 205

Gly Val Ala Met Trp Gln Phe Met Pro Pro Ala Ser Val Asp Thr Ser
    210                 215                 220

Gln Asp His Val Leu Arg Pro Pro Val Ala
225                 230


<210> SEQ ID NO 39
<211> LENGTH: 226
<212> TYPE: PRT
<213> ORGANISM: Arabidopsis thaliana

<400> SEQUENCE: 39

Met Val Ser Pro Glu Asn Thr Asn Trp Leu Ser Asp Tyr Pro Leu Ile
1               5                   10                  15

Glu Gly Ala Phe Ser Asp Gln Asn Pro Thr Phe Pro Trp Gln Ile Asp
            20                  25                  30

Gly Ser Ala Thr Val Ser Val Glu Val Asp Gly Phe Leu Cys Asp Ala
        35                  40                  45

Asp Val Ile Lys Glu Pro Ser Ser Arg Lys Arg Ile Lys Thr Glu Ser
    50                  55                  60

Cys Thr Gly Ser Asn Ser Lys Ala Cys Arg Glu Lys Gln Arg Arg Asp
65                  70                  75                  80

Arg Leu Asn Asp Lys Phe Thr Glu Leu Ser Ser Val Leu Glu Pro Gly
                85                  90                  95

Arg Thr Pro Lys Thr Asp Lys Val Ala Ile Ile Asn Asp Ala Ile Arg
            100                 105                 110

Met Val Asn Gln Ala Arg Asp Glu Ala Gln Lys Leu Lys Asp Leu Asn
        115                 120                 125

Ser Ser Leu Gln Glu Lys Ile Lys Glu Leu Lys Asp Glu Lys Asn Glu
    130                 135                 140

Leu Arg Asp Glu Lys Gln Lys Leu Lys Val Glu Lys Glu Arg Ile Asp
145                 150                 155                 160

Gln Gln Leu Lys Ala Ile Lys Thr Gln Pro Gln Pro Gln Pro Cys Phe
                165                 170                 175

Leu Pro Asn Pro Gln Thr Leu Ser Gln Ala Gln Ala Pro Gly Ser Lys
            180                 185                 190

Leu Val Pro Phe Thr Thr Tyr Pro Gly Phe Ala Met Trp Gln Phe Met
        195                 200                 205
```

-continued

```
Pro Pro Ala Ala Val Asp Thr Ser Gln Asp His Val Leu Arg Pro Pro
    210                 215                 220

Val Ala
225
```

<210> SEQ ID NO 40
<211> LENGTH: 291
<212> TYPE: PRT
<213> ORGANISM: Arabidopsis thaliana

<400> SEQUENCE: 40

```
Met Gln Thr Asn Glu Asp Asn Ile Phe Gln Asp Phe Gly Ser Cys Gly
1               5                   10                  15

Val Asn Leu Met Gln Pro Gln Gln Glu Gln Phe Asp Ser Phe Asn Gly
            20                  25                  30

Asn Leu Glu Gln Val Cys Ser Ser Phe Arg Gly Gly Asn Asn Gly Val
        35                  40                  45

Val Tyr Ser Ser Ser Ile Gly Ser Ala Gln Leu Asp Leu Ala Ala Ser
    50                  55                  60

Phe Ser Gly Val Leu Gln Gln Glu Thr His Gln Val Cys Gly Phe Arg
65                  70                  75                  80

Gly Gln Asn Asp Asp Ser Ala Val Pro His Leu Gln Gln Gln Gln Gly
                85                  90                  95

Gln Val Phe Ser Gly Val Val Glu Ile Asn Ser Ser Ser Ser Val Gly
            100                 105                 110

Ala Val Lys Glu Glu Phe Glu Glu Glu Cys Ser Gly Lys Arg Arg Arg
        115                 120                 125

Thr Gly Ser Cys Ser Lys Pro Gly Thr Lys Ala Cys Arg Glu Lys Leu
    130                 135                 140

Arg Arg Glu Lys Leu Asn Asp Lys Phe Met Asp Leu Ser Ser Val Leu
145                 150                 155                 160

Glu Pro Gly Arg Thr Pro Lys Thr Asp Lys Ser Ala Ile Leu Asp Asp
                165                 170                 175

Ala Ile Arg Val Val Asn Gln Leu Arg Gly Glu Ala His Glu Leu Gln
            180                 185                 190

Glu Thr Asn Gln Lys Leu Leu Glu Glu Ile Lys Ser Leu Lys Ala Asp
        195                 200                 205

Lys Asn Glu Leu Arg Glu Glu Lys Leu Val Leu Lys Ala Glu Lys Glu
    210                 215                 220

Lys Met Glu Gln Gln Leu Lys Ser Met Val Val Pro Ser Pro Gly Phe
225                 230                 235                 240

Met Pro Ser Gln His Pro Ala Ala Phe His Ser His Lys Met Ala Val
                245                 250                 255

Ala Tyr Pro Tyr Gly Tyr Tyr Pro Pro Asn Met Pro Met Trp Ser Pro
            260                 265                 270

Leu Pro Pro Ala Asp Arg Asp Thr Ser Arg Asp Leu Lys Asn Leu Pro
        275                 280                 285

Pro Val Ala
    290
```

<210> SEQ ID NO 41
<211> LENGTH: 320
<212> TYPE: PRT
<213> ORGANISM: Arabidopsis thaliana

<400> SEQUENCE: 41

-continued

```
Met Tyr Pro Ser Ile Glu Asp Asp Asp Asp Leu Leu Ala Ala Leu Cys
1               5                   10                  15

Phe Asp Gln Ser Asn Gly Val Glu Asp Pro Tyr Gly Tyr Met Gln Thr
            20                  25                  30

Asn Glu Asp Asn Ile Phe Gln Asp Phe Gly Ser Cys Gly Val Asn Leu
        35                  40                  45

Met Gln Pro Gln Gln Glu Gln Phe Asp Ser Phe Asn Gly Asn Leu Glu
    50                  55                  60

Gln Val Cys Ser Ser Phe Arg Gly Gly Asn Asn Gly Val Val Tyr Ser
65                  70                  75                  80

Ser Ser Ile Gly Ser Ala Gln Leu Asp Leu Ala Ala Ser Phe Ser Gly
                85                  90                  95

Val Leu Gln Gln Glu Thr His Gln Val Cys Gly Phe Arg Gly Gln Asn
            100                 105                 110

Asp Asp Ser Ala Val Pro His Leu Gln Gln Gln Gln Gly Gln Val Phe
        115                 120                 125

Ser Gly Val Val Glu Ile Asn Ser Ser Ser Ser Val Gly Ala Val Lys
    130                 135                 140

Glu Glu Phe Glu Glu Glu Cys Ser Gly Lys Arg Arg Arg Thr Gly Ser
145                 150                 155                 160

Cys Ser Lys Pro Gly Thr Lys Ala Cys Arg Glu Lys Leu Arg Arg Glu
                165                 170                 175

Lys Leu Asn Asp Lys Phe Met Asp Leu Ser Ser Val Leu Glu Pro Gly
            180                 185                 190

Arg Thr Pro Lys Thr Asp Lys Ser Ala Ile Leu Asp Asp Ala Ile Arg
        195                 200                 205

Val Val Asn Gln Leu Arg Gly Glu Ala His Glu Leu Gln Glu Thr Asn
    210                 215                 220

Gln Lys Leu Leu Glu Glu Ile Lys Ser Leu Lys Ala Asp Lys Asn Glu
225                 230                 235                 240

Leu Arg Glu Glu Lys Leu Val Leu Lys Ala Glu Lys Glu Lys Met Glu
                245                 250                 255

Gln Gln Leu Lys Ser Met Val Val Pro Ser Pro Gly Phe Met Pro Ser
            260                 265                 270

Gln His Pro Ala Ala Phe His Ser His Lys Met Ala Val Ala Tyr Pro
        275                 280                 285

Tyr Gly Tyr Tyr Pro Pro Asn Met Pro Met Trp Ser Pro Leu Pro Pro
    290                 295                 300

Ala Asp Arg Asp Thr Ser Arg Asp Leu Lys Asn Leu Pro Pro Val Ala
305                 310                 315                 320


<210> SEQ ID NO 42
<211> LENGTH: 283
<212> TYPE: PRT
<213> ORGANISM: Arabidopsis thaliana

<400> SEQUENCE: 42

Met Tyr Pro Ser Leu Asp Asp Asp Phe Val Ser Asp Leu Phe Cys Phe
1               5                   10                  15

Asp Gln Ser Asn Gly Ala Glu Leu Asp Asp Tyr Thr Gln Phe Gly Val
            20                  25                  30

Asn Leu Gln Thr Asp Gln Glu Asp Thr Phe Pro Asp Phe Val Ser Tyr
        35                  40                  45

Gly Val Asn Leu Gln Gln Glu Pro Asp Glu Val Phe Ser Ile Gly Ala
    50                  55                  60
```

-continued

```
Ser Gln Leu Asp Leu Ser Ser Tyr Asn Gly Val Leu Ser Leu Glu Pro
65                  70                  75                  80

Glu Gln Val Gly Gln Gln Asp Cys Glu Val Val Gln Glu Glu Glu Val
                85                  90                  95

Glu Ile Asn Ser Gly Ser Ser Gly Gly Ala Val Lys Glu Glu Gln Glu
            100                 105                 110

His Leu Asp Asp Asp Cys Ser Arg Lys Arg Ala Arg Thr Gly Ser Cys
        115                 120                 125

Ser Arg Gly Gly Gly Thr Lys Ala Cys Arg Glu Arg Leu Arg Arg Glu
    130                 135                 140

Lys Leu Asn Glu Arg Phe Met Asp Leu Ser Ser Val Leu Glu Pro Gly
145                 150                 155                 160

Arg Thr Pro Lys Thr Asp Lys Pro Ala Ile Leu Asp Asp Ala Ile Arg
                165                 170                 175

Ile Leu Asn Gln Leu Arg Asp Glu Ala Leu Lys Leu Glu Glu Thr Asn
            180                 185                 190

Gln Lys Leu Leu Glu Glu Ile Lys Ser Leu Lys Ala Glu Lys Asn Glu
        195                 200                 205

Leu Arg Glu Glu Lys Leu Val Leu Lys Ala Asp Lys Glu Lys Thr Glu
    210                 215                 220

Gln Gln Leu Lys Ser Met Thr Ala Pro Ser Ser Gly Phe Ile Pro His
225                 230                 235                 240

Ile Pro Ala Ala Phe Asn His Asn Lys Met Ala Val Tyr Pro Ser Tyr
                245                 250                 255

Gly Tyr Met Pro Met Trp His Tyr Met Pro Gln Ser Val Arg Asp Thr
            260                 265                 270

Ser Arg Asp Gln Glu Leu Arg Pro Pro Ala Ala
        275                 280


<210> SEQ ID NO 43
<211> LENGTH: 277
<212> TYPE: PRT
<213> ORGANISM: Arabidopsis thaliana

<400> SEQUENCE: 43

Met Asp Val Asn Leu Phe Gly His Asp Asp Ser Cys Ser Asn Gly Ala
1               5                   10                  15

Glu Leu Asp Asp Tyr Thr Gln Phe Gly Val Asn Leu Gln Thr Asp Gln
            20                  25                  30

Glu Asp Thr Phe Pro Asp Phe Val Ser Tyr Gly Val Asn Leu Gln Gln
        35                  40                  45

Glu Pro Asp Glu Val Phe Ser Ile Gly Ala Ser Gln Leu Asp Leu Ser
    50                  55                  60

Ser Tyr Asn Gly Val Leu Ser Leu Glu Pro Glu Gln Val Gly Gln Gln
65                  70                  75                  80

Asp Cys Glu Val Val Gln Glu Glu Glu Val Glu Ile Asn Ser Gly Ser
                85                  90                  95

Ser Gly Gly Ala Val Lys Glu Glu Gln Glu His Leu Asp Asp Asp Cys
            100                 105                 110

Ser Arg Lys Arg Ala Arg Thr Gly Ser Cys Ser Arg Gly Gly Gly Thr
        115                 120                 125

Lys Ala Cys Arg Glu Arg Leu Arg Arg Glu Lys Leu Asn Glu Arg Phe
    130                 135                 140

Met Asp Leu Ser Ser Val Leu Glu Pro Gly Arg Thr Pro Lys Thr Asp
```

-continued

```
145                 150                 155                 160

Lys Pro Ala Ile Leu Asp Asp Ala Ile Arg Ile Leu Asn Gln Leu Arg
                165                 170                 175

Asp Glu Ala Leu Lys Leu Glu Glu Thr Asn Gln Lys Leu Leu Glu Glu
            180                 185                 190

Ile Lys Ser Leu Lys Ala Glu Lys Asn Glu Leu Arg Glu Glu Lys Leu
        195                 200                 205

Val Leu Lys Ala Asp Lys Glu Lys Thr Glu Gln Gln Leu Lys Ser Met
    210                 215                 220

Thr Ala Pro Ser Ser Gly Phe Ile Pro His Ile Pro Ala Ala Phe Asn
225                 230                 235                 240

His Asn Lys Met Ala Val Tyr Pro Ser Tyr Gly Tyr Met Pro Met Trp
                245                 250                 255

His Tyr Met Pro Gln Ser Val Arg Asp Thr Ser Arg Asp Gln Glu Leu
            260                 265                 270

Arg Pro Pro Ala Ala
        275


<210> SEQ ID NO 44
<211> LENGTH: 337
<212> TYPE: PRT
<213> ORGANISM: Arabidopsis thaliana

<400> SEQUENCE: 44

Met Gly Ile Arg Glu Asn Gly Ile Met Leu Val Ser Arg Glu Arg Glu
1               5                   10                  15

Arg Ala Arg Arg Leu Glu Asn Arg Glu Ser Ile Phe Ala Glu Pro Pro
            20                  25                  30

Cys Leu Leu Leu Ala His Arg Ile Ser Pro Ser Pro Ser Ile Leu Pro
        35                  40                  45

Ala Glu Glu Glu Val Met Asp Val Ser Ala Arg Lys Ser Gln Lys Ala
    50                  55                  60

Gly Arg Glu Lys Leu Arg Arg Glu Lys Leu Asn Glu His Phe Val Glu
65                  70                  75                  80

Leu Gly Asn Val Leu Asp Pro Glu Arg Pro Lys Asn Asp Lys Ala Thr
                85                  90                  95

Ile Leu Thr Asp Thr Val Gln Leu Leu Lys Glu Leu Thr Ser Glu Val
            100                 105                 110

Asn Lys Leu Lys Ser Glu Tyr Thr Ala Leu Thr Asp Glu Ser Arg Glu
        115                 120                 125

Leu Thr Gln Glu Lys Asn Asp Leu Arg Glu Glu Lys Thr Ser Leu Lys
    130                 135                 140

Ser Asp Ile Glu Asn Leu Asn Leu Gln Tyr Gln Gln Arg Leu Arg Ser
145                 150                 155                 160

Met Ser Pro Trp Gly Ala Ala Met Asp His Thr Val Met Met Ala Pro
                165                 170                 175

Pro Pro Ser Phe Pro Tyr Pro Met Pro Ile Ala Met Pro Pro Gly Ser
            180                 185                 190

Ile Pro Met His Pro Ser Met Pro Ser Tyr Thr Tyr Phe Gly Asn Gln
        195                 200                 205

Asn Pro Ser Met Ile Pro Ala Pro Cys Pro Thr Tyr Met Pro Tyr Met
    210                 215                 220

Pro Pro Asn Thr Val Val Glu Gln Gln Ser Val His Ile Pro Gln Asn
225                 230                 235                 240
```

-continued

```
Pro Gly Asn Arg Ser Arg Glu Pro Arg Ala Lys Val Ser Arg Glu Ser
                245                 250                 255

Arg Ser Glu Lys Ala Glu Asp Ser Asn Glu Val Ala Thr Gln Leu Glu
            260                 265                 270

Leu Lys Thr Pro Gly Ser Thr Ser Asp Lys Asp Thr Leu Gln Arg Pro
        275                 280                 285

Glu Lys Thr Lys Arg Cys Lys Arg Asn Asn Asn Asn Asn Ser Ile Glu
    290                 295                 300

Glu Ser Ser His Ser Ser Lys Cys Ser Ser Ser Pro Ser Val Arg Asp
305                 310                 315                 320

His Ser Ser Ser Ser Ser Val Ala Gly Gly Gln Lys Pro Asp Asp Ala
                325                 330                 335

Lys


<210> SEQ ID NO 45
<211> LENGTH: 284
<212> TYPE: PRT
<213> ORGANISM: Arabidopsis thaliana

<400> SEQUENCE: 45

Met Asp Val Ser Ala Arg Lys Ser Gln Lys Ala Gly Arg Glu Lys Leu
1               5                   10                  15

Arg Arg Glu Lys Leu Asn Glu His Phe Val Glu Leu Gly Asn Val Leu
            20                  25                  30

Asp Pro Glu Arg Pro Lys Asn Asp Lys Ala Thr Ile Leu Thr Asp Thr
        35                  40                  45

Val Gln Leu Leu Lys Glu Leu Thr Ser Glu Val Asn Lys Leu Lys Ser
    50                  55                  60

Glu Tyr Thr Ala Leu Thr Asp Glu Ser Arg Glu Leu Thr Gln Glu Lys
65                  70                  75                  80

Asn Asp Leu Arg Glu Glu Lys Thr Ser Leu Lys Ser Asp Ile Glu Asn
                85                  90                  95

Leu Asn Leu Gln Tyr Gln Gln Arg Leu Arg Ser Met Ser Pro Trp Gly
            100                 105                 110

Ala Ala Met Asp His Thr Val Met Met Ala Pro Pro Pro Ser Phe Pro
        115                 120                 125

Tyr Pro Met Pro Ile Ala Met Pro Pro Gly Ser Ile Pro Met His Pro
    130                 135                 140

Ser Met Pro Ser Tyr Thr Tyr Phe Gly Asn Gln Asn Pro Ser Met Ile
145                 150                 155                 160

Pro Ala Pro Cys Pro Thr Tyr Met Pro Tyr Met Pro Pro Asn Thr Val
                165                 170                 175

Val Glu Gln Gln Ser Val His Ile Pro Gln Asn Pro Gly Asn Arg Ser
            180                 185                 190

Arg Glu Pro Arg Ala Lys Val Ser Arg Glu Ser Arg Ser Glu Lys Ala
        195                 200                 205

Glu Asp Ser Asn Glu Val Ala Thr Gln Leu Glu Leu Lys Thr Pro Gly
    210                 215                 220

Ser Thr Ser Asp Lys Asp Thr Leu Gln Arg Pro Glu Lys Thr Lys Arg
225                 230                 235                 240

Cys Lys Arg Asn Asn Asn Asn Asn Ser Ile Glu Glu Ser Ser His Ser
                245                 250                 255

Ser Lys Cys Ser Ser Ser Pro Ser Val Arg Asp His Ser Ser Ser Ser
            260                 265                 270
```

-continued

```
Ser Val Ala Gly Gly Gln Lys Pro Asp Asp Ala Lys
        275                 280


<210> SEQ ID NO 46
<211> LENGTH: 268
<212> TYPE: PRT
<213> ORGANISM: Arabidopsis thaliana

<400> SEQUENCE: 46

Met Ala Val Ser Cys Leu Phe Ile Val Ser Ser Asn Tyr Arg Gly Ala
1               5                   10                  15

Glu Met Val Val Glu Val Lys Lys Glu Ala Val Cys Ser Gln Lys Ala
            20                  25                  30

Glu Arg Glu Lys Leu Arg Arg Asp Lys Leu Lys Glu Gln Phe Leu Glu
        35                  40                  45

Leu Gly Asn Ala Leu Asp Pro Asn Arg Pro Lys Ser Asp Lys Ala Ser
    50                  55                  60

Val Leu Thr Asp Thr Ile Gln Met Leu Lys Asp Val Met Asn Gln Val
65                  70                  75                  80

Asp Arg Leu Lys Ala Glu Tyr Glu Thr Leu Ser Gln Glu Ser Arg Glu
                85                  90                  95

Leu Ile Gln Glu Lys Ser Glu Leu Arg Glu Glu Lys Ala Thr Leu Lys
            100                 105                 110

Ser Asp Ile Glu Ile Leu Asn Ala Gln Tyr Gln His Gly Ile Lys Thr
        115                 120                 125

Met Val Pro Trp Val Pro His Tyr Ser Tyr His Ile Pro Phe Val Ala
    130                 135                 140

Ile Thr Gln Gly Gln Ser Ser Phe Ile Pro Tyr Ser Ala Ser Val Asn
145                 150                 155                 160

Pro Leu Thr Glu Gln Gln Ala Ser Val Gln Gln His Ser Ser Ser Ser
                165                 170                 175

Ala Asp Ala Ser Met Lys Gln Asp Ser Lys Ile Lys Pro Leu Asp Leu
            180                 185                 190

Asp Leu Met Met Asn Ser Asn His Ser Gly Gln Gly Asn Asp Gln Lys
        195                 200                 205

Asp Asp Val Arg Leu Lys Leu Glu Leu Lys Ile His Ala Ser Ser Leu
    210                 215                 220

Ala Gln Gln Asp Val Ser Gly Lys Glu Lys Lys Val Ser Leu Thr Thr
225                 230                 235                 240

Thr Ala Ser Ser Ser Asn Ser Tyr Ser Leu Ser Gln Ala Val Gln Asp
                245                 250                 255

Ser Ser Pro Gly Thr Val Asn Asp Met Leu Lys Pro
            260                 265


<210> SEQ ID NO 47
<211> LENGTH: 286
<212> TYPE: PRT
<213> ORGANISM: Arabidopsis thaliana

<400> SEQUENCE: 47

Met Asp Gln Pro Met Lys Pro Lys Thr Cys Ser Glu Ser Asp Phe Ala
1               5                   10                  15

Asp Asp Ser Ser Ala Ser Ser Ser Ser Ser Ser Gly Gln Asn Leu Arg
            20                  25                  30

Gly Ala Glu Met Val Val Glu Val Lys Lys Glu Ala Val Cys Ser Gln
        35                  40                  45
```

-continued

```
Lys Ala Glu Arg Glu Lys Leu Arg Arg Asp Lys Leu Lys Glu Gln Phe
    50                  55                  60

Leu Glu Leu Gly Asn Ala Leu Asp Pro Asn Arg Pro Lys Ser Asp Lys
65                  70                  75                  80

Ala Ser Val Leu Thr Asp Thr Ile Gln Met Leu Lys Asp Val Met Asn
                85                  90                  95

Gln Val Asp Arg Leu Lys Ala Glu Tyr Glu Thr Leu Ser Gln Glu Ser
            100                 105                 110

Arg Glu Leu Ile Gln Glu Lys Ser Glu Leu Arg Glu Glu Lys Ala Thr
        115                 120                 125

Leu Lys Ser Asp Ile Glu Ile Leu Asn Ala Gln Tyr Gln His Arg Ile
    130                 135                 140

Lys Thr Met Val Pro Trp Val Pro His Tyr Ser Tyr His Ile Pro Phe
145                 150                 155                 160

Val Ala Ile Thr Gln Gly Gln Ser Ser Phe Ile Pro Tyr Ser Ala Ser
                165                 170                 175

Val Asn Pro Leu Thr Glu Gln Gln Ala Ser Val Gln Gln His Ser Ser
            180                 185                 190

Ser Ser Ala Asp Ala Ser Met Lys Gln Asp Ser Lys Ile Lys Pro Leu
        195                 200                 205

Asp Leu Asp Leu Met Met Asn Ser Asn His Ser Gly Gln Gly Asn Asp
    210                 215                 220

Gln Lys Asp Asp Val Arg Leu Lys Leu Glu Leu Lys Ile His Ala Ser
225                 230                 235                 240

Ser Leu Ala Gln Gln Asp Val Ser Gly Lys Glu Lys Lys Val Ser Leu
                245                 250                 255

Thr Thr Thr Ala Ser Ser Ser Asn Ser Tyr Ser Leu Ser Gln Ala Val
            260                 265                 270

Gln Asp Ser Ser Pro Gly Thr Val Asn Asp Met Leu Lys Pro
        275                 280                 285


<210> SEQ ID NO 48
<211> LENGTH: 268
<212> TYPE: PRT
<213> ORGANISM: Arabidopsis thaliana

<400> SEQUENCE: 48

Met Ala Val Ser Cys Leu Phe Ile Val Ser Ser Asn Tyr Arg Gly Ala
1               5                   10                  15

Glu Met Val Val Glu Val Lys Lys Glu Ala Val Cys Ser Gln Lys Ala
            20                  25                  30

Glu Arg Glu Lys Leu Arg Arg Asp Lys Leu Lys Glu Gln Phe Leu Glu
        35                  40                  45

Leu Gly Asn Ala Leu Asp Pro Asn Arg Pro Lys Ser Asp Lys Ala Ser
    50                  55                  60

Val Leu Thr Asp Thr Ile Gln Met Leu Lys Asp Val Met Asn Gln Val
65                  70                  75                  80

Asp Arg Leu Lys Ala Glu Tyr Glu Thr Leu Ser Gln Glu Ser Arg Glu
                85                  90                  95

Leu Ile Gln Glu Lys Ser Glu Leu Arg Glu Glu Lys Ala Thr Leu Lys
            100                 105                 110

Ser Asp Ile Glu Ile Leu Asn Ala Gln Tyr Gln His Arg Ile Lys Thr
        115                 120                 125

Met Val Pro Trp Val Pro His Tyr Ser Tyr His Ile Pro Phe Val Ala
    130                 135                 140
```

-continued

```
Ile Thr Gln Gly Gln Ser Ser Phe Ile Pro Tyr Ser Ala Ser Val Asn
145                 150                 155                 160

Pro Leu Thr Glu Gln Gln Ala Ser Val Gln Gln His Ser Ser Ser Ser
                165                 170                 175

Ala Asp Ala Ser Met Lys Gln Asp Ser Lys Ile Lys Pro Leu Asp Leu
            180                 185                 190

Asp Leu Met Met Asn Ser Asn His Ser Gly Gln Gly Asn Asp Gln Lys
        195                 200                 205

Asp Asp Val Arg Leu Lys Leu Glu Leu Lys Ile His Ala Ser Ser Leu
    210                 215                 220

Ala Gln Gln Asp Val Ser Gly Lys Glu Lys Lys Val Ser Leu Thr Thr
225                 230                 235                 240

Thr Ala Ser Ser Ser Asn Ser Tyr Ser Leu Ser Gln Ala Val Gln Asp
                245                 250                 255

Ser Ser Pro Gly Thr Val Asn Asp Met Leu Lys Pro
            260                 265


<210> SEQ ID NO 49
<211> LENGTH: 272
<212> TYPE: PRT
<213> ORGANISM: Arabidopsis thaliana

<400> SEQUENCE: 49

Met Asp Gln Pro Met Lys Pro Lys Thr Cys Ser Glu Ser Asp Phe Ala
1               5                   10                  15

Asp Asp Ser Ser Ala Ser Ser Ser Ser Ser Ser Gly Gln Asn Leu Arg
            20                  25                  30

Gly Ala Glu Met Val Val Glu Val Lys Lys Glu Ala Val Cys Ser Gln
        35                  40                  45

Lys Ala Glu Arg Glu Lys Leu Arg Arg Asp Lys Leu Lys Glu Gln Phe
    50                  55                  60

Leu Glu Leu Gly Asn Ala Leu Asp Pro Asn Arg Pro Lys Ser Asp Lys
65                  70                  75                  80

Ala Ser Val Leu Thr Asp Thr Ile Gln Met Leu Lys Asp Val Met Asn
                85                  90                  95

Gln Val Asp Arg Leu Lys Ala Glu Tyr Glu Thr Leu Ser Gln Glu Ser
            100                 105                 110

Arg Glu Leu Ile Gln Glu Lys Ser Glu Leu Arg Glu Glu Lys Ala Thr
        115                 120                 125

Leu Lys Ser Asp Ile Glu Ile Leu Asn Ala Gln Tyr Gln His Arg Ile
    130                 135                 140

Lys Thr Met Val Pro Trp Gly Gln Ser Ser Phe Ile Pro Tyr Ser Ala
145                 150                 155                 160

Ser Val Asn Pro Leu Thr Glu Gln Gln Ala Ser Val Gln Gln His Ser
                165                 170                 175

Ser Ser Ser Ala Asp Ala Ser Met Lys Gln Asp Ser Lys Ile Lys Pro
            180                 185                 190

Leu Asp Leu Asp Leu Met Met Asn Ser Asn His Ser Gly Gln Gly Asn
        195                 200                 205

Asp Gln Lys Asp Asp Val Arg Leu Lys Leu Glu Leu Lys Ile His Ala
    210                 215                 220

Ser Ser Leu Ala Gln Gln Val Ser Asp Leu Phe Asn Ser Phe Ala Asn
225                 230                 235                 240

Lys Leu Phe His Gly Leu Thr Arg Val Tyr Phe His Ala Gly Cys Phe
```

-continued

```
            245                 250                 255

Trp Lys Arg Glu Glu Ser Lys Leu Asp Asn His Cys Lys Leu Ile Glu
            260                 265                 270


<210> SEQ ID NO 50
<211> LENGTH: 237
<212> TYPE: PRT
<213> ORGANISM: Vitis vinifera

<400> SEQUENCE: 50

Met Val Ser Pro Glu Ala Thr Asn Trp Leu Tyr Glu Tyr Gly Leu Ile
1               5                   10                  15

Glu Asp Ile Pro Val Pro Asp Ser Asn Phe Ala Asn Thr Asn Ser Gly
            20                  25                  30

Phe Ala Trp Thr Pro Val Gln Ala Leu Asn Thr Ser Ala Asn Val Ser
        35                  40                  45

Gly Glu Ile Asp Gly Ser Phe Gly Asp Ser Asp Gly Ile Lys Glu Thr
    50                  55                  60

Gly Ser Lys Lys Arg Val Arg Ser Glu Ser Cys Gly Ala Ser Ser Ser
65                  70                  75                  80

Lys Ala Cys Arg Glu Lys Leu Arg Arg Asp Arg Leu Asn Asp Lys Phe
                85                  90                  95

Met Glu Leu Gly Ser Ile Leu Glu Pro Gly Arg Pro Pro Lys Thr Asp
            100                 105                 110

Lys Ser Ser Ile Leu Ile Asp Ala Val Arg Met Val Thr Gln Leu Arg
        115                 120                 125

Gly Glu Ser Gln Lys Leu Lys Asp Ser Asn Ser Ser Leu Gln Glu Lys
    130                 135                 140

Ile Lys Glu Leu Lys Ala Glu Lys Asn Glu Leu Arg Asp Glu Lys Gln
145                 150                 155                 160

Arg Leu Lys Ala Glu Lys Glu Lys Leu Glu Gln Gln Leu Lys Ala Met
                165                 170                 175

Asn Ala Gln Pro Ser Phe Leu Pro Pro Val Pro Ser Ile Pro Ala Ala
            180                 185                 190

Phe Ala Ala Gln Gly Gln Ala Gly Gly Asp Lys Leu Val Pro Phe Ile
        195                 200                 205

Gly Tyr Pro Gly Val Ala Met Trp Gln Phe Met Pro Pro Ala Ala Val
    210                 215                 220

Asp Thr Ser Gln Asp His Val Leu Arg Pro Pro Val Ala
225                 230                 235


<210> SEQ ID NO 51
<211> LENGTH: 232
<212> TYPE: PRT
<213> ORGANISM: Citrus reticulata

<400> SEQUENCE: 51

Glu Asn Thr Asn Trp Leu Leu Asp Tyr Pro Leu Ile Asp Asp Ile Thr
1               5                   10                  15

Val Pro Asp Gly Asn Phe Ser Val Ser Ala Ser Gly Phe Thr Trp Thr
            20                  25                  30

Val Gln Pro Pro Ile Asn Gly Pro Ser Asn Gly Cys Val Glu Ile Asp
        35                  40                  45

Ser Ala Phe Gly Asp Ser Asn Gly Leu Lys Glu Ser Ser Lys Lys Arg
    50                  55                  60

Val Arg Ser Glu Ser Cys Gly Ser Ser Ser Ser Lys Ala Cys Arg Glu
```

-continued

```
65                  70                  75                  80

Lys Leu Arg Arg Asp Arg Leu Asn Asp Lys Phe Val Glu Leu Ala Ser
                85                  90                  95

Ile Leu Glu Pro Gly Arg Pro Pro Lys Thr Asp Lys Ala Ala Ile Leu
            100                 105                 110

Ile Asp Ala Val Arg Met Val Thr Gln Leu Arg Ser Glu Ala Gln Lys
        115                 120                 125

Leu Lys Asp Ser Asn Ser Ser Leu Gln Glu Lys Ile Lys Glu Leu Lys
    130                 135                 140

Ala Glu Lys Asn Glu Leu Arg Asp Glu Lys Gln Arg Leu Lys Ala Glu
145                 150                 155                 160

Lys Glu Lys Ile Glu Gln Gln Leu Lys Ala Met Ser Thr Gln Pro Ser
                165                 170                 175

Phe Leu Thr Pro Pro Pro Ala Ile Pro Ala Ala Phe Ala Ala Gln Gly
            180                 185                 190

Gln Ala Pro Gly Asn Lys Leu Met Pro Phe Ile Ser Tyr Pro Gly Val
        195                 200                 205

Ala Met Trp Gln Phe Met Pro Pro Ala Ala Val Asp Thr Ser Gln Asp
    210                 215                 220

His Val Leu Arg Pro Pro Val Ala
225                 230


<210> SEQ ID NO 52
<211> LENGTH: 230
<212> TYPE: PRT
<213> ORGANISM: Medicago truncatula

<400> SEQUENCE: 52

Met Val Ser Pro Glu Asn Thr Asn Trp Leu Phe Asp Tyr Pro Leu Ile
1               5                   10                  15

Asp Glu Ile Pro Val Ser Val Asp Gly Ser Phe Ala Phe Thr Trp Pro
            20                  25                  30

Pro Pro His Leu Ser Asn Gly Gly Ile Glu Met Asp Asp Ser Ser Leu
        35                  40                  45

Val Asp Ser Asp Gly Ile Lys Glu Pro Gly Ser Lys Lys Arg Gly Arg
    50                  55                  60

Ser Asp Ser Cys Ala Pro Ser Ser Ser Lys Ala Cys Arg Glu Lys Leu
65                  70                  75                  80

Arg Arg Asp Arg Leu Asn Asp Lys Phe Val Glu Leu Gly Ser Ile Leu
                85                  90                  95

Glu Pro Gly Arg Pro Pro Lys Thr Asp Lys Ala Ala Ile Leu Ile Asp
            100                 105                 110

Ala Val Arg Met Val Thr Gln Leu Arg Gly Glu Ala Gln Lys Leu Lys
        115                 120                 125

Asp Ser Asn Ser Arg Leu Gln Glu Lys Ile Lys Glu Leu Lys Val Glu
    130                 135                 140

Lys Asn Glu Leu Arg Asp Glu Lys Gln Arg Leu Lys Ala Glu Lys Glu
145                 150                 155                 160

Lys Leu Glu Gln Gln Val Lys Ser Met Asn Thr Gln Pro Gly Phe Leu
                165                 170                 175

Thr His Pro Pro Ala Ile Pro Ala Ala Phe Ala His Gln Gly Gln Ala
            180                 185                 190

Pro Ser Asn Lys Leu Met Pro Phe Met Ser Tyr Pro Gly Val Ala Met
        195                 200                 205
```

-continued

```
Trp Gln Phe Met Pro Pro Ala Ala Val Asp Thr Ser Gln Asp His Val
    210                 215                 220

Leu Arg Pro Pro Val Ala
225                 230


<210> SEQ ID NO 53
<211> LENGTH: 229
<212> TYPE: PRT
<213> ORGANISM: Vitis vinifera

<400> SEQUENCE: 53

Met Val Ser Pro Glu Ala Thr Asn Trp Leu Tyr Glu Tyr Gly Leu Ile
1               5                   10                  15

Glu Asp Ile Pro Val Pro Asp Ser Asn Phe Ala Asn Thr Asn Ser Gly
            20                  25                  30

Phe Ala Trp Thr Pro Val Gln Ala Leu Asn Thr Ser Ala Asn Val Ser
        35                  40                  45

Gly Glu Ile Asp Gly Ser Phe Gly Asp Ser Asp Gly Ile Lys Glu Thr
    50                  55                  60

Gly Ser Lys Lys Arg Val Arg Ser Glu Ser Cys Gly Ala Ser Ser Ser
65                  70                  75                  80

Lys Ala Cys Arg Glu Lys Leu Arg Arg Asp Arg Leu Asn Asp Lys Phe
                85                  90                  95

Met Glu Leu Gly Ser Ile Leu Glu Pro Gly Arg Pro Pro Lys Thr Asp
            100                 105                 110

Lys Ser Ser Ile Leu Ile Asp Ala Val Arg Met Val Thr Gln Leu Arg
        115                 120                 125

Gly Glu Ser Gln Lys Leu Lys Asp Ser Asn Ser Ser Leu Gln Glu Lys
    130                 135                 140

Ile Lys Glu Leu Lys Ala Glu Lys Asn Glu Leu Arg Asp Glu Lys Gln
145                 150                 155                 160

Arg Leu Lys Ala Glu Lys Glu Lys Leu Glu Gln Gln Leu Lys Ala Met
                165                 170                 175

Asn Ala Gln Pro Ser Phe Leu Pro Pro Val Pro Ser Ile Pro Ala Ala
            180                 185                 190

Phe Ala Ala Gln Gly Gln Ala Gly Gly Asn Lys Leu Val Pro Phe Ile
        195                 200                 205

Gly Tyr Pro Gly Val Ala Met Trp Gln Phe Met Pro Pro Ala Ala Val
    210                 215                 220

Asp Thr Leu Thr Asp
225


<210> SEQ ID NO 54
<211> LENGTH: 238
<212> TYPE: PRT
<213> ORGANISM: Gossypium raimondii

<400> SEQUENCE: 54

Met Val Ser Pro Glu Asn Phe Asn Tyr Trp Ser His Phe Asp Tyr Ala
1               5                   10                  15

Thr Leu Ile His Asp Ile Pro Val Pro Asp Asp Pro Tyr Ala Gly Phe
            20                  25                  30

Ala Trp Ser Thr Gln Pro Ile Asp Ala Pro Ser Asn Val Val Ser Val
        35                  40                  45

Glu Ile Asp Gly Ser Phe Gly Asp Ser Asp Gly Leu Lys Glu Ser Gly
    50                  55                  60
```

-continued

```
Ser Lys Lys Arg Val Arg Ser Glu Ser Cys Asn Ala Ser Ser Ser Lys
65                  70                  75                  80

Ala Cys Arg Glu Lys Leu Arg Arg Asp Arg Leu Asn Asp Lys Phe Met
                85                  90                  95

Glu Leu Gly Ser Ile Leu Glu Pro Gly Arg Pro Pro Lys Thr Asp Lys
            100                 105                 110

Ser Ala Ile Leu Ile Asp Ala Val Arg Met Val Thr Gln Leu Arg Gly
        115                 120                 125

Glu Ala Gln Lys Leu Lys Asp Ser Asn Thr Ser Leu Gln Glu Arg Ile
    130                 135                 140

Lys Glu Leu Lys Ser Glu Lys Asn Glu Leu Arg Asp Glu Lys Gln Arg
145                 150                 155                 160

Leu Lys Ala Glu Lys Glu Arg Leu Glu Gln Gln Leu Lys Ala Met Asn
                165                 170                 175

Ala Gln Pro Ser Phe Met Pro Pro Ala Pro Pro Ala Ile Pro Ala Ala
            180                 185                 190

Phe Ala Ala Ala Pro Gly Gln Ala Pro Gly Asn Lys Leu Val Pro Leu
        195                 200                 205

Ile Gly Tyr Pro Gly Val Ala Met Trp Gln Phe Met Pro Pro Ala Ala
    210                 215                 220

Val Asp Thr Ser Gln Asp His Val Leu Arg Pro Pro Val Ala
225                 230                 235


<210> SEQ ID NO 55
<211> LENGTH: 220
<212> TYPE: PRT
<213> ORGANISM: Citrus reticulata

<400> SEQUENCE: 55

Met Val Ser Pro Glu Asn Thr Asn Trp Leu Leu Asp Tyr Pro Leu Ile
1               5                   10                  15

Asp Asp Ile Thr Val Pro Asp Gly Asn Phe Ser Val Ser Ala Ser Gly
            20                  25                  30

Phe Thr Trp Thr Val Gln Pro Pro Ile Asn Gly Pro Ser Asn Gly Cys
        35                  40                  45

Val Glu Ile Asp Ser Ala Phe Gly Asp Ser Asn Gly Leu Lys Glu Ser
    50                  55                  60

Ser Lys Lys Arg Val Arg Ser Glu Ser Cys Gly Ser Ser Ser Ser Lys
65                  70                  75                  80

Ala Cys Arg Glu Lys Leu Arg Arg Asp Arg Leu Asn Asp Lys Phe Val
                85                  90                  95

Glu Leu Ala Ser Ile Leu Glu Pro Gly Arg Pro Pro Lys Thr Asp Lys
            100                 105                 110

Ala Ala Ile Leu Ile Asp Ala Val Arg Met Val Thr Gln Leu Arg Ser
        115                 120                 125

Glu Ala Gln Lys Leu Lys Asp Ser Asn Ser Ser Leu Gln Glu Lys Ile
    130                 135                 140

Lys Glu Leu Lys Ala Glu Lys Asn Glu Leu Arg Asp Glu Lys Gln Arg
145                 150                 155                 160

Leu Lys Ala Glu Lys Glu Lys Ile Glu Gln Gln Leu Lys Ala Met Ser
                165                 170                 175

Thr Gln Pro Ser Phe Leu Thr Pro Pro Ala Ile Pro Ala Ala Phe Ala
            180                 185                 190

Ala Gln Gly Gln Ala Pro Gly Asn Lys Leu Met Pro Phe Ile Ser Tyr
        195                 200                 205
```

-continued

```
Pro Gly Val Ala Met Trp Gln Phe Met Pro Pro Ala
    210                 215                 220


<210> SEQ ID NO 56
<211> LENGTH: 233
<212> TYPE: PRT
<213> ORGANISM: Solanum tuberosum

<400> SEQUENCE: 56

Met Val Ser Pro Glu Asn Thr Asn Trp Leu Tyr Asp Tyr Gly Phe Glu
1               5                   10                  15

Asp Ser Ser Val Pro Asp Ser Asn Phe Ser Pro Ser Ala Ser Gly Phe
            20                  25                  30

Asn Trp Pro Val Gln Asn Leu Asn Gly Ser Arg Asn Val Ser Ser Glu
        35                  40                  45

Ile Asp Gly Ser Ile Gly Glu Ser Asp Tyr Pro Lys Glu Ser Gly Ser
    50                  55                  60

Lys Lys Arg Ala Arg Val Glu Ser Cys Ala Pro Thr Ser Ser Lys Ala
65                  70                  75                  80

Cys Arg Glu Lys Leu Arg Arg Asp Lys Leu Asn Asp Lys Phe Met Glu
                85                  90                  95

Leu Gly Ala Leu Leu Glu Pro Gly Arg Pro Pro Lys Thr Asp Lys Ser
            100                 105                 110

Ala Ile Leu Val Asp Ala Val Arg Met Val Thr Gln Leu Arg Asp Glu
        115                 120                 125

Ala Gln Lys Leu Lys Asp Ser Asn Leu Asn Leu Gln Glu Lys Ile Lys
    130                 135                 140

Glu Leu Lys Val Glu Lys Thr Glu Leu Arg Asp Glu Lys Gln Arg Leu
145                 150                 155                 160

Lys Ala Glu Lys Glu Lys Leu Glu Gln Gln Leu Lys Thr Thr Ser Ala
                165                 170                 175

Gln Pro Ser Phe Leu Pro Pro Ala Ile Pro Ser Ala Phe Ala Ala His
            180                 185                 190

Gly Gln Phe Pro Gly Ser Lys Leu Val Pro Ile Met Ser Tyr Pro Gly
        195                 200                 205

Val Ala Met Trp Gln Phe Met Pro Pro Ala Ala Val Asp Thr Ser Gln
    210                 215                 220

Asp His Val Leu Arg Pro Pro Val Ala
225                 230


<210> SEQ ID NO 57
<211> LENGTH: 233
<212> TYPE: PRT
<213> ORGANISM: Solanum tuberosum

<400> SEQUENCE: 57

Met Val Ser Pro Glu Asn Thr Asn Trp Leu Tyr Asp Tyr Gly Phe Glu
1               5                   10                  15

Asp Ser Ser Val Pro Asp Ser Asn Phe Ser Ala Ser Ala Ser Gly Phe
            20                  25                  30

Asn Trp Pro Val Gln Asn Leu Asn Gly Ser Arg Asn Val Ser Ser Glu
        35                  40                  45

Ile Asp Gly Ser Ile Gly Glu Ser Asp Tyr Pro Lys Glu Ser Gly Ser
    50                  55                  60

Lys Lys Arg Ala Arg Val Glu Ser Cys Ala Pro Thr Ser Ser Lys Ala
65                  70                  75                  80
```

-continued

```
Cys Arg Glu Lys Leu Arg Arg Asp Lys Leu Asn Asp Lys Phe Met Glu
                85                  90                  95

Leu Gly Ala Leu Leu Glu Pro Gly Arg Pro Pro Lys Thr Asp Lys Ser
            100                 105                 110

Ala Ile Leu Val Asp Ala Val Arg Met Val Thr Gln Leu Arg Asp Glu
        115                 120                 125

Ala Gln Lys Leu Lys Asp Ser Asn Leu Asn Leu Gln Glu Lys Ile Lys
    130                 135                 140

Glu Leu Lys Val Glu Lys Thr Glu Leu Arg Asp Glu Lys Gln Arg Leu
145                 150                 155                 160

Lys Ala Glu Lys Glu Lys Leu Glu Gln Gln Leu Lys Thr Thr Ser Ala
                165                 170                 175

Gln Pro Ser Phe Leu Pro Pro Ala Val Pro Ser Ala Phe Ala Ala His
            180                 185                 190

Gly Gln Phe Pro Gly Ser Lys Leu Val Pro Ile Met Ser Tyr Pro Gly
        195                 200                 205

Val Ala Met Trp Gln Phe Met Pro Pro Ala Ala Val Asp Thr Ser Gln
    210                 215                 220

Asp His Val Leu Arg Pro Pro Val Ala
225                 230


<210> SEQ ID NO 58
<211> LENGTH: 233
<212> TYPE: PRT
<213> ORGANISM: Solanum tuberosum

<400> SEQUENCE: 58

Met Val Ser Pro Glu Asn Thr Asn Trp Leu Tyr Asp Tyr Gly Phe Glu
1               5                   10                  15

Asp Ser Ser Val Pro Asp Ser Asn Phe Ser Ala Ser Ala Ser Gly Phe
            20                  25                  30

Asn Trp Pro Val Gln Asn Leu Asn Gly Ser Arg Asn Val Ser Ser Glu
        35                  40                  45

Ile Asp Gly Ser Ile Gly Glu Ser Asp Tyr Pro Lys Glu Ser Gly Ser
    50                  55                  60

Lys Lys Arg Ala Arg Val Glu Ser Cys Ala Pro Thr Ser Ser Lys Ala
65                  70                  75                  80

Cys Arg Glu Lys Leu Arg Arg Asp Lys Leu Asn Asp Lys Phe Met Glu
                85                  90                  95

Leu Gly Ala Leu Leu Glu Pro Gly Arg Pro Pro Lys Thr Asp Lys Ser
            100                 105                 110

Ala Ile Leu Val Asp Ala Val Arg Met Val Thr Gln Leu Arg Asp Glu
        115                 120                 125

Ala Gln Lys Leu Lys Asp Ser Asn Leu Asn Leu Gln Glu Lys Ile Lys
    130                 135                 140

Glu Leu Lys Val Glu Lys Thr Glu Leu Arg Asp Glu Lys Gln Arg Leu
145                 150                 155                 160

Lys Ala Glu Lys Glu Lys Leu Glu Gln Gln Leu Lys Thr Thr Ser Ala
                165                 170                 175

Gln Pro Ser Phe Leu Pro Pro Ala Ile Pro Ser Ala Phe Ala Ala His
            180                 185                 190

Gly Gln Phe Pro Gly Ser Lys Leu Val Pro Ile Met Ser Tyr Pro Gly
        195                 200                 205

Val Ala Met Trp Gln Phe Met Pro Pro Ala Ala Val Asp Thr Ser Gln
```

210 215 220

Asp His Val Leu Arg Pro Pro Val Ala
225 230

<210> SEQ ID NO 59
<211> LENGTH: 223
<212> TYPE: PRT
<213> ORGANISM: Vitis vinifera

<400> SEQUENCE: 59

Leu Ile Glu Asp Ile Pro Val Pro Asp Ser Asn Phe Ala Asn Thr Asn
1 5 10 15

Ser Gly Phe Ala Trp Thr Pro Val Gln Ala Leu Asn Thr Ser Ala Asn
20 25 30

Val Ser Gly Glu Ile Asp Gly Ser Phe Gly Asp Ser Asp Gly Ile Lys
35 40 45

Glu Thr Gly Ser Lys Lys Arg Val Arg Ser Glu Ser Cys Gly Ala Ser
50 55 60

Ser Ser Lys Ala Cys Arg Glu Lys Leu Arg Arg Asp Arg Leu Asn Asp
65 70 75 80

Lys Phe Met Glu Leu Gly Ser Ile Leu Glu Pro Gly Arg Pro Pro Lys
85 90 95

Thr Asp Lys Ser Ser Ile Leu Ile Asp Ala Val Arg Met Val Thr Gln
100 105 110

Leu Arg Gly Glu Ser Gln Lys Leu Lys Asp Ser Asn Ser Ser Leu Gln
115 120 125

Glu Lys Ile Lys Glu Leu Lys Ala Glu Lys Asn Glu Leu Arg Asp Glu
130 135 140

Lys Gln Arg Leu Lys Ala Glu Lys Glu Lys Leu Glu Gln Gln Leu Lys
145 150 155 160

Ala Met Asn Ala Gln Pro Ser Phe Leu Pro Pro Val Pro Ser Ile Pro
165 170 175

Ala Ala Phe Ala Ala Gln Gly Gln Ala Gly Gly Asn Lys Leu Val Pro
180 185 190

Phe Ile Gly Tyr Pro Gly Val Ala Met Trp Gln Phe Met Pro Pro Ala
195 200 205

Ala Val Asp Thr Ser Gln Asp His Val Leu Arg Pro Pro Val Ala
210 215 220

<210> SEQ ID NO 60
<211> LENGTH: 214
<212> TYPE: PRT
<213> ORGANISM: Glycine max

<400> SEQUENCE: 60

Glu Asn Ser Asn Trp Leu Phe Asp Tyr Pro Leu Ile Asp Asp Asp Val
1 5 10 15

Ile Pro Val Gly Asp Ser Ser Phe Ala Val Ser Ala Ser Thr Phe Ser
20 25 30

Trp Pro Pro Pro Pro Ala Asn Val Ser Val Glu Ile Asp Ala Ser Leu
35 40 45

Gly Asp Ser Asp Gly Leu Lys Asn Pro Ala Leu Lys Lys Arg Thr Lys
50 55 60

Ser Asp Ser Ser Thr Ala Ser Ser Ser Lys Ala Cys Arg Glu Lys Leu
65 70 75 80

Arg Arg Asp Arg Leu Asn Asp Lys Phe Val Glu Leu Gly Ser Ile Leu

-continued

```
                85                  90                  95

Glu Pro Gly Arg Pro Pro Lys Thr Asp Lys Ala Ser Ile Leu Ile Asp
            100                 105                 110

Ala Ala Arg Met Val Thr Gln Leu Arg Asp Glu Ala Leu Lys Leu Lys
        115                 120                 125

Asp Ser Asn Thr Ser Leu Gln Glu Lys Ile Lys Glu Leu Lys Ala Glu
    130                 135                 140

Lys Asn Glu Leu Arg Asp Glu Lys Gln Arg Leu Lys Ala Glu Lys Glu
145                 150                 155                 160

Lys Leu Glu Val Gln Val Lys Ser Met Asn Ala Gln Pro Ala Phe Leu
                165                 170                 175

Pro Pro Pro Pro Ala Ile Pro Ala Ala Phe Ala Pro Gln Gly Gln Ala
            180                 185                 190

Pro Gly Asn Lys Leu Val Pro Phe Ile Ser Tyr Pro Gly Val Ala Met
        195                 200                 205

Trp Gln Phe Met Pro Pro
    210


<210> SEQ ID NO 61
<211> LENGTH: 233
<212> TYPE: PRT
<213> ORGANISM: Solanum tuberosum

<400> SEQUENCE: 61

Met Val Ser Pro Glu Asn Thr Asn Trp Leu Tyr Asp Tyr Gly Phe Glu
1               5                   10                  15

Asp Ser Ser Val Pro Asp Ser Asn Phe Ser Ala Ser Ala Ser Gly Phe
            20                  25                  30

Asn Trp Pro Val Gln Asn Leu Asn Gly Ser Arg Asn Val Ser Ser Glu
        35                  40                  45

Ile Asp Gly Ser Ile Gly Glu Ser Asp Cys Pro Lys Glu Ser Gly Ser
    50                  55                  60

Lys Lys Arg Ala Arg Val Glu Ser Cys Ala Pro Thr Ser Ser Lys Ala
65                  70                  75                  80

Cys Arg Glu Lys Leu Arg Arg Asp Lys Leu Asn Asp Lys Phe Met Glu
                85                  90                  95

Leu Gly Ala Leu Leu Glu Pro Gly Arg Pro Pro Lys Thr Asp Lys Ser
            100                 105                 110

Ala Ile Leu Val Asp Ala Val Arg Met Val Thr Gln Leu Arg Asp Glu
        115                 120                 125

Ala Gln Lys Leu Lys Asp Ser Asn Leu Asn Leu Gln Glu Lys Ile Lys
    130                 135                 140

Glu Leu Lys Val Glu Lys Thr Glu Leu Arg Asp Glu Lys Gln Arg Leu
145                 150                 155                 160

Lys Ala Glu Lys Glu Lys Leu Glu Gln Gln Leu Lys Thr Thr Ser Ala
                165                 170                 175

Gln Pro Ser Phe Leu Pro Pro Ala Ile Pro Ser Ala Phe Ala Ala His
            180                 185                 190

Gly Gln Phe Pro Gly Ser Lys Leu Val Pro Ile Met Ser Tyr Pro Gly
        195                 200                 205

Val Ala Met Trp Gln Phe Met Pro Pro Ala Ala Val Asp Thr Ser Gln
    210                 215                 220

Asp His Val Leu Arg Pro Pro Val Ala
225                 230
```

-continued

<210> SEQ ID NO 62
<211> LENGTH: 192
<212> TYPE: PRT
<213> ORGANISM: Citrus reticulata

<400> SEQUENCE: 62

```
Pro Ser Asn Gly Cys Val Glu Ile Asp Ser Ala Phe Gly Asp Ser Asn
1               5                   10                  15

Gly Leu Lys Glu Ser Ser Lys Lys Arg Val Arg Ser Glu Ser Cys Gly
            20                  25                  30

Ser Ser Ser Ser Lys Ala Cys Arg Glu Lys Leu Arg Arg Asp Arg Leu
        35                  40                  45

Asn Asp Lys Phe Val Glu Leu Ala Ser Ile Leu Glu Pro Gly Arg Pro
    50                  55                  60

Pro Lys Thr Asp Lys Ala Ala Ile Leu Ile Asp Ala Val Arg Met Val
65                  70                  75                  80

Thr Gln Leu Arg Ser Glu Ala Gln Lys Leu Lys Asp Ser Asn Ser Ser
                85                  90                  95

Leu Gln Glu Lys Ile Lys Glu Leu Lys Ala Glu Lys Asn Glu Leu Arg
            100                 105                 110

Asp Glu Lys Gln Arg Leu Lys Ala Glu Lys Glu Lys Ile Glu Gln Gln
        115                 120                 125

Leu Lys Ala Met Ser Thr Gln Pro Ser Phe Leu Thr Pro Pro Ala Ile
    130                 135                 140

Pro Ala Ala Phe Ala Ala Gln Gly Gln Ala Pro Gly Asn Lys Leu Met
145                 150                 155                 160

Pro Phe Ile Ser Tyr Pro Gly Val Ala Met Trp Gln Phe Met Pro Pro
                165                 170                 175

Ala Ala Val Asp Thr Ser Gln Asp His Val Leu Arg Pro Pro Val Ala
            180                 185                 190
```

<210> SEQ ID NO 63
<211> LENGTH: 230
<212> TYPE: PRT
<213> ORGANISM: Thellungiella halophila

<400> SEQUENCE: 63

```
Glu Asn Ala Asn Trp Ile Cys Asp Leu Ile Asp Ala Asp Tyr Gly Ser
1               5                   10                  15

Phe Thr Ile Gln Gly Pro Gly Phe Ser Trp Pro Val Gln Gln Pro Ile
            20                  25                  30

Gly Val Ser Ser Asn Ser Ser Ala Gly Val Asp Val Ser Ala Gly Asn
        35                  40                  45

Ser Glu Ala Ser Lys Glu Pro Gly Ser Lys Lys Arg Gly Arg Cys Glu
    50                  55                  60

Ser Ser Ser Ala Thr Gly Ser Lys Ala Cys Arg Glu Lys Leu Arg Arg
65                  70                  75                  80

Asp Arg Leu Asn Asp Lys Phe Thr Glu Leu Gly Ala Ile Leu Glu Pro
                85                  90                  95

Gly Asn Pro Pro Lys Thr Asp Lys Ala Ala Ile Leu Val Asp Ala Val
            100                 105                 110

Arg Met Val Ala Gln Leu Arg Gly Glu Ala Gln Lys Leu Lys Asp Ser
        115                 120                 125

Asn Ser Ser Leu Gln Asp Lys Ile Lys Glu Leu Lys Thr Glu Lys Asn
    130                 135                 140
```

-continued

```
Glu Leu Arg Asp Glu Lys Gln Arg Leu Lys Thr Glu Lys Glu Lys Leu
145                 150                 155                 160

Glu Gln Gln Leu Lys Thr Met Asn Ala Pro Gln Pro Ser Phe Phe Pro
                165                 170                 175

Ala Pro Pro Met Met Pro Thr Ala Phe Ala Ser Ala Gln Gly Gln Ala
            180                 185                 190

Pro Gly Asn Lys Met Val Pro Ile Ile Ser Tyr Pro Gly Val Ala Met
        195                 200                 205

Trp Gln Phe Met Pro Pro Ala Ser Val Asp Thr Ser Gln Asp His Val
    210                 215                 220

Leu Arg Pro Pro Val Ala
225                 230


<210> SEQ ID NO 64
<211> LENGTH: 238
<212> TYPE: PRT
<213> ORGANISM: Populus tremuloides

<400> SEQUENCE: 64

Glu Asn Asp Asn Trp Val Phe Asp Cys Gly Leu Ile Glu Asp Ile Ser
1               5                   10                  15

Val Pro Gly Gly Asp Leu Leu Gly Leu Glu Ser Leu Asp Glu Thr Pro
            20                  25                  30

Asn Gly Ser Leu Trp Ser Ser His Asn Phe Thr Asp Ser Ala Phe Leu
        35                  40                  45

Ser Val Glu Phe Asn Asn Ser Tyr Glu Asn Ser Asp Gly His Lys Glu
    50                  55                  60

Ser Gly Cys Arg Lys Arg Val Arg Pro Gly Ser Ser Asn Ala Thr Gly
65                  70                  75                  80

Ser Lys Ala Cys Arg Glu Lys Leu Arg Arg Asp Arg Leu Asn Asp Arg
                85                  90                  95

Phe Met Glu Leu Gly Ala Leu Leu Asp Pro Gly Arg Pro Pro Lys Val
            100                 105                 110

Asp Lys Ser Ala Ile Leu Val Asp Ala Ala Arg Met Val Thr Gln Leu
        115                 120                 125

Arg Asp Glu Ser Gln Lys Leu Lys Glu Ser Asn Val Ser Leu Gln Glu
    130                 135                 140

Lys Ile Asp Glu Leu Lys Ala Glu Lys Asn Glu Leu Arg Asp Glu Lys
145                 150                 155                 160

Gln Arg Leu Lys Thr Glu Lys Glu Asn Leu Glu Arg Gln Val Lys Ala
                165                 170                 175

Leu Ser Ala Pro Pro Asn Phe Leu Pro His Pro Ser Ala Ile Pro Ala
            180                 185                 190

Pro Phe Ser Ala Pro Gly Gln Val Val Gly Ser Lys Met Met Pro Phe
        195                 200                 205

Val Gly Tyr Pro Gly Ile Ser Met Trp Gln Phe Met Pro Pro Ala Val
    210                 215                 220

Val Asp Thr Ser Gln Asp His Val Leu Arg Pro Pro Val Ala
225                 230                 235


<210> SEQ ID NO 65
<211> LENGTH: 232
<212> TYPE: PRT
<213> ORGANISM: Vitis vinifera

<400> SEQUENCE: 65
```

-continued

```
Met Val Ser Pro Glu Glu Asp Pro Asn Trp Ile Phe Asp Tyr Gly Leu
1               5                   10                  15

Ile Asp Asp Val Pro Val Pro Ser Leu Gln Ala Thr Phe Asn Trp Pro
            20                  25                  30

Ser His Asp Phe Thr Ala Ser Val Ala Leu Gly Val Glu Phe Asp Asp
        35                  40                  45

Ser Pro Val Asn Leu Asp Asp Val Lys Glu Asn His Ser Arg Lys Arg
    50                  55                  60

Met Arg Ser Gly Leu Cys Ser Ala Ser Gly Ser Lys Ala Cys Arg Glu
65                  70                  75                  80

Lys Val Arg Arg Asp Arg Leu Asn Asp Arg Phe Leu Glu Leu Gly Ser
                85                  90                  95

Ile Leu Glu Pro Gly Arg Pro Pro Lys Met Asp Lys Ala Val Ile Leu
            100                 105                 110

Ser Asp Ala Leu Arg Met Met Thr Gln Leu Arg Ser Glu Gly Gln Lys
        115                 120                 125

Leu Lys Lys Ser Cys Glu Asp Leu Gln Glu Lys Ile Asn Glu Leu Lys
    130                 135                 140

Ala Glu Lys Asn Glu Leu Arg Asp Glu Lys Gln Arg Leu Lys Thr Glu
145                 150                 155                 160

Lys Glu Asn Ile Val Gln Gln Ile Lys Ala Leu Ser Thr Gln Ala Gly
                165                 170                 175

Phe Leu Pro His Pro Ser Ala Ile Pro Ala Pro Phe Ala Ala Pro Gly
            180                 185                 190

Gln Val Val Gly Ser Lys Leu Met Pro Phe Ile Gly Tyr Pro Gly Val
        195                 200                 205

Ser Met Trp Gln Phe Met Pro Pro Ala Ala Val Asp Thr Ser Gln Asp
    210                 215                 220

His Val Leu Arg Pro Pro Val Ala
225                 230
```

<210> SEQ ID NO 66
<211> LENGTH: 191
<212> TYPE: PRT
<213> ORGANISM: Brassica napus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid

<400> SEQUENCE: 66

```
Ser Xaa Val Met Leu Ser Trp Lys Phe Arg Ser His Gln Gly Thr Cys
1               5                   10                  15

Ser Lys Lys Arg Ala Arg Cys Glu Ser Ser Ser Ala Thr Ser Ser Lys
            20                  25                  30

Ala Cys Arg Glu Lys Gln Arg Arg Asp Arg Leu Asn Asp Lys Phe Met
        35                  40                  45

Glu Leu Gly Ala Ile Leu Glu Pro Gly Asn Pro Pro Xaa Thr Asp Lys
    50                  55                  60

Ala Ala Ile Leu Val Asp Ala Val Arg Met Val Thr Gln Leu Arg Gly
65                  70                  75                  80

Glu Ala Gln Lys Leu Lys Asp Ser Asn Ser Ser Leu Gln Asp Lys Ile
                85                  90                  95
```

-continued

```
Lys Glu Leu Lys Thr Glu Lys Asn Glu Leu Arg Asp Glu Lys Gln Arg
            100                 105                 110

Leu Lys Thr Glu Lys Glu Lys Leu Glu Gln Gln Leu Lys Ala Met Asn
        115                 120                 125

Ala Pro Pro Gln Pro Ser Phe Phe Pro Ala Pro Pro Met Met Pro Thr
    130                 135                 140

Ala Phe Ala Ser Ala Gln Gly Gln Ala Pro Gly Asn Lys Met Val Pro
145                 150                 155                 160

Val Ile Ser Tyr Pro Gly Val Ala Met Trp Gln Phe Met Pro Pro Ala
                165                 170                 175

Ser Val Asp Thr Ser Gln Asp His Val Leu Arg Pro Pro Val Ala
            180                 185                 190


<210> SEQ ID NO 67
<211> LENGTH: 181
<212> TYPE: PRT
<213> ORGANISM: Vitis vinifera

<400> SEQUENCE: 67

Asp Ser Asp Gly Ile Lys Glu Thr Gly Ser Lys Lys Arg Val Arg Ser
1               5                   10                  15

Glu Ser Cys Gly Ala Ser Ser Ser Lys Ala Cys Arg Glu Lys Leu Arg
            20                  25                  30

Arg Asp Arg Leu Asn Asp Lys Ser Met Glu Leu Gly Ser Ile Leu Glu
        35                  40                  45

Pro Gly Arg Pro Pro Lys Thr Asp Lys Ser Ser Ile Leu Ile Asp Ala
    50                  55                  60

Val Arg Met Val Thr Gln Leu Arg Gly Glu Ser Gln Lys Leu Lys Asp
65                  70                  75                  80

Ser Asn Ser Ser Leu Gln Glu Lys Ile Lys Glu Leu Lys Ala Glu Lys
                85                  90                  95

Asn Glu Leu Arg Asp Glu Lys Gln Arg Leu Lys Ala Glu Lys Glu Lys
            100                 105                 110

Leu Glu Gln Gln Leu Lys Ala Met Asn Ala Gln Pro Ser Phe Leu Pro
        115                 120                 125

Pro Val Pro Ser Ile Pro Ala Ala Phe Ala Ala Gln Gly Gln Ala Gly
    130                 135                 140

Gly Asn Lys Leu Val Pro Phe Ile Gly Tyr Pro Gly Val Ala Met Trp
145                 150                 155                 160

Gln Phe Met Pro Pro Ala Ala Val Asp Thr Ser Gln Asp His Val Leu
                165                 170                 175

Arg Pro Pro Val Ala
            180


<210> SEQ ID NO 68
<211> LENGTH: 237
<212> TYPE: PRT
<213> ORGANISM: Gossypium raimondii

<400> SEQUENCE: 68

Met Val Ser Pro Glu Asn Thr Asn Tyr Trp Ser Ser Phe Asp Tyr Ala
1               5                   10                  15

Thr Leu Ile Asn Asp Ile Pro Ala Pro Asp Gly Pro Tyr Ser Gly Phe
            20                  25                  30

Ser Trp Pro Thr Arg Pro Ile Asn Ala Ser Ser Asn Val Phe Ser Val
        35                  40                  45
```

-continued

```
Glu Thr Asp Gly Ser Phe Glu Asp Ser Asp Gly Leu Lys Glu Ser Gly
    50                  55                  60

Ser Lys Lys Arg Val Arg Ser Glu Ser Cys Asn Val Ser Ser Ser Lys
65                  70                  75                  80

Ala Cys Arg Glu Lys Leu Arg Arg Asp Lys Leu Asn Glu Lys Phe Met
                85                  90                  95

Glu Leu Ser Ser Ile Leu Glu Pro Glu Lys Pro Pro Lys Thr Asp Lys
            100                 105                 110

Ala Ala Ile Leu Val Asp Ala Val Arg Met Val Thr Gln Leu Arg Gly
        115                 120                 125

Glu Ala Gln Lys Leu Lys Asp Ser Ile Ser Ser Leu His Asp Arg Ile
    130                 135                 140

Lys Glu Leu Lys Ala Glu Lys Asn Glu Leu Arg Asp Glu Lys Gln Arg
145                 150                 155                 160

Leu Lys Ala Glu Lys Glu Lys Leu Glu Gln Gln Leu Lys Ala Met Asn
                165                 170                 175

Ser Gln Pro Ser Phe Met Pro Pro Ala Pro Ala Phe Pro Ala Ala Phe
            180                 185                 190

Ala Thr Ala Gln Gly Gln Val Pro Gly Asn Lys Leu Val Pro Phe Phe
        195                 200                 205

Gly Tyr Pro Gly Val Ala Met Trp Gln Phe Met Leu Pro Ala Ser Leu
    210                 215                 220

Asp Thr Ser Glu Asp His Val Leu Arg Pro Pro Val Ala
225                 230                 235


<210> SEQ ID NO 69
<211> LENGTH: 238
<212> TYPE: PRT
<213> ORGANISM: Populus tremuloides

<400> SEQUENCE: 69

Glu Asn Asp Asn Trp Val Phe Asp Cys Gly Leu Ile Glu Asp Ile Ser
1               5                   10                  15

Val Pro Gly Gly Asp Leu Leu Gly Leu Glu Ser Leu Asp Glu Thr Pro
            20                  25                  30

Asn Gly Ser Leu Trp Ser Ser His Asn Phe Thr Asp Ser Ala Phe Leu
        35                  40                  45

Ser Val Glu Phe Asn Asn Ser Tyr Glu Asn Ser Asp Gly His Lys Glu
    50                  55                  60

Ser Gly Cys Arg Lys Arg Val Arg Pro Gly Ser Ser Asn Ala Thr Gly
65                  70                  75                  80

Ser Lys Ala Cys Arg Glu Lys Leu Arg Arg Asp Arg Leu Asn Asp Arg
                85                  90                  95

Phe Met Glu Leu Gly Ala Leu Leu Asp Pro Gly Arg Pro Pro Lys Val
            100                 105                 110

Asp Lys Ser Ala Ile Leu Val Asp Ala Ala Arg Met Val Thr Gln Leu
        115                 120                 125

Arg Asp Glu Ser Gln Lys Leu Lys Glu Ser Asn Val Ser Leu Gln Glu
    130                 135                 140

Lys Ile Asp Glu Leu Lys Ala Glu Lys Asn Glu Leu Arg Asp Glu Lys
145                 150                 155                 160

Gln Arg Leu Lys Thr Glu Lys Glu Asn Leu Glu Arg Gln Val Lys Ala
                165                 170                 175

Leu Ser Ala Pro Pro Asn Phe Leu Pro His Pro Ser Ala Ile Pro Ala
            180                 185                 190
```

-continued

```
Pro Phe Ser Ala Pro Gly Gln Val Val Gly Ser Lys Met Met Pro Phe
        195                 200                 205

Val Gly Tyr Pro Gly Ile Ser Met Trp Gln Phe Met Pro Pro Ala Val
    210                 215                 220

Val Asp Thr Ser Gln Asp His Val Leu Arg Pro Ser Val Ala
225                 230                 235


<210> SEQ ID NO 70
<211> LENGTH: 170
<212> TYPE: PRT
<213> ORGANISM: Prunus dulcis

<400> SEQUENCE: 70

Lys Arg Val Arg Thr Glu Ser Cys Ser Gly Ser Ser Ser Lys Ala Cys
1               5                   10                  15

Arg Glu Lys Leu Arg Arg Asp Arg Leu Asn Asp Lys Phe Leu Glu Leu
            20                  25                  30

Gly Ser Ile Leu Glu Pro Gly Arg Pro Pro Lys Thr Asp Lys Ala Ala
        35                  40                  45

Ile Leu Val Asp Ala Val Arg Met Val Asn Gln Leu Arg Gly Glu Ala
    50                  55                  60

Gln Lys Leu Lys Asp Ser Asn Ser Ser Leu Gln Glu Lys Ile Lys Glu
65                  70                  75                  80

Leu Lys Ala Glu Lys Asn Glu Leu Arg Asp Glu Lys Gln Arg Leu Lys
                85                  90                  95

Leu Glu Lys Glu Lys Leu Glu Gln Gln Leu Lys Ala Met Asn Ala Gln
            100                 105                 110

Pro Gly Phe Leu Pro Pro Pro Pro Ala Ile Pro Ala Ala Phe Ala Ala
        115                 120                 125

Gln Gly Gln Ala His Gly Asn Lys Leu Val Pro Phe Ile Gly Tyr Pro
    130                 135                 140

Gly Val Ala Met Trp Gln Phe Met Pro Pro Ala Ser Val Asp Thr Ser
145                 150                 155                 160

Gln Asp His Val Leu Arg Pro Pro Val Ala
                165                 170


<210> SEQ ID NO 71
<211> LENGTH: 170
<212> TYPE: PRT
<213> ORGANISM: Glycine max

<400> SEQUENCE: 71

Lys Arg Thr Lys Ser Asp Ser Ser Thr Ala Ser Ser Ser Lys Ala Cys
1               5                   10                  15

Arg Glu Lys Leu Arg Arg Asp Arg Leu Asn Asp Lys Phe Val Glu Leu
            20                  25                  30

Gly Ser Ile Leu Glu Pro Gly Arg Pro Pro Lys Thr Asp Lys Ala Ser
        35                  40                  45

Ile Leu Ile Asp Ala Ala Arg Met Val Thr Gln Leu Arg Asp Glu Ala
    50                  55                  60

Leu Lys Leu Lys Asp Ser Asn Thr Ser Leu Gln Glu Lys Ile Lys Glu
65                  70                  75                  80

Leu Lys Ala Glu Lys Asn Glu Leu Arg Asp Glu Lys Gln Arg Leu Lys
                85                  90                  95

Ala Glu Lys Glu Lys Leu Glu Val Gln Val Lys Ser Met Asn Ala Gln
            100                 105                 110
```

-continued

```
Pro Ala Phe Leu Pro Pro Pro Pro Ala Ile Pro Ala Ala Phe Ala Pro
        115                 120                 125

Gln Gly Gln Ala Pro Gly Asn Lys Leu Val Pro Phe Ile Ser Tyr Pro
    130                 135                 140

Gly Val Ala Met Trp Gln Phe Met Pro Pro Ala Ala Val Asp Thr Ser
145                 150                 155                 160

Gln Asp His Val Leu Arg Pro Pro Val Ala
                165                 170


<210> SEQ ID NO 72
<211> LENGTH: 181
<212> TYPE: PRT
<213> ORGANISM: Medicago truncatula

<400> SEQUENCE: 72

Asp Ser Asp Gly Leu Lys Glu Ser Gly Ser Lys Lys Arg Val Arg Ser
1               5                   10                  15

Glu Ser Cys Ala Ala Thr Ser Ser Lys Ala Cys Arg Glu Lys Leu Arg
            20                  25                  30

Arg Asp Arg Leu Asn Asp Lys Phe Ile Glu Leu Gly Ser Ile Leu Glu
        35                  40                  45

Pro Gly Arg Pro Ala Lys Thr Asp Lys Ala Ala Ile Leu Ile Asp Ala
    50                  55                  60

Val Arg Met Val Thr Gln Leu Arg Gly Glu Ala Gln Lys Leu Lys Asp
65                  70                  75                  80

Ala Asn Ser Gly Leu Gln Glu Lys Ile Lys Glu Leu Lys Val Glu Lys
                85                  90                  95

Asn Glu Leu Arg Asp Glu Lys Gln Arg Leu Lys Ala Glu Lys Glu Lys
            100                 105                 110

Leu Glu Gln Gln Leu Lys Ser Met Asn Ala Pro Pro Ser Phe Leu Pro
        115                 120                 125

Thr Pro Thr Ala Leu Pro Ala Ala Phe Ala Ala Gln Gly Gln Ala His
    130                 135                 140

Gly Asn Lys Leu Val Pro Phe Ile Ser Tyr Pro Gly Val Ala Met Trp
145                 150                 155                 160

Gln Phe Met Pro Pro Ala Ala Val Asp Thr Ser Gln Asp His Val Leu
                165                 170                 175

Arg Pro Pro Val Ala
            180


<210> SEQ ID NO 73
<211> LENGTH: 189
<212> TYPE: PRT
<213> ORGANISM: Medicago truncatula

<400> SEQUENCE: 73

Ala Glu Val Asp Gly Ser Leu Gly Asp Ser Asp Gly Leu Lys Glu Ser
1               5                   10                  15

Gly Ser Lys Lys Arg Val Arg Ser Glu Ser Cys Ala Ala Thr Ser Ser
            20                  25                  30

Lys Ala Cys Arg Glu Lys Leu Arg Arg Asp Arg Leu Asn Asp Lys Phe
        35                  40                  45

Ile Glu Leu Gly Ser Ile Leu Glu Pro Gly Gly Pro Ala Lys Thr Asp
    50                  55                  60

Lys Ala Ala Ile Leu Ile Asp Ala Val Arg Met Val Thr Gln Leu Arg
65                  70                  75                  80
```

-continued

```
Gly Glu Ala Gln Lys Leu Lys Asp Ala Asn Ser Gly Leu Gln Glu Lys
                85                  90                  95

Ile Lys Glu Leu Lys Val Glu Lys Asn Glu Leu Arg Asp Glu Lys Gln
            100                 105                 110

Arg Leu Lys Ala Glu Lys Glu Lys Leu Glu Gln Gln Leu Lys Ser Met
        115                 120                 125

Asn Ala Pro Pro Ser Phe Leu Pro Thr Pro Thr Ala Leu Pro Ala Ala
    130                 135                 140

Phe Ala Ala Gln Gly Gln Ala His Gly Asn Lys Leu Val Pro Phe Ile
145                 150                 155                 160

Ser Tyr Pro Gly Val Ala Met Trp Gln Phe Met Pro Pro Ala Ala Val
                165                 170                 175

Asp Thr Ser Gln Asp His Val Leu Arg Pro Pro Val Ala
            180                 185


<210> SEQ ID NO 74
<211> LENGTH: 169
<212> TYPE: PRT
<213> ORGANISM: Glycine max

<400> SEQUENCE: 74

Arg Ala Arg Cys Asp Ser Ser Thr Ala Ser Ser Ser Lys Ala Cys Arg
1               5                   10                  15

Glu Lys Leu Arg Arg Asp Arg Leu Asn Asp Lys Phe Val Glu Leu Gly
            20                  25                  30

Ser Ile Leu Glu Pro Gly Arg Pro Pro Lys Thr Asp Lys Ala Ala Ile
        35                  40                  45

Leu Ile Asp Ala Ala Arg Met Val Thr Gln Leu Arg Asp Glu Ala Leu
    50                  55                  60

Lys Leu Lys Asp Ser Asn Thr Ser Leu Gln Glu Lys Ile Lys Glu Leu
65                  70                  75                  80

Lys Ala Glu Lys Asn Glu Leu Arg Asp Glu Lys Gln Arg Leu Lys Ala
                85                  90                  95

Glu Lys Glu Lys Leu Glu Met Gln Val Lys Ser Met Asn Ala Gln Pro
            100                 105                 110

Ala Phe Leu Pro Pro Pro Pro Ala Ile Pro Ala Ala Phe Ala Pro Gln
        115                 120                 125

Gly Gln Ala Pro Gly Asn Lys Leu Met Pro Phe Ile Arg Tyr Pro Gly
    130                 135                 140

Val Ala Met Trp Gln Phe Met Pro Pro Ala Thr Met Asp Thr Ser Gln
145                 150                 155                 160

Asp His Val Leu Arg Pro Pro Val Ala
                165


<210> SEQ ID NO 75
<211> LENGTH: 158
<212> TYPE: PRT
<213> ORGANISM: Vitis vinifera

<400> SEQUENCE: 75

Thr Lys Ala Cys Arg Glu Lys Leu Arg Arg Asp Arg Leu Asn Glu Arg
1               5                   10                  15

Phe Leu Glu Leu Gly Ser Ile Leu Glu Pro Gly Arg Pro Pro Lys Thr
            20                  25                  30

Asp Lys Ala Ala Ile Leu Ser Asp Ala Val Arg Met Val Thr Gln Leu
        35                  40                  45
```

-continued

```
Arg Ser Glu Ala Gln Lys Leu Lys Glu Ser Asn Gly Asp Leu Gln Glu
    50                  55                  60

Lys Ile Lys Glu Leu Lys Ala Glu Lys Asn Glu Leu Arg Asp Glu Lys
65                  70                  75                  80

Gln Arg Leu Lys Ala Glu Lys Glu Lys Leu Glu Gln Gln Val Lys Ala
                85                  90                  95

Ile Ser Ala Gln Pro Gly Phe Leu Pro His Pro Ser Ala Met Pro Ala
            100                 105                 110

Ala Phe Ala Ala Gln Gly Arg Ala Pro Gly Asn Lys Leu Met Pro Phe
        115                 120                 125

Ile Gly Tyr Pro Ser Val Ala Met Trp Gln Phe Met Pro Pro Ala Ala
    130                 135                 140

Val Asp Thr Ser Gln Asp His Val Leu Arg Pro Pro Val Ala
145                 150                 155


<210> SEQ ID NO 76
<211> LENGTH: 181
<212> TYPE: PRT
<213> ORGANISM: Glycine soja

<400> SEQUENCE: 76

Asp Ser Asp Ser Leu Lys Glu Ser Gly Ser Lys Lys Arg Val Arg Ser
1               5                   10                  15

Glu Ser Cys Ala Ala Ser Gly Ser Lys Ala Cys Arg Glu Lys Leu Arg
            20                  25                  30

Arg Asp Arg Leu Asn Asp Lys Phe Val Glu Leu Gly Ala Ile Leu Glu
        35                  40                  45

Pro Gly Arg Pro Ala Lys Thr Asp Lys Ala Ala Ile Leu Ile Asp Ala
    50                  55                  60

Val Arg Met Val Thr Gln Leu Arg Gly Glu Ala Gln Lys Leu Lys Asp
65                  70                  75                  80

Thr Asn Gln Gly Leu Gln Glu Lys Ile Lys Glu Leu Lys Ala Glu Lys
                85                  90                  95

Asn Glu Leu Arg Asp Glu Lys Gln Arg Leu Lys Ala Glu Lys Glu Lys
            100                 105                 110

Leu Glu Gln Gln Leu Lys Ser Leu Asn Ala Gln Pro Ser Phe Met Pro
        115                 120                 125

Pro Pro Ala Ala Met Pro Ala Ala Phe Ala Ala Gln Gly Gln Ala His
    130                 135                 140

Gly Asn Lys Leu Val Pro Phe Ile Ser Tyr Ser Gly Ser Cys Met Trp
145                 150                 155                 160

Gln Phe Met Pro Pro Ala Ala Val Asp Thr Ser Gln Asp His Val Leu
                165                 170                 175

Arg Pro Pro Val Ser
            180


<210> SEQ ID NO 77
<211> LENGTH: 235
<212> TYPE: PRT
<213> ORGANISM: Solanum tuberosum

<400> SEQUENCE: 77

Asn Trp Leu Phe Asp Tyr Glu Leu Ile Thr Asp Ile Thr Ser Ala Ala
1               5                   10                  15

Ser Val Thr Val Thr Asp Phe Gln Ser Pro Ala Thr Ile Asp Phe Ser
            20                  25                  30
```

-continued

```
Trp Pro Ala Gln Thr Ile Tyr Ala Ser Ser Asn Leu Ile Ala Glu Thr
        35                  40                  45

Asp Tyr Thr Phe Ala Asp Ser Glu Val Ser Lys Glu Ala Ser Ser Arg
    50                  55                  60

Lys Arg Leu Lys Ser Glu Trp Cys Ser Ser Pro Arg Ser Lys Ala Cys
65                  70                  75                  80

Arg Glu Lys Leu Arg Arg Asp Arg Leu Asn Glu Arg Phe Leu Glu Leu
                85                  90                  95

Ser Ser Val Leu Asp Pro Gly Arg Pro Pro Lys Thr Glu Lys Val Ala
            100                 105                 110

Ile Leu Ser Asp Ala Gln Arg Met Leu Ile Glu Leu Arg Thr Glu Thr
        115                 120                 125

Gln Lys Leu Lys Glu Ser Asn Glu Glu Leu Gln Glu Lys Ile Lys Glu
    130                 135                 140

Leu Lys Ala Glu Lys Asn Glu Leu Arg Asp Glu Lys Arg Arg Leu Lys
145                 150                 155                 160

Glu Glu Lys Glu Asn Leu Glu Gln Gln Val Lys Ser Leu Ala Ser Lys
                165                 170                 175

Pro Gly Phe Leu Ser His Pro Ser Ala Val Gly Ala Ala Phe Thr Ala
            180                 185                 190

Gln Gly Gln Val Ala Ala Gly Asn Lys Leu Met Pro Phe Ile Gly Tyr
        195                 200                 205

Pro Ser Val Ala Met Trp Gln Phe Met Gln Pro Ala Val Val Asp Thr
    210                 215                 220

Ser Gln Asp His Val Leu Arg Pro Pro Val Ala
225                 230                 235


<210> SEQ ID NO 78
<211> LENGTH: 229
<212> TYPE: PRT
<213> ORGANISM: Gossypium raimondii

<400> SEQUENCE: 78

Met Val Ser Pro Glu Asn Thr Asn Tyr Trp Ser Ser Phe Asp Tyr Ala
1               5                   10                  15

Thr Leu Ile Asn Asp Ile Pro Ala Pro Asp Gly Pro Tyr Ser Gly Phe
            20                  25                  30

Ser Trp Pro Thr Arg Pro Ile Asn Ala Ser Ser Asn Val Phe Ser Val
        35                  40                  45

Glu Ile Asp Gly Ser Phe Glu Asp Ser Asp Gly Leu Lys Glu Ser Gly
    50                  55                  60

Ser Lys Lys Arg Val Arg Ser Glu Ser Cys Asn Val Ser Ser Ser Lys
65                  70                  75                  80

Ala Cys Arg Glu Lys Leu Arg Arg Asp Lys Leu Asn Glu Lys Phe Met
                85                  90                  95

Glu Leu Ser Ser Ile Leu Glu Pro Glu Lys Pro Pro Lys Thr Asp Lys
            100                 105                 110

Ala Ala Ile Leu Val Asp Ala Val Arg Met Val Thr Gln Leu Arg Gly
        115                 120                 125

Glu Ala Gln Lys Leu Lys Asp Ser Ile Ser Ser Leu His Asp Arg Ile
    130                 135                 140

Lys Glu Leu Lys Ala Glu Lys Asn Glu Leu Arg Asp Glu Lys Gln Arg
145                 150                 155                 160

Leu Lys Ala Glu Lys Glu Lys Leu Glu Gln Gln Leu Lys Ala Met Asn
```

-continued

```
                165                 170                 175

Ser Gln Pro Ser Phe Met Pro Pro Ala Pro Ala Phe Pro Ala Ala Phe
            180                 185                 190

Ala Thr Ala Gln Gly Gln Val Pro Gly Asn Lys Leu Val Pro Phe Phe
        195                 200                 205

Gly Tyr Pro Gly Val Ala Met Trp Gln Phe Met Leu Pro Ala Ser Leu
    210                 215                 220

Asp Thr Ser Glu Asp
225


<210> SEQ ID NO 79
<211> LENGTH: 218
<212> TYPE: PRT
<213> ORGANISM: Vitis vinifera
<220> FEATURE:
<221> NAME/KEY: misc_feature
<222> LOCATION: (197)..(197)
<223> OTHER INFORMATION: Xaa can be any naturally occurring amino acid

<400> SEQUENCE: 79

Met Val Ser Pro Glu Ala Thr Asn Trp Leu Tyr Glu Tyr Gly Leu Ile
1               5                   10                  15

Glu Asp Ile Pro Val Pro Asp Ser Asn Phe Ala Asn Thr Asn Ser Gly
            20                  25                  30

Phe Ala Trp Thr Pro Val Gln Ala Leu Asn Thr Ser Ala Asn Val Ser
        35                  40                  45

Gly Glu Ile Asp Gly Ser Phe Gly Asp Ser Asp Gly Ile Lys Glu Thr
    50                  55                  60

Gly Ser Lys Lys Arg Val Arg Ser Glu Ser Cys Gly Ala Ser Ser Ser
65                  70                  75                  80

Lys Ala Cys Arg Glu Lys Leu Arg Arg Asp Arg Leu Asn Asp Lys Ser
                85                  90                  95

Met Glu Leu Gly Ser Ile Leu Glu Pro Gly Arg Pro Pro Lys Thr Asp
            100                 105                 110

Lys Ser Ser Ile Leu Ile Asp Ala Val Arg Met Val Thr Gln Leu Arg
        115                 120                 125

Gly Glu Ser Gln Lys Leu Lys Asp Ser Asn Ser Ser Leu Gln Glu Lys
    130                 135                 140

Ile Lys Glu Leu Lys Ala Glu Lys Asn Glu Leu Arg Asp Glu Lys Gln
145                 150                 155                 160

Arg Leu Lys Ala Glu Lys Glu Lys Leu Glu Gln Gln Leu Lys Ala Met
                165                 170                 175

Asn Ala Gln Pro Ser Phe Leu Pro Pro Val Pro Ser Ile Pro Ala Ala
            180                 185                 190

Phe Ala Ala Gln Xaa Gln Ala Gly Gly Asn Lys Leu Val Pro Phe Ile
        195                 200                 205

Gly Tyr Pro Gly Val Ala Met Trp Gln Phe
    210                 215


<210> SEQ ID NO 80
<211> LENGTH: 222
<212> TYPE: PRT
<213> ORGANISM: Lycopersicon esculentum

<400> SEQUENCE: 80

Met Val Ser Pro Glu Ser Thr Asn Trp Leu Tyr Asp Tyr Gly Phe Glu
1               5                   10                  15
```

-continued

```
Asp Ser Cys Val Pro Asp Ser Asn Phe Ser Ala Ser Ala Ser Gly Phe
            20                  25                  30

Asn Trp Ser Val Gln Asn Leu Asn Gly Ser Arg Asn Val Ser Ser Glu
        35                  40                  45

Ile Asp Gly Ser Ile Gly Glu Ser Asp Tyr Pro Lys Glu Ser Gly Ser
    50                  55                  60

Lys Lys Arg Ala Arg Val Glu Ser Cys Ala Pro Thr Ser Ser Lys Ala
65                  70                  75                  80

Cys Arg Glu Lys Leu Arg Arg Asp Arg Leu Asn Asp Lys Phe Met Glu
                85                  90                  95

Leu Gly Ala Leu Leu Glu Pro Gly Arg Pro Pro Lys Thr Asp Lys Ser
            100                 105                 110

Ala Ile Leu Val Asp Ala Val Arg Leu Val Thr Gln Leu Arg Asp Glu
        115                 120                 125

Ala Gln Lys Leu Lys Asp Ser Asn Leu Asn Leu Gln Glu Lys Ile Lys
    130                 135                 140

Glu Leu Lys Val Glu Lys Thr Glu Leu Arg Asp Glu Lys His Arg Leu
145                 150                 155                 160

Lys Ala Glu Lys Glu Lys Leu Glu Gln Gln Leu Lys Thr Thr Ser Ala
                165                 170                 175

Arg Pro Ser Tyr Leu Pro Pro Ala Ile Pro Ser Ala Phe Ala Ala His
            180                 185                 190

Gly Gln Phe Pro Gly Ser Lys Leu Val Pro Ile Met Ser Tyr Pro Cys
        195                 200                 205

Val Pro Met Trp Gln Phe Met Pro Pro Ala Ala Val Asp Thr
    210                 215                 220


<210> SEQ ID NO 81
<211> LENGTH: 238
<212> TYPE: PRT
<213> ORGANISM: Pinus taeda

<400> SEQUENCE: 81

Met Ser Ser Pro Gln Ser Asn Lys Trp Leu Ser Tyr Phe Asp Glu Pro
1               5                   10                  15

Leu Leu Asp Asp Val Gly Val Gly Gln Pro Ala Asn Pro Phe Phe Trp
            20                  25                  30

Cys Gly Gln Gly Ile Asn Asp Gln Pro Asp Val Ser Gly Ser Val Glu
        35                  40                  45

Ile Asp Gly Pro Asn Lys Asp Met Asp Glu Gln Asp Lys Leu Cys Pro
    50                  55                  60

Arg Lys Arg Ser Arg Glu Glu Ser Ser Gly Gly Pro Gly Ser Lys Ala
65                  70                  75                  80

Cys Arg Glu Lys Met Arg Arg Asp Arg Leu Asn Asp Arg Phe Met Glu
                85                  90                  95

Leu Ser Ser Val Leu Glu Pro Gly Arg Pro Pro Lys Thr Ala Asp Lys
            100                 105                 110

Ala Thr Ile Leu Ser Asp Ala Ala Arg Val Met Thr Gln Leu Arg Thr
        115                 120                 125

Glu Ala Gln Asn Leu Lys Ala Glu Asn Glu Arg Leu Gln Glu Ala Ile
    130                 135                 140

Lys Asp Leu Lys Ala Glu Lys Asn Glu Leu Arg Asp Glu Lys Leu Arg
145                 150                 155                 160

Met Lys Ala Glu Lys Glu Lys Leu Glu Gln Gln Val Lys Ala Met Ala
                165                 170                 175
```

-continued

```
Leu Pro Thr Gly Phe Val Pro His Pro Ala Ala Phe His Ala Ala Ala
            180                 185                 190

Ala Phe Ala Ala Gln Ser Gln Ala Ala Ala Asn Lys Thr Met Pro Val
        195                 200                 205

Pro Gly Tyr Pro Gly Met Ala Met Trp Gln Trp Met Pro Pro Ala Val
    210                 215                 220

Val Asp Thr Ser Gln Asp His Val Leu Arg Pro Pro Val Ala
225                 230                 235


<210> SEQ ID NO 82
<211> LENGTH: 783
<212> TYPE: DNA
<213> ORGANISM: Lolium perenne

<400> SEQUENCE: 82

tccgtcgcca tggcgtcccc ggagggcgcc aactgggtct tcgactgccc gctcatggac      60

gaccttgctg ccgccgactt caccgcaccg cccgcaggag gcttctactg ggcaccaccg     120

atgcagccgc agatgcacac ccaggccccg gccgtctccg ccaccccgcc tcccaaccac     180

tgtgccgaaa tcaatagccc tatttctgtg gactgggacc atgccaaagg acagccaaca     240

aataaacgtc ctaggtcaga atctggtgct caacccagct ccaaagcatg cagggagaaa     300

gcgagaaggg acaagctaaa cgagaggttc ttggaattgg gtgctgtctt ggatccaggg     360

aaaacaccta aaatcgacaa gtgtgctata ttgaatgatg ctattcgtgc ggtgactgag     420

ctacgtagtg aagcagagaa gctgaaggat tcaaacgagt ctctccaaga gaagatcaaa     480

gagctgaagg ctgagaagaa tgagctgcgg gatgagaagc aaaagctgaa ggcagagaaa     540

gagagcctgg agcagcagat caagttcatg aatgcccgtc agagcctcgt accacaccta     600

ccgcaccctt cggttatccc agcggctgca tttgctgctc cccaagggca agtgccaggg     660

cagaagctga tgatgcctgt cattggctac catggatttc ccatgtggca attcatgcca     720

ccttctgatg ttgatacctc cgatgatccc aagtcgtgcc ctcctgttgc ataagccagc     780

taa                                                                   783


<210> SEQ ID NO 83
<211> LENGTH: 1040
<212> TYPE: DNA
<213> ORGANISM: Oryza sativa

<400> SEQUENCE: 83

gtgagcggcc ccaccccccc gcagccatgg cctccccgga gggctccacg tgggtcttcg      60

actgccctct gatggacgac ctcgccgccg ccgccggctt cgacgccgcc cccgccggag     120

gcttctactg gacgacgccc gctcctccgc aggcggcgct acagccgccg ccgccgcagc     180

agcagcccgt cgcccctgcc accgcggctc cgaacgcctg tgctgaaatc aatggctctg     240

tggactgtga acatggcaaa gaacagccaa caaataaacg tccgagatca gaaagtggca     300

ctcgaccaag ctccaaagca tgcagggaaa aagtaagaag ggacaagttg aacgagaggt     360

tcttggaact gggtgctgtc ctggaaccag ggaagacacc caaaatggac aaatcgtcta     420

tattgaacga tgctattcgt gtaatggctg agctgcgtag tgaggcacag aagttgaagg     480

aatcaaatga gagtctccaa gagaaaatca aagagttgaa ggctgagaaa aacgagctgc     540

gtgatgagaa gcaaaagctg aaggcagaga aagagagcct ggagcagcag ataaagttcc     600

tgaatgctcg accaagcttc gtaccacacc ctccggttat cccagccagt gcattcactg     660
```

-continued

```
ctcctcaagg gcaagctgcc gggcagaagc tgatgatgcc tgtgattggc tacccaggat    720

ttccgatgtg gcagttcatg ccgccttctg atgttgatac cacagatgac accaagtcat    780

gccctcctgt tgcataagtc aaagcaaaga tcaatttgcc tcgccttgta ggaaagaggt    840

gaaactgcct tccattcaag cccagtttgg tcgtcagtgt ttaaactacc tagctaatcc    900

caggattaaa ccgaagcttc gctgtatcga agtatcaacc ggtgacatgt gaactgacga    960

aagatgacac cgttgtatat tacatattag taaataaatt ccatctgtcc aattaaatga   1020

gaattagatg ccatataatt                                               1040


<210> SEQ ID NO 84
<211> LENGTH: 762
<212> TYPE: DNA
<213> ORGANISM: Oryza sativa

<400> SEQUENCE: 84

atgtccggta ccccggcgga cggcggcggc ggaggcggcg gaggcggcgg agggagcggg     60

gacgactggt tcctcgactg cggcatcctc gaggacctcc cggcggccgc gtgcggggcc    120

ttcccgtggg acgcatcccc gtcctgctcc aacccgagtg tggaagtaag cagctatgtg    180

aacaccacct cttatgtcct caaggaacct ggcagtaata aacgtgtaag gtcagggtct    240

tgtggtaggc caacatcaaa agcttccagg gaaaagatca gaagagataa gatgaatgat    300

aggtttcttg aattggggac tactttggag cctgggaagc cagtaaaatc tgacaaagct    360

gctatcctaa gtgatgccac tcgcatggta attcaacttc gtgctgaagc gaagcagcta    420

aaggatacta acgagagtct tgaagataag attaaagaac tgaaggcaga gaaggacgag    480

cttcgtgatg agaagcagaa gctgaaagta gagaaggaga cattagagca gcaggtgaag    540

attctgactg caactccagc ctacatgcct caccccacat tgatgccagc accgtaccca    600

caagcaccac ttgccccctt ccaccatgcc caggggcaag ccgcggggca gaagctgatg    660

atgccttttg ttggataccc ggggtacccg atgtggcagt tcatgccgcc ttccgaagtc    720

gacacctcca aggacagcga agcgtgcccg cctgtcgcgt aa                       762


<210> SEQ ID NO 85
<211> LENGTH: 711
<212> TYPE: DNA
<213> ORGANISM: Oryza sativa

<400> SEQUENCE: 85

atggacggag gcggagaccc cgttgacgag ttcctcatcg gcggcggcgg cgaggacggc     60

gacctcggcg tcttctgcga cggtgtgccg acgctgccct gcgatggagg acttgggatt    120

gatgatgtca gtggagatac ttgttgcctt gaccaatctg ttttagggaa aagaggtaga    180

gatgaatcat catcatctgg tccaaagtcc aaagcttgcc gtgagaaaat tcggagggat    240

agactgaatg acaggttcct tgagttatct tccgttatca atcctgacaa gcaagctaag    300

ttggataaag caaatatctt gagtgatgca gctcgtctgt tggcagaact cagaggcgag    360

gcagaaaagc ttaaagaatc taatgagaag ctacgagaaa caatcaagga ccttaaggtg    420

gagaagaatg aactccgtga tgagaaagtt actctgaagg cagagaagga gaggctggaa    480

cagcaagtta aagcattgag tgttgctcct acaggatttg ttcctcatct ccctcatcca    540

gctgcattcc atcccgctgc attccctcca tttataccac cttatcaagc tctgggcaac    600

aaaaatgctc ctacgcccgc agcattccaa gggatggcaa tgtggcagtg gttgcctcca    660

actgctgtgg acacaactca agatccaaag ctttggccac caaatgctta a             711
```

-continued

<210> SEQ ID NO 86
<211> LENGTH: 775
<212> TYPE: DNA
<213> ORGANISM: Triticum aestivum

<400> SEQUENCE: 86
ctgccccctc atggacgacc ttgctgccgc cgacttcgcc gcggcatccg caggaggctt 60
ctactggacc ccgccgatgc agccgcagat gcacactctt gcgcaggccg tctccgccac 120
cccggctccc aatccctgtg ctgaaatcaa tagctctgtt tcggtggact gggaccatgc 180
caaaggacaa ccgaaaaata aacgtcctag gtcagaaact ggtgctcaac ctagctccaa 240
agcatgcagg gagaaagtga gaagggacaa gctaaacgag aggttcttgg aattgggtgc 300
tgtcttggat ccggggaaaa cacctaaaat cgacaaatgt gctatattaa atgatgctat 360
ccgtgcggta actgaattgc gtagtgaagc acagaagttg aaggattcca atgagtctct 420
ccaagagaag attagagagc taaaggctga caagaatgag ctacgacatg agaagcaaaa 480
gatgaaggcg gagaaagaga gcctggagca gcagattaag ttcatgaatg cccgtcagag 540
cctcgtacca cacccttctg tcatcccagc tgctgcattc gctgccgccc aaggccaagc 600
ggcagggcac aagctgatga tgcctgtgat gagctaccca ggatttccca tgtggcagtt 660
catgccgcct tcagatgttg atacctccga tgaccccaag tcatgccctc cggttgcata 720
agccagcaaa aatcatttgc ctcatctatc tcatggggaa ggatggctaa aaagc 775

<210> SEQ ID NO 87
<211> LENGTH: 674
<212> TYPE: DNA
<213> ORGANISM: Hordeum vulgare

<400> SEQUENCE: 87
ccgcgaaacc ctagtccccc ggcaaccttc gctggacccg gggagccgct ccggcgccat 60
ggcatccccg gaaggatcaa actgggtctt cgactgcccc ctcatggacg accttgctgc 120
cgccgacttc gccgcggtac ccgcaggagg cttctactgg aacccgccga tgccgccgca 180
gatgcacact ctggcgcagg ccgtctccgc caccccggct cccaatccct gtgctgaaat 240
caatagctct gtttcggtgg actgggacca tgccaaagga caaccgaaaa ataaacgtcc 300
tagatcagaa actggtgctc aacctagctc caaagcatgc agggagaaag ttagaaggga 360
caagctaaat gagaggttct tggaattggg tgctgtcttg gacccgggga aaacacctaa 420
aatcgacaaa tgtgctatat taaatgatgc tatccgtgcg gtaactgaat tgcgtagtga 480
agcagagaag ttgaaggatt caaatgagtc tctccaagag aagattagag agctgaaggc 540
tgagaagaat gagctgcgag atgagaagca aaagctgaag gcggaaaaag agagcctgga 600
gcagcagatt aagttcatga atgcccgtca gagactcgta ccacaccctt ctgtcatccc 660
agctactgca ttcg 674

<210> SEQ ID NO 88
<211> LENGTH: 820
<212> TYPE: DNA
<213> ORGANISM: Oryza sativa

<400> SEQUENCE: 88
ccgcccccaa atctcctcgc gacctcgaaa ccctagcctc ctccggccac cgtcgccggc 60
cacggtgagc ggccccaccc ccccgcagcc atggcctccc cggagggctc cacgtgggtc 120

-continued

```
ttcgactgcc ctctgatgga cgacctcgcc gccgccgccg gcttcgacgc cgccccgcc    180

ggaggcttct actggacgac gcccgctcct ccgcaggcgg cgctacagcc gccgccgccg    240

cagcagcagc ccgtcgcccc tgccaccgcg gctccgaacg cctgtgctga aatcaatggc    300

tctgtggact gtgaacatgg caaagaacag ccaacaaata aacgtccgag atcagaaagt    360

ggcactcgac caagctccaa agcatgcagg gaaaaagtaa gaagggacaa gttgaacgag    420

aggttcttgg aactgggtgc tgtcctggaa ccagggaaga cacccaaaat ggacaaatcg    480

tctatattga acgatgctat tcgtgtaatg gctgagctgc gtagtgaggc acagaagttg    540

aaggaatcaa atgagagtct ccaagagaaa atcaaagagt tgaaggctga gaaaaacgag    600

ctgcgtgatg agaagcaaaa gctgaaggca gagaaagaga gcctggagca gcagataaag    660

ttcctgaatg ctcgaccaag cttcgtacca caccctccgg ttatcccagc cagtgcattc    720

actgctcctc aagggcaagc tgccgggcag aagctgatga tgcctgtgat tggctaccca    780

ggatttccga tgtggcagtt catgccgcct tctgatgttg                          820


<210> SEQ ID NO 89
<211> LENGTH: 703
<212> TYPE: DNA
<213> ORGANISM: Triticum aestivum
<220> FEATURE:
<221> NAME/KEY: misc_feature
<222> LOCATION: (34)..(34)
<223> OTHER INFORMATION: n is a, c, g, or t

<400> SEQUENCE: 89

aggaattcgg cacgaggccg cttccccgct accnccccaa ccccgaaata tcccccaatt     60

ccgacgcgac cgcggaaccc tagcccccg gcaatcttcg ctggacccgg agagccgctc    120

cggcgccatg gcatccccgg aaggatcaaa ctgggtattc gactgccccc tcatggacga    180

ccttgctgcc gccgacttcg ccgcggcatc cgcaggaggc ttctactgga ccccgccgat    240

gcagccgcag atgcacactc ttgcgcaggc cgtctccgcc accccggctc ccaatccctg    300

tgctgaaatc aatagctctg tttcggtgga ctgggaccat gccaaaggac aaccgaaaaa    360

taaacgtcct aggtcagaaa ctggtgctca acctagctcc aaagcatgca gggagaaagt    420

gagaagggac aagctaaacg agaggttctt ggaattgggt gctgtcttgg atccggggaa    480

aacacctaaa atcgacaaat gtgctatatt aaatgatgct atccgtgcgg taactgaatt    540

gcgtagtgaa gcagagaagt tgaaggattc caatgagtct ctccaagaga agattagaga    600

gctaaaggct gagaagaatg agctacgaga tgagaagcaa aagttgaagg cggagaaaga    660

gagcctggag cagcagatta agttcatgaa tgcccgtcag agc                      703


<210> SEQ ID NO 90
<211> LENGTH: 586
<212> TYPE: PRT
<213> ORGANISM: Triticum aestivum

<400> SEQUENCE: 90

Cys Cys Gly Cys Thr Cys Cys Gly Gly Cys Gly Cys Cys Ala Thr Gly
1               5                   10                  15

Gly Cys Ala Thr Cys Cys Cys Cys Gly Gly Ala Ala Gly Gly Ala Thr
            20                  25                  30

Cys Ala Ala Ala Cys Thr Gly Gly Gly Thr Ala Thr Thr Cys Gly Ala
        35                  40                  45

Cys Thr Gly Cys Cys Cys Thr Cys Thr Cys Ala Thr Gly Gly Ala Cys
    50                  55                  60
```

-continued

```
Gly Ala Cys Cys Thr Thr Gly Cys Thr Gly Cys Cys Gly Cys Cys Gly
65                  70                  75                  80

Ala Cys Thr Thr Cys Gly Cys Cys Gly Cys Gly Gly Cys Ala Thr Cys
                85                  90                  95

Cys Ala Cys Ala Gly Gly Ala Gly Gly Cys Thr Thr Cys Thr Ala Cys
            100                 105                 110

Thr Gly Gly Ala Cys Cys Cys Cys Gly Cys Cys Gly Ala Thr Gly Cys
        115                 120                 125

Ala Gly Cys Cys Gly Cys Ala Gly Ala Thr Gly Cys Ala Cys Ala Cys
    130                 135                 140

Thr Cys Thr Thr Gly Cys Gly Cys Ala Gly Gly Cys Cys Gly Thr Cys
145                 150                 155                 160

Thr Cys Cys Gly Cys Cys Ala Cys Cys Cys Cys Gly Gly Cys Thr Cys
                165                 170                 175

Cys Cys Ala Ala Thr Cys Cys Cys Thr Gly Thr Gly Cys Thr Gly Ala
            180                 185                 190

Ala Ala Thr Cys Ala Ala Thr Ala Gly Cys Thr Cys Thr Gly Thr Thr
        195                 200                 205

Thr Cys Gly Gly Thr Gly Gly Ala Cys Thr Gly Gly Ala Cys Cys
    210                 215                 220

Ala Thr Gly Cys Cys Ala Ala Ala Gly Gly Ala Cys Ala Ala Cys Cys
225                 230                 235                 240

Gly Ala Ala Ala Ala Ala Thr Ala Ala Ala Cys Gly Thr Cys Cys Thr
                245                 250                 255

Ala Gly Gly Thr Cys Ala Gly Ala Ala Ala Cys Thr Gly Gly Thr Gly
            260                 265                 270

Cys Thr Cys Ala Ala Cys Cys Thr Ala Gly Cys Thr Cys Cys Ala Ala
        275                 280                 285

Ala Gly Cys Ala Thr Gly Cys Ala Gly Gly Gly Ala Gly Ala Ala Ala
    290                 295                 300

Gly Thr Gly Ala Gly Ala Ala Gly Gly Gly Ala Cys Ala Ala Gly Cys
305                 310                 315                 320

Thr Ala Ala Ala Cys Gly Ala Gly Ala Gly Gly Thr Thr Cys Thr Thr
                325                 330                 335

Gly Gly Ala Ala Thr Thr Gly Gly Gly Thr Gly Cys Thr Gly Thr Cys
            340                 345                 350

Thr Thr Gly Gly Ala Thr Cys Cys Gly Gly Gly Gly Ala Ala Ala Ala
        355                 360                 365

Cys Ala Cys Cys Thr Ala Ala Ala Ala Thr Cys Gly Ala Cys Ala Ala
    370                 375                 380

Ala Thr Gly Thr Gly Cys Thr Ala Thr Ala Thr Thr Ala Ala Ala Thr
385                 390                 395                 400

Gly Ala Thr Gly Cys Thr Ala Thr Cys Cys Gly Thr Gly Cys Ala Gly
                405                 410                 415

Thr Ala Ala Cys Thr Gly Ala Ala Thr Thr Gly Cys Gly Thr Ala Gly
            420                 425                 430

Thr Gly Ala Gly Gly Cys Ala Gly Ala Gly Ala Ala Gly Thr Thr Gly
        435                 440                 445

Ala Ala Gly Gly Ala Thr Thr Cys Ala Ala Ala Cys Gly Ala Cys Thr
    450                 455                 460

Cys Thr Cys Thr Cys Cys Ala Ala Gly Ala Gly Ala Ala Gly Ala Thr
465                 470                 475                 480
```

-continued

```
Thr Ala Gly Ala Gly Ala Gly Cys Thr Ala Ala Ala Gly Gly Cys Thr
                485                 490                 495

Gly Ala Gly Ala Ala Gly Ala Ala Thr Gly Ala Gly Cys Thr Gly Cys
            500                 505                 510

Gly Ala Gly Ala Thr Gly Ala Gly Ala Ala Gly Cys Ala Ala Ala Ala
        515                 520                 525

Gly Thr Thr Gly Ala Ala Gly Gly Cys Gly Gly Ala Gly Ala Ala Ala
    530                 535                 540

Gly Ala Gly Ala Gly Cys Cys Thr Gly Gly Ala Gly Cys Ala Gly Cys
545                 550                 555                 560

Ala Gly Ala Thr Thr Ala Ala Gly Thr Thr Cys Ala Thr Gly Ala Ala
                565                 570                 575

Thr Gly Cys Cys Cys Gly Thr Cys Ala Gly
            580                 585


<210> SEQ ID NO 91
<211> LENGTH: 651
<212> TYPE: DNA
<213> ORGANISM: Hordeum vulgare

<400> SEQUENCE: 91

cggcacgagg ccaccccggc tcccaatccc tgtgctgaaa taatagctct gtttcggtgg     60

actgggacca tgccaaagga caaccgaaaa ataaacgtcc tagatcagaa actggtgctc    120

aacctagctc caaagcatgc agggagaaag ttagaaggga caagctaaat gagaggttct    180

tggaattggg tgctgtcttg gacccgggga aaacacctaa aatcgacaaa tgtgctatat    240

taaatgatgc tatccgtgcg gtaactgaat tgcgtagtga agcagagaag ttgaaggatt    300

caaatgagtc tctccaagag aagattagag agctgaaggc tgagaagaat gagctgcgag    360

atgagaagca aaagctgaag gcggaaaaag agagcctgga gcagcagatt aagttcatga    420

atgcccgtca gagactcgta ccacaccctt ctgtcatccc agctactgca ttcgctgccg    480

cccaaggcca agcggcaggg cataagctta tgatgcctgt aatgagctac ccaggatttc    540

ccatgtggca gttcatgccg ccttcagatg ttgatacctc ggatgaccct aagtcatgcc    600

ctcctgttgc ataagccagc gaaaatcatt tgcctcatct atctcatggg g             651


<210> SEQ ID NO 92
<211> LENGTH: 590
<212> TYPE: DNA
<213> ORGANISM: Triticum aestivum
<220> FEATURE:
<221> NAME/KEY: misc_feature
<222> LOCATION: (21)..(21)
<223> OTHER INFORMATION: n is a, c, g, or t

<400> SEQUENCE: 92

gagggactgc cccctcatgg nacgaccttg ctgccgccga cttcgccgcg gcatccgcag     60

gaggcttcta ctggaccccg ccgatgcagc cgcagatgca cactcttgcg caggccgtct    120

ccgccacccc ggctcccaat ccctgtgctg aaatcaatag ctctgtttcg gtggactggg    180

accatgccaa aggacaaccg aaaaataaac gtcctaggtc agaaactggt gctcaaccta    240

gctccaaagc atgcagggag aaagtgagaa gggacaagct aaacgagagg ttcttggaat    300

tgggtgctgt cttggatccg ggaaaacac ctaaaatcga caaatgtgct atattaaatg    360

atgctatccg tgcggtaact gaattgcgta gtgaagcaga gaagttgaag gattccaatg    420

agtctctcca agagaagatt agagagctaa aggctgagaa gaatgagcta cgagatgaga    480
```

-continued

```
agcaaaagtt gaaggcggag aaagagagcc tggagcagca gattaagttc atgaatgccc    540

gtcagagcct cgtaccacac ccttctgtca tcccagctgc tgcattcgct               590


<210> SEQ ID NO 93
<211> LENGTH: 845
<212> TYPE: DNA
<213> ORGANISM: Oryza sativa

<400> SEQUENCE: 93

ctttttttaa ttggacagat ggaatttatt tactaatatg caatatacaa cggtgtcatc     60

tttcgtcagt tcacatgtca ccggttgata cttcgataca gcgaagcttc ggtttaatcc    120

tgggtttagc taggtagtaa acactgacga ccaaactggg cttgaatgga aggcagtttc    180

acctctttcc tacaaggcga ggcaaattga tctttgcttt gacttatgca acaggagggc    240

atgacttggt gtcatctgtg gtatcaacat cagaaggcgg catgaactgc cacatcggaa    300

atcctgggta gccaatcaca ggcatcatca gcttctgccc ggcagcttga ccttgaggag    360

cagtgaatgc actggctggg ataaccggag ggtgtggtac gaagcttggt cgagcattca    420

ggaactttat ctgctgctcc aggctatctt tctctgcctt cagcttttgc ttctcatcac    480

gcagctcgtt tttctcagcc ttcaactctt tgattttctc ttggagactc tcatttgatt    540

ccttcaactt ctgtgcctca ctacgcagct cagccattac acgaatagca tcgttcaata    600

tagacgattt gtccattttg ggtgtcttcc ctggttccag gacagcaccc agttccaaga    660

acctctcgtt caacttgtcc cttcttactt tttccctgca tgctttggag cttggtcgag    720

tgccactttc tgatctcgga cgtttatttg ttggctgttc tttgccatgt tcacagtcca    780

cagagccatt gatttcagca ctagtgaaaa aaataaactt gtacttcagt atgccatatg    840

tcatg                                                                845


<210> SEQ ID NO 94
<211> LENGTH: 730
<212> TYPE: DNA
<213> ORGANISM: Triticum aestivum
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 94

ggtatttatt tactaacaat atacacggtt tncaagataa tnaatgttcc cgggtgatac     60

aacgacgacg cttcagttcg gttcttgatt taactacata tagtaacact aaacggcttc    120

tgcatagtaa cactgacgac taagatatac tttaacggac ggctttttag ccatccttcc    180

ccatgagata gatgaggcaa atgatttttg ctggcttatg caaccggagg gcatgacttg    240

gggtcatcgg aggtatcaac atctgaaggc ggcatgaact gccacatggg aaatcctggg    300

tagctcatca caggcatcat cagcttgtgc cctgccgctt ggccttgggc ggcagcgaat    360

gcagcagctg ggatgacaga agggtgtggt acgaggctct gacgggcatt catgaactta    420

atctgctgct ccaggctctc tttctccgcc ttcaactttt gcttctcatc tcgtagctca    480

ttcttctcag cctttagctc tctaatcttc tcttggagag actcattgga atccttcaac    540

ttctctgctt cactacgcaa ttcagttacc gcacggatag catcatttaa tatagcacat    600

ttgtcgattt taggtgtttt ccccggatcc aagacagcac ccaattccaa gaacctctcg    660
```

-continued

```
tttagcttgt cccttctcac tttctccctg catgctttgg agctaggttg agcaccagtt    720

tctgacctag                                                           730


<210> SEQ ID NO 95
<211> LENGTH: 770
<212> TYPE: DNA
<213> ORGANISM: Sorghum bicolor
<220> FEATURE:
<221> NAME/KEY: misc_feature
<222> LOCATION: (559)..(559)
<223> OTHER INFORMATION: n is a, c, g, or t

<400> SEQUENCE: 95

cctactggac gaccgcttcc gccccagtcc ccaccgccct cgaccccgat tcccccaatc     60

cctgccgcga ccgctgaacc ctagcctact ccggccatct gccgctggcc ccggcgatcc    120

cccgccatgg cctcccccga gggaaccacg tgggtcttcg actgtcccct catggacgac    180

ctcgcggtgg ccgccgactt cgcggcagcc cccgcggggg gatttttctg ggcagcgccg    240

ccgtcgctac agccgcaggt ggtgcaggcg ccggtccagt ctgtcgttgc cgcgtcggct    300

cccaacccat gtgtggaaat cagtagctct gtggactgtg gtcagggaaa agaacagcca    360

acaaataaac gtcctaggtc agaaagtacc gcagaaccaa gcacaaaagc atccagggag    420

aaaattagaa gggataagct gaacgagaga ttcctggaat tgggtgccat tttggagcca    480

gggaaaactc ctaaaatgga caagtcagct atattaaatg atgctattcg tgtagtaggt    540

gaattgcgta gcgaagcana agagctcaag gattcaaatg agagcctaca agagaagatt    600

aaagagctaa aggctgagaa gaatgagctg cgagacgaga agcaaaggct gaaggccgag    660

aaggagagcc tggagcagca gatcaagttc ctgaatgccc gcccaagtct ggtaccacac    720

cacccagtga tctcagcctc tgccttcact gctccccaag ggccggcagt               770


<210> SEQ ID NO 96
<211> LENGTH: 761
<212> TYPE: DNA
<213> ORGANISM: Sorghum bicolor

<400> SEQUENCE: 96

ggactgtggt cagggaaaag aacagccaac aaataaacgt cctaggtcag aaagtaccgc     60

agaaccaagc acaaaagcat ccagggagaa aattagaagg gataagctga acgagagatt    120

cctggaattg ggtgccattt tggacccagg gaaaactcct aaaatggaca agtcagctat    180

attaaatgat gctattcgtg tagtaggtga attgcgtagc gaagcaaaag agttcaagga    240

ttcaaatgag agcctacaag agaagattaa agagctaaag gctgagaaga atgagttgcg    300

agacgagaag caaaggctga aggccgagaa ggagagcctg gagcagcaga tcaagttcct    360

gaatgcccgc ccaagtctgg taccacacca cccagtgatt tcagcctctg ccttcactgc    420

tccccagggg ccggcagtcg ccgggcacaa gctgatgatg cctgtgcttg gctaccctgg    480

attcccgatg tggcagttca tgccgccttc tgatgttgac acctctgatg accccaagtc    540

ttgcccacct gtggcgtaag caagtgaaga ggcgatgctg ccctccattg attcaagtct    600

agatcgtgat cagtctgcag tgttgttggt gtagttgact ccactctcca gaatggaagg    660

gaaggttata tgtgtcggat ggtgacatgg ggtgatctga tgacccettt gtatattata    720

tggtaaatga ataaattccg tgaccagttg caaatgagga t                        761


<210> SEQ ID NO 97
```

-continued

<211> LENGTH: 630
<212> TYPE: DNA
<213> ORGANISM: Sorghum bicolor

<400> SEQUENCE: 97
ggggtcatca gaggtgtcaa catcagaagg cggcatgaac tgccacatcg ggaatccagg 60
gtagccaagc acaggcatca tcagcttgtg cccggcgact gccggcccct ggggagcagt 120
gaaggcagag gctgagatca ctgggtggtg tggtaccaga cttgggcggg cattcaggaa 180
cttgatctgc tgctccaggc tctccttctc ggccttcagc ctttgcttct cgtctcgcag 240
ctcattcttc tcagccttta gctctttaat cttctcttgt aggctctcat ttgaatcctt 300
gagctctttt gcttcgctac gcaattcacc tactacacga atagcatcat ttaatatagc 360
tgacttgtcc attttaggag ttttccctgg ctccaaaatg gcacccaatt ccaggaatct 420
ctcgttcagc ttatcccttc taattttctc cctggatgct tttgtgcttg gttctgcggt 480
actttctgac ctaggacgtt tatttgttgg ctgttctttt ccctgaccac agtccacaga 540
gctactgatt tccacacatg ggttgggagc cgacgcggca acgacagact ggaccggcgc 600
ctgcaccacc tgcggcgtag cgacggcggc 630

<210> SEQ ID NO 98
<211> LENGTH: 639
<212> TYPE: DNA
<213> ORGANISM: Zea mays

<400> SEQUENCE: 98
accctagcat actccggcat ctgctgcggc cccggcgatc ccccgccatg gcctcccccg 60
agggcacaac gtgggtcttc gactgtcccc ttatggacga cctcgcggtc gccgccgact 120
tcgcggcagc ccccgcggga ggatttttct gggcagcgcc gccgtcgctg cagccgcagg 180
cgccagtgca gtctgtcgtt gccgcgtcgg ctcccaaccc atgtatggaa atcagtagct 240
ctgtggactg tggtcaggaa aaagaacagc caacaaataa acgtccaagg tcagaaagta 300
ctacagaatc aagcacaaaa gcatccaggg agaaaattag aagggacaag ctgaacgaga 360
gattcttgga attgggtgcc attttggagc cagggaaaac tcctaaaatg gacaaaacag 420
ctatattgag tgatgctatt cgtgtagtag gtgaattgcg tagtgaagca aaaaagctca 480
aggattcaaa tgagaatctc caagagaaga ttaaagagct gaaggccgag aagaatgagc 540
tgcgagacga gaagcaaagg ctgaaggccg agaaggagag cctggagcag cagatcaagt 600
tcctgaatgc ccggccaagc ctcgtaccac accacccag 639

<210> SEQ ID NO 99
<211> LENGTH: 633
<212> TYPE: DNA
<213> ORGANISM: Sorghum bicolor

<400> SEQUENCE: 99
gaggtgtcaa catcagaagg cggcatgaac tgccacatcg ggaatccagg gtagccaagc 60
acaggcatca tcagcttgtg cccggcgact gccggcccct gggggagcag tgaaggcaga 120
ggctgagatc actgggtggt gtggtaccag acttgggcgg gcattcagga acttgatctg 180
ctgctccagg ctctccttct cggccttcag cctttgcttc tcgtctcgca gctcattctt 240
ctcagccttt agctctttaa tcttctcttg taggctctca tttgaatcct tgagctcttt 300
tgcttcgcta cgcaattcac ctactacacg aatagcatca tttaatatag ctgacttgtc 360
cattttagga gttttccctg gctccaaaat ggcacccaat tccaggaatc tctcgttcag 420

-continued

```
cttatccctt ctaattttct ccctggatgc ttttgtgctt ggttctgcgg tactttctga    480

cctaggacgt ttatttgttg gctgttcttt tccctgacca cagtccacag agctactgat    540

ttccacacat gggttgggag ccgacgcggc aacgacagac tggaccggcg cctgcaccac    600

ctgcggctgt agcgacggcg gcgggggggc ccg                                 633


<210> SEQ ID NO 100
<211> LENGTH: 622
<212> TYPE: DNA
<213> ORGANISM: Zea mays
<220> FEATURE:
<221> NAME/KEY: misc_feature
<222> LOCATION: (591)..(591)
<223> OTHER INFORMATION: n is a, c, g, or t

<400> SEQUENCE: 100

gcacgagctc gcggtcgccg ccgacttcgc ggcagccccc gcgggaggat ttttctgggc     60

agcgccgccg tcgctgcagc cgcaggcgcc agtgcagtct gtcgttgccg cgtcggctcc    120

caacccatgt atggaaatca gtagctctgt ggactgtggt caggaaaaag aacagccaac    180

aaataaacgt ccaaggtcag aaagtactac agaatcaagc acaaaagcat ccagggagaa    240

aattagaagg gacaagctga acgagagatt cttggaattg ggtgccattt tggagccagg    300

gaaaactcct aaaatggaca aaacagctat attgagtgat gctattcgtg tagtaggtga    360

attgcgtagt gaagcaaaaa agctcaagga ttcaaatgag aatctccaag agaagattaa    420

agagctgaag gccgagaaga atgagctgcg agacgagaag caaaggctga aggccgagaa    480

ggagagcctg gagcagcaga tcaagttcct gaatgcccgg ccaagcctcg taccacacca    540

cccagtgatc ccagcctctg cgttccctgc tccccagggg ccagcaaccg ncgccaggca    600

caagctgatg atgcctgtga tt                                             622


<210> SEQ ID NO 101
<211> LENGTH: 705
<212> TYPE: DNA
<213> ORGANISM: Saccharum officinarum

<400> SEQUENCE: 101

cgtagtgacc gggtcgaccc acgcgtccgc cgccctcgac cccgaatccc ccaatccctg     60

acgtgaccgc tgaaccctag cctactccgg ccatctgccg ctggccccgg cgatcccccg    120

ccatggcctc ccccgaggga accacgtggg tcttcgactg tccccttatg gacgacctcg    180

cggtggccgc tgacttcgcg gcagcccccg cggggggggtt tttctgggcg gcgccgccgt    240

cgctgcagcc gcaggtggtg caggcgccgg tgcagtctgt cgttgccgcg tcggctccta    300

accccccatg tgtggaaatt agtagctctg tggattgtgg tcagggaaaa gaacaaccaa    360

caaataaacg tcctaggtca gaaagtactg cagaaccaag cacaaaagca tccagggaga    420

aaattagaag ggacaagctg aacaagagat tcctggaatg gggtgccatt ttggagccag    480

gggaaactcc taaaatggac aaatcagcta tattgaatga tgctattcgt gcagtaggtg    540

aattgcgtag cgaagcaaaa aagctgaagg actcaaatga gagtttgcag gagaagatta    600

aagagctgaa ggctgagaag aatgagtcgc gagacgagaa gcaaaggctg aaagccgaga    660

acgagagcct ggagcagcag atcaagttcc tgaatgcccg cccaa                    705


<210> SEQ ID NO 102
<211> LENGTH: 624
<212> TYPE: DNA
```

-continued

<213> ORGANISM: Saccharum officinarum
<220> FEATURE:
<221> NAME/KEY: misc_feature
<222> LOCATION: (598)..(598)
<223> OTHER INFORMATION: n is a, c, g, or t

<400> SEQUENCE: 102

```
attttgttta caatgccatg ttatttgttt tcttgctgct tattatggtg cattatcttg      60

atatttggca tcctaacatt ggcttctatt ttagcagtgt ggaaattagt agctctgtgg     120

attgtggtca gggaaaagaa caaccaacaa ataaacgtcc taggtcagaa agtactgcag     180

aaccaagcac aaaagcatcc agggagaaaa ttagaaggga caagctgaac aagagattcc     240

tggaattggg tgccattttg gagccagggg aaactcctaa aatggacaaa tcagctatat     300

tgaatgatgc tattcgtgca gtaggtgaat tgcgtagcga agcaaaaaag ctgaaggact     360

caaatgagag tttgcaggag aagattaaag agctgaaggc tgagaagaat gagttgcgag     420

acgagaagca aaggctgaag gccgagaagg agaagcctga gcagcagatc aagttcctga     480

atgcccgccc aagcctggta ccacaccact cggtgatccc agcctctgcc ttcgctgctc     540

cccaggggcc ggcagcagct gggcacaaac tgatgctgcc tgtgcttggc taccctgnat     600

tcccaatgtg gcagttcatg cccc                                            624
```

<210> SEQ ID NO 103
<211> LENGTH: 671
<212> TYPE: DNA
<213> ORGANISM: Sorghum bicolor

<400> SEQUENCE: 103

```
agggataagc tgaacgagag attcctggaa ttgggtgcca ttttggagcc agggaaaact      60

cctaaaatgg acaagtcagc tatattaaat gatgctattc gtgtagtagg tgaattgcgt     120

agcgaagcaa aagagctcaa ggattcaaat gagagcctac aagagaagat taaagagcta     180

aaggctgaga agaatgagtt gcgagacgag aagcaaaggc tgaaggccga gaaggagagc     240

ctggagcagc agatcaagtt cctgaatgcc cgcccaagtc tggtaccaca ccaccccagt     300

gatttcagct tctgccttca ttgctcccca ggggccggca gtcgccgggc acaagctgat     360

gatgcctgtg cttggctacc ctggattccc gatgtggcag ttcatgccgc cttctgatgt     420

tgacacctct gatgacccca agtcttgccc acctgtggcg taagcaagtg aagaggcgat     480

gctgccctcc attgattcaa gtctagatcg tgatcagtct gcagtgttgt tggtgtagtt     540

gactccactc tccagaatgg aagggaaggt tatatgtgtc ggatggtgac atggggtgat     600

ctgatgaccc ctttgtatat tatatggtaa atgaataaat tccgtgacca gttgcaaatg     660

aggattagca g                                                          671
```

<210> SEQ ID NO 104
<211> LENGTH: 610
<212> TYPE: DNA
<213> ORGANISM: Triticum aestivum
<220> FEATURE:
<221> NAME/KEY: misc_feature
<222> LOCATION: (592)..(592)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t

<400> SEQUENCE: 104

```
tggtatttat ttactaacaa tatacaacgg tttcacaaga taatcaaatg ttcccgggtg      60
```

-continued

```
atacaacgac gacgcttcag ttcggttctt gatttaacta catatagtaa cactaaacgg    120

cttctgcata gtaacactga cgactaagat atactttaac ggacggcttt ttagccatcc    180

ttccccatga gatagatgag gcaaatgatt tttgctggct tatgcaaccg gagggcatga    240

cttggggtca tcggaggtat caacatctga aggcggcatg aactgccaca tgggaaatcc    300

tgggtagctc atcacaggca tcatcagctt gtgccctgcc gcttggcctt gggcggcagc    360

gaatgcagca gctgggatga cagaagggtg tggtacgagg ctctgacggg cattcatgaa    420

cttaatctgc tgctccaggc tctctttctc cgccttcaac ttttgcttct catctcgtag    480

ctcattcttc tcagccttta gctctctaat cttctcttgg agagactcat tggaatcctt    540

caacttctct gcttcactac gcaattcagt taccgcacgg atagcatcat tnaatatagc    600

acatttgncg                                                           610


<210> SEQ ID NO 105
<211> LENGTH: 628
<212> TYPE: DNA
<213> ORGANISM: Triticum aestivum
<220> FEATURE:
<221> NAME/KEY: misc_feature
<222> LOCATION: (47)..(47)
<223> OTHER INFORMATION: n is a, c, g, or t

<400> SEQUENCE: 105

ggttagatct ccccaaggat tccggcagca ataaacgctt aaggtcngag ccctgtggta     60

ggccgacatc taaggcttgt agggaaaaag tgagaagaga caagctgaat gacaggttcc    120

ttgaattggg tactacattg gatcctggta agccagtaaa agctgacaaa gctgctatcc    180

tgagtgatgc gactcgcatg gttactcagc ttcgtgctga agcgcagcag ctaaaggata    240

ctaatggaag tctagaagac aagattaaag agttgaaggc agagaaggat gaacttcgtg    300

atgagaagca gaagctgaaa ctagagaaag agacattaga gcaccagatg aaacttttga    360

cggcaactcc agcctatatg cctcatccta ctatgatgcc ctccccgttc gctcaggctc    420

cgatggctcc cttccatgca cagggacaag ctctaggaca gaaactgatg atgccctttg    480

ttggttaccc aggatatccg atgtggcagt tgatgccgcc ctctgaagtc gacacctcaa    540

aggacagcga agcatgcccg cctgttgcgt gatatgcttg gaccgcttaa atcgcatgaa    600

ctcatggtaa cctaaaacag catagttg                                       628


<210> SEQ ID NO 106
<211> LENGTH: 1136
<212> TYPE: DNA
<213> ORGANISM: Triticum aestivum
<220> FEATURE:
<221> NAME/KEY: misc_feature
<222> LOCATION: (9)..(9)
<223> OTHER INFORMATION: n is a, c, g, or t

<400> SEQUENCE: 106

ggtgatacna gagcggccgc ccttttttttt tttttagtt agaaaaggaa agcatcccat     60

tcgaattgtg attcgtttct aggcggagat cagaacaaga acgagcattc tttctttctc    120

gagaaaaaat gtattataca gtggacgaag ggtagtagac tctatagagc gcacaactgc    180

cagcattctc ctcatcaaca aaaactaccg catgagaaca atagttaatc tgaatcagag    240

agactatgcg caaccaatgg atcaaacaac tatgctgttt taggtgacca ggggttcatg    300

cgatttaagc ggtccaagca tatcacgcaa caggcgggca tgcttcgctg tcctttgagg    360
```

-continued

```
tgtcgacttc agagggcggc atcaactgcc acatcggata tcctgggtaa ccaacaaagg    420

gcatcatcag tttctgtcct agagcttgtc cctgtgcatg gaagggagcc atcggagcct    480

gagcgaacgg ggagggcatc atagtaggat gaggcatata ggctggagtt gccgtcaaaa    540

gtttcatctg gtgctctaat gtctctttct ctagtttcag cttctgcttc tcatcacgaa    600

gttcatcctt ctctgccttc aactctttaa tcttgtcttc tagacttcca ttagtatcct    660

ttagctgctg cgcttcagca cgaagctgag taaccatgcg agtcgcatca ctcaggatag    720

cagctttgtc agcttttact ggcttaccag gatccaatgt agtacccaat tcaaggaacc    780

tgtcattcag cttgtctctt ctcacttttt ccctacaagc cttagatgtt ggcctaccaa    840

aagggctctg acttaagcgg ttattggtgc cggaatcctt ggggaaaact aaattggtca    900

attgggtgcc taattcccca ctgggattgg accaagaaaa cgatgctttc ccggggaaaa    960

cgccccaagc agcggccggg aggtccttca agattccgca atcgaggaac caactgtctc   1020

ccccttcgg tcggagggaa aaaaattggg gccgggggaa cttacctccc gtttgtgctc   1080

cagcggtccc ccaaaggggg gggggcaatt ttccgcccca tcttgtgttg ggtgtt       1136
```

```
<210> SEQ ID NO 107
<211> LENGTH: 646
<212> TYPE: DNA
<213> ORGANISM: Zea mays
<220> FEATURE:
<221> NAME/KEY: misc_feature
<222> LOCATION: (614)..(614)
<223> OTHER INFORMATION: n is a, c, g, or t

<400> SEQUENCE: 107

ttttttttt ttttttgccc gcggaattta tttataccat accatatata atatacaaag     60

gggtcatcag atcaccccat gtcaccgtcc gacacatgta acatcccctt cagttctgga    120

atcaactaca ccaacaacac tgcggaccga tcaagatttg aatcaatgga aggcagcatc    180

gcctctttcc aacaggattt cgcacggctt ctacgccaca ggaggacaag acctagggtc    240

atcagaggtg tcaacatctg aaggcggcat gaactgccac atcgggaatc cagggtagcc    300

aatcacaggc atcatcagct tgtgcctggc ggcggctgct ggcccctggg gagcagggaa    360

cgcagaggct gggatcactg ggtggtgtgg tacgaggctt ggccgggcat tcaggaactt    420

gatctgctgc tccaggctct ccttctcggc cttcagcctt tgcttctcgt ctcgcagctc    480

attcttctcg gccttcagct ctttaatctt ctcttggaga ttctcatttg aatccttgag    540

cttttttgct tcactacgca attcacctac tacacgaata gcatcactca atatagctgt    600

tttgtccatt ttangagttt tccctggctc caaaatggca cccaat                   646
```

```
<210> SEQ ID NO 108
<211> LENGTH: 916
<212> TYPE: DNA
<213> ORGANISM: Zea mays

<400> SEQUENCE: 108

gcacgcggta aggtctctct tcggcggcgg cgatgtctct ccccccctgac ccggcgggcg    60

gcggcgccgg caccggcacc ggcgacgact ggttcctcga ctgcggcatc ctcgacgacc    120

tcccggccgc ggcctgcggg gccttcccgt gggacgcgtc cccgtcttct tccaacccca    180

gtgtggaagt gggcagctat gtgaacacca atgatgtttt caaggagccc aatgatgtct    240

tcaaggagcc tggcagcaat aagcgtttga ggtcaggatc caatgatgtg catgtgccaa    300

catctaaagc ttctagggaa aaaatgagga ggaacaagct gaatgacagg ttccttgaat    360
```

-continued

```
tggggtctac attagaacca gggaagccag taaaagctga caaagctgct atcctaagtg    420

atgctactcg catggttatt cagcttcgtt cagaagcaca gcagctgaag gaaactaatg    480

gtagtcttga agaaaagatc aaagaactca aggccgagaa ggatgaactt cgtgatgaga    540

agcagaagct gaaattggag aaggagagtt tagaacacca gatgaagctg atgacatcga    600

ctccaaccta catgcctcat ccaaccctga tgccggcgcc tttccctcag gcacccctag    660

cgccgttcca tgcccagggg caagctgcag ggcagaagct gatgatgccc tttgtcagct    720

atccggggta cccaatgtgg cagttcatgc cgccttcaga ggtcgacacc tcgaaggaca    780

gtgaagcgtg ccctcctgtt gcataatcgc ttcgactggc ggctggtcgt gctcacacca    840

tgcgaattag tcgcaactga agcccccccc ctagctgtcg atccattgat tggctataac    900

tgctgttgtt atattt                                                     916
```

<210> SEQ ID NO 109
<211> LENGTH: 778
<212> TYPE: DNA
<213> ORGANISM: Sorghum bicolor

<400> SEQUENCE: 109

```
gaattttgtt atagtcccca aaaggtctct tcggcggcgg ctgcggcggt ggcgatgtct     60

ctccccccgg acggcggcgg tgtcaccggc gacgactggt tcctcgactg cggcatcctc    120

gacgacctcc cgtgggacgc gtccccgtcg tcttcttccc cagtgtggaa gtgggcagct    180

atgtgaacac aaatgatgtc ttcaaggagc ccaatgatgt cttcaaggag cctggcagca    240

ataaacgttt aaggtcagga tccaatgatg tgccaacatc taaagcttct agggaaaaaa    300

tgaggaggaa caaactgaat gataggtttc ttgaattggg gtctacatta gaaccaggga    360

agccagtaaa agctgacaag gctgctatcc taagtgatgc tactcgcatg gttattcagc    420

ttcgttcaga agcacagcag ctcaaggaaa ctaatggtag ccttgaagaa aagattaaag    480

aactaaaggc tgagaaggat gagcttcgtg atgagaagca gaagttgaaa ttagagaagg    540

agagtttaga gcaccagatg aagcttatga cctcaactcc agcctacatg cctcatccga    600

ccctgatgcc agcgcctttc cctcaggcgc ccttagcacc attccatgcc caggggcaag    660

ctgcagggca gaagctgatg atgccctttg tcagctatcc ggggtaccca atgtggcagt    720

tcatgccgcc atcagaagtt gacacctcga aggacagcga agcgtgccct cctgttgc      778
```

<210> SEQ ID NO 110
<211> LENGTH: 832
<212> TYPE: DNA
<213> ORGANISM: Sorghum bicolor

<400> SEQUENCE: 110

```
caaggagcct ggcagcaata aacgtttaag gtcaggatcc aatgatgtgc caacatctaa     60

agcttctagg gaaaaaatga ggaggaacaa actgaatgat aggtttcttg aattggggtc    120

tacattagaa ccagggaagc cagtaaaagc tgacaaggct gctatcctaa gtgatgctac    180

tcgcatggtt attcagcttc gttcagaagc acagcagctc aaggaaacta atggtagcct    240

tgaagaaaag attaaagaac taaaggctga gaaggatgag cttcgtgatg agaagcagaa    300

gttgaaatta gagaaggaga gtttagagca ccagatgaag cttatgacct caactccagc    360

ctacatgcct catccgaccc tgatgccagc gcctttccct caggcgccct tagcaccatt    420

ccatgcccag gggcaagctg cagggcagaa gctgatgatg ccctttgtca gctatccggg    480
```

-continued

```
gtacccaatg tggcagttca tgccgccatc agaagttgac acctcgaagg acagcgaagc    540

gtgccctcct gttgcgtaat tgcttcggtc gactggccac gcttgcacca tgtgaattaa    600

tcacaactga agcccccccc tagtcgttga tccattgatt gggtataact atttgttctt    660

atgtggtagt tcattggtaa cgaagtaaag ctgctgatgt aagcgtccta ctatatagag    720

gctactactg ctgccccttc aatggctgta caatttttgt ggagaaaaga agaatgttcg    780

ttcttgttct ccatagcaac aatgtgacgc tatctatatg tcatatatat tc            832
```

<210> SEQ ID NO 111
<211> LENGTH: 636
<212> TYPE: DNA
<213> ORGANISM: Hordeum vulgare
<220> FEATURE:
<221> NAME/KEY: misc_feature
<222> LOCATION: (15)..(15)
<223> OTHER INFORMATION: n is a, c, g, or t

<400> SEQUENCE: 111

```
gaaacgctta aggtnagggc cctgtggtag gccaacatct aaggcttgta gggaaaaagt     60

gagaagagac aagctgaatg acaggttcct tgaattgggt actacattgg atcctggtaa    120

gccagtaaaa gctgacaaag ctgctatcct aagtgatgcg actcgcatgg ttactcagct    180

tcgtgctgaa gcgaagcagc taaaggatac caatggaagt ctagaagaca agattaaaga    240

gttgaaggca gagaaggatg aacttcgtga cgagaagcag aagctgaaat tagagaaaga    300

gacattagag caccagatga aactattgac tgcaactcca gcctatatgc ctcatcctac    360

catgatgcac tccccatttg ctcaggcgcc aatggctccc ttccatgcac aggggcacgc    420

ttcagcacag aaactgatga tgccctttgt tggttacccg ggatatccga tgtggcagtt    480

gatgccgccc tccgaagtcg acacctcaaa ggacagcgaa gcttgcccgc ctgttgcgtg    540

atgcttggac cgtttaaatc acatgaactc atggtaacct taaacagcgt agttgtttga    600

tccattggtt gcgcatagtc tctctgattc agatta                              636
```

<210> SEQ ID NO 112
<211> LENGTH: 644
<212> TYPE: DNA
<213> ORGANISM: Sorghum bicolor

<400> SEQUENCE: 112

```
agtcagctat attaaatgat gctattcgtg tagtaggtga attgcgtagc gaagcaaaag     60

agctcaagga ttcaaatgag agcctacaag agaagattaa agagctaaag gctgagaaga    120

atgagctgcg agacgagaag caaaggctga aggccgagaa ggagagcctg gagcagcaga    180

tcaagttcct gaatgcccgc ccaagtctgg taccacacca cccagtgatc tcagcctctg    240

ccttcactgc tccccagggg ccggcagtcg ccgggcacaa gctgatgatg cctgtgcttg    300

gctaccctgg attcccgatg tggcagttca tgccgccttc tgatgttgac acctctgatg    360

accccaagtc ttgcccacct gtggcgtaag caagtgaaga ggcgatgctg ccctccattg    420

attcaagtct agatcgtgat cagtctgcag tgttgttggt gtagttgact ccactctcca    480

gaatggaagg gaaggttata tgtgtcggat ggtgacatgg ggtgatctga tgaccccttt    540

gtatattata tggtaaatga ataaattccg tgaccagttg caaatgagga ttagcagact    600

agctcatgtc tattcctgct tttgtcgta taaaccacgt tgtg                      644
```

<210> SEQ ID NO 113
<211> LENGTH: 731

-continued

<212> TYPE: DNA
<213> ORGANISM: Zea mays

<400> SEQUENCE: 113
tttttttttt tttttccag ccagcgtgga tataaacatg caaaacattg tcttacacta 60
tagactgtac tgtttacaga gtaaaattta aaatagggag taagatagag aataggatag 120
agaggctgct ggagatagcc taagaacatc agttataccc catcaatgga tcgacaacga 180
caactagttg cggctaatcc acatggtgtg agcaggacca gccccatcaa ggtgatcatg 240
cgacaggagg gcacgcctcg ctgtccttcg aggtgtcgac ctctgaaggc ggcatgaact 300
gccacattgg gtaccctggg tagccgacga agggcatcat cagcttctgc cctgcagctt 360
ggccctgggc atggaatgga gctaggggcg cctgggcgaa aggcgccggc atcagggtcg 420
gatggggcat gtaggctgga gccgatgcca tcagcttcat ctggtgctct agactctcct 480
tctccagttt cagtttctgc ttctcgtcgc gaagctcgtc cttctcggcc tttagttctt 540
taatcttttc ttcgaggctg ccattagtct ccttcagttg ctgtgattct gaacggagct 600
gaataaccat gcgagtagca tcgcttagga tggcagcttt gtcagctttc actggcttcc 660
caggttctaa tgcagacccc agttcaagaa acctgtcatt cagcttgttc ctcctcattc 720
tttccctgca a 731

<210> SEQ ID NO 114
<211> LENGTH: 572
<212> TYPE: DNA
<213> ORGANISM: Zea mays

<400> SEQUENCE: 114
tataccatac catatataat atacaaaggg gtcatcagat caccccatgt caccgtccga 60
cacatgtaac atccccttca gttctgcgaa tcaactacac caacaacact gcggaccgat 120
caagatttga atcaagggaa ggcagcatcg cctctttcca acaggatttc gcacggcttc 180
tacgccacag gaggacaaga cctagggtca tcagaggtgt caacatctga aggcggcatg 240
aactgccaca tcgggaatcc agggtagcca atcacaggca tcatcagctt gtgcctggcg 300
gcggctgctg gcccctgggg agcagggaac gcagaggctg ggatcactgg gcggtgtggt 360
acgaggcttg gccgggcatt caggaacttg atctgctgct ccaggctctc cttctcggcc 420
ttcagccttt gcttctcgtc tcgcagctca ttcttctcgg ccttcagctc tttaatcttc 480
tcttggagat tctcatttga atccttgagc ttttttgctt cactacgcaa ttcacctact 540
acacgaatag catcactcaa tatagctgtt tt 572

<210> SEQ ID NO 115
<211> LENGTH: 705
<212> TYPE: DNA
<213> ORGANISM: Arabidopsis thaliana

<400> SEQUENCE: 115
atggtgtcac ccgaaaacgc taattggatt tgtgacttga tcgatgctga ttacggaagt 60
ttcacaatcc aaggtcctgg tttctcttgg cctgttcagc aacctattgg tgtttcttct 120
aactccagtg ctggagttga tggctcggct ggaaactcag aagctagcaa agaacctgga 180
tccaaaaaga gggggagatg tgaatcatcc tctgccacta gctcgaaagc atgtagagag 240
aagcagcgac gggacaggtt gaatgacaag tttatggaat tgggtgcaat tttggagcct 300
ggaaatcctc ccaaaacaga caaggctgct atcttggttg atgctgtccg catggtgaca 360

-continued

```
cagctacggg gcgaggccca gaagctgaag gactccaatt caagtcttca ggacaaaatc    420

aaagagttaa agactgagaa aaacgagctg cgagatgaga aacagaggct gaagacagag    480

aaagaaaagc tggagcagca gctgaaagcc atgaatgctc ctcaaccaag tttttttccca    540

gccccaccta tgatgcctac tgcttttgct tcagcgcaag gccaagctcc tggaaacaag    600

atggtgccaa tcatcagtta cccaggagtt gccatgtggc agttcatgcc tcctgcttca    660

gtcgatactt ctcaggatca tgtccttcgt cctcctgttg cttaa                    705
```

<210> SEQ ID NO 116
<211> LENGTH: 705
<212> TYPE: DNA
<213> ORGANISM: Arabidopsis thaliana

<400> SEQUENCE: 116

```
atggtgtcac ccgaaaacgc taattggatt tgtgacttga tcgatgctga ttacggaagt     60

ttcacaatcc aaggtcctgg tttctcttgg cctgttcagc aacctattgg tgtttcttct    120

aactccagtg ctggagttga tggctcggct ggaaactcag aagctagcaa agaacctgga    180

tccaaaaaga gggggagatg tgaatcatcc tctgccacta gctcgaaagc atgtagagag    240

aagcagcgac gggacaggtt gaatgacaag tttatggaat tgggtgcaat tttggagcct    300

ggaaatcctc ccaaaacaga caaggctgct atcttggttg atgctgtccg catggtgaca    360

cagctacggg gcgaggccca gaagctgaag gactccaatt caagtcttca ggacaaaatc    420

aaagagttaa agactgagaa aaacgagctg cgagatgaga aacagaggct gaagacagag    480

aaagaaaagc tggagcagca gctgaaagcc attaatgctc ctcaaccaag tttttttccca    540

gccccaccta tgatgcctac tgcttttgct tcagcgcaag gccaagctcc tggaaacaag    600

atggtgccaa tcatcagtta cccaggagtt gccatgtggc agttcatgcc tcctgcttca    660

gtcgatactt ctcaggatca tgtccttcgt cctcctgttg cttaa                    705
```

<210> SEQ ID NO 117
<211> LENGTH: 681
<212> TYPE: DNA
<213> ORGANISM: Arabidopsis thaliana

<400> SEQUENCE: 117

```
atggtgtctc cggagaatac gaactggctt agtgattacc ctttgattga aggtgctttc     60

tctgatcaga accccacttt cccttggcag atagatggct cagctactgt cagtgttgaa    120

gtggatggct tcctttgtga tgcagatgtg atcaaagaac caagttcaag gaagaggatc    180

aaaactgaat cttgcactgg ttctaactcg aaagcttgta gggagaaaca aagacgtgat    240

agactaaatg acaagtttac ggagttgagt tccgtattgg aacctgggag aactccaaaa    300

acagacaagg ttgctattat caatgatgca attcgcatgg tgaatcaagc aagagatgaa    360

gcgcagaaac taaaggactt gaactcaagc ctccaggaga aatcaagga gttgaaggat     420

gagaagaacg agctgcgtga tgagaaacag aagcttaagg tcgagaagga gagaatcgat    480

cagcaactga aagctattaa gacacagcct cagcctcaac cttgtttctt accaaatccg    540

caaacactct ctcaagctca agctcctgga agcaagcttg tccctttcac aacttatccc    600

ggctttgcaa tgtggcaatt catgcctcct gctgctgttg atacctcaca ggaccatgtc    660

cttcgtcctc cagttgctta a                                              681
```

<210> SEQ ID NO 118
<211> LENGTH: 876

-continued

<212> TYPE: DNA
<213> ORGANISM: Arabidopsis thaliana

<400> SEQUENCE: 118

```
atgcaaacaa atgaagataa catatttcag gattttgggt cttgtggtgt gaatctgatg     60
cagccacaac aagaacaatt tgattctttt aatggaaatc ttgagcaagt ttgtagtagc    120
tttagaggag gaaacaatgg agttgtttat agtagtagca ttggatcagc acaattggat    180
ttggctgcat cgtttagtgg agttttgcag caagagacac atcaagtctg tggctttaga    240
ggacaaaacg acgattctgc agtgcctcat ttgcagcagc aacaaggaca ggtgtttagt    300
ggtgtagtgg aaatcaattc ttcgtcatct gttggagctg ttaaggaaga gtttgaggaa    360
gaatgttcgg ggaagaggag acgaactgga tcatgtagca agccaggaac caaagcctgt    420
cgcgagaaac taagaaggga aaagctaaat gacaagttca tggacttgag ctctgtttta    480
gagcctggca ggactccaaa gacggataaa tcagctatac tcgacgatgc aatccgggtt    540
gtgaatcagc ttagaggtga agctcatgag cttcaagaaa ccaaccaaaa gcttctagaa    600
gagatcaaga gtctaaaggc ggataaaaac gagctacgag aggaaaagct ggtgttgaag    660
gcggagaagg agaagatgga gcaacagtta aaatctatgg tggttccatc accaggtttc    720
atgccctccc agcatccagc agctttccat tcccataaga tggcggtggc ttacccttac    780
ggctactatc ctccaaacat gccaatgtgg tcacccttac ctcctgctga ccgtgatacg    840
tctcgtgatc tcaaaaatct tcctcctgtt gcttaa                              876
```

<210> SEQ ID NO 119
<211> LENGTH: 963
<212> TYPE: DNA
<213> ORGANISM: Arabidopsis thaliana

<400> SEQUENCE: 119

```
atgtatccat caatcgaaga cgatgatgat cttctcgctg ctctttgttt tgatcaaagc     60
aatggagtag aagatcctta tggatatatg caaacaaatg aagataacat atttcaggat    120
tttgggtctt gtggtgtgaa tctgatgcag ccacaacaag aacaatttga ttcttttaat    180
ggaaatcttg agcaagtttg tagtagcttt agaggaggaa acaatggagt tgtttatagt    240
agtagcattg gatcagcaca attggatttg gctgcatcgt ttagtggagt tttgcagcaa    300
gagacacatc aagtctgtgg ctttagagga caaaacgacg attctgcagt gcctcatttg    360
cagcagcaac aaggacaggt gtttagtggt gtagtggaaa tcaattcttc gtcatctgtt    420
ggagctgtta aggaagagtt tgaggaagaa tgttcgggga agaggagacg aactggatca    480
tgtagcaagc caggaaccaa agcctgtcgc gagaaactaa gaagggaaaa gctaaatgac    540
aagttcatgg acttgagctc tgttttagag cctggcagga ctccaaagac ggataaatca    600
gctatactcg acgatgcaat ccgggttgtg aatcagctta gaggtgaagc tcatgagctt    660
caagaaacca accaaaagct tctagaagag atcaagagtc taaaggcgga taaaaacgag    720
ctacgagagg aaaagctggt gttgaaggcg gagaaggaga agatggagca acagttaaaa    780
tctatggtgg ttccatcacc aggtttcatg ccctcccagc atccagcagc tttccattcc    840
cataagatgg cggtggctta cccttacggc tactatcctc caaacatgcc aatgtggtca    900
cccttacctc ctgctgaccg tgatacgtct cgtgatctca aaaatcttcc tcctgttgct    960
taa                                                                  963
```

<210> SEQ ID NO 120

-continued

<211> LENGTH: 852
<212> TYPE: DNA
<213> ORGANISM: Arabidopsis thaliana

<400> SEQUENCE: 120

```
atgtatcctt ctctcgacga tgatttcgtc tctgatttgt tttgcttcga tcaaagcaat      60
ggagcagaac ttgatgatta cacacagttt ggtgtaaatt tgcagactga tcaagaggat     120
acctttccag attttgtgtc atatggtgtg aatttgcagc aggagccaga tgaagtcttt     180
agtattggag cttctcaatt ggatttgtcc tcgtataatg gagttttgtc gctagagcca     240
gaacaggtgg ggcaacaaga ttgtgaagtt gtgcaggaag aagaagtaga gatcaattct     300
ggttcatctg gtggagctgt taaggaagaa caggaacatt tagatgacga ttgctccaga     360
aagcgggcaa ggactggatc gtgtagcaga ggaggaggaa ctaaagcgtg tcgtgaaagg     420
ttgaggaggg agaagctaaa tgagaggttt atggatttga gctcggtttt ggagcctggg     480
aggactccta agactgataa accggctata ctcgatgatg caatccgtat attgaatcaa     540
cttagagatg aagctcttaa gcttgaagaa actaaccaga agcttttaga ggagatcaag     600
agtctcaagg cggagaagaa cgagctgagg gaggaaaagc tggtgttgaa ggcggataaa     660
gagaagacag aacaacagtt aaagtctatg acggctccat cttcagggtt catacctcat     720
attccagctg catttaacca caacaaaatg gctgtttatc caagttacgg ttacatgcca     780
atgtggcatt atatgcctca atccgttcgt gacacatctc gtgatcaaga actcaggcct     840
cctgctgctt aa                                                         852
```

<210> SEQ ID NO 121
<211> LENGTH: 834
<212> TYPE: DNA
<213> ORGANISM: Arabidopsis thaliana

<400> SEQUENCE: 121

```
atggatgtga atctttttgg tcatgatgac tcttgtagca atggagcaga acttgatgat      60
tacacacagt ttggtgtaaa tttgcagact gatcaagagg atacctttcc agattttgtg     120
tcatatggtg tgaatttgca gcaggagcca gatgaagtct ttagtattgg agcttctcaa     180
ttggatttgt cctcgtataa tggagttttg tcgctagagc cagaacaggt ggggcaacaa     240
gattgtgaag ttgtgcagga agaagaagta gagatcaatt ctggttcatc tggtggagct     300
gttaaggaag aacaggaaca tttagatgac gattgctcca gaaagcgggc aaggactgga     360
tcgtgtagca gaggaggagg aactaaagcg tgtcgtgaaa ggttgaggag ggagaagcta     420
aatgagaggt ttatggattt gagctcggtt ttggagcctg ggaggactcc taagactgat     480
aaaccggcta tactcgatga tgcaatccgt atattgaatc aacttagaga tgaagctctt     540
aagcttgaag aaactaacca gaagctttta gaggagatca agagtctcaa ggcggagaag     600
aacgagctga gggaggaaaa gctggtgttg aaggcggata aagagaagac agaacaacag     660
ttaaagtcta tgacggctcc atcttcaggg ttcatacctc atattccagc tgcatttaac     720
cacaacaaaa tggctgttta tccaagttac ggttacatgc caatgtggca ttatatgcct     780
caatccgttc gtgacacatc tcgtgatcaa gaactcaggc ctcctgctgc ttaa           834
```

<210> SEQ ID NO 122
<211> LENGTH: 1014
<212> TYPE: DNA
<213> ORGANISM: Arabidopsis thaliana

<400> SEQUENCE: 122

-continued

```
atggggataa gagaaaatgg aataatgctt gtgagcagag agagagagcg agcgaggagg      60
ctagagaatc gagaatcgat cttcgccgaa ccaccttgtc ttctcttagc tcatcgaatc     120
tctccgtcgc cgtcgattct tcccgccgaa gaggaggtca tggacgtttc tgctagaaag     180
tcacaaaaag ctgggcgcga aaagttgagg agggaaaaac tgaatgagca ttttgttgaa     240
ctgggaaatg tactcgatcc agagagaccc aagaatgaca aagccacgat tctgactgat     300
actgttcagt tgttgaaaga gctcacatct gaagtcaaca aactgaaatc tgagtacacc     360
gcattgacag atgagtcccg cgagttgaca caggagaaaa acgacctgag agaagaaaag     420
acatcgctga aatcagatat agagaatctc aatcttcaat accagcagag attaaggtca     480
atgtctccat ggggagctgc gatggatcac acagtcatga tggctccacc accctccttt     540
ccatacccta tgcctattgc tatgcctccc gggtcaatcc caatgcatcc atcaatgcca     600
tcttacacat actttgggaa ccagaaccct agcatgatcc cagctccatg tcctacatac     660
atgccctaca tgcctcctaa tacagtcgtt gagcaacaat ccgtgcacat tccacagaac     720
cccggtaacc gttctcggga acctagagca aaggtttcaa gagagagcag atctgagaaa     780
gcagaggact ccaacgaagt tgcaacacaa ctcgaattaa aaacccctgg atctacttct     840
gataaggata cattgcaaag gccagagaag acaaagagat gtaagagaaa caacaacaac     900
aactcaatag aagaaagctc tcattctagc aagtgttcat cttctccgag cgtacgagac     960
cacagttctt ccagtagcgt agctggtggc caaaaacctg atgatgcaaa atga          1014
```

<210> SEQ ID NO 123
<211> LENGTH: 855
<212> TYPE: DNA
<213> ORGANISM: Arabidopsis thaliana

<400> SEQUENCE: 123

```
atggacgttt ctgctagaaa gtcacaaaaa gctgggcgcg aaaagttgag gagggaaaaa      60
ctgaatgagc attttgttga actgggaaat gtactcgatc cagagagacc caagaatgac     120
aaagccacga ttctgactga tactgttcag ttgttgaaag agctcacatc tgaagtcaac     180
aaactgaaat ctgagtacac cgcattgaca gatgagtccc gcgagttgac acaggagaaa     240
aacgacctga gagaagaaaa gacatcgctg aaatcagata tagagaatct caatcttcaa     300
taccagcaga gattaaggtc aatgtctcca tggggagctg cgatggatca cacagtcatg     360
atggctccac caccctcctt tccataccct atgcctattg ctatgcctcc cgggtcaatc     420
ccaatgcatc catcaatgcc atcttacaca tactttggga accagaaccc tagcatgatc     480
ccagctccat gtcctacata catgccctac atgcctccta atacagtcgt tgagcaacaa     540
tccgtgcaca ttccacagaa ccccggtaac cgttctcggg aacctagagc aaaggtttca     600
agagagagca gatctgagaa agcagaggac tccaacgaag ttgcaacaca actcgaatta     660
aaaacccctg gatctacttc tgataaggat acattgcaaa ggccagagaa gacaaagaga     720
tgtaagagaa acaacaacaa caactcaata gaagaaagct ctcattctag caagtgttca     780
tcttctccga gcgtacgaga ccacagttct tccagtagcg tagctggtgg ccaaaaacct     840
gatgatgcaa aatga                                                     855
```

<210> SEQ ID NO 124
<211> LENGTH: 807
<212> TYPE: DNA
<213> ORGANISM: Arabidopsis thaliana -continued

<400> SEQUENCE: 124
atggctgtgt catgtttatt catagtttcg tctaattaca gaggagctga gatggtggtg 60
gaagtgaaga aggaagcagt ttgttcccag aaagcagagc gagagaagct tcgtagagat 120
aagcttaagg aacagtttct tgagcttgga aatgcacttg atccgaatag gcctaagagt 180
gacaaagcct cagttctcac tgatacaata caaatgctca aggatgtaat gaaccaagtt 240
gatagactaa aagctgagta tgaaacacta tctcaagagt ctcgtgagct aattcaagag 300
aagagtgagc tgagagagga gaaagcgact ttaaagtctg atatcgagat tcttaatgct 360
caatatcagc atggaatcaa aaccatggtt ccatgggtac ctcattacag ttatcatatc 420
cccttcgtag ccataactca gggtcagtcc agttttatac cttattcagc ctctgtcaat 480
cctctaaccg aacaacaagc atcggttcag cagcattctt cttcttctgc cgatgcttca 540
atgaaacaag attccaaaat caagccgtta gatttggatc tgatgatgaa cagtaaccat 600
tcaggtcaag gaaatgatca aaaagatgat gttcgtttaa agctcgagct taaaatccat 660
gcctcttctt tagctcaaca ggatgtttct ggaaaagaga agaaagtaag cttgacaacc 720
actgcaagct catcgaatag ttactcatta tctcaagctg ttcaagatag ttcccccggt 780
accgtaaatg acatgttgaa gccataa 807

<210> SEQ ID NO 125
<211> LENGTH: 861
<212> TYPE: DNA
<213> ORGANISM: Arabidopsis thaliana

<400> SEQUENCE: 125
atggatcaac caatgaaacc aaaaacttgc tctgaatctg attttgctga tgattcctct 60
gcttcttctt cttcttcttc gggacaaaat ctcagaggag ctgagatggt ggtggaagtg 120
aagaaggaag cagtttgttc ccagaaagca gagcgagaga agcttcgtag agataagctt 180
aaggaacagt ttcttgagct tggaaatgca cttgatccga ataggcctaa gagtgacaaa 240
gcctcagttc tcactgatac aatacaaatg ctcaaggatg taatgaacca agttgataga 300
ctaaaagctg agtatgaaac actatctcaa gagtctcgtg agctaattca agagaagagt 360
gagctgagag aggagaaagc gactttaaag tctgatatcg agattcttaa tgctcaatat 420
cagcatagaa tcaaaaccat ggttccatgg gtacctcatt acagttatca tatccccttc 480
gtagccataa ctcagggtca gtccagtttt ataccttatt cagcctctgt caatcctcta 540
accgaacaac aagcatcggt tcagcagcat tcttcttctt ctgccgatgc ttcaatgaaa 600
caagattcca aatcaagcc gttagatttg gatctgatga tgaacagtaa ccattcaggt 660
caaggaaatg atcaaaaaga tgatgttcgt ttaaagctcg agcttaaaat ccatgcctct 720
tctttagctc aacaggatgt ttctggaaaa gagaagaaag taagcttgac aaccactgca 780
agctcatcga atagttactc attatctcaa gctgttcaag atagttcccc cggtaccgta 840
aatgacatgt tgaagccata a 861

<210> SEQ ID NO 126
<211> LENGTH: 807
<212> TYPE: DNA
<213> ORGANISM: Arabidopsis thaliana

<400> SEQUENCE: 126
atggctgtgt catgtttatt catagtttcg tctaattaca gaggagctga gatggtggtg 60
gaagtgaaga aggaagcagt ttgttcccag aaagcagagc gagagaagct tcgtagagat 120

-continued

```
aagcttaagg aacagtttct tgagcttgga aatgcacttg atccgaatag gcctaagagt    180

gacaaagcct cagttctcac tgatacaata caaatgctca aggatgtaat gaaccaagtt    240

gatagactaa aagctgagta tgaaacacta tctcaagagt ctcgtgagct aattcaagag    300

aagagtgagc tgagagagga gaaagcgact ttaaagtctg atatcgagat tcttaatgct    360

caatatcagc atagaatcaa aaccatggtt ccatgggtac ctcattacag ttatcatatc    420

cccttcgtag ccataactca gggtcagtcc agttttatac cttattcagc ctctgtcaat    480

cctctaaccg aacaacaagc atcggttcag cagcattctt cttcttctgc cgatgcttca    540

atgaaacaag attccaaaat caagccgtta gatttggatc tgatgatgaa cagtaaccat    600

tcaggtcaag gaaatgatca aaaagatgat gttcgtttaa agctcgagct taaaatccat    660

gcctcttctt tagctcaaca ggatgtttct ggaaaagaga agaaagtaag cttgacaacc    720

actgcaagct catcgaatag ttactcatta tctcaagctg ttcaagatag ttcccccggt    780

accgtaaatg acatgttgaa gccataa                                        807
```

<210> SEQ ID NO 127
<211> LENGTH: 819
<212> TYPE: DNA
<213> ORGANISM: Arabidopsis thaliana

<400> SEQUENCE: 127

```
atggatcaac caatgaaacc aaaaacttgc tctgaatctg attttgctga tgattcctct     60

gcttcttctt cttcttcttc gggacaaaat ctcagaggag ctgagatggt ggtggaagtg    120

aagaaggaag cagtttgttc ccagaaagca gagcgagaga agcttcgtag agataagctt    180

aaggaacagt ttcttgagct tggaaatgca cttgatccga ataggcctaa gagtgacaaa    240

gcctcagttc tcactgatac aatacaaatg ctcaaggatg taatgaacca agttgataga    300

ctaaaagctg agtatgaaac actatctcaa gagtctcgtg agctaattca agagaagagt    360

gagctgagag aggagaaagc gactttaaag tctgatatcg agattcttaa tgctcaatat    420

cagcatagaa tcaaaaccat ggttccatgg ggtcagtcca gttttatacc ttattcagcc    480

tctgtcaatc ctctaaccga acaacaagca tcggttcagc agcattcttc ttcttctgcc    540

gatgcttcaa tgaaacaaga ttccaaaatc aagccgttag atttggatct gatgatgaac    600

agtaaccatt caggtcaagg aaatgatcaa aaagatgatg ttcgtttaaa gctcgagctt    660

aaaatccatg cctcttcttt agctcaacag gtgagtgatc tcttcaatag ttttgccaac    720

aagctctttc atggactgac cagagtttac ttccatgcag gatgtttctg gaaaagagaa    780

gaaagtaagc ttgacaacca ctgcaagctc atcgaatag                           819
```

<210> SEQ ID NO 128
<211> LENGTH: 799
<212> TYPE: DNA
<213> ORGANISM: Vitis vinifera

<400> SEQUENCE: 128

```
ccctaacgcg ctcctccctc tcccgggaaa ttgcaccggg cctcctcgat ttttcggagg     60

ttccttcgag atggtttctc cagaagccac caattggctg tacgagtacg ggctcatcga    120

ggacatccct gtccctgatt caaacttcgc taatacgaat tcagggttcg cctggactcc    180

tgtgcaggcc ttgaacactt ctgctaatgt cagtggggaa attgatggtt catttgggga    240

ctctgacggc attaaggaaa ctggatcaaa gaagagggtg agatctgaat catgtggtgc    300
```

-continued

```
atctagctcg aaggcatgta gggagaagtt gcggagggac aggctaaatg acaagtttat    360

ggaattgggt tctatcctgg agcctggaag gcctccaaaa acagacaagt cttctatttt    420

gattgatgca gttcgaatgg taactcagtt acgaggtgag tcgcagaagt tgaaggactc    480

aaattctagt ctccaggaga agattaaaga attgaaggct gagaagaatg agcttcgtga    540

tgagaagcaa aggctaaagg ccgagaaaga gaaactggag cagcaactga aagcaatgaa    600

tgctcaacct agtttcctgc ctcccgttcc ttcaatccct gctgcatttg cagctcaagg    660

ccaagctggc ggcgacaagt tggttccatt catcggctac ccaggagttg ctatgtggca    720

attcatgcca cctgctgcag ttgatacctc acaagatcat gtgctccgtc caccagttgc    780

ttaaatcagc aactcaacc                                                 799
```

<210> SEQ ID NO 129
<211> LENGTH: 839
<212> TYPE: DNA
<213> ORGANISM: Citrus reticulata

<400> SEQUENCE: 129

```
ttttttttt tttttttcaa tacagtcacc caccaatcat taaagacttc ggaaaaacta      60

atacagtcag agaacaatga taaaaccaat acacttgttg ggtgcaaatt gcaaacccaa    120

atcattgtag gttgcatact taagcaaccg gaggacggag tacatgatcc tgtgaggtat    180

ccactgcagc aggaggcatg aattgccaca ttgcgactcc agggtagctg atgaaaggca    240

tcagcttgtt tccaggtgct tggccttggg cagcaaatgc agcagggatt gcaggaggag    300

gagttaagaa actgggttgt gtgctcatag ctttgagttg ctgctctatc ttctctttct    360

ctgcctttag cctctgcttc tcatcacgaa gctcattctt ctcagccttc aactctttga    420

tcttctcctg gagacttgaa tttgagtcct tcaacttctg ggcttcactg cgtaattgag    480

tcaccatccg gacggcatca atcaaaatag ctgccttatc tgttttgggg ggccttccag    540

gctctaagat agaggctaac tccacaaact tgtcattaag acgatcccta cgcaactttt    600

ccctgcacgc cttggagcta gaagacccac atgattctga tctaaccctc ttttttgagc    660

tttccttgag accatttgaa tccccaaatg cagaatcaat ttccacacag ccatttgacg    720

gcccgttaat tggcggctga acggtccaag tgaaacccga agcggaaacg gagaaattgc    780

catcagggac agtgatatcg tcgatcaagg ggtaatctaa tagccaattc gtattttcc     839
```

<210> SEQ ID NO 130
<211> LENGTH: 730
<212> TYPE: DNA
<213> ORGANISM: Medicago truncatula

<400> SEQUENCE: 130

```
ttttccggga aattccccca ctatggtttc cccggaaaac accaattggc ttttcgatta      60

ccctttgatt gatgaaattc ctgtttctgt tgatggctcc tttgccttca cgtggccccc    120

acctcacctc tccaatggcg gtattgaaat ggatgatagc tctctagtgg attctgatgg    180

tatcaaagaa cctggttcga agaagagagg tagatcagat tcatgtgctc cttccagctc    240

taaggcatgt cgagagaagt tgcggaggga taggctgaac gacaagtttg ttgaattagg    300

ctccatcttg gagcctggaa ggcctcctaa aacagacaag gcggcaattc tgattgatgc    360

tgtccgaatg gtgacacagt tgcggggtga agcccaaaag ttgaaagact caaattcacg    420

tcttcaagag aagattaaag agttaaaggt tgagaagaat gaactccgcg atgagaagca    480

gaggcttaag gctgagaagg agaagttgga gcagcaggtg aaatcaatga acacccaacc    540
```

-continued

```
cggtttcttg acacaccctc ctgcaatccc tgctgcattt gctcatcaag gccaagcccc    600

aagcaacaag ttaatgcctt tcatgagtta tccaggagtt gccatgtggc aattcatgcc    660

accagccgcc gtggatacct cacaggatca tgtactccgt ccaccagttg cctaaattgg    720

cactgtacaa                                                           730
```

<210> SEQ ID NO 131
<211> LENGTH: 811
<212> TYPE: DNA
<213> ORGANISM: Vitis vinifera

<400> SEQUENCE: 131

```
cttttctccc tcgagaaaac cccccttttc tctctcccca aacaccctaa cgcgctcctc     60

cctctcccgg gaaattgcac cgggcctcct cgatttttcg gaggttcctt cgagatggtt    120

tctccagaag ccaccaattg gctgtacgag tacgggctca tcgaggacat ccctgtccct    180

gattcaaact tcgctaatac gaattcaggg ttcgcctgga ctcctgtgca ggccttgaac    240

acttctgcta atgtcagtgg ggaaattgat ggttcatttg gggactctga cggcattaag    300

gaaactggat caaagaagag ggtgagatct gaatcatgtg gtgcatctag ctcgaaggca    360

tgtagggaga agttgcggag ggacaggcta aatgacaagt ttatggaatt gggttctatc    420

ctggagcctg gaaggcctcc aaaaacagac aagtcttcta ttttgattga tgcagttcga    480

atggtaactc agttacgagg tgagtcgcag aagttgaagg actcaaattc tagtctccag    540

gagaagatta aagaattgaa ggctgagaag aatgagcttc gtgatgagaa gcaaaggcta    600

aaggccgaga aagagaaact ggagcagcaa ctgaaagcaa tgaatgctca acctagtttc    660

ctgcctcccg ttccttcaat ccctgctgca tttgcagctc aaggccaagc tggcggcaac    720

aagttggttc cattcatcgg ctacccagga gttgctatgt ggcaattcat gccacctgct    780

gcagttgata ccctcacaga tcatgtgctc c                                   811
```

<210> SEQ ID NO 132
<211> LENGTH: 833
<212> TYPE: DNA
<213> ORGANISM: Gossypium raimondii

<400> SEQUENCE: 132

```
cggagaatgg tgtcccctga aaactttaat tattggtctc acttcgatta tgctaccttg     60

atccacgata tccctgtccc tgatgatcct tatgccggtt ttgcttggtc tacgcagcca    120

atcgacgccc cttctaatgt tgtcagtgtg gaaattgatg gctcatttgg agattcagac    180

ggtctaaagg aatctggttc aaagaagagg gttagatccg aatcatgcaa tgcatctagc    240

tccaaagcat gtagggagaa gttgcgtaga gataggctaa atgacaagtt tatggagttg    300

ggttctattt tggaacctgg aaggcctccc aaaactgata agtctgctat tttgattgat    360

gctgtccgaa tggtgaccca gttacgaggt gaagcccaga aattgaagga ttcaaatact    420

agtctacagg aaaggattaa agagttgaag tctgaaaaga atgagcttcg tgacgaaaag    480

caaaggctga aggcagagaa agaaaggctg gagcagcaac tcaaagcaat gaatgcacaa    540

cctagcttca tgccgcccgc accaccagca atccctgctg catttgctgc ggctccgggt    600

caagctcctg ggaacaagtt ggtacctctc attggctatc ctggagttgc aatgtggcag    660

ttcatgccgc ctgcagcagt ggatacttca caggaccatg tcctccgccc tccggttgcc    720

taagttggca accaacaatg attggggttg cattttgatg caaacaaggg tataacgtaa    780
```

-continued

```
tgttctgggc tgtttagatt tcgctgaagt ttttctaact ggctttgttg ggt          833


<210> SEQ ID NO 133
<211> LENGTH: 745
<212> TYPE: DNA
<213> ORGANISM: Citrus reticulata

<400> SEQUENCE: 133

aggtgaaact caaccgctgt ttgtttccca ggaaaatttc tctccgccgg aaaacccata     60

aatattatcc tggaaattca aaatggtttc tccggaaaat acgaattggc tattagatta    120

ccccttgatc gacgatatca ctgtccctga tggcaatttc tccgtttccg cttcgggttt    180

cacttggacc gttcagccgc caattaacgg gccgtcaaat ggctgtgtgg aaattgattc    240

tgcatttggg gattcaaatg gtctcaagga aagctcaaaa aagagggtta gatcagaatc    300

atgtgggtct tctagctcca aggcgtgcag ggaaaagttg cgtagggatc gtcttaatga    360

caagtttgtg gagttagcct ctatcttaga gcctggaagg ccccccaaaa cagataaggc    420

agctattctg attgatgccg tccggatggt gactcaatta cgcagtgaag cccagaagtt    480

gaaggactca aattcaagtc tccaggagaa gatcaaagag ttgaaggctg agaagaatga    540

gcttcgtgat gagaagcaga ggctaaaggc agagaaagag aagatagagc agcaactcaa    600

agctatgagc acacaaccca gtttcttaac tcctcctgca atccctgctg catttgctgc    660

ccaaggccaa gcacctggaa acaagctgat gcctttcatc agctaccctg gagtcgcaat    720

gtggcaattc atgcctcctg ctgca                                          745


<210> SEQ ID NO 134
<211> LENGTH: 916
<212> TYPE: DNA
<213> ORGANISM: Solanum tuberosum

<400> SEQUENCE: 134

gataatccaa acagcaattg gaaaccctca tcggagaatt ttccgggaga attatttttt     60

tcatcttctg gccggcgatt gatcggagat ggtttcaccg gagaacacca actggcttta    120

tgattatgga tttgaagata gttccgtccc tgattcgaat ttctcacctt ctgcatctgg    180

gtttaactgg cctgtgcaga atttgaatgg ttcaaggaat gttagttctg aaattgatgg    240

gtcgattggt gaatcagatt acccaaagga aagtggttct aagaaacggg caagggttga    300

atcatgtgct ccaacaagtt ccaaagcttg cagagagaaa ctgcgaagag ataagctgaa    360

tgacaagttc atggaattgg gtgcactcct tgagcctggc aggcccccca aaacagacaa    420

atccgctatt cttgttgatg ctgttcgcat ggtgacccag ttacgtgatg aagctcaaaa    480

gttgaaagac tcaaacttga atctgcaaga aaagatcaag gagttaaagg ttgagaaaac    540

cgagcttcga gatgaaaaac agaggctgaa agctgaaaag gagaagctag agcaacaact    600

aaagactaca agtgcgcaac ctagtttctt gcctcctgct ataccttctg catttgctgc    660

tcatggtcaa tttccaggaa gcaagctggt gccaatcatg agttaccctg gtgtcgcgat    720

gtggcaattc atgcctcctg ctgctgttga tacttcacag gaccatgtcc tccgtcctcc    780

agttgcttaa cttgttgcag cttaaagcct acgaaggttg ccttcactgt cccgttaaat    840

taatcgtcta gttaatgtcc ttcggttgta ttagttttgg ctcaactccc cttcctgtat    900

ttggtggatg atagat                                                    916


<210> SEQ ID NO 135
<211> LENGTH: 959
```

-continued

```
<212> TYPE: DNA
<213> ORGANISM: Solanum tuberosum

<400> SEQUENCE: 135

gatccctcat cggagaattt tccgggagaa ttattttttt catcttctgg ccggcgattg      60

atccgagatg gtttcaccgg agaacaccaa ctggctttat gattatggat tcgaagatag     120

ttccgtccct gattcgaatt tctcagcttc tgcatctggg tttaactggc ctgtgcagaa     180

tttgaatggt tcaaggaatg ttagttctga aattgatggg tcgattggtg aatcagatta     240

cccaaaggaa agtggttcta agaaacgggc aagggttgaa tcatgtgctc caacaagttc     300

caaagcttgc agagagaaac tgcgaagaga taagctgaat gacaagttca tggaattggg     360

tgcactcctt gagcctggca ggccccccaa aacagacaaa tccgctattc ttgttgatgc     420

tgttcgcatg gtgacccagt tacgtgacga agctcaaaag ttgaaagact caaacttgaa     480

tctgcaagaa aagatcaagg agttaaaggt tgagaaaacc gagcttcgag atgaaaaaca     540

gaggttgaaa gctgaaaagg agaagctaga gcaacaacta aagactacaa gtgcgcaacc     600

tagtttcttg cctcctgctg taccttctgc atttgctgct catggtcaat ttccaggaag     660

caagctggtg ccaatcatga gttaccctgg tgtcgcgatg tggcaattca tgcctcctgc     720

tgctgttgat acttcacagg accatgtcct ccgtcctcca gttgcttaac ttgttgcagc     780

ttaatgccta caactgtccc attaaattaa tcgtctagtc aatgttcttc ggttgtatta     840

gttttggctc aactcccctt actgtatttt ggtggatgat agataacttg tgactttgaa     900

acttataacg gtttaatgct tgctttatgt gtaaaattaa ataaatttaa actataaaa      959


<210> SEQ ID NO 136
<211> LENGTH: 943
<212> TYPE: DNA
<213> ORGANISM: Solanum tuberosum

<400> SEQUENCE: 136

gtaattggaa accctcatcg gagaattttc cgggagaatt atttttttca tcttctggcc      60

ggcgattgat ccggagatggt ttcaccggag aacaccaact ggctttatga ttatggattc    120

gaagatagtt ccgtccctga ttcgaatttc tcagcttctg catctgggtt taactggcct     180

gtgcagaatt tgaatggttc aaggaatgtt agttctgaaa ttgatgggtc gattggtgaa     240

tcagattacc caaaggaaag tggttctaag aaacgggcaa gggttgaatc atgtgctcca     300

acaagttcca aagcttgcag agagaaattg cgaagagata agctgaatga caagttcatg     360

gaattgggtg cactccttga gcctggcagg ccccccaaaa cagacaaatc tgctattctt     420

gttgatgctg ttcgcatggt gacccagtta cgtgatgaag ctcaaaagtt gaaagactca     480

aacttgaatc tgcaagaaaa gatcaaggag ttaaaggttg agaaaaccga gcttcgagat     540

gaaaaacaga ggctgaaagc tgaaaaggag aagctagagc aacaactaaa gactacaagt     600

gcgcaaccta gtttcttgcc tcctgctata ccttctgcat ttgctgctca tggtcaattt     660

ccaggaagca agctggtgcc aatcatgagt taccctggtg tcgcgatgtg gcaattcatg     720

cctcctgctg ctgttgatac ttcacaggac catgtcctcc gtcctccagt tgcttaactt     780

gttgcagctt aaagcctaca aaggttgcct tcactgtccc gttaaattaa tcgtctagtc     840

aatgtccttc ggttgtatta gttttggctc aactcccctt actgtatttg gtggatgata     900

gataacttgt gactttgaaa cttataacgg tttaatgctt gct                       943


<210> SEQ ID NO 137
```

<211> LENGTH: 917
<212> TYPE: DNA
<213> ORGANISM: Vitis vinifera

<400> SEQUENCE: 137

```
tttttttttt tttttttttt tttttttttt ccagattaaa cttattgaga tttacatgca    60
aataccatca ctaattcagg taagttctta aattgcaaac atcttccatc acccacgaaa   120
tccagttaga accaggaaca ctaatagtct aatacagtcc agaaacgaca aaatgaaagt   180
aaacttcttt ggggcaaaat gcaaacccaa atcattagag gttgagttgc tgatttaagc   240
aactggggga cggagcacat gatcttgtga ggtatcaact gcagcagggg gcatgaattg   300
ccacatagca actcctgggt agccgatgaa tggaaccaac ttgttgccgc cagcttggcc   360
ttgagctgca aatgcagcag ggattgaagg aacgggaggc aggaaactag gttgagcatt   420
cattgctttc agttgctgct ccagtttctc tttctcggcc tttagccttt gcttctcatc   480
acgaagctca ttcttctcag ccttcaattc tttaatcttc tcctggagac tagaatttga   540
gtccttcaac ttctgcgact cacctcgtaa ctgagttacc attcgaactg catcaatcaa   600
aatagaagac ttgtctgttt ttggaggcct tccaggctcc aggatagaac ccaattccat   660
aaacttgtca tttagcctgt ccctccgcaa cttctcccta catgccttcg agctagatgc   720
accacatgat tcagatctca ccctcttctt tgatccagtt tccttaatgc cgtcagagtc   780
cccaaatgaa ccatcaattt ccccactgac attagcagaa gtgttcaagg cctgcacagg   840
agtccaggcg aaccctgaat tcgtattagc gaagtttgaa tcagggacag ggatgtcctc   900
gatgagcccg tactcgt                                                   917
```

<210> SEQ ID NO 138
<211> LENGTH: 652
<212> TYPE: DNA
<213> ORGANISM: Glycine max

<400> SEQUENCE: 138

```
tccaaagcgg aaaacagcaa ttggctgttt gattacccgt tgatcgacga cgacgttatt    60
cccgtcggcg actcctcctt cgccgtctcc gcttccacct tctcctggcc cccacctccc   120
gccaatgtca gtgtcgaaat tgatgcttcg cttggggatt ctgatggcct aaaaaatcct   180
gctttgaaga aaaggactaa atctgattca agtactgctt ctagctccaa agcgtgtcgg   240
gagaagttga ggagggatag gcttaatgac aagtttgttg aattgggctc catcttggag   300
cccggaaggc ctcccaaaac agacaaggct tccattctga ttgatgctgc ccgaatggtg   360
acacagctgc gggatgaagc cctgaagttg aaagactcaa atacgagtct tcaagagaag   420
attaaagagt taaaggctga gaagaatgaa cttcgtgatg agaaacagag gcttaaggca   480
gagaaagaga agttggaggt gcaggtaaaa tcaatgaatg ctcaacctgc tttcttgcca   540
cccccctcctg caatccctgc tgcatttgct ccacaaggcc aagcccctgg caacaagttg   600
gtgcctttca tcagctatcc gggagttgcc atgtggcaat ttatgcctcc gg           652
```

<210> SEQ ID NO 139
<211> LENGTH: 955
<212> TYPE: DNA
<213> ORGANISM: Solanum tuberosum

<400> SEQUENCE: 139

```
gatcaattgg aaaccctcat cggagaattt tccgggagaa ttatttttt catattctgg     60
ccggcgattg atcggagatg gtttcaccgg agaacaccaa ctggctttat gattatggat   120
```

-continued

```
ttgaagatag ttccgtccct gattcgaatt tctcagcttc tgcatctggg tttaactggc    180

ctgtgcagaa tttgaatggt tcaaggaatg ttagttctga aattgatggg tcgattggtg    240

aatcagattg cccaaaggaa agtggttcta agaaacgggc aagggttgaa tcatgtgctc    300

caacaagttc caaagcttgc agagagaaac tgcgaagaga taagctgaat gacaagttca    360

tggaattggg tgcactcctt gagcctggca ggccccccaa aacagacaaa tccgctattc    420

ttgttgatgc tgttcgcatg gtgacccagt tacgtgatga agctcaaaag ttgaaagact    480

caaatttgaa tctgcaagaa aagatcaagg agttaaaggt tgagaaaacc gagcttcgag    540

atgaaaaaca gaggctgaaa gctgaaaagg agaagctaga gcaacaacta aagactacaa    600

gtgcgcaacc tagtttcttg cctcctgcta taccttctgc atttgctgct catggtcaat    660

ttccaggaag caagctggtg ccaatcatga gttaccctgg tgtcgcgatg tggcaattca    720

tgcctcctgc tgctgttgat acttcacagg accatgtcct ccgtcctcca gttgcttaac    780

ttgttgcagc ttaaagccta caaaggttgc cttcactgtc ccgttaaatt aatcgtctag    840

tcaatgtcct tcggttgtat tagatttggc tcaactcccc ttactgtatt tggtggatga    900

tagataactt gtgactttga aacttataac ggttttatgc ttgctttatg tgtaa         955
```

<210> SEQ ID NO 140
<211> LENGTH: 792
<212> TYPE: DNA
<213> ORGANISM: Citrus reticulata

<400> SEQUENCE: 140

```
cctttttgc cgacgaactt attgaaattt acatgcaaaa gccagcaaca atccactatt     60

gacagagaga ttcaaataca gtcacccacc aatcattaaa gacttcggaa aaactaatac    120

agtcagagaa caatgataaa acgaatacac ttgttgggtg caaattgcaa acccaaatca    180

ttgtaggttg catacttaag caaccggagg acggagtaca tgatcctgtg aggtatccac    240

tgcagcagga ggcatgaatt gccacattgc gactccaggg tagctgatga aaggcatcag    300

cttgtttcca ggtgcttggc cttgggcagc aaatgcagca gggattgcag gaggagttaa    360

gaaactgggt tgtgtgctca tagctttgag ttgctgctct atcttctctt tctctgcctt    420

tagcctctgc ttctcatcac gaagctcatt cttctcagcc ttcaactctt tgatcttctc    480

ctggagactt gaatttgagt ccttcaactt ctgggcttca ctgcgtaatt gagtcaccat    540

ccggacggca tcaatcagaa tagctgcctt atctgttttg gggggccttc caggctctaa    600

gatagaggct aactccacaa acttgtcatt aagacgatcc ctacgcaact tttccctgca    660

cgccttggag ctagaagacc cacatgattc tgatctaacc ctcttttttg agctttcctt    720

gagaccattt gaatccccaa atgcagaatc aatttccaca cagccatttg acggcccgtt    780

aattggcggc tg                                                        792
```

<210> SEQ ID NO 141
<211> LENGTH: 840
<212> TYPE: DNA
<213> ORGANISM: Thellungiella halophila

<400> SEQUENCE: 141

```
ggcacgaggc ctcgtgccga attcggcacg aggccgaaaa cgctaattgg atttgcgacc     60

tgattgatgc cgactatgga agtttcacaa tccaaggtcc aggtttctct tggcccgtgc    120

agcaacctat tggcgtttct tcaaactcca gcgcgggagt tgatgtctca gctggaaatt    180
```

-continued

```
cagaagccag caaggaacct ggctccaaaa agaggggtag atgtgaatca tcctctgcca    240

ctggctcaaa agcatgtaga gagaagctgc gacgtgacag attgaatgac aagtttacgg    300

aattgggtgc aattttggag cctgggaatc ctcccaaaac agacaaggct gcaatcttgg    360

ttgatgctgt ccgcatggtg gcacagctac ggggcgaagc ccagaagttg aaggactcca    420

attcaagtct ccaggacaaa atcaaagagt taaagactga gaaaaacgag ttgcgagatg    480

agaaacagag gctgaagaca gagaaagaga agctggagca acagctgaaa accatgaatg    540

ctcctcaacc aagctttttc ccagctccac ctatgatgcc aactgctttt gcttctgcac    600

aaggccaagc tcccggaaac aagatggtgc caatcatcag ttacccagga gttgccatgt    660

ggcagttcat gcctcctgct tcagtcgata cttctcagga tcatgtcctt cgtccaccag    720

ttgcttaact gggagacaaa gacctcagga aaaaaaatca tcaattggtt tggcttctcg    780

cttacgctga aaggaaaggc tccatttgtt ttgcctctct ctttttcggc tctcttagcc    840
```

<210> SEQ ID NO 142
<211> LENGTH: 822
<212> TYPE: DNA
<213> ORGANISM: Populus tremuloides
<220> FEATURE:
<221> NAME/KEY: misc_feature
<222> LOCATION: (788)..(788)
<223> OTHER INFORMATION: n is a, c, g, or t

<400> SEQUENCE: 142

```
cggcggctca ccggaacaca cgccgggaac cttgaattcc ggcggagatg gtgttaccta     60

atgaaaatga taactgggtt tttgattgtg ggttgattga ggacatttcg gtccctggtg    120

gtgaccttct tggtcttgaa tctcttgatg aaaccccgaa tgggtctctg tggtcttctc    180

ataatttcac tgattctgcc ttcttaagtg tggaattcaa taattcatat gagaattcgg    240

atggccataa ggaaagtggg tgtcggaaac gagtgaggcc tggatcaagt aatgcaactg    300

gctccaaagc atgtagagag aaactgcggc gggataggct gaacgacagg ttcatggaat    360

tgggtgctct tctagatcct ggaaggcctc ctaaagtgga caaatctgct atactggttg    420

atgctgctcg aatggtgact cagttacgag atgaatctca gaagctgaaa gagtctaatg    480

tgagtctaca ggagaagatc gatgaattga aggcggagaa gaatgagctt cgtgatgaga    540

aacagaggct aaagacagaa aaggagaacc tagagcggca agtgaaagcc ttgagtgctc    600

caccaaactt cctgcctcat ccctctgcca ttccagctcc attttctgcc ccaggccaag    660

ttgttggcag caagatgatg ccctttgttg gttatcctgg aatttctatg tggcagttca    720

tgccccctgc tgttgttgat acctctcagg atcatgttct acgccctcca gttgcttaag    780

ttattcangc agaaatttta tgtctacgtc ctcgcagagc at                       822
```

<210> SEQ ID NO 143
<211> LENGTH: 911
<212> TYPE: DNA
<213> ORGANISM: Vitis vinifera

<400> SEQUENCE: 143

```
atgtgaacgg tggtgtgtga tggtgaatgg tgccaccgat ccctaaaacc agaaaaaaaa     60

agaagaaaaa aacccaaatt catttctctt ctcaccaccg actttaattt cgccggagaa    120

aactccggta tggtatctcc agaagaagat ccaaattgga tcttcgacta cggcttgatc    180

gacgacgttc ctgtcccctc cctccaagca acctttaatt ggccttctca tgatttcact    240

gcttccgtcg ccctcggtgt ggaatttgat gactcacctg tgaatttgga tgatgtgaag    300
```

-continued

```
gaaaatcact cccggaaaag gatgaggtct ggactgtgca gcgcgtctgg ctccaaagca    360

tgtcgggaga aagtacggag ggataggctg aatgacaggt tcctagaatt gggttctatc    420

ctggagcctg gaagaccccc taaaatggac aaggctgtta tattaagtga tgctcttaga    480

atgatgactc agctgcgtag tgaaggacag aagctgaaga aatcatgtga ggatctgcaa    540

gagaagatca atgaattgaa ggctgagaag aatgagcttc gtgatgagaa gcagaggctg    600

aagacagaga aagagaacat tgtgcagcaa ataaaagctc tgagtaccca agcaggcttc    660

ctgccacacc cttctgcaat cccagctcca tttgccgctc caggccaagt tgttggcagc    720

aagctgatgc ctttcattgg ctaccctgga gtttccatgt ggcagttcat gccacctgct    780

gccgttgata cttcacagga tcatgttctc cggcccccag ttgcttaaat ttgaaggcgt    840

taactgtgga tcttccttcc ctgtggatcg agcatgattc tatgatctgg gttttcttct    900

ggctcttgaa g                                                         911
```

<210> SEQ ID NO 144
<211> LENGTH: 849
<212> TYPE: DNA
<213> ORGANISM: Brassica napus

<400> SEQUENCE: 144

```
tgttataaga agataacacc ggagaagacc aaagcaacca taagactaag aaagccgaga     60

aagaggagag caaaacaaat ggacttttct tgcttttttt cttttttttcc ggrgragcaa   120

gaagcaaacc agttgatgat tttcttgagg gtcgtcccag ttaagcaact ggtggacgaa    180

ggacgtgatc ctgagaagta tcgactgaag caggaggcat gaactgccac atggcaactc    240

ctgggtaact gatgactggc accatcttgt ttccgggagc ttggccttgc gcagaagcaa    300

aagcagttgg catcataggt ggggctggga agaagcttgg ttgaggagga gcattcatgg    360

ctttcagctg ttgctccagc ttctctttct ctgtcttcag cctctgcttc tcatctcgca    420

gctcgttctt ctcggtcttt aactctttga ttttgtcttg aagactcgaa ttggagtcct    480

tcaacttctg cgcctcgcca cgtagttgtg taaccatgcg gacagcatcg accaagattg    540

cagccttgtc tgtsttggga ggattccccg gctccaaaat tgcacccaat tccataaact    600

tgtcattcag cctgtcacgt cgctgcttct ctctacaggc tttagagcta gtggcagagg    660

acgattcaca tctcgccctc tttttggagc aggttccttg gtggcttctg aatttccagc    720

tgagcatcac tchagactgg aacgccatag gtgctggtga gaggcaggag agcaggcttg    780

aatgtgaact tcatagtctg cgtygatcaw tcggtatcaa tagcgtttcg gggcacatct    840

ctcaactca                                                            849
```

<210> SEQ ID NO 145
<211> LENGTH: 852
<212> TYPE: DNA
<213> ORGANISM: Vitis vinifera

<400> SEQUENCE: 145

```
ttttttttt ttttttttt ttttttttc gtaatgtaag ttgccagatt aaacttattg        60

agatttacat gcaaatacca tcactaattc aggtaagttc ttaaattgca aacatcttcc    120

atcacccacg aaatccagtt agaaccagga acactaatag tctaatacag tccagaaacg    180

acaaaatgaa agtaaacttc tttggggcaa aatgcaaacc caaatcatta gaggttgagt    240

tgctgattta agcaactggg ggacggagca catgatcttg tgaggtatca actgcagcag    300
```

-continued

```
ggggcatgaa ttgccacata gcaactcctg ggtagccgat gaatggaacc aacttgttgc    360

cgccagcttg gccttgagct gcaaatgcag cagggattga aggaacggga ggcaggaaac    420

taggttgagc attcattgct ttcagttgct gctccagttt ctctttctcg gcctttagcc    480

tttgcttctc atcacgaagc tcattcttct cagccttcaa ttctttaatc ttctcctgga    540

gactagaatt tgagtccttc aacttctgcg actcacctcg taactgagtt accattcgaa    600

ctgcatcaat caaaatagaa gacttgtctg tttttggagg ccttccaggc tccaggatag    660

aacccaattc catagacttg tcatttagcc tgtccctccg caacttctcc ctacatgcct    720

tcgagctaga tgcaccacat gattcagatc tcaccctctt ctttgatcca gtttccttaa    780

tgccgtcaga gtccccaaat gaaccatcaa tttccccact gacattagca gaagtgttca    840

aggcctgcac ag                                                        852
```

<210> SEQ ID NO 146
<211> LENGTH: 837
<212> TYPE: DNA
<213> ORGANISM: Gossypium raimondii
<220> FEATURE:
<221> NAME/KEY: misc_feature
<222> LOCATION: (831)..(831)
<223> OTHER INFORMATION: n is a, c, g, or t

<400> SEQUENCE: 146

```
caccaatcct ctgtgtcccg ccctttgttc ttatttttct ctcttgccaa acagaaactc     60

cattttcttt gccaaaagcc ggaaatcaaa ccaaaccctt ccggctaaaa gcaaattcag    120

tggagaatgg tatcacctga aaacaccaat tattggtcta gcttcgatta tgcaaccttg    180

atcaacgata tccctgcccc tgacggacct tattccggat tttcttggcc cactcggcca    240

atcaatgcat cttctaatgt tttcagtgtg gaaactgacg gctcgtttga ggattcagat    300

ggccttaagg aatctggttc aaagaagaga gttagatctg agtcttgcaa tgtttcaagc    360

tccaaagcat gcagggagaa gttgcgtagg gataagctaa atgagaagtt tatggagctg    420

agttctattt tggaacctga aaagcctccc aagacagaca aggctgctat tttggttgat    480

gctgtccgaa tggtaaccca gttacgaggt gaagcccaga aattgaagga ttcaatttca    540

agtctccatg acaggattaa agaattgaag gctgaaaaga atgaacttcg tgatgaaaag    600

caaaggctga aggccgagaa ggaaaagctg gagcaacagc tgaaggccat gaattcacaa    660

cccagcttca tgcctcctgc acctgcattc cctgctgcat ttgctactgc ccaaggtcaa    720

gttccaggaa acaagttggt tcctttcttt ggttatcctg gagttgccat gtggcagttt    780

atgctgcctg cgtcgttaga cacctcagag gatcatgtac tccgccctcc ngttgcc       837
```

<210> SEQ ID NO 147
<211> LENGTH: 806
<212> TYPE: DNA
<213> ORGANISM: Populus tremuloides

<400> SEQUENCE: 147

```
cggcggctca ccggaacaca cgccgggaac cttgaattcc ggcggagatg gtgttaccta     60

atgaaaatga taactgggtt tttgattgtg ggttgattga ggacatttcg gtccctggtg    120

gtgaccttct tggtcttgaa tctcttgatg aaaccccgaa tgggtctctg tggtcttctc    180

ataatttcac tgattctgcc ttcttaagtg tggaattcaa taattcatat gagaattcgg    240

atggccataa ggaaagtggg tgtcggaaac gagtgaggcc tggatcaagt aatgcaactg    300

gctccaaagc atgtagagag aaactgcggc gggataggct gaacgacagg ttcatggaat    360
```

-continued

```
tgggtgctct tctagatcct ggaaggcctc ctaaagtgga caaatctgct atactggttg    420

atgctgctcg aatggtgact cagttacgag atgaatctca gaagctgaaa gagtctaatg    480

tgagtctaca ggagaagatc gatgaattga aggcggagaa gaatgagctt cgtgatgaga    540

aacagaggct aaagacagaa aaggagaacc tagagcggca agtgaaagcc ttgagtgctc    600

caccaaactt cctgcctcat ccctctgcca ttccagctcc attttctgcc ccaggccaag    660

ttgttggcag caagatgatg ccctttgttg gttatcctgg aatttctatg tggcagttca    720

tgccccctgc tgttgttgat acctctcagg atcatgttct acgcccctca gttgcttaag    780

ttattcaggc agggatttta tgtcta                                         806
```

<210> SEQ ID NO 148
<211> LENGTH: 598
<212> TYPE: DNA
<213> ORGANISM: Prunus dulcis

<400> SEQUENCE: 148

```
caaaaaagag ggtcagaact gaatcatgca gtggatctag ttccaaggca tgcagggaga     60

agttgcgaag ggataggcta aacgacaagt ttctcgaatt gggctctata ttggagcctg    120

gaaggccccc caagactgac aaggctgcta tattggtgga tgctgtccga atggtgaatc    180

agttacgcgg tgaagcccaa aagttgaagg actcaaattc aagcctccag gagaagatca    240

aggaattgaa ggcagagaag aatgaacttc gtgatgagaa gcagaggttg aagttagaga    300

aagagaagtt ggagcagcaa ctgaaggcca tgaatgcaca gccaggcttc ttgcctcccc    360

ctcctgcaat tcctgctgca tttgctgccc aaggccaagc tcacggcaac aagctggtgc    420

ctttcattgg ataccctggg gttgccatgt ggcagttcat gccacctgcc tcagtggata    480

cttcgcagga tcatgtactc cgcccaccag ttgcttaagt tggcaagatc taagatgatt    540

cggctgattt gggataacat tttgtcccca acatgtttat tgtcctgtca ttgctctt      598
```

<210> SEQ ID NO 149
<211> LENGTH: 568
<212> TYPE: DNA
<213> ORGANISM: Glycine max

<400> SEQUENCE: 149

```
cctgctttga agaaaaggac taaatctgat tcaagtactg cttctagctc caaagcgtgt     60

cgggagaagt tgaggaggga taggcttaat gacaagtttg ttgaattggg ctccatcttg    120

gagcccggaa ggcctcccaa aacagacaag gcttccattc tgattgatgc tgcccgaatg    180

gtgacacagc tgcgggatga agccctgaag ttgaaagact caaatacgag tcttcaagag    240

aagattaaag agttaaaggc tgagaagaat gaacttcgtg atgagaaaca gaggcttaag    300

gcagagaaag agaagttgga ggtgcaggta aaatcaatga atgctcaacc tgctttcttg    360

ccaccccctc ctgcaatccc tgctgcattt gctccacaag gccaagcccc tggcaacaag    420

ttggtgcctt tcatcagcta tccgggagtt gccatgtggc aatttatgcc tccggccgcc    480

gtggatacct cacaggatca tgtactccgt ccaccggttg cctaagttgg cattgtacaa    540

ttatttgggc ttccattttg gctcaaaa                                       568
```

<210> SEQ ID NO 150
<211> LENGTH: 708
<212> TYPE: DNA
<213> ORGANISM: Medicago truncatula -continued

<400> SEQUENCE: 150
atagaaaact aacaaagcaa gaaggtattg gtgataggat acaatcttga gctaaaatgg 60
aagcccggag aattgcacag agccagctta ggcaactgga ggacgaagta catgatcctg 120
tgaggtatcc actgcagcag gtggcataaa ttgccacatt gcaactccag gataactaat 180
aaagggtacc aatttgttgc catgggcttg gccttgtgca gcaaatgccg cagggagtgc 240
agtgggggta ggcaagaaac taggaggtgc attcatagat ttcagctgct gctccaactt 300
ctctttctct gccttgagcc tctgtttctc gtcacggagt tcgttcttct caacctttaa 360
ctctttaatc ttttcttgaa gacccgagtt ggcatctttc aacttttggg cttcacccct 420
taactgtgtc accattcgga cagcatcaat caggatggca gccttgtctg ttttggcagg 480
ccttccaggc tccaaaatgg agcccaattc aataaacttg tcgttaagcc tatctctacg 540
caacttctcc cgacatgctt tggagctagt agcagcacat gactcagatc taaccctctt 600
ctttgaacca gactctttga gaccgtcaga atcccctatg agcccatcac ttcagcactg 660
acattggaaa aaaggttgaa ggggggctga attggccagg tgaaagcg 708

<210> SEQ ID NO 151
<211> LENGTH: 797
<212> TYPE: DNA
<213> ORGANISM: Medicago truncatula

<400> SEQUENCE: 151
ttaattcata agtattcata agccaaatac aaacggaagc cactgggtcc agttagaata 60
gatagaaaac taacaaagca agaaggtatt ggtgatagga tacaatcttg agctaaaatg 120
gaagcccgga gaattgcaca gagccagctt aggcaactgg aggacgaagt acatgatcct 180
gtgaggtatc cactgcagca ggtggcataa attgccacat tgcaactcca ggataactaa 240
taaagggtac caatttgttg ccatgggctt ggccttgtgc agcaaatgcc gcagggagtg 300
cagtgggggt aggcaagaaa ctaggaggtg cattcataga tttcagctgc tgctccaact 360
tctctttctc tgccttgagc ctctgtttct cgtcacggag ttcgttcttc tcaaccttta 420
actctttaat cttttcttga agacccgagt tggcatcttt caacttttgg gcttcacccc 480
ttaactgtgt caccattcgg acagcatcaa tcaggatggc agccttgtct gttttggcag 540
gccctccagg ctccaaaatg gagcccaatt caataaactt gtcgttaagc ctatctctac 600
gcaacttctc ccgacatgct ttggagctag tagcagcaca tgactcagat ctaaccctct 660
tctttgaacc agactctttg agaccgtcag aatcccctaa tgagccatca acttcagcac 720
ccattctcat gtcaacagca tcagtccatg gaaagttgca ctgtttgaag ttagacagcg 780 taccccctatc tcactaa 797

<210> SEQ ID NO 152
<211> LENGTH: 524
<212> TYPE: DNA
<213> ORGANISM: Glycine max

<400> SEQUENCE: 152
agggctagat gtgattcaag tactgcttct agctctaaag cgtgtcggga gaagttgcgg 60
agggataggc ttaatgacaa atttgttgaa ttgggctcca tcttggagcc tggaaggcct 120
cccaaaacag acaaggctgc cattctgatt gatgctgccc gaatggtaac acagctgcgg 180
gatgaagccc tgaagttgaa agactcaaat acgagtcttc aagagaagat taaagagtta 240
aaggctgaga agaatgaact tcgtgacgag aaacagaggc ttaaggcaga gaaagagaag 300

-continued

```
ttggagatgc aggtaaaatc aatgaatgct caacctgctt tcttgccacc ccctcctgca    360

atccctgctg catttgctcc acaaggccaa gcccccggca acaagttgat gcctttcatc    420

aggtacccgg gagttgccat gtggcaattt atgcctccgg ccaccatgga tacctcccag    480

gatcatgttc tccgtccacc agttgcctaa gttggcattg taca                     524
```

<210> SEQ ID NO 153
<211> LENGTH: 738
<212> TYPE: DNA
<213> ORGANISM: Vitis vinifera

<400> SEQUENCE: 153

```
cgcaagtgtt tgttccaaag atgtacttgg cttacttcaa cagttgattt aaaaacatac     60

aacaatcata tttgcttatt gtattttaca tgcaatcagc agaaatccaa gggagtcatt    120

ggtttctgat aacaatgaca aagtaaaata gacgaggaac tctttgggca ctgagaatgt    180

agaccaacca ttgatgtcct ccaacttaag ccactggggg acggagaaca tgatcctgtg    240

atgtgtcaac tgcagcaggt ggcatgaatt gccacatggc aacactaggg taaccaatga    300

aaggcatcag cttgttgcca ggagctcggc cttgggcagc aaatgcagct ggcattgcag    360

aaggatgagg cagaaagcct ggctgtgcac taatggcttt gacttgctgc tccagcttct    420

ccttttcggc ttttaacctt tgcttctcat cccgaagctc atttttctca gccttcaact    480

ccttaatctt ctcttgcaaa tccccatttg actccttcag cttctgtgct tcacttcgta    540

attgagtcac cattcgaaca gcatcactca gaatagcagc cttgtccgtt ttgggtggcc    600

ttccaggctc caagatagaa cccaattcca agaacctctc attcagccta tccctccgca    660

atttttcccg gcaagctttg gtgccagttg caccacatga gattcatgct tcaaccgttt    720

tcggggtcca agttcttt                                                   738
```

<210> SEQ ID NO 154
<211> LENGTH: 559
<212> TYPE: DNA
<213> ORGANISM: Glycine soja

<400> SEQUENCE: 154

```
tgatggctcg ttgggggatt ctgacagtct caaagagtct ggctcaaaga aaagggttag     60

gtctgagtca tgtgctgctt ctggctccaa ggcatgtcgg gagaagttga gaagggatag    120

gcttaatgac aagtttgttg aattgggcgc catttttggag cctggaaggc ctgccaaaac    180

agacaaggct gctatcctga ttgatgctgt ccgaatggtg acccagttac ggggtgaagc    240

ccagaagttg aaagacacta atcagggtct tcaagaaaag attaaagagt taaaggctga    300

gaagaacgaa cttcgcgatg agaaacagag gctcaaggca gagaaggaga aactggagca    360

gcagctgaaa tctttgaatg cacagcctag tttcatgcct ccccctgctg caatgcctgc    420

tgcatttgcg gcacaaggcc aagcccatgg caacaagttg gtacctttta ttagttattc    480

cggaagttgc atgtggcaat tcatgccacc tgctgcagtg gatacctcac aggatcatgt    540

tctccgtcca ccagtttcc                                                  559
```

<210> SEQ ID NO 155
<211> LENGTH: 943
<212> TYPE: DNA
<213> ORGANISM: Solanum tuberosum

<400> SEQUENCE: 155

-continued

```
gtgggaatcc taattggtta tttgattatg agttgataac ggatattact tctgctgctt     60

ctgttaccgt cactgatttt cagtctccgg ctactattga tttcagctgg cctgctcaaa    120

caatctatgc ttcctctaat ctcattgctg aaacagatta cacatttgcg gattcagaag    180

tcagtaagga ggcaagctca cgaaagaggt taaaaagtga atggtgcagc tctccgagat    240

ctaaggcatg ccgagagaaa ttgcggaggg acagactgaa tgagaggttc ctcgaattga    300

gctctgtcct tgatcctgga aggccaccaa aaactgagaa agttgcaatt ctgagtgatg    360

ctcaaaggat gctgattgag ctgcgaactg aaacccagaa gctgaaggag tcaaatgagg    420

agctgcaaga gaagataaaa gaacttaagg cagagaagaa tgagctccgt gatgaaaagc    480

gaaggctaaa ggaagaaaag gagaatttgg agcagcaggt taaaagctta gcttctaaac    540

caggatttct ctcccatcct tctgccgtgg gagctgcatt tactgcacaa ggacaagtcg    600

ctgcaggcaa caaattgatg cctttcattg gttatcccag tgttgcaatg tggcaattca    660

tgcaacctgc tgttgttgac acatctcaag atcatgtgct ccgtcctcca gttgcttaaa    720

ctgaatttgc caggtgactt gctactggaa ctttgttctt tttgttgctc ctgtgagtgc    780

taaaggtgac aaacaactga gacaatttgc tggttgtatt tatatgtcta gcttttatgt    840

atgagtcagt cttgatgatt tgctaaatca tgtatatgac gggtatatac tcacccgaaa    900

aacagttacg tattatgatt ccctagatgg gactccttct gaa                      943
```

<210> SEQ ID NO 156
<211> LENGTH: 831
<212> TYPE: DNA
<213> ORGANISM: Gossypium raimondii

<400> SEQUENCE: 156

```
ctcccaccaa tcctctgtgt cccgccctct ttttttagtt ttctctcttg ccaaacagaa     60

actccattct tttttgccaa aagccggaaa tcaaaccaaa cccttccggc taaaagcaaa    120

ttcagtggag aatggtatca cctgaaaaca ccaattattg gtctagcttc gattatgcaa    180

ccttgatcaa cgatatccct gcccctgacg gaccttattc cggattttct tggcccactc    240

ggccaatcaa tgcatcttct aatgttttca gtgtggaaat tgacggctcg tttgaggatt    300

cagatggcct taaggaatct ggttcaaaga agagagttag atctgagtct tgcaatgttt    360

caagctccaa agcatgcagg gagaagttgc gtagggataa gctaaatgag aagtttatgg    420

agctgagttc tattttggaa cctgaaaagc ctcccaagac agacaaggct gctattttgg    480

ttgatgctgt ccgaatggta acccagttac gaggtgaagc ccagaaattg aaggattcaa    540

tttcaagtct ccatgacagg attaaagaat tgaaggctga aaagaatgaa cttcgtgatg    600

aaaagcaaag gctgaaggcc gagaaggaaa agctggagca acagctgaag gccatgaatt    660

cacaacccag cttcatgcct cctgcacctg cattccctgc tgcatttgct actgcccaag    720

gtcaagttcc aggaaacaag ttggttcctt tctttggtta tcctggagtt gccatgtggc    780

agtttatgct gcctgcgtcg ttagacacct cagaggatca tgtactccgc c             831
```

<210> SEQ ID NO 157
<211> LENGTH: 791
<212> TYPE: DNA
<213> ORGANISM: Vitis vinifera
<220> FEATURE:
<221> NAME/KEY: misc_feature
<222> LOCATION: (725)..(725)
<223> OTHER INFORMATION: n is a, c, g, or t

<400> SEQUENCE: 157

-continued

```
catttttccc actcggattc ccttttctcc ctcgagaaaa ccccccttt ctctctcccc     60

aaacacccta acgcgctcct ccctctcccg ggaaattgca ccgggcctcc tcgatttttc    120

ggaggttcct tcgagatggt ttctccagaa gccaccaatt ggctgtacga gtacgggctc    180

atcgaggaca tccctgtccc tgattcaaac ttcgctaata cgaattcagg gttcgcctgg    240

actcctgtgc aggccttgaa cacttctgct aatgtcagtg ggaaattga tggttcattt    300

ggggactctg acggcattaa ggaaactgga tcaaagaaga gggtgagatc tgaatcatgt    360

ggtgcatcta gctcgaaggc atgtagggag aagttgcgga gggacaggct aaatgacaag    420

tctatggaat tgggttctat cctggagcct ggaaggcctc caaaaacaga caagtcttct    480

attttgattg atgcagttcg aatggtaact cagttacgag gtgagtcgca gaagttgaag    540

gactcaaatt ctagtctcca ggagaagatt aaagaattga aggctgagaa gaatgagctt    600

cgtgatgaga agcaaaggct aaaggccgag aaagagaaac tggagcagca actgaaagca    660

atgaatgctc aacctagttt cctgcctccc gttccttcaa tccctgctgc atttgcagct    720

caagnccaag ctggcggcaa caagttggtt ccattcatcg gctacccagg agttgctatg    780

tggcaattca t                                                         791
```

<210> SEQ ID NO 158
<211> LENGTH: 693
<212> TYPE: DNA
<213> ORGANISM: Lycopersicon esculentum

<400> SEQUENCE: 158

```
catcttctgg ccggcgactg atcggagatg gtttcaccgg agagtaccaa ttggctttat     60

gattacggat tcgaagatag ttgcgtccct gattcgaatt tctcagcttc tgcatctggg    120

tttaactggt ctgtgcagaa tttgaatggt tcaaggaatg ttagttctga aatcgatggg    180

tcaattggtg aatcagatta ccccaaggaa agtggttcta agaaacgggc aagggttgaa    240

tcatgtgctc caacaagttc caaagcttgc agagagaaac tgcgaagaga taggctgaat    300

gacaagttca tggaattggg tgcactcctt gagcctggaa gaccccctaa aacagacaaa    360

tccgctattc ttgttgatgc tgttcgcttg gtgacccagt tacgtgatga agctcaaaag    420

ttgaaagact caaacttgaa tctgcaagaa aagatcaagg agttaaaggt tgagaaaacc    480

gagcttcgag atgaaaaaca caggctgaaa gctgaaaagg agaagctaga gcaacaacta    540

aagactacaa gtgcacggcc tagttacttg cctcctgcta taccttctgc atttgctgct    600

catggtcaat ttccaggaag caagctggtg ccaatcatga gttacccctg tgtcccgatg    660

tggcaattca tgcctcctgc tgctgttgat act                                693
```

<210> SEQ ID NO 159
<211> LENGTH: 877
<212> TYPE: DNA
<213> ORGANISM: Pinus taeda

<400> SEQUENCE: 159

```
ctggacacct cgaatctcct ccggtcattt tttgttttga cagggccggt ttggtgatta     60

gggtttcaga taacaggagg acaagtgttc gaattcgaga gaagccagaa tgagctctcc    120

gcagagcaat aagtggctgt catatttcga cgagccattg ttggatgatg taggcgtggg    180

gcagccggcc aatccattct tctggtgcgg tcagggcata aatgatcagc ccgacgtaag    240

tggtagtgta gaaattgatg gccccaataa ggacatggac gagcaagata aattatgtcc    300
```

-continued

```
tagaaagagg tcacgggaag aatctagtgg gggacctggg tcaaaagctt gccgtgagaa    360

gatgcggagg gacagactta atgataggtt catggagcta agctctgtgt tagaaccggg    420

taggcctccc aagacggcag acaaagccac aattttgtct gatgctgcac gtgttatgac    480

ccagctacga actgaggcgc agaacctgaa agctgagaat gaacgactgc aggaagccat    540

taaagatctg aaggcagaga aaaatgaact tcgtgatgaa aagctgagaa tgaaagcaga    600

aaaggaaaaa ttggagcaac aagtaaaagc aatggctttg cccacaggct ttgtgccgca    660

tcctgcagca tttcatgcgg ctgctgcttt tgcagcccaa agtcaagcag cagcaaacaa    720

aactatgcct gttccaggat atcctggaat ggcaatgtgg caatggatgc ctccagctgt    780

ggttgatact tcgcaggatc atgtgctaag gcctcctgtt gcttgaagca ggctcttatt    840

ttatattcca aactggtgct actatttctt tggccct                             877


<210> SEQ ID NO 160
<211> LENGTH: 25
<212> TYPE: PRT
<213> ORGANISM: Artificial
<220> FEATURE:
<223> OTHER INFORMATION: plant consensus
<220> FEATURE:
<221> NAME/KEY: MISC_FEATURE
<222> LOCATION: (1)..(1)
<223> OTHER INFORMATION: H, F or Y
<220> FEATURE:
<221> NAME/KEY: MISC_FEATURE
<222> LOCATION: (2)..(2)
<223> OTHER INFORMATION: G, A, K, E or R
<220> FEATURE:
<221> NAME/KEY: MISC_FEATURE
<222> LOCATION: (4)..(4)
<223> OTHER INFORMATION: S, T, N or G
<220> FEATURE:
<221> NAME/KEY: MISC_FEATURE
<222> LOCATION: (7)..(7)
<223> OTHER INFORMATION: G, E, D, N or Y
<220> FEATURE:
<221> NAME/KEY: MISC_FEATURE
<222> LOCATION: (8)..(8)
<223> OTHER INFORMATION: K or R
<220> FEATURE:
<221> NAME/KEY: MISC_FEATURE
<222> LOCATION: (9)..(9)
<223> OTHER INFORMATION: A, S, V, G or T
<220> FEATURE:
<221> NAME/KEY: MISC_FEATURE
<222> LOCATION: (10)..(10)
<223> OTHER INFORMATION: F or Y
<220> FEATURE:
<221> NAME/KEY: MISC_FEATURE
<222> LOCATION: (11)..(11)
<223> OTHER INFORMATION: A, P, S or G
<220> FEATURE:
<221> NAME/KEY: MISC_FEATURE
<222> LOCATION: (12)..(12)
<223> OTHER INFORMATION: S or T
<220> FEATURE:
<221> NAME/KEY: MISC_FEATURE
<222> LOCATION: (21)..(21)
<223> OTHER INFORMATION: A or T
<220> FEATURE:
<221> NAME/KEY: MISC_FEATURE
<222> LOCATION: (25)..(25)
<223> OTHER INFORMATION: K, S, I, P, T or V

<400> SEQUENCE: 160

Xaa Xaa Cys Xaa Val Cys Xaa Xaa Xaa Xaa Xaa Xaa Tyr Gln Ala Leu
1               5                   10                  15

Gly Gly His Lys Xaa Ser His Arg Xaa
            20                  25
```

<210> SEQ ID NO 161
<211> LENGTH: 25
<212> TYPE: PRT
<213> ORGANISM: Artificial
<220> FEATURE:
<223> OTHER INFORMATION: dicotyledonous consensus
<220> FEATURE:
<221> NAME/KEY: MISC_FEATURE
<222> LOCATION: (1)..(1)
<223> OTHER INFORMATION: H, F or Y
<220> FEATURE:
<221> NAME/KEY: MISC_FEATURE
<222> LOCATION: (2)..(2)
<223> OTHER INFORMATION: G, A, K, E or R
<220> FEATURE:
<221> NAME/KEY: MISC_FEATURE
<222> LOCATION: (4)..(4)
<223> OTHER INFORMATION: S, T, N or G
<220> FEATURE:
<221> NAME/KEY: MISC_FEATURE
<222> LOCATION: (7)..(7)
<223> OTHER INFORMATION: G, E, D, N or Y
<220> FEATURE:
<221> NAME/KEY: MISC_FEATURE
<222> LOCATION: (9)..(9)
<223> OTHER INFORMATION: A, S, G or T
<220> FEATURE:
<221> NAME/KEY: MISC_FEATURE
<222> LOCATION: (11)..(11)
<223> OTHER INFORMATION: A, P, S or G
<220> FEATURE:
<221> NAME/KEY: MISC_FEATURE
<222> LOCATION: (21)..(21)
<223> OTHER INFORMATION: A or T
<220> FEATURE:
<221> NAME/KEY: MISC_FEATURE
<222> LOCATION: (25)..(25)
<223> OTHER INFORMATION: K, S, I, P, T or V

<400> SEQUENCE: 161

```
Xaa Xaa Cys Xaa Val Cys Xaa Lys Xaa Phe Xaa Ser Tyr Gln Ala Leu
1               5                   10                  15

Gly Gly His Lys Xaa Ser His Arg Xaa
            20                  25
```

<210> SEQ ID NO 162
<211> LENGTH: 25
<212> TYPE: PRT
<213> ORGANISM: Artificial
<220> FEATURE:
<223> OTHER INFORMATION: monocotyledonous consensus
<220> FEATURE:
<221> NAME/KEY: MISC_FEATURE
<222> LOCATION: (1)..(1)
<223> OTHER INFORMATION: H, F or Y
<220> FEATURE:
<221> NAME/KEY: MISC_FEATURE
<222> LOCATION: (2)..(2)
<223> OTHER INFORMATION: G, A, K, E or R
<220> FEATURE:
<221> NAME/KEY: MISC_FEATURE
<222> LOCATION: (8)..(8)
<223> OTHER INFORMATION: K or R
<220> FEATURE:
<221> NAME/KEY: MISC_FEATURE
<222> LOCATION: (9)..(9)
<223> OTHER INFORMATION: A, S, V or G
<220> FEATURE:
<221> NAME/KEY: MISC_FEATURE
<222> LOCATION: (10)..(10)
<223> OTHER INFORMATION: A, S, V or G
<220> FEATURE:
<221> NAME/KEY: MISC_FEATURE
<222> LOCATION: (11)..(11)

<223> OTHER INFORMATION: A, P, S or G
<220> FEATURE:
<221> NAME/KEY: MISC_FEATURE
<222> LOCATION: (21)..(21)
<223> OTHER INFORMATION: A or T
<220> FEATURE:
<221> NAME/KEY: MISC_FEATURE
<222> LOCATION: (25)..(25)
<223> OTHER INFORMATION: K, P, T or V

<400> SEQUENCE: 162

```
Xaa Xaa Cys Ser Val Cys Gly Xaa Xaa Xaa Xaa Ser Tyr Gln Ala Leu
1               5                   10                  15

Gly Gly His Lys Xaa Ser His Arg Xaa
            20                  25
```

<210> SEQ ID NO 163
<211> LENGTH: 228
<212> TYPE: PRT
<213> ORGANISM: Lolium perenne

<400> SEQUENCE: 163

```
Met Ala Val Glu Ala Val Leu Glu Ala Ala Ala Met Ile Gln Ser Pro
1               5                   10                  15

Pro Ser Lys Lys Met Glu Ala Ser Ser Ser Ser Asp Glu Ala Phe Glu
            20                  25                  30

Ala Leu Gln Gln His Thr Glu Gly Trp Ser Lys Lys Lys Arg Ser Arg
        35                  40                  45

Arg Pro Arg Ala Leu Glu Pro Ser Glu Glu Glu Tyr Leu Ala Phe Cys
    50                  55                  60

Leu Val Met Leu Ala Arg Gly His Arg Asp Ala Ala Pro Glu His Gly
65                  70                  75                  80

Cys Ser Val Cys Gly Lys Ala Phe Ala Ser Tyr Gln Ala Leu Gly Gly
                85                  90                  95

His Lys Ala Ser His Arg Lys Pro Pro Thr Ala Pro Ala Ala Val Ala
            100                 105                 110

Ala Ser Ala Val Pro Glu Glu Asp Lys Pro Arg Ala Ala Ala Ser Ser
        115                 120                 125

Ser Ser Gly Ser Gly Asp Ala Ala Gly Gly Gly Lys Val His Glu Cys
    130                 135                 140

Asn Val Cys Gln Lys Thr Phe Pro Thr Gly Gln Ala Leu Gly Gly His
145                 150                 155                 160

Lys Arg Cys His Tyr Asp Gly Thr Ile Gly Ser Ala Ala Ala Pro Thr
                165                 170                 175

Val Lys Ala Ala Lys Ala Ala Ala Ala Ala Ser Ala Pro Thr Ala Thr
            180                 185                 190

Asn Arg Gly Phe Asp Leu Asn Val Pro Ala Leu Pro Gly Leu Ala Glu
        195                 200                 205

Glu Gly Glu Glu Val Leu Ser Pro Val Ser Phe Lys Lys Pro Arg Leu
    210                 215                 220

Met Ile Thr Ala
225
```

<210> SEQ ID NO 164
<211> LENGTH: 250
<212> TYPE: PRT
<213> ORGANISM: Oryza sativa

<400> SEQUENCE: 164

-continued

```
Met Ala Val Glu Ala Val Leu Glu Ala Ser Arg Ser Ser Ser Glu Glu
1               5                   10                  15

Glu Ala Glu Val Ile Val Thr His Gly Gly Gly Gly Gly Gly Gly Gly
            20                  25                  30

Gly Gly Gly Gln Val Glu Gly Trp Gly Lys Arg Lys Arg Ser Arg Arg
        35                  40                  45

Arg Arg Pro Gln Leu Pro Pro Ser Glu Glu Glu Tyr Leu Ala Leu Cys
    50                  55                  60

Leu Leu Met Leu Ala Arg Gly Arg Arg Asp Gly Asp Asp Val Ala Ala
65                  70                  75                  80

Ser Ala Ser Ala Ala Ala Ala Ala Val Glu His Arg Cys Ser Val Cys
                85                  90                  95

Gly Lys Ala Phe Ala Ser Tyr Gln Ala Leu Gly Gly His Lys Ala Ser
            100                 105                 110

His Arg Lys Pro Pro Pro Pro Pro Pro Pro Ala Met Val Asp Asp Asp
        115                 120                 125

Glu Val Val Val Glu Thr Lys Pro Ala Ala Ile Ala Thr Pro Ser Ser
    130                 135                 140

Ser Ala Ser Gly Val Ser Gly Gly Gly Gly Gly Arg Ala His Glu Cys
145                 150                 155                 160

Asn Val Cys Gly Lys Ala Phe Pro Thr Gly Gln Ala Leu Gly Gly His
                165                 170                 175

Lys Arg Cys His Tyr Asp Gly Thr Ile Gly Ser Ala Ala Gly Ala Gly
            180                 185                 190

Ala Ser Lys Pro Ala Ala Lys Thr Thr Val Ala Val Ala Ala Ser Arg
        195                 200                 205

Gly Phe Asp Leu Asn Leu Pro Ala Leu Pro Asp Val Ala Ala Ala Ala
    210                 215                 220

Asp Gln Arg Cys Ala Ala Glu Asp Asp Glu Val Leu Ser Pro Leu Ala
225                 230                 235                 240

Phe Lys Lys Pro Arg Leu Met Ile Pro Ala
                245                 250


<210> SEQ ID NO 165
<211> LENGTH: 238
<212> TYPE: PRT
<213> ORGANISM: Oryza sativa

<400> SEQUENCE: 165

Met Ala Val Glu Glu Val Leu Asp Gly Ala Ala Pro Met Leu Ser Ser
1               5                   10                  15

Ser Pro Ala Ala Ser Gly Glu Glu Val Gly Ala Arg Lys Pro Gln Gln
            20                  25                  30

Arg Cys Gly Gly Ala Glu Gly Trp Ser Lys Arg Lys Arg Ser Arg Arg
        35                  40                  45

Arg His Arg Asp Arg Ala Ala Ala Pro Pro Pro His Gly Ser Glu Glu
    50                  55                  60

Glu His Leu Ala Leu Ser Leu Leu Met Leu Ala Arg Gly His Arg Asp
65                  70                  75                  80

Pro Ser Pro Ala Pro Gln Glu Gln His Gly Cys Ser Val Cys Gly Arg
                85                  90                  95

Val Phe Ser Ser Tyr Gln Ala Leu Gly Gly His Lys Thr Ser His Arg
            100                 105                 110

Pro Arg Thr Pro Pro Thr Met Ala Ala Val Val Val Val Asp Glu Pro
        115                 120                 125
```

-continued

```
Ala Ala Thr Thr Ala Ser Pro Ala Ala Ser Ser Ser Asn Ser Gly Ser
    130                 135                 140

Gly Ser Gly Gly Gly Gly Gly Asn Lys Val His Glu Cys Ser Val Cys
145                 150                 155                 160

Lys Lys Thr Phe Pro Thr Gly Gln Ala Leu Gly Gly His Lys Arg Cys
                165                 170                 175

His Tyr Glu Gly Pro Ile Gly Ser Gly Gly Gly Ala Ala Val Ala Gly
            180                 185                 190

Arg Gly Phe Asp Leu Asn Leu Pro Ala Val Ala Leu Pro Asp Ile Met
        195                 200                 205

Thr Glu Arg Cys Leu Pro Ala Ala Ala Glu Glu Glu Glu Val Leu Ser
    210                 215                 220

Pro Leu Ala Ser Phe Lys Lys Pro Arg Leu Met Ile Pro Ala
225                 230                 235


<210> SEQ ID NO 166
<211> LENGTH: 261
<212> TYPE: PRT
<213> ORGANISM: Triticum aestivum

<400> SEQUENCE: 166

Met Ser Ser Ser Ala Met Glu Ala Leu His Ala Leu Ile Pro Glu Gln
1               5                   10                  15

His Gln Leu Asp Val Glu Ala Ala Ala Ala Val Ser Ser Ala Thr Ser
            20                  25                  30

Gly Glu Glu Ser Gly His Val Leu Gln Gly Trp Ala Lys Arg Lys Arg
        35                  40                  45

Ser Arg Arg Gln Arg Ser Glu Glu Glu Asn Leu Ala Leu Cys Leu Leu
    50                  55                  60

Met Leu Ser Arg Gly Gly Lys Gln Arg Val Gln Ala Pro Gln Pro Glu
65                  70                  75                  80

Ser Phe Ala Ala Pro Val Pro Ala Glu Phe Lys Cys Ser Val Cys Gly
                85                  90                  95

Lys Ser Phe Ser Ser Tyr Gln Ala Leu Gly Gly His Lys Thr Ser His
            100                 105                 110

Arg Val Lys Gln Pro Ser Pro Pro Ser Asp Ala Ala Ala Ala Pro Leu
        115                 120                 125

Val Ala Leu Pro Ala Val Ala Ala Ile Leu Pro Ser Ala Glu Pro Ala
    130                 135                 140

Thr Ser Ser Thr Ala Ala Ser Ser Asp Gly Ala Thr Asn Arg Val His
145                 150                 155                 160

Arg Cys Ser Ile Cys Gln Lys Glu Phe Pro Thr Gly Gln Ala Leu Gly
                165                 170                 175

Gly His Lys Arg Lys His Tyr Asp Gly Gly Val Gly Ala Ala Ala Ser
            180                 185                 190

Ser Thr Glu Leu Leu Ala Ala Ala Ala Ala Glu Ser Glu Val Gly Ser
        195                 200                 205

Thr Gly Asn Gly Ser Ser Ala Ala Arg Ala Phe Asp Leu Asn Ile Pro
    210                 215                 220

Ala Val Pro Glu Phe Val Trp Arg Pro Cys Ala Lys Gly Lys Met Met
225                 230                 235                 240

Trp Glu Asp Asp Glu Glu Val Gln Ser Pro Leu Ala Phe Lys Lys Pro
                245                 250                 255

Arg Leu Leu Thr Ala
```

260

<210> SEQ ID NO 167
<211> LENGTH: 269
<212> TYPE: PRT
<213> ORGANISM: Oryza sativa

<400> SEQUENCE: 167

```
Met Ser Ser Ala Ser Ser Met Glu Ala Leu His Ala Ala Val Leu Lys
1               5                   10                  15

Glu Glu Gln Gln Gln His Glu Val Glu Glu Ala Thr Val Val Thr Ser
            20                  25                  30

Ser Ser Ala Thr Ser Gly Glu Glu Gly Gly His Leu Pro Gln Gly Trp
        35                  40                  45

Ala Lys Arg Lys Arg Ser Arg Arg Gln Arg Ser Glu Glu Glu Asn Leu
    50                  55                  60

Ala Leu Cys Leu Leu Met Leu Ala Arg Gly Gly His His Arg Val Gln
65                  70                  75                  80

Ala Pro Pro Pro Leu Ser Ala Ser Ala Pro Pro Pro Ala Gly Ala Glu
                85                  90                  95

Phe Lys Cys Ser Val Cys Gly Lys Ser Phe Ser Ser Tyr Gln Ala Leu
            100                 105                 110

Gly Gly His Lys Thr Ser His Arg Val Lys Leu Pro Thr Pro Pro Ala
        115                 120                 125

Ala Pro Val Leu Ala Pro Ala Pro Val Ala Ala Leu Leu Pro Ser Ala
    130                 135                 140

Glu Asp Arg Glu Pro Ala Thr Ser Ser Thr Ala Ala Ser Ser Asp Gly
145                 150                 155                 160

Met Thr Asn Arg Val His Arg Cys Ser Ile Cys Gln Lys Glu Phe Pro
                165                 170                 175

Thr Gly Gln Ala Leu Gly Gly His Lys Arg Lys His Tyr Asp Gly Gly
            180                 185                 190

Val Gly Ala Gly Ala Gly Ala Ser Ser Thr Glu Leu Leu Ala Thr Val
        195                 200                 205

Ala Ala Glu Ser Glu Val Gly Ser Ser Gly Asn Gly Gln Ser Ala Thr
    210                 215                 220

Arg Ala Phe Asp Leu Asn Leu Pro Ala Val Pro Glu Phe Val Trp Arg
225                 230                 235                 240

Pro Cys Ser Lys Gly Lys Lys Met Trp Asp Glu Glu Glu Glu Val Gln
                245                 250                 255

Ser Pro Leu Ala Phe Lys Lys Pro Arg Leu Leu Thr Ala
            260                 265
```

<210> SEQ ID NO 168
<211> LENGTH: 220
<212> TYPE: PRT
<213> ORGANISM: Oryza sativa

<400> SEQUENCE: 168

```
Met Ala Leu Asp Gly Lys Pro Pro Val Pro Pro Pro Ser Thr Pro Pro
1               5                   10                  15

Met Asp Ser Trp Ala Cys Gly Gly Arg Arg Ser Lys Arg Arg Gly Gly
            20                  25                  30

Gly Gly Gly Ser Ser Gly Ser Ser Gly Ser Ser Gly Gly Gly Gly Gly
        35                  40                  45

Gly Glu Ser Glu Glu Glu Tyr Leu Ala Ala Cys Leu Leu Met Leu Ala
```

-continued

```
    50                  55                  60

His Gly Val Arg Asp Glu Ala Glu Val Val Gly Val Ala Ala Ala Thr
65                  70                  75                  80

Ala Lys Pro Gln His Gly Tyr Glu Cys Ser Val Cys Gly Lys Val Tyr
                85                  90                  95

Gly Ser Tyr Gln Ala Leu Gly Gly His Lys Thr Ser His Arg Lys Pro
            100                 105                 110

Pro Ser Pro Ala Ala Glu Pro Ala Ala Gly Glu Glu Pro Ser Ser Gly
        115                 120                 125

Gly Val Ala Gly Glu Ala Lys Val His Arg Cys Ser Ile Cys Leu Arg
    130                 135                 140

Thr Phe Pro Ser Gly Gln Ala Leu Gly Gly His Lys Arg Leu His Tyr
145                 150                 155                 160

Glu Gly Gly Ala Val Gly Asp Ala Val Lys Glu Lys Asn Ser Leu Lys
                165                 170                 175

Thr Lys Ala Ala Val Ala Thr Ala Val Leu Lys Asp Phe Asp Leu Asn
            180                 185                 190

Leu Pro Ala Ala Ala Thr Thr Ala Gly Asp Glu Ala Glu Ser Ser Pro
        195                 200                 205

Pro Glu Ala Lys Arg Ala Arg Leu Leu Leu Leu Val
    210                 215                 220


<210> SEQ ID NO 169
<211> LENGTH: 189
<212> TYPE: PRT
<213> ORGANISM: Aegilops speltoides

<400> SEQUENCE: 169

Met Ala Val Asp Ala Val Arg Asp Ala Ala Ala Met Val Ser Glu Glu
1               5                   10                  15

Glu Glu Glu Gly Gln Leu Arg Cys Asp Glu Gly Trp Gly Lys Arg Arg
            20                  25                  30

Arg Pro Arg Arg Gln Arg Gln Arg Ala Pro Ser Glu Glu Glu His Leu
        35                  40                  45

Ala Leu Ser Leu Leu Met Leu Ala Arg Gly His Arg Asp Arg His Leu
    50                  55                  60

Leu Gly Ser Ser Glu Pro Ala Gln Glu His Arg Cys Ser Val Cys Gly
65                  70                  75                  80

Lys Gly Phe Pro Ser Tyr Gln Ala Leu Gly Gly His Lys Ala Ser His
                85                  90                  95

Arg Pro Lys Pro Ala Pro Ala Gly Ala Asp Glu Pro Ala Ala Thr Thr
            100                 105                 110

Ala Ala Ser Pro Ala Ala Ser Ser Ser Thr Thr Ser Ser Gly Ala Gly
        115                 120                 125

Gly Gly Gly Arg Val His Glu Cys Ser Val Cys Lys Lys Thr Phe Pro
    130                 135                 140

Thr Gly Gln Ala Leu Gly Gly His Lys Arg Cys His Tyr Glu Gly Pro
145                 150                 155                 160

Ile Gly Ala Thr Val Val Ala Ser Arg Gly Phe Asp Leu Asn Leu Pro
                165                 170                 175

Ala Leu Pro Asp Ile Val Thr Glu Arg Glu Arg Cys Met
            180                 185


<210> SEQ ID NO 170
<211> LENGTH: 184
```

-continued

<212> TYPE: PRT
<213> ORGANISM: Secale cereale

<400> SEQUENCE: 170

Arg Arg Arg Pro Arg Arg Gln Arg Gln Arg Ala Pro Ser Glu Glu Glu
1 5 10 15

His Leu Ala Leu Ser Leu Leu Met Leu Ala Arg Gly His Arg Asp Arg
20 25 30

His Leu Pro Pro Ser Ser Glu Pro Ala Gln Glu His Arg Cys Ser Val
35 40 45

Cys Gly Lys Gly Phe Pro Ser Tyr Gln Ala Leu Gly Gly His Lys Ala
50 55 60

Ser His Arg Pro Lys Pro Ala Pro Ala Gly Ala Asp Glu Pro Ala Ala
65 70 75 80

Thr Ala Ala Ala Ser Pro Ala Ala Ser Ser Ser Thr Thr Ser Ser Gly
85 90 95

Ala Gly Val Lys Val His Glu Cys Ser Val Cys Lys Lys Thr Phe Pro
100 105 110

Thr Gly Gln Ala Leu Gly Gly His Lys Arg Cys His Tyr Glu Gly Pro
115 120 125

Ile Gly Gly Gly Gly Ala Pro Ala Val Ala Ser Arg Gly Phe Asp Leu
130 135 140

Asn Leu Pro Ala Leu Pro Asp Ile Val Thr Glu Arg Glu Arg Cys Met
145 150 155 160

Pro Ala Pro Ala Asp Glu Glu Glu Val Leu Ser Pro Leu Ala Phe Lys
165 170 175

Lys Pro Arg Leu Met Ile Pro Ala
180

<210> SEQ ID NO 171
<211> LENGTH: 200
<212> TYPE: PRT
<213> ORGANISM: Saccharum officinarum

<400> SEQUENCE: 171

Asp Val Val Ala Ala Ala Ala Asp Gln Val Ala Thr Thr Ser Asn Ser
1 5 10 15

Ser Gly Thr Ala Ala Glu Glu Asp Lys Asp Val Lys Thr Ala Val Gln
20 25 30

Gln Glu His Gly Gln Gly Leu Ala Lys Arg Lys Arg Ser Arg Arg Arg
35 40 45

Arg Asp Arg Glu Gln Gln Gln Leu Pro Lys Glu His Pro Thr Gln Glu
50 55 60

Glu Tyr Leu Ala Gln Cys Leu Val Met Leu Ala Thr Gly Arg Arg Asp
65 70 75 80

Gly Asp Val Pro Ala Leu Ala Ser Ala Pro Pro Pro Pro Gln Gly Gln
85 90 95

Gln Gln Asp His Ala Cys Ser Val Cys Gly Lys Ala Phe Pro Thr Tyr
100 105 110

Gln Ala Leu Gly Gly His Lys Ala Ser His Arg Thr Arg Pro Ser Pro
115 120 125

Pro Ser Ala Ala Thr Glu Val Val Gly Asp His His Glu Glu Gln Lys
130 135 140

Pro Val Leu Pro Ser Ser Ser Ser Ala Ala Ser Ala Gly Ala Asp Asn
145 150 155 160

-continued

```
Asn Lys Pro Ala Ala Ala His Glu Cys Asn Val Cys Gly Lys Ala Phe
                165                 170                 175

Pro Thr Gly Gln Ala Leu Gly Gly His Lys Arg Arg His Tyr Asp Gly
            180                 185                 190

Thr Ile Gly Ser Ala Ala Ala Pro
        195                 200


<210> SEQ ID NO 172
<211> LENGTH: 253
<212> TYPE: PRT
<213> ORGANISM: Nicotiana benthamiana

<400> SEQUENCE: 172

Met Ala Leu Glu Ala Leu Asn Ser Pro Thr Thr Thr Thr Pro Pro Thr
1               5                   10                  15

Phe Gln Phe Glu Asn Asn Gly Pro Leu Arg Tyr Leu Glu Asn Trp Thr
            20                  25                  30

Lys Gly Lys Arg Ser Lys Arg Pro Arg Ser Met Glu Arg Gln Pro Thr
        35                  40                  45

Glu Glu Glu Tyr Leu Ala Leu Cys Leu Ile Met Leu Ala Arg Ser Asp
    50                  55                  60

Gly Ser Ala Asn Arg Glu Gln Ser Leu Pro Pro Pro Pro Val Pro Val
65                  70                  75                  80

Met Lys Ile His Ala Pro Pro Glu Glu Lys Met Val Tyr Lys Cys Ser
                85                  90                  95

Val Cys Gly Lys Gly Phe Gly Ser Tyr Gln Ala Leu Gly Gly His Lys
            100                 105                 110

Ala Ser His Arg Lys Leu Val Ala Gly Gly Gly Gly Gly Asp Asp Gln
        115                 120                 125

Ser Thr Thr Ser Thr Thr Thr Asn Ala Thr Gly Thr Thr Ser Ser Ala
    130                 135                 140

Asn Gly Asn Gly Asn Gly Ser Gly Lys Thr His Glu Cys Ser Ile Cys
145                 150                 155                 160

His Lys Arg Phe Pro Thr Gly Gln Ala Leu Gly Gly His Lys Arg Cys
                165                 170                 175

His Tyr Asp Gly Gly Asn Ser Asn Gly Gly Val Ser Val Ser Ala Ser
            180                 185                 190

Val Gly Leu Thr Ser Ser Glu Gly Val Gly Ser Thr Val Ser His Arg
        195                 200                 205

Asp Phe Asp Leu Asn Ile Pro Ala Leu Pro Glu Phe Trp Pro Gly Phe
    210                 215                 220

Gly Ser Gly Glu Asp Glu Val Glu Ser Pro His Pro Thr Lys Lys Ser
225                 230                 235                 240

Arg Leu Ser Leu Pro Pro Lys Phe Glu Leu Phe Arg Glu
                245                 250


<210> SEQ ID NO 173
<211> LENGTH: 261
<212> TYPE: PRT
<213> ORGANISM: Capsicum annuum

<400> SEQUENCE: 173

Met Ala Leu Glu Ala Leu Asn Ser Pro Thr Gly Thr Pro Thr Pro Pro
1               5                   10                  15

Pro Phe Gln Phe Glu Ser Asp Gly Gln Gln Leu Arg Tyr Ile Glu Asn
            20                  25                  30
```

-continued

```
Trp Arg Lys Gly Lys Arg Ser Lys Arg Ser Arg Ser Met Glu His Gln
        35                  40                  45

Pro Thr Glu Glu Glu Tyr Leu Ala Leu Cys Leu Ile Met Leu Ala Arg
    50                  55                  60

Ser Gly Gly Ser Val Asn His Gln Arg Ser Leu Pro Pro Pro Ala Pro
65                  70                  75                  80

Val Met Lys Leu His Ala Pro Ser Ser Ser Ser Ala Ala Glu Glu Glu
                85                  90                  95

Lys Glu Lys Met Val Tyr Lys Cys Ser Val Cys Gly Lys Gly Phe Gly
            100                 105                 110

Ser Tyr Gln Ala Leu Gly Gly His Lys Ala Ser His Arg Lys Leu Val
        115                 120                 125

Pro Gly Gly Asp Asp Gln Ser Thr Thr Ser Thr Thr Thr Asn Ala Thr
    130                 135                 140

Gly Thr Thr Thr Ser Val Asn Gly Asn Gly Asn Arg Ser Gly Arg Thr
145                 150                 155                 160

His Glu Cys Ser Ile Cys His Lys Cys Phe Pro Thr Gly Gln Ala Leu
                165                 170                 175

Gly Gly His Lys Arg Cys His Tyr Asp Gly Gly Ile Gly Asn Gly Asn
            180                 185                 190

Ala Asn Ser Gly Val Ser Ala Ser Val Gly Val Thr Ser Ser Glu Gly
        195                 200                 205

Val Gly Ser Thr Val Ser His Arg Asp Phe Asp Leu Asn Ile Pro Ala
    210                 215                 220

Leu Pro Glu Phe Trp Leu Gly Phe Gly Ser Gly Glu Asp Glu Val Glu
225                 230                 235                 240

Ser Pro His Pro Ala Lys Lys Ser Arg Leu Cys Leu Pro Pro Lys Tyr
                245                 250                 255

Glu Leu Phe Gln His
            260


<210> SEQ ID NO 174
<211> LENGTH: 235
<212> TYPE: PRT
<213> ORGANISM: Medicago sativa

<400> SEQUENCE: 174

Met Ala Met Glu Ala Leu Asn Ser Pro Thr Thr Ala Thr Pro Phe Thr
1               5                   10                  15

Pro Phe Glu Glu Pro Asn Leu Ser Tyr Leu Glu Thr Pro Trp Thr Lys
            20                  25                  30

Gly Lys Arg Ser Lys Arg Ser Arg Met Asp Gln Ser Ser Cys Thr Glu
        35                  40                  45

Glu Glu Tyr Leu Ala Leu Cys Leu Ile Met Leu Ala Arg Ser Gly Asn
    50                  55                  60

Asn Asn Asp Lys Lys Ser Asp Ser Val Ala Thr Pro Leu Thr Thr Val
65                  70                  75                  80

Lys Leu Ser His Lys Cys Ser Val Cys Asn Lys Ala Phe Ser Ser Tyr
                85                  90                  95

Gln Ala Leu Gly Gly His Lys Ala Ser His Arg Lys Ala Val Met Ser
            100                 105                 110

Ala Thr Thr Ala Glu Asp Gln Ile Thr Thr Thr Ser Ser Ala Val Thr
        115                 120                 125

Thr Ser Ser Ala Ser Asn Gly Lys Asn Lys Thr His Glu Cys Ser Ile
    130                 135                 140
```

-continued

```
Cys His Lys Ser Phe Pro Thr Gly Gln Ala Leu Gly Gly His Lys Arg
145                 150                 155                 160

Cys His Tyr Glu Gly Ser Val Gly Ala Gly Ala Gly Ala Gly Ser Asn
                165                 170                 175

Ala Val Thr Ala Ser Glu Gly Val Gly Leu Ser His Ser His His Arg
            180                 185                 190

Asp Phe Asp Leu Asn Leu Pro Ala Phe Pro Asp Phe Ser Lys Lys Phe
        195                 200                 205

Phe Val Asp Asp Glu Val Phe Ser Pro Leu Pro Ala Ala Lys Lys Pro
    210                 215                 220

Cys Leu Phe Lys Leu Glu Ile Pro Ser His Tyr
225                 230                 235


<210> SEQ ID NO 175
<211> LENGTH: 240
<212> TYPE: PRT
<213> ORGANISM: Glycine max

<400> SEQUENCE: 175

Met Ala Leu Glu Ala Leu Asn Ser Pro Thr Thr Thr Ala Pro Ser Phe
1               5                   10                  15

Pro Phe Asp Asp Pro Thr Ile Pro Trp Ala Lys Arg Lys Arg Ser Lys
            20                  25                  30

Arg Ser Arg Asp His Pro Ser Glu Glu Glu Tyr Leu Ala Leu Cys Leu
        35                  40                  45

Ile Met Leu Ala Arg Gly Gly Thr Thr Thr Val Asn Asn Arg His Val
    50                  55                  60

Ser Pro Pro Pro Leu Gln Pro Gln Pro Gln Pro Thr Pro Asp Pro Ser
65                  70                  75                  80

Thr Lys Leu Ser Tyr Lys Cys Ser Val Cys Asp Lys Ser Phe Pro Ser
                85                  90                  95

Tyr Gln Ala Leu Gly Gly His Lys Ala Ser His Arg Lys Leu Ala Gly
            100                 105                 110

Ala Ala Glu Asp Gln Pro Pro Ser Thr Thr Thr Ser Ser Ala Ala Ala
        115                 120                 125

Thr Ser Ser Ala Ser Gly Gly Lys Ala His Glu Cys Ser Ile Cys His
    130                 135                 140

Lys Ser Phe Pro Thr Gly Gln Ala Leu Gly Gly His Lys Arg Cys His
145                 150                 155                 160

Tyr Glu Gly Asn Gly Asn Gly Asn Asn Asn Asn Ser Asn Ser Val Val
                165                 170                 175

Thr Val Ala Ser Glu Gly Val Gly Ser Thr His Thr Val Ser His Gly
            180                 185                 190

His His Arg Asp Phe Asp Leu Asn Ile Pro Ala Phe Pro Asp Phe Ser
        195                 200                 205

Thr Lys Val Gly Glu Asp Glu Val Glu Ser Pro His Pro Val Met Lys
    210                 215                 220

Lys Pro Arg Leu Phe Val Ile Pro Lys Ile Glu Ile Pro Gln Phe Gln
225                 230                 235                 240


<210> SEQ ID NO 176
<211> LENGTH: 265
<212> TYPE: PRT
<213> ORGANISM: Arabidopsis thaliana

<400> SEQUENCE: 176
```

-continued

```
Met Val Ala Tyr Pro Thr Lys Lys Thr Ala Ile Lys Gln Phe Leu His
1               5                   10                  15

Cys Asn Ser Gln Ala Thr Phe Lys Leu Lys Leu Glu Arg Gln Glu Ile
            20                  25                  30

Leu Arg Ile Phe Asn Leu Met Ala Leu Glu Ala Leu Thr Ser Pro Arg
        35                  40                  45

Leu Ala Ser Pro Ile Pro Pro Leu Phe Glu Asp Ser Ser Val Phe His
    50                  55                  60

Gly Val Glu His Trp Thr Lys Gly Lys Arg Ser Lys Arg Ser Arg Ser
65                  70                  75                  80

Asp Phe His His Gln Asn Leu Thr Glu Glu Glu Tyr Leu Ala Phe Cys
                85                  90                  95

Leu Met Leu Leu Ala Arg Asp Asn Arg Gln Pro Pro Pro Pro Pro Ala
            100                 105                 110

Val Glu Lys Leu Ser Tyr Lys Cys Ser Val Cys Asp Lys Thr Phe Ser
        115                 120                 125

Ser Tyr Gln Ala Leu Gly Gly His Lys Ala Ser His Arg Lys Asn Leu
    130                 135                 140

Ser Gln Thr Leu Ser Gly Gly Gly Asp Asp His Ser Thr Ser Ser Ala
145                 150                 155                 160

Thr Thr Thr Ser Ala Val Thr Thr Gly Ser Gly Lys Ser His Val Cys
                165                 170                 175

Thr Ile Cys Asn Lys Ser Phe Pro Ser Gly Gln Ala Leu Gly Gly His
            180                 185                 190

Lys Arg Cys His Tyr Glu Gly Asn Asn Asn Ile Asn Thr Ser Ser Val
        195                 200                 205

Ser Asn Ser Glu Gly Ala Gly Ser Thr Ser His Val Ser Ser Ser His
    210                 215                 220

Arg Gly Phe Asp Leu Asn Ile Pro Pro Ile Pro Glu Phe Ser Met Val
225                 230                 235                 240

Asn Gly Asp Asp Glu Val Met Ser Pro Met Pro Ala Lys Lys Pro Arg
                245                 250                 255

Phe Asp Phe Pro Val Lys Leu Gln Leu
            260                 265


<210> SEQ ID NO 177
<211> LENGTH: 227
<212> TYPE: PRT
<213> ORGANISM: Arabidopsis thaliana

<400> SEQUENCE: 177

Met Ala Leu Glu Ala Leu Thr Ser Pro Arg Leu Ala Ser Pro Ile Pro
1               5                   10                  15

Pro Leu Phe Glu Asp Ser Ser Val Phe His Gly Val Glu His Trp Thr
            20                  25                  30

Lys Gly Lys Arg Ser Lys Arg Ser Arg Ser Asp Phe His His Gln Asn
        35                  40                  45

Leu Thr Glu Glu Glu Tyr Leu Ala Phe Cys Leu Met Leu Leu Ala Arg
    50                  55                  60

Asp Asn Arg Gln Pro Pro Pro Pro Pro Ala Val Glu Lys Leu Ser Tyr
65                  70                  75                  80

Lys Cys Ser Val Cys Asp Lys Thr Phe Ser Ser Tyr Gln Ala Leu Gly
                85                  90                  95

Gly His Lys Ala Ser His Arg Lys Asn Leu Ser Gln Thr Leu Ser Gly
```

```
            100                 105                 110

Gly Gly Asp Asp His Ser Thr Ser Ser Ala Thr Thr Thr Ser Ala Val
        115                 120                 125

Thr Thr Gly Ser Gly Lys Ser His Val Cys Thr Ile Cys Asn Lys Ser
    130                 135                 140

Phe Pro Ser Gly Gln Ala Leu Gly Gly His Lys Arg Cys His Tyr Glu
145                 150                 155                 160

Gly Asn Asn Asn Ile Asn Thr Ser Ser Val Ser Asn Ser Glu Gly Ala
                165                 170                 175

Gly Ser Thr Ser His Val Ser Ser Ser His Arg Gly Phe Asp Leu Asn
            180                 185                 190

Ile Pro Pro Ile Pro Glu Phe Ser Met Val Asn Gly Asp Asp Glu Val
        195                 200                 205

Met Ser Pro Met Pro Ala Lys Lys Pro Arg Phe Asp Phe Pro Val Lys
    210                 215                 220

Leu Gln Leu
225


<210> SEQ ID NO 178
<211> LENGTH: 247
<212> TYPE: PRT
<213> ORGANISM: Datisca glomerata

<400> SEQUENCE: 178

Met Ala Leu Glu Ala Leu Asn Ser Pro Thr Thr Ala Thr Pro Val Phe
1               5                   10                  15

His Tyr Asp Asp Pro Ser Leu Asn Tyr Leu Glu Pro Trp Thr Lys Arg
            20                  25                  30

Lys Arg Ser Lys Arg Thr Arg Leu Asp Ser Pro His Thr Glu Glu Glu
        35                  40                  45

Tyr Leu Ala Phe Cys Leu Ile Met Leu Ala Arg Gly Arg Val Ala Ser
    50                  55                  60

Ala Asn Arg Arg Asp Ser Gln Ser Ser Ile Gln Ile Gln Pro Glu Ala
65                  70                  75                  80

Thr Thr Ser Ala Thr Lys Val Ser Tyr Lys Cys Ser Val Cys Asp Lys
                85                  90                  95

Ala Phe Ser Ser Tyr Gln Ala Leu Gly Gly His Lys Ala Ser His Arg
            100                 105                 110

Lys Leu Ala Gly Gly Glu Asp Gln Ser Thr Ser Phe Ala Thr Thr Asn
        115                 120                 125

Ser Ala Thr Val Thr Thr Thr Thr Ala Ser Gly Gly Gly Gly Arg Ser
    130                 135                 140

His Glu Cys Ser Ile Cys His Lys Ser Phe Pro Thr Gly Gln Ala Leu
145                 150                 155                 160

Gly Gly His Lys Arg Cys His Tyr Glu Gly Ser Ile Gly Gly Asn Ser
                165                 170                 175

Ile His His His Asn Asn Thr Thr Asn Ser Gly Ser Asn Gly Gly Met
            180                 185                 190

Ser Met Thr Ser Glu Val Gly Ser Thr His Thr Val Ser His Ser His
        195                 200                 205

Arg Asp Phe Asp Leu Asn Ile Pro Ala Leu Pro Glu Phe Arg Ser Asn
    210                 215                 220

Phe Phe Ile Ser Gly Asp Asp Glu Val Glu Ser Pro His Pro Ala Lys
225                 230                 235                 240
```

```
Lys Pro Arg Ile Leu Met Lys
                245


<210> SEQ ID NO 179
<211> LENGTH: 227
<212> TYPE: PRT
<213> ORGANISM: Arabidopsis thaliana

<400> SEQUENCE: 179

Met Ala Leu Glu Ala Leu Thr Ser Pro Arg Leu Ala Ser Pro Ile Pro
1               5                   10                  15

Pro Leu Phe Glu Asp Ser Ser Val Phe His Gly Val Glu His Trp Thr
            20                  25                  30

Lys Gly Lys Arg Ser Lys Arg Ser Arg Ser Asp Phe His His Gln Asn
        35                  40                  45

Leu Thr Glu Glu Glu Tyr Leu Ala Phe Trp Leu Met Leu Leu Ala Arg
    50                  55                  60

Asp Asn Arg Gln Pro Pro Pro Pro Pro Ala Val Glu Lys Leu Ser Tyr
65                  70                  75                  80

Lys Cys Ser Val Cys Asp Lys Thr Phe Ser Ser Tyr Gln Ala Leu Gly
                85                  90                  95

Gly His Lys Ala Ser His Arg Lys Asn Leu Ser Gln Thr Leu Ser Gly
            100                 105                 110

Gly Gly Asp Asp His Ser Thr Ser Ser Ala Thr Thr Thr Ser Ala Val
        115                 120                 125

Thr Thr Gly Ser Gly Lys Ser His Val Cys Thr Ile Cys Asn Lys Ser
    130                 135                 140

Phe Pro Ser Gly Gln Ala Leu Gly Gly His Lys Arg Cys His Tyr Glu
145                 150                 155                 160

Gly Asn Asn Asn Ile Asn Thr Ser Ser Val Ser Asn Ser Glu Gly Ala
                165                 170                 175

Gly Ser Thr Ser His Val Ser Ser Ser His Arg Gly Phe Asp Leu Asn
            180                 185                 190

Ile Pro Pro Ile Pro Glu Phe Ser Met Val Asn Gly Asp Asp Glu Val
        195                 200                 205

Met Ser Pro Met Pro Ala Lys Lys Pro Arg Phe Asp Phe Pro Val Lys
    210                 215                 220

Leu Gln Leu
225


<210> SEQ ID NO 180
<211> LENGTH: 253
<212> TYPE: PRT
<213> ORGANISM: Petunia x hybrida

<400> SEQUENCE: 180

Met Ala Leu Glu Ala Leu Asn Ser Pro Thr Thr Thr Thr Pro Pro Ser
1               5                   10                  15

Phe Gln Phe Glu Asn Asn Gly Leu Lys Tyr Leu Glu Ser Trp Thr Lys
            20                  25                  30

Gly Lys Arg Ser Lys Arg Gln Arg Ser Met Glu Arg Gln Cys Thr Glu
        35                  40                  45

Glu Glu Tyr Leu Ala Leu Cys Leu Ile Met Leu Ala Arg Ser Asp Gly
    50                  55                  60

Ser Val Asn Asn Ser Arg Ser Leu Pro Pro Pro Pro Leu Pro Pro Ser
65                  70                  75                  80
```

-continued

```
Val Pro Val Thr Ser Gln Ile Asn Ala Thr Leu Leu Glu Gln Lys Asn
                85                  90                  95

Leu Tyr Lys Cys Ser Val Cys Gly Lys Gly Phe Gly Ser Tyr Gln Ala
            100                 105                 110

Leu Gly Gly His Lys Ala Ser His Arg Lys Leu Val Ser Met Gly Gly
        115                 120                 125

Asp Glu Gln Ser Thr Thr Ser Thr Thr Thr Asn Val Thr Gly Thr Ser
    130                 135                 140

Ser Ala Asn Val Asn Gly Asn Gly Arg Thr His Glu Cys Ser Ile Cys
145                 150                 155                 160

His Lys Cys Phe Pro Thr Gly Gln Ala Leu Gly Gly His Lys Arg Cys
                165                 170                 175

His Tyr Asp Gly Gly Asn Gly Asn Gly Asn Gly Ser Val Ser Val Gly
            180                 185                 190

Val Thr Ser Ser Glu Gly Val Gly Ser Thr Ile Ser His His Arg Asp
        195                 200                 205

Phe Asp Leu Asn Ile Pro Ala Leu Pro Glu Phe Trp Pro Gly Phe Gly
    210                 215                 220

Ser Gly Glu Asp Glu Val Glu Ser Pro His Pro Ala Lys Lys Ser Arg
225                 230                 235                 240

Leu Ser Leu Pro Pro Lys Leu Glu Leu Phe Lys Gly Leu
                245                 250


<210> SEQ ID NO 181
<211> LENGTH: 273
<212> TYPE: PRT
<213> ORGANISM: Arabidopsis thaliana

<400> SEQUENCE: 181

Met Ala Leu Glu Ala Met Asn Thr Pro Thr Ser Ser Phe Thr Arg Ile
1               5                   10                  15

Glu Thr Lys Glu Asp Leu Met Asn Asp Ala Val Phe Ile Glu Pro Trp
            20                  25                  30

Leu Lys Arg Lys Arg Ser Lys Arg Gln Arg Ser His Ser Pro Ser Ser
        35                  40                  45

Ser Ser Ser Ser Pro Pro Arg Ser Arg Pro Lys Ser Gln Asn Gln Asp
    50                  55                  60

Leu Thr Glu Glu Glu Tyr Leu Ala Leu Cys Leu Leu Met Leu Ala Lys
65                  70                  75                  80

Asp Gln Pro Ser Gln Thr Arg Phe His Gln Gln Ser Gln Ser Leu Thr
                85                  90                  95

Pro Pro Pro Glu Ser Lys Asn Leu Pro Tyr Lys Cys Asn Val Cys Glu
            100                 105                 110

Lys Ala Phe Pro Ser Tyr Gln Ala Leu Gly Gly His Lys Ala Ser His
        115                 120                 125

Arg Ile Lys Pro Pro Thr Val Ile Ser Thr Thr Ala Asp Asp Ser Thr
    130                 135                 140

Ala Pro Thr Ile Ser Ile Val Ala Gly Glu Lys His Pro Ile Ala Ala
145                 150                 155                 160

Ser Gly Lys Ile His Glu Cys Ser Ile Cys His Lys Val Phe Pro Thr
                165                 170                 175

Gly Gln Ala Leu Gly Gly His Lys Arg Cys His Tyr Glu Gly Asn Leu
            180                 185                 190

Gly Gly Gly Gly Gly Gly Gly Ser Lys Ser Ile Ser His Ser Gly Ser
        195                 200                 205
```

```
Val Ser Ser Thr Val Ser Glu Glu Arg Ser His Arg Gly Phe Ile Asp
    210                 215                 220

Leu Asn Leu Pro Ala Leu Pro Glu Leu Ser Leu His His Asn Pro Ile
225                 230                 235                 240

Val Asp Glu Glu Ile Leu Ser Pro Leu Thr Gly Lys Lys Pro Leu Leu
                245                 250                 255

Leu Thr Asp His Asp Gln Val Ile Lys Lys Glu Asp Leu Ser Leu Lys
            260                 265                 270

Ile


<210> SEQ ID NO 182
<211> LENGTH: 238
<212> TYPE: PRT
<213> ORGANISM: Arabidopsis thaliana

<400> SEQUENCE: 182

Met Ala Leu Glu Thr Leu Thr Ser Pro Arg Leu Ser Ser Pro Met Pro
1               5                   10                  15

Thr Leu Phe Gln Asp Ser Ala Leu Gly Phe His Gly Ser Lys Gly Lys
            20                  25                  30

Arg Ser Lys Arg Ser Arg Ser Glu Phe Asp Arg Gln Ser Leu Thr Glu
        35                  40                  45

Asp Glu Tyr Ile Ala Leu Cys Leu Met Leu Leu Ala Arg Asp Gly Asp
    50                  55                  60

Arg Asn Arg Asp Leu Asp Leu Pro Ser Ser Ser Ser Ser Pro Pro Leu
65                  70                  75                  80

Leu Pro Pro Leu Pro Thr Pro Ile Tyr Lys Cys Ser Val Cys Asp Lys
                85                  90                  95

Ala Phe Ser Ser Tyr Gln Ala Leu Gly Gly His Lys Ala Ser His Arg
            100                 105                 110

Lys Ser Phe Ser Leu Thr Gln Ser Ala Gly Gly Asp Glu Leu Ser Thr
        115                 120                 125

Ser Ser Ala Ile Thr Thr Ser Gly Ile Ser Gly Gly Gly Gly Gly Ser
    130                 135                 140

Val Lys Ser His Val Cys Ser Ile Cys His Lys Ser Phe Ala Thr Gly
145                 150                 155                 160

Gln Ala Leu Gly Gly His Lys Arg Cys His Tyr Glu Gly Lys Asn Gly
                165                 170                 175

Gly Gly Val Ser Ser Ser Val Ser Asn Ser Glu Asp Val Gly Ser Thr
            180                 185                 190

Ser His Val Ser Ser Gly His Arg Gly Phe Asp Leu Asn Ile Pro Pro
        195                 200                 205

Ile Pro Glu Phe Ser Met Val Asn Gly Asp Glu Glu Val Met Ser Pro
    210                 215                 220

Met Pro Ala Lys Lys Leu Arg Phe Asp Phe Pro Gly Lys Pro
225                 230                 235


<210> SEQ ID NO 183
<211> LENGTH: 238
<212> TYPE: PRT
<213> ORGANISM: Arabidopsis thaliana

<400> SEQUENCE: 183

Met Ala Leu Glu Thr Leu Thr Ser Pro Arg Leu Ser Ser Pro Met Pro
1               5                   10                  15
```

-continued

```
Thr Leu Phe Gln Asp Ser Ala Leu Gly Phe His Gly Ser Lys Gly Lys
            20                  25                  30

Arg Ser Lys Arg Ser Arg Ser Glu Phe Asp Arg Gln Ser Leu Thr Glu
        35                  40                  45

Asp Glu Tyr Ile Ala Leu Cys Leu Met Leu Leu Ala Arg Asp Gly Asp
    50                  55                  60

Arg Asn Arg Asp Leu Asp Leu Pro Ser Ser Ser Ser Ser Pro Pro Leu
65                  70                  75                  80

Leu Pro Pro Leu Pro Thr Pro Ile Tyr Lys Cys Ser Val Cys Asp Lys
                85                  90                  95

Ala Phe Ser Ser Tyr Gln Ala Leu Gly Gly His Lys Ala Ser His Arg
            100                 105                 110

Lys Ser Phe Ser Leu Thr Gln Ser Ala Gly Gly Asp Glu Leu Ser Thr
        115                 120                 125

Ser Ser Ala Ile Thr Thr Ser Gly Ile Ser Gly Gly Gly Gly Gly Ser
    130                 135                 140

Val Lys Ser His Val Cys Ser Ile Cys His Lys Ser Phe Ala Thr Gly
145                 150                 155                 160

Gln Ala Leu Gly Gly His Lys Arg Cys His Tyr Glu Gly Lys Asn Gly
                165                 170                 175

Gly Gly Val Ser Ser Ser Val Ser Asn Ser Glu Asp Val Gly Ser Thr
            180                 185                 190

Ser His Val Ser Ser Gly His Arg Gly Phe Asp Leu Asn Ile Pro Pro
        195                 200                 205

Ile Pro Glu Phe Ser Met Val Asn Gly Asp Glu Glu Val Met Ser Pro
    210                 215                 220

Met Pro Ala Lys Lys Leu Arg Phe Asp Phe Pro Glu Lys Pro
225                 230                 235


<210> SEQ ID NO 184
<211> LENGTH: 235
<212> TYPE: PRT
<213> ORGANISM: Brassica rapa

<400> SEQUENCE: 184

Met Ala Leu Glu Thr Leu Asn Ser Pro Thr Ser Ala Thr Ala Ser Ala
1               5                   10                  15

Arg Pro Leu Leu Arg Tyr Arg Glu Glu Met Glu Pro Glu Asn Leu Glu
            20                  25                  30

Gln Trp Ala Lys Arg Lys Arg Thr Lys Arg Gln Arg Phe Asp Gln Ser
        35                  40                  45

Arg Leu Asn Gln Glu Thr Ala Pro Ser Glu Glu Glu Tyr Leu Ala Leu
    50                  55                  60

Cys Leu Leu Met Leu Ala Arg Gly Ser Ala Val Gln Ser Pro Leu Pro
65                  70                  75                  80

Pro Ser Ser Ser Ser Asp His Arg Gly Tyr Lys Cys Thr Val Cys Gly
                85                  90                  95

Lys Ser Phe Ser Ser Tyr Gln Ala Leu Gly Gly His Lys Thr Ser His
            100                 105                 110

Arg Lys Pro Ala Ser Asn Val Asn Val Pro Ile Asn Gln Glu Gln Ser
        115                 120                 125

Asn Asn Ser His Ser Asn Ser Asn Gly Gly Ser Val Val Ile Asn Gly
    130                 135                 140

Asn Gly Val Ser Gln Ser Gly Lys Ile His Thr Cys Ser Ile Cys Phe
145                 150                 155                 160
```

-continued

```
Lys Ser Phe Ser Ser Gly Gln Ala Leu Gly Gly His Lys Arg Cys His
                165                 170                 175

Tyr Asp Ala Gly Asn Asn Gly Asn Gly Asn Gly Ser Ser Ser Asn Ser
            180                 185                 190

Val Glu Val Val Gly Gly Ser Asp Gly Ser Tyr Val Asp Asp Glu Arg
        195                 200                 205

Ser Ser Glu Gln Ser Ala Thr Gly Asp Asn Arg Gly Phe Asp Leu Asn
    210                 215                 220

Leu Pro Ala Asp Gln Val Ala Val Val Ile Ser
225                 230                 235
```

<210> SEQ ID NO 185
<211> LENGTH: 237
<212> TYPE: PRT
<213> ORGANISM: Brassica rapa

<400> SEQUENCE: 185

```
Met Ala Leu Glu Thr Leu Asn Ser Pro Thr Ser Ala Thr Ala Ser Ala
1               5                   10                  15

Arg Pro Leu Leu Arg Tyr Arg Glu Glu Met Glu Pro Glu Asn Leu Glu
            20                  25                  30

Gln Trp Ala Lys Arg Lys Arg Thr Lys Arg Gln Arg Phe Asp Gln Ser
        35                  40                  45

Arg Leu Asn Gln Glu Thr Ala Pro Ser Glu Glu Glu Tyr Leu Ala Leu
    50                  55                  60

Cys Leu Leu Met Leu Ala Arg Gly Ser Ala Val Gln Ser Pro Leu Pro
65                  70                  75                  80

Pro Ser Ser Ser Ser Asp His Arg Gly Tyr Lys Cys Thr Val Cys Gly
                85                  90                  95

Lys Ser Phe Ser Ser Tyr Gln Ala Leu Gly Gly His Lys Thr Ser His
            100                 105                 110

Arg Lys Pro Ala Ser Asn Val Asn Val Pro Ile Asn Gln Glu Gln Ser
        115                 120                 125

Asn Asn Ser His Ser Asn Ser Asn Gly Gly Ser Val Ala Ile Asn Gly
    130                 135                 140

Asn Gly Val Ser Gln Ser Gly Lys Ile His Thr Cys Ser Ile Cys Phe
145                 150                 155                 160

Lys Ser Phe Ser Ser Gly Gln Ala Leu Gly Gly His Lys Arg Cys His
                165                 170                 175

Tyr Asp Ala Gly Ile Asn Gly Asn Gly Asn Gly Ser Ser Ser Asn Ser
            180                 185                 190

Val Glu Val Val Gly Gly Ser Asp Gly Asn Tyr Val Asp Asp Glu Arg
        195                 200                 205

Ser Ser Glu Gln Ser Ala Thr Gly Asp Asn Arg Gly Phe Asp Leu Asn
    210                 215                 220

Leu Pro Ala Asp Gln Val Ala Val Val Ile Ser Lys Arg
225                 230                 235
```

<210> SEQ ID NO 186
<211> LENGTH: 273
<212> TYPE: PRT
<213> ORGANISM: Nicotiana tabacum

<400> SEQUENCE: 186

```
Met Thr Leu Glu Ala Leu Lys Ser Pro Thr Ala Ala Thr Pro Thr Leu
1               5                   10                  15
```

-continued

```
Pro Pro Arg Tyr Glu Asp Asp Asp Glu Ile His Asn Leu Asp Ser Trp
            20                  25                  30

Ala Lys Gly Lys Arg Ser Lys Arg Pro Arg Ile Asp Ala Pro Pro Thr
        35                  40                  45

Glu Glu Glu Tyr Leu Ala Leu Cys Leu Ile Met Leu Ala Arg Ser Gly
    50                  55                  60

Thr Gly Thr Arg Thr Gly Leu Thr Asp Ala Thr Thr Ser Gln Gln Pro
65                  70                  75                  80

Ala Asp Lys Lys Thr Ala Glu Leu Pro Pro Val His Lys Lys Glu Val
                85                  90                  95

Ala Thr Glu Gln Ala Glu Gln Ser Tyr Lys Cys Ser Val Cys Asp Lys
            100                 105                 110

Ala Phe Ser Ser Tyr Gln Ala Leu Gly Gly His Lys Ala Ser His Arg
        115                 120                 125

Lys Thr Thr Thr Thr Ala Thr Ala Ala Ser Asp Asp Asn Asn Pro Ser
    130                 135                 140

Thr Ser Thr Ser Thr Gly Ala Val Asn Ile Ser Ala Leu Asn Pro Thr
145                 150                 155                 160

Gly Arg Ser His Val Cys Ser Ile Cys His Lys Ala Phe Pro Thr Gly
                165                 170                 175

Gln Ala Leu Gly Gly His Lys Arg Arg His Tyr Glu Gly Lys Leu Gly
            180                 185                 190

Gly Asn Ser Arg Asp Leu Gly Gly Gly Gly Gly Gly Gly His Ser Gly
        195                 200                 205

Ser Val Leu Thr Thr Ser Asp Gly Gly Ala Ser Thr His Thr Leu Arg
    210                 215                 220

Asp Phe Asp Leu Asn Met Pro Ala Ser Pro Glu Leu Gln Leu Gly Leu
225                 230                 235                 240

Ser Ile Asp Cys Gly Arg Lys Ser Gln Leu Leu Pro Met Val Gln Glu
                245                 250                 255

Val Glu Ser Pro Met Pro Ala Lys Lys Pro Arg Leu Leu Phe Ser Leu
            260                 265                 270

Gly
```

<210> SEQ ID NO 187
<211> LENGTH: 274
<212> TYPE: PRT
<213> ORGANISM: Petunia x hybrida

<400> SEQUENCE: 187

```
Met Ala Leu Glu Ala Leu Lys Ser Pro Thr Ala Ala Thr Pro Ser Leu
1               5                   10                  15

Pro Pro Arg Tyr Glu Asp His Val Asp Met Asn Asn Leu Asp Ser Trp
            20                  25                  30

Val Lys Gly Lys Arg Ser Lys Arg Pro Arg Ile Glu Thr Pro Pro Ser
        35                  40                  45

Glu Glu Glu Tyr Leu Ala Leu Cys Leu Ile Met Leu Ala Arg Ser Gly
    50                  55                  60

Asn Gly Thr Thr Pro Gly Ser Thr Asp Thr Thr Ile Thr Thr Thr Ile
65                  70                  75                  80

Ser Lys Glu Pro Glu Lys Lys Asn Arg Glu Leu Thr Pro Val His Gln
                85                  90                  95

Glu Thr Glu Gln Ser Tyr Lys Cys Ser Val Cys Asp Lys Ser Phe Ser
            100                 105                 110
```

-continued

```
Ser Tyr Gln Ala Leu Gly Gly His Lys Ala Ser His Arg Lys Ile Thr
        115                 120                 125

Thr Ile Ala Thr Thr Ala Leu Leu Asp Asp Asn Asn Asn Asn Pro Thr
    130                 135                 140

Thr Ser Asn Ser Thr Ser Gly Asn Val Val Asn Asn Ile Ser Ala Leu
145                 150                 155                 160

Asn Pro Ser Gly Arg Ser His Val Cys Ser Ile Cys His Lys Ala Phe
                165                 170                 175

Pro Thr Gly Gln Ala Leu Gly Gly His Lys Arg Arg His Tyr Glu Gly
            180                 185                 190

Lys Leu Gly Gly Asn Asn Asn Asn His Arg Asp Gly Gly Gly His Ser
        195                 200                 205

Gly Ser Val Val Thr Thr Ser Asp Gly Gly Ala Ser Thr His Thr Leu
    210                 215                 220

Arg Asp Phe Asp Leu Asn Met Leu Pro Pro Ser Pro Glu Leu Gln Leu
225                 230                 235                 240

Gly Leu Ser Ile Asp Cys Asp Leu Lys Ser Gln Ile Pro Ile Glu Gln
                245                 250                 255

Glu Val Glu Ser Pro Met Pro Leu Lys Lys Pro Arg Leu Leu Phe Ser
            260                 265                 270

Met Asp


<210> SEQ ID NO 188
<211> LENGTH: 193
<212> TYPE: PRT
<213> ORGANISM: Arabidopsis thaliana

<400> SEQUENCE: 188

Met Ala Leu Glu Ala Leu Asn Ser Pro Arg Leu Val Glu Asp Pro Leu
1               5                   10                  15

Arg Phe Asn Gly Val Glu Gln Trp Thr Lys Cys Lys Lys Arg Ser Lys
            20                  25                  30

Arg Ser Arg Ser Asp Leu His His Asn His Arg Leu Thr Glu Glu Glu
        35                  40                  45

Tyr Leu Ala Phe Cys Leu Met Leu Leu Ala Arg Asp Gly Gly Asp Leu
    50                  55                  60

Asp Ser Val Thr Val Ala Glu Lys Pro Ser Tyr Lys Cys Gly Val Cys
65                  70                  75                  80

Tyr Lys Thr Phe Ser Ser Tyr Gln Ala Leu Gly Gly His Lys Ala Ser
                85                  90                  95

His Arg Ser Leu Tyr Gly Gly Gly Glu Asn Asp Lys Ser Thr Pro Ser
            100                 105                 110

Thr Ala Val Lys Ser His Val Cys Ser Val Cys Gly Lys Ser Phe Ala
        115                 120                 125

Thr Gly Gln Ala Leu Gly Gly His Lys Arg Cys His Tyr Asp Gly Gly
    130                 135                 140

Val Ser Asn Ser Glu Gly Val Gly Ser Thr Ser His Val Ser Ser Ser
145                 150                 155                 160

Ser His Arg Gly Phe Asp Leu Asn Ile Ile Pro Val Gln Gly Phe Ser
                165                 170                 175

Pro Asp Asp Glu Val Met Ser Pro Met Ala Thr Lys Lys Pro Arg Leu
            180                 185                 190

Lys
```

<210> SEQ ID NO 189
<211> LENGTH: 193
<212> TYPE: PRT
<213> ORGANISM: Arabidopsis thaliana

<400> SEQUENCE: 189

```
Met Ala Leu Glu Ala Leu Asn Ser Pro Arg Leu Val Glu Asp Pro Leu
1               5                   10                  15

Arg Phe Asn Gly Val Glu Gln Trp Thr Lys Cys Lys Lys Arg Ser Lys
            20                  25                  30

Arg Ser Arg Ser Asp Leu His His Asn His Arg Leu Thr Glu Glu Glu
        35                  40                  45

Tyr Leu Ala Phe Cys Leu Met Leu Leu Ala Arg Asp Gly Gly Asp Leu
    50                  55                  60

Asp Ser Val Thr Val Glu Glu Lys Pro Ser Tyr Lys Cys Gly Val Cys
65                  70                  75                  80

Tyr Lys Thr Phe Ser Ser Tyr Gln Ala Leu Gly Gly His Lys Ala Ser
                85                  90                  95

His Arg Ser Leu Tyr Gly Gly Gly Asp Asn Asp Lys Ser Thr Pro Ser
            100                 105                 110

Thr Ala Val Lys Ser His Val Cys Ser Val Cys Gly Lys Ser Phe Ala
        115                 120                 125

Thr Gly Gln Ala Leu Gly Gly His Lys Arg Cys His Tyr Asp Gly Gly
    130                 135                 140

Val Ser Asn Ser Glu Gly Val Gly Ser Thr Ser His Val Ser Ser Ser
145                 150                 155                 160

Ser His Arg Gly Phe Asp Leu Asn Ile Leu Pro Val Gln Gly Phe Ser
                165                 170                 175

Arg Asp Asp Glu Val Met Ser Pro Met Ala Thr Lys Lys Pro Arg Leu
            180                 185                 190

Lys
```

<210> SEQ ID NO 190
<211> LENGTH: 215
<212> TYPE: PRT
<213> ORGANISM: Arabidopsis thaliana

<400> SEQUENCE: 190

```
Met Ala Leu Asp Thr Leu Asn Ser Pro Thr Ser Thr Thr Thr Thr Thr
1               5                   10                  15

Ala Pro Pro Pro Phe Leu Arg Cys Leu Asp Glu Thr Glu Pro Glu Asn
            20                  25                  30

Leu Glu Ser Trp Thr Lys Arg Lys Arg Thr Lys Arg His Arg Ile Asp
        35                  40                  45

Gln Pro Asn Pro Pro Pro Ser Glu Glu Glu Tyr Leu Ala Leu Cys Leu
    50                  55                  60

Leu Met Leu Ala Arg Gly Ser Ser Asp His His Ser Pro Pro Ser Asp
65                  70                  75                  80

His His Ser Leu Ser Pro Leu Ser Asp His Gln Lys Asp Tyr Lys Cys
                85                  90                  95

Ser Val Cys Gly Lys Ser Phe Pro Ser Tyr Gln Ala Leu Gly Gly His
            100                 105                 110

Lys Thr Ser His Arg Lys Pro Val Ser Val Asp Val Asn Asn Ser Asn
        115                 120                 125

Gly Thr Val Thr Asn Asn Gly Asn Ile Ser Asn Gly Leu Val Gly Gln
```

-continued

```
    130                 135                 140

Ser Gly Lys Thr His Asn Cys Ser Ile Cys Phe Lys Ser Phe Pro Ser
145                 150                 155                 160

Gly Gln Ala Leu Gly Gly His Lys Arg Cys His Tyr Asp Gly Gly Asn
                165                 170                 175

Gly Asn Ser Asn Gly Asp Asn Ser His Lys Phe Asp Leu Asn Leu Pro
            180                 185                 190

Ala Asp Gln Val Ser Asp Glu Thr Ile Gly Lys Ser Gln Leu Ser Gly
        195                 200                 205

Glu Glu Thr Lys Ser Val Leu
    210                 215


<210> SEQ ID NO 191
<211> LENGTH: 277
<212> TYPE: PRT
<213> ORGANISM: Petunia x hybrida

<400> SEQUENCE: 191

Met Ala Leu Glu Ala Leu Lys Ser Pro Thr Ala Ala Thr Pro Thr Leu
1               5                   10                  15

Pro Pro Arg Tyr Glu Asp Gln Val Asp Met Ser Asn Leu Asp Ser Trp
            20                  25                  30

Val Lys Gly Lys Arg Ser Lys Arg Pro Arg Ile Glu Thr Pro Pro Ser
        35                  40                  45

Glu Glu Glu Tyr Leu Ala Leu Cys Leu Ile Met Leu Ala Arg Ser Gly
    50                  55                  60

Asn Gly Thr Thr Pro Ser Ser Ile Pro Gly Ser Thr Asp Thr Thr Thr
65                  70                  75                  80

Ile Ser Lys Glu Pro Glu Lys Lys Asn Arg Asp Val Ala Pro Val Tyr
                85                  90                  95

Gln Glu Thr Glu Gln Ser Tyr Lys Cys Ser Val Cys Asp Lys Ser Phe
            100                 105                 110

Ser Ser Tyr Gln Ala Leu Gly Gly His Lys Ala Ser His Arg Lys Ile
        115                 120                 125

Thr Thr Ile Ala Thr Thr Ala Leu Leu Asp Asp Asn Asn Asn Asn Pro
    130                 135                 140

Thr Thr Ser Asn Ser Thr Asn Gly Asn Val Val Asn Asn Ile Ser Thr
145                 150                 155                 160

Leu Asn Pro Ser Gly Arg Ser His Val Cys Ser Ile Cys His Lys Ala
                165                 170                 175

Phe Pro Ser Gly Gln Ala Leu Gly Gly His Lys Arg Arg His Tyr Glu
            180                 185                 190

Gly Lys Leu Gly Gly Asn Asn Asn Asn Asn His Arg Asp Gly Gly Gly
        195                 200                 205

His Ser Gly Ser Val Val Thr Thr Ser Asp Gly Gly Ala Ser Thr His
    210                 215                 220

Thr Leu Arg Asp Phe Asp Leu Asn Met Leu Pro Pro Ser Pro Glu Leu
225                 230                 235                 240

Gln Leu Gly Leu Ser Ile Asp Cys Gly Leu Lys Ser Gln Gln Val Pro
                245                 250                 255

Ile Glu Gln Glu Val Glu Ser Pro Met Pro Leu Lys Lys Pro Arg Leu
            260                 265                 270

Leu Phe Ser Met Asp
        275
```

-continued

<210> SEQ ID NO 192
<211> LENGTH: 245
<212> TYPE: PRT
<213> ORGANISM: Arabidopsis thaliana

<400> SEQUENCE: 192

Met Ala Leu Glu Thr Leu Asn Ser Pro Thr Ala Thr Thr Thr Ala Arg
1 5 10 15

Pro Leu Leu Arg Tyr Arg Glu Glu Met Glu Pro Glu Asn Leu Glu Gln
20 25 30

Trp Ala Lys Arg Lys Arg Thr Lys Arg Gln Arg Phe Asp His Gly His
35 40 45

Gln Asn Gln Glu Thr Asn Lys Asn Leu Pro Ser Glu Glu Glu Tyr Leu
50 55 60

Ala Leu Cys Leu Leu Met Leu Ala Arg Gly Ser Ala Val Gln Ser Pro
65 70 75 80

Pro Leu Pro Pro Leu Pro Ser Arg Ala Ser Pro Ser Asp His Arg Asp
85 90 95

Tyr Lys Cys Thr Val Cys Gly Lys Ser Phe Ser Ser Tyr Gln Ala Leu
100 105 110

Gly Gly His Lys Thr Ser His Arg Lys Pro Thr Asn Thr Ser Ile Thr
115 120 125

Ser Gly Asn Gln Glu Leu Ser Asn Asn Ser His Ser Asn Ser Gly Ser
130 135 140

Val Val Ile Asn Val Thr Val Asn Thr Gly Asn Gly Val Ser Gln Ser
145 150 155 160

Gly Lys Ile His Thr Cys Ser Ile Cys Phe Lys Ser Phe Ala Ser Gly
165 170 175

Gln Ala Leu Gly Gly His Lys Arg Cys His Tyr Asp Gly Gly Asn Asn
180 185 190

Gly Asn Gly Asn Gly Ser Ser Ser Asn Ser Val Glu Leu Val Ala Gly
195 200 205

Ser Asp Val Ser Asp Val Asp Asn Glu Arg Trp Ser Glu Glu Ser Ala
210 215 220

Ile Gly Gly His Arg Gly Phe Asp Leu Asn Leu Pro Ala Asp Gln Val
225 230 235 240

Ser Val Thr Thr Ser
245

<210> SEQ ID NO 193
<211> LENGTH: 248
<212> TYPE: PRT
<213> ORGANISM: Solanum tuberosum

<400> SEQUENCE: 193

Ile Glu Met Ala Leu Glu Ala Leu Asn Ser Pro Thr Gly Thr Ser Asn
1 5 10 15

Pro Gln Thr Phe Lys Phe Glu Ser Lys Gly Gln Gln Gln Leu Arg Tyr
20 25 30

Leu Glu Asn Trp Thr Lys Gly Lys Arg Ser Lys Arg Ser Arg Ser Met
35 40 45

Glu Arg Gln Pro Thr Glu Glu Glu Tyr Leu Ala Ile Cys Leu Ile Met
50 55 60

Leu Ala Arg Ser Asp Gly Ser Val Asn Gln Val Arg Ser Leu Pro Pro
65 70 75 80

-continued

```
Pro Val Pro Val Met Lys Ile His Ala Pro Ser Glu Lys Met Glu Tyr
                85                  90                  95

Lys Cys Ser Val Cys Gly Lys Gly Phe Gly Ser Tyr Gln Ala Leu Gly
            100                 105                 110

Gly His Lys Ala Ser His Arg Lys Leu Ile Ala Gly Val Ser Gly Gly
        115                 120                 125

Gly Asp Asp Gln Ser Thr Thr Ser Thr Thr Thr Asn Ala Thr Gly Thr
    130                 135                 140

Thr Ser Ser Gly Asn Gly Asn Gly Ser Gly Arg Thr His Glu Cys Ser
145                 150                 155                 160

Ile Cys His Lys Cys Phe Pro Thr Gly Gln Ala Leu Gly Gly His Lys
                165                 170                 175

Arg Cys His Tyr Asp Gly Gly Asn Gly Asn Gly Asn Ala Asn Ser Ser
            180                 185                 190

Val Ser Ala Ser Val Gly Val Thr Ser Ser Glu Gly Val Gly Ser Thr
        195                 200                 205

Ile Ser His Arg Asp Phe Asp Leu Asn Ile Pro Ala Leu Pro Glu Phe
    210                 215                 220

Trp Pro Gly Phe Gly Ser Gly Glu Asp Glu Val Glu Ser Pro His Pro
225                 230                 235                 240

Ala Lys Lys Ser Arg Leu Ser Leu
                245


<210> SEQ ID NO 194
<211> LENGTH: 269
<212> TYPE: PRT
<213> ORGANISM: Gossypium raimondii

<400> SEQUENCE: 194

Leu Ala Leu Cys Phe Cys Ser Gln Thr Arg Arg Asp Ser Glu Val Phe
1               5                   10                  15

Asp Met Ala Leu Glu Ala Leu Asn Ser Pro Ala Thr Pro Phe Thr Asn
            20                  25                  30

Lys Tyr Asp Asp Val Asp Asn Asn Tyr Val Glu Thr Trp Lys Lys Gly
        35                  40                  45

Lys Arg Ser Lys Arg Gln Arg Gly Asp Ser Pro Ala Ala Val Glu Leu
    50                  55                  60

Gln Pro Thr Thr Glu Glu Glu Tyr Leu Ala Leu Cys Leu Ile Met Leu
65                  70                  75                  80

Ala Arg Gly Ser Ser Gly Ala Asp Leu Asp Val Ile Arg Arg Ser Ser
                85                  90                  95

Ser Ser Ser Ser Pro Pro Pro Pro Pro Pro Ala Leu Lys Leu Ser Tyr
            100                 105                 110

Lys Cys Ser Val Cys Asp Lys Ala Phe Pro Ser Tyr Gln Ala Leu Gly
        115                 120                 125

Gly His Lys Ala Ser His Arg Lys Pro Leu Ser Ala Asp Ala Ala Thr
    130                 135                 140

Thr Thr Ala Ala Ala Asn Val Asp Asn Pro Ser Thr Thr Ser Thr Ala
145                 150                 155                 160

Thr Thr Ala Thr Ser Ser Gly Arg Leu His Glu Cys Ser Ile Cys His
                165                 170                 175

Lys Ser Phe Pro Thr Gly Gln Ala Leu Gly Gly His Lys Arg Cys His
            180                 185                 190

Tyr Glu Gly Gly Asn Asn Asn Asn Asn Asn Asn Lys Asn Asn Asn Asn
        195                 200                 205
```

-continued

```
Ser Gly Ser Val Ser Val Ser Gly Val Thr Ser Ser Asp Gly Gly Ala
    210                 215                 220

Leu Ser His Asn His Arg Ala Val Asp Phe Asp Phe Asp Leu Asn Leu
225                 230                 235                 240

Pro Ala Leu Pro Glu Phe Ser Gln Met Tyr Pro Asp Glu Glu Glu Val
                245                 250                 255

Gln Ser Pro Leu Pro Thr Gln Lys Pro Arg Phe Leu Ile
            260                 265


<210> SEQ ID NO 195
<211> LENGTH: 195
<212> TYPE: PRT
<213> ORGANISM: Vitis aestivalis

<400> SEQUENCE: 195

Glu Ser Trp Ala Lys Arg Lys Arg Ser Lys Arg Pro Arg Phe Asp Asn
1               5                   10                  15

Gln Pro Thr Glu Glu Glu Tyr Leu Ala Leu Cys Leu Ile Met Leu Ala
            20                  25                  30

Arg Gly Gly Ala Ala Ser Ser Thr Val Ser His Arg Arg His Leu Ser
        35                  40                  45

Pro Pro Pro Ala Leu Gln Val Glu Ala Pro Lys Leu Thr Tyr Lys Cys
    50                  55                  60

Ser Val Cys Asn Lys Ala Phe Ala Ser Tyr Gln Ala Leu Gly Gly His
65                  70                  75                  80

Lys Ala Ser His Arg Lys Gln Ser Gly Ser Asp Asp Leu Ser Ala Ser
                85                  90                  95

Ile Thr Thr Thr Ser Thr Ala Ala Ala Ala Ser Gly Gly Arg Thr His
            100                 105                 110

Glu Cys Ser Ile Cys His Lys Thr Phe Pro Thr Gly Gln Ala Leu Gly
        115                 120                 125

Gly His Lys Arg Cys His Tyr Glu Gly Gly Ala Ser Val Ser Ser Gly
    130                 135                 140

Val Thr Ser Ser Glu Gly Val Gly Ser Thr His Ser His Arg Asp Phe
145                 150                 155                 160

Asp Leu Asn Leu Pro Ala Phe Pro Glu Leu Trp Ser Ala Arg Arg Phe
                165                 170                 175

Pro Val Asp Asp Glu Val Glu Ser Pro Leu Pro Thr Lys Lys Pro Arg
            180                 185                 190

Leu Gln Met
        195


<210> SEQ ID NO 196
<211> LENGTH: 226
<212> TYPE: PRT
<213> ORGANISM: Lycopersicon esculentum

<400> SEQUENCE: 196

Met Ala Leu Glu Ala Leu Asn Ser Pro Thr Gly Thr Thr Ser Asn Pro
1               5                   10                  15

Gln Thr Phe Gln Phe Glu Ser Lys Gly Gln Gln Gln Leu Arg Tyr Leu
            20                  25                  30

Glu Asn Trp Thr Lys Gly Lys Arg Ser Lys Arg Ser Arg Ser Met Asp
        35                  40                  45

Arg Gln Pro Thr Glu Glu Glu Tyr Leu Ala Leu Cys Leu Ile Met Leu
    50                  55                  60
```

```
Ala Arg Ser Asp Gly Ser Val Asn His Val Arg Ser Leu Pro Pro Pro
65                  70                  75                  80

Val Pro Val Met Lys Ile His Glu Thr Ala Glu Lys Met Leu Tyr Arg
                85                  90                  95

Cys Ser Val Cys Gly Lys Gly Phe Gly Ser Tyr Gln Ala Leu Gly Gly
            100                 105                 110

His Lys Ala Ser His Arg Lys Leu Ile Ala Gly Gly Asp Asp Gln Ser
        115                 120                 125

Thr Thr Ser Thr Thr Thr Asn Ala Asn Gly Thr Thr Ser Ser Gly Asn
    130                 135                 140

Gly Asn Gly Asn Gly Ser Gly Thr Gly Arg Thr His Glu Cys Ser Ile
145                 150                 155                 160

Cys His Lys Cys Phe Pro Thr Gly Gln Ala Leu Gly Gly His Lys Arg
                165                 170                 175

Cys His Tyr Asp Gly Gly Asn Ser Asn Gly Asn Gly Asn Ala Asn Ala
            180                 185                 190

Asn Ser Ser Ile Ser Ala Ser Val Gly Val Thr Ser Ser Glu Gly Val
        195                 200                 205

Gly Ser Thr Ile Ser His Arg Asp Phe Asp Leu Asn Ile Pro Ala Leu
    210                 215                 220

Pro Gly
225


<210> SEQ ID NO 197
<211> LENGTH: 198
<212> TYPE: PRT
<213> ORGANISM: Medicago truncatula

<400> SEQUENCE: 197

Trp Thr Lys Gly Lys Arg Ser Lys Arg Ser Arg Met Asp Gln Ser Ser
1               5                   10                  15

Cys Thr Glu Glu Glu Tyr Leu Ala Leu Cys Leu Ile Met Leu Ala Arg
            20                  25                  30

Ser Gly Asn Asn Asn Asp Asn Lys Thr Glu Ser Val Pro Val Pro Ala
        35                  40                  45

Pro Leu Thr Thr Val Lys Leu Ser His Lys Cys Ser Val Cys Asn Lys
    50                  55                  60

Ala Phe Ser Ser Tyr Gln Ala Leu Gly Gly His Lys Ala Ser His Arg
65                  70                  75                  80

Lys Ala Val Met Ser Ala Thr Thr Val Glu Asp Gln Thr Thr Thr Thr
                85                  90                  95

Ser Ser Ala Val Thr Thr Ser Ser Ala Ser Asn Gly Lys Asn Lys Thr
            100                 105                 110

His Glu Cys Ser Ile Cys His Lys Ser Phe Pro Thr Gly Gln Ala Leu
        115                 120                 125

Gly Gly His Lys Arg Cys His Tyr Glu Gly Ser Val Gly Ala Gly Ala
    130                 135                 140

Gly Ser Ser Ala Val Thr Ala Ala Ser Glu Gly Val Gly Ser Ser His
145                 150                 155                 160

Ser His His Arg Asp Phe Asp Leu Asn Leu Pro Ala Phe Pro Asp Phe
                165                 170                 175

Ser Lys Lys Phe Phe Val Asp Asp Glu Val Ser Ser Pro Leu Pro Ala
            180                 185                 190

Ala Lys Lys Pro Cys Leu
```

-continued

```
        195


<210> SEQ ID NO 198
<211> LENGTH: 219
<212> TYPE: PRT
<213> ORGANISM: Populus sp.
<220> FEATURE:
<221> NAME/KEY: misc_feature
<222> LOCATION: (199)..(199)
<223> OTHER INFORMATION: Xaa can be any naturally occurring amino acid

<400> SEQUENCE: 198

Lys Lys Asn Ser Val Ser Arg Ile Gln Ile Met Ala Leu Glu Ala Leu
1               5                   10                  15

Asn Ser Pro Thr Thr Ala Ala Pro Leu Asn Tyr Glu Glu Thr Trp Ile
            20                  25                  30

Lys Arg Lys Arg Ser Lys Arg Pro Arg Ser Glu Ser Pro Ser Thr Glu
        35                  40                  45

Glu Glu Tyr Leu Ala Phe Cys Leu Ile Met Leu Ala Arg Gly Gly Ser
    50                  55                  60

Thr Ala Ala Thr Ala Lys Lys Thr Ala Ser Ala Ser Pro Ala Pro Pro
65                  70                  75                  80

Gln Pro Pro Thr Leu Asp Leu Ser Tyr Lys Cys Thr Val Cys Asn Lys
                85                  90                  95

Ala Phe Ser Ser Tyr Gln Ala Leu Gly Gly His Lys Ala Ser His Arg
            100                 105                 110

Lys Ser Ser Ser Glu Ser Thr Val Ala Thr Ala Ala Glu Asn Pro Ser
        115                 120                 125

Ala Ser Thr Thr Thr Asn Thr Thr Thr Thr Thr Thr Asn Gly Arg Thr
    130                 135                 140

His Glu Cys Ser Ile Cys His Lys Thr Phe Leu Thr Gly Gln Ala Leu
145                 150                 155                 160

Gly Gly His Lys Arg Cys His Tyr Glu Gly Thr Ile Gly Gly Asn Asn
                165                 170                 175

Ser Ser Ser Ala Ser Ala Ala Ile Thr Thr Ser Asp Gly Gly Ala Val
            180                 185                 190

Gly Gly Gly Gly Val Ser Xaa Ser Lys Ser Gln Arg Ser Gly Gly Gly
        195                 200                 205

Phe Asp Phe Asp Leu Asn Leu Pro Ala Leu Pro
    210                 215


<210> SEQ ID NO 199
<211> LENGTH: 240
<212> TYPE: PRT
<213> ORGANISM: Citrus sinensis
<220> FEATURE:
<221> NAME/KEY: misc_feature
<222> LOCATION: (235)..(236)
<223> OTHER INFORMATION: Xaa can be any naturally occurring amino acid

<400> SEQUENCE: 199

Arg Tyr Glu Asp Ser Trp Thr Lys Arg Arg Arg Ser Lys Arg Leu Arg
1               5                   10                  15

Thr Asp Glu Ser Pro Gln Leu Pro Ala Ala Ala Ala Ala Pro Thr Glu
            20                  25                  30

Glu Glu Tyr Met Ala Leu Cys Leu Ile Met Leu Ala Arg Gly Thr Thr
        35                  40                  45

Thr Ala Asn Thr Ala Pro Ala Glu Arg Thr Pro Thr Leu Ala Pro Glu
    50                  55                  60
```

-continued

```
Gln Lys Pro Leu Asp Gln Phe Pro Glu Pro Pro Ser Leu Lys Leu Ser
65                  70                  75                  80

Tyr Lys Cys Ser Val Cys Asn Lys Ala Phe Ser Ser Tyr Gln Ala Leu
                85                  90                  95

Gly Gly His Lys Ala Ser His Arg Lys Asn Ala Ala Asp Ala Ser Ala
            100                 105                 110

Ser Pro Asn Ala Ala Ala Ala Ser Asp Val Thr Pro Pro Pro Ser Ala
        115                 120                 125

Thr Ala Ser Ser Gly Ser Gly Gly Arg Thr His Glu Cys Ser Ile Cys
    130                 135                 140

His Lys Ser Phe Pro Thr Gly Gln Ala Leu Gly Gly His Lys Arg Cys
145                 150                 155                 160

His Tyr Glu Gly Gly Ile Asn Asn Asn Asn Asn Ser Ser Ser Asn Asn
                165                 170                 175

Asn Lys Ser Asn Asn Asn Ser Asp Val Val Thr Ser Gly Ser Ala Ser
            180                 185                 190

Val Gly Ala Ser Ala Val Thr Phe Ser Glu Gly Gly Gly Ser Ser Ser
        195                 200                 205

Gln Arg Gly Phe Asp Leu Asn Leu Pro Ala Leu Pro Glu Phe Trp Ser
    210                 215                 220

Gln Glu Val Glu Ser Pro Leu Pro Ala Lys Xaa Xaa Lys Leu Leu Met
225                 230                 235                 240


<210> SEQ ID NO 200
<211> LENGTH: 196
<212> TYPE: PRT
<213> ORGANISM: Lotus corniculatus

<400> SEQUENCE: 200

Trp Ala Lys Arg Lys Arg Ser Lys Arg Ser Arg Thr Asp Ser His His
1               5                   10                  15

Asn His Ala Ser Cys Thr Glu Glu Glu Tyr Leu Ala Leu Cys Leu Ile
            20                  25                  30

Met Leu Ala Arg Gly Ser Thr Ala Val Thr Pro Lys Leu Thr Leu Ser
        35                  40                  45

Arg Pro Ala Pro Val Thr Ala Glu Lys Leu Ser Tyr Lys Cys Ser Val
    50                  55                  60

Cys Glu Lys Thr Phe Pro Ser Tyr Gln Ala Leu Gly Gly His Lys Ala
65                  70                  75                  80

Ser His Arg Lys Leu Ala Gly Ala Ala Ala Glu Asp His Ser Thr Ser
                85                  90                  95

Ser Ala Val Thr Thr Ser Ser Ala Ser Asn Gly Gly Gly Lys Val His
            100                 105                 110

Gln Cys Ser Ile Cys Gln Lys Ser Phe Pro Thr Gly Gln Ala Leu Gly
        115                 120                 125

Gly His Lys Arg Cys His Tyr Glu Gly Gly Gly Gly Ala Ser Ser Thr
    130                 135                 140

Ala Thr Ala Thr Ala Ser Glu Gly Val Gly Ser Thr His Ser His Gln
145                 150                 155                 160

Arg Asn Phe Asp Leu Asn Leu Pro Ala Phe Pro Asp Phe Ser Ala Ser
                165                 170                 175

Lys Phe Phe Val Glu Glu Glu Val Ser Ser Pro Leu Pro Ser Lys Lys
            180                 185                 190

Pro Arg Leu Leu
```

-continued

195

<210> SEQ ID NO 201
<211> LENGTH: 687
<212> TYPE: DNA
<213> ORGANISM: Lolium perenne

<400> SEQUENCE: 201
atggccgtgg aggcggttct cgaagcggcg gcgatgatac agtcgccgcc gagcaagaag 60
atggaggcgt ctagtagcag cgacgaggcg ttcgaggcgt tgcagcagca cacggagggg 120
tggtccaaga agaagcgctc gaggcggcca cgggcgctcg agcccagcga ggaggagtac 180
ctcgcgttct gcctcgtcat gctggcgcgc ggccaccgcg acgccgcgcc ggagcacggg 240
tgctccgtct gcggcaaggc gttcgcgtcg taccaggcgc tcggcggcca caaggccagc 300
caccggaagc cacccacagc tccagccgcg gtggcagcaa gcgccgtccc cgaggaggac 360
aagccacggg cggctgcctc gtcctcgtct gggtccggcg atgccgctgg cggcggcaag 420
gtccacgagt gcaacgtgtg ccagaagacg ttcccgacgg ggcaggcgct gggcggccac 480
aagcggtgcc actacgacgg caccatcggc agcgccgccg cgcccacggt gaaggctgcc 540
aaggccgccg ccgcggcgag cgcgccgacg gcgacgaacc gggggttcga cctgaacgtg 600
ccggcgctgc cgggactcgc ggaggagggg gaggaggtgc tcagcccggt atccttcaag 660
aagccgaggc tcatgatcac cgcgtga 687

<210> SEQ ID NO 202
<211> LENGTH: 753
<212> TYPE: DNA
<213> ORGANISM: Oryza sativa

<400> SEQUENCE: 202
atggcggtgg aggcggttct tgaggcgtcg agaagtagta gtgaggagga ggcggaggtg 60
atcgtcacgc acggcggcgg cggcggcggc ggaggaggag gaggacaggt ggaggggtgg 120
gggaagcgga agcggtcgcg gcggcggcga ccgcagctgc cgccctccga ggaggagtac 180
ctcgcgctct gcctcctcat gctggcgcgc gggcgacgcg acggcgacga cgtggcggcg 240
tcggcgtcgg cggcggcggc ggcggtggag caccggtgct ccgtctgcgg caaggcgttc 300
gcgtcctacc aggctctcgg cggccacaag gccagccacc ggaagccgcc gccgccgccg 360
ccgcccgcca tggtcgacga cgacgaggtg gtggtggaga cgaaaccggc ggctatcgcg 420
acgccgtcct cgtcggcgtc gggcgtctcc ggcggcggcg gcgggagggc gcacgagtgc 480
aacgtgtgcg gcaaggcgtt cccgacgggg caggcgctgg gcggccacaa gcgatgccac 540
tacgacggca cgatcggcag cgccgccggc gccggcgcgt ccaagccggc ggcgaagacg 600
accgtggcgg tggcggcgag ccggggcttc gacctcaacc tgccggcgct gccggacgtc 660
gccgccgccg ccgaccagcg gtgcgcggcg gaggacgacg aggtgctcag ccctctcgcc 720
ttcaagaagc ccaggctcat gatcccggca tag 753

<210> SEQ ID NO 203
<211> LENGTH: 717
<212> TYPE: DNA
<213> ORGANISM: Oryza sativa

<400> SEQUENCE: 203
atggcggtgg aggaggttct tgatggcgcc gcgccgatgc tgtcgtcgtc gccggcggcg 60
agcggcgagg aggtgggggc gcggaagccg cagcaacggt gcggcggcgc cgaggggtgg 120

-continued

```
tccaagcgga agcgctcgag gcggcgccac cgcgaccgcg ccgctgcgcc gccgcctcac    180

ggttcggagg aggagcacct cgcgctcagc ctcctcatgc tggcgcgcgg ccaccgcgac    240

ccctcgccgg cgccgcagga gcagcacggg tgctccgtgt gcggcagggt gttctcgtcc    300

taccaggcgc tcggcggcca caagacgagc caccgcccca ggacgccgcc gacgatggcg    360

gccgttgtcg tcgtagacga gccggcagcg acgacggcct cgccggccgc gtcctcgtcc    420

aattccggct ccggcagcgg cggcggcggc ggaaacaagg tgcacgagtg ctccgtgtgc    480

aagaagacgt tcccgacggg gcaggcgctg ggcgggcaca agcggtgcca ctacgagggc    540

ccgatcggaa gcggcggcgg cgccgctgtc gccggccgcg ggttcgatct gaacctgccg    600

gcggtggcgc tgccggacat catgacggag cggtgcttgc cggcggcggc cgaggaggag    660

gaggtgctca gcccgcttgc aagcttcaag aagccaaggc taatgatccc tgcttaa       717
```

```
<210> SEQ ID NO 204
<211> LENGTH: 786
<212> TYPE: DNA
<213> ORGANISM: Triticum aestivum

<400> SEQUENCE: 204

atgtcgtcgt cggccatgga agcgctccac gccctgatcc cggagcagca ccagctggac     60

gttgaggcgg ctgcggctgt cagcagcgcc accagcggcg aggagagcgg ccacgtgctg    120

caggggtggg ccaagaggaa gcgatcgcgc cgccagcgct ccgaggagga gaacctcgcg    180

ctctgcctcc tcatgctctc gcgcggcggc aagcagcgtg ttcaggcgcc gcagccggag    240

tcgttcgctg cgccggtgcc tgccgagttc aagtgctccg tctgcggcaa gtccttcagc    300

tcctaccagg cgctcggagg ccacaagacg agccaccggg tgaagcagcc gtctcctccc    360

tctgatgccg ctgctgcccc actcgtggcc ctcccggccg tcgccgccat cctgccgtcc    420

gccgagccgg ccacgtcgtc caccgccgcg tcctccgacg gcgcgaccaa cagagtccac    480

aggtgctcca tctgccaaaa ggagttcccg actgggcagg cgctcggcgg gcacaagagg    540

aagcactacg acggaggcgt gggcgccgcc gcctcgtcga ccgagcttct ggccgccgcg    600

gccgccgagt ctgaggtggg gagcaccggc aacgggagct ccgccgcccg ggccttcgac    660

ctgaacattc cggccgtgcc ggagttcgtg tggaggccgt gcgccaaggg caagatgatg    720

tgggaggacg atgaggaggt gcagagcccc ctcgccttca agaagcctcg gcttctcacc    780

gcttga                                                               786
```

```
<210> SEQ ID NO 205
<211> LENGTH: 810
<212> TYPE: DNA
<213> ORGANISM: Oryza sativa

<400> SEQUENCE: 205

atgtcgagcg cgtcgtccat ggaagcgctc cacgccgcgg tgctcaagga ggagcagcag     60

cagcacgagg tggaggaggc gacggtcgtg acgagcagca gcgccacgag cggggaggag    120

ggcggacacc tgccccaggg gtgggcgaag cggaagcggt cgcgccgcca gcgatcggag    180

gaggagaacc tcgcgctctg cctcctcatg ctcgcccgcg gcggccacca ccgcgtccag    240

gcgccgcctc cgctctcggc ttcggcgccc ccgccggcag gtgcggagtt caagtgctcc    300

gtctgcggca agtccttcag ctcctaccag gcgctcggcg gccacaagac gagccaccgg    360

gtcaagctgc cgactccgcc cgcagctccc gtcttggctc ccgcccccgt cgccgccttg    420
```

-continued

```
ctgccttccg ccgaggaccg cgagccagcc acgtcatcca ccgccgcgtc ctccgacggc    480

atgaccaaca gagtccacag gtgttccatc tgccagaagg agttccccac cgggcaggcg    540

ctcggcgggc acaagaggaa gcactacgac ggtggcgtag gcgccggcgc cggcgcatct    600

tcaaccgagc tcctggccac ggtggccgcc gagtccgagg tgggaagctc cggcaacggc    660

cagtccgcca cccgggcgtt cgacctcaac ctcccggccg tgccggagtt cgtgtggcgg    720

ccgtgctcca agggcaagaa gatgtgggac gaggaggagg aggtccagag ccccctcgcc    780

ttcaagaagc cccggcttct caccgcgtaa                                     810
```

<210> SEQ ID NO 206
<211> LENGTH: 663
<212> TYPE: DNA
<213> ORGANISM: Oryza sativa

<400> SEQUENCE: 206

```
atggcgctcg acgggaagcc accggtgccg ccgccgtcca cgccgccgat ggactcgtgg     60

gcctgcggtg gtcgccgctc caagcgccgc ggcggcggcg gcgggagcag cgggagtagt    120

ggcagctccg gcggcggcgg cggcggcgag tccgaggagg agtacctcgc ggcctgcctc    180

ttgatgctcg cgcatggcgt ccgcgacgag gccgaggtcg tcggcgtcgc ggcggcgacg    240

gcgaagccac agcatgggta cgagtgctcg gtgtgcggca aggtgtacgg gtcctaccag    300

gcgctgggcg ggcacaagac gagccaccgc aagccgccgt cgccggcggc cgaaccggcg    360

gccggcgaag agccgtcctc cggcggggtg gccggcgagg cgaaggtgca ccgttgctcc    420

atctgcctcc gcacgttccc gtccgggcag gcgctgggcg ggcacaagcg gctgcactac    480

gagggcggcg ccgtcggaga cgccgtcaag gagaagaact ccctgaagac caaggcggcg    540

gtggcgacag cggtgctgaa ggacttcgac ctgaacctgc cggccgcggc gacgacggcg    600

ggggacgagg ccgagagctc accaccggag gccaagagag cacgtctgct gcttctcgtc    660

taa                                                                  663
```

<210> SEQ ID NO 207
<211> LENGTH: 737
<212> TYPE: DNA
<213> ORGANISM: Aegilops speltoides

<400> SEQUENCE: 207

```
tcggcacgag gccctgctcc atcaccacta gccagtagct agctactccc tcgcctcact     60

tccttcccga accactagct aactactgcc caccactcct ccttcgtgcc agagagaata    120

agcaacacgt tcttgcgtgt gttggatcgg cgtacgtgcg tgcatggcgg tggacgcggt    180

tcgcgacgcg gcggcgatgg tgagcgagga ggaggaggag gggcagctgc ggtgcgacga    240

ggggtggggc aagcggaggc gcccgaggcg ccagcggcag cgcgcgccca gcgaggagga    300

gcacctcgcg ctcagcctcc tcatgctggc gcgcggtcac cgcgaccggc acctgcttgg    360

gtcgtccgag ccggcgcagg agcaccgctg ctccgtgtgc ggcaaggggt tcccgtccta    420

ccaggccctg ggcgggcaca aggcgagcca ccgcccgaag ccggcgcccg ccggcgcgga    480

cgagcccgct gccacgacgg cggcctcgcc cgccgcatcc tcgtcaacga cgtccagcgg    540

cgcgggcgga ggtggcaggg tgcacgagtg ctccgtgtgc aagaagacct tcccgaccgg    600

gcaggcgctg ggcgggcaca agcggtgcca ctacgagggc cccatcggcg ccaccgtggt    660

tgcgagccga gggttcgacc tgaacctgcc ggcgctgccg gacatcgtca ccgagcgcga    720

gcggtgcatg ccggcac                                                   737
```

-continued

<210> SEQ ID NO 208
<211> LENGTH: 655
<212> TYPE: DNA
<213> ORGANISM: Secale cereale

<400> SEQUENCE: 208
gcggaggcgc ccgaggcggc agcggcagcg cgcgcccagc gaggaggagc acctcgcgct 60
cagcctcctc atgctggcgc gcggtcaccg cgaccggcac ctgcctccgt cgtccgagcc 120
ggcacaggag caccgctgct ccgtgtgcgg caaggggttc ccgtcctacc aggccctcgg 180
cgggcacaag gcgagccacc gcccgaagcc ggcgcccgcc ggcgcggacg agcccgctgc 240
cacggcggcg gcctcgcccg ccgcatcctc gtcaacgacg tccagcggcg cgggtgtcaa 300
ggtgcacgag tgctccgtgt gcaagaagac cttcccgacg gggcaggcgc tgggcgggca 360
caagcggtgc cactacgagg gccccatcgg cggcggcggt gcccccgcgg ttgcgagccg 420
agggttcgac ctgaaccttc cggcgctgcc ggacatcgtc accgagcgcg agcggtgcat 480
gccggcgccg gccgatgagg aggaggtgct cagcccgctg gcgttcaaga agccgaggct 540
aatgatcccg gcataattaa atcatcaaag aattaatgag tgaattgcgt cggtgtgtat 600
tctttttgga ttgcttatgc tcggctggtt ggtgtaaaaa aaaaaaaaaa aaaaa 655

<210> SEQ ID NO 209
<211> LENGTH: 666
<212> TYPE: DNA
<213> ORGANISM: Saccharum officinarum
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (666)..(666)
<223> OTHER INFORMATION: n is a, c, g, or t

<400> SEQUENCE: 209
ggacgacgtg gtggcggctg cagcggatca ggtcgccacg accagcaaca gcagcggcac 60
ggcggcagag gaggacaagg atgtcaagac ggcggtgcag caggagcatg gccaagggct 120
ggcgaagcgg aagcgctcca ggcgccgccg cgaccgcgag cagcagcagc tgcccaagga 180
gcaccccacc caggaggagt acctggcgca gtgcctcgtc atgctggcca ccggccgccg 240
cgacggcgac gtcccggccc tggcctccgc gccgccgccg ccgcaggggc agcagcagga 300
ccacgcgtgc tccgtctgcg gcaaggcgtt cccgacgtac caggcgctcg gcgggcacaa 360
ggccagccac cgcaccaggc cctcgccgcc gtcggcggca acggaagtag taggggatca 420
ccacgaggag cagaagccgg tgctgccgtc ctcgtcgtcc gcggcctccg ctggcgccga 480

-continued caacaacaag cccgcggcgg cgcacgagtg caacgtgtgc ggcaaggcgt tcccgacggg 540
gcaggcgctg ggcggccaca agcgccgcca ctacgacggc accatcggca gcgccgccgc 600
gcccgcgcgc gcgtnctnct nctnctncgc gggcggcggc caacagcagc cgcgccacgc 660 cggcgn 666

<210> SEQ ID NO 210
<211> LENGTH: 762
<212> TYPE: DNA
<213> ORGANISM: Nicotiana benthamiana

<400> SEQUENCE: 210
atggcacttg aagctttgaa ttctccaact acaacaactc caccaacttt ccaatttgag 60
aacaacggcc cgcttcgata ccttgaaaat tggactaaag gtaaaagatc aaaaaggcct 120
cgtagtatgg aacgacagcc tactgaagaa gagtatttgg ctctttgttt gattatgcta 180
gcgcgtagcg atggctctgc taatcgggaa cagtctctac caccaccgcc agttccagtg 240
atgaaaatac acgcgccacc ggaggagaag atggtgtaca agtgttcagt ttgtggtaag 300
ggttttggat cttatcaagc tttaggagga cacaaggcta gtcaccggaa gctcgtcgcc 360
ggcggtggag gaggagatga ccagtcaact acctccacaa ccactaacgc tacaggaact 420
actagctctg ctaacggtaa cggtaacgga agcggaaaaa ctcacgagtg ttcaatttgc 480
cacaagcgtt ttcctactgg acaggctttg ggtggacaca aaaggtgtca ctacgacggc 540
ggtaacagta acggtggcgt tagcgttagt gctagcgttg gactgacgtc atcagaaggt 600
gtggggtcca ctgtgagtca ccgtgacttt gacttgaaca ttccggcgtt gccggaattc 660
tggcccggat ttggttccgg cgaggatgaa gtggagagtc ctcatccgac gaagaaatcg 720
cggctatctc tgcctccaaa atttgaatta ttccgggaat ag 762

<210> SEQ ID NO 211
<211> LENGTH: 786
<212> TYPE: DNA
<213> ORGANISM: Capsicum annuum

<400> SEQUENCE: 211
atggcacttg aagctttgaa ttctccaact ggtacaccaa ctccgccacc gtttcaattt 60
gagagcgacg gccaacagct tcgatatatc gaaaactgga ggaagggaaa gagatctaaa 120
aggtcacgca gcatggagca ccagcctact gaggaagaat acttagcgct ttgtttgatc 180
atgcttgcac gtagcggtgg ctccgttaat catcaacgat ctctaccacc gccggctccg 240
gtgatgaaac tgcacgcgcc gtcgtcatca tcggcggcgg aggaggagaa ggagaagatg 300
gtgtataagt gttcggtttg tggtaaggga tttgggtctt atcaagcttt aggtggacac 360
aaagctagtc accggaaact cgtacccggc ggagatgatc agtcaactac ctccacaacc 420
actaacgcaa ccggaacaac aacctccgtt aacggcaacg gcaacagaag tggaaggact 480
cacgagtgtt cgatttgtca caagtgtttt cccactggac aagctttagg tggacacaaa 540
aggtgtcact acgacggcgg tatcggtaac ggaaacgcta acagtggcgt tagtgctagc 600
gttggagtga cgtcatcgga gggtgtgggg tccacagtca gtcaccggga tttcgacttg 660
aacattccgg cgttgccgga attctggctg ggatttggtt ccggcgaaga tgaggtggag 720
agtccacatc cggcgaagaa atcgcggtta tgtttgcctc caaaatatga attatttcaa 780
cattaa 786

-continued

<210> SEQ ID NO 212
<211> LENGTH: 708
<212> TYPE: DNA
<213> ORGANISM: Medicago sativa

<400> SEQUENCE: 212
atggctatgg aagcacttaa ctcacccacc actgctactc ctttcacacc ctttgaggaa 60
ccaaatctga gttatcttga aacaccgtgg acgaaaggta aacgatcaaa gcgttctcgc 120
atggatcaat cttcatgcac tgaagaagag tatctcgctc tttgtctcat catgcttgct 180
cgcagcggta acaacaacga caaaaagtct gattcggtgg cgacgccgct aaccaccgtt 240
aaactcagtc acaaatgctc agtctgcaac aaagctttct catcttatca agccctaggt 300
ggacacaaag ccagtcaccg gaaagctgtt atgtccgcaa ccaccgctga agatcagatc 360
accaccactt catccgccgt gactaccagc tctgcttcca acggtaagaa caagactcat 420
gagtgttcca tctgtcacaa atccttccct actggacagg ctttgggagg acacaagcgt 480
tgtcactacg aaggcagcgt tggtgccggt gccggtgctg gaagtaacgc tgtaactgcc 540
tctgaaggag ttggattgtc acacagccac caccgtgatt ttgatcttaa cctcccggct 600
tttccggact tttcaaagaa gtttttcgtg gatgacgagg tttttagtcc tttacctgct 660
gcaaagaagc cctgtctttt caagctggaa attccttctc attactga 708

<210> SEQ ID NO 213
<211> LENGTH: 723
<212> TYPE: DNA
<213> ORGANISM: Artificial
<220> FEATURE:
<223> OTHER INFORMATION: Glycine max

<400> SEQUENCE: 213
atggctttgg aagctctcaa ctcaccaaca acaaccgctc catcttttcc ctttgacgac 60
ccaactattc catgggcgaa acgaaaacgt tcaaagcgtt ctcgcgacca tccttctgaa 120
gaagagtacc tcgccctctg cctcatcatg ctcgctcgcg gcggcaccac caccgtcaac 180
aaccgccacg tcagccctcc gccgctacag ccacagccac agccgacacc agatccttcc 240
accaagctca gttacaaatg ctccgtttgc gacaagagct tcccctctta ccaagcgctc 300
ggtggacaca aggccagtca ccggaaactc gccggcgccg ccgaagacca accccccagc 360
accaccactt cctccgccgc cgccaccagc tccgcctccg gaggtaaggc ccatgagtgc 420
tccatttgcc acaaatcctt ccccaccgga caggcccttg gcggacacaa acgttgtcac 480
tacgaaggta acggtaacgg aaataacaac aacagtaaca gcgttgtcac cgtcgcctcg 540
gaaggcgtgg gctccaccca cactgtcagt cacggccacc accgcgactt cgatctcaac 600
atcccggcct ttccggattt ttcgaccaag gtcggagaag acgaggttga gagccctcac 660
cctgtcatga agaagcctcg cctcttcgtc attcccaaga tcgaaatccc ccaatttcaa 720
tga 723

<210> SEQ ID NO 214
<211> LENGTH: 798
<212> TYPE: DNA
<213> ORGANISM: Arabidopsis thaliana

<400> SEQUENCE: 214
atggttgcat acccaaccaa aaaaacagca attaaacaat ttcttcactg caattcacaa 60
gcaaccttca aactaaaact cgagagacaa gaaatcctca gaatctttaa cttaatggcg 120

-continued

```
ctcgaggctc ttacatcacc aagattagct tctccgattc ctcctttgtt cgaagattct    180

tcagtcttcc atggagtcga gcactggaca aagggtaagc gatctaagag atcaagatcc    240

gatttccacc accaaaacct cactgaggaa gagtatctag ctttttgcct catgcttctc    300

gctcgcgaca accgtcagcc tcctcctcct ccggcggtgg agaagttgag ctacaagtgt    360

agcgtctgcg acaagacgtt ctcttcttac caagctctcg gtggtcacaa ggcaagccac    420

cgtaagaact tatcacagac tctctccggc ggaggagatg atcattcaac ctcgtcggcg    480

acaaccacat ccgccgtgac tactggaagt gggaaatcac acgtttgcac catctgtaac    540

aagtcttttc cttccggtca agctctcggc ggacacaagc ggtgccacta cgaaggaaac    600

aacaacatca acactagtag cgtgtccaac tccgaaggtg cggggtccac tagccacgtt    660

agcagtagcc accgtgggtt tgacctcaac atccctccga tccctgaatt ctcgatggtc    720

aacggagacg acgaagtcat gagccctatg ccggcgaaga agcctcggtt tgactttccg    780

gtcaaacttc aactttaa                                                   798


<210> SEQ ID NO 215
<211> LENGTH: 684
<212> TYPE: DNA
<213> ORGANISM: Arabidopsis thaliana

<400> SEQUENCE: 215

atggcgctcg aggctcttac atcaccaaga ttagcttctc cgattcctcc tttgttcgaa     60

gattcttcag tcttccatgg agtcgagcac tggacaaagg gtaagcgatc taagagatca    120

agatccgatt tccaccacca aaacctcact gaggaagagt atctagcttt ttgcctcatg    180

cttctcgctc gcgacaaccg tcagcctcct cctcctccgg cggtggagaa gttgagctac    240

aagtgtagcg tctgcgacaa gacgttctct tcttaccaag ctctcggtgg tcacaaggca    300

agccaccgta agaacttatc acagactctc tccggcggag gagatgatca ttcaacctcg    360

tcggcgacaa ccacatccgc cgtgactact ggaagtggga aatcacacgt ttgcaccatc    420

tgtaacaagt cttttccttc cggtcaagct ctcggcggac acaagcggtg ccactacgaa    480

ggaaacaaca acatcaacac tagtagcgtg tccaactccg aaggtgcggg gtccactagc    540

cacgttagca gtagccaccg tgggtttgac ctcaacatcc ctccgatccc tgaattctcg    600

atggtcaacg gagacgacga agtcatgagc cctatgccgg cgaagaagcc tcggtttgac    660

tttccggtca aacttcaact ttaa                                           684


<210> SEQ ID NO 216
<211> LENGTH: 744
<212> TYPE: DNA
<213> ORGANISM: Datisca glomerata

<400> SEQUENCE: 216

atggctctag aagcgctcaa ctctccgacc acagctacgc cggtgtttca ctacgacgac     60

cccagcttga attaccttga gccatggacc aagcgtaagc gttccaagcg tacgcgctta    120

gatagccctc ataccgagga agagtacctt gctttctgcc tcatcatgct cgctcgtggc    180

cgcgttgcct ctgcaaatcg acgggattct cagtcttcca ttcagattca gcctgaagca    240

acgacttcgg ctaccaaagt cagttataag tgctctgtgt gcgataaggc cttttcgtct    300

tatcaggctt tgggtgggca caaggccagc cacagaaagc tcgctggcgg cgaagatcaa    360

tcgacttcct ttgccaccac gaattcagcc accgtcacta ccaccacagc ctccggaggt    420

ggtggcaggt ctcatgagtg ttctatttgc cacaaatcgt tcccgactgg ccaggccttg    480
```

-continued

```
ggtggtcaca agcgctgcca ctacgaaggc agtatcggcg gcaatagtat tcaccaccac    540
aacaatacca ccaacagcgg aagcaacggt ggcatgagca tgacctccga agtaggttcc    600
acacacacag tcagccacag tcaccgtgac ttcgatctca acatcccggc cttgccggag    660
tttcggtcga atttcttcat atccggggat gacgaggtcg agagtcctca tccggccaag    720
aaaccccgta tattgatgaa ataa                                          744
```

<210> SEQ ID NO 217
<211> LENGTH: 684
<212> TYPE: DNA
<213> ORGANISM: Arabidopsis thaliana

<400> SEQUENCE: 217

```
atggcgctcg aggctcttac atcaccaaga ttagcttctc cgattcctcc tttgttcgaa     60
gattcttcag tcttccatgg agtcgagcac tggacaaagg gtaagcgatc taagagatca    120
agatccgatt tccaccacca aaacctcact gaggaagagt atctagcttt ttggctcatg    180
cttctcgctc gcgacaaccg tcagcctcct cctcctccgg cggtggagaa gttgagctac    240
aagtgtagcg tctgcgacaa gacgttctct tcttaccaag ctctcggtgg tcacaaggca    300
agccaccgta agaacttatc acagactctc tccggcggag gagatgatca ttcaacctcg    360
tcggcgacaa ccacatccgc cgtgactact ggaagtggga aatcacacgt ttgcaccatc    420
tgtaacaagt cttttccttc cggtcaagct ctcggcggac acaagcggtg ccactacgaa    480
ggaaacaaca acatcaacac tagtagcgtg tccaactccg aaggtgcggg gtccactagc    540
cacgttagca gtagccaccg tgggtttgac ctcaacatcc ctccgatccc tgaattctcg    600
atggtcaacg gagacgacga agtcatgagc cctatgccgg cgaagaagcc tcggtttgac    660
tttccggtca aacttcaact ttaa                                          684
```

<210> SEQ ID NO 218
<211> LENGTH: 762
<212> TYPE: DNA
<213> ORGANISM: Petunia x hybrida

<400> SEQUENCE: 218

```
atggcacttg aagcattgaa ttctccaact acaacaacac caccatcatt ccaatttgag     60
aacaacgggc ttaagtacct tgagagttgg acaaaaggta aaagatcaaa aaggcaacgc    120
agcatggaac gacagtgtac tgaagaagag tatttagcac tttgtcttat catgctagca    180
cgtagcgatg gttctgttaa taactcacgg tctctaccac caccaccact accaccatca    240
gttccagtaa cgtcgcaaat aaacgcgacg ttattggaac agaagaattt gtacaagtgt    300
tccgtttgtg gtaaagggtt tgggtcttat caagctttag gtggacataa agcaagtcac    360
cggaaacttg tcagcatggg aggagatgaa caatctacta cttccactac tactaacgta    420
acgggaacta gttccgctaa cgttaacggt aacggaagaa ctcacgaatg ttcaatttgt    480
cacaagtgct ttcctactgg acaagcttta ggtggtcata aaaggtgcca ctatgacggt    540
ggtaacggta acggtaacgg aagtgtaagt gttggggtga cgtcatctga aggtgtgggg    600
tccactatta gtcatcaccg tgactttgac ttgaatattc ccgcgttgcc ggagttttgg    660
ccgggatttg gttccggcga ggatgaggtg gagagtcctc atccagcaaa gaagtcaagg    720
ctatctcttc cacctaaact tgaattattc aaaggattat ag                      762
```

<210> SEQ ID NO 219

-continued

<211> LENGTH: 822
<212> TYPE: DNA
<213> ORGANISM: Arabidopsis thaliana

<400> SEQUENCE: 219
atggccctcg aagcgatgaa cactccaact tcttctttca ccagaatcga aacgaaagaa 60
gatttgatga acgacgccgt tttcattgag ccgtggctta aacgcaaacg ctccaaacgt 120
cagcgttctc acagcccttc ttcgtcttct tcctcaccgc ctcgatctcg acccaaatcc 180
cagaatcaag atcttacgga agaagagtat ctcgctcttt gtctcctcat gctcgctaaa 240
gatcaaccgt cgcaaacgcg atttcatcaa cagtcgcaat cgttaacgcc gccgccagaa 300
tcaaagaacc ttccgtacaa gtgtaacgtc tgtgaaaaag cgtttccttc ctatcaggct 360
ttaggcggtc acaaagcaag tcaccgaatc aaaccaccaa ccgtaatctc aacaaccgcc 420
gatgattcaa cagctccgac catctccatc gtcgccggag aaaaacatcc gattgctgcc 480
tccggaaaga tccacgagtg ttcaatctgt cataaagtgt ttccgacggg tcaagcttta 540
ggcggtcaca aacgttgtca ctacgaaggc aacctcggcg gcggaggagg aggaggaagc 600
aaatcaatca gtcacagtgg aagcgtgtcg agcacggtat cggaagaaag gagccaccgt 660
ggattcatcg atctaaacct accggcgtta cctgaactca gccttcatca caatccaatc 720
gtcgacgaag agatcttgag tccgttgacc ggtaaaaaac cgcttttgtt gaccgatcac 780
gaccaagtca tcaagaaaga agatttatct ttaaaaatct aa 822

<210> SEQ ID NO 220
<211> LENGTH: 717
<212> TYPE: DNA
<213> ORGANISM: Arabidopsis thaliana

<400> SEQUENCE: 220
atggcacttg aaactcttac ttctccaaga ttatcttctc cgatgccgac tctgtttcaa 60
gattcagcac tagggtttca tggaagcaaa ggcaaacgat ctaagcgatc aagatctgaa 120
ttcgaccgtc agagtctcac ggaggatgaa tatatcgctt tatgtctcat gcttcttgct 180
cgcgacggag atagaaaccg tgaccttgac ctgccttctt cttcgtcttc acctcctctg 240
cttcctcctc ttcctactcc gatctacaag tgtagcgtct gtgacaaggc gttttcgtct 300
taccaggctc ttggtggaca caaggcaagt caccggaaaa gcttttcgct tactcaatct 360
gccggaggag atgagctgtc gacatcgtcg gcgataacca cgtctggtat atccggtggc 420
gggggaggaa gtgtgaagtc gcacgtttgc tctatctgtc ataaatcgtt cgccaccggt 480
caagctctcg gcggccacaa acggtgccac tacgaaggaa agaacggagg cggtgtgagt 540
agtagcgtgt cgaattctga agatgtgggg tctacaagcc acgtcagcag tggccaccgt 600
gggtttgacc tcaacatacc gccgataccg gaattctcga tggtcaacgg agacgaagag 660
gtgatgagtc ctatgccggc gaagaaactc cggtttgact tcccggggaa accctaa 717

<210> SEQ ID NO 221
<211> LENGTH: 717
<212> TYPE: DNA
<213> ORGANISM: Arabidopsis thaliana

<400> SEQUENCE: 221
atggcacttg aaactcttac ttctccaaga ttatcttctc cgatgccgac tctgtttcaa 60
gattcagcac tagggtttca tggaagcaaa ggcaaacgat ctaagcgatc aagatctgaa 120
ttcgaccgtc agagtctcac ggaggatgaa tatatcgctt tatgtctcat gcttcttgct 180

-continued

```
cgcgacggag atagaaaccg tgaccttgac ctgccttctt cttcgtcttc acctcctctg    240

cttcctcctc ttcctactcc gatctacaag tgtagcgtct gtgacaaggc gttttcgtct    300

taccaggctc ttggtggaca caaggcaagt caccggaaaa gcttttcgct tactcaatct    360

gccggaggag atgagctgtc gacatcgtcg gcgataacca cgtctggtat atccggtggc    420

gggggaggaa gtgtgaagtc gcacgtttgc tctatctgtc ataaatcgtt cgccaccggt    480

caagctctcg gcggccacaa acggtgccac tacgaaggaa agaacggagg cggtgtgagt    540

agtagcgtgt cgaattctga agatgtgggg tctacaagcc acgtcagcag tggccaccgt    600

gggtttgacc tcaacatacc gccgataccg gaattctcga tggtcaacgg agacgaagag    660

gtgatgagtc ctatgccggc gaagaaactc cggtttgact tcccggagaa accctaa       717
```

<210> SEQ ID NO 222
<211> LENGTH: 708
<212> TYPE: DNA
<213> ORGANISM: Brassica rapa

<400> SEQUENCE: 222

```
atggctcttg agactctcaa ttctccgact tcagccaccg cctccgctcg gcctcttctc     60

cggtatcgcg aagaaatgga gccggagaat ctcgagcaat gggctaaaag aaaacgcacc    120

aaacgacaac gttttgatca gagtcgtctg aatcaagaaa cggctccttc agaagaagag    180

tatctcgctc tttgtctcct catgctcgct cgtggctccg ccgtgcaatc tcctctccct    240

ccgtcttcgt cctccgacca ccgtggttac aagtgtacgg tctgcggaaa gtcgttttcc    300

tcttaccaag ccttaggtgg acacaagacg agtcaccgga aaccggcgag caacgttaac    360

gttcccatca accaagagca gtctaataac agtcatagta acagcaacgg tggttccgtc    420

gttatcaacg gtaacggcgt tagtcaaagc gggaagattc atacttgctc gatatgtttc    480

aagtcgtttt cgtcaggtca ggctttgggt ggacacaaac ggtgtcacta tgacgctggt    540

aataacggaa acggtaacgg cagtagcagc aacagcgtgg aggtcgtcgg tggcagtgac    600

ggcagctatg tggatgatga aagatcgtca gaacagagcg cgaccggcga caaccggggg    660

tttgacttga atttaccggc tgatcaagtc gcagttgtga tatcttaa                 708
```

<210> SEQ ID NO 223
<211> LENGTH: 714
<212> TYPE: DNA
<213> ORGANISM: Brassica rapa

<400> SEQUENCE: 223

```
atggctcttg agactctcaa ttctccgact tcagccaccg cctccgctcg gcctcttctc     60

cggtatcgcg aagaaatgga gccggagaat ctcgagcaat gggctaaaag aaaacgcacc    120

aaacgacaac gttttgatca gagtcgtctg aatcaagaaa cggctccttc agaagaagag    180

tatctcgctc tttgtctcct catgctcgct cgtggctccg ccgtgcaatc tcctctccct    240

ccgtcttcgt cctccgacca ccgtggttac aagtgtacgg tctgcggaaa gtcgttttcc    300

tcttaccaag ccttaggtgg acacaagacg agtcaccgga aaccggcgag caacgttaac    360

gttcccatca accaagagca gtctaataac agtcatagta acagcaacgg tggttccgtc    420

gctatcaacg gtaacggcgt tagtcaaagc gggaagattc atacttgctc gatatgtttc    480

aagtcgtttt cgtcaggtca ggctttgggt ggacacaaac ggtgtcacta tgacgctggt    540

attaacggaa acggtaacgg cagtagcagc aacagcgtgg aggtcgtcgg tggcagtgac    600
```

-continued

```
ggcaactatg tggatgatga aagatcgtca gaacagagcg cgaccggcga caaccggggg    660

tttgacttga atttaccggc tgatcaagtc gcagttgtga tatctaaacg ttga          714
```

<210> SEQ ID NO 224
<211> LENGTH: 822
<212> TYPE: DNA
<213> ORGANISM: Nicotiana tabacum

<400> SEQUENCE: 224

```
atgactcttg aagctttgaa gtcacctacg gcggcaacgc cgactctacc accacgctat     60

gaagatgatg atgaaattca taatttggat tcttgggcta aaggaaaacg atcaaaacgg    120

ccccgtattg atgccccacc gactgaagaa gagtatttag ccctctgtct catcatgctc    180

gctcgcagcg gaaccggaac cagaaccggt ttaactgatg ctactacttc ccaacaacct    240

gccgataaaa aaaccgccga gttgccgccg gttcataaga aagaggtggc aacagagcaa    300

gcagagcaat cttacaagtg tagcgtgtgt gacaaggctt tttcttctta tcaagcactc    360

ggtgggcata aagcaagtca ccgtaaaact actactactg ctaccgccgc ctctgatgat    420

aacaatcctt caacttcaac ttccactggc gccgttaata tctctgctct taatccaact    480

ggtcgttcac acgtctgttc tatttgccac aaggcttttc ctactggcca agctttgggt    540

gggcacaagc gccgccacta tgaaggcaaa ctcggtggta acagccgcga cttaggcggc    600

ggcggcggcg gcggtcatag tggaagcgtc ttgactactt cagacggcgg cgcgtcgact    660

cacacgctac gtgactttga cctgaacatg cctgcttcgc cggaattgca actgggtctg    720

agtattgatt gtggacggaa aagtcaactg ttgccgatgg tccaagaggt ggaaagtcct    780

atgcctgcaa agaaaccgcg tttattgttt tcgttgggtt ga                       822
```

<210> SEQ ID NO 225
<211> LENGTH: 825
<212> TYPE: DNA
<213> ORGANISM: Petunia x hybrida

<400> SEQUENCE: 225

```
atggctcttg aagctttaaa gtcacccaca gcagcaacac catctctacc accacgttat     60

gaagatcatg ttgatatgaa taatttggat tcttgggtta aaggaaaacg atccaaacga    120

cctcgaattg aaaccccacc ttctgaagaa gaatatttag cactttgtct tattatgctt    180

gcccgtagcg gtaacggaac tacacccggt tcaactgata ctactattac tactactatt    240

tctaaagaac cggagaagaa aaaccgtgag ctgacaccgg ttcatcaaga aacagaacaa    300

tcttacaagt gtagcgtgtg tgacaagtct tttagttctt atcaagctct tggtggacac    360

aaagcaagtc ataggaaaat tacaactatt gccaccaccg ccttattaga tgacaacaac    420

aataatccta caacgtcaaa ttctacaagt ggcaacgttg ttaataatat ttctgcttta    480

aacccaagtg gacgttcaca cgtatgttct atatgtcaca aggcttttcc aactggacaa    540

gctttaggtg gacacaaacg ccgccactat gaaggcaaac taggtggtaa caacaacaac    600

caccgtgacg gcggtggtca tagtggaagt gtcgtgacaa cttctgatgg tggcgcgtct    660

actcacacgc tccgtgactt tgacttgaac atgttgcctc cttccccaga attgcaattg    720

gggttgagta ttgactgtga tttgaaaagt caaataccaa ttgaacaaga agttgaaagt    780

cctatgcctt tgaagaaacc gcgtttattg ttttctatgg attga                    825
```

<210> SEQ ID NO 226
<211> LENGTH: 582

<212> TYPE: DNA
<213> ORGANISM: Arabidopsis thaliana

<400> SEQUENCE: 226
atggcgcttg aagctcttaa ttcaccaaga ttggtcgagg atcccttaag attcaatggc 60
gttgagcagt ggaccaaatg taagaaacga tccaaacgtt cgagatctga tcttcatcat 120
aaccaccgtc tcactgagga agagtatcta gctttctgtc tcatgcttct tgctcgggat 180
ggcggcgatc ttgactctgt gacggttgcg gagaagccga gttataagtg tggcgtttgt 240
tacaagacgt tttcgtctta ccaagctctc ggcggtcata aagcgagcca ccggagctta 300
tacggtggtg gagagaatga taaatcgaca ccatccaccg ccgtgaaatc tcacgtttgt 360
tcggtttgcg ggaaatcttt cgccaccggt caagctctcg gcggccacaa gcggtgccac 420
tacgatggtg gcgtttcgaa ctcggaaggt gtggggtcta ctagccacgt cagcagtagt 480
agccaccgtg gatttgacct taatattata ccggtgcagg gattttcgcc ggacgacgaa 540
gtgatgagtc cgatggcgac taagaagcct cgcctgaagt aa 582

<210> SEQ ID NO 227
<211> LENGTH: 582
<212> TYPE: DNA
<213> ORGANISM: Arabidopsis thaliana

<400> SEQUENCE: 227
atggctcttg aagctcttaa ttcaccaaga ttggtcgagg atcccttaag attcaatggc 60
gttgagcagt ggaccaaatg taagaaacga tccaaacgtt cgagatctga tcttcatcat 120
aaccaccgtc tcactgagga agagtatcta gctttctgtc tcatgcttct tgctcgtgat 180
ggcggcgatc ttgattctgt gacggttgag gagaagccga gttataagtg tggcgtttgt 240
tacaagacgt tttcgtctta ccaagctctc ggtggtcaca aagcgagtca ccggagttta 300
tacggtggtg gagataacga taagtcgaca ccatccaccg ccgtgaaatc tcacgtttgt 360
tcggtttgcg ggaaatcttt cgccaccggt caagctctcg gcggccacaa gcggtgccac 420
tatgatggtg gcgtttcgaa ctcggaaggt gtggggtcta ctagccacgt tagtagtagt 480
agccaccgtg gatttgacct taatatttta ccggtgcagg gattctcgcg ggacgacgaa 540
gtgatgagtc cgatggcgac taagaagcct cgcctgaagt aa 582

<210> SEQ ID NO 228
<211> LENGTH: 648
<212> TYPE: DNA
<213> ORGANISM: Arabidopsis thaliana

<400> SEQUENCE: 228
atggctctcg acactctcaa ttctcccacc tccaccacca caaccaccgc tcctcctcct 60
ttcctccgtt gcctcgacga aaccgagccc gaaaacctcg aatcatggac caaaagaaaa 120
cgtacaaaac gtcaccgtat agatcaacca aaccctcctc cttctgaaga agagtatctc 180
gctctttgcc tccttatgct cgctcgtggc tcctccgatc atcactctcc accgtcggat 240
catcactctc tttctccact gtccgatcat cagaaagatt acaagtgttc cgtctgtggc 300
aaatctttcc cgtcttacca agcgttaggt ggacacaaaa caagtcaccg gaaaccggtt 360
agtgtcgatg ttaataatag taacggaacc gttactaata acggaaatat tagtaacggt 420
ttagttggtc aaagtgggaa gactcataac tgctctatat gttttaagtc gtttccctct 480
ggtcaagcat tgggtggtca caaacgttgt cactatgatg gtggtaacgg taacagtaac 540

-continued

```
ggtgacaata gccacaagtt tgacctaaat ttaccggctg atcaagttag tgatgagaca    600

attggaaaaa gtcaactctc cggtgaagaa acaaagtcgg tgttgtga                648
```

<210> SEQ ID NO 229
<211> LENGTH: 834
<212> TYPE: DNA
<213> ORGANISM: Petunia x hybrida

<400> SEQUENCE: 229

```
atggctcttg aagctttaaa atcacccaca gcagcaacac caactctacc accacgttat     60

gaagatcaag ttgatatgag taatttggat tcatgggtta aaggaaaacg atccaaacga    120

cctcggattg aaaccccacc ttctgaagaa gaatatctag cactttgtct tatcatgctt    180

gcccgtagcg gtaacggaac tacacccagt tcaattcccg gttcaactga tacaactact    240

atttctaaag aaccggagaa gaaaaaccgt gacgtggcac cggtttatca agaaacagaa    300

caatcttaca agtgtagcgt gtgtgacaag tcttttagtt cttatcaagc tcttggcgga    360

cacaaagcaa gtcataggaa aattacaact attgccacca ccgccttatt agatgacaac    420

aacaataatc ctacaacgtc aaattctaca aatggcaacg ttgttaataa tatttctact    480

ttgaacccaa gtggacgttc acacgtgtgt tctatatgtc acaaggcttt tccaagtgga    540

caagctttag gtggacacaa gcgccgtcac tatgaaggca aacttggcgg caacaacaac    600

aacaaccacc gtgacggcgg tggtcatagt ggaagtgttg tgacaacttc tgatggtggc    660

gcgtctactc acacgctccg tgactttgac ttgaacatgt tgcctccttc cccagagttg    720

caattggggt tgagtattga ctgtggtttg aaaagtcaac aagttcctat tgaacaagaa    780

gttgaaagtc ctatgccttt gaagaaaccg cgtttattgt tttccatgga ttga          834
```

<210> SEQ ID NO 230
<211> LENGTH: 738
<212> TYPE: DNA
<213> ORGANISM: Arabidopsis thaliana

<400> SEQUENCE: 230

```
atggctctcg agactctcaa ttctccaaca gctaccacca ccgctcggcc tcttctccgg     60

tatcgtgaag aaatggagcc tgagaatctc gagcaatggg ctaaaagaaa acgaacaaaa    120

cgtcaacgtt ttgatcacgg tcatcagaat caagaaacga acaagaacct tccttctgaa    180

gaagagtatc tcgctctttg tctcctcatg ctcgctcgtg gctccgccgt acaatctcct    240

cctcttcctc ctctaccgtc acgtgcgtca ccgtccgatc accgagatta caagtgtacg    300

gtctgtggga agtccttttc gtcataccaa gccttaggtg gacacaagac gagtcaccgg    360

aaaccgacga acactagtat cacttccggt aaccaagaac tgtctaataa cagtcacagt    420

aacagcggtt ccgttgttat taacgttacc gtgaacactg gtaacggtgt tagtcaaagc    480

ggaaagattc acacttgctc aatctgtttc aagtcgtttg cgtctggtca agccttaggt    540

ggacacaaac ggtgtcacta tgacggtggc aacaacggta acggtaacgg aagtagcagc    600

aacagcgtag aactcgtcgc tggtagtgac gtcagcgatg ttgataatga gagatggtcc    660

gaagaaagtg cgatcggtgg ccaccgtgga tttgacctaa acttaccggc tgatcaagtc    720

tcagtgacga cttcttaa                                                   738
```

<210> SEQ ID NO 231
<211> LENGTH: 846
<212> TYPE: DNA
<213> ORGANISM: Solanum tuberosum -continued

<400> SEQUENCE: 231

```
ctcacaaaac ttctcaagtt ttataatatt cttaacactc tctctctcta aacaaaacag     60
acgaataatt caatcaaatt gatattgaga tggcccttga agctttgaat tctccaactg    120
gtacttcaaa tccgcagacg tttaaatttg agagcaaagg ccagcagcag cttcggtacc    180
ttgagaattg gactaaaggg aagagatcta agaggtcacg gagtatggaa cgccagccga    240
ctgaagagga atatttggcg atttgtttga ttatgcttgc gcgtagcgat ggctctgtta    300
atcaggtacg atctctacca ccgccggtgc cagtgatgaa aatccacgcg ccgtcggaga    360
agatggagta taagtgttcg gtttgtggta agggatttgg atcttatcaa gctttaggag    420
gacataaagc tagtcaccgg aaactcatcg ccggcgtcag cggcggcgga gatgatcagt    480
caactacctc tactactact aacgctaccg gaactactag ctccggtaac ggtaacggta    540
gtggaaggac tcacgagtgt tcgatttgtc acaagtgttt tcctactgga caagctttgg    600
gaggacacaa acggtgtcac tacgacggtg gtaacggtaa cggaaacgct aacagtagcg    660
ttagcgctag cgtcggagtt acgtcgtcgg agggcgtggg gtcaacaatc agccaccgtg    720
attttgactt gaacatcccg gcgttgccgg aattctggcc tggatttggt tccggcgagg    780
atgaggtgga gagtccacat ccggcgaaga aatcacggct atctctacct ccaaaatttg    840
aattat                                                               846
```

<210> SEQ ID NO 232
<211> LENGTH: 819
<212> TYPE: DNA
<213> ORGANISM: Gossypium raimondii

<400> SEQUENCE: 232

```
ttacttttag ctctctgttt ttgctctcaa actcgaaggg attcggaagt atttgatatg     60
gcgcttgaag ctctgaactc gccggcgacg cctttcacca acaaatacga tgacgtggac    120
aacaattacg tcgagacatg gaagaaaggc aagcgttcga agcgacaacg tggcgactct    180
cctgctgctg ttgaacttca acccaccacc gaagaagagt acctcgctct ttgtctcatc    240
atgctcgctc gcggctcttc cggtgctgat cttgatgtta ttcgtcggtc ttcctcttcg    300
tcgtcaccgc ctccgccgcc gcctgctttg aagttgtctt acaagtgtag tgtttgtgac    360
aaggcgttcc cttcttatca agctttgggc ggtcataaag ccagccaccg caaacccctt    420
tccgccgacg ccgctaccac caccgccgcc gccaacgtcg ataacccatc aacaaccagc    480
accgccacca ccgccaccag cagcggtagg cttcacgagt gttccatctg ccacaagagt    540
ttccctacag gccaagcctt gggtggtcat aaacgctgcc actacgaagg tggcaacaac    600
aacaacaaca acaacaaaaa taacaacaac agcggtagcg ttagcgttag cggggtgact    660
tcttcggatg ggggcgcgtt gagccacaac caccgtgcag tcgactttga ctttgacctc    720
aacttgccgg ccttgccgga gttcagtcaa atgtacccag atgaagaaga ggtccaaagc    780
ccattgccga cccagaaacc acgtttcttg atcgccaag                           819
```

<210> SEQ ID NO 233
<211> LENGTH: 705
<212> TYPE: DNA
<213> ORGANISM: Vitis aestivalis

<400> SEQUENCE: 233

```
cctctttcat ggctctggaa gctctcaact caccaaccac acccacgcct tcctttcact     60
```

-continued

```
acgaacaacc cagcctccac tctctggagt catgggccaa gcgcaagcgt tccaagcgtc    120

ctcgcttcga caaccaacct acagaggaag agtatctggc tctctgcctc atcatgttgg    180

ctcgaggagg cgccgcctcc tccaccgtct cacaccgccg ccatctctct ccccctcctg    240

ccctgcaggt ggaagctcct aaactcacat acaaatgttc agtttgtaac aaggccttcg    300

catcctacca ggcactaggg ggacacaagg ccagccaccg taagcagtcc ggatccgatg    360

acctgtcggc ctccatcacc accacaagca ccgcggccgc tgccagcggt ggtaggactc    420

atgagtgttc catctgtcac aagactttcc ccactggaca ggctttgggt ggacacaagc    480

gatgccacta cgaaggcggc gccagcgtca gcagtggcgt tacctcctcc gaaggtgtgg    540

ggtcaaccca cagccaccgt gacttcgacc tcaacctgcc ggcctttccc gaattatggt    600

ccgcacgtcg attcccagtc gatgacgagg tcgagagtcc tctaccgaca aagaagcccc    660

gtctccagat gctgccgcca aaaaccgaaa ttctctcaga ttacc                    705
```

```
<210> SEQ ID NO 234
<211> LENGTH: 742
<212> TYPE: DNA
<213> ORGANISM: Lycopersicon esculentum

<400> SEQUENCE: 234

acactctcga taactctgaa cgaacaattt gaattaaatt gatatcgaaa tggctcttga     60

agctttgaat tctccaactg gtactacttc aaatccgcaa acgtttcaat ttgagagcaa    120

aggccagcag cagcttcggt accttgagaa ttggactaaa gggaagagat ctaagaggtc    180

acggagtatg gatcgtcaac cgactgaaga ggaatatttg gcgctttgtt tgattatgct    240

tgcaaggagc gatggctctg ttaatcacgt acggtctcta ccaccgccgg tgccagtgat    300

gaaaattcac gagacggcgg agaagatgtt gtataggtgt tcggtttgtg gtaagggatt    360

cggatcttat caagctttag gaggacataa agctagtcac cggaaactca tcgccggcgg    420

agatgatcag tcgactacct ctactactac gaacgctaac ggaactacaa gctccggtaa    480

cggtaacggt aacggtagtg gaactggaag gactcacgag tgttcgattt gtcacaagtg    540

ttttccgact gggcaagctt tgggaggaca caaacggtgt cactacgacg gtggtaacag    600

taacggtaac ggaaatgcta acgctaacag tagcattagc gctagcgtcg gagttacgtc    660

gtcggagggc gtgggttcaa caatcagcca ccgtgatttt gacttgaaca ttccggcgtt    720

gccgggattc tggcctggat tt                                             742
```

```
<210> SEQ ID NO 235
<211> LENGTH: 804
<212> TYPE: DNA
<213> ORGANISM: Medicago truncatula

<400> SEQUENCE: 235

cgctactcct ttccaccctt tgaggaacca aatctgagtt atcttgaaac accgtggacg     60

aaaggtaaac gttcaaagcg ttctcgtatg gatcaatctt catgcactga agaagagtat    120

ctcgctcttt gtctcatcat gcttgctcgc agcggaaaca acaacgacaa caagactgaa    180

tcggtgccgg tgccggcgcc gctaaccacc gttaaactca gtcacaaatg ctcagtctgc    240

aacaaagctt tttcatctta tcaagcccta ggtggacaca aagccagtca ccggaaagct    300

gttatgtccg caaccaccgt tgaagatcag accaccacca cttcatctgc cgtgactacc    360

agctctgcat ccaacggtaa gaacaagact catgagtgtt ccatctgtca caaatccttt    420

cctactggac aggctttggg aggacacaag cgttgtcact acgaaggcag cgttggtgcc    480
```

-continued

```
ggtgccggaa gtagcgctgt aactgccgcc tctgaaggag ttggatcgtc tcacagtcac    540
caccgtgatt ttgatcttaa cctaccggct tttccggact tttcaaagaa gtttttcgtg    600
gatgacgagg tttctagtcc tttacctgct gcaaagaagc cctgtctttt caagcttgaa    660
attccttctc attactgatc aataatagat ccaattttat tgttattatt agtaataatt    720
attatcgctt agggcatagt tattttcttt tttctttcaa tattttggat caatttgttc    780
tgtacataca aattgggact ggct                                            804
```

<210> SEQ ID NO 236
<211> LENGTH: 743
<212> TYPE: DNA
<213> ORGANISM: Populus sp.
<220> FEATURE:
<221> NAME/KEY: misc_feature
<222> LOCATION: (680)..(680)
<223> OTHER INFORMATION: n is a, c, g, or t

<400> SEQUENCE: 236

```
tccctcctcc ctgtctctct caataccttt cttcctctcc ttggaaatct tgttcgtttg     60
taccccctcgt tgcccactca cacaagaaaa actcagtatc aagaatccaa atcatggctc    120
ttgaagctct gaactctcct acaacagccg ctcctttaaa ttatgaagaa acatggatta    180
agaggaaacg ctctaagaga cctcgtagtg agtccccttc gaccgaggaa gaatacctcg    240
ctttttgcct tatcatgctt gctcgtggcg gctccactgc cgcaaccgcc aaaaaaaccg    300
cttccgcctc ccctgcacca ccccaaccac caactttgga tctttcttac aagtgtacgg    360
tttgcaacaa ggctttctct tcttaccagg ctctcggcgg gcacaaagcc agtcacagga    420
aatcctcctc cgagtcaacc gtcgccacag ccgctgaaaa cccatcagcc tccaccacaa    480
ctaacacaac caccacgacc accaatggta ggactcatga gtgttctatc tgccacaaga    540
ctttccttac tggacaggcc ttaggcggac acaaacgttg tcactatgag ggcacaattg    600
gaggcaacaa cagcagcagt gctagcgctg caatcaccac ctcagacggt ggtgctgttg    660
gaggcggtgg cgtgagccan agtaagagtc aaagaagcgg tggtggattt gactttgacc    720
tgaacttgcc tgctttgcct gaa                                             743
```

<210> SEQ ID NO 237
<211> LENGTH: 894
<212> TYPE: DNA
<213> ORGANISM: Citrus sinensis
<220> FEATURE:
<221> NAME/KEY: misc_feature
<222> LOCATION: (872)..(874)
<223> OTHER INFORMATION: n is a, c, g, or t

<400> SEQUENCE: 237

```
ggggatcatt tccatccatt tgaaatcacc tctctctctc tctcgaaact caacagattc     60
aaccacaaga gtcgagaatt cactaacaag aaaagaaaaa attcacgact atggctctag    120
aagctctaaa ctcccctaca acaagcaccc acaatcatca tccgtttaga tacgaagact    180
catggactaa aagaaggcgc tcaaaacgac tccgtaccga cgagtcccca caactaccag    240
cagcagcagc agctcccacg gaagaagagt acatggctct ctgtctcatc atgctcgccc    300
gcggtaccac caccgccaac accgctccgg ccgaaagaac cccaaccctg gcgccggaac    360
agaagccgct ggatcagttc ccggagccgc caagtttgaa actctcttac aagtgcagtg    420
tgtgcaacaa ggctttctct tcgtaccagg cccttggtgg gcacaaagcc agccaccgca    480
```

-continued

```
agaacgctgc tgacgcctcg gcttctccca acgccgcagc cgccagtgac gtcaccccac    540
caccgtcggc aacggcgagc agcggaagcg gtggtaggac ccacgagtgc tctatttgtc    600
acaagtcttt tcccacggga caagctctag gaggccacaa gcggtgtcac tatgaaggcg    660
gcatcaacaa caacaacaac agcagcagca ataataataa aagtaataat aatagcgacg    720
ttgttactag tggtagcgct agcgttggtg caagtgcggt gacgttttcg gaaggcggag    780
ggagcagcag tcaacgcgga tttgacctga acttgccggc gttgccggag ttttggtcac    840
aggaagttga gtctccgttg ccggccaaga annncaagtt gttgatgcac tact          894
```

<210> SEQ ID NO 238
<211> LENGTH: 900
<212> TYPE: DNA
<213> ORGANISM: Lotus corniculatus

<400> SEQUENCE: 238

```
tcaccaacca ccgccgctcc aaccttcact cccttccagg aaccgaacca cagctacatg     60
gtcgacgcac cgtgggcgaa gagaaagcgt tccaagcgtt ctcgcacgga cagccatcac    120
aaccacgctt cctgcacgga ggaagagtat ctcgctctct gcctcatcat gctcgctcgc    180
ggcagcaccg ccgtaacacc caagctcact ctgtctcgtc cggcaccggt aaccgctgaa    240
aagctcagtt acaagtgctc tgtctgcgaa aaaaccttcc cctcttacca agcccttggc    300
ggacacaagg ccagccaccg gaaactcgcc ggcgccgccg ctgaggacca ctccacctcc    360
tccgccgtga ccaccagctc tgcctccaac ggtggaggca aggtccacca gtgctccatc    420
tgccagaaat ccttccctac aggacaggcc ttgggaggac acaagcgttg ccactatgaa    480
ggcggtggtg gtgctagtag caccgccaca gccaccgcat cggaaggtgt gggatccaca    540
cacagccacc agcgcaactt cgatctgaac ctgccggctt ttccggactt ctccgccagc    600
aaatttttcg tggaagaaga ggtttccagt cccctgcctt cgaagaagcc acgtcttttg    660
cccaagattg aaatccctca ttattattaa ttaattaatg catttagatc aaagttaatt    720
agtgcttaat tagcttttca attgtttggg aattgggatt tgatttgttc ttgtacatat    780
acagtagcta gctagctgga cttggagctt attagctggt tttaggattt cttctacatt    840
gtattttgac agtcattcat tatcatataa ttcaattcat ttattcaatc tatctattta    900
```

<210> SEQ ID NO 239
<211> LENGTH: 1178
<212> TYPE: DNA
<213> ORGANISM: Lolium perenne
<220> FEATURE:
<221> NAME/KEY: misc_feature
<222> LOCATION: (681)..(681)
<223> OTHER INFORMATION: n is a, c, g, or t

<400> SEQUENCE: 239

```
ggctggtaaa acaaatataa gtattaatat aaatataata caatagaagg aaaataaata     60
aaatttccct ctgtgccgtg caaaaatgca cggcaatggg ctggcccgca cggcaaaggc    120
atcgttgccg tgtccacggc aatgggttgg cccgcacggc aaaggcatcg ttgccgtgtc    180
cacgtcttcg ccgtgcgcct tggctctatc tttgccgtga agcgttcttt gccgtgtgcc    240
ttttatttct ttgccgtggg atgctgcctt tgccgagcgc tgagctggcg ctttgccgtg    300
cgcgtattgt ttgccgtgcg tcgtcccaga gctgtacggc aaagaattca ctgccgtgca    360
cgagacacac gggaaagaag ttttgcatgg caaagggcgc tgacagcaca cggcaaagag    420
cctggcacgg cattgagctt ttttcccgta atgatagacg gcataatata atggacgcac    480
```

-continued

```
atgctgatgt caggatgtca cccactcatc ctagtatttg tgggacgtga attctttgtg    540
agatgggcaa tggggtgtga acaaaataag ttttgtacta gtagataaac atttttaccc    600
ataaacaatt gttctgtatt gaatgagaaa ttattttgta ctggatgaaa attttctgag    660
taactgtgta agattaacat naatcaagag acaaatccaa tggctacaaa gtcaactaat    720
acttgttaaa agttccgata cttaaaatta tcaaaactga tatatagaat attgcccatc    780
tcgccaccgt gctagtttaa cagacgatgg acgaatatca gtcttgtatt ggataatcga    840
tgcatgcgag ctatcggcca cctgtccatg cttccagaag gagccgagac gtggcgactt    900
cgtccgacgc gccgactatc tgcacacgcc cggcttctcg tcgtgggcga gtcagcagtt    960
acgggctttc cgcctaccaa ctcacacgta gcgccctatc gtggcgcttg atcgatgcaa   1020
cagcgatgcc tatcccagct cctcaagctg cttataagta tgtcctcggc catcactgct   1080
tacacaacaa acacagctac ttatcgcagt gtactaaaca agacgtacta gctagatttc   1140
gtgaggtaaa atcagtgcaa tatcacttgt gcaagatg                           1178
```

<210> SEQ ID NO 240
<211> LENGTH: 5214
<212> TYPE: DNA
<213> ORGANISM: Artificial
<220> FEATURE:
<223> OTHER INFORMATION: genetic construct

<400> SEQUENCE: 240

```
ggcgcgcctt aattaacggg ctggtaaaac aaatataagt attaatataa atataataca     60
atagaaggaa aataaataaa atttccctct gtgccgtgca aaaatgcacg gcaatgggtt    120
ggcccgcacg gcaaaggcat cgttgccgtg tccacggcaa tgggttggcc cgcacggcaa    180
aggcatcgtt gccgtgtcca cgtctttgcc gtgcgccttg gctctatctt tgccgtgaag    240
cgttctttgc cgtgtgcctt ttatttcttt gccgtgggat gctgcctttg ccgagcgctg    300
agctggcgct ttgccgtgcg cgtattgttt gccgtgcgtc ctcccagagc tgtacggcaa    360
agaattcatt gccgtgcacg aggcacacgg gaaagaagtt tcgcatggca aagggcgctg    420
acagcacacg gcaaagagcc cggcacggca ttgagctttt tttcccgtaa tgatagacgg    480
cataatataa tggacgcaca tgctgatgtc aggatgtcac ccactcatcc tagtatttgt    540
gggacgtgaa ttctttgtga gatgggcaat gggatgtgaa caaaataagt tttgtactag    600
tagataaaca tttttaccca taaacaattg ttctgtattg aatgaaaaat tattttgtac    660
tggatgaaaa tcttctgagt aactgtgtaa gattaacatg aatcaagaga caaatccaat    720
ggctacaaag tcaactaata cttgttaaaa gttccgatac ttaaaattat caaaactgat    780
atatagaata ttgcccatct cgccaccgtg ctagtttaac agacgatgga cgaatatcag    840
tcttgtattg gataatcgat gcatgcgagc tatcggtcac ctgtccatgc ttccagaagg    900
agccgagacg tggcgacttc gtccgacgcg ccgactatct gcacacgccc ggcttctcgt    960
cgtgggcgag tcagcagtca caggctttcc gcctaccaac tcacacgtag cgccctatcg   1020
tggcgcttga tcgatgcaac agcgatgcct atcccagctc ctcaagctgc ttataagtat   1080
gtcctcggcc atcactgctt acacaacaaa cacagctact tatcgcagtg tactaaacaa   1140
gacgtactag ctagatttcg tgaggtaaaa tcagtgcaat atcacttgtg caagccatta   1200
gttccgtcgc catggcgtcc ccggagggcg ccaactgggt cttcgactgc ccgctcatgg   1260
acgaccttgc tgccgccgac ttcaccgcac cgcccgcagg aggcttctac tgggcaccac   1320
```

-continued

```
cgatgcagcc gcagatgcac acccaggccc cggccgtctc cgccaccccg cctcccaacc   1380
actgtgccga aatcaatagc cctatttctg tggactggga ccatgccaaa ggacagccaa   1440
caaataaacg tcctaggtca gaatctggtg ctcaacccag ctccaaagca tgcagggaga   1500
aagcgagaag ggacaagcta aacgagaggt tcttggaatt gggtgctgtc ttggatccag   1560
ggaaaacacc taaaatcgac aagtgtgcta tattgaatga tgctattcgt gcggtgactg   1620
agctacgtag tgaagcagag aagctgaagg attcaaacga gtctctccaa gagaagatca   1680
aagagctgaa ggctgagaag aatgagctgc gggatgagaa gcaaaagctg aaggcagaga   1740
aagagagcct ggagcagcag atcaagttca tgaatgcccg tcagagcctc gtaccacacc   1800
taccgcaccc ttcggttatc ccagcggctg catttgctgc tccccaaggg caagtgccag   1860
ggcagaagct gatgatgcct gtcattggct accatggatt tcccatgtgg caattcatgc   1920
caccttctga tgttgatacc tccgatgatc ccaagtcgtg ccctcctgtt gcataagcca   1980
gctaaaggcc tggtttctcc ataataatgt gtgagtagtt cccagataag ggaattaggg   2040
ttcctatagg gtttcgctca tgtgttgagc atataagaaa cccttagtat gtatttgtat   2100
ttgtaaaata cttctatcaa taaaatttct aattcctaaa accaaaatcc agtactaaaa   2160
tccagatccc ccgaattaat tcggcgttaa ttcagtatcg gcgcgcctta attaaaatcg   2220
aatttcgacc atatgggaga gctcccaacg cgttggatgc atagcttgag tattctatag   2280
tgtcacctaa atagcttggc gtaatcatgg tcatagctgt ttcctgtgtg aaattgttat   2340
ccgctcacaa ttccacacaa catacgagcc ggaagcataa agtgtaaagc ctggggtgcc   2400
taatgagtga gctaactcac attaattgcg ttgcgctcac tgcccgcttt ccagtcggga   2460
aacctgtcgt gccagctgca ttaatgaatc ggccaacgcg cggggagagg cggtttgcgt   2520
attgggcgct cttccgcttc ctcgctcact gactcgctgc gctcggtcgt tcggctgcgg   2580
cgagcggtat cagctcactc aaaggcggta atacggttat ccacagaatc aggggataac   2640
gcaggaaaga acatgtgagc aaaaggccag caaaaggcca ggaaccgtaa aaaggccgcg   2700
ttgctggcgt ttttccatag gctccgcccc cctgacgagc atcacaaaaa tcgacgctca   2760
agtcagaggt ggcgaaaccc gacaggacta taaagatacc aggcgtttcc ccctggaagc   2820
tccctcgtgc gctctcctgt tccgaccctg ccgcttaccg gatacctgtc cgcctttctc   2880
ccttcgggaa gcgtggcgct ttctcatagc tcacgctgta ggtatctcag ttcggtgtag   2940
gtcgttcgct ccaagctggg ctgtgtgcac gaaccccccg ttcagcccga ccgctgcgcc   3000
ttatccggta actatcgtct tgagtccaac ccggtaagac acgacttatc gccactggca   3060
gcagccactg gtaacaggat tagcagagcg aggtatgtag gcggtgctac agagttcttg   3120
aagtggtggc ctaactacgg ctacactaga agaacagtat ttggtatctg cgctctgctg   3180
aagccagtta ccttcggaaa aagagttggt agctcttgat ccggcaaaca aaccaccgct   3240
ggtagcggtg gtttttttgt ttgcaagcag cagattacgc gcagaaaaaa aggatctcaa   3300
gaagatcctt tgatcttttc tacggggtct gacgctcagt ggaacgaaaa ctcacgttaa   3360
gggattttgg tcatgagatt atcaaaaagg atcttcacct agatcctttt aaattaaaaa   3420
tgaagtttta aatcaatcta aagtatatat gagtaaactt ggtctgacag ttaccaatgc   3480
ttaatcagtg aggcacctat ctcagcgatc tgtctatttc gttcatccat agttgcctga   3540
ctccccgtcg tgtagataac tacgatacgg gagggcttac catctggccc cagtgctgca   3600
atgataccgc gagacccacg ctcaccggct ccagatttat cagcaataaa ccagccagcc   3660
ggaagggccg agcgcagaag tggtcctgca actttatccg cctccatcca gtctattaat   3720
```

-continued

```
tgttgccggg aagctagagt aagtagttcg ccagttaata gtttgcgcaa cgttgttgcc   3780

attgctacag gcatcgtggt gtcacgctcg tcgtttggta tggcttcatt cagctccggt   3840

tcccaacgat caaggcgagt tacatgatcc cccatgttgt gcaaaaaagc ggttagctcc   3900

ttcggtcctc cgatcgttgt cagaagtaag ttggccgcag tgttatcact catggttatg   3960

gcagcactgc ataattctct tactgtcatg ccatccgtaa gatgcttttc tgtgactggt   4020

gagtactcaa ccaagtcatt ctgagaatag tgtatgcggc gaccgagttg ctcttgcccg   4080

gcgtcaatac gggataatac cgcgccacat agcagaactt taaaagtgct catcattgga   4140

aaacgttctt cggggcgaaa actctcaagg atcttaccgc tgttgagatc cagttcgatg   4200

taacccactc gtgcacccaa ctgatcttca gcatctttta ctttcaccag cgtttctggg   4260

tgagcaaaaa caggaaggca aaatgccgca aaaaagggaa taagggcgac acggaaatgt   4320

tgaatactca tactcttcct ttttcaatat tattgaagca tttatcaggg ttattgtctc   4380

atgagcggat acatatttga atgtatttag aaaaataaac aaataggggt tccgcgcaca   4440

tttccccgaa aagtgccacc tgatgcggtg tgaaataccg cacagatgcg taaggagaaa   4500

ataccgcatc aggaaattgt aagcgttaat attttgttaa aattcgcgtt aaatttttgt   4560

taaatcagct catttttta ccaataggcc gaaatcggca aaatccctta taaatcaaaa   4620

gaatagaccg agatagggtt gagtgttgtt ccagtttgga acaagagtcc actattaaag   4680

aacgtggact ccaacgtcaa agggcgaaaa accgtctatc agggcgatgg cccactacgt   4740

gaaccatcac cctaatcaag ttttttgggg tcgaggtgcc gtaaagcact aaatcggaac   4800

cctaaaggga gcccccgatt tagagcttga cggggaaagc cggcgaacgt ggcgagaaag   4860

gaagggaaga aagcgaaagg agcgggcgct agggcgctgg caagtgtagc ggtcacgctg   4920

cgcgtaacca ccacacccgc cgcgcttaat gcgccgctac agggcgcgtc cattcgccat   4980

tcaggctgcg caactgttgg gaagggcgat cggtgcgggc ctcttcgcta ttacgccagc   5040

tggcgaaagg gggatgtgct gcaaggcgat taagttgggt aacgccaggg ttttcccagt   5100

cacgacgttg taaaacgacg gccagtgaat tgtaatacga ctcactatag ggcgaattgg   5160

gcccgacgtc gcatgctccc ggccgccatg gcggccgcgg gaattcgatt gatt         5214
```

```
<210> SEQ ID NO 241
<211> LENGTH: 5118
<212> TYPE: DNA
<213> ORGANISM: Artificial
<220> FEATURE:
<223> OTHER INFORMATION: genetic construct

<400> SEQUENCE: 241
```

```
ggcgcgcctt aattaacggg ctggtaaaac aaatataagt attaatataa atataataca     60

atagaaggaa aataaataaa atttccctct gtgccgtgca aaaatgcacg gcaatgggtt    120

ggcccgcacg gcaaaggcat cgttgccgtg tccacggcaa tgggttggcc cgcacggcaa    180

aggcatcgtt gccgtgtcca cgtctttgcc gtgcgccttg gctctatctt tgccgtgaag    240

cgttctttgc cgtgtgcctt ttatttcttt gccgtgggat gctgcctttg ccgagcgctg    300

agctggcgct ttgccgtgcg cgtattgttt gccgtgcgtc ctcccagagc tgtacggcaa    360

agaattcatt gccgtgcacg aggcacacgg gaaagaagtt tcgcatggca aagggcgctg    420

acagcacacg gcaaagagcc cggcacggca ttgagctttt tttcccgtaa tgatagacgg    480

cataatataa tggacgcaca tgctgatgtc aggatgtcac ccactcatcc tagtatttgt    540
```

-continued

```
gggacgtgaa ttctttgtga gatgggcaat gggatgtgaa caaaataagt tttgtactag    600
tagataaaca tttttaccca taaacaattg ttctgtattg aatgaaaaat tattttgtac    660
tggatgaaaa tcttctgagt aactgtgtaa gattaacatg aatcaagaga caaatccaat    720
ggctacaaag tcaactaata cttgttaaaa gttccgatac ttaaaattat caaaactgat    780
atatagaata ttgcccatct cgccaccgtg ctagtttaac agacgatgga cgaatatcag    840
tcttgtattg gataatcgat gcatgcgagc tatcggtcac ctgtccatgc ttccagaagg    900
agccgagacg tggcgacttc gtccgacgcg ccgactatct gcacacgccc ggcttctcgt    960
cgtgggcgag tcagcagtca caggctttcc gcctaccaac tcacacgtag cgccctatcg   1020
tggcgcttga tcgatgcaac agcgatgcct atcccagctc ctcaagctgc ttataagtat   1080
gtcctcggcc atcactgctt acacaacaaa cacagctact tatcgcagtg tactaaacaa   1140
gacgtactag ctagatttcg tgaggtaaaa tcagtgcaat atcacttgtg caagccatta   1200
gtatggccgt ggaggcggtt ctcgaagcgg cggcgatgat acagtcgccg ccgagcaaga   1260
agatggaggc gtctagtagc agcgacgagg cgttcgaggc gttgcagcag cacacggagg   1320
ggtggtccaa gaagaagcgc tcgaggcggc cacgggcgct cgagcccagc gaggaggagt   1380
acctcgcgtt ctgcctcgtc atgctggcgc gcggccaccg cgacgccgcg ccggagcacg   1440
ggtgctccgt ctgcggcaag gcgttcgcgt cgtaccaggc gctcggcggc cacaaggcca   1500
gccaccggaa gccacccaca gctccagccg cggtggcagc aagcgccgtc cccgaggagg   1560
acaagccacg ggcggctgcc tcgtcctcgt ctgggtccgg cgatgccgct ggcggcggca   1620
aggtccacga gtgcaacgtg tgccagaaga cgttcccgac ggggcaggcg ctgggcggcc   1680
acaagcggtg ccactacgac ggcaccatcg gcagcgccgc cgcgcccacg gtgaaggctg   1740
ccaaggccgc cgccgcggcg agcgcgccga cggcgacgaa ccgggggttc gacctgaacg   1800
tgccggcgct gccgggactc gcggaggagg gggaggaggt gctcagcccg gtatccttca   1860
agaagccgag gctcatgatc accgcgtgaa ggcctggttt ctccataata atgtgtgagt   1920
agttcccaga taagggaatt agggttccta tagggtttcg ctcatgtgtt gagcatataa   1980
gaaaccctta gtatgtattt gtatttgtaa aatacttcta tcaataaaat ttctaattcc   2040
taaaaccaaa atccagtact aaaatccaga tcccccgaat taattcggcg ttaattcagt   2100
atcggcgcgc cttaattaaa atcgaatttc gaccatatgg gagagctccc aacgcgttgg   2160
atgcatagct tgagtattct atagtgtcac ctaaatagct tggcgtaatc atggtcatag   2220
ctgtttcctg tgtgaaattg ttatccgctc acaattccac acaacatacg agccggaagc   2280
ataaagtgta aagcctgggg tgcctaatga gtgagctaac tcacattaat tgcgttgcgc   2340
tcactgcccg ctttccagtc gggaaacctg tcgtgccagc tgcattaatg aatcggccaa   2400
cgcgcgggga gaggcggttt gcgtattggg cgctcttccg cttcctcgct cactgactcg   2460
ctgcgctcgg tcgttcggct gcggcgagcg gtatcagctc actcaaaggc ggtaatacgg   2520
ttatccacag aatcagggga taacgcagga aagaacatgt gagcaaaagg ccagcaaaag   2580
gccaggaacc gtaaaaaggc cgcgttgctg gcgtttttcc ataggctccg cccccctgac   2640
gagcatcaca aaaatcgacg ctcaagtcag aggtggcgaa acccgacagg actataaaga   2700
taccaggcgt ttccccctgg aagctccctc gtgcgctctc ctgttccgac cctgccgctt   2760
accggatacc tgtccgcctt tctcccttcg ggaagcgtgg cgctttctca tagctcacgc   2820
tgtaggtatc tcagttcggt gtaggtcgtt cgctccaagc tgggctgtgt gcacgaaccc   2880
cccgttcagc ccgaccgctg cgccttatcc ggtaactatc gtcttgagtc caacccggta   2940
```

-continued agacacgact tatcgccact ggcagcagcc actggtaaca ggattagcag agcgaggtat 3000
gtaggcggtg ctacagagtt cttgaagtgg tggcctaact acggctacac tagaagaaca 3060
gtatttggta tctgcgctct gctgaagcca gttaccttcg gaaaaagagt tggtagctct 3120
tgatccggca aacaaaccac cgctggtagc ggtggttttt ttgtttgcaa gcagcagatt 3180
acgcgcagaa aaaaaggatc tcaagaagat cctttgatct tttctacggg gtctgacgct 3240
cagtggaacg aaaactcacg ttaagggatt ttggtcatga gattatcaaa aaggatcttc 3300
acctagatcc ttttaaatta aaaatgaagt tttaaatcaa tctaaagtat atatgagtaa 3360
acttggtctg acagttacca atgcttaatc agtgaggcac ctatctcagc gatctgtcta 3420
tttcgttcat ccatagttgc ctgactcccc gtcgtgtaga taactacgat acgggagggc 3480
ttaccatctg gccccagtgc tgcaatgata ccgcgagacc cacgctcacc ggctccagat 3540
ttatcagcaa taaaccagcc agccggaagg gccgagcgca gaagtggtcc tgcaacttta 3600
tccgcctcca tccagtctat taattgttgc cgggaagcta gagtaagtag ttcgccagtt 3660
aatagtttgc gcaacgttgt tgccattgct acaggcatcg tggtgtcacg ctcgtcgttt 3720
ggtatggctt cattcagctc cggttcccaa cgatcaaggc gagttacatg atcccccatg 3780
ttgtgcaaaa aagcggttag ctccttcggt cctccgatcg ttgtcagaag taagttggcc 3840
gcagtgttat cactcatggt tatggcagca ctgcataatt ctcttactgt catgccatcc 3900
gtaagatgct tttctgtgac tggtgagtac tcaaccaagt cattctgaga atagtgtatg 3960
cggcgaccga gttgctcttg cccggcgtca atacgggata ataccgcgcc acatagcaga 4020
actttaaaag tgctcatcat tggaaaacgt tcttcggggc gaaaactctc aaggatctta 4080
ccgctgttga gatccagttc gatgtaaccc actcgtgcac ccaactgatc ttcagcatct 4140
tttactttca ccagcgtttc tgggtgagca aaaacaggaa ggcaaaatgc cgcaaaaaag 4200
ggaataaggg cgacacggaa atgttgaata ctcatactct tcctttttca atattattga 4260
agcatttatc agggttattg tctcatgagc ggatacatat ttgaatgtat ttagaaaaat 4320
aaacaaatag gggttccgcg cacatttccc cgaaaagtgc cacctgatgc ggtgtgaaat 4380
accgcacaga tgcgtaagga gaaaataccg catcaggaaa ttgtaagcgt taatattttg 4440
ttaaaattcg cgttaaattt ttgttaaatc agctcatttt ttaaccaata ggccgaaatc 4500
ggcaaaatcc cttataaatc aaaagaatag accgagatag ggttgagtgt tgttccagtt 4560
tggaacaaga gtccactatt aaagaacgtg gactccaacg tcaaagggcg aaaaaccgtc 4620
tatcagggcg atggcccact acgtgaacca tcaccctaat caagtttttt ggggtcgagg 4680
tgccgtaaag cactaaatcg gaaccctaaa gggagccccc gatttagagc ttgacgggga 4740
aagccggcga acgtggcgag aaaggaaggg aagaaagcga aaggagcggg cgctagggcg 4800
ctggcaagtg tagcggtcac gctgcgcgta accaccacac ccgccgcgct taatgcgccg 4860
ctacagggcg cgtccattcg ccattcaggc tgcgcaactg ttgggaaggg cgatcggtgc 4920
gggcctcttc gctattacgc cagctggcga aagggggatg tgctgcaagg cgattaagtt 4980
gggtaacgcc agggttttcc cagtcacgac gttgtaaaac gacggccagt gaattgtaat 5040
acgactcact atagggcgaa ttgggcccga cgtcgcatgc tcccggccgc catggcggcc 5100
gcgggaattc gattgatt 5118

<210> SEQ ID NO 242
<211> LENGTH: 10821
<212> TYPE: DNA

-continued

<213> ORGANISM: Artificial
<220> FEATURE:
<223> OTHER INFORMATION: genetic construct

<400> SEQUENCE: 242
gaatttctag ttctagatgc atgctcgaaa ttcgattggc gcgccttaat taataagagc 60
agcttgccaa catggtggag cacgacactc tcgtctactc caagaatatc aaagatacag 120
tctcagaaga ccaaagggct attgagactt ttcaacaaag ggtaatatcg ggaaacctcc 180
tcggattcca ttgcccagct atctgtcact tcatcaaaag gacagtagaa aaggaaggtg 240
gcacctacaa atgccatcat tgcgataaag gaaaggctat cgttcaagat gcctctgccg 300
acagtggtcc caaagatgga cccccaccca cgaggagcat cgtggaaaaa gaagacgttc 360
caaccacgtc ttcaaagcaa gtggattgat gtgaacatgg tggagcacga cactctcgtc 420
tactccaaga atatcaaaga tacagtctca gaaggccaaa gggctattga gacttttcaa 480
caaagggtaa tatcgggaaa cctcctcgga ttccattgcc cagctatctg tcacttcatc 540
aaaaggacag tagaaaagga aggtggcacc tacaaatgcc atcattgcga taaaggaaag 600
gctatcgttc aagatgctct gccgacagtg gtcccaaaga tggaccccca cccacgagga 660
gcatcgtgga aaaagaagac gttccaacca cgtcttcaaa gcaagtggat tgatgtgata 720
tctccactga cgtaagggat gacgcacaat cccactatcc ttcgcaagac ccttcctcta 780
tataaggaag ttcatttcat ttggagagga cacgctgaaa tcaccagtct ctctctacaa 840
atctatctct ctccattagt tccgtcgcca tggcgtcccc ggagggcgcc aactgggtct 900
tcgactgccc gctcatggac gaccttgctg ccgccgactt caccgcaccg cccgcaggag 960
gcttctactg ggcaccaccg atgcagccgc agatgcacac ccaggccccg gccgtctccg 1020
ccaccccgcc tcccaaccac tgtgccgaaa tcaatagccc tatttctgtg gactgggacc 1080
atgccaaagg acagccaaca aataaacgtc ctaggtcaga atctggtgct caacccagct 1140
ccaaagcatg cagggagaaa gcgagaaggg acaagctaaa cgagaggttc ttggaattgg 1200
gtgctgtctt ggatccaggg aaaacaccta aaatcgacaa gtgtgctata ttgaatgatg 1260
ctattcgtgc ggtgactgag ctacgtagtg aagcagagaa gctgaaggat tcaaacgagt 1320
ctctccaaga gaagatcaaa gagctgaagg ctgagaagaa tgagctgcgg gatgagaagc 1380
aaaagctgaa ggcagagaaa gagagcctgg agcagcagat caagttcatg aatgcccgtc 1440
agagcctcgt accacaccta ccgcaccctt cggttatccc agcggctgca tttgctgctc 1500
cccaagggca agtgccaggg cagaagctga tgatgcctgt cattggctac catggatttc 1560
ccatgtggca attcatgcca ccttctgatg ttgatacctc cgatgatccc aagtcgtgcc 1620
ctcctgttgc ataagccagc taaaggcctg gtttctccat aataatgtgt gagtagttcc 1680
cagataaggg aattagggtt cctatagggt ttcgctcatg tgttgagcat ataagaaacc 1740
cttagtatgt atttgtattt gtaaaatact tctatcaata aaatttctaa ttcctaaaac 1800
caaaatccag tactaaaatc cagatccccc gaattaattc ggcgttaatt cagtatcggc 1860
gcgccttaat taaaatcgaa tttcgaccat actagtggat ccccctcgga ctagaagctt 1920
ggcactggcc gtcgttttac aacgtcgtga ctgggaaaac cctggcgtta cccaacttaa 1980
tcgccttgca gcacatcccc ctttcgccag ctggcgtaat agcgaagagg cccgcaccga 2040
tcgcccttcc caacagttgc gcagcctgaa tggcgaatgc tagagcagct tgagcttgga 2100
tcagattgtc gtttcccgcc ttcagtttaa actatcagtg tttgacagga tatattggcg 2160
ggtaaaccta agagaaaaga gcgtttatta gaataacgga tatttaaaag ggcgtgaaaa 2220

-continued

```
ggtttatccg ttcgtccatt tgtatgtgca tgccaaccac agggttcccc tcgggatcaa   2280
agtactttga tccaacccct ccgctgctat agtgcagtcg gcttctgacg ttcagtgcag   2340
ccgtcttctg aaaacgacat gtcgcacaag tcctaagtta cgcgacaggc tgccgccctg   2400
cccttttcct ggcgttttct tgtcgcgtgt tttagtcgca taaagtagaa tacttgcgac   2460
tagaaccgga gacattacgc catgaacaag agcgccgccg ctggcctgct gggctatgcc   2520
cgcgtcagca ccgacgacca ggacttgacc aaccaacggg ccgaactgca cgcggccggc   2580
tgcaccaagc tgttttccga gaagatcacc ggcaccaggc gcgaccgccc ggagctggcc   2640
aggatgcttg accacctacg ccctggcgac gttgtgacag tgaccaggct agaccgcctg   2700
gcccgcagca cccgcgacct actggacatt gccgagcgca tccaggaggc cggcgcgggc   2760
ctgcgtagcc tggcagagcc gtgggccgac accaccacgc cggccggccg catggtgttg   2820
accgtgttcg ccggcattgc cgagttcgag cgttccctaa tcatcgaccg cacccggagc   2880
gggcgcgagg ccgccaaggc ccgaggcgtg aagtttggcc cccgccctac cctcaccccg   2940
gcacagatcg cgcacgcccg cgagctgatc gaccaggaag gccgcaccgt gaaagaggcg   3000
gctgcactgc ttggcgtgca tcgctcgacc ctgtaccgcg cacttgagcg cagcgaggaa   3060
gtgacgccca ccgaggccag gcggcgcggt gccttccgtg aggacgcatt gaccgaggcc   3120
gacgccctgg cggccgccga gaatgaacgc caagaggaac aagcatgaaa ccgcaccagg   3180
acggccagga cgaaccgttt ttcattaccg aagagatcga ggcggagatg atcgcggccg   3240
ggtacgtgtt cgagccgccc gcgcacgtct caaccgtgcg gctgcatgaa atcctggccg   3300
gtttgtctga tgccaagctg gcggcctggc cggccagctt ggccgctgaa gaaaccgagc   3360
gccgccgtct aaaaaggtga tgtgtatttg agtaaaacag cttgcgtcat gcggtcgctg   3420
cgtatatgat gcgatgagta aataaacaaa tacgcaaggg gaacgcatga aggttatcgc   3480
tgtacttaac cagaaaggcg ggtcaggcaa gacgaccatc gcaacccatc tagcccgcgc   3540
cctgcaactc gccggggccg atgttctgtt agtcgattcc gatccccagg gcagtgcccg   3600
cgattgggcg gccgtgcggg aagatcaacc gctaaccgtt gtcggcatcg accgcccgac   3660
gattgaccgc gacgtgaagg ccatcggccg gcgcgacttc gtagtgatcg acggagcgcc   3720
ccaggcggcg gacttggctg tgtccgcgat caaggcagcc gacttcgtgc tgattccggt   3780
gcagccaagc ccttacgaca tatgggccac cgccgacctg gtggagctgg ttaagcagcg   3840
cattgaggtc acggatggaa ggctacaagc ggcctttgtc gtgtcgcggg cgatcaaagg   3900
cacgcgcatc ggcggtgagg ttgccgaggc gctggccggg tacgagctgc ccattcttga   3960
gtcccgtatc acgcagcgcg tgagctaccc aggcactgcc gccgccggca caaccgttct   4020
tgaatcagaa cccgagggcg acgctgcccg cgaggtccag gcgctggccg ctgaaattaa   4080
atcaaaactc atttgagtta atgaggtaaa gagaaaatga gcaaaagcac aaacacgcta   4140
agtgccggcc gtccgagcgc acgcagcagc aaggctgcaa cgttggccag cctggcagac   4200
acgccagcca tgaagcgggt caactttcag ttgccggcgg aggatcacac caagctgaag   4260
atgtacgcgg tacgccaagg caagaccatt accgagctgc tatctgaata catcgcgcag   4320
ctaccagagt aaatgagcaa atgaataaat gagtagatga attttagcgg ctaaaggagg   4380
cggcatggaa aatcaagaac aaccaggcac cgacgccgtg gaatgcccca tgtgtggagg   4440
aacgggcggt tggccaggcg taagcggctg ggttgtctgc cggccctgca atggcactgg   4500
aacccccaag cccgaggaat cggcgtgacg gtcgcaaacc atccggcccg gtacaaatcg   4560
```

-continued

```
gcgcggcgct gggtgatgac ctggtggaga agttgaaggc cgcgcaggcc gcccagcggc   4620
aacgcatcga ggcagaagca cgccccggtg aatcgtggca agcggccgct gatcgaatcc   4680
gcaaagaatc ccggcaaccg ccggcagccg gtgcgccgtc gattaggaag ccgcccaagg   4740
gcgacgagca accagatttt ttcgttccga tgctctatga cgtgggcacc cgcgatagtc   4800
gcagcatcat ggacgtggcc gttttccgtc tgtcgaagcg tgaccgacga gctggcgagg   4860
tgatccgcta cgagcttcca gacgggcacg tagaggtttc cgcagggccg gccggcatgg   4920
ccagtgtgtg ggattacgac ctggtactga tggcggtttc ccatctaacc gaatccatga   4980
accgataccg ggaagggaag ggagacaagc ccggccgcgt gttccgtcca cacgttgcgg   5040
acgtactcaa gttctgccgg cgagccgatg gcggaaagca gaaagacgac ctggtagaaa   5100
cctgcattcg gttaaacacc acgcacgttg ccatgcagcg tacgaagaag gccaagaacg   5160
gccgcctggt gacggtatcc gagggtgaag ccttgattag ccgctacaag atcgtaaaga   5220
gcgaaaccgg gcggccggag tacatcgaga tcgagctagc tgattggatg taccgcgaga   5280
tcacagaagg caagaacccg gacgtgctga cggttcaccc cgattacttt ttgatcgatc   5340
ccggcatcgg ccgttttctc taccgcctgg cacgccgcgc cgcaggcaag gcagaagcca   5400
gatggttgtt caagacgatc tacgaacgca gtggcagcgc cggagagttc aagaagttct   5460
gtttcaccgt gcgcaagctg atcgggtcaa atgacctgcc ggagtacgat ttgaaggagg   5520
aggcggggca ggctggcccg atcctagtca tgcgctaccg caacctgatc gagggcgaag   5580
catccgccgg ttcctaatgt acggagcaga tgctagggca aattgcccta gcaggggaaa   5640
aaggtcgaaa aggtctcttt cctgtggata gcacgtacat tgggaaccca aagccgtaca   5700
ttgggaaccg gaacccgtac attgggaacc caaagccgta cattgggaac cggtcacaca   5760
tgtaagtgac tgatataaaa gagaaaaaag gcgatttttc cgcctaaaac tctttaaaac   5820
ttattaaaac tcttaaaacc cgcctggcct gtgcataact gtctggccag cgcacagccg   5880
aagagctgca aaaagcgcct acccttcggt cgctgcgctc cctacgcccc gccgcttcgc   5940
gtcggcctat cgcggccgct ggccgctcaa aaatggctgg cctacggcca ggcaatctac   6000
cagggcgcgg acaagccgcg ccgtcgccac tcgaccgccg gcgcccacat caaggcaccc   6060
tgcctcgcgc gtttcggtga tgacggtgaa aacctctgac acatgcagct cccggagacg   6120
gtcacagctt gtctgtaagc ggatgccggg agcagacaag cccgtcaggg cgcgtcagcg   6180
ggtgttggcg ggtgtcgggg cgcagccatg acccagtcac gtagcgatag cggagtgtat   6240
actggcttaa ctatgcggca tcagagcaga ttgtactgag agtgcaccat atgcggtgtg   6300
aaataccgca cagatgcgta aggagaaaat accgcatcag gcgctcttcc gcttcctcgc   6360
tcactgactc gctgcgctcg gtcgttcggc tgcggcgagc ggtatcagct cactcaaagg   6420
cggtaatacg gttatccaca gaatcagggg ataacgcagg aaagaacatg tgagcaaaag   6480
gccagcaaaa ggccaggaac cgtaaaaagg ccgcgttgct ggcgtttttc cataggctcc   6540
gcccccctga cgagcatcac aaaaatcgac gctcaagtca gaggtggcga aacccgacag   6600
gactataaag ataccaggcg tttccccctg gaagctccct cgtgcgctct cctgttccga   6660
ccctgccgct taccggatac ctgtccgcct ttctcccttc gggaagcgtg gcgctttctc   6720
atagctcacg ctgtaggtat ctcagttcgg tgtaggtcgt tcgctccaag ctgggctgtg   6780
tgcacgaacc ccccgttcag cccgaccgct gcgccttatc cggtaactat cgtcttgagt   6840
ccaacccggt aagacacgac ttatcgccac tggcagcagc cactggtaac aggattagca   6900
gagcgaggta tgtaggcggt gctacagagt tcttgaagtg gtggcctaac tacggctaca   6960
```

-continued

```
ctagaaggac agtatttggt atctgcgctc tgctgaagcc agttaccttc ggaaaaagag   7020
ttggtagctc ttgatccggc aaacaaacca ccgctggtag cggtggtttt tttgtttgca   7080
agcagcagat tacgcgcaga aaaaaaggat ctcaagaaga tcctttgatc ttttctacgg   7140
ggtctgacgc tcagtggaac gaaaactcac gttaagggat tttggtcatg cattctaggt   7200
actaaaacaa ttcatccagt aaaatataat attttatttt ctcccaatca ggcttgatcc   7260
ccagtaagtc aaaaaatagc tcgacatact gttcttcccc gatatcctcc ctgatcgacc   7320
ggacgcagaa ggcaatgtca taccacttgt ccgccctgcc gcttctccca agatcaataa   7380
agccacttac tttgccatct ttcacaaaga tgttgctgtc tcccaggtcg ccgtgggaaa   7440
agacaagttc ctcttcgggc ttttccgtct ttaaaaaatc atacagctcg cgcggatctt   7500
taaatggagt gtcttcttcc cagttttcgc aatccacatc ggccagatcg ttattcagta   7560
agtaatccaa ttcggctaag cggctgtcta agctattcgt atagggacaa tccgatatgt   7620
cgatggagtg aaagagcctg atgcactccg catacagctc gataatcttt tcagggcttt   7680
gttcatcttc atactcttcc gagcaaagga cgccatcggc ctcactcatg agcagattgc   7740
tccagccatc atgccgttca aagtgcagga cctttggaac aggcagcttt ccttccagcc   7800
atagcatcat gtccttttcc cgttccacat cataggtggt ccctttatac cggctgtccg   7860
tcatttttaa atataggttt tcattttctc ccaccagctt atataccttta gcaggagaca   7920
ttccttccgt atcttttacg cagcggtatt tttcgatcag tttttcaat tccggtgata   7980
ttctcatttt agccatttat tatttccttc ctcttttcta cagtatttaa agatacccca   8040
agaagctaat tataacaaga cgaactccaa ttcactgttc cttgcattct aaaaccttaa   8100
ataccagaaa acagcttttt caaagttgtt ttcaaagttg gcgtataaca tagtatcgac   8160
ggagccgatt ttgaaaccgc ggtgatcaca ggcagcaacg ctctgtcatc gttacaatca   8220
acatgctacc ctccgcgaga tcatccgtgt ttcaaacccg gcagcttagt tgccgttctt   8280
ccgaatagca tcggtaacat gagcaaagtc tgccgcctta caacggctct cccgctgacg   8340
ccgtcccgga ctgatgggct gcctgtatcg agtggtgatt ttgtgccgag ctgccggtcg   8400
gggagctgtt ggctggctgg tggcaggata tattgtggtg taaacaaatt gacgcttaga   8460
caacttaata acacattgcg gacgttttta atgtactgaa ttaacgccga attaattcgg   8520
gggatctgga ttttagtact ggattttggt tttaggaatt agaaatttta ttgatagaag   8580
tattttacaa atacaaatac atactaaggg tttcttatat gctcaacaca tgagcgaaac   8640
cctataggaa ccctaattcc cttatctggg aactactcac acattattat ggagaaactc   8700
gagcttgtcg atcgacagat ccggtcggca tctactctat ttctttgccc tcggacgagt   8760
gctggggcgt cggtttccac tatcggcgag tacttctaca cagccatcgg tccagacggc   8820
cgcgcttctg cgggcgattt gtgtacgccc gacagtcccg gctccggatc ggacgattgc   8880
gtcgcatcga ccctgcgccc aagctgcatc atcgaaattg ccgtcaacca agctctgata   8940
gagttggtca agaccaatgc ggagcatata cgcccggagt cgtggcgatc ctgcaagctc   9000
cggatgcctc cgctcgaagt agcgcgtctg ctgctccata caagccaacc acggcctcca   9060
gaagaagatg ttggcgacct cgtattggga atccccgaac atcgcctcgc tccagtcaat   9120
gaccgctgtt atgcggccat tgtccgtcag gacattgttg gagccgaaat ccgcgtgcac   9180
gaggtgccgg acttcggggc agtcctcggc ccaaagcatc agctcatcga gagcctgcgc   9240
gacggacgca ctgacggtgt cgtccatcac agtttgccag tgatacacat ggggatcagc   9300
```

-continued

```
aatcgcgcat atgaaatcac gccatgtagt gtattgaccg attccttgcg gtccgaatgg   9360

gccgaacccg ctcgtctggc taagatcggc cgcagcgatc gcatccatag cctccgcgac   9420

cggttgtaga acagcgggca gttcggtttc aggcaggtct tgcaacgtga caccctgtgc   9480

acggcgggag atgcaatagg tcaggctctc gctaaactcc ccaatgtcaa gcacttccgg   9540

aatcgggagc gcggccgatg caaagtgccg ataaacataa cgatctttgt agaaaccatc   9600

ggcgcagcta tttacccgca ggacatatcc acgccctcct acatcgaagc tgaaagcacg   9660

agattcttcg ccctccgaga gctgcatcag gtcggagacg ctgtcgaact tttcgatcag   9720

aaacttctcg acagacgtcg cggtgagttc aggctttttc atatctcatt gcccccccgg   9780

atctgcgaaa gctcgagaga gatagatttg tagagagaga ctggtgattt cagcgtgtcc   9840

tctccaaatg aaatgaactt ccttatatag aggaaggtct tgcgaaggat agtgggattg   9900

tgcgtcatcc cttacgtcag tggagatatc acatcaatcc acttgctttg aagacgtggt   9960

tggaacgtct tctttttcca cgatgctcct cgtgggtggg ggtccatctt tgggaccact  10020

gtcggcagag gcatcttgaa cgatagcctt tcctttatcg caatgatggc atttgtaggt  10080

gccaccttcc ttttctactg tccttttgat gaagtgacag atagctgggc aatggaatcc  10140

gaggaggttt cccgatatta ccctttgttg aaaagtctca atagcccttt ggtcttctga  10200

gactgtatct ttgatattct tggagtagac gagagtgtcg tgctccacca tgttatcaca  10260

tcaatccact tgctttgaag acgtggttgg aacgtcttct ttttccacga tgctcctcgt  10320

gggtgggggt ccatctttgg gaccactgtc ggcagaggca tcttgaacga tagcctttcc  10380

tttatcgcaa tgatggcatt tgtaggtgcc accttccttt tctactgtcc ttttgatgaa  10440

gtgacagata gctgggcaat ggaatccgag gaggtttccc gatattaccc tttgttgaaa  10500

agtctcaata gccctttggt cttctgagac tgtatctttg atattcttgg agtagacgag  10560

agtgtcgtgc tccaccatgt tggcaagctg ctctagccaa tacgcaaacc gcctctcccc  10620

gcgcgttggc cgattcatta atgcagctgg cacgacaggt ttcccgactg gaaagcgggc  10680

agtgagcgca acgcaattaa tgtgagttag ctcactcatt aggcacccca ggctttacac  10740

tttatgcttc cggctcgtat gttgtgtgga attgtgagcg gataacaatt tcacacagga  10800

aacagctatg accatgatta c                                            10821
```

```
<210> SEQ ID NO 243
<211> LENGTH: 10905
<212> TYPE: DNA
<213> ORGANISM: Artificial
<220> FEATURE:
<223> OTHER INFORMATION: genetic construct

<400> SEQUENCE: 243
```

```
gaatttctag ttctagatgc atgctcgaaa ttcgattggc gcgccttaat taataagagc     60

agcttgccaa catggtggag cacgacactc tcgtctactc caagaatatc aaagatacag    120

tctcagaaga ccaaagggct attgagactt ttcaacaaag ggtaatatcg ggaaacctcc    180

tcggattcca ttgcccagct atctgtcact tcatcaaaag gacagtagaa aaggaaggtg    240

gcacctacaa atgccatcat tgcgataaag gaaaggctat cgttcaagat gcctctgccg    300

acagtggtcc caaagatgga cccccaccca cgaggagcat cgtggaaaaa gaagacgttc    360

caaccacgtc ttcaaagcaa gtggattgat gtgaacatgg tggagcacga cactctcgtc    420

tactccaaga atatcaaaga tacagtctca gaaggccaaa gggctattga gacttttcaa    480

caaagggtaa tatcgggaaa cctcctcgga ttccattgcc cagctatctg tcacttcatc    540
```

-continued

```
aaaaggacag tagaaaagga aggtggcacc tacaaatgcc atcattgcga taaaggaaag    600
gctatcgttc aagatgctct gccgacagtg gtcccaaaga tggaccccca cccacgagga    660
gcatcgtgga aaaagaagac gttccaacca cgtcttcaaa gcaagtggat tgatgtgata    720
tctccactga cgtaagggat gacgcacaat cccactatcc ttcgcaagac ccttcctcta    780
tataaggaag ttcatttcat ttggagagga cacgctgaaa tcaccagtct ctctctacaa    840
atctatctct ctccattagt ttgcccactg cttgctgcta ctctctcgat ctgtagttgc    900
tcaggtgtgc aagaaagata ctcacacgcg agcttgcttg gcatggccgt ggaggcggtt    960
ctcgaagcgg cggcgatgat acagtcgccg ccgagcaaga agatggaggc gtctagtagc   1020
agcgacgagg cgttcgaggc gttgcagcag cacacggagg ggtggtccaa gaagaagcgc   1080
tcgaggcggc cacgggcgct cgagcccagc gaggaggagt acctcgcgtt ctgcctcgtc   1140
atgctggcgc gcggccaccg cgacgccgcg ccggagcacg ggtgctccgt ctgcggcaag   1200
gcgttcgcgt cgtaccaggc gctcggcggc cacaaggcca gccaccggaa gccacccaca   1260
gctccagccg cggtggcagc aagcgccgtc cccgaggagg acaagccacg ggcggctgcc   1320
tcgtcctcgt ctgggtccgg cgatgccgct ggcggcggca aggtccacga gtgcaacgtg   1380
tgccagaaga cgttcccgac ggggcaggcg ctgggcggcc acaagcggtg ccactacgac   1440
ggcaccatcg gcagcgccgc cgcgcccacg gtgaaggctg ccaaggccgc cgccgcggcg   1500
agcgcgccga cggcgacgaa ccgggggttc gacctgaacg tgccggcgct gccgggactc   1560
gcggaggagg gggaggaggt gctcagcccg gtatccttca agaagccgag gctcatgatc   1620
accgcgtgat ttgaccatac aatctgcata tagttggtca aaatcaaggg ttcttctgta   1680
gcttagcttc tgttagtgat tgccgtacat agattgttgg tgattgaagg cctggtttct   1740
ccataataat gtgtgagtag ttcccagata agggaattag ggttcctata gggtttcgct   1800
catgtgttga gcatataaga aacccttagt atgtatttgt atttgtaaaa tacttctatc   1860
aataaaattt ctaattccta aaaccaaaat ccagtactaa aatccagatc ccccgaatta   1920
attcggcgtt aattcagtat cggcgcgcct taattaaaat cgaatttcga ccatactagt   1980
ggatccccct cggactagaa gcttggcact ggccgtcgtt ttacaacgtc gtgactggga   2040
aaaccctggc gttacccaac ttaatcgcct tgcagcacat ccccctttcg ccagctggcg   2100
taatagcgaa gaggcccgca ccgatcgccc ttcccaacag ttgcgcagcc tgaatggcga   2160
atgctagagc agcttgagct tggatcagat tgtcgtttcc cgccttcagt ttaaactatc   2220
agtgtttgac aggatatatt ggcgggtaaa cctaagagaa aagagcgttt attagaataa   2280
cggatattta aaagggcgtg aaaaggttta tccgttcgtc catttgtatg tgcatgccaa   2340
ccacagggtt cccctcggga tcaaagtact ttgatccaac ccctccgctg ctatagtgca   2400
gtcggcttct gacgttcagt gcagccgtct tctgaaaacg acatgtcgca caagtcctaa   2460
gttacgcgac aggctgccgc cctgcccttt tcctggcgtt ttcttgtcgc gtgttttagt   2520
cgcataaagt agaatacttg cgactagaac cggagacatt acgccatgaa caagagcgcc   2580
gccgctggcc tgctgggcta tgcccgcgtc agcaccgacg accaggactt gaccaaccaa   2640
cgggccgaac tgcacgcggc cggctgcacc aagctgtttt ccgagaagat caccggcacc   2700
aggcgcgacc gcccggagct ggccaggatg cttgaccacc tacgccctgg cgacgttgtg   2760
acagtgacca ggctagaccg cctggcccgc agcacccgcg acctactgga cattgccgag   2820
cgcatccagg aggccggcgc gggcctgcgt agcctggcag agccgtgggc cgacaccacc   2880
```

-continued

```
acgccggccg gccgcatggt gttgaccgtg ttcgccggca ttgccgagtt cgagcgttcc   2940
ctaatcatcg accgcacccg gagcgggcgc gaggccgcca aggcccgagg cgtgaagttt   3000
ggcccccgcc ctaccctcac cccggcacag atcgcgcacg cccgcgagct gatcgaccag   3060
gaaggccgca ccgtgaaaga ggcggctgca ctgcttggcg tgcatcgctc gaccctgtac   3120
cgcgcacttg agcgcagcga ggaagtgacg cccaccgagg ccaggcggcg cggtgccttc   3180
cgtgaggacg cattgaccga ggccgacgcc ctggcggccg ccgagaatga acgccaagag   3240
gaacaagcat gaaaccgcac caggacggcc aggacgaacc gtttttcatt accgaagaga   3300
tcgaggcgga gatgatcgcg gccgggtacg tgttcgagcc gcccgcgcac gtctcaaccg   3360
tgcggctgca tgaaatcctg gccggtttgt ctgatgccaa gctggcggcc tggccggcca   3420
gcttggccgc tgaagaaacc gagcgccgcc gtctaaaaag gtgatgtgta tttgagtaaa   3480
acagcttgcg tcatgcggtc gctgcgtata tgatgcgatg agtaaataaa caaatacgca   3540
aggggaacgc atgaaggtta tcgctgtact taaccagaaa ggcgggtcag gcaagacgac   3600
catcgcaacc catctagccc gcgccctgca actcgccggg gccgatgttc tgttagtcga   3660
ttccgatccc cagggcagtg cccgcgattg ggcggccgtg cgggaagatc aaccgctaac   3720
cgttgtcggc atcgaccgcc cgacgattga ccgcgacgtg aaggccatcg gccggcgcga   3780
cttcgtagtg atcgacggag cgccccaggc ggcggacttg gctgtgtccg cgatcaaggc   3840
agccgacttc gtgctgattc cggtgcagcc aagcccttac gacatatggg ccaccgccga   3900
cctggtggag ctggttaagc agcgcattga ggtcacggat ggaaggctac aagcggcctt   3960
tgtcgtgtcg cgggcgatca aaggcacgcg catcggcggt gaggttgccg aggcgctggc   4020
cgggtacgag ctgcccattc ttgagtcccg tatcacgcag cgcgtgagct acccaggcac   4080
tgccgccgcc ggcacaaccg ttcttgaatc agaacccgag ggcgacgctg cccgcgaggt   4140
ccaggcgctg gccgctgaaa ttaaatcaaa actcatttga gttaatgagg taaagagaaa   4200
atgagcaaaa gcacaaacac gctaagtgcc ggccgtccga gcgcacgcag cagcaaggct   4260
gcaacgttgg ccagcctggc agacacgcca gccatgaagc gggtcaactt tcagttgccg   4320
gcggaggatc acaccaagct gaagatgtac gcggtacgcc aaggcaagac cattaccgag   4380
ctgctatctg aatacatcgc gcagctacca gagtaaatga gcaaatgaat aaatgagtag   4440
atgaatttta gcggctaaag gaggcggcat ggaaaatcaa gaacaaccag gcaccgacgc   4500
cgtggaatgc cccatgtgtg gaggaacggg cggttggcca ggcgtaagcg gctgggttgt   4560
ctgccggccc tgcaatggca ctggaacccc caagcccgag gaatcggcgt gacggtcgca   4620
aaccatccgg cccggtacaa atcggcgcgg cgctgggtga tgacctggtg gagaagttga   4680
aggccgcgca ggccgcccag cggcaacgca tcgaggcaga agcacgcccc ggtgaatcgt   4740
ggcaagcggc cgctgatcga atccgcaaag aatcccggca accgccggca gccggtgcgc   4800
cgtcgattag gaagccgccc aagggcgacg agcaaccaga tttttcgtt ccgatgctct    4860
atgacgtggg cacccgcgat agtcgcagca tcatggacgt ggccgttttc cgtctgtcga   4920
agcgtgaccg acgagctggc gaggtgatcc gctacgagct tccagacggg cacgtagagg   4980
tttccgcagg gccggccggc atggccagtg tgtgggatta cgacctggta ctgatggcgg   5040
tttcccatct aaccgaatcc atgaaccgat accgggaagg gaagggagac aagcccggcc   5100
gcgtgttccg tccacacgtt gcggacgtac tcaagttctg ccggcgagcc gatggcggaa   5160
agcagaaaga cgacctggta gaaacctgca ttcggttaaa caccacgcac gttgccatgc   5220
agcgtacgaa gaaggccaag aacggccgcc tggtgacggt atccgagggt gaagccttga   5280
```

-continued

```
ttagccgcta caagatcgta aagagcgaaa ccgggcggcc ggagtacatc gagatcgagc   5340
tagctgattg gatgtaccgc gagatcacag aaggcaagaa cccggacgtg ctgacggttc   5400
accccgatta ctttttgatc gatcccggca tcggccgttt tctctaccgc ctggcacgcc   5460
gcgccgcagg caaggcagaa gccagatggt tgttcaagac gatctacgaa cgcagtggca   5520
gcgccggaga gttcaagaag ttctgtttca ccgtgcgcaa gctgatcggg tcaaatgacc   5580
tgccggagta cgatttgaag gaggaggcgg ggcaggctgg cccgatccta gtcatgcgct   5640
accgcaacct gatcgagggc gaagcatccg ccggttccta atgtacggag cagatgctag   5700
ggcaaattgc cctagcaggg gaaaaaggtc gaaaaggtct ctttcctgtg gatagcacgt   5760
acattgggaa cccaaagccg tacattggga accggaaccc gtacattggg aacccaaagc   5820
cgtacattgg gaaccggtca cacatgtaag tgactgatat aaaagagaaa aaaggcgatt   5880
tttccgccta aaactcttta aaacttatta aaactcttaa aacccgcctg gcctgtgcat   5940
aactgtctgg ccagcgcaca gccgaagagc tgcaaaaagc gcctaccctt cggtcgctgc   6000
gctccctacg ccccgccgct tcgcgtcggc ctatcgcggc cgctggccgc tcaaaaatgg   6060
ctggcctacg gccaggcaat ctaccagggc gcggacaagc cgcgccgtcg ccactcgacc   6120
gccggcgccc acatcaaggc accctgcctc gcgcgtttcg gtgatgacgg tgaaaacctc   6180
tgacacatgc agctcccgga gacggtcaca gcttgtctgt aagcggatgc cgggagcaga   6240
caagcccgtc agggcgcgtc agcgggtgtt ggcgggtgtc ggggcgcagc catgacccag   6300
tcacgtagcg atagcggagt gtatactggc ttaactatgc ggcatcagag cagattgtac   6360
tgagagtgca ccatatgcgg tgtgaaatac cgcacagatg cgtaaggaga aaataccgca   6420
tcaggcgctc ttccgcttcc tcgctcactg actcgctgcg ctcggtcgtt cggctgcggc   6480
gagcggtatc agctcactca aaggcggtaa tacggttatc cacagaatca ggggataacg   6540
caggaaagaa catgtgagca aaaggccagc aaaaggccag gaaccgtaaa aaggccgcgt   6600
tgctggcgtt tttccatagg ctccgccccc ctgacgagca tcacaaaaat cgacgctcaa   6660
gtcagaggtg gcgaaacccg acaggactat aaagatacca ggcgtttccc cctggaagct   6720
ccctcgtgcg ctctcctgtt ccgaccctgc cgcttaccgg atacctgtcc gcctttctcc   6780
cttcgggaag cgtggcgctt tctcatagct cacgctgtag gtatctcagt tcggtgtagg   6840
tcgttcgctc caagctgggc tgtgtgcacg aaccccccgt tcagcccgac cgctgcgcct   6900
tatccggtaa ctatcgtctt gagtccaacc cggtaagaca cgacttatcg ccactggcag   6960
cagccactgg taacaggatt agcagagcga ggtatgtagg cggtgctaca gagttcttga   7020
agtggtggcc taactacggc tacactagaa ggacagtatt tggtatctgc gctctgctga   7080
agccagttac cttcggaaaa agagttggta gctcttgatc cggcaaacaa accaccgctg   7140
gtagcggtgg tttttttgtt tgcaagcagc agattacgcg cagaaaaaaa ggatctcaag   7200
aagatccttt gatcttttct acggggtctg acgctcagtg gaacgaaaac tcacgttaag   7260
ggattttggt catgcattct aggtactaaa acaattcatc cagtaaaata taatatttta   7320
ttttctccca atcaggcttg atccccagta agtcaaaaaa tagctcgaca tactgttctt   7380
ccccgatatc ctccctgatc gaccggacgc agaaggcaat gtcataccac ttgtccgccc   7440
tgccgcttct cccaagatca ataaagccac ttactttgcc atctttcaca aagatgttgc   7500
tgtctcccag gtcgccgtgg gaaaagacaa gttcctcttc gggcttttcc gtctttaaaa   7560
aatcatacag ctcgcgcgga tctttaaatg gagtgtcttc ttcccagttt tcgcaatcca   7620
```

-continued

```
catcggccag atcgttattc agtaagtaat ccaattcggc taagcggctg tctaagctat   7680

tcgtataggg acaatccgat atgtcgatgg agtgaaagag cctgatgcac tccgcataca   7740

gctcgataat cttttcaggg ctttgttcat cttcatactc ttccgagcaa aggacgccat   7800

cggcctcact catgagcaga ttgctccagc catcatgccg ttcaaagtgc aggacctttg   7860

gaacaggcag ctttccttcc agccatagca tcatgtcctt ttcccgttcc acatcatagg   7920

tggtcccttt ataccggctg tccgtcattt ttaaatatag gttttcattt tctcccacca   7980

gcttatatac cttagcagga gacattcctt ccgtatcttt tacgcagcgg tatttttcga   8040

tcagtttttt caattccggt gatattctca ttttagccat ttattatttc cttcctcttt   8100

tctacagtat ttaaagatac cccaagaagc taattataac aagacgaact ccaattcact   8160

gttccttgca ttctaaaacc ttaaatacca gaaaacagct ttttcaaagt tgttttcaaa   8220

gttggcgtat aacatagtat cgacggagcc gattttgaaa ccgcggtgat cacaggcagc   8280

aacgctctgt catcgttaca atcaacatgc taccctccgc gagatcatcc gtgtttcaaa   8340

cccggcagct tagttgccgt tcttccgaat agcatcggta acatgagcaa agtctgccgc   8400

cttacaacgg ctctcccgct gacgccgtcc cggactgatg ggctgcctgt atcgagtggt   8460

gattttgtgc cgagctgccg gtcggggagc tgttggctgg ctggtggcag gatatattgt   8520

ggtgtaaaca aattgacgct tagacaactt aataacacat tgcggacgtt tttaatgtac   8580

tgaattaacg ccgaattaat tcgggggatc tggattttag tactggattt tggttttagg   8640

aattagaaat tttattgata gaagtatttt acaaatacaa atacatacta agggtttctt   8700

atatgctcaa cacatgagcg aaaccctata ggaaccctaa ttcccttatc tgggaactac   8760

tcacacatta ttatggagaa actcgagctt gtcgatcgac agatccggtc ggcatctact   8820

ctatttcttt gccctcggac gagtgctggg gcgtcggttt ccactatcgg cgagtacttc   8880

tacacagcca tcggtccaga cggccgcgct tctgcgggcg atttgtgtac gcccgacagt   8940

cccggctccg gatcggacga ttgcgtcgca tcgaccctgc gcccaagctg catcatcgaa   9000

attgccgtca accaagctct gatagagttg gtcaagacca atgcggagca tatacgcccg   9060

gagtcgtggc gatcctgcaa gctccggatg cctccgctcg aagtagcgcg tctgctgctc   9120

catacaagcc aaccacggcc tccagaagaa gatgttggcg acctcgtatt gggaatcccc   9180

gaacatcgcc tcgctccagt caatgaccgc tgttatgcgg ccattgtccg tcaggacatt   9240

gttggagccg aaatccgcgt gcacgaggtg ccggacttcg gggcagtcct cggcccaaag   9300

catcagctca tcgagagcct gcgcgacgga cgcactgacg gtgtcgtcca tcacagtttg   9360

ccagtgatac acatggggat cagcaatcgc gcatatgaaa tcacgccatg tagtgtattg   9420

accgattcct tgcggtccga atgggccgaa cccgctcgtc tggctaagat cggccgcagc   9480

gatcgcatcc atagcctccg cgaccggttg tagaacagcg ggcagttcgg tttcaggcag   9540

gtcttgcaac gtgacaccct gtgcacggcg ggagatgcaa taggtcaggc tctcgctaaa   9600

ctccccaatg tcaagcactt ccggaatcgg gagcgcggcc gatgcaaagt gccgataaac   9660

ataacgatct ttgtagaaac catcggcgca gctatttacc cgcaggacat atccacgccc   9720

tcctacatcg aagctgaaag cacgagattc ttcgccctcc gagagctgca tcaggtcgga   9780

gacgctgtcg aacttttcga tcagaaactt ctcgacagac gtcgcggtga gttcaggctt   9840

tttcatatct cattgccccc ccggatctgc gaaagctcga gagagataga tttgtagaga   9900

gagactggtg atttcagcgt gtcctctcca aatgaaatga acttccttat atagaggaag   9960

gtcttgcgaa ggatagtggg attgtgcgtc atcccttacg tcagtggaga tatcacatca  10020
```

```
atccacttgc tttgaagacg tggttggaac gtcttctttt tccacgatgc tcctcgtggg  10080
tgggggtcca tctttgggac cactgtcggc agaggcatct tgaacgatag cctttccttt  10140
atcgcaatga tggcatttgt aggtgccacc ttccttttct actgtccttt tgatgaagtg  10200
acagatagct gggcaatgga atccgaggag gtttcccgat attacccttt gttgaaaagt  10260
ctcaatagcc ctttggtctt ctgagactgt atctttgata ttcttggagt agacgagagt  10320
gtcgtgctcc accatgttat cacatcaatc cacttgcttt gaagacgtgg ttggaacgtc  10380
ttctttttcc acgatgctcc tcgtgggtgg gggtccatct ttgggaccac tgtcggcaga  10440
ggcatcttga acgatagcct ttcctttatc gcaatgatgg catttgtagg tgccaccttc  10500
cttttctact gtcctttga tgaagtgaca gatagctggg caatggaatc cgaggaggtt  10560
tcccgatatt accctttgtt gaaaagtctc aatagccctt tggtcttctg agactgtatc  10620
tttgatattc ttggagtaga cgagagtgtc gtgctccacc atgttggcaa gctgctctag  10680
ccaatacgca aaccgcctct ccccgcgcgt tggccgattc attaatgcag ctggcacgac  10740
aggtttcccg actggaaagc gggcagtgag cgcaacgcaa ttaatgtgag ttagctcact  10800
cattaggcac cccaggcttt acactttatg cttccggctc gtatgttgtg tggaattgtg  10860
agcggataac aatttcacac aggaaacagc tatgaccatg attac                10905
```

<210> SEQ ID NO 244
<211> LENGTH: 7
<212> TYPE: PRT
<213> ORGANISM: Artificial
<220> FEATURE:
<223> OTHER INFORMATION: motif found in SEQ ID NO: 201 from Lolium perenne

<400> SEQUENCE: 244

```
Gln Ala Leu Gly Gly His Lys
1               5
```

<210> SEQ ID NO 245
<211> LENGTH: 120
<212> TYPE: PRT
<213> ORGANISM: Triticum aestivum

<400> SEQUENCE: 245

```
Met Ala Ser Pro Glu Gly Ser Asn Trp Val Phe Asp Cys Pro Leu Met
1               5                   10                  15

Asp Asp Leu Ala Ala Ala Asp Phe Ala Ala Ala Pro Ala Gly Gly Phe
            20                  25                  30

Tyr Trp Thr Pro Pro Met Gln Pro Gln Met His Thr Leu Ala Gln Ala
        35                  40                  45

Val Ser Ala Thr Pro Ala Pro Asn Pro Cys Ala Glu Ile Asn Ser Ser
    50                  55                  60

Val Ser Val Cys Trp Asp His Ala Lys Gly Gln Pro Lys Asn Lys Arg
65                  70                  75                  80

Pro Arg Ser Glu Thr Gly Ala Gln Pro Ser Ser Lys Ala Cys Arg Glu
                85                  90                  95

Lys Ala Arg Arg Asp Lys Leu Asn Glu Arg Phe Leu Glu Ser Ser Ala
            100                 105                 110

Asp Leu Asp Pro Gly Asn Thr Pro
        115                 120
```

<210> SEQ ID NO 246

-continued

<211> LENGTH: 135
<212> TYPE: PRT
<213> ORGANISM: Secale cereale
<220> FEATURE:
<221> NAME/KEY: misc_feature
<222> LOCATION: (86)..(86)
<223> OTHER INFORMATION: Unknown

<400> SEQUENCE: 246

```
Met Ala Ser Pro Glu Gly Ser Asn Trp Val Phe Asp Cys Pro Leu Met
1               5                   10                  15

Asp Asp Leu Ala Ala Ala Asp Phe Ala Ala Ala Pro Ala Gly Gly Phe
            20                  25                  30

Tyr Trp Thr Pro Gln Met His Thr Leu Ala Gln Ala Val Ser Ala Thr
        35                  40                  45

Pro Ala Pro Asn Gly Gly Ala Glu Ile Asn Ser Ser Val Ser Val Asp
    50                  55                  60

Cys Asp His Val Lys Gly Gln Pro Lys Asn Lys Arg Pro Arg Ser Glu
65                  70                  75                  80

Thr Gly Ala Gln Pro Xaa Ser Lys Ala Cys Arg Glu Lys Val Arg Arg
                85                  90                  95

Asp Lys Leu Asn Glu Arg Phe Leu Glu Leu Gly Ala Val Leu Asp Pro
            100                 105                 110

Gly Lys Thr Pro Lys Ile Asp Lys Cys Ala Ile Leu Asn Asp Ala Ile
        115                 120                 125

Arg Ala Val Thr Glu Leu Arg
    130                 135
```

<210> SEQ ID NO 247
<211> LENGTH: 151
<212> TYPE: PRT
<213> ORGANISM: Oryza sativa

<400> SEQUENCE: 247

```
Met Ala Ser Pro Glu Gly Ser Thr Trp Val Phe Asp Cys Pro Leu Met
1               5                   10                  15

Asp Asp Leu Ala Ala Ala Ala Gly Phe Asp Ala Ala Pro Ala Gly Gly
            20                  25                  30

Phe Tyr Trp Thr Thr Pro Ala Pro Pro Gln Ala Ala Leu Gln Pro Pro
        35                  40                  45

Pro Pro Gln Gln Gln Pro Val Ala Pro Ala Thr Ala Ala Pro Asn Ala
    50                  55                  60

Cys Ala Glu Ile Asn Gly Ser Val Asp Cys Glu His Gly Lys Glu Gln
65                  70                  75                  80

Pro Thr Asn Lys Arg Pro Arg Ser Glu Ser Gly Thr Arg Pro Ser Ser
                85                  90                  95

Lys Ala Cys Arg Glu Lys Val Arg Arg Asp Lys Leu Asn Glu Arg Phe
            100                 105                 110

Leu Glu Leu Gly Ala Val Leu Glu Pro Gly Lys Thr Pro Lys Met Asp
        115                 120                 125

Lys Ser Ser Ile Leu Asn Asp Ala Ile Arg Val Met Ala Glu Leu Arg
    130                 135                 140

Ser Glu Ala Gln Lys Val Glu
145                 150
```